(12) United States Patent
Lindström et al.

(10) Patent No.: US 11,667,651 B2
(45) Date of Patent: Jun. 6, 2023

(54) AMINOPYRIDINE DERIVATIVES AS PHOSPHATIDYLINOSITOL PHOSPHATE KINASE INHIBITORS

(71) Applicant: HiberCell, Inc., New York, NY (US)

(72) Inventors: Johan Lindström, Holo (SE); Lars Boukharta Persson, Uppsala (SE); Jenny Viklund, Hägersten (SE); Edward A. Kesicki, New York, NY (US); Eugene R. Hickey, Danbury, CT (US); Markus K. Dahlgren, Shelton, CT (US); Aleksey I. Gerasyuto, Flemington, NJ (US)

(73) Assignee: HiberCell, Inc., New York, NY (US)

( * ) Notice: Subject to any disclaimer, the term of this patent is extended or adjusted under 35 U.S.C. 154(b) by 0 days.

(21) Appl. No.: 16/956,971

(22) PCT Filed: Dec. 21, 2018

(86) PCT No.: PCT/US2018/067264
§ 371 (c)(1),
(2) Date: Jun. 22, 2020

(87) PCT Pub. No.: WO2019/126731
PCT Pub. Date: Jun. 27, 2019

(65) Prior Publication Data
US 2021/0317136 A1    Oct. 14, 2021

Related U.S. Application Data

(60) Provisional application No. 62/609,568, filed on Dec. 22, 2017.

(51) Int. Cl.
| | |
|---|---|
| C07D 498/14 | (2006.01) |
| A61P 35/00 | (2006.01) |
| C07D 213/74 | (2006.01) |
| C07D 401/12 | (2006.01) |
| C07D 401/14 | (2006.01) |
| C07D 405/14 | (2006.01) |
| C07D 413/14 | (2006.01) |
| C07D 417/14 | (2006.01) |
| C07D 498/04 | (2006.01) |
| C07D 513/14 | (2006.01) |
| C07D 519/00 | (2006.01) |
| C07F 5/02 | (2006.01) |

(52) U.S. Cl.
CPC ............ *C07D 498/14* (2013.01); *A61P 35/00* (2018.01); *C07D 213/74* (2013.01); *C07D 401/12* (2013.01); *C07D 401/14* (2013.01); *C07D 405/14* (2013.01); *C07D 413/14* (2013.01); *C07D 417/14* (2013.01); *C07D 498/04* (2013.01); *C07D 513/14* (2013.01); *C07D 519/00* (2013.01); *C07F 5/02* (2013.01)

(58) Field of Classification Search
CPC .................................................... C07D 498/14
See application file for complete search history.

(56) References Cited

U.S. PATENT DOCUMENTS

| | | |
|---|---|---|
| 6,608,052 B2 | 8/2003 | Breitfelder et al. |
| 6,703,525 B2 | 3/2004 | Kapadia et al. |
| 7,049,310 B2 | 5/2006 | Burgess et al. |
| 7,615,643 B2 | 11/2009 | Kuntz et al. |
| 7,683,064 B2 | 3/2010 | Dewdney et al. |
| 7,906,509 B2 | 3/2011 | Kennedy-Smith et al. |
| 8,058,045 B2 | 11/2011 | Collins et al. |
| 8,124,604 B2 | 2/2012 | Dewdney et al. |
| 8,153,652 B2 | 4/2012 | Burgess et al. |
| 8,367,658 B2 | 2/2013 | Collins et al. |
| 8,445,505 B2 | 5/2013 | Marsilje, III et al. |
| 8,618,098 B2 | 12/2013 | Dewdney et al. |
| 8,703,938 B2 | 4/2014 | Or et al. |
| 8,759,332 B2 | 6/2014 | Qiu et al. |
| 8,815,928 B2 | 8/2014 | Or et al. |
| 8,822,457 B2 | 9/2014 | Dewdney et al. |
| 8,822,700 B2 | 9/2014 | Qiu et al. |
| 8,927,709 B2 | 1/2015 | Qiu et al. |
| RE47,739 E | 11/2019 | Barvian et al. |

(Continued)

FOREIGN PATENT DOCUMENTS

| | | |
|---|---|---|
| EP | 1165516 B1 | 10/2004 |
| EP | 1466906 A1 | 10/2004 |

(Continued)

OTHER PUBLICATIONS

Chemical Abstracts Registry No. 2133413-24-6, indexed in the Registry file on STN CAS Online on Oct. 9, 2017. (Year: 2017).*
Golub et al. "Molecular Classification of Cancer: Class Discovery and Class Prediction by Gene Expression Monitoring" Science, vol. 286, Oct. 15, 1999, pp. 531-537.
Grant, R., Grant, C. (1987). Grant & Hackh's Chemical Dictionary (5th ed.). New York, NY: McGraw-Hill, p. 313.
Hinchliffe et al. "The type II PIPkins (PtdIns5P 4-kinases): enzymes in search of a function?", Biochem. Soc. Trans., (1999), 27(4), p. 657-661.
http://butane.chem.uiuc.edu/jsmoore/chem232/notes_current/Stereochemistry/NOTES-Stereoisomers.pdf, Dec. 2009. (Year: 2009).
International Search Report and Written Opinion for PCT Application No. PCT/US2018/067264 dated Apr. 16, 2019.

(Continued)

*Primary Examiner* — Laura L Stockton
(74) *Attorney, Agent, or Firm* — Goodwin Procter LLP

(57) ABSTRACT

The invention relates to inhibitors of PI5P4K inhibitors useful in the treatment of cancers, neurodegenerative diseases, inflammatory disorders, and metabolic diseases, having the Formula:

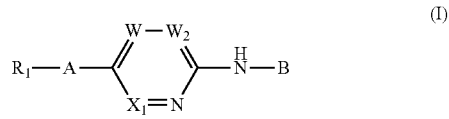

where A, B, $R_1$, $X_1$, $X_2$, and W are described herein.

11 Claims, No Drawings

(56) References Cited

U.S. PATENT DOCUMENTS

| | | | |
|---|---|---|---|
| 2005/0101518 | A1 | 5/2005 | Solow-Cordero et al. |
| 2007/0149508 | A1 | 6/2007 | Noronha et al. |
| 2010/0273797 | A1 | 10/2010 | Boman et al. |
| 2011/0172217 | A1 | 7/2011 | Fujioka et al. |
| 2013/0035336 | A1 | 2/2013 | Borland et al. |
| 2016/0251376 | A1 | 9/2016 | Dahlgren et al. |
| 2018/0161329 | A1 | 6/2018 | Mizuno et al. |
| 2019/0076539 | A1 | 3/2019 | Phillips et al. |
| 2020/0216417 | A1 | 7/2020 | Bernales et al. |
| 2020/0331913 | A1 | 10/2020 | Lindstrom et al. |
| 2020/0392156 | A1 | 12/2020 | Kesicki |
| 2020/0392162 | A1 | 12/2020 | Kesicki |
| 2021/0253600 | A1 | 8/2021 | Lindstrom et al. |
| 2021/0317136 | A1 | 10/2021 | Lindstrom et al. |
| 2022/0372046 | A1 | 11/2022 | Kesicki |

FOREIGN PATENT DOCUMENTS

| | | |
|---|---|---|
| EP | 1690854 A1 | 8/2006 |
| EP | 3053577 A1 | 8/2016 |
| WO | WO2000/055139 A2 | 9/2000 |
| WO | WO2001/027103 A1 | 4/2001 |
| WO | WO2002/083642 A1 | 10/2002 |
| WO | WO2002/096876 A1 | 12/2002 |
| WO | WO2003/022273 A1 | 3/2003 |
| WO | WO2003/029210 A2 | 4/2003 |
| WO | WO2003/062234 A1 | 7/2003 |
| WO | WO2003/062236 A1 | 7/2003 |
| WO | WO2003/068223 A1 | 8/2003 |
| WO | WO2003/088897 A2 | 10/2003 |
| WO | WO2004/030637 A2 | 4/2004 |
| WO | WO2004/082586 A2 | 9/2004 |
| WO | WO2005/018624 A2 | 3/2005 |
| WO | WO2005/021529 A1 | 3/2005 |
| WO | WO2005/023761 A2 | 3/2005 |
| WO | WO2006/016680 A1 | 2/2006 |
| WO | WO2007/030359 A1 | 3/2007 |
| WO | WO2007/030366 A1 | 3/2007 |
| WO | WO2007/056075 A2 | 5/2007 |
| WO | WO2007/058990 A2 | 5/2007 |
| WO | WO2007/071598 A1 | 6/2007 |
| WO | WO2007/084786 A1 | 7/2007 |
| WO | WO2007/091703 A1 | 8/2007 |
| WO | WO2007/095588 A1 | 8/2007 |
| WO | WO2007/110340 A2 | 10/2007 |
| WO | WO2007/143456 A2 | 12/2007 |
| WO | WO2007/146712 A2 | 12/2007 |
| WO | WO2008/099000 A2 | 8/2008 |
| WO | WO2008/138889 A2 | 11/2008 |
| WO | WO2009/016118 A1 | 2/2009 |
| WO | WO2009/044162 A1 | 4/2009 |
| WO | WO2009/050227 A1 | 4/2009 |
| WO | WO2009/085185 A1 | 7/2009 |
| WO | WO2009/108838 A1 | 9/2009 |
| WO | WO2009/156966 A1 | 12/2009 |
| WO | WO2009/158431 A2 | 12/2009 |
| WO | WO2010/014939 A1 | 2/2010 |
| WO | WO2010/020675 A1 | 2/2010 |
| WO | WO-2010/027002 A1 | 3/2010 |
| WO | WO2010/057833 A1 | 5/2010 |
| WO | WO2010/075074 A1 | 7/2010 |
| WO | WO2010/075282 A1 | 7/2010 |
| WO | WO010/100070 A1 | 9/2010 |
| WO | WO-2010/115264 A1 | 10/2010 |
| WO | WO2010/139731 A1 | 12/2010 |
| WO | WO2010/144345 A1 | 12/2010 |
| WO | WO-2011/021678 A1 | 2/2011 |
| WO | WO-2011/022473 A1 | 2/2011 |
| WO | WO-2011/031934 A1 | 3/2011 |
| WO | WO-2011/090738 A2 | 7/2011 |
| WO | WO-2011/101409 A1 | 8/2011 |
| WO | WO-2011/130232 A1 | 10/2011 |
| WO | WO-2012/035023 A1 | 3/2012 |
| WO | WO-2012/045124 A1 | 4/2012 |
| WO | WO-2012/095781 A1 | 7/2012 |
| WO | WO-2012/103806 A1 | 8/2012 |
| WO | WO-2012/158785 A1 | 11/2012 |
| WO | WO-2013/052394 A1 | 4/2013 |
| WO | WO-2013/106612 A1 | 7/2013 |
| WO | WO-2013/106614 A1 | 7/2013 |
| WO | WO-2013/106641 A1 | 7/2013 |
| WO | WO-2013/157540 A1 | 10/2013 |
| WO | WO-2013/192098 A1 | 12/2013 |
| WO | WO-2014/028459 A1 | 2/2014 |
| WO | WO-2014/060395 A1 | 4/2014 |
| WO | WO-2014/106800 A2 | 7/2014 |
| WO | WO-2014/110297 A1 | 7/2014 |
| WO | WO-2015/016206 A1 | 2/2015 |
| WO | WO-2015/098991 A1 | 7/2015 |
| WO | WO-2015/112441 A1 | 7/2015 |
| WO | WO-2015/131080 A1 | 9/2015 |
| WO | WO-2015/180642 A1 | 12/2015 |
| WO | WO-2016/015605 A1 | 2/2016 |
| WO | WO-2016/022644 A1 | 2/2016 |
| WO | WO-2016/027904 A1 | 2/2016 |
| WO | WO-2016/038583 A1 | 3/2016 |
| WO | WO-2016/070107 A1 | 5/2016 |
| WO | WO-2016/089208 A2 | 6/2016 |
| WO | WO-2016/128343 A1 | 8/2016 |
| WO | WO-2016/194831 A * | 8/2016 ........... C07D 471/04 |
| WO | WO-2016/138352 A1 | 9/2016 |
| WO | WO-2016/166250 A1 | 10/2016 |
| WO | WO-2016/194831 A1 | 12/2016 |
| WO | WO-2016/210296 A1 | 12/2016 |
| WO | WO-2017/019804 A2 | 2/2017 |
| WO | WO-2017/071516 A1 | 5/2017 |
| WO | WO-2017/100726 A1 | 6/2017 |
| WO | WO-2017/101763 A1 | 6/2017 |
| WO | WO-2017/161045 A1 | 9/2017 |
| WO | WO-2017/185031 A1 | 10/2017 |
| WO | WO-2017/190086 A1 | 11/2017 |
| WO | WO-2017/197051 A1 | 11/2017 |
| WO | WO-2018/045956 A1 | 3/2018 |
| WO | WO-2018/045957 A1 | 3/2018 |
| WO | WO-2018/106870 A1 | 6/2018 |
| WO | WO-2018136202 A2 | 7/2018 |
| WO | WO-2018/177403 A1 | 10/2018 |
| WO | WO-2018/183112 A1 | 10/2018 |
| WO | WO-2018/232039 A1 | 12/2018 |
| WO | WO-2019/052535 A1 | 3/2019 |
| WO | WO-2019/079783 A1 | 4/2019 |
| WO | WO-2019/090198 A1 | 5/2019 |
| WO | WO-2019/126559 A1 | 6/2019 |
| WO | WO-2019/126731 A1 | 6/2019 |
| WO | WO-2019/152809 A1 | 8/2019 |
| WO | WO-2019/161224 A1 | 8/2019 |
| WO | WO-2019/191092 A1 | 10/2019 |
| WO | WO-2019/191229 A1 | 10/2019 |
| WO | WO-2019/213340 A1 | 11/2019 |
| WO | WO-2020/005873 A1 | 1/2020 |
| WO | WO-2020/023480 A1 | 1/2020 |
| WO | WO-2020/081450 A1 | 4/2020 |
| WO | WO-2020/097265 A1 | 5/2020 |
| WO | WO-2020/108661 A1 | 6/2020 |
| WO | WO-2020/109191 A1 | 6/2020 |
| WO | WO-2020/114487 A1 | 6/2020 |
| WO | WO-2020/114519 A1 | 6/2020 |
| WO | WO-2020/132700 A1 | 6/2020 |
| WO | WO-2020/142742 A1 | 7/2020 |
| WO | WO-2020/163409 A1 | 8/2020 |
| WO | WO-2020/163544 A1 | 8/2020 |
| WO | WO-2020/168197 A1 | 8/2020 |
| WO | WO-2020/207260 A1 | 10/2020 |
| WO | WO-2020/224568 A1 | 11/2020 |
| WO | WO-2020/231977 A1 | 11/2020 |
| WO | WO-2020/257271 A1 | 12/2020 |

OTHER PUBLICATIONS van den Bout et al. "PIP5K-driven PtdIns(4,5) $P_2$ synthesis: regulation and cellular functions" Journal of Cell Science 122, pp. 3837-3850 Published by The Company of Biologists 2009.

(56) References Cited

OTHER PUBLICATIONS

CHEMCATS file; CAS Registry No. 2061527-02-2, STN entry date: Jan. 30, 2017; chemical name: 2-Pyrazinamine, 5-[1-(2-methyl-4-pyrimidinyl)-3-piperidinyl]-N-2-pyrazinyl-.

CHEMCATS file; CAS Registry No. 2060404-38-6, STN entry date: Jan. 27, 2017; chemical name: 2-Pyrazinamine, N-(6-methyl-2-pyridinyl)-5-[1-(4-pyrimidinyl)-3-piperidinyl]-.

CHEMCATS file: CAS Registry No. 2060404-08-0; STN entry date: Jan. 27, 2017; chemical name: 1-Piperidineacetamide, N,N-dimethyl-3-[5-(2-pyrazinylamino)-2-pyrazinyl]-.

CHEMCATS file: CAS Registry No. 1794062-09-1; STN entry date: Jul. 5, 2015; chemical name: 1-Piperidineacetamide, 2-[6-[(4,6-dimethyl-2-pyrimidinyl)amino]-3-pyridinyl]-N,N-dimethyl-.

CHEMCATS file: CAS Registry No. 1381025-64-4; STN entry date: Jul. 4, 2012; chemical name: 2-Pyrazinamine, 5-[1-(6-methyl-4-pyrimidinyl)-3-piperidinyl]-N-2-pyrazinyl-.

CHEMCATS file: CAS Registry No. 1381020-11-6; STN entry date: Jul. 4, 2012; chemical name: 2-Pyrimidinamine, N-[5-[1-(6-methyl-4-pyrimidinyl)-3-piperidinyl]-2-pyrazinyl]-.

CHEMCATS file: CAS Registry No. 1381019-89-1; STN entry date: Jul. 4, 2012; chemical name: 2-Pyrazinamine, N-2-pyrazinyl-5-[1-(2-pyrimidinyl)-3-piperidinyl]-.

CHEMCATS file: CAS Registry No. 1380993-08-7; STN entry date: Jul. 4, 2012; chemical name: 1-Piperidineacetamide, N,N-dimethyl-3-[5-[(6-methyl-2-pyridinyl)amino]-2-pyrazinyl]-.

CHEMCATS file: CAS Registry No. 1380992-98-2; STN entry date Jul. 4, 2012; chemical name: 1-Piperidineacetamide, N,N-dimethyl-3-[5-(2-pyridinylamino)-2-pyrazinyl]-.

CHEMCATS file: CAS Registry No. 1380898-52-1; STN entry date: Jul. 3, 2012; chemical name: 2-Pyrazinamine, 5-[1-(2-pyrimidinyl)-3-piperidinyl]-N-2-thiazolyl-.

CHEMCATS file: CAS Registry No. 1380855-52-6; STN entry date: Jul. 3, 2012; chemical name: 2-Pyrazinamine, N-2-pyridinyl-5-[1-(2-pyrimidinyl)-3-piperidinyl]-.

CHEMCATS file: CAS Registry No. 1380854-25-0; STN entry date: Jul. 3, 2012; chemical name: 2-Pyrazinamine, N-(6-methyl-2-pyridinyl)-5-[1-(2-pyrimidinyl)-3-piperidinyl]-.

CHEMCATS file: CAS Registry No. 1380852-13-0; STN entry date: Jul. 3, 2012; chemical name: 2-Pyrazinamine, 5-[1-(6-methyl-4-pyrimidinyl)-3-piperidinyl)-N-2-pyridinyl-.

* cited by examiner

AMINOPYRIDINE DERIVATIVES AS PHOSPHATIDYLINOSITOL PHOSPHATE KINASE INHIBITORS

CROSS-REFERENCE TO RELATED APPLICATIONS

This application is a U.S. National Phase Application, filed under 35 U.S.C. 371, of International Application No. PCT/US2018/067264, filed on Dec. 21, 2018, which claims the benefit of priority of U.S. Provisional Application No. 62/609,568, filed Dec. 22, 2017, which the entire disclosure of each are incorporated herein by reference in their entirety.

FIELD OF INVENTION

The present invention is directed to inhibitors of phosphatidylinositol-5-phosphate-4-kinase (PI5P4K) useful in the treatment of diseases or disorders associated with PI5P4K enzymes. In particular, the invention is concerned with compounds and compositions inhibiting PI5P4K, methods of treating diseases or disorders associated with PI5P4K, and methods of synthesis of these compounds.

BACKGROUND OF THE INVENTION

A minor but ubiquitous component of cells, phosphoinositol lipids are pivotal players in many intracellular signal transduction pathways. Phosphoinositol lipids are formed when phosphatidylinositol (PtdIns) is converted, by the catalytic action of lipid kinases, to polyphosphoinositides. As a prototypic example, the membrane associated phospholipid, phosphatidylinositol-4,5-bisphosphate (PtdIns(4, 5)P2), is formed by two successive phosphorylations of PtdIns by the phosphatidylinositol phosphate kinases (PIP kinases).

PtdIns(4,5)P2 is a substrate for phospholipase C (PLC) and is converted into the second messengers inositol-1,4,5-trisphosphate and diacylglycerol (DAG). Phosphoinositides are involved in regulating a broad spectrum of activities from cytoskeletal assembly and motility to vesicle trafficking and exocytosis to transduction of intracellular signals including stimulating the release of intracellular calcium stores (Hinchliffe et al., Biochem. Soc. Trans., 1999, 27, 657-661).

PIP kinases comprise a unique and promiscuous family of enzymes that catalyze the production of poly-phosphorylated inositol lipids from mono-phosphorylated phosphoinositides. isolation and purification of several different PIP kinase enzymes able to catalyze phosphorylation of phosphatidylinositol 4-phosphate and produce PtdIns(4,5)P2 led to the further categorization of these enzymes, dubbed the phosphatidylinositol 4-phosphate 5-kinases (PIP5Ks), into two types having different activities. The PIP kinases have no homology to other lipid or protein kinases at the primary sequence level, and are distinguished from each other by their lack of immuno-cross reactivity and by the fact that type I PIP5Ks are stimulated in vitro by phosphatidic acid, whereas the type II PIP5Ks are not. Furthermore, the recent discovery that the type II PTP5Ks are able to phosphorylate multiple lipid substrates in vitro suggests that this family of kinases is potentially able to generate several distinct, often subcellularly compartmentalized, phosphoinositol products for regulation of a variety of physiologically important processes (Hinchliffe et al., Biochem. Soc. Trans., 1999, 27, 657-661).

One particular species of PI, phosphatidylinositol 5-phosphate (PI5P), has been implicated in the regulation of the tumor suppressor ING2 and the oncogene AKT. The phosphatidylinositol 5-phosphate 4-kinase (PI5P4K) family (α, β, γ isoforms) catalyzes the conversion of PI5P to PI4, 5 P2. These enzymes therefore represent one means by which cells can regulate endogenous PI5P levels. Mice deficient for PI5P4Kβ (PI5P4Kβ-/-) have been shown to exhibit enhanced insulin sensitivity and activation of AKT in skeletal muscle.

The pharmacological modulation of PIP5KII-beta activity and/or expression is therefore believed to be an appropriate point of therapeutic intervention in pathological conditions in which cell differentiation, proliferation, and/or motility are compromised, such as cancer or inflammation, and in metabolic disorders.

Currently, there are no known therapeutic agents which effectively inhibit the synthesis of PIP5KII-beta. Inhibition of PI5P4K with small molecule inhibitors, therefore, has the potential to be a treatment for cancers and other disorders. For this reason, there remains a considerable need for novel and potent small molecule inhibitors and agents capable of effectively inhibiting PIP5KII-beta function.

SUMMARY OF THE INVENTION

A first aspect of the invention relates to compounds of Formula (I):

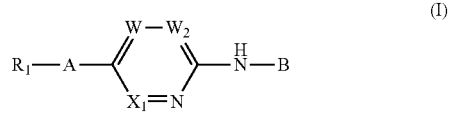

and pharmaceutically acceptable salts, prodrugs, solvates, hydrates, isomers, and tautomers thereof,
wherein:
A is $C_{3-8}$ cycloalkyl, $C_{4-8}$ cycloalkenyl, $C_{2-6}$ alkynyl, aryl, spiroheterocyclyl, heterocyclyl, or 6-membered heteroaryl, wherein the cycloalkyl, heterocyclyl, aryl spiroheterocyclyl, or heteroaryl is optionally substituted with one or more $R_5$;

B is heterocyclyl or heteroaryl, wherein the heterocyclyl group is optionally substituted with one or more $R_7$ and the heteroaryl is optionally substituted with one or more $R_8$, provided that when B is heteroaryl, B is not bonded through its heteroatom;

$X_1$ is $C(R_5)$;
$X_2$ is $C(R_5)$ or N;
W is $C(R_6)$ or N; provided that only one of $X_1$, $X_2$, or W can be N;
$R_1$ is $-N(R_2)C(O)R_3$, $-C(O)N(R_2)(R_3)$, $-S(O)_2N(R_2)(R_3)$, $-N(R_2)S(O)_2R_3$, $-R_2C(O)N(R_2)(R_3)$, or heteroaryl, wherein heteroaryl is optionally substituted with one or more $R_7$;
$R_2$ is independently, at each occurrence, $C_{1-6}$ alkyl, $C_{2-6}$ alkenyl, or $C_{2-6}$ alkynyl, wherein the alkyl, alkenyl, or alkynyl is optionally substituted with one or more $R_4$;
$R_3$ is independently, at each occurrence, $-H$, $C_{1-6}$ alkyl, $C_{2-6}$ alkenyl, or $C_{2-6}$ alkynyl, wherein the alkyl, alkenyl, or alkynyl is optionally substituted with one or more $R_4$; or
$R_2$ and $R_3$ when taken together with the atom to which they are each attached form a heterocycle optionally substituted with one or more $R_4$;

$R_4$ is independently —H, halogen, —OH, —NH$_2$, —NO$_2$, —CN, C$_{1-6}$ alkyl, C$_{1-6}$ alkoxy, C$_{3-8}$ cycloalkyl, heterocyclyl, aryl, or heteroaryl, wherein the alkyl, alkoxy, cycloalkyl, heterocyclyl, aryl, or heteroaryl is optionally substituted with one or more $R_7$;

$R_5$ is independently —H, halogen, —OH, —CN, C$_{1-6}$ alkyl, methoxy, —OC$_3$-C$_6$ alkyl, C$_{3-8}$ cycloalkyl, heterocyclyl, aryl, or heteroaryl;

$R_6$ is —H, halogen, —OH, —NH$_2$, —NO$_2$, —CN, —CO$_2$H, —C(O)NH$_2$, C$_{1-6}$ alkoxy, C$_{3-8}$ cycloalkyl, heterocyclyl, —O—C$_{3-8}$ cycloalkyl, or C$_{1-6}$ alkyl, wherein the alkyl, alkoxy, heterocyclyl, or cycloalkyl is optionally substituted with —OH, C$_{1-6}$ alkyl, C$_{1-6}$ alkoxy, C$_{3-8}$ cycloalkyl, —NH$_2$, —NH(C$_{1-6}$ alkyl), or —N(C$_{1-6}$ alkyl)$_2$; or $R_5$ and $R_6$ when on adjacent carbons and when taken together with the carbon atom to which they are each attached form a 5- to 6-membered heteroaryl ring;

$R_7$ is —H, halogen, —OH, oxo, C$_{1-6}$ alkyl, C$_{1-6}$ alkoxy, C$_{3-8}$ cycloalkyl, heterocyclyl, aryl, or heteroaryl, wherein the alkyl, alkoxy, cycloalkyl, heterocyclyl, aryl or heteroaryl is optionally substituted with one or more $R_{14}$;

$R_8$ is —H, —CN, oxo, C$_{1-6}$ alkyl, heterocyclyl, aryl, heteroaryl —N(R$_9$)C(O)R$_{10}$, —N(R$_9$)C(O)OR$_{10}$, —N(R$_9$)C(O)N(R$_9$)(R$_{10}$), —N(R$_9$)S(O)$_2$R$_{10}$, —S(O)$_2$R$_{10}$, —C(O)R$_9$, —N(R$_9$)(R$_{10}$), —OR$_{10}$, —C(O)R$_9$—NR$_{10}$, —N(R$_9$)C(O)R$_{13}$, or —C(O)N(R$_9$)(R$_{10}$), wherein the alkyl, heterocyclyl, aryl, or heteroaryl is optionally substituted with one or more $R_{15}$; or two $R_8$ groups, together with the atoms to which they are attached, form a C$_{3-6}$ cycloalkyl, C$_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$ or the aryl or heteroaryl is optionally substituted with one or more $R_{24}$;

each $R_9$ or $R_{10}$ is independently, at each occurrence, —H, C$_{1-6}$ alkyl, C$_{2-6}$ alkenyl, C$_{2-6}$ alkynyl, C$_{3-8}$ cycloalkyl, aryl, heteroaryl, or heterocyclyl, wherein the alkyl, cycloalkyl, or heterocyclyl is optionally substituted with one or more $R_{11}$; or $R_9$ and $R_{10}$ when taken together with the atom to which they are each attached form a heterocycle ring optionally substituted with one or more $R_{12}$;

$R_{11}$ is —H, halogen, —CN, oxo, —OH, —N(R$_{23}$)(R$_{25}$), —OR$_{23}$, C$_{1-6}$ alkyl, C$_{1-6}$ alkoxy, C$_{3-8}$ cycloalkyl, heterocyclyl, heteroaryl, aryl, —C(O)R$_{17}$, —C(O)R$_{17}$, —C(O)OR$_{17}$, —OC(O)R$_{17}$, or —C(O)N(R$_{23}$)(R$_{23}$), wherein the alkyl, alkoxy, aryl, heterocyclyl, heteroaryl, or cycloalkyl is optionally substituted with one or more $R_{17}$;

$R_{12}$ is independently —C(O)OR$_{21}$, —C(O)R$_{13}$; oxo, —OH, C$_{1-6}$ alkyl, heterocycle, —(C$_{1-6}$ alkyl)-heteroaryl, —(C$_{1-6}$ alkyl)-heterocycle, —(C$_{1-6}$alkyl)-C$_{3-6}$ cycloalkyl, —(C$_{1-6}$ alkyl)-aryl, wherein any alkyl, heteroaryl, heterocycle, cycloalkyl, or aryl is optionally substituted with one or more $R_{18}$; or two $R_{12}$ together with the atoms to which they are attached form an aryl ring optionally substituted with one or more $R_{18}$;

each $R_{13}$ is aryl, heterocyclyl, cycloalkyl, or heteroaryl, wherein the aryl or heteroaryl group is optionally substituted with one or more $R_{19}$ and the heterocyclyl or cycloalkyl is optionally substituted with one or more $R_{20}$;

$R_{14}$ is independently —H, halogen, —CN, —NO$_2$, —OH, —NH$_2$, C$_{1-6}$ alkyl, C$_{3-8}$ cycloalkyl, heterocyclyl, aryl, or heteroaryl;

$R_{15}$ is —H, halogen, oxo, —OH, —NH$_2$, —NO$_2$, C$_{1-6}$ alkyl, C$_{1-6}$ alkoxy, C$_{3-8}$ cycloalkyl, heterocyclyl, aryl, heteroaryl, —C(O)N(R$_{21}$)(R$_{23}$), —(CH$_2$)$_o$—C(O)R$_{23}$, —OC(O)R$_{23}$, —C(O)OR$_{23}$, —SO$_2$R$_{23}$, —N(R$_{23}$)C(O)—Ar—N(R$_{23}$)-G or —N(R$_{23}$)C(O)—Ar—N(R$_{23}$)C(O)-G, wherein the alkyl, alkoxy, cycloalkyl, heterocyclyl, heteroaryl, or aryl is optionally substituted with one or more $R_{23}$; or two $R_{15}$ groups, together with the atoms to which they are attached, form a heterocyclyl, C$_{3-6}$ cycloalkyl, C$_{5-6}$ spirocycloalkyl, aryl, or heteroaryl, wherein cycloalkyl, heterocyclyl, spirocycloalkyl, heteroaryl, or aryl is optionally substituted with one or more $R_{20}$;

Ar is aryl;

G is —H, C$_{1-6}$ alkyl, C$_{1-6}$ alkoxy, C$_{2-6}$ alkenyl, C$_{2-6}$ alkynyl, C$_{3-8}$ cycloalkyl, heterocyclyl, aryl, heteroaryl, —C(O)OR$_{23}$, —C(O)CH═CHCH$_2$N(R$_{23}$)(R$_{23}$), or —C(O)N(R$_{21}$)(R$_{23}$); or two $R_{15}$ when on adjacent atoms may be taken together with the atoms to which they are each attached to form a heterocycle optionally substituted with one or more $R_{16}$;

$R_{16}$ is independently C$_{1-6}$ alkyl, C$_{3-6}$ cycloalkyl, —C(O)R$_{23}$, —C(O)R$_{23}$, —C(O)OR$_{23}$, —S(O)$_2$R$_{23}$, or oxo;

$R_{17}$ is —H, —CN, C$_{1-6}$ alkyl, C$_{1-6}$ alkoxy, heteroaryl, aryl, —N(R$_{23}$)(R$_{23}$), —N(R$_{23}$)C(O)OR$_{23}$, —C(O)N(R$_{23}$)(R$_{23}$), —N(R$_{23}$)C(O) R$_{23}$, —N(R$_{23}$)C(O)—U—Z, or —N(R$_{23}$)C(O)—U—N(R$_{23}$)—Z;

Z is —H, C$_{1-6}$ alkyl, C$_{1-6}$ alkoxy, C$_{2-6}$ alkenyl, C$_{2-6}$ alkynyl, C$_{3-8}$ cycloalkyl, heterocyclyl, aryl, heteroaryl, or —C(O)—U—N(R$_{23}$)(R$_{23}$);

U is —(CH$_2$)$_p$—, —(CH$_2$)$_p$—Ar—, —CH═CH(CH$_2$)$_p$—, or heterocyclyl;

$R_{18}$ is independently C$_{1-6}$ alkyl, heteroaryl, heterocyclyl, cycloalkyl, aryl, —OR$_{23}$, —N(R$_{23}$)(R$_{23}$), or —N(R$_{23}$)C(O)—V—N(R$_{23}$)-E, wherein the heteroaryl, heterocyclyl, cycloalkyl, or aryl is optionally substituted with one or more $R_{19}$;

V is —(CH$_2$)$_n$—, —(CH$_2$)$_n$—Ar—, or —CH═CH(CH$_2$)$_n$—,

E is —H, C$_{1-6}$ alkyl or —C(O)—V—N(R$_{23}$)(R$_{23}$);

$R_{19}$ is halogen, C$_{1-6}$ alkyl, C$_{3-6}$ cycloalkyl, —OR$_{21}$, —N(R$_{21}$)(R$_{22}$), —C(O)R$_{21}$, —N(R$_{23}$)C(O)OR$_{23}$, —N(R$_{23}$)C(O)-Q-N(R$_{23}$)—F, or —N(R$_{23}$)-Q-N(R$_{23}$)—F;

Q is —CH═CH(CH$_2$)$_m$—, —(CH$_2$)$_m$—, —(CH$_2$O)$_m$, —(CH$_2$)$_m$Ar—, or —(CH$_2$CH$_2$O)$_o$—(CH$_2$)$_m$—,

F is —H, C$_{1-6}$ alkyl, aryl, heteroaryl, —C(O)-Q-R$_{23}$, or —C(O)-Q-N(R$_{23}$)(R$_{23}$), wherein the alkyl, aryl, or heteroaryl is optionally substituted with one or more $R_{23}$; or $R_{20}$ is independently —H, halogen, —OH, —NH$_2$, oxo, —C(O)R$_{21}$, —OR$_{23}$, C$_{3-6}$ cycloalkyl, or C$_{1-6}$ alkyl; or $R_{21}$ is —H, C$_{1-6}$ alkyl, C$_{2-6}$ alkenyl, C$_{2-6}$ alkynyl, C$_{3-8}$ cycloalkyl, heterocyclyl, aryl, or heteroaryl, wherein the alkyl, alkenyl, alkynyl, cycloalkyl, heterocyclyl, heteroaryl, or aryl is optionally substituted with one or more —H, halogen, —CN, —OH, C$_{1-6}$ alkyl, C$_{1-6}$ alkoxy, C$_{3-8}$-cycloalkyl, heterocyclyl, heteroaryl, or aryl;

$R_{22}$ is —H, C$_{1-6}$ alkyl, or —C(O)R$_{23}$; and each $R_{23}$ is independently —H, C$_{1-6}$ alkyl, C$_{1-6}$ alkoxy, C$_{2-6}$ alkenyl, C$_{2-6}$ alkynyl, C$_{3-8}$ cycloalkyl, heterocyclyl, aryl, or heteroaryl, wherein the alkyl, alkenyl, alkynyl, cycloalkyl, heterocyclyl, heteroaryl, or aryl is optionally substituted with one or more —H, halogen, —CN, —OH, —NH$_2$, C$_{1-6}$ alkyl, C$_{1-6}$ alkoxy, C$_{3-8}$ cycloalkyl, heterocyclyl, heteroaryl, aryl, or R$_{24}$;

R$_{24}$ is —H, C$_{1-6}$ alkyl, C$_{2-6}$ alkenyl, C$_{2-6}$ alkynyl, C$_{3-8}$ cycloalkyl, heterocyclyl, aryl, or heteroaryl, C(O)N(C$_{1-6}$ alkyl)(C$_{1-6}$ alkyl), —C(O)—C$_{1-6}$ alkyl, —C(O)—C$_{2-6}$ alkenyl, —C(O)O—C$_{1-6}$ alkyl, wherein the alkyl, alkenyl, alkynyl, cycloalkyl, heterocyclyl, heteroaryl, or aryl is optionally substituted with one or more —H, halogen, —CN, —OH, —NH$_2$, C$_{1-6}$ alkyl, C$_{1-6}$ alkoxy, C$_{3-8}$ cycloalkyl, heterocyclyl, heteroaryl, or aryl;

R$_{25}$ is independently C$_{1-6}$ alkyl, C$_{1-6}$ alkoxy, C$_{2-6}$ alkenyl, C$_{2-6}$ alkynyl, C$_{3-8}$ cycloalkyl, heterocyclyl, aryl, or heteroaryl, wherein the alkyl, alkenyl, alkynyl, cycloalkyl, heterocyclyl, heteroaryl, or aryl is optionally substituted with one or more —H, halogen, —CN, —OH, —NH$_2$, C$_{1-6}$ alkyl, C$_{1-6}$ alkoxy, C$_{3-8}$ cycloalkyl, heterocyclyl, heteroaryl, aryl, or R$_{24}$;

each p is independently 1-4;
each n is independently 1-4;
each m is independently 1-4; and
each o is independently 0-4.

Another aspect of the invention relates to a method of treating a disease or disorder associated with modulation of PI5P4K. The method comprises administering to a patient in need of a treatment for diseases or disorders associated with modulation of PI5P4K an effective amount of a compound of Formula (I), or a pharmaceutically acceptable salt, hydrate, solvate, prodrug, stereoisomer, or tautomer thereof.

Another aspect of the invention is directed to a method of inhibiting PI5P4K. The method involves administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating cancer. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating a neurodegenerative disease. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating a viral infection or disease. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating an inflammatory disease or condition. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of inducing cell cycle arrest, apoptosis in tumor cells and/or enhanced tumor-specific T-cell immunity. The method comprises contacting the cells with an effective amount of a compound of Formula (I), or a pharmaceutically acceptable salt, hydrate, solvate, prodrug, stereoisomer, or tautomer thereof.

Another aspect of the invention is directed to pharmaceutical compositions comprising a compound of Formula (I), or a pharmaceutically acceptable salt, hydrate, solvate, prodrug, stereoisomer, or tautomer thereof and a pharmaceutically acceptable carrier. The pharmaceutical acceptable carrier may further include an excipient, diluent, or surfactant.

Another aspect of the present invention relates to a compound of Formula (I), or a pharmaceutically acceptable salt, hydrate, solvate, prodrug, stereoisomer, or tautomer thereof, for use in the manufacture of a medicament for treating a disease associated with inhibiting PI5P4K.

Another aspect of the present invention relates to the use of a compound of Formula (I), or a pharmaceutically acceptable salt, hydrate, solvate, prodrug, stereoisomer, or tautomer thereof, in the treatment of a disease associated with inhibiting PI5P4K.

The present invention further provides methods of treating a disease or disorder associated with modulation of PI5P4K including, cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases, comprising administering to a patient suffering from at least one of said diseases or disorder a compound of Formula (I), or a pharmaceutically acceptable salt, hydrate, solvate, prodrug, stereoisomer, or tautomer thereof.

The present invention provides inhibitors of PI5P4K that are therapeutic agents in the treatment of diseases such as cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases.

The present invention further provides compounds and compositions with an improved efficacy and safety profile relative to known PI5P4K inhibitors. The present disclosure also provides agents with novel mechanisms of action toward PI5P4K enzymes in the treatment of various types of diseases including cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases. Ultimately the present invention provides the medical community with a novel pharmacological strategy for the treatment of diseases and disorders associated with PI5P4K enzymes.

DETAILED DESCRIPTION OF THE INVENTION

The present invention relates to compounds and compositions that are capable of inhibiting the activity PI5P4K. The invention features methods of treating, preventing or ameliorating a disease or disorder in which PI5P4K plays a role by administering to a patient in need thereof a therapeutically effective amount of a compound of Formula (I), or a pharmaceutically acceptable salt, hydrate, solvate, prodrug, stereoisomer, or tautomer thereof. The methods of the present invention can be used in the treatment of a variety of PI5P4K dependent diseases and disorders by inhibiting the activity of PI5P4K enzymes. Inhibition of PI5P4K provides a novel approach to the treatment, prevention, or amelioration of diseases including, but not limited to, cancer and metastasis, neurodegenerative diseases, immunological disorders, osteoporosis, arthritis inflammatory disorders, cardiovascular diseases, ischemic diseases, viral infections and diseases, and bacterial infections and diseases.

In a first aspect of the invention, the compounds of Formula (I) are described:

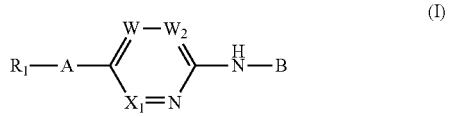

(I)

and pharmaceutically acceptable salts, hydrates, solvates, prodrugs, stereoisomers, and tautomers thereof, wherein A, B, $R_1$, $X_1$, $X_2$, and W are described herein above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have one or more substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—($C_1$-$C_6$) alkyl, ($C_1$-$C_6$) alkyl, ($C_1$-$C_6$) alkoxy, ($C_1$-$C_6$) haloalkyl, ($C_1$-$C_6$) haloalkoxy, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O ($C_1$-$C_6$) alkyl, —NH$_2$, —NH(($C_1$-$C_6$) alkyl), —N(($C_1$-$C_6$) alkyl)$_2$, —NHC(O)($C_1$-$C_6$) alkyl, —C(O)NH($C_1$-$C_6$) alkyl, —S(O)$_2$($C_1$-$C_6$) alkyl, —S(O)NH($C_1$-$C_6$)alkyl, and —S(O) N(($C_1$-$C_6$)alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$)alkyl, ($C_1$-$C_6$)alkyl, —O— ($C_2$-$C_6$)alkenyl, —O—($C_2$-$C_6$) alkynyl, ($C_2$-$C_6$)alkenyl, ($C_2$-$C_6$)alkynyl, —OH, —OP(O)(OH)$_2$, —OC(O)($C_1$-$C_6$) alkyl, —C(O)($C_1$-$C_6$) alkyl, —OC(O)O($C_1$-$C_6$)alkyl, —NH$_2$, —NH(($C_1$-$C_6$)alkyl), —N(($C_1$-$C_6$)alkyl)$_2$, —S(O)$_2$ —($C_1$-$C_6$) alkyl, —S(O)NH($C_1$-$C_6$)alkyl, and —S(O)N (($C_1$-$C_6$)alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic or a polycyclic aromatic radical of 5 to 24 ring atoms, containing one or more ring heteroatoms selected from N, O, S, P, or B, the remaining ring atoms being C. A polycyclic aromatic radical includes two or more fused rings and may further include two or more spiro-fused rings, e.g., bicyclic, tricyclic, tetracyclic, and the like. Unless otherwise specifically defined, "fused" means two rings sharing two ring atoms. Unless otherwise specifically defined, "spiro-fused" means two rings sharing one ring atom. Heteroaryl as herein defined also means a bicyclic heteroaromatic group wherein the heteroatom is selected from N, O, S, P, or B. Heteroaryl as herein defined also means a tricyclic heteroaromatic group containing one or more ring heteroatoms selected from N, O, S, P, or B. Heteroaryl as herein defined also means a tetracyclic heteroaromatic group containing one or more ring heteroatoms selected from N, O, S, P, or B. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b] pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2, 3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3, 4-b]pyridinyl, pyrrolo[3,2-b]pyridinyl, imidazo[5,4-b] pyridinyl, pyrrolo[1,2-a]pyrimidinyl, tetrahydro pyrrolo[1,2-a]pyrimidinyl, 3,4-dihydro-2H-1-pyrrolo[2,1-b] pyrimidine, dibenzo[b,d] thiophene, pyridin-2-one, furo[3,2-c]pyridinyl, furo[2,3-c]pyridinyl, 1H-pyrido[3,4-b][1,4] thiazinyl, benzooxazolyl, benzoisoxazolyl, furo[2,3-b] pyridinyl, benzothiophenyl, 1,5-naphthyridinyl, furo[3,2-b] pyridine, [1,2,4]triazolo[1,5-a]pyridinyl, benzo[1,2,3]triazolyl, imidazo[1,2-a]pyrimidinyl, [1,2,4]triazolo[4,3-b] pyridazinyl, benzo[c][1,2,5]thiadiazolyl, benzo[c][1,2,5] oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d] thiazolyl, imidazo[2,1-b][1,3,4]thiadiazolyl, thieno[2,3-b] pyrrolyl, 3H-indolyl, and derivatives thereof. Furthermore, when containing two or more fused rings, the heteroaryl groups defined herein may have one or more saturated or partially unsaturated ring fused with one or more fully unsaturated ring. In heteroaryl ring systems containing more than two fused rings, a saturated or partially unsaturated ring may further be fused with a saturated or partially unsaturated ring described herein. Furthermore, when containing three or more fused rings, the heteroaryl groups defined herein may have one or more saturated or partially unsaturated ring spiro-fused. Any saturated or partially unsaturated ring described herein is optionally substituted with one or more oxo. Exemplary ring systems of these heteroaryl groups include, for example, indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuranyl, benzofuranonyl, indolinyl, oxindolyl, indolyl, 1,6-dihydro-7H-pyrazolo[3,4-c]pyridin-7-onyl, 7,8-dihydro-6H-pyrido[3,2-b] pyrrolizinyl, 8H-pyrido[3,2-b]pyrrolizinyl, 1,5,6,7-tetrahydrocyclopenta[b]pyrazolo[4,3-e]pyridinyl, 7,8-dihydro-6H-pyrido[3,2-b]pyrrolizine, pyrazolo[1,5-a] pyrimidin-7(4H)-only, 3,4-dihydropyrazino[1,2-a]indol-1 (2H)-onyl, benzo[c][1,2]oxaborol-1(3H)-olyl, 6,6a,7,8-tetrahydro-9H-pyrido[2,3-b]puyrrolo[1,2-d][1,4]oxazin-9-onyl, or 6a',7'-dihydro-6'H,9'H-spiro[cyclopropane-1,8'-pyrido[2,3-b]pyrrolo[1,2-d][1,4]oxazin]-9'-onyl.

Halogen or "halo" refers to fluorine, chlorine, bromine, or iodine.

Alkyl refers to a straight or branched chain saturated hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, i.e., —O(alkyl). Examples of alkoxy groups include without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

The term "alkylene" or "alkylenyl" refers to a divalent alkyl radical. Any of the above mentioned monovalent alkyl groups may be an alkylene by abstraction of a second hydrogen atom from the alkyl. As herein defined, alkylene may also be a $C_1$-$C_6$ alkylene. An alkylene may further be a $C_1$-$C_4$ alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

"Cycloalkyl" means monocyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norbornyl, norborenyl, bicyclo[2.2.2]octanyl, or bicyclo[2.2.2] octenyl.

"Cycloalkylalkyl" means monocyclic saturated carbon rings containing 3-24 carbon atoms further substituted with ($C_1$-$C_6$) alkyl groups. In general cycloalkylalkyl groups herein described display the following formula

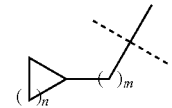

where m is an integer from 1 to 6 and n is an integer from 1 to 16. The cycloalkyl ring or carbocycle may be optionally substituted by one or more substituents, e.g., 1 to 5 substituents, at any point of attachment. The substituents can themselves be optionally substituted. Examples of cycloalkyl groups include, without limitations, cyclopropyl, cyclobutyl, cyclopentyl, cyclohexyl, cycloheptanyl, cyclooctanyl, norbornyl, norborenyl, bicyclo[2.2.2]octanyl, bicyclo[2.2.2]octenyl, decahydronaphthalenyl, octahydro-TH-indenyl, cyclopentenyl, cyclohexenyl, cyclohexa-1,4-dienyl, cyclohexa-1,3-dienyl, 1,2,3,4-tetrahydronaphthalenyl, octahydropentalenyl, 3a,4,5,6,7,7a-hexahydro-1H-indenyl, 1,2,3,3a-tetrahydropentalenyl, bicyclo[3.1.0] hexanyl, bicyclo[2.1.0]pentanyl, spiro[3.3]heptanyl, bicyclo [2.2.1]heptanyl, bicyclo[2.2.1]hept-2-enyl, bicyclo[2.2.2] octanyl, 6-methylbicyclo[3.1.1]heptanyl, 2,6,6-trimethylbicyclo[3.1.1]heptanyl, and derivatives thereof.

"Heterocyclyl" or "heterocycloalkyl" monocyclic rings contain carbon and one or more heteroatoms selected from N, O, S, P, or B and wherein the rings are not aromatic. The heterocycloalkyl ring structure may be substituted by one or more substituents. The substituents can themselves be optionally substituted. Examples of heterocyclyl rings include, but are not limited to, oxetanyl, azetidinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl.

The term "aromatic" means a planar ring having 4n+2 electrons in a conjugated system. As used herein, "conjugated system" means a system of connected p-orbitals with delocalized electrons, and the system may include lone electron pairs.

The term "hydroxyalkyl" means an alkyl group as defined above, where the alkyl group is substituted with one or more OH groups. Examples of hydroxyalkyl groups include HO—CH$_2$—, HO—CH$_2$—CH$_2$— and CH$_3$—CH(OH)—.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., C≡N.

The term "amine" as used herein refers to primary (R—NH$_2$, R≠H), secondary (R$_2$—NH, R$_2$≠H) and tertiary (R$_3$—N, R≠H) amines. A substituted amine is intended to mean an amine where at least one of the hydrogen atoms has been replaced by the substituent.

The term "amino" as used herein means a substituent containing at least one nitrogen atom. Specifically, —NH$_2$, —NH(alkyl) or alkylamino, —N(alkyl)$_2$ or dialkylamino, amide-, carbamide-, urea, and sulfamide substituents are included in the term "amino".

The term "dialkylamino" as used herein refers to an amino or —NH$_2$ group where both of the hydrogens have been replaced with alkyl groups, as defined herein above, i.e., —N(alkyl)$_2$. The alkyl groups on the amino group can be the same or different alkyl groups. Example of alkylamino groups include, but are not limited to, dimethylamino (i.e., —N(CH$_3$)$_2$), diethylamino, dipropylamino, diisopropylamino, di-n-butylamino, di-sec-butylamino, di-tert-butylamino, methyl(ethyl)amino, methyl(butylamino), etc.

"Spirocycloalkyl" or "spirocyclyl" means carbogenic bicyclic ring systems with both rings connected through a single atom. The ring can be different in size and nature, or identical in size and nature. Examples include spiropentane, spriohexane, sprioheptane, spriooctane, sprinonane, or spirodecane. One or both of the rings in a spirocycle can be fused to another ring carbocyclic, heterocyclic, aromatic, or heteroaromatic ring. One or more of the carbon atoms in the spirocycle can be substituted with a heteroatom (e.g., O, N, S, or P). A (C$_3$-C$_{12}$) spirocycloalkyl is a spirocycle containing between 3 and 12 carbon atoms. One or more of the carbon atoms can be substituted with a heteroatom.

The term "spiroheterocycloalkyl" or "spiroheterocyclyl" is understood to mean a spirocycle wherein at least one of the rings is a heterocycle (e.g., at least one of the rings is furanyl, morpholinyl, or piperidinyl).

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The present invention also contemplates isotopically-labelled compounds of Formula I (e.g., those labeled with $^2$H and $^{14}$C). Deuterated (i.e., $^2$H or D) and carbon-14 (i.e., $^{14}$C) isotopes are particularly preferred for their ease of preparation and detectability. Further, substitution with heavier isotopes such as deuterium may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples herein below, by substituting an appropriate isotopically labelled reagent for a non-isotopically labelled reagent.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzoate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate, pantothenate, phosphate/diphosphate, picrate, polygalacturonate, propionate, p-toluenesulfonate, salicylate, stearate, subacetate, succinate, sulfate, sulfosalicylate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The present invention relates to compounds or pharmaceutically acceptable salts, hydrates, solvates, prodrugs, stereoisomers, or tautomers thereof, capable of inhibiting PI5P4K, which are useful for the treatment of diseases and disorders associated with modulation of a PI5P4K enzyme. The invention further relates to compounds, or pharmaceutically acceptable salts, hydrates, solvates, prodrugs, stereoisomers, or tautomers thereof, which are useful for inhibiting PI5P4K.

In another embodiment, the compounds of Formula (I) have the structure of Formula (Ia):

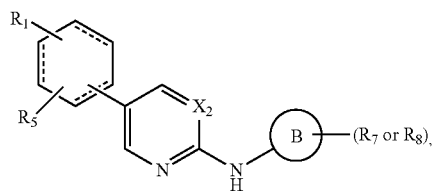

(Ia)

wherein:

------- represents an optional double bond.

In one embodiment, the compounds of Formula (I) have the structure of Formula (Ib):

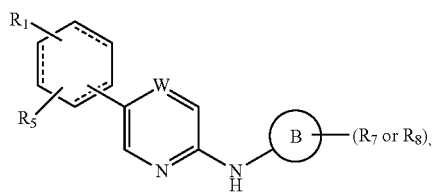

(Ib)

wherein ------- represents an optional double bond conferring partial unsaturation or aromaticity to the ring.

In another embodiment, the compounds of Formula (I) have the structure of Formula (Ic):

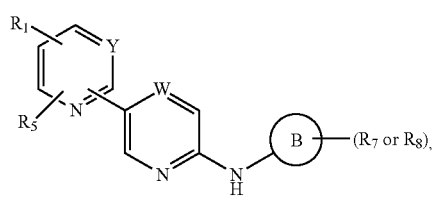

(Ic)

wherein Y is $C(R_5)$ or N.

In another embodiment, the compounds of Formula (I) have the structure of Formula (Id):

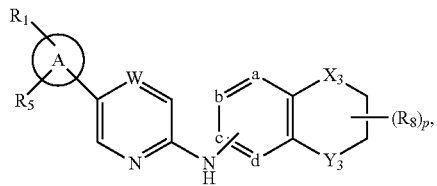

(Id)

wherein a, b, c, and d, are each independently C or N, wherein at least one of a, b, c, and d is N, and no more than two of a, b, c, and d, are N;

$X_3$ and $Y_3$ are each independently —O—, —$CH_2$—, or —$N(R_8)$—;

$\rho$ is 1, 2, or 3.

In another embodiment, the compounds of Formula (I) have the structure of Formula (Ie):

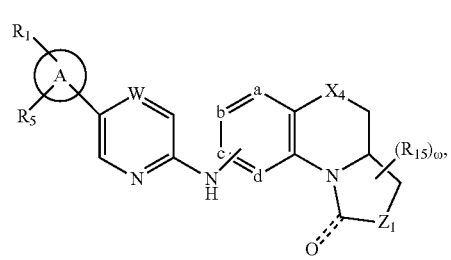

(Ie)

wherein:

------- represents an optional double bond;

a, b, c, and d, are each independently C or N, wherein at least one of a, b, c, and d is N; and no more than two of a, b, c, d, and e, are N;

$X_4$ and $Z_1$ are each independently —O—, —$N(R_{15})$—, or —$C(R_{15})(R_{15})$—; and $\omega$ is 1, 2, or 3.

In another embodiment, the compounds of Formula (I) have the structure of Formula (If):

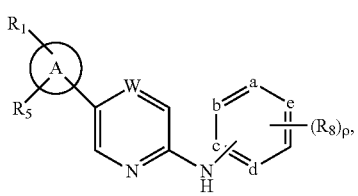

(If)

wherein:

a, b, c, d, and e, are each independently C or N, wherein at least one of a, b, c, d, and e is N, and no more than two of a, b, c, d, and e, are N; and $\rho$ is 1, 2, or 3.

In another embodiment, the compounds of Formula (I) have the structure of Formula (Ig):

(Ig)

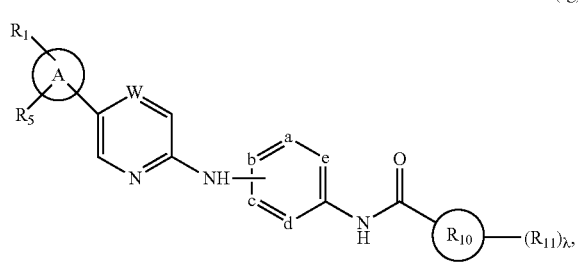

wherein:
a, b, c, d, and e, are each independently C or N, wherein at least one of a, b, c, d, and e is N, and no more than two of a, b, c, d, and e, are N; and
λ is 1, 2, or 3.

In another embodiment, the compounds of Formula (I) have the structure of Formula (Ih):

(Ih)

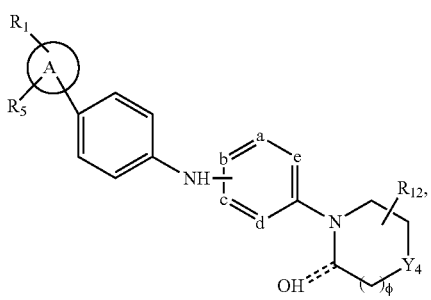

wherein:
------- represents an optional double bond;
a, b, c, d, and e, are each independently C or N, wherein at least one of a, b, c, d, and e is N, and no more than two of a, b, c, d, and e, are N;
$Y_4$ is —O—, —N($R_{12}$)—, or —C($R_{12}$)($R_2$)—; and
Φ is 0, 1, or 2.

In another embodiment, the compounds of Formula (I) have the structure of Formula (Ii):

(Ii)

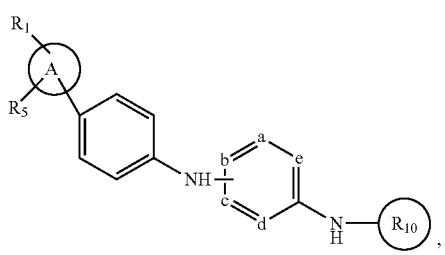

wherein:
a, b, c, d, and e, are each independently C or N, wherein at least one of a, b, c, d, and e is N, and no more than two of a, b, c, d, and e, are N.

In another embodiment, the compounds of Formula (I) have the structure of Formula (IJ):

(Ij)

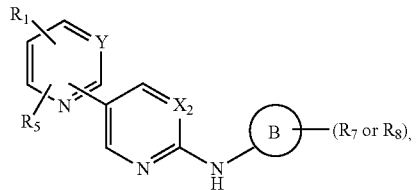

wherein:
Y is C($R_5$) or N.

In another embodiment, the compounds of Formula (I) have the structure of Formula (Ik):

(Ik)

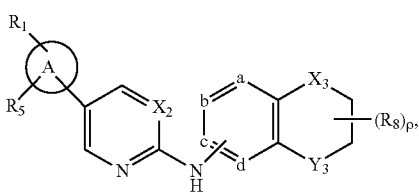

wherein:
a, b, c, and d, are each independently C or N, wherein at least one of a, b, c, and d is N, and no more than two of a, b, c, and d, are N;
$X_3$ and $Y_3$ are each independently —O—, —CH$_2$—, or —N($R_8$)—;
ρ is 1, 2, or 3.

In another embodiment, the compounds of Formula (I) have the structure of Formula (Il):

(Il)

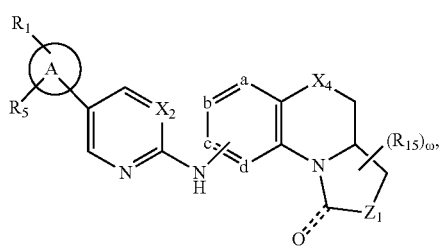

wherein:
------- represents an optional double bond;
a, b, c, and d, are each independently C or N, wherein at least one of a, b, c, and d is N; and no more than two of a, b, c, d, and e, are N;
$X_4$ and $Z_1$ are each independently —O—, —N($R_{15}$)—, or —C($R_{15}$)($R_{15}$)—; and
ω is 1, 2, or 3.

In another embodiment, the compounds of Formula (I) have the structure of Formula (Im):

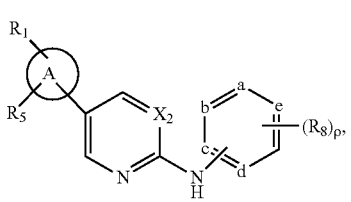

(Im)

wherein:
  a, b, c, d, and e, are each independently C or N, wherein at least one of a, b, c, d, and e is N, and no more than two of a, b, c, d, and e, are N; and
  ρ is 1, 2, or 3.

In another embodiment, the compounds of Formula (I) have the structure of Formula (In):

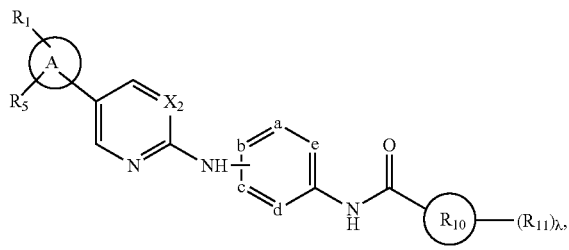

(In)

wherein:
  a, b, c, d, and e, are each independently C or N, wherein at least one of a, b, c, d, and e is N, and no more than two of a, b, c, d, and e, are N; and
  λ is 1, 2, or 3.

In another embodiment, the compounds of Formula (I) have the structure of Formula (Io):

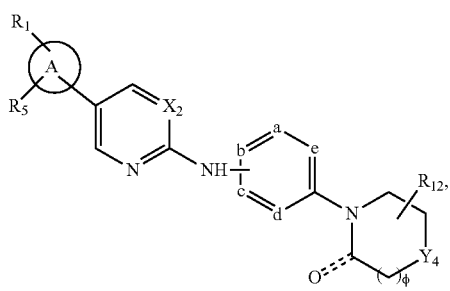

(Io)

wherein:
  ------- represents an optional double bond;
  a, b, c, d, and e, are each independently C or N, wherein at least one of a, b, c, d, and e is N, and no more than two of a, b, c, d, and e, are N;
  $Y_4$ is —O—, —N($R_{12}$)—, or —C($R_{12}$)($R_{12}$)—; and
  Φ is 0, 1, or 2.

In another embodiment, the compounds of Formula (I) have the structure of Formula (Ip):

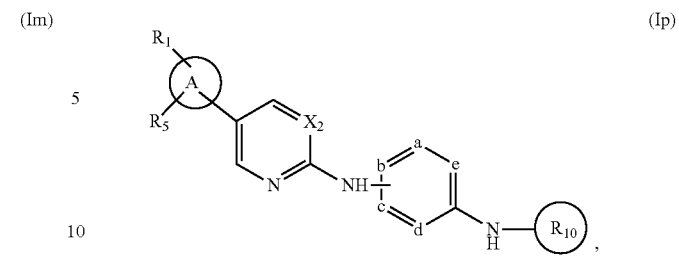

(Ip)

wherein:
  a, b, c, d, and e, are each independently C or N, wherein at least one of a, b, c, d, and e is N, and no more than two of a, b, c, d, and e, are N.

In some embodiments of the compounds of Formula I, $R_1$ is —N($R_2$)C(O)$R_3$, —C(O)N($R_2$)($R_3$), —S(O)$_2$N($R_2$)($R_3$), —N($R_2$)S(O)$_2$$R_3$, or heteroaryl, wherein heteroaryl is optionally substituted with $R_7$. In another embodiment $R_1$ is —N($R_2$)C(O)$R_3$, —C(O)N($R_2$)($R_3$), —S(O)$_2$N($R_2$)($R_3$), —N($R_2$)S(O)$_2$$R_3$, or heteroaryl. In another embodiment, $R_1$ is —N($R_2$)C(O)$R_3$, —C(O)N($R_2$)($R_3$), —S(O)$_2$N($R_2$)($R_3$), or —N($R_2$)S(O)$_2$$R_3$. In another embodiment, $R_1$ is —N($R_2$)C(O)$R_3$, —C(O)N($R_2$)($R_3$), or —S(O)$_2$N($R_2$)($R_3$). In another embodiment, $R_1$ is —N($R_2$)C(O)$R_3$ or —C(O)N($R_2$)($R_3$). In another embodiment, $R_1$ is —N($R_2$)C(O)$R_3$. In another embodiment, $R_1$ is —C(O)N($R_2$)($R_3$). In another embodiment, $R_1$ is —S(O)$_2$N($R_2$)($R_3$). In another embodiment, $R_1$ is —N($R_2$)S(O)$_2$$R_3$. In another embodiment, $R_1$ is heteroaryl. In another embodiment, $R_1$ is heteroaryl, wherein heteroaryl is optionally substituted with $R_7$.

In some embodiments of the compounds of Formula I, W is C($R_6$) or N. In another embodiment, W is C($R_6$). In another embodiment, W is N.

In some embodiments of the compounds of Formula I, A is $C_{3-8}$ cycloalkyl, $C_{4-8}$ cycloalkenyl, $C_{2-6}$ alkynyl, aryl, spiroheterocyclyl, heterocyclyl, or 6-membered heteroaryl. In another embodiment, A is $C_{3-8}$ cycloalkyl, $C_{4-8}$ cycloalkenyl, $C_{2-6}$ alkynyl, aryl, heterocyclyl, or 6-membered heteroaryl. In another embodiment, A is $C_{3-8}$ cycloalkyl, $C_{4-8}$ cycloalkenyl, $C_{2-6}$ alkynyl, aryl, or heterocyclyl. In another embodiment, A is $C_{3-8}$ cycloalkyl, $C_{4-8}$ cycloalkenyl, $C_{2-6}$ alkynyl, or aryl. In another embodiment, A is $C_{3-8}$ cycloalkyl, $C_{4-8}$ cycloalkenyl, or $C_{2-6}$ alkynyl. In another embodiment, A is $C_{3-8}$ cycloalkyl or $C_{4-8}$ cycloalkenyl. In another embodiment, A is $C_{3-8}$ cycloalkyl. In another embodiment, A is $C_{4-8}$ cycloalkenyl. In another embodiment, A is $C_{2-6}$ alkynyl. In another embodiment, A is spiroheterocyclyl. In another embodiment, A is aryl. In another embodiment, A is heterocyclyl. In another embodiment, A is 6-membered heteroaryl. In another embodiment, A is $C_{3-8}$ cycloalkyl optionally substituted with one or more $R_5$. In another embodiment, A is $C_{4-8}$ cycloalkenyl optionally substituted with one or more $R_5$. In another embodiment, A is $C_{2-6}$ alkynyl optionally substituted with one or more $R_5$. In another embodiment, A is spiroheterocyclyl optionally substituted with one or more $R_5$. In another embodiment, A is aryl optionally substituted with one or more $R_5$. In another embodiment, A is heterocyclyl optionally substituted with one or more $R_5$. In another embodiment, A is 6-membered heteroaryl optionally substituted with one or more $R_5$.

In some embodiments of the compounds of Formula I, B is heterocyclyl or heteroaryl. In one embodiment, B is heterocyclyl. In one embodiment, B is heteroaryl. In one embodiment, B is heterocyclyl optionally substituted with one or more $R_7$. In one embodiment, B is heteroaryl optionally substituted with one or more $R_5$.

In some embodiments of the compounds of Formula I, $X_1$ is $C(R_5)$. In one embodiment, $X_1$ is $C(R_5)$.

In some embodiments of the compounds of Formula I, $X_2$ is $C(R_5)$ or N. In one embodiment, $X_2$ is $C(R_5)$. In one embodiment, $X_2$ is N.

In some embodiments of the compounds of Formula I, $R_2$ is $C_{1-6}$ alkyl, $C_{2-6}$ alkenyl, or $C_{2-6}$ alkynyl. In another embodiment, $R_2$ is $C_{1-6}$ alkyl. In another embodiment, $R_2$ is $C_{2-6}$ alkenyl. In another embodiment, $R_2$ is $C_{2-6}$ alkynyl. In another embodiment, $R_2$ is $C_{1-6}$ alkyl optionally substituted with one or more $R_4$. In another embodiment, $R_2$ is $C_{2-6}$ alkenyl optionally substituted with one or more $R_4$. In another embodiment, $R_2$ is $C_{2-6}$ alkynyl optionally substituted with one or more $R_4$.

In some embodiments of the compounds of Formula I, $R_3$ is —H, $C_{1-6}$ alkyl, $C_{2-6}$ alkenyl, or $C_{2-6}$ alkynyl. In another embodiment, $R_3$ is —H. In another embodiment, $R_3$ is $C_{1-6}$ alkyl. In another embodiment, $R_3$ is $C_{2-6}$ alkenyl. In another embodiment, $R_3$ is $C_{2-6}$ alkynyl. In another embodiment, $R_3$ is $C_{1-6}$ alkyl optionally substituted with one or more $R_4$. In another embodiment, $R_3$ is $C_{2-6}$ alkenyl optionally substituted with one or more $R_4$. In another embodiment, $R_3$ is $C_{2-6}$ alkynyl optionally substituted with one or more $R_4$.

In other embodiments of the compounds of Formula I, $R_2$ and $R_3$ when taken together with the atom to which they are attached form a heterocycle. In another embodiment, $R_2$ and $R_3$ when taken together with the atom to which they are attached form a heterocycle optionally substituted with one or more $R_4$.

In other embodiments of the compounds of Formula I, $R_4$ is —H, halogen, —OH, —$NH_2$, —$NO_2$, —CN, $C_{1-6}$ alkyl, $C_{1-6}$ alkoxy, $C_{3-8}$ cycloalkyl, heterocyclyl, aryl, or heteroaryl, wherein heterocyclyl is optionally substituted with one or more $R_7$. In another embodiment, $R_4$ is —H, halogen, —OH, —$NH_2$, —$NO_2$, —CN, $C_{1-6}$ alkyl, $C_{1-6}$ alkoxy, $C_{3-8}$ cycloalkyl, heterocyclyl, or aryl. In another embodiment, $R_4$ is —H, halogen, —OH, —$NH_2$, —$NO_2$, —CN, $C_{1-6}$ alkyl, $C_{1-6}$ alkoxy, $C_{3-8}$ cycloalkyl, or heterocyclyl. In another embodiment, $R_4$ is —H, halogen, —OH, —$NH_2$, —$NO_2$, —CN, $C_{1-6}$ alkyl, $C_{1-6}$ alkoxy, or $C_{3-8}$ cycloalkyl. In another embodiment, $R_4$ is —H, halogen, —OH, —$NH_2$, —$NO_2$, —CN, $C_{1-6}$ alkyl, or $C_{1-6}$ alkoxy. In another embodiment, $R_4$ is —H, halogen, —OH, —$NH_2$, —$NO_2$, —CN, or $C_{1-6}$ alkyl. In another embodiment, $R_4$ is —H, halogen, —OH, —$NH_2$, —$NO_2$, or —CN. In another embodiment, $R_4$ is —H, halogen, —OH, —$NH_2$, or —$NO_2$. In another embodiment, $R_4$ is —H, halogen, —OH, or —$NH_2$. In another embodiment, $R_4$ is —H, halogen, or —OH. In another embodiment, $R_4$ is —H or halogen. In another embodiment, $R_4$ is —H. In another embodiment, $R_4$ is halogen. In another embodiment, $R_4$ is —OH. In another embodiment, $R_4$ is —$NH_2$. In another embodiment, $R_4$ is —$NO_2$. In another embodiment, $R_4$ is —CN. In another embodiment, $R_4$ is $C_{1-6}$ alkyl. In another embodiment, $R_4$ is $C_{1-6}$ alkoxy. In another embodiment, $R_4$ is $C_{3-8}$ cycloalkyl. In another embodiment, $R_4$ is heterocyclyl. In another embodiment, $R_4$ is aryl. In another embodiment, $R_4$ is heteroaryl. In another embodiment, $R_4$ is heterocyclyl optionally substituted with $R_7$. In another embodiment, $R_4$ is alkyl, alkoxy, cycloalkyl, heterocyclyl, aryl, or heteroaryl is optionally substituted with one or more $R_7$. In another embodiment, $R_4$ is alkyl optionally substituted with one or more $R_7$. In another embodiment, $R_4$ is alkoxy substituted with one or more $R_7$. In another embodiment, $R_4$ is cycloalkyl optionally substituted with one or more $R_7$. In another embodiment, $R_4$ is aryl optionally substituted with one or more $R_7$. In another embodiment, $R_4$ is heteroaryl optionally substituted with one or more $R_7$.

In other embodiments of the compounds of Formula I, $R_5$ is —H, halogen, —OH, —CN, $C_{1-6}$ alkyl, methoxy, —$OC_3$-$C_6$ alkyl, $C_{3-8}$ cycloalkyl, heterocyclyl, aryl, or heteroaryl. In another embodiment, $R_5$ is —H, halogen, —OH, —CN, $C_{1-6}$ alkyl, $C_{1-6}$ alkoxy, $C_{3-8}$ cycloalkyl, heterocyclyl, or aryl. In another embodiment, $R_5$ is —H, halogen, —OH, —$NO_2$, —CN, $C_{1-6}$ alkyl, $C_{1-6}$ alkoxy, $C_{3-8}$ cycloalkyl, or heterocyclyl. In another embodiment, $R_5$ is —H, halogen, —OH, —CN, $C_{1-6}$ alkyl, $C_{1-6}$ alkoxy, or $C_{3-8}$ cycloalkyl. In another embodiment, $R_5$ is —H, halogen, —OH, —CN, $C_{1-6}$ alkyl, or $C_{1-6}$ alkoxy. In another embodiment, $R_5$ is —H, halogen, —OH, —CN, or $C_{1-6}$ alkyl. In another embodiment, $R_5$ is —H, halogen, —OH, or —CN. In another embodiment, $R_5$ is —H, halogen, or —$NO_2$. In another embodiment, $R_5$ is —H, halogen, or —OH. In another embodiment, $R_5$ is —H, halogen, or —OH. In another embodiment, $R_5$ is —H or halogen. In another embodiment, $R_5$ is —H. In another embodiment, $R_5$ is halogen. In another embodiment, $R_5$ is —OH. In another embodiment, $R_5$ is —CN. In another embodiment, $R_5$ is $C_{1-6}$ alkyl. In another embodiment, $R_5$ is $C_{1-6}$ alkoxy. In another embodiment, $R_5$ is $C_{3-8}$ cycloalkyl. In another embodiment, $R_5$ is heterocyclyl. In another embodiment, $R_5$ is aryl. In another embodiment, $R_5$ is heteroaryl.

In other embodiments of the compounds of Formula I, $R_6$ is —H, halogen, —OH, —$NH_2$, —$NO_2$, —CN, —$CO_2H$, —$C(O)NH_2$, $C_{1-6}$ alkoxy, $C_{3-8}$ cycloalkyl, heterocyclyl, —O—$C_{3-8}$ cycloalkyl, or $C_{1-6}$ alkyl. In other embodiments of the compounds of Formula I, $R_6$ is $C_{1-6}$ alkoxy, $C_{3-8}$ cycloalkyl, heterocyclyl, —O—$C_{3-8}$ cycloalkyl, or $C_{1-6}$ alkyl, wherein the alkyl, alkoxy, heterocyclyl, or cycloalkyl is optionally substituted with one or more —OH, $C_{1-6}$ alkoxy, $C_{3-8}$ cycloalkyl, —$NH_2$, —$NH(C_{1-6}$ alkyl), or —$N(C_{1-6}$ alkyl)$_2$. In other embodiments of the compounds of Formula I, $R_6$ is —H, halogen, —OH, —$NH_2$, —$NO_2$, —CN, —$CO_2H$, —$C(O)NH_2$, $C_{1-6}$ alkoxy, $C_{3-8}$ cycloalkyl, or $C_{1-6}$ alkyl. In other embodiments of the compounds of Formula I, $R_6$ is —H, halogen, —OH, —$NH_2$, —$NO_2$, —CN, —$CO_2H$, —$C(O)NH_2$, or $C_{1-6}$ alkyl. In another embodiment, $R_6$ is —H, halogen, —OH, —$NH_2$, —$NO_2$, —CN, —$CO_2H$, or —$C(O)NH_2$. In another embodiment, $R_6$ is H, halogen, —OH, $NH_2$, $NO_2$, CN, or —$CO_2H$. In another embodiment, $R_6$ is H, halogen, —OH, $NH_2$, $NO_2$, or CN. In another embodiment, $R_5$ is H, halogen, —OH, $NH_2$, or $NO_2$. In another embodiment, $R_6$ is H, halogen, —OH, or $NH_2$. In another embodiment, $R_6$ is H, halogen, or —OH. In another embodiment, $R_6$ is H or halogen. In another embodiment, $R_6$ is H. In another embodiment, $R_6$ is halogen. In another embodiment, $R_6$ is —OH. In another embodiment, $R_6$ is $NH_2$. In another embodiment, $R_6$ is $NO_2$. In another embodiment, $R_6$ is CN. In another embodiment, $R_6$ is $C_{1-6}$ alkyl. In another embodiment, $R_6$ is —$CO_2H$. In another embodiment, $R_6$ is —$C(O)NH_2$. In another embodiment, $R_6$ is $C_{1-6}$ alkyl substituted with —OH. In another embodiment, $R_6$ is $C_{1-6}$ alkyl substituted with $C_{1-6}$ alkoxy. In another embodiment, $R_6$ is $C_{1-6}$ alkyl substituted with $C_{1-6}$ cycloalkyl. In another embodiment, $R_6$ is $C_{1-6}$ alkyl is substituted with —$NH_2$. In another embodiment, $R_6$ is $C_{1-6}$ alkyl is substituted with —$NH(C_{1-6}$ alkyl). In another embodiment, $R_6$ is $C_{1-6}$ alkyl is substituted with —$N(C_{1-6}$ alkyl)$_2$. In another embodiment, $R_6$ is $C_{1-6}$ alkoxy substituted with —OH. In another embodiment, $R_6$ is $C_{1-6}$ alkoxy substituted with $C_{1-6}$ alkoxy. In another embodiment, $R_6$ is $C_{1-6}$ alkoxy substituted with $C_{1-6}$ cycloalkyl. In another embodiment, $R_6$ is $C_{1-6}$ alkoxy is substituted with —$NH_2$. In another embodiment, $R_6$ is $C_{1-6}$ alkoxy is substituted with —NH($C_{1-6}$ alkyl). In another embodiment, $R_6$ is $C_{1-6}$ alkoxy is substituted with —N($C_{1-6}$ alkyl)$_2$. In another embodiment, $R_6$ is heterocyclyl substituted with —OH. In another embodiment, $R_6$ is heterocyclyl substituted with $C_{1-6}$ alkoxy. In another embodiment, $R_6$ is heterocyclyl substituted with $C_{1-6}$ cycloalkyl. In another embodiment, $R_6$ is heterocyclyl is substituted with —NH$_2$. In another embodiment, $R_6$ is heterocyclyl is substituted with —NH($C_{1-6}$ alkyl). In another embodiment, $R_6$ is heterocyclyl is substituted with —N($C_{1-6}$ alkyl)$_2$. In another embodiment, $R_6$ is cycloalkyl substituted with —OH. In another embodiment, $R_6$ is cycloalkyl substituted with $C_{1-6}$ alkoxy. In another embodiment, $R_6$ is cycloalkyl substituted with $C_{1-6}$ cycloalkyl. In another embodiment, $R_6$ is cycloalkyl is substituted with —NH$_2$. In another embodiment, $R_6$ is cycloalkyl is substituted with —NH($C_{1-6}$ alkyl). In another embodiment, $R_6$ is cycloalkyl is substituted with —N($C_{1-6}$ alkyl)$_2$.

In other embodiments of the compounds of Formula I, $R_5$ and $R_6$ when on adjacent carbons and when taken together with the carbon atom to which they are each attached form a 5- to 6-membered heteroaryl ring. In another embodiment, $R_5$ and $R_6$ when on adjacent carbons and when taken together with the carbon atom to which they are each attached form a 5-membered heteroaryl ring. In another embodiment, $R_5$ and $R_6$ when on adjacent carbons and when taken together with the carbon atom to which they are each attached form a 6-membered heteroaryl ring.

In other embodiments of the compounds of Formula I, $R_7$ is —H, halogen, —OH, oxo, $C_{1-6}$ alkyl, $C_{1-6}$ alkoxy, $C_{3-8}$ cycloalkyl, heterocyclyl, aryl, or heteroaryl. In another embodiment, $R_7$ is —H, halogen, —OH, oxo, $C_{1-6}$ alkyl, $C_{1-6}$ alkoxy, $C_{3-8}$ cycloalkyl, heterocyclyl, or aryl. In another embodiment, $R_7$ is —H, halogen, —OH, oxo, $C_{1-6}$ alkyl, $C_{1-6}$ alkoxy, $C_{3-8}$ cycloalkyl, or heterocyclyl. In another embodiment, $R_7$ is —H, halogen, —OH, oxo, $C_{1-6}$ alkyl, $C_{1-6}$ alkoxy, or $C_{3-8}$ cycloalkyl. In another embodiment, $R_7$ is —H, halogen, —OH, oxo, $C_{1-6}$ alkyl, or $C_{1-6}$ alkoxy. In another embodiment, $R_7$ is —H, halogen, —OH, oxo, or $C_{1-6}$ alkyl. In another embodiment, $R_7$ is —H, halogen, —OH, or oxo. In another embodiment, $R_7$ is —H, halogen, —OH, or oxo. In another embodiment, $R_7$ is —H, halogen, or —OH. In another embodiment, $R_7$ is —H or halogen. In another embodiment, $R_7$ is —H. In another embodiment, $R_7$ is halogen. In another embodiment, $R_7$ is —OH. In another embodiment, $R_7$ is oxo. In another embodiment, $R_7$ is $C_{1-6}$ alkyl. In another embodiment, $R_7$ is $C_{1-6}$ alkoxy. In another embodiment, $R_7$ is $C_{3-8}$ cycloalkyl. In another embodiment, $R_7$ is heterocyclyl. In another embodiment, $R_7$ is aryl. In another embodiment, $R_7$ is heteroaryl. In another embodiment, $R_7$ is $C_{1-6}$ alkyl optionally substituted with one or more $R_{14}$. In another embodiment, $R_7$ is $C_{1-6}$ alkoxy optionally substituted with one or more $R_{14}$. In another embodiment, $R_7$ is $C_{3-8}$ cycloalkyl optionally substituted with one or more $R_{14}$. In another embodiment, $R_7$ is heterocyclyl optionally substituted with one or more $R_{14}$. In another embodiment, $R_7$ is aryl optionally substituted with one or more $R_{14}$. In another embodiment, $R_7$ is heteroaryl optionally substituted with one or more $R_{14}$.

In other embodiments of the compounds of Formula I, $R_5$ is H, —CN, oxo, $C_{1-6}$ alkyl, heterocyclyl, aryl, heteroaryl —N($R_9$)C(O)$R_{10}$, —N($R_9$)C(O)O$R_{10}$, —N($R_9$)C(O)N($R_9$)($R_{10}$), —N($R_9$)S(O)$_2R_{10}$, —S(O)$_2R_{10}$, C(O)$R_9$—N($R_9$)($R_{10}$), —O$R_{10}$, —N($R_9$)C(O)$R_{13}$, or —C(O)N($R_9$)($R_{10}$). In another embodiment, $R_5$ is H. In another embodiment, $R_5$ is —CN. In another embodiment, $R_5$ is oxo. In another embodiment, $R_5$ is $C_{1-6}$ alkyl. In another embodiment, $R_5$ is heterocyclyl. In another embodiment, $R_5$ is aryl. In another embodiment, $R_5$ is heteroaryl. In another embodiment, $R_5$ is —N($R_9$)C(O)$R_{10}$. In another embodiment, $R_5$ is —N($R_9$)C(O)O$R_{10}$. In another embodiment, $R_5$ is —N($R_9$)C(O)N($R_9$)($R_{10}$). In another embodiment, $R_5$ is —N($R_9$)S(O)$_2R_{10}$. In another embodiment, $R_5$ is —S(O)$_2R_{10}$. In another embodiment, $R_5$ is C(O)$R_9$. In another embodiment, $R_5$ is —N($R_9$)($R_{10}$). In another embodiment, $R_5$ is —O$R_{10}$. In another embodiment, $R_5$ is —N($R_9$)C(O)$R_{13}$. In another embodiment, $R_5$ is —C(O)N($R_9$)($R_{10}$). In another embodiment, $R_5$ is $C_{1-6}$ alkyl optionally substituted with one or more $R_{15}$. In another embodiment, $R_5$ is $C_{3-8}$ cycloalkyl optionally substituted with one or more $R_{15}$. In another embodiment, $R_5$ is heterocyclyl optionally substituted with one or more $R_{15}$. In another embodiment, $R_5$ is aryl optionally substituted with one or more $R_{15}$. In another embodiment, $R_5$ is heteroaryl optionally substituted with one or more $R_{15}$.

In other embodiments of the compounds of Formula I, $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl. In some embodiments, $R_8$ groups, together with the atoms to which they are attached, form a $C_{3-6}$ cycloalkyl. In some embodiments, $R_8$ groups, together with the atoms to which they are attached, form a $C_{5-6}$ spirocycloalkyl. In some embodiments, $R_8$ groups, together with the atoms to which they are attached, form a spiroheterocycloalkyl. In some embodiments, $R_8$ groups, together with the atoms to which they are attached, form a heterocyclyl. In some embodiments, $R_8$ groups, together with the atoms to which they are attached, form an aryl. In some embodiments, $R_8$ groups, together with the atoms to which they are attached, form a heteroaryl. In some embodiments, $R_8$ groups, together with the atoms to which they are attached, form a $C_{3-6}$ cycloalkyl optionally substituted with one or more $R_{15}$. In some embodiments, $R_8$ groups, together with the atoms to which they are attached, form a $C_{5-6}$ spirocycloalkyl optionally substituted with one or more $R_{15}$. In some embodiments, $R_8$ groups, together with the atoms to which they are attached, form a spiroheterocycloalkyl optionally substituted with one or more $R_{15}$. In some embodiments, $R_8$ groups, together with the atoms to which they are attached, form a heterocyclyl optionally substituted with one or more $R_{15}$. In some embodiments, $R_8$ groups, together with the atoms to which they are attached, form an aryl optionally substituted with one or more $R_{24}$. In some embodiments, $R_8$ groups, together with the atoms to which they are attached, form a heteroaryl optionally substituted with one or more $R_{24}$.

In some embodiments of the compounds of Formula I, $R_9$ is —H, $C_{1-6}$ alkyl, $C_{2-6}$ alkenyl, $C_{2-6}$ alkynyl, $C_{3-8}$ cycloalkyl, aryl, heteroaryl, or heterocyclyl. In another embodiment, $R_9$ is —H. In another embodiment, $R_9$ is $C_{1-6}$ alkyl. In another embodiment, $R_9$ is $C_{2-6}$ alkenyl. In another embodiment, $R_9$ is $C_{2-6}$ alkynyl. In another embodiment, $R_9$ is $C_{3-8}$ cycloalkyl. In another embodiment, $R_9$ is heterocyclyl. In another embodiment, $R_9$ is aryl. In another embodiment, $R_9$ is heteroaryl. In another embodiment, $R_9$ is $C_{1-6}$ alkyl optionally substituted with one or more $R_{11}$. In another embodiment, $R_9$ is $C_{2-6}$ alkenyl optionally substituted with one or more $R_{11}$. In another embodiment, $R_9$ is $C_{2-6}$ alkynyl optionally substituted with one or more $R_{11}$. In another embodiment, $R_9$ is $C_{3-8}$ cycloalkyl optionally substituted with one or more $R_{11}$. In another embodiment, $R_9$ is heterocyclyl optionally substituted with one or more $R_{11}$. In another embodiment, $R_9$ is aryl optionally substituted with one or more $R_{11}$. In another embodiment, $R_9$ is heteroaryl optionally substituted with one or more $R_{11}$.

In some embodiments of the compounds of Formula I, $R_{10}$ is —H, $C_{1-6}$ alkyl, $C_{2-6}$ alkenyl, $C_{2-6}$ alkynyl, $C_{3-8}$ cycloalkyl, aryl, heteroaryl, or heterocyclyl. In another embodiment, $R_{10}$ is —H. In another embodiment, $R_{10}$ is $C_{1-6}$ alkyl. In another embodiment, $R_{10}$ is $C_{2-6}$ alkenyl. In another embodiment, $R_{10}$ is $C_{2-6}$ alkynyl. In another embodiment, $R_{10}$ is $C_{3-8}$ cycloalkyl. In another embodiment, $R_{10}$ is heterocyclyl. In another embodiment, $R_{10}$ is aryl. In another embodiment, $R_{10}$ is heteroaryl. In another embodiment, $R_{10}$ is $C_{1-6}$ alkyl optionally substituted with one or more $R_{11}$. In another embodiment, $R_{10}$ is $C_{2-6}$ alkenyl optionally substituted with one or more $R_{11}$. In another embodiment, $R_{10}$ is $C_{2-6}$ alkynyl optionally substituted with one or more $R_{11}$. In another embodiment, $R_{10}$ is $C_{3-8}$ cycloalkyl optionally substituted with one or more $R_{11}$. In another embodiment, $R_{10}$ is heterocyclyl optionally substituted with one or more $R_{11}$. In another embodiment, $R_{10}$ is aryl optionally substituted with one or more $R_{11}$. In another embodiment, $R_{10}$ is heteroaryl optionally substituted with one or more $R_{11}$.

In other embodiments of the compounds of Formula I, $R_9$ and $R_{10}$ when taken together with the atom to which they are each attached form a heterocycle ring. In another embodiment, $R_9$ and $R_{10}$ when taken together with the atom to which they are each attached form a heterocycle ring optionally substituted with one or more $R_{12}$.

In other embodiments of the compounds of Formula I, $R_1$ is —H, halogen, —CN, oxo, —OH, —N($R_{23}$)($R_{25}$), —O$R_{23}$, $C_{1-6}$ alkyl, $C_{1-6}$ alkoxy, $C_{3-8}$ cycloalkyl, heterocyclyl, heteroaryl, aryl, —C(O)$R_{17}$, —C(O)$R_{17}$, —C(O)O$R_{17}$, —OC(O)$R_{17}$, or —C(O)N($R_{23}$)($R_{23}$). In another embodiment, $R_1$ is —H. In another embodiment, $R_1$ is halogen. In another embodiment, $R_1$ is —CN. In another embodiment, $R_1$ is oxo. In another embodiment, $R_1$ is —OH. In another embodiment, $R_1$ is —N($R_{23}$)($R_{25}$). In another embodiment, $R_1$ is —O$R_{23}$. In another embodiment, $R_1$ is $C_{1-6}$ alkyl. In another embodiment, $R_1$ is $C_{1-6}$ alkoxy. In another embodiment, $R_1$ is $C_{3-8}$ cycloalkyl. In another embodiment, $R_1$ is heterocyclyl. In another embodiment, $R_1$ is heteroaryl. In another embodiment, $R_1$ is aryl. In another embodiment, $R_1$ is —C(O)$R_{17}$. In another embodiment, $R_1$ is —C(O)O$R_{17}$. In another embodiment, $R_1$ is —OC(O)$R_{17}$. In another embodiment, $R_1$ is —C(O)N($R_{23}$)($R_{23}$). In another embodiment, $R_1$ is $C_{1-6}$ alkyl optionally substituted with one or more $R_{17}$. In another embodiment, $R_{11}$ is $C_{1-6}$ alkoxy optionally substituted with one or more $R_{17}$. In another embodiment, $R_{11}$ is $C_{3-8}$ cycloalkyl optionally substituted with one or more $R_{17}$. In another embodiment, $R_{11}$ is heterocyclyl optionally substituted with one or more $R_{17}$. In another embodiment, $R_{11}$ is heteroaryl. In another embodiment, $R_{11}$ is aryl optionally substituted with one or more $R_{17}$. In another embodiment, $R_{11}$ is heterocyclyl optionally substituted with one or more $R_{17}$.

In other embodiments of the compounds of Formula I, each $R_{12}$ is —C(O)O$R_{21}$, —C(O)$R_{13}$; oxo, —OH, $C_{1-6}$ alkyl, heterocycle, —($C_{1-6}$ alkyl)-heteroaryl, —($C_{1-6}$ alkyl)-heterocycle, —($C_{1-6}$alkyl)-$C_{3-6}$ cycloalkyl, or —($C_{1-6}$ alkyl)-aryl. In another embodiment, $R_{12}$ is —C(O)O$R_{21}$. In another embodiment, $R_{12}$ is —C(O)$R_{13}$. In another embodiment, $R_{12}$ is oxo. In another embodiment, $R_{12}$ is —OH. In another embodiment, $R_{12}$ is $C_{1-6}$ alkyl. In another embodiment, $R_{12}$ is heterocycle. In another embodiment, $R_{12}$ is —($C_{1-6}$ alkyl)-heteroaryl. In another embodiment, $R_{12}$ is —($C_{1-6}$alkyl)-$C_{3-6}$ cycloalkyl. In another embodiment, $R_{12}$ is —($C_{1-6}$ alkyl)-aryl. In another embodiment, $R_{12}$ is $C_{1-6}$ alkyl optionally substituted with one or more $R_{15}$. In another embodiment, $R_{12}$ is heterocycle optionally substituted with one or more $R_{15}$. In another embodiment, $R_{12}$ is —($C_{1-6}$ alkyl)-heteroaryl optionally substituted with one or more $R_{11}$. In another embodiment, $R_{12}$ is —($C_{1-6}$alkyl)-$C_{3-6}$ cycloalkyl optionally substituted with one or more $R_{18}$. In another embodiment, $R_{12}$ is —($C_{1-6}$ alkyl)-aryl optionally substituted with one or more $R_{18}$.

In other embodiments of the compounds of Formula I, two $R_{12}$ together with the atoms to which they are attached form an aryl ring. In another embodiment, two $R_{12}$ together with the atoms to which they are attached form an aryl ring optionally substituted with one or more $R_{11}$.

In some embodiments of the compounds of Formula I, $R_{13}$ is aryl, heterocyclyl, cycloalkyl, or heteroaryl. In another embodiment, $R_{13}$ is aryl. In another embodiment, $R_{13}$ is heterocyclyl. In another embodiment, $R_{13}$ is $C_{3-8}$ cycloalkyl. In another embodiment, $R_{13}$ is heteroaryl. In another embodiment, $R_{13}$ is aryl optionally substituted with one or more $R_{19}$. In another embodiment, $R_{13}$ is heterocyclyl optionally substituted with one or more $R_{20}$. In another embodiment, $R_{13}$ is $C_{3-8}$ cycloalkyl optionally substituted with one or more $R_{20}$. In another embodiment, $R_{13}$ is heteroaryl optionally substituted with one or more $R_{19}$.

In some embodiments of the compounds of Formula I, $R_{14}$ is —H, halogen, —CN, —NO$_2$, —OH, —NH$_2$, $C_{1-6}$ alkyl, $C_{3-8}$ cycloalkyl, heterocyclyl, aryl, or heteroaryl. In another embodiment, $R_{14}$ is —H. In another embodiment, $R_{14}$ is halogen. In another embodiment, $R_{14}$ is —CN. In another embodiment, $R_{14}$ is NO$_2$. In another embodiment, $R_{14}$ is —OH. In another embodiment, $R_{14}$ is —NH$_2$. In another embodiment, $R_{14}$ is $C_{1-6}$alkyl. In another embodiment, $R_{14}$ is $C_{3-8}$ cycloalkyl. In another embodiment, $R_{14}$ is heterocyclyl. In another embodiment, $R_{14}$ is aryl. In another embodiment, $R_{14}$ is heteroaryl.

In some embodiments of the compounds of Formula I, $R_5$ is H, halogen, oxo, —OH, —NH$_2$, —NO$_2$, $C_{1-6}$ alkyl, $C_{1-6}$ alkoxy, $C_{3-8}$ cycloalkyl, heterocyclyl, aryl, heteroaryl, —C(O)N($R_{21}$)($R_{23}$), —(CH$_2$)$_o$—C(O)$R_{23}$, —OC(O)$R_{23}$, —C(O)O$R_{23}$, —SO$_2R_{23}$, —N($R_{23}$)C(O)—Ar—N($R_{23}$)-G, or —N($R_{23}$)C(O)—Ar—N($R_{23}$)C(O)-G. In one embodiment, $R_{15}$ is H. In one embodiment, $R_{15}$ is halogen. In one embodiment, $R_{15}$ is oxo. In one embodiment, $R_{15}$ is —OH. In one embodiment, $R_{15}$ is —NH$_2$. In one embodiment, $R_{15}$ is —NO$_2$. In one embodiment, $R_{15}$ is $C_{1-6}$ alkyl. In one embodiment, $R_{15}$ is $C_{1-6}$ alkoxy. In one embodiment, $R_{15}$ is $C_{3-8}$ cycloalkyl. In one embodiment, $R_{15}$ is heterocyclyl. In one embodiment, $R_{15}$ is aryl. In one embodiment, $R_{15}$ is heteroaryl. In one embodiment, $R_{15}$ is —C(O)N($R_{21}$)($R_{23}$). In one embodiment, $R_5$ is —(CH$_2$)$_o$—C(O)$R_{23}$. In one embodiment, $R_{15}$ is —OC(O)$R_{23}$. In one embodiment, $R_{15}$ is —C(O)O$R_{23}$. In one embodiment, $R_{15}$ is —SO$_2R_{23}$. In one embodiment, $R_5$ is —N($R_{23}$)C(O)—Ar—N($R_{23}$)-G. In one embodiment, $R_{15}$ is —N($R_{23}$)C(O)—Ar—N($R_{23}$)C(O)-G. In one embodiment, $R_{15}$ is $C_{1-6}$ alkyl optionally substituted with one or more $R_{23}$. In one embodiment, $R_{15}$ is $C_{1-6}$ alkoxy optionally substituted with one or more $R_{23}$. In one embodiment, $R_{15}$ is $C_{3-8}$ cycloalkyl optionally substituted with one or more $R_{23}$. In one embodiment, $R_{15}$ is heterocyclyl optionally substituted with one or more $R_{23}$. In one embodiment, $R_{15}$ is aryl optionally substituted with one or more $R_{23}$. In one embodiment, $R_{15}$ is heteroaryl optionally substituted with one or more $R_{23}$.

In other embodiments of the compounds of Formula I, two $R_{15}$ groups, together with the atoms to which they are attached, form a $C_{3-6}$ cycloalkyl or $C_{5-6}$ spirocycloalkyl. In another embodiment, two $R_{15}$ groups, together with the atoms to which they are attached, form a $C_{3-6}$ cycloalkyl. In another embodiment, two $R_{15}$ groups, together with the atoms to which they are attached, form a $C_{5-6}$ spirocycloalkyl. In another embodiment, two $R_{15}$ when on adjacent atoms may be taken together with the atoms to which they are each attached to form a heterocycle. In another embodiment, two $R_{15}$ when on adjacent atoms may be taken together with the atoms to which they are each attached to form a heterocycle substituted with one or more $R_{16}$.

In some embodiments of the compounds of Formula I, Ar is aryl.

In some embodiments of the compounds of Formula I, G is H, $C_{1-6}$ alkyl, $C_{1-6}$ alkoxy, $C_{2-6}$ alkenyl, $C_{2-6}$ alkynyl, $C_{3-8}$ cycloalkyl, heterocyclyl, aryl, heteroaryl, —C(O)O$R_{23}$, —C(O)CH=CHCH$_2$N($R_{23}$)($R_{23}$), or —C(O)N($R_{21}$)($R_{23}$). In one embodiment, G is H. In one embodiment, G is $C_{1-6}$ alkyl. In one embodiment, G is $C_{1-6}$ alkoxy. In one embodiment, G is $C_{2-6}$ alkenyl. In one embodiment, G is $C_{2-6}$ alkynyl. In one embodiment, G is $C_{3-8}$ cycloalkyl. In one embodiment, G is heterocyclyl. In one embodiment, G is aryl. In one embodiment, G is heteroaryl. In one embodiment, G is —C(O)O$R_{23}$. In one embodiment, G is —C(O)CH=CHCH$_2$N($R_{23}$)($R_{23}$). In one embodiment, G is —C(O)N($R_{21}$)($R_{23}$).

In some embodiments of the compounds of Formula I, $R_{16}$ is $C_{1-6}$ alkyl, $C_{3-6}$ cycloalkyl, —C(O)$R_{23}$, —C(O)O$R_{23}$, —S(O)$_2$$R_{23}$, or oxo. In another embodiment, $R_{16}$ is $C_{1-6}$ alkyl. In another embodiment, $R_{16}$ is $C_{3-8}$ cycloalkyl. In another embodiment, $R_{16}$ is —C(O)$R_{23}$ In another embodiment, $R_{16}$ is —C(O)O$R_{23}$. In another embodiment, $R_{16}$ is —S(O)$_2$$R_{23}$. In another embodiment, $R_{16}$ is oxo.

In some embodiments of the compounds of Formula I, $R_{17}$ is —H, —CN, $C_{1-6}$ alkyl, $C_{1-6}$ alkoxy, heteroaryl, aryl, —N($R_{23}$)($R_{23}$), —N($R_{23}$)C(O)O$R_{23}$, —C(O)N($R_{23}$)($R_{23}$), —N($R_{23}$)C(O) $R_{23}$, —N($R_{23}$)C(O)—U—Z, or —N($R_{23}$)C(O)—U—N($R_{23}$)—Z. In one embodiment, $R_{17}$ is —H. In one embodiment, $R_{17}$ is —CN. In one embodiment, $R_{17}$ is $C_{1-6}$ alkyl. In one embodiment, $R_{17}$ is $C_{1-6}$ alkoxy. In one embodiment, $R_{17}$ is heteroaryl. In one embodiment, $R_{17}$ is aryl. In one embodiment, $R_{17}$ is —N($R_{23}$)($R_{23}$). In one embodiment, $R_{17}$ is —N($R_{23}$)C(O)O$R_{23}$. In one embodiment, $R_{17}$ is —C(O)N($R_{23}$)($R_{23}$). In one embodiment, $R_{17}$ is —N($R_{23}$)C(O) $R_{23}$. In one embodiment, $R_{17}$ is —N($R_{23}$)C(O)—U—Z. In one embodiment, $R_{17}$ is —N($R_{23}$)C(O)—U—N($R_{23}$)—Z.

In other embodiments of the compounds of Formula I, Z is —H, $C_{1-6}$ alkyl, $C_{1-6}$ alkoxy, $C_{2-6}$ alkenyl, $C_{2-6}$ alkynyl, $C_{3-8}$ cycloalkyl, heterocyclyl, aryl, heteroaryl, or —C(O)—U—N($R_{23}$)($R_{23}$). In one embodiment, Z is —H. In one embodiment, Z is $C_{1-6}$ alkyl. In one embodiment, Z is $C_{1-6}$ alkoxy. In one embodiment, Z is $C_{2-6}$ alkenyl. In one embodiment, Z is $C_{2-6}$ alkynyl. In one embodiment, Z is $C_{3-8}$ cycloalkyl. In one embodiment, Z is heterocyclyl. In one embodiment, Z is aryl. In one embodiment, Z is heteroaryl. In one embodiment, Z is —C(O)—U—N($R_{23}$)($R_{23}$).

In other embodiments of the compounds of Formula I, U is —(CH$_2$)$_p$—, —(CH$_2$)$_p$—Ar—, —CH=CH(CH$_2$)$_p$— or heterocyclyl. In one embodiment, U is —(CH$_2$)$_p$—. In one embodiment, U is —(CH$_2$)$_p$—Ar—. In one embodiment, U is —CH=CH(CH$_2$)$_p$—. In one embodiment, U is heterocyclyl.

In some embodiments of the compounds of Formula I, $R_1$ is $C_{1-6}$ alkyl, heteroaryl, heterocyclyl, cycloalkyl, aryl, —O$R_{23}$, —N($R_{23}$)($R_{23}$), or —N($R_{23}$)C(O)—V—N($R_{23}$)-E. In another embodiment, $R_{18}$ is $C_{1-6}$ alkyl. In another embodiment, $R_{18}$ is heteroaryl. In another embodiment, $R_{18}$ is heterocyclyl. In another embodiment, $R_{18}$ is cycloalkyl. In another embodiment, $R_{18}$ is aryl. In another embodiment, $R_{18}$ is —O$R_{23}$. In another embodiment, $R_{18}$ is —N($R_{23}$)($R_{23}$). In another embodiment, $R_{18}$ is —N($R_{23}$)C(O)—V—N($R_{23}$)-E. In another embodiment, $R_{18}$ is $C_{1-6}$ alkyl optionally substituted with one or more $R_{19}$. In another embodiment, $R_{18}$ is heteroaryl optionally substituted with one or more $R_{19}$. In another embodiment, $R_{18}$ is heterocyclyl optionally substituted with one or more $R_{19}$. In another embodiment, $R_{18}$ is cycloalkyl optionally substituted with one or more $R_{19}$. In another embodiment, $R_{18}$ is aryl optionally substituted with one or more $R_{19}$.

In other embodiments of the compounds of Formula I, V is —(CH$_2$)$_n$—, —(CH$_2$)$_n$—Ar—, or —CH=CH(CH$_2$)$_n$—. In one embodiment, V is —(CH$_2$)$_n$—. In one embodiment, V is —(CH$_2$)$_n$—Ar—. In one embodiment, V is —CH=CH(CH$_2$)$_n$—.

In some embodiments of the compounds of Formula I, E is H, $C_{1-6}$ alkyl or —C(O)—V—N($R_{23}$)($R_{23}$). In one embodiment, E is H. In one embodiment, E is $C_{1-6}$ alkyl. In one embodiment, E is —C(O)—V—N($R_{23}$)($R_{23}$).

In some embodiments of the compounds of Formula I, $R_{19}$ is halogen, $C_{1-6}$ alkyl, $C_{3-6}$ cycloalkyl, —O$R_{21}$, —N($R_{21}$)($R_{22}$), —C(O)$R_{21}$, —N($R_{23}$)C(O)O$R_{23}$, —N($R_{23}$)C(O)-Q-N($R_{23}$)—F, or —N($R_{23}$)-Q-N($R_{23}$)—F. In another embodiment, $R_{19}$ is halogen. In another embodiment, $R_{19}$ is $C_{1-6}$ alkyl. In another embodiment, $R_{19}$ is $C_{3-6}$ cycloalkyl. In another embodiment, $R_{19}$ is —O$R_{21}$. In another embodiment, $R_{19}$ is —N($R_{21}$)($R_{22}$). In another embodiment, $R_{19}$ is —C(O)$R_{21}$. In another embodiment, $R_{19}$ is —N($R_{23}$)C(O)O$R_{23}$. In another embodiment, $R_{19}$ is —N($R_{23}$)C(O)-Q-N($R_{23}$)—F. In another embodiment, $R_{19}$ is —N($R_{23}$)-Q-N($R_{23}$)—F.

In other embodiments of the compounds of Formula I, Q is —CH=CH(CH$_2$)$_m$—, —(CH$_2$)$_m$—, —(CH$_2$O)$_m$—, —(CH$_2$)$_m$Ar—, or —(CH$_2$CH$_2$O)$_o$—(CH$_2$)$_m$—. In another embodiment, Q is —CH=CH(CH$_2$)$_m$—. In another embodiment, Q is —(CH$_2$)$_m$—. In another embodiment, Q is —(CH$_2$O)$_m$—. In another embodiment, Q is —(CH$_2$)$_m$Ar—. In another embodiment, Q is —(CH$_2$CH$_2$O)$_o$—(CH$_2$)$_m$—.

In other embodiments of the compounds of Formula I, F is H, $C_{1-6}$ alkyl, aryl, heteroaryl, —C(O)-Q-$R_{23}$, or —C(O)-Q-N($R_{23}$)($R_{23}$). In another embodiment, F is H. In another embodiment, F is $C_{1-6}$ alkyl. In another embodiment, F is aryl. In another embodiment, F is heteroaryl. In another embodiment, F is —C(O)-Q-$R_{23}$. In another embodiment, F is —C(O)-Q-N($R_{23}$)($R_{23}$). In another embodiment, F is $C_{1-6}$ alkyl optionally substituted with one or more $R_{23}$. In another embodiment, F is aryl optionally substituted with one or more $R_{23}$. In another embodiment, F is heteroaryl optionally substituted with one or more $R_{23}$.

In some embodiments of the compounds of Formula I, $R_{20}$ is H, halogen, —OH, —NH$_2$, oxo, —C(O)$R_{21}$, —O$R_{23}$, $C_{3-6}$ cycloalkyl, or $C_{1-6}$ alkyl. In another embodiment, $R_{20}$ is —H. In another embodiment, $R_{20}$ is halogen. In another embodiment, $R_{20}$ is —OH. In another embodiment, $R_{20}$ is —NH$_2$. In another embodiment, $R_{20}$ is oxo. In another embodiment, $R_{20}$ is —C(O)$R_{21}$. In another embodiment, $R_{20}$ is —O$R_{23}$. In another embodiment, $R_{20}$ is $C_{3-6}$ cycloalkyl. In another embodiment, $R_{20}$ is $C_{1-6}$ alkyl.

In some embodiments of the compounds of Formula I, $R_{21}$ is —H, $C_{1-6}$ alkyl, $C_{2-6}$ alkenyl, $C_{2-6}$ alkynyl, $C_{3-8}$ cycloalkyl, heterocyclyl, aryl, or heteroaryl. In another embodiment, $R_{21}$ is —H. In another embodiment, $R_{21}$ is $C_{1-6}$ alkyl. In another embodiment, $R_{21}$ is $C_{2-6}$ alkenyl. In another embodiment, $R_{21}$ is $C_{2-6}$ alkynyl. In another embodiment, $R_{21}$ is $C_{3-8}$ cycloalkyl. In another embodiment, $R_{21}$ is heterocyclyl. In another embodiment, $R_{21}$ is aryl. In another embodiment, $R_{21}$ is heteroaryl. In another embodiment, $R_{21}$ is $C_{1-6}$ alkyl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{21}$ is $C_{2-6}$ alkenyl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{21}$ is $C_{2-6}$ alkynyl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{21}$ is $C_{3-8}$ cycloalkyl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{21}$ is heterocyclyl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{21}$ is aryl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{21}$ is heteroaryl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl.

In other embodiments of the compounds of Formula I, $R_{22}$ is —H, $C_{1-6}$ alkyl, or —C(O)$R_{23}$. In one embodiment, $R_{22}$ is —H. In one embodiment, $R_{22}$ is $C_{1-6}$ alkyl. In one embodiment, $R_{22}$ is —C(O)$R_{23}$.

In other embodiment of the compounds of Formula I, $R_{23}$ is —H, $C_{1-6}$ alkyl, $C_{1-6}$ alkoxy, $C_{2-6}$ alkenyl, $C_{2-6}$ alkynyl, $C_{3-8}$ cycloalkyl, heterocyclyl, aryl, or heteroaryl. In another embodiment, $R_{23}$ is —H. In another embodiment, $R_{23}$ is $C_{1-6}$ alkyl. In another embodiment, $R_{23}$ is $C_{1-6}$ alkoxy. In another embodiment, $R_{23}$ is $C_{2-6}$ alkenyl. In another embodiment, $R_{23}$ is $C_{2-6}$ alkynyl. In another embodiment, $R_{23}$ is $C_{3-8}$ cycloalkyl. In another embodiment, $R_{23}$ is heterocyclyl. In another embodiment, $R_{23}$ is aryl. In another embodiment, $R_{23}$ is heteroaryl. In another embodiment, $R_{23}$ is $C_{1-6}$ alkyl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{23}$ is $C_{1-6}$ alkoxy optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{23}$ is $C_{2-6}$ alkenyl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{23}$ is $C_{2-6}$ alkynyl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{23}$ is $C_{3-8}$ cycloalkyl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{23}$ is heterocyclyl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{23}$ is aryl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{23}$ is heteroaryl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl.

In one embodiment of the compounds of Formula I, $R_{24}$ is —H, $C_{1-6}$ alkyl, $C_{2-6}$ alkenyl, $C_{2-6}$ alkynyl, $C_{3-8}$ cycloalkyl, heterocyclyl, aryl, heteroaryl, C(O)N($C_{1-6}$ alkyl)($C_{1-6}$ alkyl), —C(O)—$C_{1-6}$ alkyl, —OC(O)—$C_{1-6}$ alkyl or —C(O)O—$C_{1-6}$ alkyl. In another embodiment, $R_{24}$ is-H. In another embodiment, $R_{24}$ is $C_{1-6}$ alkyl. In another embodiment, $R_{24}$ is $C_{2-6}$ alkenyl. In another embodiment, $R_{24}$ is $C_{2-6}$ alkynyl. In another embodiment, $R_{24}$ is $C_{3-8}$ cycloalkyl. In another embodiment, $R_{24}$ is heterocyclyl. In another embodiment, $R_{24}$ is aryl. In another embodiment, $R_{24}$ is heteroaryl. In another embodiment, $R_{24}$ is —C(O)N($C_{1-6}$ alkyl)($C_{1-6}$ alkyl). In another embodiment, $R_{24}$ is —C(O)—$C_{1-6}$ alkyl. In another embodiment, $R_{24}$ is —OC(O)—$C_{1-6}$ alkyl. In another embodiment, $R_{24}$ is —C(O)O—$C_{1-6}$ alkyl. In another embodiment, $R_{24}$ is $C_{1-6}$ alkyl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{24}$ is $C_{2-6}$ alkenyl optionally substituted with one or more —H, halogen, —CN, —OH, $C_{1-6}$ alkyl, $C_{1-6}$ alkoxy, $C_{3-8}$-cycloalkyl, heterocyclyl, heteroaryl, or aryl. In another embodiment, $R_{24}$ is $C_{2-6}$ alkynyl optionally substituted with one or more —H, halogen, —CN, —OH, $C_{1-6}$ alkyl, $C_{1-6}$ alkoxy, $C_{3-8}$-cycloalkyl, heterocyclyl, heteroaryl, or aryl. In another embodiment, $R_{24}$ is $C_{3-8}$ cycloalkyl optionally substituted with one or more —H, halogen, —CN, —OH, $C_{1-6}$ alkyl, $C_{1-6}$ alkoxy, $C_{3-8}$-cycloalkyl, heterocyclyl, heteroaryl, or aryl. In another embodiment, $R_{24}$ is heterocyclyl optionally substituted with one or more —H, halogen, —CN, —OH, $C_{1-6}$ alkyl, $C_{1-6}$ alkoxy, $C_{3-8}$-cycloalkyl, heterocyclyl, heteroaryl, or aryl. In another embodiment, $R_{24}$ is aryl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{24}$ is heteroaryl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{24}$ is C(O)N($C_{1-6}$ alkyl)($C_{1-6}$ alkyl) optionally substituted with one or more —H, halogen, —CN, —OH, $C_{1-6}$ alkyl, $C_{1-6}$ alkoxy, $C_{3-8}$-cycloalkyl, heterocyclyl, heteroaryl, or aryl. In another embodiment, $R_{24}$ is —C(O)—$C_{1-6}$ alkyl optionally substituted with one or more —H, halogen, —CN, —OH, $C_{1-6}$ alkyl, $C_{1-6}$ alkoxy, $C_{3-8}$-cycloalkyl, heterocyclyl, heteroaryl, or aryl. In another embodiment, $R_{24}$ is —OC(O)—$C_{1-6}$ alkyl optionally substituted with one or more —H, halogen, —CN, —OH, $C_{1-6}$ alkyl, $C_{1-6}$ alkoxy, $C_{3-8}$-cycloalkyl, heterocyclyl, heteroaryl, or aryl. In another embodiment, $R_{24}$ is —C(O)O—$C_{1-6}$ alkyl optionally substituted with one or more —H, halogen, —CN, —OH, $C_{1-6}$ alkyl, $C_{1-6}$ alkoxy, $C_{3-8}$-cycloalkyl, heterocyclyl, heteroaryl, or aryl.

In other embodiment of the compounds of Formula I, $R_{25}$ is $C_{1-6}$ alkyl, $C_{1-6}$ alkoxy, $C_{2-6}$ alkenyl, $C_{2-6}$ alkynyl, $C_{3-8}$ cycloalkyl, heterocyclyl, aryl, or heteroaryl. In another embodiment, $R_{25}$ is $C_{1-6}$ alkyl. In another embodiment, $R_{25}$ is $C_{1-6}$ alkoxy. In another embodiment, $R_{25}$ is $C_{2-6}$ alkenyl. In another embodiment, $R_{25}$ is $C_{2-6}$ alkynyl. In another embodiment, $R_{25}$ is $C_{3-8}$ cycloalkyl. In another embodiment, $R_{25}$ is heterocyclyl. In another embodiment, $R_{25}$ is aryl. In another embodiment, $R_{25}$ is heteroaryl. In another embodiment, $R_{25}$ is $C_{1-6}$ alkyl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{25}$ is $C_{1-6}$ alkoxy optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{25}$ is $C_{2-6}$ alkenyl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{25}$ is $C_{2-6}$ alkynyl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{25}$ is $C_{3-8}$ cycloalkyl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{25}$ is heterocyclyl optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl. In another embodiment, $R_{25}$ is aryl optionally substituted with one or more —H, halogen, —CN, —OH, $C_{1-6}$ alkyl, $C_{1-6}$ alkoxy, $C_{3-8}$-cycloalkyl, heterocyclyl, heteroaryl, or aryl. In another embodiment, $R_{25}$ is heteroaryl optionally substituted with one or more —H, halogen, —CN, —OH, $C_{1-6}$ alkyl, $C_{1-6}$ alkoxy, $C_{3-8}$-cycloalkyl, heterocyclyl, heteroaryl, or aryl.

In one embodiment, p is 1, 2, 3, or 4. In another embodiment p is 1, 2, or 3. In another embodiment p is 1 or 2. In another embodiment p is 1. In another embodiment p is 2. In another embodiment p is 3. In another embodiment p is 4.

In one embodiment, n is 1, 2, 3, or 4. In another embodiment n is 1, 2, or 3. In another embodiment n is 1 or 2. In another embodiment n is 1. In another embodiment n is 2. In another embodiment n is 3. In another embodiment n is 4.

In one embodiment, m is 1, 2, 3, or 4. In another embodiment m is 1, 2, or 3. In another embodiment m is 1 or 2. In another embodiment m is 1. In another embodiment m is 2. In another embodiment m is 3. In another embodiment m is 4.

In one embodiment, o is 1, 2, or 3. In another embodiment o is 1 or 2. In another embodiment o is 1. In another embodiment o is 2. In another embodiment o is 3.

In one embodiment of the compounds of Formula I, A is $C_{3-8}$ cycloalkyl, B is heteroaryl, $X_1$ is $C(R_5)$, $X_2$ is $C(R_5)$, W is $C(R_6)$, and $R_1$ is —$N(R_2)C(O)R_3$.

In one embodiment of the compounds of Formula I, A is $C_{4-8}$ cycloalkenyl, B is heteroaryl, $X_1$ is $C(R_5)$, $X_2$ is $C(R_5)$, W is $C(R_6)$, and $R_1$ is —$N(R_2)C(O)R_3$.

In one embodiment of the compounds of Formula I, A is 6-membered heteroaryl, B is heteroaryl, $X_1$ is $C(R_5)$, $X_2$ is $C(R_5)$, W is $C(R_6)$, and $R_1$ is —$N(R_2)C(O)R_3$.

In one embodiment of the compounds of Formula I, A is $C_{2-6}$ alkynyl, B is heteroaryl, $X_1$ is $C(R_5)$, $X_2$ is $C(R_5)$, W is $C(R_6)$, and $R_1$ is —$N(R_2)C(O)R_3$.

In one embodiment of the compounds of Formula I, A is aryl, B is heteroaryl, $X_1$ is $C(R_5)$, $X_2$ is $C(R_5)$, W is $C(R_6)$, and $R_1$ is —$N(R_2)C(O)R_3$.

In one embodiment of the compounds of Formula I, A is heterocyclyl, B is heteroaryl, $X_1$ is $C(R_5)$, $X_2$ is $C(R_5)$, W is $C(R_6)$, and $R_1$ is —$N(R_2)C(O)R_3$.

In one embodiment of the compounds of Formula I, A is $C_{3-8}$ cycloalkyl, B is heteroaryl, $X_1$ is $C(R_5)$, $X_2$ is $C(R_5)$, W is $C(R_6)$, and $R_1$ is —$C(O)N(R_2)(R_3)$.

In one embodiment of the compounds of Formula I, A is $C_{4-8}$ cycloalkenyl, B is heteroaryl, $X_1$ is $C(R_5)$, $X_2$ is $C(R_5)$, W is $C(R_6)$, and $R_1$ is —$C(O)N(R_2)(R_3)$.

In one embodiment of the compounds of Formula I, A is 6-membered heteroaryl, B is heteroaryl, $X_1$ is $C(R_5)$, $X_2$ is $C(R_5)$, W is $C(R_6)$, and $R_1$ is —$C(O)N(R_2)(R_3)$.

In one embodiment of the compounds of Formula I, A is $C_{2-6}$ alkynyl, B is heteroaryl, $X_1$ is $C(R_5)$, $X_2$ is $C(R_5)$, W is $C(R_6)$, and $R_1$ is —$C(O)N(R_2)(R_3)$.

In one embodiment of the compounds of Formula I, A is aryl, B is heteroaryl, $X_1$ is $C(R_5)$, $X_2$ is $C(R_5)$, W is $C(R_6)$, and $R_1$ is —$C(O)N(R_2)(R_3)$.

In one embodiment of the compounds of Formula I, A is heterocyclyl, B is heteroaryl, $X_1$ is $C(R_5)$, $X_2$ is $C(R_5)$, W is $C(R_6)$, and $R_1$ is —$C(O)N(R_2)(R_3)$.

In one embodiment of the compounds of Formula I, A is $C_{3-8}$ cycloalkyl, B is heteroaryl, $X_1$ is $C(R_5)$, $X_2$ is $C(R_5)$, W is $C(R_6)$, and $R_1$ is —$S(O)_2N(R_2)(R_3)$.

In one embodiment of the compounds of Formula I, A is $C_{4-8}$ cycloalkenyl, B is heteroaryl, $X_1$ is $C(R_5)$, $X_2$ is $C(R_5)$, W is $C(R_6)$, and $R_1$ is —$S(O)_2N(R_2)(R_3)$.

In one embodiment of the compounds of Formula I, A is 6-membered heteroaryl, B is heteroaryl, $X_1$ is $C(R_5)$, $X_2$ is $C(R_5)$, W is $C(R_6)$, and $R_1$ is —$S(O)_2N(R_2)(R_3)$.

In one embodiment of the compounds of Formula I, A is $C_{2-6}$ alkynyl, B is heteroaryl, $X_1$ is $C(R_5)$, $X_2$ is $C(R_5)$, W is $C(R_6)$, and $R_1$ is —$S(O)_2N(R_2)(R_3)$.

In one embodiment of the compounds of Formula I, A is aryl, B is heteroaryl, $X_1$ is $C(R_5)$, $X_2$ is $C(R_5)$, W is $C(R_6)$, and $R_1$ is —$S(O)_2N(R_2)(R_3)$.

In one embodiment of the compounds of Formula I, A is heterocyclyl, B is heteroaryl, $X_1$ is $C(R_5)$, $X_2$ is $C(R_5)$, W is $C(R_6)$, and $R_1$ is —$S(O)_2N(R_2)(R_3)$.

In one embodiment of the compounds of Formula I, A is $C_{3-8}$ cycloalkyl, B is heteroaryl, $X_1$ is $C(R_5)$, $X_2$ is $C(R_5)$, W is $C(R_6)$, and $R_1$ is heteroaryl.

In one embodiment of the compounds of Formula I, A is $C_{4-8}$ cycloalkenyl, B is heteroaryl, $X_1$ is $C(R_5)$, $X_2$ is $C(R_5)$, W is $C(R_6)$, and $R_1$ is heteroaryl.

In one embodiment of the compounds of Formula I, A is 6-membered heteroaryl, B is heteroaryl, $X_1$ is $C(R_5)$, $X_2$ is $C(R_5)$, W is $C(R_6)$, and $R_1$ is heteroaryl.

In one embodiment of the compounds of Formula I, A is $C_{2-6}$ alkynyl, B is heteroaryl, $X_1$ is $C(R_5)$, $X_2$ is $C(R_5)$, W is $C(R_6)$, and $R_1$ is heteroaryl.

In one embodiment of the compounds of Formula I, A is aryl, B is heteroaryl, $X_1$ is $C(R_5)$, $X_2$ is $C(R_5)$, W is $C(R_6)$, and $R_1$ is heteroaryl.

In one embodiment of the compounds of Formula I, A is heterocyclyl, B is heteroaryl, $X_1$ is $C(R_5)$, $X_2$ is $C(R_5)$, W is $C(R_6)$, and $R_1$ is heteroaryl.

In one embodiment of the compounds of Formula I, A is $C_{3-8}$ cycloalkyl, B is heteroaryl, $X_1$ is $C(R_5)$, $X_2$ is $C(R_5)$, W is $C(R_6)$, and $R_1$ is —$N(R_2)S(O)_2R_3$.

In one embodiment of the compounds of Formula I, A is $C_{4-8}$ cycloalkenyl, B is heteroaryl, $X_1$ is $C(R_5)$, $X_2$ is $C(R_5)$, W is $C(R_6)$, and $R_1$ is —$N(R_2)S(O)_2R_3$.

In one embodiment of the compounds of Formula I, A is 6-membered heteroaryl, B is heteroaryl, $X_1$ is $C(R_5)$, $X_2$ is $C(R_5)$, W is $C(R_6)$, and $R_1$ is —$N(R_2)S(O)_2R_3$.

In one embodiment of the compounds of Formula I, A is $C_{2-6}$ alkynyl, B is heteroaryl, $X_1$ is $C(R_5)$, $X_2$ is $C(R_5)$, W is $C(R_6)$, and $R_1$ is —$N(R_2)S(O)_2R_3$.

In one embodiment of the compounds of Formula I, A is aryl, B is heteroaryl, $X_1$ is $C(R_5)$, $X_2$ is $C(R_5)$, W is $C(R_6)$, and $R_1$ is —$N(R_2)S(O)_2R_3$.

In one embodiment of the compounds of Formula I, A is heterocyclyl, B is heteroaryl, $X_1$ is $C(R_5)$, $X_2$ is $C(R_5)$, W is $C(R_6)$, and $R_1$ is —$N(R_2)S(O)_2R_3$.

In one embodiment of the compounds of Formula I, A is $C_{3-8}$ cycloalkyl, B is heterocyclyl, $X_1$ is $C(R_5)$, $X_2$ is $C(R_5)$, W is $C(R_6)$, and $R_1$ is —$N(R_2)C(O)R_3$.

In one embodiment of the compounds of Formula I, A is $C_{4-8}$ cycloalkenyl, B is heterocyclyl, $X_1$ is $C(R_5)$, $X_2$ is $C(R_5)$, W is $C(R_6)$, and $R_1$ is —$N(R_2)C(O)R_3$.

In one embodiment of the compounds of Formula I, A is 6-membered heteroaryl, B is heterocyclyl, $X_1$ is $C(R_5)$, $X_2$ is $C(R_5)$, W is $C(R_6)$, and $R_1$ is —$N(R_2)C(O)R_3$.

In one embodiment of the compounds of Formula I, A is $C_{2-6}$ alkynyl, B is heterocyclyl, $X_1$ is $C(R_5)$, $X_2$ is $C(R_5)$, W is $C(R_6)$, and $R_1$ is —$N(R_2)C(O)R_3$.

In one embodiment of the compounds of Formula I, A is aryl, B is heterocyclyl, $X_1$ is $C(R_5)$, $X_2$ is $C(R_5)$, W is $C(R_6)$, and $R_1$ is —$N(R_2)C(O)R_3$.

In one embodiment of the compounds of Formula I, A is heterocyclyl, B is heterocyclyl, $X_1$ is $C(R_5)$, $X_2$ is $C(R_5)$, W is $C(R_6)$, and $R_1$ is $-N(R_2)C(O)R_3$.

In one embodiment of the compounds of Formula I, A is $C_{3-8}$ cycloalkyl, B is heterocyclyl, $X_1$ is $C(R_5)$, $X_2$ is $C(R_5)$, W is $C(R_6)$, and $R_1$ is $-C(O)N(R_2)(R_3)$.

In one embodiment of the compounds of Formula I, A is $C_{4-8}$ cycloalkenyl, B is heterocyclyl, $X_1$ is $C(R_5)$, $X_2$ is $C(R_5)$, W is $C(R_6)$, and $R_1$ is $-C(O)N(R_2)(R_3)$.

In one embodiment of the compounds of Formula I, A is 6-membered heteroaryl, B is heterocyclyl, $X_1$ is $C(R_5)$, $X_2$ is $C(R_5)$, W is $C(R_6)$, and $R_1$ is $-C(O)N(R_2)(R_3)$.

In one embodiment of the compounds of Formula I, A is $C_{2-6}$ alkynyl, B is heterocyclyl, $X_1$ is $C(R_5)$, $X_2$ is $C(R_5)$, W is $C(R_6)$, and $R_1$ is $-C(O)N(R_2)(R_3)$.

In one embodiment of the compounds of Formula I, A is aryl, B is heterocyclyl, $X_1$ is $C(R_5)$, $X_2$ is $C(R_5)$, W is $C(R_6)$, and $R_1$ is $-C(O)N(R_2)(R_3)$.

In one embodiment of the compounds of Formula I, A is heterocyclyl, B is heterocyclyl, $X_1$ is $C(R_5)$, $X_2$ is $C(R_5)$, W is $C(R_6)$, and $R_1$ is $-C(O)N(R_2)(R_3)$.

In one embodiment of the compounds of Formula I, A is $C_{3-8}$ cycloalkyl, B is heteroaryl optionally substituted with one or more $R_8$, $X_1$ is $C(R_5)$, $X_2$ is $C(R_5)$, W is $C(R_6)$, and $R_1$ is $-N(R_2)C(O)R_3$.

In one embodiment of the compounds of Formula I, A is $C_{4-8}$ cycloalkenyl, B is heteroaryl optionally substituted with one or more $R_8$, $X_1$ is $C(R_5)$, $X_2$ is $C(R_5)$, W is $C(R_6)$, and $R_1$ is $-N(R_2)C(O)R_3$.

In one embodiment of the compounds of Formula I, A is 6-membered heteroaryl, B is heteroaryl optionally substituted with one or more $R_8$, $X_1$ is $C(R_5)$, $X_2$ is $C(R_5)$, W is $C(R_6)$, and $R_1$ is $-N(R_2)C(O)R_3$.

In one embodiment of the compounds of Formula I, A is $C_{2-6}$ alkynyl, B is heteroaryl optionally substituted with one or more $R_8$, $X_1$ is $C(R_5)$, $X_2$ is $C(R_5)$, W is $C(R_6)$, and $R_1$ is $-N(R_2)C(O)R_3$.

In one embodiment of the compounds of Formula I, A is aryl, B is heteroaryl optionally substituted with one or more $R_8$, $X_1$ is $C(R_5)$, $X_2$ is $C(R_5)$, W is $C(R_6)$, and $R_1$ is $-N(R_2)C(O)R_3$.

In one embodiment of the compounds of Formula I, A is heterocyclyl, B is heteroaryl optionally substituted with one or more $R_8$, $X_1$ is $C(R_5)$, $X_2$ is $C(R_5)$, W is $C(R_6)$, and $R_1$ is $-N(R_2)C(O)R_3$.

In one embodiment of the compounds of Formula I, A is $C_{3-8}$ cycloalkyl, B is heteroaryl optionally substituted with one or more $R_8$, $X_1$ is $C(R_5)$, $X_2$ is $C(R_5)$, W is $C(R_6)$, and $R_1$ is $-C(O)N(R_2)(R_3)$.

In one embodiment of the compounds of Formula I, A is $C_{4-8}$ cycloalkenyl, B is heteroaryl optionally substituted with one or more $R_8$, $X_1$ is $C(R_5)$, $X_2$ is $C(R_5)$, W is $C(R_6)$, and $R_1$ is $-C(O)N(R_2)(R_3)$.

In one embodiment of the compounds of Formula I, A is 6-membered heteroaryl, B is heteroaryl optionally substituted with one or more $R_8$, $X_1$ is $C(R_5)$, $X_2$ is $C(R_5)$, W is $C(R_6)$, and $R_1$ is $-C(O)N(R_2)(R_3)$.

In one embodiment of the compounds of Formula I, A is $C_{2-6}$ alkynyl, B is heteroaryl optionally substituted with one or more $R_8$, $X_1$ is $C(R_5)$, $X_2$ is $C(R_5)$, W is $C(R_6)$, and $R_1$ is $-C(O)N(R_2)(R_3)$.

In one embodiment of the compounds of Formula I, A is aryl, B is heteroaryl optionally substituted with one or more $R_8$, $X_1$ is $C(R_5)$, $X_2$ is $C(R_5)$, W is $C(R_6)$, and $R_1$ is $-C(O)N(R_2)(R_3)$.

In one embodiment of the compounds of Formula I, A is heterocyclyl, B is heteroaryl optionally substituted with one or more $R_8$, $X_1$ is $C(R_5)$, $X_2$ is $C(R_5)$, W is $C(R_6)$, and $R_1$ is $-C(O)N(R_2)(R_3)$.

In one embodiment of the compounds of Formula I, A is $C_{3-8}$ cycloalkyl, B is heterocyclyl optionally substituted with one or more $R_7$, $X_1$ is $C(R_5)$, $X_2$ is $C(R_5)$, W is $C(R_6)$, and $R_1$ is $-N(R_2)C(O)R_3$.

In one embodiment of the compounds of Formula I, A is $C_{4-8}$ cycloalkenyl, B is heterocyclyl optionally substituted with one or more $R_7$, $X_1$ is $C(R_5)$, $X_2$ is $C(R_5)$, W is $C(R_6)$, and $R_1$ is $-N(R_2)C(O)R_3$.

In one embodiment of the compounds of Formula I, A is 6-membered heteroaryl, B is heterocyclyl optionally substituted with one or more $R_7$, $X_1$ is $C(R_5)$, $X_2$ is $C(R_5)$, W is $C(R_6)$, and $R_1$ is $-N(R_2)C(O)R_3$.

In one embodiment of the compounds of Formula I, A is $C_{2-6}$ alkynyl, B is heterocyclyl optionally substituted with one or more $R_7$, $X_1$ is $C(R_5)$, $X_2$ is $C(R_5)$, W is $C(R_6)$, and $R_1$ is $-N(R_2)C(O)R_3$.

In one embodiment of the compounds of Formula I, A is aryl, B is heterocyclyl optionally substituted with one or more $R_7$, $X_1$ is $C(R_5)$, $X_2$ is $C(R_5)$, W is $C(R_6)$, and $R_1$ is $-N(R_2)C(O)R_3$.

In one embodiment of the compounds of Formula I, A is heterocyclyl, B is heterocyclyl optionally substituted with one or more $R_7$, $X_1$ is $C(R_5)$, $X_2$ is $C(R_5)$, W is $C(R_6)$, and $R_1$ is $-N(R_2)C(O)R_3$.

In one embodiment of the compounds of Formula I, A is $C_{3-8}$ cycloalkyl, B is heterocyclyl optionally substituted with one or more $R_7$, $X_1$ is $C(R_5)$, $X_2$ is $C(R_5)$, W is $C(R_6)$, and $R_1$ is $-C(O)N(R_2)(R_3)$.

In one embodiment of the compounds of Formula I, A is $C_{4-8}$ cycloalkenyl, B is heterocyclyl optionally substituted with one or more $R_7$, $X_1$ is $C(R_5)$, $X_2$ is $C(R_5)$, W is $C(R_6)$, and $R_1$ is $-C(O)N(R_2)(R_3)$.

In one embodiment of the compounds of Formula I, A is 6-membered heteroaryl, B is heterocyclyl optionally substituted with one or more $R_7$, $X_1$ is $C(R_5)$, $X_2$ is $C(R_5)$, W is $C(R_6)$, and $R_1$ is $-C(O)N(R_2)(R_3)$.

In one embodiment of the compounds of Formula I, A is $C_{2-6}$ alkynyl, B is heterocyclyl optionally substituted with one or more $R_7$, $X_1$ is $C(R_5)$, $X_2$ is $C(R_5)$, W is $C(R_6)$, and $R_1$ is $-C(O)N(R_2)(R_3)$.

In one embodiment of the compounds of Formula I, A is aryl, B is heterocyclyl optionally substituted with one or more $R_7$, $X_1$ is $C(R_5)$, $X_2$ is $C(R_5)$, W is $C(R_6)$, and $R_1$ is $-C(O)N(R_2)(R_3)$.

In one embodiment of the compounds of Formula I, A is heterocyclyl, B is heterocyclyl optionally substituted with one or more $R_7$, $X_1$ is $C(R_5)$, $X_2$ is $C(R_5)$, W is $C(R_6)$, and $R_1$ is $-C(O)N(R_2)(R_3)$.

In one embodiment of the compounds of Formula I, A is $C_{3-8}$ cycloalkyl, B is heteroaryl, $X_1$ is $C(R_5)$, $X_2$ is N, W is $C(R_6)$, and $R_1$ is $-N(R_2)C(O)R_3$.

In one embodiment of the compounds of Formula I, A is $C_{4-8}$ cycloalkenyl, B is heteroaryl, $X_1$ is $C(R_5)$, $X_2$ is N, W is $C(R_6)$, and $R_1$ is $-N(R_2)C(O)R_3$.

In one embodiment of the compounds of Formula I, A is 6-membered heteroaryl, B is heteroaryl, $X_1$ is $C(R_5)$, $X_2$ is N, W is $C(R_6)$, and $R_1$ is $-N(R_2)C(O)R_3$.

In one embodiment of the compounds of Formula I, A is $C_{2-6}$ alkynyl, B is heteroaryl, $X_1$ is $C(R_5)$, $X_2$ is N, W is $C(R_6)$, and $R_1$ is $-N(R_2)C(O)R_3$.

In one embodiment of the compounds of Formula I, A is aryl, B is heteroaryl, $X_1$ is $C(R_5)$, $X_2$ is N, W is $C(R_6)$, and $R_1$ is $-N(R_2)C(O)R_3$.

In one embodiment of the compounds of Formula I, A is heterocyclyl, B is heteroaryl, $X_1$ is $C(R_5)$, $X_2$ is N, W is $C(R_6)$, and $R_1$ is —$N(R_2)C(O)R_3$.

In one embodiment of the compounds of Formula I, A is $C_{3-8}$ cycloalkyl, B is heteroaryl, $X_1$ is $C(R_5)$, $X_2$ is N, W is $C(R_6)$, and $R_1$ is —$C(O)N(R_2)(R_3)$.

In one embodiment of the compounds of Formula I, A is $C_{4-8}$ cycloalkenyl, B is heteroaryl, $X_1$ is $C(R_5)$, $X_2$ is N, W is $C(R_6)$, and $R_1$ is —$C(O)N(R_2)(R_3)$.

In one embodiment of the compounds of Formula I, A is 6-membered heteroaryl, B is heteroaryl, $X_1$ is $C(R_5)$, $X_2$ is N, W is $C(R_6)$, and $R_1$ is —$C(O)N(R_2)(R_3)$.

In one embodiment of the compounds of Formula I, A is $C_{2-6}$ alkynyl, B is heteroaryl, $X_1$ is $C(R_5)$, $X_2$ is N, W is $C(R_6)$, and $R_1$ is —$C(O)N(R_2)(R_3)$.

In one embodiment of the compounds of Formula I, A is aryl, B is heteroaryl, $X_1$ is $C(R_5)$, $X_2$ is N, W is $C(R_6)$, and $R_1$ is —$C(O)N(R_2)(R_3)$.

In one embodiment of the compounds of Formula I, A is heterocyclyl, B is heteroaryl, $X_1$ is $C(R_5)$, $X_2$ is N, W is $C(R_6)$, and $R_1$ is —$C(O)N(R_2)(R_3)$.

In one embodiment of the compounds of Formula I, A is $C_{3-8}$ cycloalkyl, B is heteroaryl, $X_1$ is $C(R_5)$, $X_2$ is N, W is $C(R_6)$, and $R_1$ is —$S(O)_2N(R_2)(R_3)$.

In one embodiment of the compounds of Formula I, A is $C_{4-8}$ cycloalkenyl, B is heteroaryl, $X_1$ is $C(R_5)$, $X_2$ is N, W is $C(R_6)$, and $R_1$ is —$S(O)_2N(R_2)(R_3)$.

In one embodiment of the compounds of Formula I, A is 6-membered heteroaryl, B is heteroaryl, $X_1$ is $C(R_5)$, $X_2$ is N, W is $C(R_6)$, and $R_1$ is —$S(O)_2N(R_2)(R_3)$.

In one embodiment of the compounds of Formula I, A is $C_{2-6}$ alkynyl, B is heteroaryl, $X_1$ is $C(R_5)$, $X_2$ is N, W is $C(R_6)$, and $R_1$ is —$S(O)_2N(R_2)(R_3)$.

In one embodiment of the compounds of Formula I, A is aryl, B is heteroaryl, $X_1$ is $C(R_5)$, $X_2$ is N, W is $C(R_6)$, and $R_1$ is —$S(O)_2N(R_2)(R_3)$.

In one embodiment of the compounds of Formula I, A is heterocyclyl, B is heteroaryl, $X_1$ is $C(R_5)$, $X_2$ is N, W is $C(R_6)$, and $R_1$ is —$S(O)_2N(R_2)(R_3)$.

In one embodiment of the compounds of Formula I, A is $C_{3-8}$ cycloalkyl, B is heteroaryl, $X_1$ is $C(R_5)$, $X_2$ is N, W is $C(R_6)$, and $R_1$ is heteroaryl.

In one embodiment of the compounds of Formula I, A is $C_{4-8}$ cycloalkenyl, B is heteroaryl, $X_1$ is $C(R_5)$, $X_2$ is N, W is $C(R_6)$, and $R_1$ is heteroaryl.

In one embodiment of the compounds of Formula I, A is 6-membered heteroaryl, B is heteroaryl, $X_1$ is $C(R_5)$, $X_2$ is N, W is $C(R_6)$, and $R_1$ is heteroaryl.

In one embodiment of the compounds of Formula I, A is $C_{2-6}$ alkynyl, B is heteroaryl, $X_1$ is $C(R_5)$, $X_2$ is N, W is $C(R_6)$, and $R_1$ is heteroaryl.

In one embodiment of the compounds of Formula I, A is aryl, B is heteroaryl, $X_1$ is $C(R_5)$, $X_2$ is N, W is $C(R_6)$, and $R_1$ is heteroaryl.

In one embodiment of the compounds of Formula I, A is heterocyclyl, B is heteroaryl, $X_1$ is $C(R_5)$, $X_2$ is N, W is $C(R_6)$, and $R_1$ is heteroaryl.

In one embodiment of the compounds of Formula I, A is $C_{3-8}$ cycloalkyl, B is heteroaryl, $X_1$ is $C(R_5)$, $X_2$ is N, W is $C(R_6)$, and $R_1$ is —$N(R_2)S(O)_2R_3$.

In one embodiment of the compounds of Formula I, A is $C_{4-8}$ cycloalkenyl, B is heteroaryl, $X_1$ is $C(R_5)$, $X_2$ is N, W is $C(R_6)$, and $R_1$ is —$N(R_2)S(O)_2R_3$.

In one embodiment of the compounds of Formula I, A is 6-membered heteroaryl, B is heteroaryl, $X_1$ is $C(R_5)$, $X_2$ is N, W is $C(R_6)$, and $R_1$ is —$N(R_2)S(O)_2R_3$.

In one embodiment of the compounds of Formula I, A is $C_{2-6}$ alkynyl, B is heteroaryl, $X_1$ is $C(R_5)$, $X_2$ is N, W is $C(R_6)$, and $R_1$ is —$N(R_2)S(O)_2R_3$.

In one embodiment of the compounds of Formula I, A is aryl, B is heteroaryl, $X_1$ is $C(R_5)$, $X_2$ is N, W is $C(R_6)$, and $R_1$ is —$N(R_2)S(O)_2R_3$.

In one embodiment of the compounds of Formula I, A is heterocyclyl, B is heteroaryl, $X_1$ is $C(R_5)$, $X_2$ is N, W is $C(R_6)$, and $R_1$ is —$N(R_2)S(O)_2R_3$.

In one embodiment of the compounds of Formula I, A is $C_{3-8}$ cycloalkyl, B is heterocyclyl, $X_1$ is $C(R_5)$, $X_2$ is N, W is $C(R_6)$, and $R_1$ is —$N(R_2)C(O)R_3$.

In one embodiment of the compounds of Formula I, A is $C_{4-8}$ cycloalkenyl, B is heterocyclyl, $X_1$ is $C(R_5)$, $X_2$ is N, W is $C(R_6)$, and $R_1$ is —$N(R_2)C(O)R_3$.

In one embodiment of the compounds of Formula I, A is 6-membered heteroaryl, B is heterocyclyl, $X_1$ is $C(R_5)$, $X_2$ is N, W is $C(R_6)$, and $R_1$ is —$N(R_2)C(O)R_3$.

In one embodiment of the compounds of Formula I, A is $C_{2-6}$ alkynyl, B is heterocyclyl, $X_1$ is $C(R_5)$, $X_2$ is N, W is $C(R_6)$, and $R_1$ is —$N(R_2)C(O)R_3$.

In one embodiment of the compounds of Formula I, A is aryl, B is heterocyclyl, $X_1$ is $C(R_5)$, $X_2$ is N, W is $C(R_6)$, and $R_1$ is —$N(R_2)C(O)R_3$.

In one embodiment of the compounds of Formula I, A is heterocyclyl, B is heterocyclyl, $X_1$ is $C(R_5)$, $X_2$ is N, W is $C(R_6)$, and $R_1$ is —$N(R_2)C(O)R_3$.

In one embodiment of the compounds of Formula I, A is $C_{3-8}$ cycloalkyl, B is heterocyclyl, $X_1$ is $C(R_5)$, $X_2$ is N, W is $C(R_6)$, and $R_1$ is —$C(O)N(R_2)(R_3)$.

In one embodiment of the compounds of Formula I, A is $C_{4-8}$ cycloalkenyl, B is heterocyclyl, $X_1$ is $C(R_5)$, $X_2$ is N, W is $C(R_6)$, and $R_1$ is —$C(O)N(R_2)(R_3)$.

In one embodiment of the compounds of Formula I, A is 6-membered heteroaryl, B is heterocyclyl, $X_1$ is $C(R_5)$, $X_2$ is N, W is $C(R_6)$, and $R_1$ is —$C(O)N(R_2)(R_3)$.

In one embodiment of the compounds of Formula I, A is $C_{2-6}$ alkynyl, B is heterocyclyl, $X_1$ is $C(R_5)$, $X_2$ is N, W is $C(R_6)$, and $R_1$ is —$C(O)N(R_2)(R_3)$.

In one embodiment of the compounds of Formula I, A is aryl, B is heterocyclyl, $X_1$ is $C(R_5)$, $X_2$ is N, W is $C(R_6)$, and $R_1$ is —$C(O)N(R_2)(R_3)$.

In one embodiment of the compounds of Formula I, A is heterocyclyl, B is heterocyclyl, $X_1$ is $C(R_5)$, $X_2$ is N, W is $C(R_6)$, and $R_1$ is —$C(O)N(R_2)(R_3)$.

In one embodiment of the compounds of Formula I, A is $C_{3-8}$ cycloalkyl, B is heteroaryl optionally substituted with one or more $R_8$, $X_1$ is $C(R_5)$, $X_2$ is N, W is $C(R_6)$, and $R_1$ is —$N(R_2)C(O)R_3$.

In one embodiment of the compounds of Formula I, A is $C_{4-8}$ cycloalkenyl, B is heteroaryl optionally substituted with one or more $R_8$, $X_1$ is $C(R_5)$, $X_2$ is N, W is $C(R_6)$, and $R_1$ is —$N(R_2)C(O)R_3$.

In one embodiment of the compounds of Formula I, A is 6-membered heteroaryl, B is heteroaryl optionally substituted with one or more $R_8$, $X_1$ is $C(R_5)$, $X_2$ is N, W is $C(R_6)$, and $R_1$ is —$N(R_2)C(O)R_3$.

In one embodiment of the compounds of Formula I, A is $C_{2-6}$ alkynyl, B is heteroaryl optionally substituted with one or more $R_8$, $X_1$ is $C(R_5)$, $X_2$ is N, W is $C(R_6)$, and $R_1$ is —$N(R_2)C(O)R_3$.

In one embodiment of the compounds of Formula I, A is aryl, B is heteroaryl optionally substituted with one or more $R_8$, $X_1$ is $C(R_5)$, $X_2$ is N, W is $C(R_6)$, and $R_1$ is —$N(R_2)C(O)R_3$.

In one embodiment of the compounds of Formula I, A is heterocyclyl, B is heteroaryl optionally substituted with one or more $R_8$, $X_1$ is $C(R_5)$, $X_2$ is N, W is $C(R_6)$, and $R_1$ is —$N(R_2)C(O)R_3$.

In one embodiment of the compounds of Formula I, A is $C_{3-8}$ cycloalkyl, B is heteroaryl optionally substituted with one or more $R_8$, $X_1$ is $C(R_5)$, $X_2$ is N, W is $C(R_6)$, and $R_1$ is —$C(O)N(R_2)(R_3)$.

In one embodiment of the compounds of Formula I, A is $C_{4-8}$ cycloalkenyl, B is heteroaryl optionally substituted with one or more $R_8$, $X_1$ is $C(R_5)$, $X_2$ is N, W is $C(R_6)$, and $R_1$ is —$C(O)N(R_2)(R_3)$.

In one embodiment of the compounds of Formula I, A is 6-membered heteroaryl, B is heteroaryl optionally substituted with one or more $R_8$, $X_1$ is $C(R_5)$, $X_2$ is N, W is $C(R_6)$, and $R_1$ is —$C(O)N(R_2)(R_3)$.

In one embodiment of the compounds of Formula I, A is $C_{2-6}$ alkynyl, B is heteroaryl optionally substituted with one or more $R_8$, $X_1$ is $C(R_5)$, $X_2$ is N, W is $C(R_6)$, and $R_1$ is —$C(O)N(R_2)(R_3)$.

In one embodiment of the compounds of Formula I, A is aryl, B is heteroaryl optionally substituted with one or more $R_8$, $X_1$ is $C(R_5)$, $X_2$ is N, W is $C(R_6)$, and $R_1$ is —$C(O)N(R_2)(R_3)$.

In one embodiment of the compounds of Formula I, A is heterocyclyl, B is heteroaryl optionally substituted with one or more $R_8$, $X_1$ is $C(R_5)$, $X_2$ is N, W is $C(R_6)$, and $R_1$ is —$C(O)N(R_2)(R_3)$.

In one embodiment of the compounds of Formula I, A is $C_{3-8}$ cycloalkyl, B is heterocyclyl optionally substituted with one or more $R_7$, $X_1$ is $C(R_5)$, $X_2$ is N, W is $C(R_6)$, and $R_1$ is —$N(R_2)C(O)R_3$.

In one embodiment of the compounds of Formula I, A is $C_{4-8}$ cycloalkenyl, B is heterocyclyl optionally substituted with one or more $R_7$, $X_1$ is $C(R_5)$, $X_2$ is N, W is $C(R_6)$, and $R_1$ is —$N(R_2)C(O)R_3$.

In one embodiment of the compounds of Formula I, A is 6-membered heteroaryl, B is heterocyclyl optionally substituted with one or more $R_7$, $X_1$ is $C(R_5)$, $X_2$ is N, W is $C(R_6)$, and $R_1$ is —$N(R_2)C(O)R_3$.

In one embodiment of the compounds of Formula I, A is $C_{2-6}$ alkynyl, B is heterocyclyl optionally substituted with one or more $R_7$, $X_1$ is $C(R_5)$, $X_2$ is N, W is $C(R_6)$, and $R_1$ is —$N(R_2)C(O)R_3$.

In one embodiment of the compounds of Formula I, A is aryl, B is heterocyclyl optionally substituted with one or more $R_7$, $X_1$ is $C(R_5)$, $X_2$ is N, W is $C(R_6)$, and $R_1$ is —$N(R_2)C(O)R_3$.

In one embodiment of the compounds of Formula I, A is heterocyclyl, B is heterocyclyl optionally substituted with one or more $R_7$, $X_1$ is $C(R_5)$, $X_2$ is N, W is $C(R_6)$, and $R_1$ is —$N(R_2)C(O)R_3$.

In one embodiment of the compounds of Formula I, A is $C_{3-8}$ cycloalkyl, B is heterocyclyl optionally substituted with one or more $R_7$, $X_1$ is $C(R_5)$, $X_2$ is N, W is $C(R_6)$, and $R_1$ is —$C(O)N(R_2)(R_3)$.

In one embodiment of the compounds of Formula I, A is $C_{4-8}$ cycloalkenyl, B is heterocyclyl optionally substituted with one or more $R_7$, $X_1$ is $C(R_5)$, $X_2$ is N, W is $C(R_6)$, and $R_1$ is —$C(O)N(R_2)(R_3)$.

In one embodiment of the compounds of Formula I, A is 6-membered heteroaryl, B is heterocyclyl optionally substituted with one or more $R_7$, $X_1$ is $C(R_5)$, $X_2$ is N, W is $C(R_6)$, and $R_1$ is —$C(O)N(R_2)(R_3)$.

In one embodiment of the compounds of Formula I, A is $C_{2-6}$ alkynyl, B is heterocyclyl optionally substituted with one or more $R_7$, $X_1$ is $C(R_5)$, $X_2$ is N, W is $C(R_6)$, and $R_1$ is —$C(O)N(R_2)(R_3)$.

In one embodiment of the compounds of Formula I, A is aryl, B is heterocyclyl optionally substituted with one or more $R_7$, $X_1$ is $C(R_5)$, $X_2$ is N, W is $C(R_6)$, and $R_1$ is —$C(O)N(R_2)(R_3)$.

In one embodiment of the compounds of Formula I, A is heterocyclyl, B is heterocyclyl optionally substituted with one or more $R_7$, $X_1$ is $C(R_5)$, $X_2$ is N, W is $C(R_6)$, and $R_1$ is —$C(O)N(R_2)(R_3)$.

In one embodiment of the compounds of Formula I, A is $C_{3-8}$ cycloalkyl, B is heteroaryl optionally substituted with one or more $R_8$, wherein $R_8$ is —H, —CN, oxo, —$N(R_9)C(O)R_{10}$, —$N(R_9)C(O)OR_{10}$, —$N(R_9)C(O)N(R_9)(R_{10})$, —$N(R_9)S(O)_2R_{10}$, —$S(O)_2R_{10}$, $C(O)R_9$—$N(R_9)(R_{10})$, —$OR_{10}$, —$N(R_9)C(O)R_{13}$, or —$C(O)N(R_9)(R_{10})$, $X_1$ is $C(R_5)$, $X_2$ is $C(R_5)$, W is $C(R_6)$, and $R_1$ is —$N(R_2)C(O)R_3$.

In one embodiment of the compounds of Formula I, A is $C_{4-8}$ cycloalkenyl, B is heteroaryl optionally substituted with one or more $R_8$, wherein $R_8$ is —H, —CN, oxo, —$N(R_9)C(O)R_{10}$, —$N(R_9)C(O)OR_{10}$, —$N(R_9)C(O)N(R_9)(R_{10})$, —$N(R_9)S(O)_2R_{10}$, —$S(O)_2R_{10}$, $C(O)R_9$—$N(R_9)(R_{10})$, —$OR_{10}$, —$N(R_9)C(O)R_3$, or —$C(O)N(R_9)(R_{10})$, $X_1$ is $C(R_5)$, $X_2$ is $C(R_5)$, W is $C(R_6)$, and $R_1$ is —$N(R_2)C(O)R_3$.

In one embodiment of the compounds of Formula I, A is 6-membered heteroaryl, B is heteroaryl optionally substituted with one or more $R_8$, wherein $R_8$ is —H, —CN, oxo, —$N(R_9)C(O)R_{10}$, —$N(R_9)C(O)OR_{10}$, —$N(R_9)C(O)N(R_9)(R_{10})$, —$N(R_9)S(O)_2R_{10}$, —$S(O)_2R_{10}$, $C(O)R_9$—$N(R_9)(R_{10})$, —$OR_{10}$, —$N(R_9)C(O)R_3$, or —$C(O)N(R_9)(R_{10})$, $X_1$ is $C(R_5)$, $X_2$ is $C(R_5)$, W is $C(R_6)$, and $R_1$ is —$N(R_2)C(O)R_3$.

In one embodiment of the compounds of Formula I, A is $C_{2-6}$ alkynyl, B is heteroaryl optionally substituted with one or more $R_8$, wherein $R_8$ is —H, —CN, oxo, —$N(R_9)C(O)R_{10}$, —$N(R_9)C(O)OR_{10}$, —$N(R_9)C(O)N(R_9)(R_{10})$, —$N(R_9)S(O)_2R_{10}$, —$S(O)_2R_{10}$, $C(O)R_9$—$N(R_9)(R_{10})$, —$OR_{10}$, —$N(R_9)C(O)R_3$, or —$C(O)N(R_9)(R_{10})$, $X_1$ is $C(R_5)$, $X_2$ is $C(R_5)$, W is $C(R_6)$, and $R_1$ is —$N(R_2)C(O)R_3$.

In one embodiment of the compounds of Formula I, A is aryl, B is heteroaryl optionally substituted with one or more $R_8$, $X_1$ is $C(R_5)$, wherein $R_8$ is —H, —CN, oxo, —$N(R_9)C(O)R_{10}$, —$N(R_9)C(O)OR_{10}$, —$N(R_9)C(O)N(R_9)(R_{10})$, —$N(R_9)S(O)_2R_{10}$, —$S(O)_2R_{10}$, $C(O)R_9$—$N(R_9)(R_{10})$, —$OR_{10}$, —$N(R_9)C(O)R_{13}$, or —$C(O)N(R_9)(R_{10})$, $X_2$ is $C(R_5)$, W is $C(R_6)$, and $R_1$ is —$N(R_2)C(O)R_3$.

In one embodiment of the compounds of Formula I, A is heterocyclyl, B is heteroaryl optionally substituted with one or more $R_8$, wherein $R_8$ is —H, —CN, oxo, —$N(R_9)C(O)R_{10}$, —$N(R_9)C(O)OR_{10}$, —$N(R_9)C(O)N(R_9)(R_{10})$, —$N(R_9)S(O)_2R_{10}$, —$S(O)_2R_{10}$, $C(O)R_9$—$N(R_9)(R_{10})$, —$OR_{10}$, —$N(R_9)C(O)R_{13}$, or —$C(O)N(R_9)(R_{10})$, $X_1$ is $C(R_5)$, $X_2$ is $C(R_5)$, W is $C(R_6)$, and $R_1$ is —$N(R_2)C(O)R_3$.

In one embodiment of the compounds of Formula I, A is $C_{3-8}$ cycloalkyl, B is heteroaryl optionally substituted with one or more $R_8$, wherein $R_8$ is —H, —CN, oxo, —$N(R_9)C(O)R_{10}$, —$N(R_9)C(O)OR_{10}$, —$N(R_9)C(O)N(R_9)(R_{10})$, —$N(R_9)S(O)_2R_{10}$, —$S(O)_2R_{10}$, $C(O)R_9$—$N(R_9)(R_{10})$, —$OR_{10}$, —$N(R_9)C(O)R_{13}$, or —$C(O)N(R_9)(R_{10})$, $X_1$ is $C(R_5)$, $X_2$ is $C(R_5)$, W is $C(R_6)$, and $R_1$ is —$C(O)N(R_2)(R_3)$.

In one embodiment of the compounds of Formula I, A is $C_{4-8}$ cycloalkenyl, B is heteroaryl optionally substituted with one or more $R_8$, wherein $R_8$ is —H, —CN, oxo, —$N(R_9)C(O)R_{10}$, —$N(R_9)C(O)OR_{10}$, —$N(R_9)C(O)N(R_9)(R_{10})$, —$N(R_9)S(O)_2R_{10}$, —$S(O)_2R_{10}$, $C(O)R_9$—$N(R_9)(R_{10})$, —OR$_{10}$, —N(R$_9$)C(O)R$_{13}$, or —C(O)N(R$_9$)(R$_{10}$), X$_1$ is C(R$_5$), X$_2$ is C(R$_5$), W is C(R$_6$), and R$_1$ is —C(O)N(R$_2$)(R$_3$).

In one embodiment of the compounds of Formula I, A is 6-membered heteroaryl, B is heteroaryl optionally substituted with one or more R$_8$, wherein R$_8$ is —H, —CN, oxo, —N(R$_9$)C(O)R$_{10}$, —N(R$_9$)C(O)OR$_{10}$, —N(R$_9$)C(O)N(R$_9$)(R$_{10}$), —N(R$_9$)S(O)$_2$R$_{10}$, —S(O)$_2$R$_{10}$, C(O)R$_9$—N(R$_9$)(R$_{10}$), —OR$_{10}$, —N(R$_9$)C(O)R$_{13}$, or —C(O)N(R$_9$)(R$_{10}$), X$_1$ is C(R$_5$), X$_2$ is C(R$_5$), W is C(R$_6$), and R$_1$ is —C(O)N(R$_2$)(R$_3$).

In one embodiment of the compounds of Formula I, A is C$_{2-6}$ alkynyl, B is heteroaryl optionally substituted with one or more R$_8$, wherein R$_8$ is —H, —CN, oxo, —N(R$_9$)C(O)R$_{10}$, —N(R$_9$)C(O)OR$_{10}$, —N(R$_9$)C(O)N(R$_9$)(R$_{10}$), —N(R$_9$)S(O)$_2$R$_{10}$, —S(O)$_2$R$_{10}$, C(O)R$_9$—N(R$_9$)(R$_{10}$), —OR$_{10}$, —N(R$_9$)C(O)R$_{13}$, or —C(O)N(R$_9$)(R$_{10}$), X$_1$ is C(R$_5$), X$_2$ is C(R$_5$), W is C(R$_6$), and R$_1$ is —C(O)N(R$_2$)(R$_3$).

In one embodiment of the compounds of Formula I, A is aryl, B is heteroaryl optionally substituted with one or more R$_8$, wherein R$_8$ is —H, —CN, oxo, —N(R$_9$)C(O)R$_{10}$, —N(R$_9$)C(O)OR$_{10}$, —N(R$_9$)C(O)N(R$_9$)(R$_{10}$), —N(R$_9$)S(O)$_2$R$_{10}$, —S(O)$_2$R$_{10}$, C(O)R$_9$—N(R$_9$)(R$_{10}$), —OR$_{10}$, —N(R$_9$)C(O)R$_3$, or —C(O)N(R$_9$)(R$_{10}$), X$_1$ is C(R$_5$), X$_2$ is C(R$_5$), W is C(R$_6$), and R$_1$ is —C(O)N(R$_2$)(R$_3$).

In one embodiment of the compounds of Formula I, A is heterocyclyl, B is heteroaryl optionally substituted with one or more R$_8$, wherein R$_8$ is —H, —CN, oxo, —N(R$_9$)C(O)R$_{10}$, —N(R$_9$)C(O)OR$_{10}$, —N(R$_9$)C(O)N(R$_9$)(R$_{10}$), —N(R$_9$)S(O)$_2$R$_{10}$, —S(O)$_2$R$_{10}$, C(O)R$_9$—N(R$_9$)(R$_{10}$), —OR$_{10}$, —N(R$_9$)C(O)R$_{13}$, or —C(O)N(R$_9$)(R$_{10}$), X$_1$ is C(R$_5$), X$_2$ is C(R$_5$), W is C(R$_6$), and R$_1$ is —C(O)N(R$_2$)(R$_3$).

In one embodiment of the compounds of Formula I, A is C$_{3-8}$ cycloalkyl, B is heteroaryl optionally substituted with one or more R$_8$, R$_8$ is C$_{1-6}$ alkyl, heterocyclyl, aryl, or heteroaryl, wherein the alkyl, heterocyclyl, aryl, or heteroaryl is optionally substituted with one or more R$_{15}$, X$_1$ is C(R$_5$), X$_2$ is C(R$_5$), W is C(R$_6$), and R$_1$ is —N(R$_2$)C(O)R$_3$.

In one embodiment of the compounds of Formula I, A is C$_{4-8}$ cycloalkenyl, B is heteroaryl optionally substituted with one or more R$_8$, R$_8$ is C$_{1-6}$ alkyl, heterocyclyl, aryl, or heteroaryl, wherein the alkyl, heterocyclyl, aryl, or heteroaryl is optionally substituted with one or more R$_{15}$, X$_1$ is C(R$_5$), X$_2$ is C(R$_5$), W is C(R$_6$), and R$_1$ is —N(R$_2$)C(O)R$_3$.

In one embodiment of the compounds of Formula I, A is 6-membered heteroaryl, B is heteroaryl optionally substituted with one or more R$_8$, R$_8$ is C$_{1-6}$ alkyl, heterocyclyl, aryl, or heteroaryl, wherein the alkyl, heterocyclyl, aryl, or heteroaryl is optionally substituted with one or more R$_{15}$, X$_1$ is C(R$_5$), X$_2$ is C(R$_5$), W is C(R$_6$), and R$_1$ is —N(R$_2$)C(O)R$_3$.

In one embodiment of the compounds of Formula I, A is C$_{2-6}$ alkynyl, B is heteroaryl optionally substituted with one or more R$_8$, R$_8$ is C$_{1-6}$ alkyl, heterocyclyl, aryl, or heteroaryl, wherein the alkyl, heterocyclyl, aryl, or heteroaryl is optionally substituted with one or more R$_{15}$, X$_1$ is C(R$_5$), X$_2$ is C(R$_5$), W is C(R$_6$), and R$_1$ is —N(R$_2$)C(O)R$_3$.

In one embodiment of the compounds of Formula I, A is aryl, B is heteroaryl optionally substituted with one or more R$_8$, X$_1$ is C(R$_5$), R$_8$ is C$_{1-6}$ alkyl, heterocyclyl, aryl, or heteroaryl, wherein the alkyl, heterocyclyl, aryl, or heteroaryl is optionally substituted with one or more R$_{15}$, X$_2$ is C(R$_5$), W is C(R$_6$), and R$_1$ is —N(R$_2$)C(O)R$_3$.

In one embodiment of the compounds of Formula I, A is heterocyclyl, B is heteroaryl optionally substituted with one or more R$_8$, R$_8$ is C$_{1-6}$ alkyl, heterocyclyl, aryl, or heteroaryl, wherein the alkyl, heterocyclyl, aryl, or heteroaryl is optionally substituted with one or more R$_{15}$, X$_1$ is C(R$_5$), W is C(R$_6$), and R$_1$ is —N(R$_2$)C(O)R$_3$.

In one embodiment of the compounds of Formula I, A is C$_{3-8}$ cycloalkyl, B is heteroaryl optionally substituted with one or more R$_8$, R$_8$ is C$_{1-6}$ alkyl, heterocyclyl, aryl, or heteroaryl, wherein the alkyl, heterocyclyl, aryl, or heteroaryl is optionally substituted with one or more R$_{15}$, X$_1$ is C(R$_5$), X$_2$ is C(R$_5$), W is C(R$_6$), and R$_1$ is —C(O)N(R$_2$)(R$_3$).

In one embodiment of the compounds of Formula I, A is C$_{4-8}$ cycloalkenyl, B is heteroaryl optionally substituted with one or more R$_8$, R$_8$ is C$_{1-6}$ alkyl, heterocyclyl, aryl, or heteroaryl, wherein the alkyl, heterocyclyl, aryl, or heteroaryl is optionally substituted with one or more R$_{15}$, X$_1$ is C(R$_5$), X$_2$ is C(R$_5$), W is C(R$_6$), and R$_1$ is —C(O)N(R$_2$)(R$_3$).

In one embodiment of the compounds of Formula I, A is 6-membered heteroaryl, B is heteroaryl optionally substituted with one or more R$_8$, R$_8$ is C$_{1-6}$ alkyl, heterocyclyl, aryl, or heteroaryl, wherein the alkyl, heterocyclyl, aryl, or heteroaryl is optionally substituted with one or more R$_{15}$, X$_1$ is C(R$_5$), X$_2$ is C(R$_5$), W is C(R$_6$), and R$_1$ is —C(O)N(R$_2$)(R$_3$).

In one embodiment of the compounds of Formula I, A is C$_{2-6}$ alkynyl, B is heteroaryl optionally substituted with one or more R$_8$, R$_8$ is C$_{1-6}$ alkyl, heterocyclyl, aryl, or heteroaryl, wherein the alkyl, heterocyclyl, aryl, or heteroaryl is optionally substituted with one or more R$_{15}$, X$_1$ is C(R$_5$), X$_2$ is C(R$_5$), W is C(R$_6$), and R$_1$ is —C(O)N(R$_2$)(R$_3$).

In one embodiment of the compounds of Formula I, A is aryl, B is heteroaryl optionally substituted with one or more R$_8$, R$_8$ is C$_{1-6}$ alkyl, heterocyclyl, aryl, or heteroaryl, wherein the alkyl, heterocyclyl, aryl, or heteroaryl is optionally substituted with one or more R$_{15}$, X$_1$ is C(R$_5$), X$_2$ is C(R$_5$), W is C(R$_6$), and R$_1$ is —C(O)N(R$_2$)(R$_3$).

In one embodiment of the compounds of Formula I, A is heterocyclyl, B is heteroaryl optionally substituted with one or more R$_8$, R$_8$ is C$_{1-6}$ alkyl, heterocyclyl, aryl, or heteroaryl, wherein the alkyl, heterocyclyl, aryl, or heteroaryl is optionally substituted with one or more R$_{15}$, X$_1$ is C(R$_5$), X$_2$ is C(R$_5$), W is C(R$_6$), and R$_1$ is —C(O)N(R$_2$)(R$_3$).

In one embodiment of the compounds of Formula I, A is C$_{3-8}$ cycloalkyl, B is heteroaryl optionally substituted with one or more R$_8$, wherein R$_8$ is —H, —CN, oxo, —N(R$_9$)C(O)R$_{10}$, —N(R$_9$)C(O)OR$_{10}$, —N(R$_9$)C(O)N(R$_9$)(R$_{10}$), —N(R$_9$)S(O)$_2$R$_{10}$, —S(O)$_2$R$_{10}$, C(O)R$_9$—N(R$_9$)(R$_{10}$), —OR$_{10}$, —N(R$_9$)C(O)R$_3$, or —C(O)N(R$_9$)(R$_{10}$), X$_1$ is C(R$_5$), X$_2$ is N, W is C(R$_6$), and R$_1$ is —N(R$_2$)C(O)R$_3$.

In one embodiment of the compounds of Formula I, A is C$_{4-8}$ cycloalkenyl, B is heteroaryl optionally substituted with one or more R$_8$, wherein R$_8$ is —H, —CN, oxo, —N(R$_9$)C(O)R$_{10}$, —N(R$_9$)C(O)OR$_{10}$, —N(R$_9$)C(O)N(R$_9$)(R$_{10}$), —N(R$_9$)S(O)$_2$R$_{10}$, —S(O)$_2$R$_{10}$, C(O)R$_9$—N(R$_9$)(R$_{10}$), —OR$_{10}$, —N(R$_9$)C(O)R$_3$, or —C(O)N(R$_9$)(R$_{10}$), X$_1$ is C(R$_5$), X$_2$ is N, W is C(R$_6$), and R$_1$ is —N(R$_2$)C(O)R$_3$.

In one embodiment of the compounds of Formula I, A is 6-membered heteroaryl, B is heteroaryl optionally substituted with one or more R$_8$, wherein R$_8$ is —H, —CN, oxo, —N(R$_9$)C(O)R$_{10}$, —N(R$_9$)C(O)OR$_{10}$, —N(R$_9$)C(O)N(R$_9$)(R$_{10}$), —N(R$_9$)S(O)$_2$R$_{10}$, —S(O)$_2$R$_{10}$, C(O)R$_9$—N(R$_9$)(R$_{10}$), —OR$_{10}$, —N(R$_9$)C(O)R$_{13}$, or —C(O)N(R$_9$)(R$_{10}$), X$_1$ is C(R$_5$), X$_2$ is N, W is C(R$_6$), and R$_1$ is —N(R$_2$)C(O)R$_3$.

In one embodiment of the compounds of Formula I, A is C$_{2-6}$ alkynyl, B is heteroaryl optionally substituted with one or more R$_8$, wherein R$_8$ is —H, —CN, oxo, —N(R$_9$)C(O)R$_{10}$, —N(R$_9$)C(O)OR$_{10}$, —N(R$_9$)C(O)N(R$_9$)(R$_{10}$), —N(R$_9$)S(O)$_2$R$_{10}$, —S(O)$_2$R$_{10}$, C(O)R$_9$—N(R$_9$)(R$_{10}$), —OR$_{10}$, —N(R$_9$)C(O)R$_3$, or —C(O)N(R$_9$)(R$_{10}$), X$_1$ is C(R$_5$), X$_2$ is N, W is C(R$_6$), and R$_1$ is —N(R$_2$)C(O)R$_3$.

In one embodiment of the compounds of Formula I, A is aryl, B is heteroaryl optionally substituted with one or more $R_8$, $X_1$ is $C(R_5)$, wherein $R_8$ is —H, —CN, oxo, —N($R_9$)C(O)$R_{10}$, —N($R_9$)C(O)O$R_{10}$, —N($R_9$)C(O)N($R_9$)($R_{10}$), —N($R_9$)S(O)$_2R_{10}$, —S(O)$_2R_{10}$, C(O)$R_9$—N($R_9$)($R_{10}$), —O$R_{10}$, —N($R_9$)C(O)$R_3$, or —C(O)N($R_9$)($R_{10}$), $X_2$ is N, W is $C(R_6)$, and $R_1$ is —N($R_2$)C(O)$R_3$.

In one embodiment of the compounds of Formula I, A is heterocyclyl, B is heteroaryl optionally substituted with one or more $R_8$, wherein $R_8$ is —H, —CN, oxo, —N($R_9$)C(O)$R_{10}$, —N($R_9$)C(O)O$R_{10}$, —N($R_9$)C(O)N($R_9$)($R_{10}$), —N($R_9$)S(O)$_2R_{10}$, —S(O)$_2R_{10}$, C(O)$R_9$—N($R_9$)($R_{10}$), —O$R_{10}$, —N($R_9$)C(O)$R_3$, or —C(O)N($R_9$)($R_{10}$), $X_1$ is $C(R_5)$, $X_2$ is N, W is $C(R_6)$, and $R_1$ is —N($R_2$)C(O)$R_3$.

In one embodiment of the compounds of Formula I, A is $C_{3-8}$ cycloalkyl, B is heteroaryl optionally substituted with one or more $R_8$, wherein $R_8$ is —H, —CN, oxo, —N($R_9$)C(O)$R_{10}$, —N($R_9$)C(O)O$R_{10}$, —N($R_9$)C(O)N($R_9$)($R_{10}$), —N($R_9$)S(O)$_2R_{10}$, —S(O)$_2R_{10}$, C(O)$R_9$—N($R_9$)($R_{10}$), —O$R_{10}$, —N($R_9$)C(O)$R_3$, or —C(O)N($R_9$)($R_{10}$), $X_1$ is $C(R_5)$, $X_2$ is N, W is $C(R_6)$, and $R_1$ is —C(O)N($R_2$)($R_3$).

In one embodiment of the compounds of Formula I, A is $C_{4-8}$ cycloalkenyl, B is heteroaryl optionally substituted with one or more $R_8$, wherein $R_8$ is —H, —CN, oxo, —N($R_9$)C(O)$R_{10}$, —N($R_9$)C(O)O$R_{10}$, —N($R_9$)C(O)N($R_9$)($R_{10}$), —N($R_9$)S(O)$_2R_{10}$, —S(O)$_2R_{10}$, C(O)$R_9$—N($R_9$)($R_{10}$), —O$R_{10}$, —N($R_9$)C(O)$R_3$, or —C(O)N($R_9$)($R_{10}$), $X_1$ is $C(R_5)$, $X_2$ is N, W is $C(R_6)$, and $R_1$ is —C(O)N($R_2$)($R_3$).

In one embodiment of the compounds of Formula I, A is 6-membered heteroaryl, B is heteroaryl optionally substituted with one or more $R_8$, wherein $R_8$ is —H, —CN, oxo, —N($R_9$)C(O)$R_{10}$, —N($R_9$)C(O)O$R_{10}$, —N($R_9$)C(O)N($R_9$)($R_{10}$), —N($R_9$)S(O)$_2R_{10}$, —S(O)$_2R_{10}$, C(O)$R_9$—N($R_9$)($R_{10}$), —O$R_{10}$, —N($R_9$)C(O)$R_{13}$, or —C(O)N($R_9$)($R_{10}$), $X_1$ is $C(R_5)$, $X_2$ is N, W is $C(R_6)$, and $R_1$ is —C(O)N($R_2$)($R_3$).

In one embodiment of the compounds of Formula I, A is $C_{2-6}$ alkynyl, B is heteroaryl optionally substituted with one or more $R_8$, wherein $R_8$ is —H, —CN, oxo, —N($R_9$)C(O)$R_{10}$, —N($R_9$)C(O)O$R_{10}$, —N($R_9$)C(O)N($R_9$)($R_{10}$), —N($R_9$)S(O)$_2R_{10}$, —S(O)$_2R_{10}$, C(O)$R_9$—N($R_9$)($R_{10}$), —O$R_{10}$, —N($R_9$)C(O)$R_3$, or —C(O)N($R_9$)($R_{10}$), $X_1$ is $C(R_5)$, $X_2$ is N, W is $C(R_6)$, and $R_1$ is —C(O)N($R_2$)($R_3$).

In one embodiment of the compounds of Formula I, A is aryl, B is heteroaryl optionally substituted with one or more $R_8$, wherein $R_8$ is —H, —CN, oxo, —N($R_9$)C(O)$R_{10}$, —N($R_9$)C(O)O$R_{10}$, —N($R_9$)C(O)N($R_9$)($R_{10}$), —N($R_9$)S(O)$_2R_{10}$, —S(O)$_2R_{10}$, C(O)$R_9$—N($R_9$)($R_{10}$), —O$R_{10}$, —N($R_9$)C(O)$R_3$, or —C(O)N($R_9$)($R_{10}$), $X_1$ is $C(R_5)$, $X_2$ is N, W is $C(R_6)$, and $R_1$ is —C(O)N($R_2$)($R_3$).

In one embodiment of the compounds of Formula I, A is heterocyclyl, B is heteroaryl optionally substituted with one or more $R_8$, wherein $R_8$ is —H, —CN, oxo, —N($R_9$)C(O)$R_{10}$, —N($R_9$)C(O)O$R_{10}$, —N($R_9$)C(O)N($R_9$)($R_{10}$), —N($R_9$)S(O)$_2R_{10}$, —S(O)$_2R_{10}$, C(O)$R_9$—N($R_9$)($R_{10}$), —O$R_{10}$, —N($R_9$)C(O)$R_3$, or —C(O)N($R_9$)($R_{10}$), $X_1$ is $C(R_5)$, $X_2$ is N, W is $C(R_6)$, and $R_1$ is —C(O)N($R_2$)($R_3$).

In one embodiment of the compounds of Formula I, A is $C_{3-8}$ cycloalkyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, and $R_1$ is —N($R_2$)C(O)$R_3$.

In one embodiment of the compounds of Formula I, A is $C_{4-8}$ cycloalkenyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, and $R_1$ is —N($R_2$)C(O)$R_3$.

In one embodiment of the compounds of Formula I, A is 6-membered heteroaryl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, and $R_1$ is —N($R_2$)C(O)$R_3$.

In one embodiment of the compounds of Formula I, A is $C_{2-6}$ alkynyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, and $R_1$ is —N($R_2$)C(O)$R_3$.

In one embodiment of the compounds of Formula I, A is aryl, B is heteroaryl optionally substituted with one or more $R_8$, $X_1$ is $C(R_5)$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_2$ is N, W is $C(R_6)$, and $R_1$ is —N($R_2$)C(O)$R_3$.

In one embodiment of the compounds of Formula I, A is heterocyclyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, and $R_1$ is —N($R_2$)C(O)$R_3$.

In one embodiment of the compounds of Formula I, A is $C_{3-8}$ cycloalkyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, and $R_1$ is —C(O)N($R_2$)($R_3$).

In one embodiment of the compounds of Formula I, A is $C_{4-8}$ cycloalkenyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, and $R_1$ is —C(O)N($R_2$)($R_3$).

In one embodiment of the compounds of Formula I, A is 6-membered heteroaryl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, and $R_1$ is —C(O)N($R_2$)($R_3$).

In one embodiment of the compounds of Formula I, A is $C_{2-6}$ alkynyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, and $R_1$ is —C(O)N($R_2$)($R_3$).

In one embodiment of the compounds of Formula I, A is aryl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, and $R_1$ is —C(O)N($R_2$)($R_3$).

In one embodiment of the compounds of Formula I, A is heterocyclyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, and $R_1$ is —C(O)N($R_2$)($R_3$).

In one embodiment of the compounds of Formula I, A is $C_{3-8}$ cycloalkyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is H, halogen, oxo, —OH, —NH$_2$, —NO$_2$, —C(O)N$(R_2)(R_{23})$, —(CH$_2$)$_o$—C(O)R$_{23}$, —OC(O)R$_{23}$, —C(O)OR$_{23}$, —SO$_2$R$_{23}$, or —N(R$_{23}$)C(O)—Ar—N(R$_{23}$)C(O)-G.

In one embodiment of the compounds of Formula I, A is $C_{4-8}$ cycloalkenyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is H, halogen, oxo, —OH, —NH$_2$, —NO$_2$, —C(O)N$(R_2)(R_{23})$, —(CH$_2$)$_o$—C(O)R$_{23}$, —OC(O)R$_{23}$, —C(O)OR$_{23}$, —SO$_2$R$_{23}$, or —N(R$_{23}$)C(O)—Ar—N(R$_{23}$)C(O)-G.

In one embodiment of the compounds of Formula I, A is 6-membered heteroaryl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is H, halogen, oxo, —OH, —NH$_2$, —NO$_2$, —C(O)N$(R_{21})(R_{23})$, —(CH$_2$)—C(O)R$_{23}$, —OC(O)R$_{23}$, —C(O)OR$_{23}$, —SO$_2$R$_{23}$, or —N(R$_{23}$)C(O)—Ar—N(R$_{23}$)C(O)-G.

In one embodiment of the compounds of Formula I, A is $C_{2-6}$ alkynyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is H, halogen, oxo, —OH, —NH$_2$, —NO$_2$, —C(O)N$(R_{21})(R_{23})$, —(CH$_2$)—C(O)R$_{23}$, —OC(O)R$_{23}$, —C(O)OR$_{23}$, —SO$_2$R$_{23}$, or —N(R$_{23}$)C(O)—Ar—N(R$_{23}$)C(O)-G.

In one embodiment of the compounds of Formula I, A is aryl, B is heteroaryl optionally substituted with one or more $R_8$, $X_1$ is $C(R_5)$, $R_5$ is $C_{1-6}$ alkyl, heterocyclyl, aryl, or heteroaryl, wherein the alkyl, heterocyclyl, aryl, or heteroaryl is optionally substituted with one or more $R_{15}$, $X_2$ is $C(R_5)$, W is $C(R_6)$, $R_1$ is —$N(R_2)C(O)R_3$, and $R_{15}$ is H, halogen, oxo, —OH, —NH$_2$, —NO$_2$, —C(O)N$(R_{21})(R_{23})$, —(CH$_2$)$_o$—C(O)R$_{23}$, —OC(O)R$_{23}$, —C(O)OR$_{23}$, —SO$_2$R$_{23}$, or —N(R$_{23}$)C(O)—Ar—N(R$_{23}$)C(O)-G.

In one embodiment of the compounds of Formula I, A is heterocyclyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is H, halogen, oxo, —OH, —NH$_2$, —NO$_2$, —C(O)N$(R_{21})(R_{23})$, —(CH$_2$)$_o$—C(O)R$_{23}$, —OC(O)R$_{23}$, —C(O)OR$_{23}$, —SO$_2$R$_{23}$, or —N(R$_{23}$)C(O)—Ar—N(R$_{23}$)C(O)-G.

In one embodiment of the compounds of Formula I, A is $C_{3-8}$ cycloalkyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is H, halogen, oxo, —OH, —NH$_2$, —NO$_2$, —C(O)N$(R_{21})(R_{23})$, —(CH$_2$)—C(O)R$_{23}$, —OC(O)R$_{23}$, —C(O)OR$_{23}$, —SO$_2$R$_{23}$, or —N(R$_{23}$)C(O)—Ar—N(R$_{23}$)C(O)-G.

In one embodiment of the compounds of Formula I, A is $C_{4-8}$ cycloalkenyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is H, halogen, oxo, —OH, —NH$_2$, —NO$_2$, —C(O)N$(R_{21})(R_{23})$, —(CH$_2$)$_o$—C(O)R$_{23}$, —OC(O)R$_{23}$, —C(O)OR$_{23}$, —SO$_2$R$_{23}$, or —N(R$_{23}$)C(O)—Ar—N(R$_{23}$)C(O)-G.

In one embodiment of the compounds of Formula I, A is 6-membered heteroaryl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is H, halogen, oxo, —OH, —NH$_2$, —NO$_2$, —C(O)N$(R_{21})(R_{23})$, —(CH$_2$)—C(O)R$_{23}$, —OC(O)R$_{23}$, —C(O)OR$_{23}$, —SO$_2$R$_{23}$, or —N(R$_{23}$)C(O)—Ar—N(R$_{23}$)C(O)-G.

In one embodiment of the compounds of Formula I, A is $C_{2-6}$ alkynyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is H, halogen, oxo, —OH, —NH$_2$, —NO$_2$, —C(O)N$(R_{21})(R_{23})$, —(CH$_2$)$_o$—C(O)R$_{23}$, —OC(O)R$_{23}$, —C(O)OR$_{23}$, —SO$_2$R$_{23}$, or —N(R$_{23}$)C(O)—Ar—N(R$_{23}$)C(O)-G.

In one embodiment of the compounds of Formula I, A is aryl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is H, halogen, oxo, —OH, —NH$_2$, —NO$_2$, —C(O)N$(R_{21})(R_{23})$, —(CH$_2$)$_o$—C(O)R$_{23}$, —OC(O)R$_{23}$, —C(O)OR$_{23}$, —SO$_2$R$_{23}$, or —N(R$_{23}$)C(O)—Ar—N(R$_{23}$)C(O)-G.

In one embodiment of the compounds of Formula I, A is $C_{3-8}$ cycloalkyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is H, halogen, oxo, —OH, —NH$_2$, —NO$_2$, —C(O)N$(R_{21})(R_{23})$, —(CH$_2$)—C(O)R$_{23}$, —OC(O)R$_{23}$, —C(O)OR$_{23}$, —SO$_2$R$_{23}$, or —N(R$_{23}$)C(O)—Ar—N(R$_{23}$)C(O)-G.

In one embodiment of the compounds of Formula I, A is $C_{4-8}$ cycloalkenyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is H, halogen, oxo, —OH, —NH$_2$, —NO$_2$, —C(O)N$(R_{21})(R_{23})$, —(CH$_2$)—C(O)R$_{23}$, —OC(O)R$_{23}$, —C(O)OR$_{23}$, —S$_2$R$_{23}$, or —N(R$_{23}$)C(O)—Ar—N(R$_{23}$)C(O)-G.

In one embodiment of the compounds of Formula I, A is 6-membered heteroaryl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is H, halogen, oxo, —OH, —NH$_2$, —NO$_2$, —C(O)N$(R_{21})(R_{23})$, —(CH$_2$)—C(O)R$_{23}$, —OC(O)R$_{23}$, —C(O)OR$_{23}$, —S$_2$R$_{23}$, or —N(R$_{23}$)C(O)—Ar—N(R$_{23}$)C(O)-G.

In one embodiment of the compounds of Formula I, A is $C_{2-6}$ alkynyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is H, halogen, oxo, —OH, —NH$_2$, —NO$_2$, —C(O)N$(R_{21})(R_{23})$, —(CH$_2$)—C(O)R$_{23}$, —OC(O)R$_{23}$, —C(O)OR$_{23}$, —SO$_2$R$_{23}$, or —N(R$_{23}$)C(O)—Ar—N(R$_{23}$)C(O)-G.

In one embodiment of the compounds of Formula I, A is aryl, B is heteroaryl optionally substituted with one or more $R_8$, $X_1$ is $C(R_5)$, $R_8$ is $C_{1-6}$ alkyl, heterocyclyl, or heteroaryl, wherein the alkyl, heterocyclyl, aryl, or heteroaryl is optionally substituted with one or more $R_{15}$, $X_2$ is N, W is $C(R_6)$, $R_1$ is —$N(R_2)C(O)R_3$, and $R_{15}$ is H, halogen, oxo, —OH, —$NH_2$, —$NO_2$, —$C(O)N(R_{21})(R_{23})$, —$(CH_2)_o$—$C(O)R_{23}$, —$OC(O)R_{23}$, —$C(O)OR_{23}$, —$SO_2R_{23}$, or —$N(R_{23})C(O)$—Ar—$N(R_{23})C(O)$-G.

In one embodiment of the compounds of Formula I, A is heterocyclyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is H, halogen, oxo, —OH, —$NH_2$, —$NO_2$, —$C(O)N(R_{21})(R_{23})$, —$(CH_2)$—$C(O)R_{23}$, —$OC(O)R_{23}$, —$C(O)OR_{23}$, —$SO_2R_{23}$, or —$N(R_{23})C(O)$—Ar—$N(R_{23})C(O)$-G.

In one embodiment of the compounds of Formula I, A is $C_{3-8}$ cycloalkyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is H, halogen, oxo, —OH, —$NH_2$, —$NO_2$, —$C(O)N(R_{21})(R_{23})$, —$(CH_2)$—$C(O)R_{23}$, —$OC(O)R_{23}$, —$C(O)OR_{23}$, —$SO_2R_{23}$, or —$N(R_{23})C(O)$—Ar—$N(R_{23})C(O)$-G.

In one embodiment of the compounds of Formula I, A is $C_{4-8}$ cycloalkenyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is H, halogen, oxo, —OH, —$NH_2$, —$NO_2$, —$C(O)N(R_2)(R_{23})$, —$(CH_2)_o$—$C(O)R_{23}$, —$OC(O)R_{23}$, —$C(O)OR_{23}$, —$SO_2R_{23}$, or —$N(R_{23})C(O)$—Ar—$N(R_{23})C(O)$-G.

In one embodiment of the compounds of Formula I, A is 6-membered heteroaryl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is H, halogen, oxo, —OH, —$NH_2$, —$NO_2$, —$C(O)N(R_{21})(R_{23})$, —$(CH_2)$—$C(O)R_{23}$, —$OC(O)R_{23}$, —$C(O)OR_{23}$, —$SO_2R_{23}$, or —$N(R_{23})C(O)$—Ar—$N(R_{23})C(O)$-G.

In one embodiment of the compounds of Formula I, A is $C_{2-6}$ alkynyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is H, halogen, oxo, —OH, —$NH_2$, —$NO_2$, —$C(O)N(R_{21})(R_{23})$, —$(CH_2)_o$—$C(O)R_{23}$, —$OC(O)R_{23}$, —$C(O)OR_{23}$, —$SO_2R_{23}$, or —$N(R_{23})C(O)$—Ar—$N(R_{23})C(O)$-G.

In one embodiment of the compounds of Formula I, A is aryl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is H, halogen, oxo, —OH, —$NH_2$, —$NO_2$, —$C(O)N(R_{21})(R_{23})$, —$(CH_2)_o$—$C(O)R_{23}$, —$OC(O)R_{23}$, —$C(O)OR_{23}$, —$SO_2R_{23}$, or —$N(R_{23})C(O)$—Ar—$N(R_{23})C(O)$-G.

In one embodiment of the compounds of Formula I, A is heterocyclyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is $C_{3-8}$ cycloalkyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is $C_{4-8}$ cycloalkenyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is 6-membered heteroaryl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is $C_{2-6}$ alkynyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is aryl, B is heteroaryl optionally substituted with one or more $R_8$, $X_1$ is $C(R_5)$, $R_5$ is $C_{1-6}$ alkyl, heterocyclyl, aryl, or heteroaryl, wherein the alkyl, heterocyclyl, aryl, or heteroaryl is optionally substituted with one or more $R_{15}$, $X_2$ is $C(R_5)$, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is heterocyclyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is $C_{3-8}$ cycloalkyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is $C_{4-8}$ cycloalkenyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is 6-membered heteroaryl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is $C_{2-6}$ alkynyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is aryl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is heterocyclyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is $C(R_5)$, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is heterocyclyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is $C_{3-8}$ cycloalkyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is $C_{4-8}$ cycloalkenyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is 6-membered heteroaryl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is $C_{2-6}$ alkynyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is aryl, B is heteroaryl optionally substituted with one or more $R_8$, $X_1$ is $C(R_5)$, $R_5$ is $C_{1-6}$ alkyl, heterocyclyl, aryl, or heteroaryl, wherein the alkyl, heterocyclyl, aryl, or heteroaryl is optionally substituted with one or more $R_{15}$, $X_2$ is N, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is heterocyclyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is $C_{3-8}$ cycloalkyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is $C_{4-8}$ cycloalkenyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is 6-membered heteroaryl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is $C_{2-6}$ alkynyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is aryl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is heterocyclyl, B is heteroaryl optionally substituted with one or more $R_8$, $R_8$ is $C_{1-6}$ alkyl, heterocyclyl, aryl, or heteroaryl, wherein the alkyl, heterocyclyl, aryl, or heteroaryl is optionally substituted with one or more $R_{15}$, $X_1$ is $C(R_5)$, $X_2$ is N, W is $C(R_6)$, $R_1$ is —$N(R_2)C(O)R_3$, and $R_{15}$ is $C_{1-6}$ alkyl, $C_{1-6}$ alkoxy, $C_{3-8}$ cycloalkyl, heterocyclyl, aryl, or heteroaryl, wherein the alkyl, alkoxy, cycloalkyl, heterocyclyl, heteroaryl, or aryl is optionally substituted with one or more $R_{23}$.

In one embodiment of the compounds of Formula I, A is $C_{3-8}$ cycloalkyl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is $C(R_5)$, W is $C(R_6)$, and $R_1$ is —$N(R_2)C(O)R_3$.

In one embodiment of the compounds of Formula I, A is $C_{4-8}$ cycloalkenyl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is $C(R_5)$, W is $C(R_6)$, and $R_1$ is —$N(R_2)C(O)R_3$.

In one embodiment of the compounds of Formula I, A is 6-membered heteroaryl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is $C(R_5)$, W is $C(R_6)$, and $R_1$ is —$N(R_2)C(O)R_3$.

In one embodiment of the compounds of Formula I, A is $C_{2-6}$ alkynyl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is $C(R_5)$, W is $C(R_6)$, and $R_1$ is —$N(R_2)C(O)R_3$.

In one embodiment of the compounds of Formula I, A is aryl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is $C(R_5)$, W is $C(R_6)$, and $R_1$ is —$N(R_2)C(O)R_3$.

In one embodiment of the compounds of Formula I, A is heterocyclyl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is $C(R_5)$, W is $C(R_6)$, and $R_1$ is —$N(R_2)C(O)R_3$.

In one embodiment of the compounds of Formula I, A is $C_{3-8}$ cycloalkyl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is $C(R_5)$, W is $C(R_6)$, and $R_1$ is —$C(O)N(R_2)(R_3)$.

In one embodiment of the compounds of Formula I, A is $C_{4-8}$ cycloalkenyl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is $C(R_5)$, W is $C(R_6)$, and $R_1$ is —$C(O)N(R_2)(R_3)$.

In one embodiment of the compounds of Formula I, A is 6-membered heteroaryl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is $C(R_5)$, W is $C(R_6)$, and $R_1$ is —$C(O)N(R_2)(R_3)$.

In one embodiment of the compounds of Formula I, A is $C_{2-6}$ alkynyl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is $C(R_5)$, W is $C(R_6)$, and $R_1$ is —C(O)N($R_2$)($R_3$).

In one embodiment of the compounds of Formula I, A is aryl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is $C(R_5)$, W is $C(R_6)$, and $R_1$ is —C(O)N($R_2$)($R_3$).

In one embodiment of the compounds of Formula I, A is heterocyclyl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is $C(R_5)$, W is $C(R_6)$, and $R_1$ is —C(O)N($R_2$)($R_3$).

In one embodiment of the compounds of Formula I, A is $C_{3-8}$ cycloalkyl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is N, W is $C(R_6)$, and $R_1$ is —N($R_2$)C(O)$R_3$.

In one embodiment of the compounds of Formula I, A is $C_{4-8}$ cycloalkenyl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is N, W is $C(R_6)$, and $R_1$ is —N($R_2$)C(O)$R_3$.

In one embodiment of the compounds of Formula I, A is 6-membered heteroaryl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is N, W is $C(R_6)$, and $R_1$ is —N($R_2$)C(O)$R_3$.

In one embodiment of the compounds of Formula I, A is $C_{2-6}$ alkynyl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is N, W is $C(R_6)$, and $R_1$ is —N($R_2$)C(O)$R_3$.

In one embodiment of the compounds of Formula I, A is aryl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is N, W is $C(R_6)$, and $R_1$ is —N($R_2$)C(O)$R_3$.

In one embodiment of the compounds of Formula I, A is heterocyclyl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is N, W is $C(R_6)$, and $R_1$ is —N($R_2$)C(O)$R_3$.

In one embodiment of the compounds of Formula I, A is $C_{3-8}$ cycloalkyl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is N, W is $C(R_6)$, and $R_1$ is —C(O)N($R_2$)($R_3$).

In one embodiment of the compounds of Formula I, A is $C_{4-8}$ cycloalkenyl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is N, W is $C(R_6)$, and $R_1$ is —C(O)N($R_2$)($R_3$).

In one embodiment of the compounds of Formula I, A is 6-membered heteroaryl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is N, W is $C(R_6)$, and $R_1$ is —C(O)N($R_2$)($R_3$).

In one embodiment of the compounds of Formula I, A is $C_{2-6}$ alkynyl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is N, W is $C(R_6)$, and $R_1$ is —C(O)N($R_2$)($R_3$).

In one embodiment of the compounds of Formula I, A is aryl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is N, W is $C(R_6)$, and $R_1$ is —C(O)N($R_2$)($R_3$).

In one embodiment of the compounds of Formula I, A is heterocyclyl, B is heteroaryl optionally substituted with two or more $R_8$, wherein two $R_8$ groups, together with the atoms to which they are attached, form a $C_{3-6}$ cycloalkyl, $C_{5-6}$ spirocycloalkyl, spiroheterocycloalkyl, heterocyclyl, aryl, or heteroaryl, wherein the cycloalkyl, spirocycloalkyl, spiroheterocycloalkyl, or heterocyclyl, is optionally substituted with one or more $R_{15}$, $X_1$ is $C(R_5)$, $X_2$ is N, W is $C(R_6)$, and $R_1$ is —C(O)N($R_2$)($R_3$).

Non-limiting illustrative compounds of the present disclosure include:

N,N-dimethyl-4-(6-(pyridin-3-ylamino)pyridin-3-yl)benzamide,
4-(6-((5-(3-benzyl-2-oxoimidazolidin-1-yl)pyridin-3-yl)amino)pyridin-3-yl)-N,N-dimethylbenzamide,
1-(4-(6-(pyridin-3-ylamino)pyridin-3-yl)phenyl)pyrrolidin-2-one,
N,N-dimethyl-4-(6-((5-(2-oxopyrrolidin-1-yl)pyridin-3-yl)amino)pyridin-3-yl)benzamide,
N,N-dimethyl-4-(6-((5-(N-methylmethylsulfonamido)pyridin-3-yl)amino)pyridin-3-yl)benzamide,
4-(6-((5-(1-cyanocyclopropyl)pyridin-3-yl)amino)pyridin-3-yl)-N,N-dimethylbenzamide,
N,N-dimethyl-4-(6-((1-(methylsulfonyl)-1H-pyrrolo[3,2-b]pyridin-6-yl)amino)pyridin-3-yl)benzamide,
N,N-dimethyl-4-(6-((1-(methylsulfonyl)-2,3-dihydro-1H-pyrido[2,3-b][1,4]oxazin-7-yl)amino)pyridin-3-yl)benzamide,
N,N-dimethyl-4-(6-((5-(2-oxo-3-(pyridin-3-ylmethyl)imidazolidin-1-yl)pyridin-3-yl)amino)pyridin-3-yl)benzamide,
4-(5-((5-(3-benzyl-2-oxoimidazolidin-1-yl)pyridin-3-yl)amino)pyrazin-2-yl)-N,N-dimethylbenzamide,
N,N-dimethyl-4-(5-((5-(2-oxopyrrolidin-1-yl)pyridin-3-yl)amino)pyrazin-2-yl)benzamide azetidin-1-yl(4-(6-(pyridin-3-ylamino)pyridin-3-yl)phenyl)methanone,
4-(6-((5-(N-cyclopropylmethylsulfonamido)pyridin-3-yl)amino)pyridin-3-yl)-N,N-dimethylbenzamide,
N,N-dimethyl-4-(6-((5-(2-oxo-3-(thiazol-4-ylmethyl)imidazolidin-1-yl)pyridin-3-yl)amino)pyridin-3-yl)benzamide,
4-(6-((1-acetyl-2,3-dihydro-1H-pyrido[2,3-b][1,4]oxazin-7-yl)amino)pyridin-3-yl)-N,N-dimethylbenzamide,
4-(6-((5-(3-(4-methoxybenzyl)-2-oxoimidazolidin-1-yl)pyridin-3-yl)amino)pyridin-3-yl)-N,N-dimethylbenzamide,
N,N-dimethyl-4-(6-((5-(2-oxo-3-((tetrahydrofuran-2-yl)methyl)imidazolidin-1-yl)pyridin-3-yl)amino)pyridin-3-yl)benzamide,
N,N-dimethyl-4-(6-((5-(N-methyl-2-phenylcyclopropane-1-carboxamido)pyridin-3-yl)amino)pyridin-3-yl)benzamide,
N,N-dimethyl-4-(6-((5-(2-oxoimidazolidin-1-yl)pyridin-3-yl)amino)pyridin-3-yl)benzamide,
N,N-dimethyl-4-(6-((5-(N-methylpropan-2-ylsulfonamido)pyridin-3-yl)amino)pyridin-3-yl)benzamide,
N,N-dimethyl-4-(6-((5-(N-methylcyclopropanesulfonamido)pyridin-3-yl)amino)pyridin-3-yl)benzamide,
4-(6-((5-acetamidopyridin-3-yl)amino)pyridin-3-yl)-N,N-dimethylbenzamide,
2-fluoro-N,N-dimethyl-4-(6-((5-(2-oxopyrrolidin-1-yl)pyridin-3-yl)amino)pyridin-3-yl)benzamide,
N,N-dimethyl-4-(6-((5-(3-methyl-2-oxoimidazolidin-1-yl)pyridin-3-yl)amino)pyridin-3-yl)benzamide,
3-fluoro-N,N-dimethyl-4-(6-((5-(2-oxopyrrolidin-1-yl)pyridin-3-yl)amino)pyridin-3-yl)benzamide,
N,N-dimethyl-4-(6-((5-(2-oxo-2-((pyridin-3-ylmethyl)amino)ethyl)pyridin-3-yl)amino)pyridin-3-yl)benzamide,
(S)-4-(6-((5-(4-isopropyl-2,5-dioxoimidazolidin-1-yl)pyridin-3-yl)amino)pyridin-3-yl)-N,N-dimethylbenzamide,
2,5-difluoro-N,N-dimethyl-4-(6-((5-(2-oxopyrrolidin-1-yl)pyridin-3-yl)amino)pyridin-3-yl)benzamide,
N-(furan-2-ylmethyl)-N-methyl-4-(6-(pyridin-3-ylamino)pyridin-3-yl)benzamide,
N,N-dimethyl-4-(6-((5-(3-oxomorpholino)pyridin-3-yl)amino)pyridin-3-yl)benzamide,
4-(6-((5-(2-(dimethylamino)-2-oxoethyl)pyridin-3-yl)amino)pyridin-3-yl)-N,N-dimethylbenzamide,
4-(6-((2-methoxypyrimidin-5-yl)amino)pyridin-3-yl)-N,N-dimethylbenzamide,
N,N-dimethyl-4-(4-methyl-6-(pyridin-3-ylamino)pyridin-3-yl)benzamide,
4-(6-((5-(N-isopropylmethylsulfonamido)pyridin-3-yl)amino)pyridin-3-yl)-N,N-dimethylbenzamide,
4-(6-((5-(1-carbamoylcyclopropyl)pyridin-3-yl)amino)pyridin-3-yl)-N,N-dimethylbenzamide,
4-(6-((5-methoxypyridin-3-yl)amino)pyridin-3-yl)-N,N-dimethylbenzamide,
N-ethyl-N-methyl-4-(6-(pyridin-3-ylamino)pyridin-3-yl)benzamide,
5-(4-(4-methyl-4H-1,2,4-triazol-3-yl)phenyl)-N-(pyridin-3-yl)pyridin-2-amine,
N,N-dimethyl-4-(6-(pyrimidin-5-ylamino)pyridin-3-yl)benzamide,
4-(6-((5-cyanopyridin-3-yl)amino)pyridin-3-yl)-N,N-dimethylbenzamide,
N-benzyl-N-methyl-4-(6-(pyridin-3-ylamino)pyridin-3-yl)benzamide,
N,N-dimethyl-4-(6-(pyridin-3-ylamino)pyridin-3-yl)benzenesulfonamide,
N,N,2-trimethyl-4-(6-(pyridin-3-ylamino)pyridin-3-yl)benzamide,
(4-(6-(pyridin-3-ylamino)pyridin-3-yl)phenyl)(pyrrolidin-1-yl)methanone,
N,N-dimethyl-4-(6-((2-methylpyrimidin-5-yl)amino)pyridin-3-yl)benzamide,
N,N-dimethyl-6'-(pyridin-3-ylamino)-[3,3'-bipyridine]-6-carboxamide,
4-(6-((1-benzyl-6-oxo-1,6-dihydropyridin-3-yl)amino)pyridin-3-yl)-N,N-dimethylbenzamide,
N,N-dimethyl-4-(6-((2-methylpyridin-3-yl)amino)pyridin-3-yl)benzamide,
N,N-dimethyl-6'-(pyridin-3-ylamino)-[2,3'-bipyridine]-5-carboxamide,
5-((5-(4-(dimethylcarbamoyl)phenyl)pyridin-2-yl)amino)-N,N-dimethylnicotinamide,
N,N-dimethyl-4-(6-(pyridin-3-ylamino)pyridin-3-yl)cyclohex-3-ene-1-carboxamide,
N,N-dimethyl-4-(6-(pyrazin-2-ylamino)pyridin-3-yl)benzamide,
N-methyl-4-(6-((5-(2-oxopyrrolidin-1-yl)pyridin-3-yl)amino)pyridin-3-yl)benzamide,
(1r,4r)-N,N-dimethyl-4-(6-(pyridin-3-ylamino)pyridin-3-yl)cyclohexane-1-carboxamide,
N,N,3-trimethyl-4-(6-(pyridin-3-ylamino)pyridin-3-yl)benzamide,
N-methyl-N-(4-(6-(pyridin-3-ylamino)pyridin-3-yl)phenyl)acetamide,
N-methyl-4-(6-(pyridin-3-ylamino)pyridin-3-yl)-N-(pyridin-3-ylmethyl)benzamide,
N,N-dimethyl-5-(6-(pyridin-3-ylamino)pyridin-3-yl)thiophene-2-carboxamide,
4-(6-acetamidopyridin-3-yl)-N,N-dimethylbenzamide,
N,N-dimethyl-3-(6-(pyridin-3-ylamino)pyridin-3-yl)propiolamide,
(1s,4s)-N,N-dimethyl-4-(6-(pyridin-3-ylamino)pyridin-3-yl)cyclohexane-1-carboxamide,
N,N-dimethyl-4-(6-((2-oxo-1,2-dihydropyridin-4-yl)amino)pyridin-3-yl)benzamide,
2-fluoro-N,N-dimethyl-4-(5-((5-(2-oxopyrrolidin-1-yl)pyridin-3-yl)amino)pyrazin-2-yl)benzamide, 3-fluoro-N,N-dimethyl-4-(5-((5-(2-oxopyrrolidin-1-yl)pyridin-3-yl)amino)pyrazin-2-yl)benzamide,
N,N-dimethyl-4-(5-(pyridin-3-ylamino)pyrazin-2-yl)benzamide,
2,5-difluoro-N,N-dimethyl-4-(5-((5-(2-oxopyrrolidin-1-yl)pyridin-3-yl)amino)pyrazin-2-yl)benzamide,
N,N-dimethyl-4-(6-((6-morpholinopyridin-3-yl)amino)pyridin-3-yl)benzamide,
4-(6-((1-acetyl-4-methyl-1,2,3,4-tetrahydropyrido[2,3-b]pyrazin-7-yl)amino)pyridin-3-yl)-N,N-dimethylbenzamide,
4-(6-((2,3-dihydro-1H-pyrido[2,3-b][1,4]oxazin-7-yl)amino)pyridin-3-yl)-N,N-dimethylbenzamide,
tert-butyl 7-((5-(4-(dimethylcarbamoyl)phenyl)pyridin-2-yl)amino)-2,3-dihydro-1H-pyrido[2,3-b][1,4]oxazine-1-carboxylate,
N,N-dimethyl-4-(6-((5-(1-oxoisoindolin-2-yl)pyridin-3-yl)amino)pyridin-3-yl)benzamide,
(R)—N,N-dimethyl-4-(6-((5-(2-oxo-3-(1-phenylethyl)imidazolidin-1-yl)pyridin-3-yl)amino)pyridin-3-yl)benzamide,
(S)—N,N-dimethyl-4-(6-((5-(2-oxo-3-(1-phenylethyl)imidazolidin-1-yl)pyridin-3-yl)amino)pyridin-3-yl)benzamide,
4-(4-ethyl-6-(pyridin-3-ylamino)pyridin-3-yl)-N,N-dimethylbenzamide,
4-(6-((5-(3-(cyclopropylmethyl)-2-oxoimidazolidin-1-yl)pyridin-3-yl)amino)pyridin-3-yl)-N,N-dimethylbenzamide,
4-(6-((1-benzoyl-2,3-dihydro-1H-pyrido[2,3-b][1,4]oxazin-7-yl)amino)pyridin-3-yl)-N,N-dimethylbenzamide,
(E)-4-(6-((5-(3-(4-(dimethylamino)but-2-enamido)benzamido)pyridin-3-yl)amino)pyridin-3-yl)-N,N-dimethylbenzamide,
4-(6-((5-(3-aminobenzamido)pyridin-3-yl)amino)pyridin-3-yl)-N,N-dimethylbenzamide,
tert-butyl (3-(3-((5-((5-(4-(dimethylcarbamoyl)phenyl)pyridin-2-yl)amino)pyridin-3-yl)amino)-3-oxopropyl)phenyl)carbamate,
4-(6-((5-(3-(3-aminophenyl)propanamido)pyridin-3-yl)amino)pyridin-3-yl)-N,N-dimethylbenzamide,
(E)-4-(6-((5-(3-(3-(4-(dimethylamino)but-2-enamido)phenyl)propanamido)pyridin-3-yl)amino)pyridin-3-yl)-N,N-dimethylbenzamide,
tert-butyl (3-((5-((5-(4-(dimethylcarbamoyl)phenyl)pyridin-2-yl)amino)pyridin-3-yl)carbamoyl)phenyl)carbamate,
N,N-dimethyl-4-(6-((1-picolinoyl-2,3-dihydro-1H-pyrido[2,3-b][1,4]oxazin-7-yl)amino)pyridin-3-yl)benzamide,
tert-butyl (3-(((5-((5-(4-(dimethylcarbamoyl)phenyl)pyridin-2-yl)amino)pyridin-2-yl)methyl)carbamoyl)phenyl)carbamate,
(E)-4-(6-((6-((3-(4-(dimethylamino)but-2-enamido)benzamido)methyl)pyridin-3-yl)amino)pyridin-3-yl)-N,N-dimethylbenzamide,
N,N-dimethyl-4-(6-((1-pivaloyl-2,3-dihydro-1H-pyrido[2,3-b][1,4]oxazin-7-yl)amino)pyridin-3-yl)benzamide,
4-(6-((1-(cyclopropanecarbonyl)-2,3-dihydro-1H-pyrido[2,3-b][1,4]oxazin-7-yl)amino)pyridin-3-yl)-N,N-dimethylbenzamide,
methyl 7-((5-(4-(dimethylcarbamoyl)phenyl)pyridin-2-yl)amino)-2,3-dihydro-1H-pyrido[2,3-b][1,4]oxazine-1-carboxylate,
N-methyl-4-(6-(pyridin-3-ylamino)pyridin-3-yl)-N-(thiazol-5-ylmethyl)benzamide,
1-(4-(6-((2,3-dihydro-[1,4]dioxino[2,3-b]pyridin-7-yl)amino)pyridin-3-yl)phenyl)pyrrolidin-2-one,
(R)-2-((5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one,
4-(6-((3,4-dihydro-2H-pyrano[2,3-b]pyridin-6-yl)amino)pyridin-3-yl)-N,N-dimethylbenzamide,
N,N-dimethyl-4-(6-((6-(2-morpholinoethyl)pyridin-3-yl)amino)pyridin-3-yl)benzamide,
4-(6-((2,3-dihydro-[1,4]dioxino[2,3-b]pyridin-7-yl)amino)pyridin-3-yl)-N,N-dimethylbenzamide,
4-(6-((5-(difluoromethoxy)pyridin-3-yl)amino)pyridin-3-yl)-N,N-dimethylbenzamide,
1-(4-(6-((1-acetyl-2,3-dihydro-1H-pyrido[2,3-b][1,4]oxazin-7-yl)amino)pyridin-3-yl)phenyl)pyrrolidin-2-one,
N,N-dimethyl-4-(6-((5-(2-morpholinoethyl)pyridin-3-yl)amino)pyridin-3-yl)benzamide,
4-(6-((1-(2-hydroxyacetyl)-2,3-dihydro-1H-pyrido[2,3-b][1,4]oxazin-7-yl)amino)pyridin-3-yl)-N,N-dimethylbenzamide,
N,N-dimethyl-4-(6-((2-oxo-2,3-dihydro-1H-pyrido[2,3-b][1,4]oxazin-7-yl)amino)pyridin-3-yl)benzamide,
4-(6-((5-aminopyridin-3-yl)amino)pyridin-3-yl)-N,N-dimethylbenzamide,
4-(6-((1-(2-hydroxypropanoyl)-2,3-dihydro-1H-pyrido[2,3-b][1,4]oxazin-7-yl)amino)pyridin-3-yl)-N,N-dimethylbenzamide,
1-(7-((5-(4-(dimethylcarbamoyl)phenyl)pyridin-2-yl)amino)-2,3-dihydro-1H-pyrido[2,3-b][1,4]oxazin-1-yl)-1-oxopropan-2-yl acetate,
4-(6-((1-(3-hydroxy-2,2-dimethylpropanoyl)-2,3-dihydro-1H-pyrido[2,3-b][1,4]oxazin-7-yl)amino)pyridin-3-yl)-N,N-dimethylbenzamide,
4-(6-((5-(3-(4-aminobenzyl)-2-oxoimidazolidin-1-yl)pyridin-3-yl)amino)pyridin-3-yl)-N,N-dimethylbenzamide,
4-(6-((5-(3-(3-aminobenzyl)-2-oxoimidazolidin-1-yl)pyridin-3-yl)amino)pyridin-3-yl)-N,N-dimethylbenzamide,
4-(6-((5-(3-(3-(3-aminophenyl)propanamido)benzyl)-2-oxoimidazolidin-1-yl)pyridin-3-yl)amino)pyridin-3-yl)-N,N-dimethylbenzamide,
(E)-4-(6-((5-(3-(3-(3-(4-(dimethylamino)but-2-enamido)phenyl)propanamido)benzyl)-2-oxoimidazolidin-1-yl)pyridin-3-yl)amino)pyridin-3-yl)-N,N-dimethylbenzamide,
4-(6-((5-(3-(3-(2-aminoacetamido)benzyl)-2-oxoimidazolidin-1-yl)pyridin-3-yl)amino)pyridin-3-yl)-N,N-dimethylbenzamide,
4-(6-((5-(3-(3-(2-(2-aminoethoxy)ethoxy)propanamido)benzamido)pyridin-3-yl)amino)pyridin-3-yl)-N,N-dimethylbenzamide,
(E)-N,N-dimethyl-4-(6-((5-(3-(2-methyl-6-oxo-10,13-dioxa-2,7-diazahexadec-4-en-16-amido)benzamido)pyridin-3-yl)amino)pyridin-3-yl)benzamide,
(E)-4-(6-((5-(3-(3-(2-(4-(dimethylamino)but-2-enamido)acetamido)benzyl)-2-oxoimidazolidin-1-yl)pyridin-3-yl)amino)pyridin-3-yl)-N,N-dimethylbenzamide,
N,N-dimethyl-4-(6-((2-methyloxazolo[4,5-b]pyridin-6-yl)amino)pyridin-3-yl)benzamide,
4-(6-([1,3]dioxolo[4,5-b]pyridin-6-ylamino)pyridin-3-yl)-N,N-dimethylbenzamide,
4-(6-((5-(4-aminobenzamido)pyridin-3-yl)amino)pyridin-3-yl)-N,N-dimethylbenzamide,
(E)-4-(6-((5-(4-(4-(dimethylamino)but-2-enamido)benzamido)pyridin-3-yl)amino)pyridin-3-yl)-N,N-dimethylbenzamide,
4-(6-((5-(3-(4-aminophenyl)propanamido)pyridin-3-yl)amino)pyridin-3-yl)-N,N-dimethylbenzamide, (E)-4-(6-((5-(3-(4-(4-(dimethylamino)but-2-enamido)phenyl)propanamido)pyridin-3-yl)amino)pyridin-3-yl)-N,N-dimethylbenzamide,
4-(6-((5-(3-(4-(2-aminoacetamido)benzyl)-2-oxoimidazolidin-1-yl)pyridin-3-yl)amino)pyridin-3-yl)-N,N-dimethylbenzamide,
(E)-4-(6-((5-(3-(4-(2-(4-(dimethylamino)but-2-enamido)acetamido)benzyl)-2-oxoimidazolidin-1-yl)pyridin-3-yl)amino)pyridin-3-yl)-N,N-dimethylbenzamide,
N-(3-(3-((5-((5-(4-(dimethylcarbamoyl)phenyl)pyridin-2-yl)amino)pyridin-3-yl)amino)-3-oxopropyl)phenyl)piperidine-4-carboxamide,
4-(6-((5-(3-(3-(6-aminohexanamido)phenyl)propanamido)pyridin-3-yl)amino)pyridin-3-yl)-N,N-dimethylbenzamide,
4-(6-((5-(3-(4-(3-(3-aminophenyl)propanamido)benzyl)-2-oxoimidazolidin-1-yl)pyridin-3-yl)amino)pyridin-3-yl)-N,N-dimethylbenzamide,
(E)-4-(6-((5-(3-(4-(3-(3-(4-(dimethylamino)but-2-enamido)phenyl)propanamido)benzyl)-2-oxoimidazolidin-1-yl)pyridin-3-yl)amino)pyridin-3-yl)-N,N-dimethylbenzamide,
4-(6-((5-(4-fluorobenzamido)pyridin-3-yl)amino)pyridin-3-yl)-N,N-dimethylbenzamide,
4-(6-((5-(3-fluorobenzamido)pyridin-3-yl)amino)pyridin-3-yl)-N,N-dimethylbenzamide,
4-(6-((5-(3-(3-(2-aminoacetamido)phenyl)propanamido)pyridin-3-yl)amino)pyridin-3-yl)-N,N-dimethylbenzamide,
4-(6-((5-benzamidopyridin-3-yl)amino)pyridin-3-yl)-N,N-dimethylbenzamide,
4-(6-((5-(2-cyanoacetamido)pyridin-3-yl)amino)pyridin-3-yl)-N,N-dimethylbenzamide,
N,N-dimethyl-4-(6-((5-(2-phenylacetamido)pyridin-3-yl)amino)pyridin-3-yl)benzamide,
4-(6-((5-(2-(dimethylamino)acetamido)pyridin-3-yl)amino)pyridin-3-yl)-N,N-dimethylbenzamide,
N-(5-((5-(4-(dimethylcarbamoyl)phenyl)pyridin-2-yl)amino)pyridin-3-yl)picolinamide,
N-(5-((5-(4-(dimethylcarbamoyl)phenyl)pyridin-2-yl)amino)pyridin-3-yl)isonicotinamide,
N-(5-((5-(4-(dimethylcarbamoyl)phenyl)pyridin-2-yl)amino)pyridin-3-yl)-1H-indole-6-carboxamide,
N-(5-((5-(4-(dimethylcarbamoyl)phenyl)pyridin-2-yl)amino)pyridin-3-yl)benzo[d]oxazole-6-carboxamide,
N,N-dimethyl-4-(6-((5-(3-phenylpropanamido)pyridin-3-yl)amino)pyridin-3-yl)benzamide,
N,N-dimethyl-4-(6-((5-(2-phenylcyclopropane-1-carboxamido)pyridin-3-yl)amino)pyridin-3-yl)benzamide,
4-(6-((5-(3-methoxybenzamido)pyridin-3-yl)amino)pyridin-3-yl)-N,N-dimethylbenzamide,
4-(6-((5-(4-methoxybenzamido)pyridin-3-yl)amino)pyridin-3-yl)-N,N-dimethylbenzamide,
N-(5-((5-(4-(dimethylcarbamoyl)phenyl)pyridin-2-yl)amino)pyridin-3-yl)-1H-indole-4-carboxamide,
N-(5-((5-(4-(dimethylcarbamoyl)phenyl)pyridin-2-yl)amino)pyridin-3-yl)tetrahydro-2H-pyran-4-carboxamide,
methyl (5-((5-(4-(dimethylcarbamoyl)phenyl)pyridin-2-yl)amino)pyridin-3-yl)carbamate,
N-(5-((5-(4-(dimethylcarbamoyl)phenyl)pyridin-2-yl)amino)pyridin-3-yl)nicotinamide,
N-(5-((5-(4-(dimethylcarbamoyl)phenyl)pyridin-2-yl)amino)pyridin-3-yl)-1H-benzo[d]imidazole-7-carboxamide,
(E)-4-(6-((5-(3-(3-(6-(4-(dimethylamino)but-2-enamido)hexanamido)phenyl)propanamido)pyridin-3-yl)amino)pyridin-3-yl)-N,N-dimethylbenzamide,
N,N-dimethyl-4-(6-((5-(3-methylureido)pyridin-3-yl)amino)pyridin-3-yl)benzamide,
2-amino-N-(5-((5-(4-(dimethylcarbamoyl)phenyl)pyridin-2-yl)amino)pyridin-3-yl)isonicotinamide,
(E)-4-(6-((5-(3-(2-(4-(dimethylamino)but-2-enamido)acetamido)phenyl)propanamido)pyridin-3-yl)amino)pyridin-3-yl)-N,N-dimethylbenzamide,
(E)-1-(4-(dimethylamino)but-2-enoyl)-N-(3-(3-((5-((5-(4-(dimethylcarbamoyl)phenyl)pyridin-2-yl)amino)pyridin-3-yl)amino)-3-oxopropyl)phenyl)piperidine-4-carboxamide,
N,N-dimethyl-3-((5-(4-(2-oxopyrrolidin-1-yl)phenyl)pyridin-2-yl)amino)quinoline-5-carboxamide,
1-(4-(6-((1-pivaloyl-2,3-dihydro-1H-pyrido[2,3-b][1,4]oxazin-7-yl)amino)pyridin-3-yl)phenyl)pyrrolidin-2-one,
N-methyl-N-(5-((5-(4-(2-oxopyrrolidin-1-yl)phenyl)pyridin-2-yl)amino)pyridin-3-yl)methanesulfonamide,
N-(5-((5-(4-(dimethylcarbamoyl)phenyl)pyridin-2-yl)amino)pyridin-3-yl)-1-hydroxy-1,3-dihydrobenzo[c][1,2]oxaborole-6-carboxamide,
N-methyl-3-((5-(4-(2-oxopyrrolidin-1-yl)phenyl)pyridin-2-yl)amino)quinoline-5-carboxamide,
1-(4-(6-((5-(pyrrolidine-1-carbonyl)quinolin-3-yl)amino)pyridin-3-yl)phenyl)pyrrolidin-2-one
1-(4-(6-((5-(3-hydroxypyrrolidine-1-carbonyl)quinolin-3-yl)amino)pyridin-3-yl)phenyl)pyrrolidin-2-one,
N,N-dimethyl-2-(6-(pyridin-3-ylamino)pyridin-3-yl)pyrimidine-5-carboxamide,
1-(4-(6-((1-(1-hydroxycyclopropane-1-carbonyl)-2,3-dihydro-H-pyrido[2,3-b][1,4]oxazin-7-yl)amino)pyridin-3-yl)phenyl)pyrrolidin-2-one,
N,N-dimethyl-4-(6-((5-(methylsulfonamido)pyridin-3-yl)amino)pyridin-3-yl)benzamide,
N-(5-((5-(4-(dimethylcarbamoyl)phenyl)pyridin-2-yl)amino)pyridin-3-yl)-1-hydroxy-1,3-dihydrobenzo[c][1,2]oxaborole-5-carboxamide,
4-(6-((5-(3-(3-aminobenzyl)-2-oxopyrrolidin-1-yl)pyridin-3-yl)amino)pyridin-3-yl)-N,N-dimethylbenzamide,
1-(4-(6-((1-isobutyryl-2,3-dihydro-1H-pyrido[2,3-b][1,4]oxazin-7-yl)amino)pyridin-3-yl)phenyl)pyrrolidin-2-one,
1-(4-(6-((1-(methylsulfonyl)-2,3-dihydro-1H-pyrido[2,3-b][1,4]oxazin-7-yl)amino)pyridin-3-yl)phenyl)pyrrolidin-2-one,
N-(2-methoxy-5-((5-(4-(2-oxopyrrolidin-1-yl)phenyl)pyridin-2-yl)amino)pyridin-3-yl)acetamide,
N-(2-methoxy-5-((5-(4-(2-oxopyrrolidin-1-yl)phenyl)pyridin-2-yl)amino)pyridin-3-yl)-N-methylmethanesulfonamide,
1-(5-((5-(4-(2-oxopyrrolidin-1-yl)phenyl)pyridin-2-yl)amino)pyridin-3-yl)-3-(thiazol-4-ylmethyl)imidazolidin-2-one,
1-(5-((5-(4-(2-oxopyrrolidin-1-yl)phenyl)pyrazin-2-yl)amino)pyridin-3-yl)-3-(thiazol-4-ylmethyl)imidazolidin-2-one,
methyl 7-((5-(4-(2-oxopyrrolidin-1-yl)phenyl)pyridin-2-yl)amino)-2,3-dihydro-1H-pyrido[2,3-b][1,4]oxazine-1-carboxylate,
1-(4-(6-((1-(cyclopropylsulfonyl)-2,3-dihydro-1H-pyrido[2,3-b][1,4]oxazin-7-yl)amino)pyridin-3-yl)phenyl)pyrrolidin-2-one,
N-(2-methoxy-5-((5-(4-(2-oxopyrrolidin-1-yl)phenyl)pyridin-2-yl)amino)pyridin-3-yl)methanesulfonamide,
N-(2-methoxy-5-((5-(4-(2-oxopyrrolidin-1-yl)phenyl)pyridin-2-yl)amino)pyridin-3-yl)-N-methylacetamide,
1-(4-(6-((1-(2-hydroxypropanoyl)-2,3-dihydro-1H-pyrido[2,3-b][1,4]oxazin-7-yl)amino)pyridin-3-yl)phenyl)pyrrolidin-2-one, 1-(4-(6-((1-(2-hydroxyacetyl)-2,3-dihydro-1H-pyrido[2,3-b][1,4]oxazin-7-yl)amino)pyridin-3-yl)phenyl)pyrrolidin-2-one, 1-(4-(6-((1-(cyclopropanecarbonyl)-2,3-dihydro-1H-pyrido[2,3-b][1,4]oxazin-7-yl)amino)pyridin-3-yl)phenyl)pyrrolidin-2-one, 1-(oxazol-4-ylmethyl)-3-(5-((5-(4-(2-oxopyrrolidin-1-yl)phenyl)pyridin-2-yl)amino)pyridin-3-yl)imidazolidin-2-one, (S)-2-((5-(4-((R)-4-hydroxy-2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((5-(4-((S)-4-hydroxy-2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, 1-(4-(6-((1-(2-hydroxy-2-methylpropanoyl)-2,3-dihydro-1H-pyrido[2,3-b][1,4]oxazin-7-yl)amino)pyridin-3-yl)phenyl)pyrrolidin-2-one, 1-(oxazol-5-ylmethyl)-3-(5-((5-(4-(2-oxopyrrolidin-1-yl)phenyl)pyridin-2-yl)amino)pyridin-3-yl)imidazolidin-2-one, (S)-2-((5-(4-(2-oxopyrrolidin-1-yl)phenyl)pyrazin-2-yl)amino)-6,6a,7,8-tetrahydro-9H-pyrido[2,3-b]pyrrolo[1,2-d][1,4]oxazin-9-one, 5-methoxy-N-(5-((5-(4-(2-oxopyrrolidin-1-yl)phenyl)pyridin-2-yl)amino)pyridin-3-yl)nicotinamide, 6-oxo-N-(5-((5-(4-(2-oxopyrrolidin-1-yl)phenyl)pyridin-2-yl)amino)pyridin-3-yl)-1,6-dihydropyridine-3-carboxamide, 1-(4-(6-((5-(4-(3-methoxypropanoyl)piperazin-1-yl)pyridin-3-yl)amino)pyridin-3-yl)phenyl)pyrrolidin-2-one, 1-(4-(6-((1-(isopropylsulfonyl)-2,3-dihydro-1H-pyrido[2,3-b][1,4]oxazin-7-yl)amino)pyridin-3-yl)phenyl)pyrrolidin-2-one, (S)—N,N-dimethyl-4-(6-((9-oxo-6a,7,8,9-tetrahydro-6H-pyrido[2,3-b]pyrrolo[1,2-d][1,4]oxazin-2-yl)amino)pyridin-3-yl)benzamide, 2,3-difluoro-N-(5-((5-(4-(2-oxopyrrolidin-1-yl)phenyl)pyridin-2-yl)amino)pyridin-3-yl)benzamide, (R)-1-(4-(6-((5-(4-(tetrahydrofuran-3-carbonyl)piperazin-1-yl)pyridin-3-yl)amino)pyridin-3-yl)phenyl)pyrrolidin-2-one, (S)-1-(4-(6-((5-(4-(tetrahydrofuran-3-carbonyl)piperazin-1-yl)pyridin-3-yl)amino)pyridin-3-yl)phenyl)pyrrolidin-2-one, (S)-2-((5-(3-fluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, N-(5-((5-(4-(2-oxopyrrolidin-1-yl)phenyl)pyridin-2-yl)amino)pyridin-3-yl)-2-phenylcyclopropane-1-carboxamide, 1-ethyl-6-oxo-N-(5-((5-(4-(2-oxopyrrolidin-1-yl)phenyl)pyridin-2-yl)amino)pyridin-3-yl)-1,6-dihydropyridine-3-carboxamide, 6-ethoxy-N-(5-((5-(4-(2-oxopyrrolidin-1-yl)phenyl)pyridin-2-yl)amino)pyridin-3-yl)nicotinamide, 1-(5-((5-(3-fluoro-4-(2-oxopyrrolidin-1-yl)phenyl)pyridin-2-yl)amino)pyridin-3-yl)imidazolidin-2-one, 2-methyl-N-(5-((5-(4-(2-oxopyrrolidin-1-yl)phenyl)pyridin-2-yl)amino)pyridin-3-yl)morpholine-4-carboxamide, N-(5-((5-(4-(2-oxopyrrolidin-1-yl)phenyl)pyridin-2-yl)amino)pyridin-3-yl)morpholine-4-carboxamide, (1S,2S)-2-ethoxy-N-(5-((5-(4-(2-oxopyrrolidin-1-yl)phenyl)pyridin-2-yl)amino)pyridin-3-yl)cyclopropane-1-carboxamide, 5-methoxy-N-(5-((5-(4-(2-oxopyrrolidin-1-yl)phenyl)pyridin-2-yl)amino)pyridin-3-yl)-1H-benzo[d]imidazole-7-carboxamide, N-(5-((5-(4-(2-oxopyrrolidin-1-yl)phenyl)pyridin-2-yl)amino)pyridin-3-yl)-2H-tetrazole-5-carboxamide, (S)-8,8-dimethyl-2-((5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, 3-methyl-N-(5-((5-(4-(2-oxopyrrolidin-1-yl)phenyl)pyridin-2-yl)amino)pyridin-3-yl)piperazine-1-carboxamide, 3-cyclopropyl-N-(5-((5-(4-(2-oxopyrrolidin-1-yl)phenyl)pyridin-2-yl)amino)pyridin-3-yl)piperazine-1-carboxamide, (S)-2-((5-(3-fluoro-4-(2-oxopyrrolidin-1-yl)phenyl)pyridin-2-yl)amino)-8,8-dimethyl-6,6a,7,8-tetrahydro-9H-pyrido[2,3-b]pyrrolo[1,2-d][1,4]oxazin-9-one, (E)-4-(dimethylamino)-N-(3-(3-oxo-3-((5-((5-(4-(2-oxopyrrolidin-1-yl)phenyl)pyridin-2-yl)amino)pyridin-3-yl)amino)propyl)phenyl)but-2-enamide, 4-(dimethylamino)-N-(3-(3-oxo-3-((5-((5-(4-(2-oxopyrrolidin-1-yl)phenyl)pyridin-2-yl)amino)pyridin-3-yl)amino)propyl)phenyl)butanamide, 4-(4-(dimethylamino)butanamido)-N-(5-((5-(4-(2-oxopyrrolidin-1-yl)phenyl)pyridin-2-yl)amino)pyridin-3-yl)benzamide, (6aS)-8-methyl-2-((5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (R)-2-((5-(3-fluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2'-((5-(4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one, (6aS)-2-((5-(3-fluoro-4-(2-oxopyrrolidin-1-yl)phenyl)pyridin-2-yl)amino)-8-methyl-6,6a,7,8-tetrahydro-9H-pyrido[2,3-b]pyrrolo[1,2-d][1,4]oxazin-9-one, (E)-4-(4-(dimethylamino)but-2-enamido)-N-(5-((5-(4-(2-oxopyrrolidin-1-yl)phenyl)pyridin-2-yl)amino)pyridin-3-yl)benzamide, 2-cyclopropyl-N-(5-((5-(4-(2-oxopyrrolidin-1-yl)phenyl)pyridin-2-yl)amino)pyridin-3-yl)morpholine-4-carboxamide, (S)-2-((5-(3-fluoro-4-(2-oxopyrrolidin-1-yl)phenyl)-4-methoxypyridin-2-yl)amino)-6,6a,7,8-tetrahydro-9H-pyrido[2,3-b]pyrrolo[1,2-d][1,4]oxazin-9-one, (S)-2-((4'-(difluoromethyl)-5-(2-oxopyrrolidin-1-yl)-[2,3'-bipyridin]-6'-yl)amino)-6,6a,7,8-tetrahydro-9H-pyrido[2,3-b]pyrrolo[1,2-d][1,4]oxazin-9-one, (S)-2-((5-(3-fluoro-4-(2-oxopyrrolidin-1-yl)phenyl)-4-methylpyridin-2-yl)amino)-6,6a,7,8-tetrahydro-9H-pyrido[2,3-b]pyrrolo[1,2-d][1,4]oxazin-9-one, (E)-4-(dimethylamino)-N-(2-oxo-2-((3-((2-oxo-3-(5-((5-(4-(2-oxopyrrolidin-1-yl)phenyl)pyridin-2-yl)amino)pyridin-3-yl)imidazolidin-1-yl)methyl)phenyl)amino)ethyl)but-2-enamide, (S)-2-((5-(3,5-difluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((5-(2,5-difluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one, (S)-2-((6-amino-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((6-(4-(2-oxopyrrolidin-1-yl)phenyl)pyridazin-3-yl)amino)-6,6a,7,8-tetrahydro-9H-pyrido[2,3-b]pyrrolo[1,2-d][1,4]oxazin-9-one, (S)-2-((6-methyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, N,N-dimethyl-4-(2-(pyridin-3-ylamino)pyrimidin-5-yl)benzamide, (S)-2'-((4-cyclopropyl-5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one, (S)-2-((4-cyclopropyl-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one, (R)-8-((5-(4-(2-oxopyrrolidin-1-yl)phenyl)pyridin-2-yl)amino)-3a,4-dihydro-1H,3H-oxazolo[3,4-d]pyrido[2,3-b][1,4]oxazin-1-one, (S)-2'-((4-isopropyl-5-(4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one, (S)-2-((4-(2-aminopropan-2-yl)-5-(2-fluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2'-((4-cyclopropyl-5-(4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one, (S)-2'-((5-(2-methyl-4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one, (S)-2'-((4-methoxy-5-(4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one, (S)-2'-((5-(2-methyl-4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one, (S)-2'-((4-methyl-5-(4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one, (S)-2-((5-(2-methyl-4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one, (S)-2'-((4-amino-5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one, (S)-2'-((4-methyl-5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one, (S)-2'-((4-methoxy-5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one, (S)-2-((4-amino-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one, (S)-2-((4-methyl-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one, (S)-2-((4-methoxy-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one, (S)-2'-((4-(methoxymethyl)-5-(4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one, (S)-2'-((5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one, (S)-2-((3-methyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((5-(2-methyl-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((4-cyclopropyl-5-(3-fluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((4-cyclopropyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((5-(3-fluoro-4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one, (S)-2-((5-(3-fluoro-4-(2-oxopyrrolidin-1-yl)phenyl)-4-isopropylpyridin-2-yl)amino)-6,6a,7,8-tetrahydro-9H-pyrido[2,3-b]pyrrolo[1,2-d][1,4]oxazin-9-one, (S)-2-((4-isopropyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((5-(2-fluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, 1-(4-(6-((5-(5-methyl-1,1-dioxido-1,2,5-thiadiazolidin-2-yl)pyridin-3-yl)amino)pyridin-3-yl)phenyl)pyrrolidin-2-one, (E)-4-(dimethylamino)-N-(2-oxo-2-((4-((2-oxo-3-(5-((5-(4-(2-oxopyrrolidin-1-yl)phenyl)pyridin-2-yl)amino)pyridin-3-yl)imidazolidin-1-yl)methyl)phenyl)amino)ethyl)but-2-enamide, (6aS)-2-((5-(3-fluoro-4-(2-oxopyrrolidin-1-yl)phenyl)pyridin-2-yl)amino)-8-hydroxy-6,6a,7,8-tetrahydro-9H-pyrido[2,3-b]pyrrolo[1,2-d][1,4]oxazin-9-one, (6aS)-8-hydroxy-2-((5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((4-methoxy-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((4-methyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (6aR)-2-((5-(4-(1-methyl-2-oxopyrrolidin-3-yl)phenyl)pyridin-2-yl)amino)-6,6a,7,8-tetrahydro-9H-pyrido[2,3-b]pyrrolo[1,2-d][1,4]oxazin-9-one, (6aS,8R)-2-((5-(3-fluoro-4-(2-oxopyrrolidin-1-yl)phenyl)pyridin-2-yl)amino)-8-hydroxy-8-methyl-6,6a,7,8-tetrahydro-9H-pyrido[2,3-b]pyrrolo[1,2-d][1,4]oxazin-9-one, (6aS,8R)-8-hydroxy-8-methyl-2-((5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, N-methyl-4-[6-[[5-(2-oxopyrrolidin-1-yl)-3-pyridyl]amino]-3-pyridyl]benzamide, N,N-dimethyl-4-(6-((1-(methylsulfonyl)-2,3-dihydro-1H-pyrido[2,3-b][1,4]oxazin-7-yl)amino)pyridin-3-yl)benzamide, 4'-((5-(2-(dimethylamino)-2-oxoethyl)pyridin-3-yl)amino)-N,N-dimethyl-[1,1'-biphenyl]-4-carboxamide, 1-(4-(6-((6-methoxypyridin-3-yl)amino)pyridin-3-yl)phenyl)pyrrolidin-2-one, 4-(6-((6-((3-aminobenzamido)methyl)pyridin-3-yl)amino)pyridin-3-yl)-N,N-dimethylbenzamide, N-(5-((5-(4-(dimethylcarbamoyl)phenyl)pyridin-2-yl)amino)pyridin-3-yl)-1H-benzo[d]imidazole-4-carboxamide, 3-((5-(4-(2-oxopyrrolidin-1-yl)phenyl)pyridin-2-yl)amino)quinoline-5-carboxamide, (S)-1-(4-(6-((2-methyl-1,1-dioxido-2,3,3a,4-tetrahydropyrido[2,3-b][1,2,5]thiadiazolo[2,3-d][1,4]oxazin-8-yl)amino)pyridin-3-yl)phenyl)pyrrolidin-2-one, (S)-2-((4-(methoxymethyl)-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((4-(methoxymethyl)-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one, (S)-2'-((4-(methoxymethyl)-5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one, (3S,6R)—N,N-dimethyl-6-(6-(((S)-9-oxo-6a,7,8,9-tetrahydro-6H-pyrido[2,3-b]pyrrolo[1,2-d][1,4]oxazin-2-yl)amino)pyridin-3-yl)tetrahydro-2H-pyran-3-carboxamide, (S)-2-((4-isopropyl-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one, (S)-2'-((4-isopropyl-5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one, (S)-2-((4-(3-methoxycyclobutyl)-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one, (S)-2-((1'-(4-methyl-4H-1,2,4-triazol-3-yl)-1',2',3',6'-tetrahydro-[3,4'-bipyridin]-6-yl)amino)-6,6a,7,8-tetrahydro-9H-pyrido[2,3-b]pyrrolo[1,2-d][1,4]oxazin-9-one, (S)-2-((5-(4-(4-methyl-4H-1,2,4-triazol-3-yl)piperazin-1-yl)pyridin-2-yl)amino)-6,6a,7,8-tetrahydro-9H-pyrido[2,3-b]pyrrolo[1,2-d][1,4]oxazin-9-one, (S)-2-((5-(4-(4-methylpyridazin-3-yl)phenyl)pyridin-2-yl)amino)-6,6a,7,8-tetrahydro-9H-pyrido[2,3-b]pyrrolo[1,2-d][1,4]oxazin-9-one, (S)-2-((5-(4-(4-methylisoxazol-5-yl)phenyl)pyridin-2-yl)amino)-6,6a,7,8-tetrahydro-9H-pyrido[2,3-b]pyrrolo[1,2-d][1,4]oxazin-9-one, (S)-2-((4-isopropyl-5-(4-(5-methyl-1H-1,2,3-triazol-1-yl)phenyl)pyrimidin-2-yl)amino)-6,6a,7,8-tetrahydro-9H-pyrido[2,3-b]pyrrolo[1,2-d][1,4]oxazin-9-one, (S)-2-((5-(3-methyl-2-oxo-1-oxa-3,8-diazaspiro[4.5]decan-8-yl)pyridin-2-yl)amino)-6,6a,7,8-tetrahydro-9H-pyrido[2,3-b]pyrrolo[1,2-d][1,4]oxazin-9-one, (S)-2-((4-morpholino-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one, (S)-2-((4-(4-methylpiperazin-1-yl)-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one, (S)-2-((4-(methoxymethyl)-5-(4-(4-methylisoxazol-3-yl)phenyl)pyrimidin-2-yl)amino)-6,6a,7,8-tetrahydro-9H-pyrido[2,3-b]pyrrolo[1,2-d][1,4]oxazin-9-one, (S)-2-((5-(4-(4-methylisoxazol-3-yl)phenyl)pyridin-2-yl)amino)-6,6a,7,8-tetrahydro-9H-pyrido[2,3-b]pyrrolo[1,2-d][1,4]oxazin-9-one, (S)-2-((4-cyclobutoxy-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((4-cyclopropyl-5-(4-(4-methyl-4H-1,2,4-triazol-3-yl)phenyl)pyridin-2-yl)amino)-6,6a,7,8-tetrahydro-9H-pyrido[2,3-b]pyrrolo[1,2-d][1,4]oxazin-9-one, (S)-2-((4-(3-methoxyazetidin-1-yl)-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one, (S)-2-((4-methoxy-5-(4-(4-methyl-4H-1,2,4-triazol-3-yl)phenyl)pyrimidin-2-yl)amino)-6,6a,7,8-tetrahydro-9H-pyrido[2,3-b]pyrrolo[1,2-d][1,4]oxazin-9-one, (S)-2-((4-methoxy-5-(4-(5-methyl-TH-1,2,3-triazol-1-yl)phenyl)pyrimidin-2-yl)amino)-6,6a,7,8-tetrahydro-9H-pyrido[2,3-b]pyrrolo[1,2-d][1,4]oxazin-9-one, (S)-2-((5-(4-(5-methyl-TH-1,2,3-triazol-1-yl)phenyl)pyridin-2-yl)amino)-6,6a,7,8-tetrahydro-9H-pyrido[2,3-b]pyrrolo[1,2-d][1,4]oxazin-9-one, (S)-2-((4-methoxy-5-(4-(4-methyl-4H-1,2,4-triazol-3-yl)phenyl)pyridin-2-yl)amino)-6,6a,7,8-tetrahydro-9H-pyrido[2,3-b]pyrrolo[1,2-d][1,4]oxazin-9-one, (S)-2-((5-(4-(4-methyl-4H-1,2,4-triazol-3-yl)phenyl)pyridin-2-yl)amino)-6,6a,7,8-tetrahydro-9H-pyrido[2,3-b]pyrrolo[1,2-d][1,4]oxazin-9-one, 4-(4-(2-((2-(2,6-dioxopiperidin-3-yl)-1,3-dioxoisoindolin-4-yl)oxy)acetamido)butanamido)-N-(5-((5-(4-(2-oxopyrrolidin-1-yl)phenyl)pyridin-2-yl)amino)pyridin-3-yl)benzamide, (S)-4-(4-(methoxymethyl)-2-((9-oxo-6a,7,8,9-tetrahydro-6H-pyrido[2,3-b]pyrrolo[1,2-d][1,4]oxazin-2-yl)amino)pyrimidin-5-yl)-N,N-dimethylbenzamide, (S)-4-(4-methoxy-2-((9-oxo-6a,7,8,9-tetrahydro-6H-pyrido[2,3-b]pyrrolo[1,2-d][1,4]oxazin-2-yl)amino)pyrimidin-5-yl)-N,N-dimethylbenzamide, (R)-8-((5-(3-fluoro-4-(2-oxopyrrolidin-1-yl)phenyl)pyridin-2-yl)amino)-3a,4-dihydro-1H,3H-oxazolo[3,4-d]pyrido[2,3-b][1,4]oxazin-1-one, 4-(2-(2-(2-(2-((2-(2,6-dioxopiperidin-3-yl)-1,3-dioxoisoindolin-4-yl)amino)ethoxy)ethoxy)ethoxy)acetamido)-N-(5-((5-(4-(2-oxopyrrolidin-1-yl)phenyl)pyridin-2-yl)amino)pyridin-3-yl)benzamide, (S)-2-((5-(4-(4-isobutyl-4H-1,2,4-triazol-3-yl)phenyl)pyridin-2-yl)amino)-6,6a,7,8-tetrahydro-9H-pyrido[2,3-b]pyrrolo[1,2-d][1,4]oxazin-9-one, (S)—N,N-dimethyl-4-(2-((9'-oxo-6a',7'-dihydro-6'H,9'H-spiro[cyclopropane-1,8'-pyrido[2,3-b]pyrrolo[1,2-d][1,4]oxazin]-2'-yl)amino)pyrimidin-5-yl)benzamide, (S)-2-fluoro-N,N-dimethyl-4-(2-((9-oxo-6a,7,8,9-tetrahydro-6H-pyrido[2,3-b]pyrrolo[1,2-d][1,4]oxazin-2-yl)amino)pyrimidin-5-yl)benzamide, (S)-2-((5-(4-((R)-2-methyl-5-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((5-(4-(pyrrolidine-1-carbonyl)phenyl)pyrimidin-2-yl)amino)-6,6a,7,8-tetrahydro-9H-pyrido[2,3-b]pyrrolo[1,2-d][1,4]oxazin-9-one, (S)-2-((5-(4-(azetidine-1-carbonyl)phenyl)pyrimidin-2-yl)amino)-6,6a,7,8-tetrahydro-9H-pyrido[2,3-b]pyrrolo[1,2-d][1,4]oxazin-9-one, (S)—N,N-dimethyl-4-(2-((9-oxo-6a,7,8,9-tetrahydro-6H-pyrido[2,3-b]pyrrolo[1,2-d][1,4]oxazin-2-yl)amino)pyrimidin-5-yl)benzamide, (S)-2-((9-fluoro-5,5-dimethyl-8-(2-oxopyrrolidin-1-yl)-5H-chromeno[3,4-d]pyrimidin-3-yl)amino)-6,6a,7,8-tetrahydro-9H-pyrido[2,3-b]pyrrolo[1,2-d][1,4]oxazin-9-one, and (S)-2-((5-(4-(2-oxopyrrolidin-1-yl-4,4,5,5-d4)phenyl)pyridin-2-yl)amino)-6,6a,7,8-tetrahydro-9H-pyrido[2,3-b]pyrrolo[1,2-d][1,4]oxazin-9-one.

It should be understood that all isomeric forms are included within the present invention, including mixtures thereof. If the compound contains a double bond, the substituent may be in the E or Z configuration. If the compound contains a di-substituted cycloalkyl, the cycloalkyl substituent may have a cis- or trans configuration. All tautomeric forms are also intended to be included.

Compounds of the invention, and pharmaceutically acceptable salts, hydrates, solvates, stereoisomers and prodrugs thereof may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of a chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula I may form salts which are also within the scope of this invention. Reference to a compound of the Formula herein is understood to include reference to salts thereof, unless otherwise indicated.

The present invention relates to compounds which are modulators of PI5P4K. In one embodiment, the compounds of the present invention are inhibitors of PI5P4K.

The invention is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method of Synthesizing the Compounds

The compounds of the present invention may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order will be readily apparent to those skilled in the art and they will recognize if a stereocenter exists in the compounds of Formula (I). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention can be synthesized by following the steps outlined in General Scheme 1 which comprise different sequences of assembling intermediates or compounds (II). Starting materials are either commercially available or made by known procedures in the reported literature or as illustrated below.

A compound of formula (I) may be obtained (Scheme 1) by starting from, for example, a compound of formula (II), wherein LG represents a leaving group including, but not limited to, halogen (e.g., chlorine, bromine or iodine), or an alkyl-sulfonate, aryl-sulfonate or haloalkyl-sulfonate (e.g., triflate), and reacting said compound (II) with a compound of formula B—NH$_2$, wherein B—NH$_2$ is defined below and represents a cyclic amine either as free base or a salt (e.g., HCl, TFA or acetic acid), optionally under the influence of a transition metal catalyst as described in for example *Metal-Catalyzed Cross-Coupling Reactions, 2$^{nd}$, Completely Revised and Enlarged Edition* by A. de Meijere and F. Diederich, Wiley VCH, 2004.

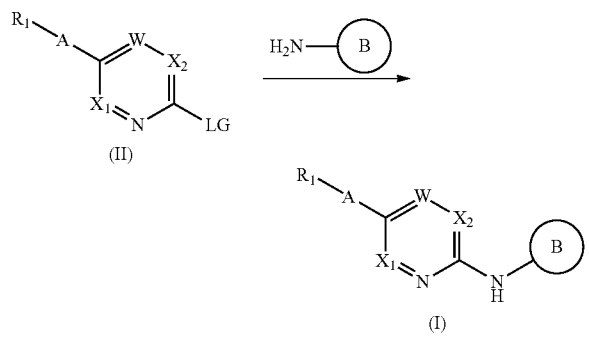

Scheme 1

The reaction may be carried out by coupling of a compound of formula (II), with an appropriate amine of formula B—NH$_2$. The reaction may also be carried out using a suitable metal catalyst including, but not limited to, a palladium catalyst, for example, (di-tert-butylphosphino) ferrocene palladium (II) dichloride, tetrakis(triphenylphosphine)palladium (0), palladium (II) (diphenylphosphino) ferrocene dichloride, palladium(II) acetate or bis (dibenzylideneacetone) palladium (0). Optionally a suitable ligand, for example, triphenylphosphine, tri-tert-butylphosphine or 2-(dicyclohexylphosphino)biphenyl or 2-dicyclohexylphosphino-2',4',6'-triisopropylbiphenyl is employed. Suitable bases, including an alkyl amine base, (e.g., triethyl amine), an alkali metal or alkaline earth metal carbonate or hydroxide, or phosphate base, (e.g., potassium carbonate, sodium carbonate, cesium carbonate, sodium hydroxide, or potassium phosphate), may be used in the reaction. Said reaction may be performed at a temperature range between +20° C. and +160° C., in suitable solvents, including, without limitation, toluene, tetrahydrofuran, 2-methyl-tetrahydrofuran, 1,4-dioxane, 1,2-dimethoxyethane, acetonitrile, water, ethanol, N,N-dimethylacetamide or N,N-dimethylformamide, or mixtures thereof. If enantiomerically pure or enriched compound (II) is used in this reaction, an enantiomerically pure or enantiomerically enriched compound (I) is obtained.

Compounds of formula (II) and B—NH$_2$ may be commercially available compounds, or known in the literature, or they are prepared by standard processes known in the art. A compound of formula (I), (II) or B—NH$_2$ may be separated into its enantiomers by standard processes known in the art by for example chromatography on a chiral stationary phase.

Methods of Using the Disclosed Compounds

Another aspect of the invention relates to a method of treating a disease or disorder associated with modulation of PI5P4K. The method comprises administering to a patient in need of a treatment for diseases or disorders associated with modulation of PI5P4K an effective amount the compositions and compounds of Formula (I).

In another aspect, the present invention is directed to a method of inhibiting PI5P4K. The method involves administering to a patient in need thereof an effective amount of a compound of Formula (I).

Another aspect of the present invention relates to a method of treating, preventing, inhibiting or eliminating a disease or disorder in a patient associated with the inhibition of PI5P4K, the method comprising administering to a patient in need thereof an effective amount of a compound of Formula (I). In one embodiment, the disease may be, but not limited to, cancer or cell proliferative disorder, a metabolic disorder, neurodegenerative disease, and an inflammatory disease.

The present invention also relates to the use of an inhibitor of PI5P4K for the preparation of a medicament used in the treatment, prevention, inhibition or elimination of a disease or condition mediated by PI5P4K, wherein the medicament comprises a compound of Formula (I).

In another aspect, the present invention relates to a method for the manufacture of a medicament for treating, preventing, inhibiting, or eliminating a disease or condition mediated by PI5P4K, wherein the medicament comprises a compound of Formula (I).

Another aspect of the present invention relates to a compound of Formula (I) for use in the manufacture of a medicament for treating a disease associated with inhibiting PI5P4K.

In another aspect, the present invention relates to the use of a compound of Formula (I) in the treatment of a disease associated with inhibiting PI5P4K.

Another aspect of the invention relates to a method of treating cancer. The method comprises administering to a patient in need thereof an effective amount of a compound of Formula (I).

In another aspect of the invention, the method relates to treating a cell proliferative disease. The method comprises administering to a patient in need thereof an effective amount of a compound of Formula (I).

In yet another aspect, the present invention relates to a method of treating a neurodegenerative disease. The method comprises administering to a patient in need thereof an effective amount of a compound of Formula (I).

In another aspect, the present invention relates to a method of treating an inflammatory disease or condition. The method comprises administering to a patient in need thereof an effective amount of a compound of Formula (I).

Another aspect of the invention relates to a method of inducing cell cycle arrest, apoptosis in tumor cells, and/or enhanced tumor-specific T cell immunity. The method comprises contacting the cells with an effective amount of a compound of Formula (I).

In one embodiment, the present invention relates to the use of an inhibitor of PI5P4K for the preparation of a medicament used in treatment, prevention, inhibition or elimination of a disease or disorder associated with cancer or cell proliferative disorder, a metabolic disorder, neurodegenerative disease, and an inflammatory disease.

In another embodiment, the present invention relates to a compound of Formula (I) or a pharmaceutical composition comprising a compound of the present invention and a pharmaceutically acceptable carrier used for the treatment of cancers or cell proliferative disorders including, but not limited to, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

In another embodiment, the present invention relates to a compound of Formula (I) or a pharmaceutical composition comprising a compound of the present invention and a pharmaceutically acceptable carrier used for the treatment of neurodegenerative diseases including, but not limited to, brain trauma, spinal cord trauma, trauma to the peripheral nervous system, Alzheimer's disease, Pick's disease, diffuse Lewy body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffman disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, and prion diseases (including Creutzfeldt-Jakob, Gerstmann-Straussler-Scheinker disease, Kuru and fatal familial insomnia, age-related dementia, vascular dementia, diffuse white matter disease (Binswanger's disease), dementia of endocrine or metabolic origin, dementia of head trauma and diffuse brain damage, dementia pugilistica or frontal lobe dementia, neurodegenerative disorders resulting from cerebral ischemia or infarction including embolic occlusion and thrombotic occlusion as well as intracranial hemorrhage of any type, intracranial and intravertebral lesions, hereditary cerebral angiopathy, normeuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis arthropathy, and Finnish and Iowa amyloidosis.

In another embodiment, the present invention relates to a compound of Formula (I) or a pharmaceutical composition comprising a compound of the present invention and a pharmaceutically acceptable carrier used for the treatment of inflammatory disease. In some embodiments, the inflammatory disease is associated with a metabolic disorder. In some embodiments the treated inflammation is associated with, but not limited to, Type II diabetes, insulin resistance cardiovascular disease, arrhythmia, atherosclerosis, coronary artery disease, hypertriglyceridemia, dyslipidemia, retinopathy, nephropathy, neuropathy, obesity, and macular edema.

In yet another embodiment, the present invention relates to a compound of Formula (I) or a pharmaceutical composition comprising a compound of the present invention and a pharmaceutically acceptable carrier used for the treatment of a metabolic disease including, but not limited, Type II diabetes, insulin resistance cardiovascular disease, arrhythmia, atherosclerosis, coronary artery disease, hypertriglyceridemia, dyslipidemia, retinopathy, nephropathy, neuropathy, obesity, and macular edema.

In another embodiment, the present invention relates to a compound of Formula (I) or a pharmaceutical composition comprising a compound of the present invention and a pharmaceutically acceptable carrier used for the treatment of inflammatory disease associated with inflammatory disease. In some embodiments the treated inflammation is associated with, but not limited to, ileitis, ulcerative colitis, Barrett's syndrome, or Crohn's disease.

In some embodiments, the patient is selected for treatment based on gene amplification and/or elevated tumor expression of PI5P4K. In other embodiments, the patient is selected for treatment based on gene amplification and/or elevated tumor expression of PI5P4Kα gene, PI5P4Kβ gene, or PI5P4Kγ gene. In other embodiments, the patient is selected for the treatment based on tumor expression of p53 mutations.

In some embodiments, administration of a compound of Formula (I) or a pharmaceutical composition comprising a compound of the present invention and a pharmaceutically acceptable carrier induces a change in the cell cycle or cell viability.

Another aspect of the invention is directed to pharmaceutical compositions comprising a compound of Formula (I) and a pharmaceutically acceptable carrier. The pharmaceutical acceptable carrier may further include an excipient, diluent, or surfactant.

In one embodiment, are provided methods of treating a disease or disorder associated with modulation of PI5P4K including, cancer or cell proliferative disorder, a metabolic disorder, neurodegenerative disease, and an inflammatory disease, comprising administering to a patient suffering from at least one of said diseases or disorder a compound of Formula (I).

One therapeutic use of the compounds or compositions of the present invention which inhibit PI5P4K is to provide treatment to patients or subjects suffering from c cancer or cell proliferative disorder, a metabolic disorder, neurodegenerative disease, and an inflammatory disease.

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, pentaneG400, pentaneG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, poly(hydroxypropyl) methacrylamide-phenol, poly(hydroxyethyl)aspanamide phenol, or poly(ethyleneoxide)-polylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula (I) and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Analytical Methods, Materials, and Instrumentation

Unless otherwise noted, reagents and solvents were used as received from commercial suppliers. All solvents used were of analytical grade and commercially available anhydrous solvents were routinely used for reactions. Starting materials were available from commercial sources, or prepared according to literature procedures. Room temperature refers to +20-25° C. Solvent mixture compositions are given as volume percentages or volume ratios.

Microwave heating was performed in a Biotage Initiator microwave cavity producing continuous irradiation at 2.45 GHz. It is understood that microwaves may be used for the heating of reaction mixtures.

Straight phase chromatography was manually performed on Merck Silica gel 60 (0.040-0.063 mm), or automatically using an ISCO Combiflash® Companion™ system using SiliaSep™ normal-phase flash columns using the solvent system indicated.

NMR spectra were recorded on a 400 MHz (or higher field) NMR spectrometer fitted with a probe of suitable configuration. Spectra were recorded at ambient temperature unless otherwise stated. Chemical shifts are given in ppm down- and upfield from TMS (0.00 ppm). The following reference signals were used: the residual solvent signal of DMSO-$d_6$ $\delta$ 2.5, CDCl3 $\delta$ 7.26 or Methanol-d4 $\delta$ 3.31. Resonance multiplicities are denoted s, d, t, q, m and br for singlet, doublet, triplet, quartet, multiplet and broad, respectively.

High pressure liquid chromatography (HPLC) was performed on a reverse phase column. A linear gradient was applied using for example mobile phase A (aqueous 0.1% $NH_3$ or aqueous 0.1% acetic acid or aqueous 0.1% formic acid) and B (acetonitrile or methanol). Mass spectrometer (MS) analyses were performed in positive ion mode using electrospray ionization (ES+).

Preparative chromatography was run on a Gilson-PREP GX271 or GX281 with Trilution 1c as software on a reverse phase column. A linear gradient was applied using for example mobile phase A (aqueous 0.1% $NH_3$ or aqueous 0.1% acetic acid or aqueous 0.1% formic acid) and B (acetonitrile or methanol).

Preparative chiral chromatography for separation of enantiomers was run on a Thar SFC using supercritical fluid chromatography on a chiral stationary phase. A linear gradient was applied using mobile phase A (carbon dioxide) and B (acetonitrile or methanol or ethanol or 2-propanol or any mixtures thereof). Additives (such as diethyl amine or isopropyl amine or ammonia or formic acid or TFA) may be used.

Abbreviations used in the following examples and elsewhere herein are:

$Ac_2O$ acetic anhydride
AcOH acetic acid
ADP adenosine diphosphate
Amphos (4-(N,N-dimethylamino)phenyl)di-tert-butyl phosphine
anh. anhydrous
aq. Aqueous
atm atmosphere
ATP adenosine triphosphate
$B_2Pin_2$ bis(pinacolato)diboron
$BH_3$.THF borane tetrahydrofuran
BINAP (±)-2,2'-bis(diphenylphosphino)-1,1'-binaphthalene
Boc tert-butyloxycarbonyl
$Boc_2O$ tert-butyloxycarbonyl anhydride
Brettphos 2-(dicyclohexylphosphino)3,6-dimethoxy-2',4',6'-triisopropyl-1,1'-biphenyl
Brettphos Pd G3 [(2-di-cyclohexylphosphino-3,6-dimethoxy-2',4',6'-triisopropyl-1,1'-biphenyl)-2-(2'-amino-1,1'-biphenyl)]palladium(II) methanesulfonate
br broad
brine saturated aqueous sodium chloride
n-BuLi n-butyl lithium
n-BuOH n-butanol
Calc'd calculated
$CDCl_3$ deuterated chloroform
$CHCl_3$ chloroform
$CoCl_2.6H_2O$ cobalt chloride hexahydrate
$Cs_2CO_3$ cesium carbonate
CuI copper iodide
DCM dichloromethane
DIAD diisopropyl azodiformate
DIPEA N,N-diisopropylethylamine
DMAc N,N-dimethyl acetamide
DMAP N,N-dimethylpyridin-4-amine
DME 1,2-Dimethoxyethane
DMEDA N,N'-Dimethylethylenediamine
DMF N,N-dimethyl formamide
DMFDMA N,N-dimethyl formamide dimethyl acetal
2,2-DMP dimethoxypropane
DMSO dimethyl sulfoxide
DMSO-$d_6$ deuterated dimethyl sulfoxide
DOPE 1,2-dioleoyl-sn-glycero-3-phosphoethanolamine
EDA ethylenediamine
EDC 1-ethyl-3-(3-dimethylaminopropyl)carbodiimide
EDCI 1-ethyl-3-(3-dimethylaminopropyl)carbodiimide
EDTA ethylenediaminetetraacetic acid
EGTA ethylene glycol-bis(β-aminoethyl ether)-N,N,N'N'-tetraacetic acid
ESI electrospray ionization
$Et_2O$ diethyl ether
EtOAc ethyl acetateEtOH ethanol
FA formic acid
Fe iron
g gram
GST glutathione S-transferase
h hour(s)
$H_2$ hydrogen gas
$H_2O_2$ hydrogen peroxide
HATU [bis(dimethylamino)methylene]-1H-1,2,3-triazolo[4,5-b]pyridinium 3-oxide hexafluorophosphate
HBTU 3-[bis(dimethylamino)methylene]-3H-benzotriazol-1-oxide hexafluorophosphate
HBr hydrobromic acid
HCl hydrochloric acid
HEPES (4-(2-hydroxyethyl)-1-piperazineethanesulfonic acid)

H₄NE 20 mM HEPES, pH 7.4, 100 mM NaCl, 0.5 mM EGTA
HPLC high pressure (or performance) liquid chromatography
Hz hertz
IPA isopropanol
J coupling constant
K₂CO₃ potassium carbonate
KMnO₄ potassium permanganate
KOAc potassium acetate
KOtBu potassium tert-butoxide
LCMS liquid chromatography mass spectrometry
LHMDS lithium bis(trimethylsilyl)amide
LiOH lithium hydroxide
m multiplet
m/z mass-to-charge ratio
MBTE methyl tert-butyl ether
MeCN acetonitrile
MeI methyl iodideMeNH₂ methylamine
Me₂NH dimethylamine
MeOH methanol
Methanol-D₄ deuterated methanol
2-MeTHF 2-methyl tetrahydrofuran
mg milligram
MgCl₂ magnesium chloride
MgSO₄ magnesium sulfate
MHz megahertz
min min
mM millimolar
mmol millimole
mL milliliter
MOPS 3-(N-morpholino)propanesulfonic acid
MS mass spectrometry
MS ES mass spectrometry electrospray
MsCl methanesulfonyl chloride
Ms₂O methanesulfonic anhydride
MTBE methyl tert-butyl ether
m/z mass-to-charge ratio
μg microgram
μM micromolar
μL microliter
N₂ nitrogen
NaBH₄ sodium borohydride
NaCl sodium chloride
Na₂CO₃ sodium carbonate
NaH sodium hydride
NaHCO₃ sodium bicarbonate
NaOtBu sodium tert-butoxide
Na₂SO₄ sodium sulfate
NaOH sodium hydroxide
NH₃ ammonia
NH₄Cl ammonium chloride
NH₄HCO₃ ammonium bicarbonate
NMR nuclear magnetic resonance
Pd/C palladium on carbon
PdCl₂(Amphos) bis(di-tert-butyl(4-dimethylaminophenyl)phosphine)dichloropalladium(II)
PdCl₂(PPh₃)₂ bis(triphenylphosphinepalladium(II) dichloride
Pd₂(dba)₃ tris(dibenzylideneacetone)dipalladium(0)
Pd(OAc)₂ palladium(II) acetate
PdCl₂(dppf) [1,1'-bis(diphenylphosphino)ferrocene]dichloropalladium(II)
Pd(t-Bu₃P)₂ bis(tri-tert-butylphosphine)palladium(0)
Pd(PPh₃)₄ tetrakis(triphenylphosphine)palladium(0)
PEPPSI-iPr [1,3-bis(2,6-Diisopropylphenyl)imidazol-2-ylidene](3-chloropyridyl)palladium(II) dichloride
pH potential of hydrogen
PI5P phosphatidylinositol 5-phosphate
PI5P4K phosphatidylinositol-5-phosphate-4-kinase
PIP4K2A phsosphatidylinositol 5-phosphate 4-kinase type-2 alpha
ppm parts per million
psi pounds per square inch
py pyridine
quant. quantitative
R_f retention factor
rt room temperature
Rt retention time
sat. saturated
SEMCl 2-(trimethylsilyl)ethoxymethyl chloride
SOCl₂ thionyl chloride
t-BuOH tert-butanol
TBAB tetrabutylammonium bromide
TEA triethylamine
TFA trifluoroacetic acid
THF tetrahydrofuran
TLC thin layer chromatography
TMEDA tetramethylethylenediamine
Triton X-100 4-(1,1,3,3-tetramethylbutyl)phenyl-polyethylene glycol
Ts₂O tosylic anhydride
TsOH tosylic acid
Tween 20 PEG(20) sorbitan monolaurate
XantPhos 4,5-bis(diphenylphosphino)-9,9-dimethylxanthene
XPhos 2-dicyclohexylphosphino-2',4',6'-triisopropylbiphenyl
XPhos Pd G1 (2-Dicyclohexylphosphino-2',4',6'-triisopropyl-1,1'-biphenyl)[2-(2-aminoethyl)phenyl)]palladium(II) chloride, (XPhos) palladium(II) phenethylamine chloride
Zn zinc Example 1: N,N-dimethyl-4-(6-(pyridin-3-ylamino)pyridin-3-yl)benzamide

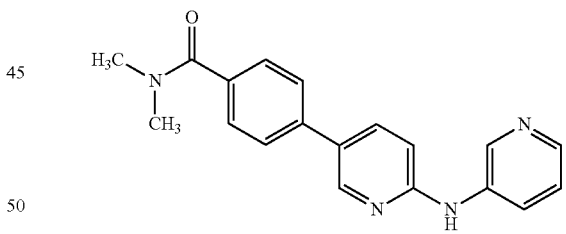

4-Iodo-N,N-dimethyl-benzamide (195 mg, 0.71 mmol), (6-chloro-3-pyridyl)boronic acid (140 mg, 0.89 mmol), Pd(PPh₃)₄ (40 mg, 0.03 mmol) and K₂CO₃ (300 mg, 2.17 mmol) were taken up in 1,4-Dioxane:H₂O:EtOH (6:3:1, 5 mL). The resulting mixture was stirred at 70° C. for 3 h and then allowed to cool to rt overnight. Water (5 mL) was added and the mixture extracted with EtOAc (3×10 mL). The combined organics were washed with brine, dried over Na₂SO₄, filtered and concentrated to give crude product (248 mg). 4-(6-chloro-3-pyridyl)-N,N-dimethyl-benzamide (180 mg, 0.69 mmol, from previous step), Pd(OAc)₂ (7.75 mg, 0.03 mmol), BINAP (43 mg, 0.07 mmol), KOtBu (232 mg, 2.07 mmol) and pyridin-3-amine (130 mg, 1.38 mmol) were taken up in 1,4-Dioxane and the resulting mixture was stirred at 90° C. overnight. When cooled to rt water (5 mL), brine (5 mL) and EtOAc (10 mL) were added, the mixture was filtered and the organic layer separated. The aqueous layer was extracted with EtOAc (2×10 mL). The combined organics were washed with brine, dried over Na₂SO₄, filtered, concentrated and purified by preparative HPLC to give product as a solid (27 mg, 12%). ¹H NMR (500 MHz, DMSO-d₆) δ 9.44 (s, 1H), 8.84 (d, J=2.2 Hz, 1H), 8.57 (d, J=1.9 Hz, 1H), 8.26 (br d, J=8.2 Hz, 1H), 8.12 (d, J=3.8 Hz, 1H), 7.99 (dd, J=2.4, 8.7 Hz, 1H), 7.72 (d, J=8.2 Hz, 2H), 7.48 (d, J=8.2 Hz, 2H), 7.31 (dd, J=4.6, 8.4 Hz, 1H), 6.97 (d, J=8.8 Hz, 1H), 3.16-2.80 (m, 6H). MS ES+m/z 319 [M+H]⁺.

Example 2: N,N,3-trimethyl-4-(6-(pyridin-3-ylamino)pyridin-3-yl)benzamide

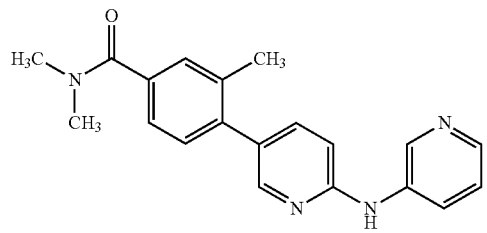 [SMILES: Cc1cc(C(=O)N(C)C)ccc1-c1ccc(Nc2cccnc2)nc1]

The title compound was synthesized in a similar way as described in Example 1, starting from 4-bromo-N,N,3-trimethyl-benzamide, to give the product as a solid (5 mg, 4%). ¹H NMR (500 MHz, DMSO-d₆) δ ppm 2.32 (s, 3H) 2.94-3.05 (m, 6H) 6.96 (d, 1H) 7.28-7.36 (m, 4H) 7.69 (dd, 1H) 8.12 (d, 1H) 8.21 (d, 1H) 8.28 (br d, 1H) 8.85 (d, 1H) 9.44 (s, 1H). MS ES+m/z 333 [M+H]⁺.

Example 3: N,N-dimethyl-6'-(pyridin-3-ylamino)-[3,3'-bipyridine]-6-carboxamide

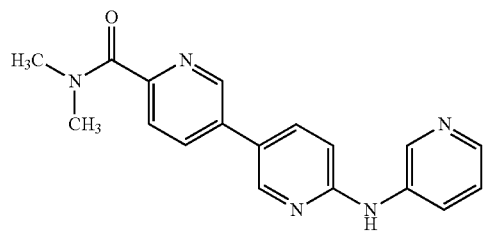 [SMILES: CN(C)C(=O)c1ccc(-c2ccc(Nc3cccnc3)nc2)cn1]

The title compound was synthesized in a similar way as described in Example 1, starting from 5-bromo-N,N-dimethyl-pyridine-2-carboxamide, to give the product as a solid (35 mg, 24%). ¹H NMR (500 MHz, DMSO-d₆) δ ppm 3.03 (d, 6H) 7.00 (d, 1H) 7.33 (dd, 1H) 7.64 (d, 1H) 8.08 (dd, 1H) 8.14 (d, 1H) 8.21 (dd, 1H) 8.27 (br d, 1H) 8.66 (d, 1H) 8.86 (d, 1H) 8.89-8.95 (m, 1H) 9.52 (s, 1H). MS ES+m/z 320 [M+H]⁺.

Example 4: N,N-dimethyl-3-(6-(pyridin-3-ylamino)pyridin-3-yl)propiolamide

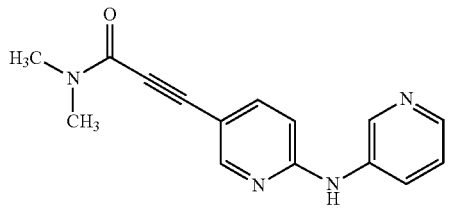 [SMILES: CN(C)C(=O)C#Cc1ccc(Nc2cccnc2)nc1]

Step 1: Intermediate 1—3-(6-Chloro-3-pyridyl)prop-2-ynoic acid

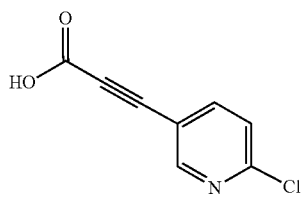 [SMILES: O=C(O)C#Cc1ccc(Cl)nc1]

2-Chloro-5-iodo-pyridine (500 mg, 2.09 mmol), prop-2-ynoic acid (154 mg, 2.19 mmol), PdCl₂(PPh₃)₂ (22 mg, 0.03 mmol) and CuI (16 mg, 0.08 mmol) were taken up in 2-MeTHF (5 mL). TEA (1 mL, 7.19 mmol) was added and the resulting mixture was stirred at rt for 2 h. EtOAc (3 mL), 2M aq. NaOH (3 mL) and water (10 mL) were added and the aqueous layer separated. The organic layer was extracted with 0.2M aq NaOH (5 mL). The combined aqueous layers were washed with EtOAc (5 mL) and filtered. pH was adjusted to ~2 using conc. HCl and the mixture was stirred at rt for 10 min. The resulting precipitate was filtered off, washed with water and dried to give the product as a solid (210 mg, 55%). MS ES+m/z 182 [M+H]⁺.

Step 2: Intermediate—3-(6-Chloro-3-pyridyl)-N,N-dimethyl-prop-2-ynamide

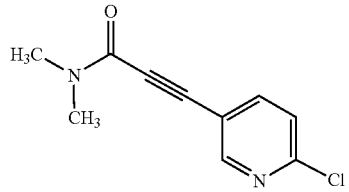

3-(6-Chloro-3-pyridyl)prop-2-ynoic acid (210 mg, 1.16 mmol) was taken up in SOCl₂ (3 mL, 41 mmol) and the resulting mixture was stirred at 80° C. for 1 h. The mixture was concentrated and the resulting residue was taken up in THF (10 mL) and cooled to 0° C. Dimethylamine HCl salt (472 mg, 5.78 mmol) and TEA (1 mL, 7.19 mmol) were added and the mixture was stirred at 0° C. for 30 min and then at rt for 1 h. The mixture was concentrated and the resulting residue was taken up in DCM (10 mL), filtered and purified on a silica gel column eluted with 0-75% EtOAc in Heptane to give the product as a solid (30 mg, 12%). MS ES+m/z 209 [M+H]+.

Step 3: N,N-dimethyl-3-(6-(pyridin-3-ylamino)pyridin-3-yl)propiolamide 3-(6-Chloro-3-pyridyl)-N,N-dimethyl-prop-2-ynamide (30 mg, 0.14 mmol), pyridin-3-amine (18 mg, 0.19 mmol), (2-Dicyclohexylphosphino-2',4',6'-triisopropyl-1,1'-biphenyl)[2-(2-aminoethyl)phenyl)]palladium(II) chloride (11 mg, 0.01 mmol) and Cs$_2$CO$_3$ (94 mg, 0.29 mmol) were taken up in 2-MeTHF (1.5 mL) and the resulting mixture was heated in a microwave reactor at 120° C. for 1 h. Heated again at 130° C. for 1 h. When cooled to rt the mixture was filtered, concentrated and purified by preparative HPLC to give the product as a solid. $^1$H NMR (500 MHz, METHANOL-d4) δ ppm 3.24-3.29 (m, 6H), 6.88 (d, J=8.51 Hz, 1H), 7.36 (dd, J=8.35, 4.57 Hz, 1H), 7.76 (dd, J=8.83, 2.21 Hz, 1H), 8.12-8.19 (m, 1H), 8.27-8.33 (m, 1H), 8.42-8.46 (m, 1H), 8.83 (d, J=2.21 Hz, 1H). MS ES+m/z 267 [M+H]+.

Example 5: N,N-dimethyl-5-(6-(pyridin-3-ylamino)pyridin-3-yl)thiophene-2-carboxamide

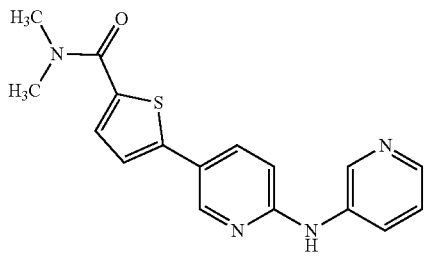 [SMILES: CN(C)C(=O)c1ccc(-c2ccc(Nc3cccnc3)nc2)s1]

Step 1: Intermediate 3 5-(6-Chloro-3-pyridyl)-N,N-dimethyl-thiophene-2-carboxamide

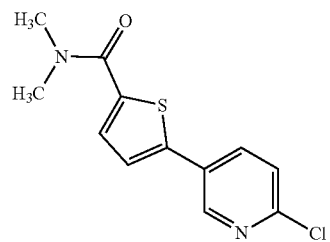 [SMILES: CN(C)C(=O)c1ccc(-c2ccc(Cl)nc2)s1]

(6-Chloro-3-pyridyl)boronic acid (185 mg, 1.17 mmol), 5-bromo-N,N-dimethyl-thiophene-2-carboxamide (183 mg, 0.78 mmol), Pd(PPh$_3$)$_4$ (45 mg, 0.04 mmol) and K$_2$CO$_3$ (324 mg, 12.35 mmol) were taken up in 1,4-Dioxane:H$_2$O:EtOH (6:3:1, 3 mL) and the resulting mixture was stirred at 80° C. overnight. Additional Pd(PPh$_3$)$_4$ (45 mg) was added and the mixture heated in a microwave reactor at 130° C. for 15 min. When cooled to rt the mixture was concentrated and the resulting residue was taken up in DCM (20 mL) and water (10 mL). The organic layer was separated and the aqueous layer extracted with DCM (2×20 mL). The combined organics were washed with water and brine, dried over Na$_2$SO$_4$, filtered, concentrated and purified on a silica gel column, eluted with 0-100% EtOAc in Heptane, to give the product as a solid (61 mg, 29%). MS ES+m/z 267 [M+H]+.

Step 2: N,N-dimethyl-5-(6-(pyridin-3-ylamino)pyridin-3-yl)thiophene-2-carboxamide PEPPSI-iPr (12 mg, 0.02 mmol), Cs$_2$CO$_3$ (126 mg, 0.39 mmol) pyridin-3-amine (32 mg, 0.34 mmol) and 5-(6-chloro-3-pyridyl)-N,N-dimethyl-thiophene-2-carboxamide (61 mg, 0.23 mmol) were dissolved in dry degassed 1,4-Dioxane:DMF (2 mL, 3:1) and the mixture was stirred at 80° C. overnight. The reaction mixture was transferred to a microwave vial and heated in a microwave reactor at 130° C. for 80 min. When cooled to rt the mixture was concentrated and the resulting residue was taken up in EtOAc (20 mL) and water (10 mL). The organic layer was separated and the aqueous layer extracted with EtOAc (2×20 mL). The combined organics were washed with water and brine, dried over Na$_2$SO$_4$, filtered, concentrated and purified by preparative HPLC to give the product as a solid (11 mg, 14%). $^1$H NMR (500 MHz, DMSO-d$_6$) δ ppm 3.33 (s, 6H) 6.94 (d, J=8.83 Hz, 1H) 7.32 (dd, J=8.35, 4.57 Hz, 1H) 7.44 (d, J=3.78 Hz, 1H) 7.47-7.54 (m, 1H) 7.95 (dd, J=8.67, 2.36 Hz, 1H) 8.14 (d, J=4.41 Hz, 1H) 8.17-8.29 (m, 1H) 8.57 (d, J=2.21 Hz, 1H) 8.83 (d, J=2.52 Hz, 1H) 9.53 (br s, 1H). MS ES+m/z 325 [M+H]+.

Example 6: N,N-dimethyl-4-(6-(pyridin-3-ylamino)pyridin-3-yl)cyclohex-3-ene-1-carboxamide

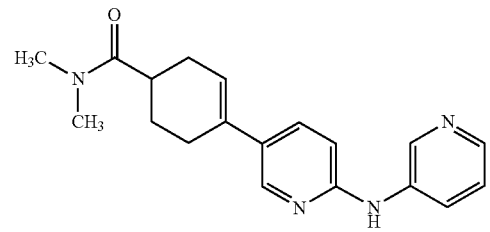 [SMILES: CN(C)C(=O)C1CC=C(c2ccc(Nc3cccnc3)nc2)CC1]

Step 1: Intermediate 4—Methyl 4-(6-chloro-3-pyridyl)cyclohex-3-ene-1-carboxylate

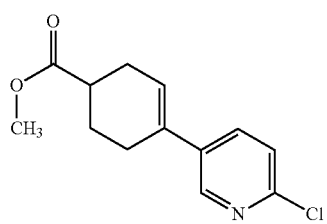 [SMILES: COC(=O)C1CC=C(c2ccc(Cl)nc2)CC1]

Methyl 4-(4,4,5,5-tetramethyl-1,3,2-dioxaborolan-2-yl)cyclohex-3-ene-1-carboxylate (1.1 g, 4.13 mmol), 2-chloro-5-iodo-pyridine (1 g, 4.18 mmol), Pd(PPh$_3$)$_4$ (250 mg, 0.22 mmol) and K$_2$CO$_3$ (1.71 g, 12.4 mmol) were taken up in 1,4-Dioxane (15 mL) and water (5 mL). The mixture was degassed with nitrogen for 5 min, then stirred at 70° C. for 5 h. When cooled to rt the mixture was filtered and the precipitate discarded. The filtrate was diluted with water (5 mL) and EtOAc (20 mL). The organic layer was separated and the aqueous layer extracted with EtOAc (2×10 mL). The combined organics were washed with brine, dried over Na$_2$SO$_4$, filtered, concentrated and purified on a silica gel column, eluted with 0-50% EtOAc in Heptane, to give the product as a solid (300 mg, 29%). MS ES+m/z 252 [M+H]$^+$.

Step 2: Intermediate 5—4-(6-Chloro-3-pyridyl)-N,N-dimethyl-cyclohex-3-ene-1-carboxamide

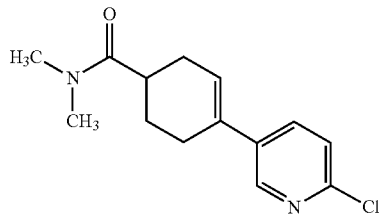 [SMILES: CN(C)C(=O)C1CC=C(c2ccc(Cl)nc2)CC1]

Methyl 4-(6-chloro-3-pyridyl)cyclohex-3-ene-1-carboxylate (300 mg, 1.19 mmol) was taken up in MeOH (3 mL), THF (5 mL) and water (1 mL). LiOH hydrate (60 mg, 1.43 mmol) was added and the resulting mixture was stirred at 50° C. overnight. The mixture was concentrated and the residue was taken up in SOCl$_2$ (4 mL, 55 mmol), stirred at 80° C. for 2 h and then concentrated. In a separate flask, dimethylamine HCl (486 mg, 5.96 mmol) and DIPEA (2 mL, 11.48 mmol) were taken up in THF at 0° C. A solution of the crude acid chloride in THF (5 mL) was added slowly and the resulting mixture was stirred at rt for 1 h. Water (10 mL) and EtOAc (10 mL) were added and the organic layer separated. The aqueous layer was extracted with EtOAc (2×5 mL) and the combined organics were washed with brine, dried over Na$_2$SO$_4$, filtered and concentrated to give the product as a solid (310 mg, 98%). MS ES+m/z 265 [M+H]$^+$.

Step 3: N,N-dimethyl-4-(6-(pyridin-3-ylamino)pyridin-3-yl)cyclohex-3-ene-1-carboxamide 4-(6-Chloro-3-pyridyl)-N,N-dimethyl-cyclohex-3-ene-1-carboxamide (310 mg, 1.17 mmol), pyridin-3-amine (143 mg, 1.52 mmol), TEA (0.08 mL, 0.59 mmol), 2-(2'-Di-tert-butylphosphine)biphenyl palladium(II) acetate (27 mg, 0.06 mmol) and NaOtBu (169 mg, 1.76 mmol) were taken up in Toluene (5 mL) and the resulting mixture was stirred at 80° C. overnight. PEPPSI-iPr (60 mg, 0.09 mmol) and DMF (2 mL) were added and the mixture was stirred at 130° C. for 1.5 h. When cooled to rt water (10 mL), EtOAc (10 mL) and brine (2 mL) were added and the organic layer separated. The aqueous layer was extracted with EtOAc (2×10 mL) and the combined organics were washed with brine, dried over Na$_2$SO$_4$, filtered, concentrated and purified by preparative HPLC to give the product as a solid (40 mg, 11%). $^1$H NMR (500 MHz, CDCl$_3$) δ=8.59 (d, J=2.5 Hz, 1H), 8.31-8.25 (m, 2H), 7.99 (d, J=8.2 Hz, 1H), 7.59 (d, J=8.3 Hz, 1H), 7.30-7.25 (m, 1H, obscured by CDCl$_3$), 6.79 (d, J=8.8 Hz, 1H), 6.63 (s, 1H), 6.11-6.08 (m, 1H), 3.15-3.11 (m, 3H), 3.00 (s, 3H), 2.87-2.81 (m, 1H), 2.60-2.42 (m, 3H), 2.36-2.29 (m, 1H), 2.07-2.00 (m, 1H), 1.95-1.80 (m, 1H). MS ES+m/z 323 [M+H]$^+$.

Example 7: (r,4r)-N,N-dimethyl-4-(6-(pyridin-3-ylamino)pyridin-3-yl)cyclohexane-1-carboxamide

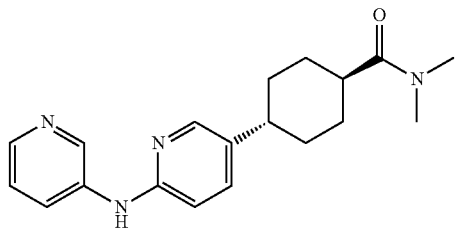 [SMILES: CN(C)C(=O)[C@H]1CC[C@H](c2ccc(Nc3cccnc3)nc2)CC1]

Pd/C (10%, 100 mg, 0.09 mmol) was weighed into a miniclave flask and covered with EtOAc (2 mL). A solution of N,N-dimethyl-4-[6-(3-pyridylamino)-3-pyridyl]cyclohex-3-ene-1-carboxamide (30 mg, 0.09 mmol) in MeOH (5 mL) was added carefully and the resulting mixture was stirred at rt under a hydrogen atmosphere (1.5 bar) for 3 h. The mixture was filtered, concentrated and purified by preparative HPLC to give the products as solids.

First isomer to elute (3 mg, 10%);

$^1$H NMR (500 MHz, CDCl$_3$) δ=8.57 (d, J=2.5 Hz, 1H), 8.24 (dd, J=1.4, 4.6 Hz, 1H), 8.11 (d, J=2.2 Hz, 1H), 7.98-7.93 (m, 1H), 7.41 (dd, J=2.2, 8.5 Hz, 1H), 7.25 (br dd, J=4.6, 8.4 Hz, 1H), 6.79 (d, J=8.2 Hz, 1H), 6.52 (s, 1H), 3.09 (s, 3H), 3.00-2.96 (m, 3H), 2.64-2.51 (m, 2H), 2.11-1.95 (m, 2H), 1.94-1.84 (m, 2H), 1.74 (dq, J=3.2, 12.8 Hz, 2H), 1.48 (dq, J=3.3, 12.9 Hz, 2H). MS ES+m/z 325 [M+H]$^+$.

Example 8: (1s,4s)-N,N-dimethyl-4-(6-(pyridin-3-ylamino)pyridin-3-yl)cyclohexane-1-carboxamide

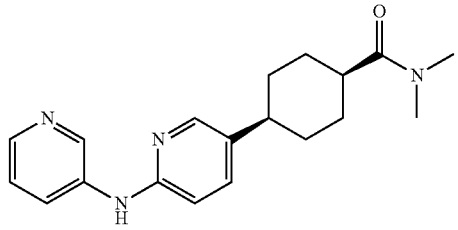 [SMILES: CN(C)C(=O)[C@H]1CC[C@@H](c2ccc(Nc3cccnc3)nc2)CC1]

Pd/C (10%, 100 mg, 0.09 mmol) was weighed into a miniclave flask and covered with EtOAc (2 mL). A solution of N,N-dimethyl-4-[6-(3-pyridylamino)-3-pyridyl]cyclohex-3-ene-1-carboxamide (30 mg, 0.09 mmol) in MeOH (5 mL) was added carefully and the resulting mixture was stirred at rt under a hydrogen atmosphere (1.5 bar) for 3 h. The mixture was filtered, concentrated and purified by preparative HPLC to give the products as solids.

Second isomer to elute (9 mg, 30%);

$^1$H NMR (500 MHz, CDCl$_3$) δ=8.55 (d, J=2.5 Hz, 1H), 8.22 (dd, J=1.3, 4.7 Hz, 1H), 8.13 (d, J=2.2 Hz, 1H), 7.97 (ddd, J=1.4, 2.6, 8.3 Hz, 1H), 7.51 (dd, J=2.2, 8.5 Hz, 1H), 7.26-7.20 (m, J=6.5, 6.5 Hz, 1H), 6.78 (d, J=8.5 Hz, 1H), 6.56 (s, 1H), 3.06 (s, 3H), 2.96 (s, 3H), 2.91-2.86 (m, 1H), 2.64-2.56 (m, 1H), 2.14-2.04 (m, 2H), 2.02-1.94 (m, 2H), 1.75-1.68 (m, 4H). MS ES+m/z 325 [M+H]$^+$.

Example 9: N,N-dimethyl-6'-(pyridin-3-ylamino)-[2,3'-bipyridine]-5-carboxamide

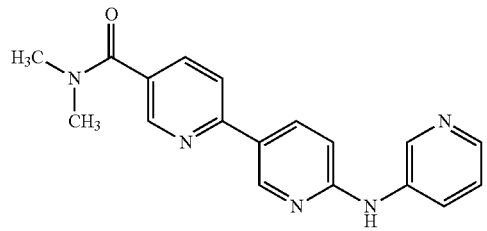

Step 1. Intermediate 6—6-(6-Fluoro-3-pyridyl)-N,N-dimethyl-pyridine-3-carboxamide

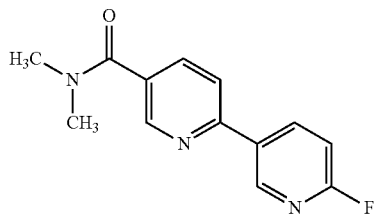 [SMILES: CN(C)C(=O)c1ccc(-c2ccc(F)nc2)nc1]

A mixture of 6-chloro-N,N-dimethyl-pyridine-3-carboxamide (383 mg, 2.07 mmol), (6-fluoro-3-pyridyl)boronic acid (351 mg, 2.49 mmol), PdCl$_2$(Amphos) (73 mg, 0.1 mmol) and K$_2$CO$_3$ (860 mg, 6.22 mmol) in DME (3.5 mL) and water (1.25 mL) was heated in a microwave reactor at 130° C. for 40 min. EtOAc (20 mL) and brine (20 mL) were added the organic layer separated. The aqueous layer was extracted with EtOAc (2×40 mL) and the combined organics were washed with brine, dried over Na$_2$SO$_4$, concentrated and purified on a silica gel column, eluted with 0-100% EtOAc in Heptane, to give the product as a solid (425 mg, 84%). MS ES+m/z 246 [M+H]$^+$.

Step 2: N,N-dimethyl-6'-(pyridin-3-ylamino)-[2,3'-bipyridine]-5-carboxamide To a solution of 3-aminopyridine (138 mg, 1.47 mmol) in 5 mL 2-MeTHF was added 1M LHMDS in THF (1.96 mL, 1.96 mmol) at 0° C. under an argon atmosphere. After 15 minutes 6-(6-fluoro-3-pyridyl)-N,N-dimethyl-pyridine-3-carboxamide (120 mg, 0.49 mmol) in 5 mL 2-MeTHF was added and the mixture was stirred at rt for 1 h. Additional 3-aminopyridine (138 mg, 1.47 mmol) and 1M LHMDS (1.96 mL, 1.96 mmol), pre-mixed in 2-MeTHF (3 mL), was added and the mixture stirred at rt overnight (repeated twice). Water (40 mL) and EtOAc (20 mL) were added, the organic layer separated and the aqueous layer was extracted with EtOAc (10 mL). The combined organics were washed with brine, dried over Na$_2$SO$_4$, concentrated and purified by preparative HPLC to give the product as a solid (30 mg, 19%). $^1$H NMR (500 MHz, DMSO-d$_6$) δ ppm 9.56 (1H, s) 8.96 (1H, d) 8.86 (1H, d) 8.67 (1H, m) 8.35 (1H, dd) 8.27 (1H, m) 8.14 (1H, dd) 7.99 (1H, m) 7.90 (1H, dd) 7.33 (1H, dd) 6.98 (1H, d) 3.02 (3H, s) 2.99 (3H, br s). MS ES+m/z 320 [M+H]$^+$.

Example 10: N,N,2-trimethyl-4-(6-(pyridin-3-ylamino)pyridin-3-yl)benzamide

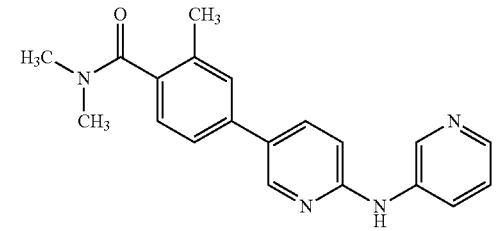 [SMILES: Cc1cc(-c2ccc(Nc3cccnc3)nc2)ccc1C(=O)N(C)C]

Step 1: Intermediate 7—[4-(Dimethylcarbamoyl)-3-methyl-phenyl]boronic acid

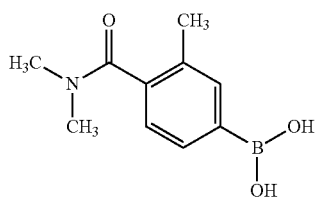

4-Carboxy-3-methylphenylboronic acid (500 mg, 2.78 mmol) was dissolved in DMF (4 mL). DIPEA (2.9 mL, 16.67 mmol) and HATU (1.27 g, 3.33 mmol) were added and the resulting mixture was stirred at rt for 10 min. Dimethylamine HCl (453 mg, 5.56 mmol) was added and the mixture stirred at rt for 3 h. Half-saturated aq. NH$_4$Cl (50 mL) and EtOAc (50 mL) were added, the organic layer was separated and the aqueous layer extracted with EtOAc (3×50 mL). The combined organic layers were washed with brine, dried over Na$_2$SO$_4$, filtered and concentrated to give the product (954 mg, 83%, 50% purity), which was used in the next step without further purification. MS ES+m/z 208 [M+H]$^+$.

Step 1: Intermediate 8—5-Bromo-N-(3-pyridyl)pyridin-2-amine

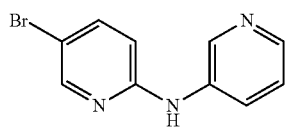 [SMILES: Brc1ccc(Nc2cccnc2)nc1]

1M LHMDS in THF (19.43 mL, 19.43 mmol) was added to a solution of pyridin-3-amine (1.83 g, 19.43 mmol) in 2-MeTHF (80 mL) at 0° C. under a nitrogen atmosphere. After 10 min 5-bromo-2-fluoro-pyridine (1 mL, 9.72 mmol) was added and the mixture was stirred at rt for 2.5 h. Water (100 mL) and EtOAc (100 mL) were added. The organic layer was separated, washed with brine, dried over Na$_2$SO$_4$, filtered, and concentrated. The residue was triturated with MeOH and dried to give the product as a solid (968 mg, 40%). MS ES+m/z 250 [M+H]$^+$.

Step 3: N,N,2-trimethyl-4-(6-(pyridin-3-ylamino)pyridin-3-yl)benzamide

A mixture of 5-bromo-N-(3-pyridyl)pyridin-2-amine (150 mg, 0.6 mmol), [4-(Dimethylcarbamoyl)-3-methyl-phenyl]boronic acid (298 mg, 0.72 mmol, 50% pure), PdCl₂ (AmPhos) (32 mg, 0.05 mmol) and K₂CO₃ (249 mg, 1.8 mmol) in DME (3 mL) and water (1 mL) was heated in a microwave reactor at 130° C. for 40 min. EtOAc (20 mL) and brine (20 mL) were added the organic layer separated. The aqueous layer was extracted with EtOAc (20 mL) and the combined organics were washed with brine, dried over Na₂SO₄, concentrated and purified by preparative HPLC to give the product as a solid (39 mg, 19%). $^1$H NMR (500 MHz, METHANOL-d4) δ ppm 2.37 (s, 3H), 2.93 (s, 3H), 3.17 (s, 3H), 6.99 (d, J=8.51 Hz, 1H), 7.29 (d, J=7.88 Hz, 1H), 7.50-7.59 (m, 3H), 7.96 (dd, J=8.67, 2.36 Hz, 1H), 8.17 (br d, J=4.10 Hz, 1H), 8.35 (m, J=8.30 Hz, 1H), 8.54 (d, J=2.21 Hz, 1H), 9.11 (br s, 1H). MS ES+m/z 333 [M+H]⁺.

Example 11: azetidin-1-yl(4-(6-(pyridin-3-ylamino)pyridin-3-yl)phenyl)methanone

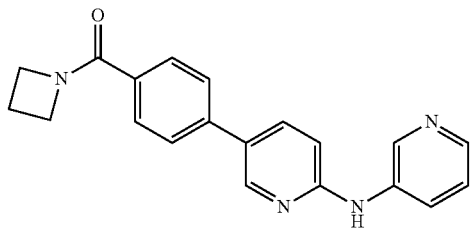 [SMILES: O=C(c1ccc(-c2ccc(Nc3cccnc3)nc2)cc1)N1CCC1]

The title compound was prepared as described in Example 10, starting from 5-Bromo-N-(3-pyridyl)pyridin-2-amine and [4-(azetidine-1-carbonyl)phenyl]boronic acid, to give the product as a solid (90 mg, 22%). $^1$H NMR (400 MHz, DMSO-d₆) δ 9.44 (s, 1H), 8.84 (d, J=2.0 Hz, 1H), 8.58 (d, J=2.4 Hz, 1H), 8.25 (d, J=8.4 Hz, 1H), 8.12 (d, J=4.4 Hz, 1H), 8.00 (dd, J=2.4, 8.8 Hz, 1H), 7.75-7.68 (m, 4H), 7.32-7.29 (m, 1H), 6.97 (d, J=8.8 Hz, 1H), 4.35-4.33 (m, 2H), 4.07-4.05 (m, 2H), 2.31-2.23 (m, 2H). MS ES+m/z 331 [M+H]⁺.

Example 12: 2-fluoro-N,N-dimethyl-4-(6-((5-(2-oxopyrrolidin-1-yl)pyridin-3-yl)amino)pyridin-3-yl)benzamide

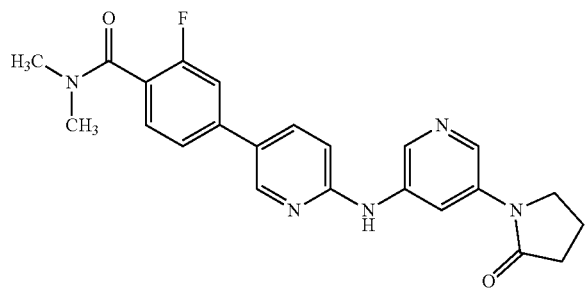 [SMILES: CN(C)C(=O)c1ccc(-c2ccc(Nc3cncc(N4CCCC4=O)c3)nc2)cc1F]

Step 1 Intermediate 9—1-[5-[(5-Bromo-2-pyridyl)amino]-3-pyridyl]pyrrolidin-2-one

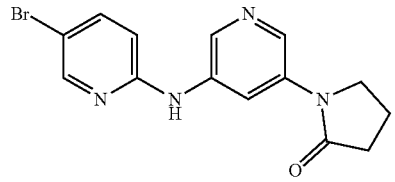 [SMILES: O=C1CCCN1c1cncc(Nc2ccc(Br)cn2)c1]

A mixture of 1-(5-bromo-3-pyridyl)pyrrolidin-2-one (2 g, 8.29 mmol), 5-bromopyridin-2-amine (1.5 g, 9.12 mmol), NaOtBu (1.6 g, 16.5 mmol) and Xantphos (0.48 g, 0.82 mmol) in 1,4-Dioxane (40 mL) was degassed with argon for 15 min. Pd₂(dba)₃ (0.75 g, 0.82 mmol) was added and mixture was stirred at 90° C. for 1 h. When cooled to rt, EtOAc was added and the mixture filtered through celite. The filtrate was concentrated and purified on a silica gel column to give the product as a solid (0.9 g, 32%). MS ES+m/z 333 [M+H]⁺.

Step 2: 2-fluoro-N,N-dimethyl-4-(6-((5-(2-oxopyrrolidin-1-yl)pyridin-3-yl)amino)pyridin-3-yl)benzamide The title compound was prepared as described in Example 10, starting from 1-[5-[(5-Bromo-2-pyridyl)amino]-3-pyridyl]pyrrolidin-2-one and [4-(dimethylcarbamoyl)-3-fluoro-phenyl]boronic acid, to give the product as a solid (19 mg, 10%). $^1$H NMR (400 MHz, DMSO-d₆) δ=9.54 (s, 1H), 8.79 (s, 1H), 8.62 (s, 1H), 8.57 (s, 1H), 8.38 (s, 1H), 8.02 (dd, J=4.0, 8.8 Hz, 2.4 Hz, 1H), 7.65-7.59 (m, 2H), 7.44 (t, 7.6 Hz, 1H), 6.97 (d, J=8 Hz, 1H), 3.88 (t, 7 Hz, 2H), 3.02 (s, 3H), 2.89 (s, 3H), 2.54-2.52 (m, 2H), 2.14-2.07 (m, 2H). MS ES+m/z 420 [M+H]⁺.

Example 13: 3-fluoro-N,N-dimethyl-4-(6-((5-(2-oxopyrrolidin-1-yl)pyridin-3-yl)amino)pyridin-3-yl)benzamide

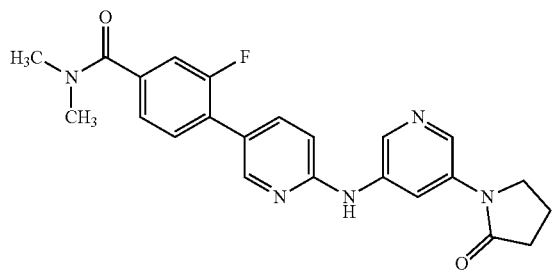

The title compound was prepared as described in Example 10, starting from 1-[5-[(5-Bromo-2-pyridyl)amino]-3-pyridyl]pyrrolidin-2-one and [4-(dimethylcarbamoyl)-2-fluoro-phenyl]boronic acid, to give the product as a solid (26 mg, 14%). $^1$H NMR (400 MHz, DMSO-d₆) δ=9.53 (s, 1H), 8.78 (s, 1H), 8.58 (s, 1H), 8.42 (s, 1H), 8.36 (s, 1H), 7.86 (d, J=8.8 Hz, 1H), 7.63 (t, J=8.0 Hz, 1H), 7.37 (d, 11.2 Hz, 1H), 7.33 (d, 9.6 Hz, 1H), 7.0 (d, J=8.4 Hz, 1H), 3.88 (t, 6.8 Hz, 2H), 2.97 (br s, 6H), 2.54-2.52 (m, 2H), 2.14-2.07 (m, 2H). MS ES+m/z 420 [M+H]⁺.

Example 14: 2,5-difluoro-N,N-dimethyl-4-(6-((5-(2-oxopyrrolidin-1-yl)pyridin-3-yl)amino)pyridin-3-yl)benzamide

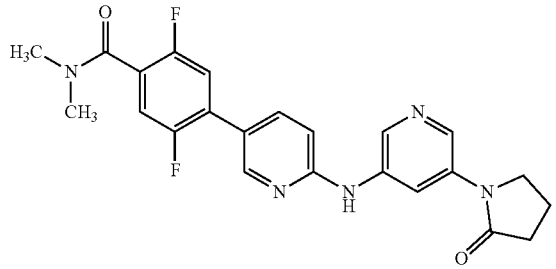 [SMILES: CN(C)C(=O)c1cc(F)c(-c2ccc(Nc3cncc(N4CCCC4=O)c3)nc2)cc1F]

Step 1: Intermediate 10—2,5-Difluoro-N,N-dimethyl-4-(4,4,5,5-tetramethyl-1,3,2-dioxaborolan-2-yl)benzamide

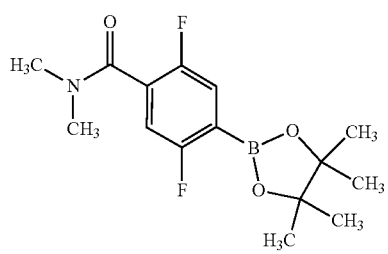

4-Bromo-2,5-difluoro-N,N-dimethyl-benzamide (0.6 g, 2.27 mmol), $B_2Pin_2$ (1.44 g, 5.68 mmol) and KOAc (0.67 g, 6.82 mmol) were taken up in 1,4-dioxane (15 mL) and the mixture was degassed with argon for 10 min. $PdCl_2$ (dppf) DCM adduct (186 mg, 0.28 mmol) was added and the mixture stirred at 100° C. overnight. Water was added and the mixture extracted with EtOAc. The combined organic layers were washed with brine, dried over $Na_2SO_4$, filtered, concentrated and purified on a silica gel column to give the product (550 mg, 78%). MS ES+ m/z 230 [M+H]$^+$ (boronic acid).

Step 2: 2,5-difluoro-N,N-dimethyl-4-(6-((5-(2-oxopyrrolidin-1-yl)pyridin-3-yl)amino)pyridin-3-yl)benzamide The title compound was prepared as described in Example 10, starting from 1-[5-[(5-bromo-2-pyridyl)amino]-3-pyridyl]pyrrolidin-2-one and 2,5-difluoro-N,N-dimethyl-4-(4,4,5,5-tetramethyl-1,3,2-dioxaborolan-2-yl)benzamide, to give the product as a solid (49 mg, 18%). $^1$H NMR (400 MHz, DMSO-d$_6$) δ=8.77 (s, 1H), 8.59 (s, 1H), 8.45 (s, 1H), 8.39 (s, 1H), 7.89 (d, J=4.0, 7.2 Hz, 1H), 7.60-7.57 (m, 1H), 7.42-7.39 (m, 1H), 7.0 (d, J=6.8 Hz, 1H), 3.88 (t, 5.6 Hz, 2H), 3.02 (s, 3H), 2.91 (s, 3H), 2.54-2.52 (m, 2H), 2.12-2.09 (m, 2H). MS ES+m/z 438 [M+H]$^+$.

Example 15: N-methyl-4-[6-[[5-(2-oxopyrrolidin-1-yl)-3-pyridyl]amino]-3-pyridyl]benzamide

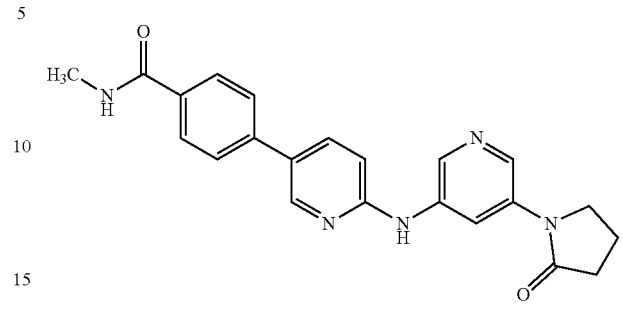

The title compound was prepared as described in Example 10, starting from 1-[5-[(5-bromo-2-pyridyl)amino]-3-pyridyl]pyrrolidin-2-one and [4-(methylcarbamoyl)phenyl]boronic acid, to give the product as a solid (100 mg, 34%). $^1$H NMR (400 MHz, DMSO-d$_6$) δ 9.51 (s, 1H), 8.78 (d, J=2.0 Hz, 1H), 8.60-8.59 (m, 2H), 8.46 (d, J=3.0 Hz, 1H), 8.38 (d, J=2.4 Hz, 1H), 8.01 (dd, J=2.4, 8.8 Hz, 1H), 7.92-7.90 (m, 2H), 7.78-7.76 (m, 2H), 6.98 (d, J=8.8 Hz, 1H), 3.88 (t, J=7.0 Hz, 1H), 2.80 (d, J=4.4 Hz, 3H), 2.54-2.50 (m, 2H), 2.14-2.07 (m, 2H). MS ES+m/z 388 [M+H]$^+$.

Example 16: N,N-dimethyl-4-(4-methyl-6-(pyridin-3-ylamino)pyridin-3-yl)benzamide

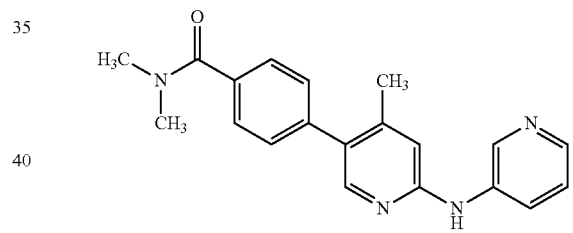

Step 1: Intermediate 11—5-Bromo-4-methyl-N-(3-pyridyl)pyridin-2-amine

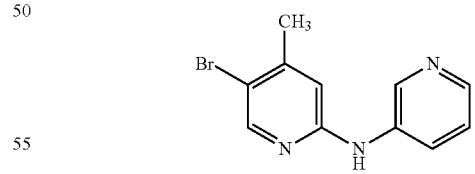

The title compound was prepared as described in Intermediate 9, starting from 2,5-dibromo-4-methyl-pyridine and pyridin-3-amine and using DMF as solvent, to give the product as a solid (150 mg, 20%). MS ES+m/z 264 [M+H]$^+$.

Step 2: N,N-dimethyl-4-(4-methyl-6-(pyridin-3-ylamino)pyridin-3-yl)benzamide The title compound was prepared as described in Example 10, starting from 5-bromo-4-methyl-N-(3-pyridyl)pyridin- 2-amine and [4-(dimethylcarbamoyl)phenyl]boronic acid, to give the product as a solid (90 mg, 21%). $^1$H NMR (400 MHz, DMSO-d$_6$) δ 9.26 (s, 1H), 8.81 (d, J=2.4 Hz, 1H), 8.23 (d, J=8.4 Hz, 1H), 8.09 (d, J=3.6 Hz, 1H), 8.03 (s, 1H), 7.48-7.42 (m, 4H), 7.30-7.26 (m, 1H), 6.8 (s, 1H), 2.9 (br s, 6H), 2.24 (s, 3H). MS ES+m/z 333 [M+H]$^+$.

Example 17: 4-(4-ethyl-6-(pyridin-3-ylamino)pyridin-3-yl)-N,N-dimethylbenzamide

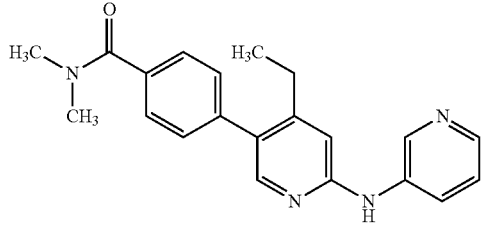 [SMILES: CCc1cc(Nc2cccnc2)ncc1-c1ccc(C(=O)N(C)C)cc1]

Step 1: Intermediate 12—4-(6-Amino-4-ethyl-3-pyridyl)-N,N-dimethyl-benzamide

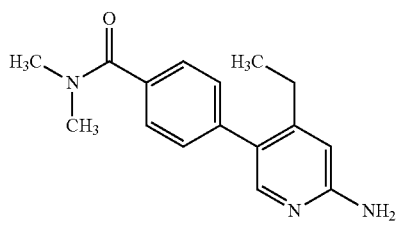 [SMILES: CCc1cc(N)ncc1-c1ccc(C(=O)N(C)C)cc1]

The title compound was prepared as described in Example 10, starting from 5-bromo-4-ethyl-pyridin-2-amine and [4-(methylcarbamoyl)phenyl]boronic acid, to give the product as a solid (400 mg, 36%). MS ES+m/z 270 [M+H]$^+$.

Step 2: 4-(4-ethyl-6-(pyridin-3-ylamino)pyridin-3-yl)-N,N-dimethylbenzamide Xantphos (22 mg, 0.04 mmol) and Pd$_2$(dba)$_3$ (17 mg, 0.02 mmol) was mixed in toluene (0.5 mL), stirred at 50° C. for 15 min and then transferred to a mixture of 4-(6-amino-4-ethyl-3-pyridyl)-N,N-dimethyl-benzamide (100 mg, 0.37 mmol), 3-bromopyridine (59 mg, 0.37 mmol) and NaOtBu (72 mg, 0.75 mmol) in toluene (3 mL). The resulting mixture was stirred at 90° C. overnight. When cooled to rt the reaction mixture was filtered through celite, concentrated and purified by preparative HPLC to give the product as a solid (25 mg, 19%). $^1$H NMR (500 MHz, DMSO-d$_6$) δ ppm 1.07 (t, J=7.41 Hz, 3H), 2.57 (q, J=7.36 Hz, 2H), 2.98 (br s, 6H), 6.84 (s, 1H), 7.28 (dd, J=8.35, 4.57 Hz, 1H), 7.40 (m, J=7.88 Hz, 2H), 7.47 (m, J=7.88 Hz, 2H), 7.99 (s, 1H), 8.09 (d, J=4.89 Hz, 1H), 8.24 (br d, J=9.46 Hz, 1H), 8.81 (d, J=2.52 Hz, 1H), 9.29 (s, 1H). MS ES+m/z 347 [M+H]$^+$.

Example 18: N,N-dimethyl-4-(5-(pyridin-3-ylamino)pyrazin-2-yl)benzamide

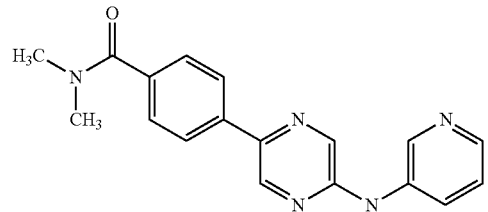

Step 1: Intermediate 13 Step 1: 4-(5-Chloropyrazin-2-yl)-N,N-dimethyl-benzamide

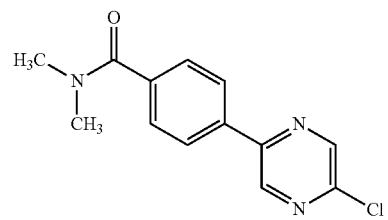 [SMILES: CN(C)C(=O)c1ccc(-c2cnc(Cl)cn2)cc1]

The title compound was prepared as described in Intermediate 3, starting from 2-bromo-5-chloro-pyrazine and [4-(dimethylcarbamoyl)phenyl]boronic acid and stirring the mixture at 70° C. for 30 min, to give the product as a solid (250 mg, 92%). MS ES+m/z 262 [M+H]$^+$.

Step 2: N,N-dimethyl-4-(5-(pyridin-3-ylamino)pyrazin-2-yl)benzamide 4-(5-Chloropyrazin-2-yl)-N,N-dimethyl-benzamide (150 mg, 0.57 mmol), pyridin-3-amine (80 mg, 0.85 mmol), KOtBu (110 mg, 0.98 mmol) and PEPPSI-IPr (7 mg, 0.01 mmol) were taken up in 1,4-Dioxane (1.5 mL) and the resulting mixture was heated in a microwave reactor at 130° C. for 1 h. When cooled to rt the mixture was diluted with EtOAc (10 mL), water (2 mL) and brine (5 mL). The organic layer was separated and the aqueous layer extracted with EtOAc (2×10 mL). The combined organics were washed with brine, dried over Na$_2$SO$_4$, filtered, concentrated and purified by preparative HPLC to give the product as a solid (7 mg, 4%). $^1$H NMR (500 MHz, DMSO) δ 9.91 (s, 1H), 8.88 (d, J=2.2 Hz, 1H), 8.83 (s, 1H), 8.37 (s, 1H), 8.30-8.21 (m, 1H), 8.19 (d, J=4.4 Hz, 1H), 8.07 (d, J=7.9 Hz, 2H), 7.50 (d, J=8.2 Hz, 2H), 7.36 (dd, J=4.7, 8.2 Hz, 1H), 3.10-2.91 (m, 6H). MS ES+m/z 320 [M+H]$^+$.

Example 19: N,N-dimethyl-4-(5-((5-(2-oxopyrrolidin-1-yl)pyridin-3-yl)amino)pyrazin-2-yl)benzamide

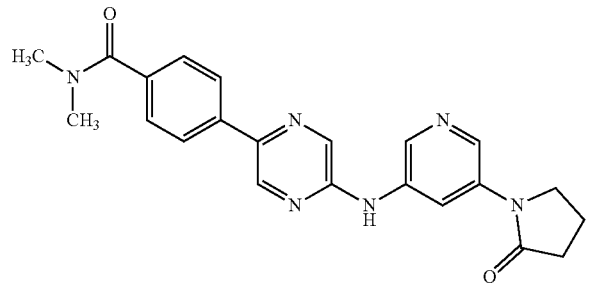 [SMILES: CN(C)C(=O)c1ccc(-c2cnc(Nc3cncc(N4CCCC4=O)c3)cn2)cc1]

Step 1 Intermediate 14—1-(5-Amino-3-pyridyl)pyrrolidin-2-one

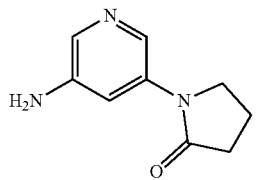 [SMILES: Nc1cncc(N2CCCC2=O)c1]

5-Bromopyridin-3-amine (10 g, 57.8 mmol), pyrrolidin-2-one (9 mL, 63.2 mmol), K$_2$CO$_3$ (15 g, 115.6 mmol), CuI (1.1 g, 5.78 mmol) and DMEDA (1.3 mL, 8.42 mmol) were taken up in 1,4-dioxane (100 mL) and the resulting mixture was refluxed overnight. When cooled to rt EtOAc was added and the mixture filtered through celite. The filtrate was concentrated and purified on a silica gel column to give the product as a solid (6 g, 59%). MS ES+m/z 178 [M+H]$^+$.

Step 2: Intermediate 15—1-[5-[(5-Bromopyrazin-2-yl)amino]-3-pyridyl]pyrrolidin-2-one

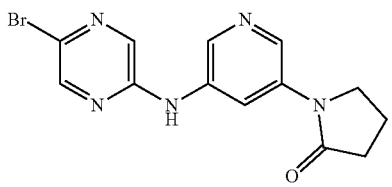 [SMILES: O=C1CCCN1c1cncc(Nc2cnc(Br)cn2)c1]

The title compound was prepared as described in Intermediate 9, starting from 1-(5-Amino-3-pyridyl)pyrrolidin-2-one and 2,5-dibromopyrazine, using Cs$_2$CO$_3$ instead of NaOtBu, to give the product as a solid (110 mg, 23%). MS ES+m/z 334 [M+H]$^+$.

Step 3: N,N-dimethyl-4-(5-((5-(2-oxopyrrolidin-1-yl)pyridin-3-yl)amino)pyrazin-2-yl)benzamide The title compound was prepared as described in Example 10, starting from 1-[5-[(5-bromopyrazin-2-yl)amino]-3-pyridyl]pyrrolidin-2-one and [4-(dimethylcarbamoyl)phenyl]boronic acid, to give the product as a solid (70 mg, 23%). $^1$H NMR (400 MHz, DMSO-d$_6$) δ 9.96 (s, 1H), 8.83 (dd, J=10.8, 1.6 Hz, 1H), 8.61 (t, J=2.2 Hz, 1H), 8.41 (d, J=2.8 Hz, 1H), 8.38 (d, J=1.2 Hz, 1H), 8.07 (d, J=4.4 Hz, 2H), 7.50 (d, J=8.4 Hz, 2H), 3.89 (t, J=6.8 Hz, 2H), 2.97 (bs, 6H), 2.55-2.52 (m, 2H), 2.15-2.07 (m, 2H). MS ES+m/z 403 [M+H]$^+$.

Example 20: 2-fluoro-N,N-dimethyl-4-(5-((5-(2-oxopyrrolidin-1-yl)pyridin-3-yl)amino)pyrazin-2-yl)benzamide

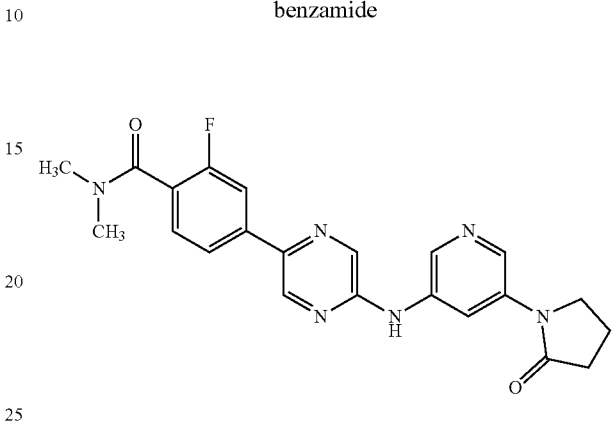

The title compound was prepared as described in Example 10, starting from 1-[5-[(5-bromopyrazin-2-yl)amino]-3-pyridyl]pyrrolidin-2-one and [4-(dimethylcarbamoyl)-3-fluoro-phenyl]boronic acid, to give the product as a solid (96 mg, 30%). $^1$H NMR (400 MHz, DMSO-d$_6$) δ 10.02 (s, 1H), 8.89 (d, J=0.8 Hz, 1H), 8.81 (d, J=2.0 Hz, 1H), 8.61 (t, J=2.2 Hz, 1H), 8.42 (d, J=2.4 Hz, 1H), 8.37 (d, J=0.8 Hz, 1H), 7.96-7.89 (m, 2H), 7.47 (t, J=7.6 Hz, 1H), 3.89 (t, J=7.2 Hz, 2H), 3.02 (s, 3H), 2.89 (s, 3H), 2.55-2.52 (m, 2H), 2.15-2.07 (m, 2H). MS ES+m/z 421 [M+H]$^+$.

Example 21: 3-fluoro-N,N-dimethyl-4-(5-((5-(2-oxopyrrolidin-1-yl)pyridin-3-yl)amino)pyrazin-2-yl)benzamide

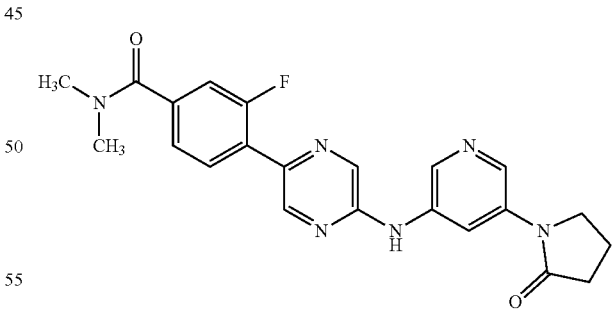

The title compound was prepared as described in Example 10, starting from 1-[5-[(5-bromopyrazin-2-yl)amino]-3-pyridyl]pyrrolidin-2-one and [4-(dimethylcarbamoyl)-2-fluoro-phenyl]boronic acid, to give the product as a solid (33 mg, 11%). $^1$H NMR (400 MHz, DMSO-d$_6$) δ 10.03 (s, 1H), 8.80 (d, J=2.0 Hz, 1H), 8.64 (d, J=2.0 Hz, 2H), 8.43 (d, J=2.4 Hz, 2H), 7.99 (t, J=2.2 Hz, 1H), 7.42-7.35 (m, 2H), 3.89 (t, J=7.0 Hz, 2H), 3.00 (s, 3H), 2.96 (s, 3H), 2.53-2.50 (m, 2H), 2.13-2.09 (m, 2H). MS ES+m/z 421 [M+H]$^+$.

Example 22: 2,5-difluoro-N,N-dimethyl-4-(5-((5-(2-oxopyrrolidin-1-yl)pyridin-3-yl)amino)pyrazin-2-yl)benzamide

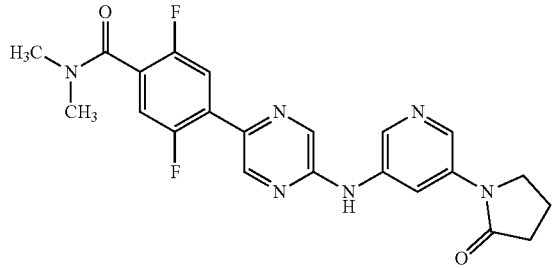 [SMILES: CN(C)C(=O)c1cc(F)c(-c2cnc(Nc3cncc(N4CCCC4=O)c3)cn2)cc1F]

The title compound was prepared as described in Example 10, starting from 1-[5-[(5-bromopyrazin-2-yl)amino]-3-pyridyl]pyrrolidin-2-one and 2,5-difluoro-N,N-dimethyl-4-(4,4,5,5-tetramethyl-1,3,2-dioxaborolan-2-yl)benzamide, to give the product as a solid (91 mg, 30%). $^1$H NMR (400 MHz, DMSO-$d_6$) δ 10.10 (s, 1H), 8.80 (d, J=2.4 Hz, 1H), 8.67-8.64 (m, 2H), 8.44-8.42 (m, 2H), 7.83-7.78 (m, 1H), 7.49-7.45 (m, 1H), 3.89 (t, J=7.2 Hz, 2H), 3.02 (s, 3H), 2.91 (s, 3H), 2.55-2.53 (m, 2H), 2.15-2.07 (m, 2H). MS ES+m/z 439 [M+H]$^+$.

Example 23: 4-(5-((5-(3-benzyl-2-oxoimidazolidin-1-yl)pyridin-3-yl)amino)pyrazin-2-yl)-N,N-dimethylbenzamide

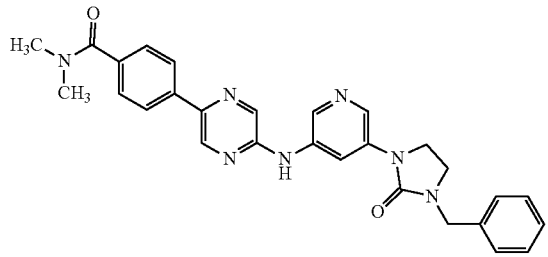 [SMILES: CN(C)C(=O)c1ccc(-c2cnc(Nc3cncc(N4CCN(Cc5ccccc5)C4=O)c3)cn2)cc1]

Step 1: Intermediate 16—4-(5-Aminopyrazin-2-yl)-N,N-dimethyl-benzamide

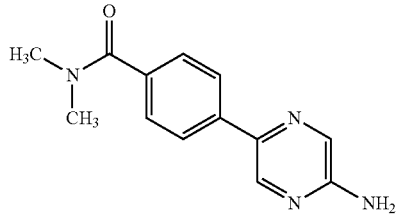 [SMILES: CN(C)C(=O)c1ccc(-c2cnc(N)cn2)cc1]

The title compound was prepared as described in Intermediate 3, starting from 5-bromopyrazin-2-amine and [4-(dimethylcarbamoyl)phenyl]boronic acid and stirring the mixture at 90° C. for 2 h, to give the product as a solid (230 mg, 83%). MS ES+m/z 243 [M+H]$^+$.

Step 2: Intermediate 17—1-(5-Bromo-3-pyridyl)-3-(2-chloroethyl)urea

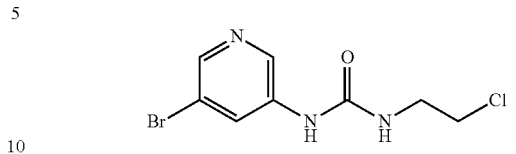

2-Chloroethyl isocyanate (640 μL, 7.5 mmol) was added dropwise over 5 min to a solution of 5-bromopyridin-3-amine (865 mg, 5 mmol) in toluene (10 mL) at 0° C. The resulting mixture was stirred at rt overnight. The formed precipitate was filtered off, washed sequentially with toluene (3 mL), pentane, (3 mL) and dried to give the product as a solid (1.3 g, 93%). MS ES+m/z 278 [M+H]$^+$.

Step 3: Intermediate 18—1-(5-Bromo-3-pyridyl)imidazolidin-2-one

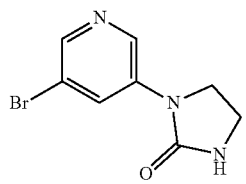 [SMILES: O=C1NCCN1c1cncc(Br)c1]

A solution of 1-(5-bromo-3-pyridyl)-3-(2-chloroethyl)urea (1.3 g, 4.67 mmol) in DMF (10 mL) was added slowly to suspension of NaH (60%, 268 mg, 7 mmol) in THF (10 mL) at 0° C. The resulting mixture was stirred at rt for 1 h. MeOH (5 mL) was added at 0° C. and the mixture concentrated. The resulting residue was partitioned between water (50 mL) and CHCl$_3$ (20 mL). The organic layer was separated and the aqueous layer extracted with CHCl$_3$ (2×20 mL). The combined organics were washed with water (20 mL), sat. aq. NaHCO$_3$ (20 mL), dried over Na$_2$SO$_4$, and concentrated. The resulting solid was triturated with EtOAc: pentane (1:3, 2×4 mL) followed by pentane (3 mL) and dried to give the product as a solid (850 mg, 75%). MS ES+m/z 242 [M+H]$^+$.

Step 4: Intermediate 19—1-Benzyl-3-(5-bromo-3-pyridyl)imidazolidin-2-one

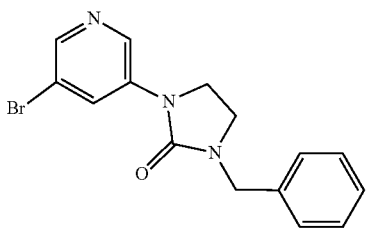 [SMILES: O=C1N(Cc2ccccc2)CCN1c1cncc(Br)c1]

1-(5-Bromo-3-pyridyl)imidazolidin-2-one (240 mg, 0.99 mmol) and TBAB (31.96 mg, 0.1 mmol) were taken up in toluene (5 mL). Aq. 2M NaOH (1.5 mL) was added followed by chloromethyl benzene (126 μL, 1.09 mmol) and the resulting mixture was stirred at 50° C. for 5 h. Additional chloromethyl benzene (126 μL, 1.09 mmol) was added and stirring continued at 50° C. overnight. When cooled to rt EtOAc (5 mL) and water (5 mL) were added. The organic layer was separated and washed with brine, dried over Na₂SO₄, filtered and concentrated to give the product as an oil (320 mg, 97%). MS ES+m/z 332 [M+H]⁺.

Step 5: 4-(5-((5-(3-benzyl-2-oxoimidazolidin-1-yl)pyridin-3-yl)amino)pyrazin-2-yl)-N,N-dimethylbenzamide The title compound was prepared as described in Intermediate 9, starting from 4-(5-aminopyrazin-2-yl)-N,N-dimethyl-benzamide and 1-benzyl-3-(5-bromo-3-pyridyl)imidazolidin-2-one, to give the product as a solid (21 mg, 10%). ¹H NMR (500 MHz, DMSO-d₆) δ ppm 2.99 (br d, J=11.98 Hz, 6H), 3.40-3.46 (m, 2H), 3.87-3.92 (m, 2H), 4.44 (s, 2H), 7.30-7.41 (m, 5H), 7.51 (m, J=8.20 Hz, 2H), 8.09 (m, J=8.20 Hz, 2H), 8.38 (s, 1H), 8.39 (s, 1H), 8.52-8.55 (m, 1H), 8.73 (d, J=2.21 Hz, 1H), 8.84 (s, 1H), 9.91 (s, 1H). MS ES+m/z 494 [M+H]⁺.

Example 24: N,N-dimethyl-4-(6-((5-(N-methylmethylsulfonamido)pyridin-3-yl)amino)pyridin-3-yl)benzamide

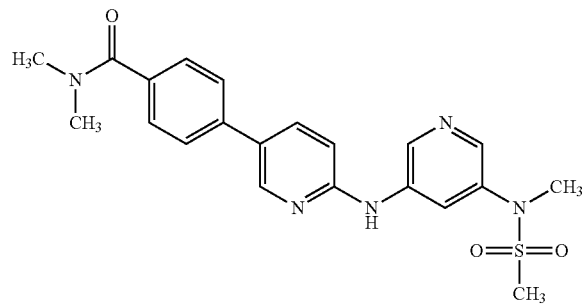 [SMILES: CN(C)C(=O)c1ccc(-c2ccc(Nc3cncc(N(C)S(C)(=O)=O)c3)nc2)cc1]

Step 1: Intermediate 20—N-(5-bromo-3-pyridyl)-N-methyl-methanesulfonamide

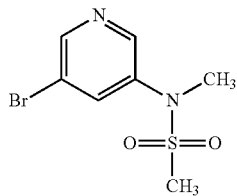

To a stirred solution of 5-bromo-N-methyl-pyridin-3-amine (518 mg, 2.77 mmol) and TEA (0.58 mL, 4.15 mmol) in THF (5 mL) was added methanesulfonyl chloride (0.26 mL, 3.32 mmol) dropwise. The resulting mixture was stirred at 60° C. for 1 h. Additional TEA (0.58 mL, 4.15 mmol) and methanesulfonyl chloride (0.26 mL, 3.32 mmol) were added and stirring continued for 30 min. Water (5 mL) was added and the THF removed in vacuo. The resulting residue was extracted with EtOAc (2×10 mL) and the combined organics were dried over Na₂SO₄, filtered and concentrated to give the product as an oil (734 mg, quant.), which was used in the next step without further purification. MS ES+m/z 267 [M+H]⁺.

Step 2: N,N-dimethyl-4-(6-((5-(N-methylmethylsulfonamido)pyridin-3-yl)amino)pyridin-3-yl)benzamide The title compound was prepared as described in Example 17, starting from 4-(6-amino-3-pyridyl)-N,N-dimethyl-benzamide and N-(5-bromo-3-pyridyl)-N-methyl-methanesulfonamide, to give the product as a solid (24 mg, 13%). ¹H NMR (500 MHz, DMSO-d₆) δ ppm 2.99 (br s, 6H), 3.06 (s, 3H), 3.31 (s, 3H), 7.00 (d, J=8.83 Hz, 1H), 7.50 (d, J=8.20 Hz, 2H), 7.75 (d, J=8.20 Hz, 2H), 8.03 (dd, J=8.67, 2.68 Hz, 1H), 8.21 (d, J=2.52 Hz, 1H), 8.31 (t, J=2.21 Hz, 1H), 8.62 (d, J=2.52 Hz, 1H), 8.82 (d, J=2.21 Hz, 1H), 9.59 (s, 1H). MS ES+m/z 426 [M+H]⁺.

Example 25: N,N-dimethyl-4-(6-((5-(N-methylcyclopropanesulfonamido)pyridin-3-yl)amino)pyridin-3-yl)benzamide

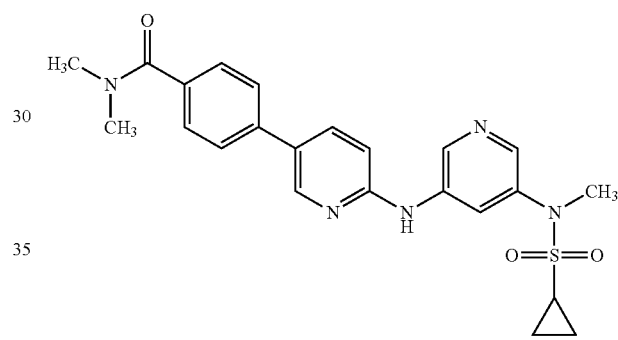

Step 1: Intermediate 21—N-(5-bromo-3-pyridyl)-N-methyl-cyclopropanesulfonamide

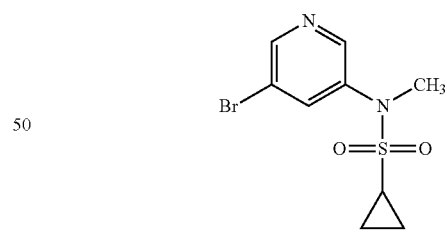

The title compound was prepared as described in Intermediate 20, using cyclopropanesulfonyl chloride and purified by preparative HPLC, to give the product (250 mg, 15%). MS ES+m/z 291 [M+H]⁺.

Step 2: N,N-dimethyl-4-(6-((5-(N-methylcyclopropanesulfonamido)pyridin-3-yl)amino)pyridin-3-yl)benzamide A mixture of XantPhos (40 mg, 0.07 mmol), Pd₂(dba)₃ (31 mg, 0.03 mmol), 4-(6-amino-3-pyridyl)-N,N-dimethyl-benzamide (166 mg, 0.69 mmol), N-(5-bromo-3-pyridyl)-

N-methyl-cyclopropanesulfonamide (200 mg, 0.69 mmol) and NaOtBu (132 mg, 1.38 mmol) in 1,4-dioxane (10 mL) was heated in a microwave reactor at 130° C. for 1 h. When cooled to rt the mixture was diluted with EtOAc and filtered through celite. The filtrate was washed with brine, dried over Na$_2$SO$_4$, filtered, concentrated and purified by preparative HPLC to give the product as a solid (125 mg, 40%). $^1$H NMR (400 MHz, DMSO-d$_6$) δ 9.59 (s, 1H), 8.78 (d, J=2.0 Hz, 1H), 8.60 (d, J=2.4 Hz, 1H), 8.38 (t, J=2.2 Hz, 1H), 8.20 (d, J=2.0 Hz, 1H), 8.01 (dd, J=7.8, 2.6 Hz, 1H), 7.73 (d, J=8.4 Hz, 2H), 7.48 (d, J=8.0 Hz, 2H), 6.98 (d, J=8.4 Hz, 1H), 3.36-3.26 (m, 3H), 2.98 (bs, 6H), 2.83-2.77 (m, 1H), 1.05-1.00 (m, 2H), 0.90-0.86 (m, 2H). MS ES+m/z 452 [M+H]$^+$.

Example 26: N,N-dimethyl-4-(6-((5-(N-methylpropan-2-ylsulfonamido)pyridin-3-yl)amino)pyridin-3-yl)benzamide

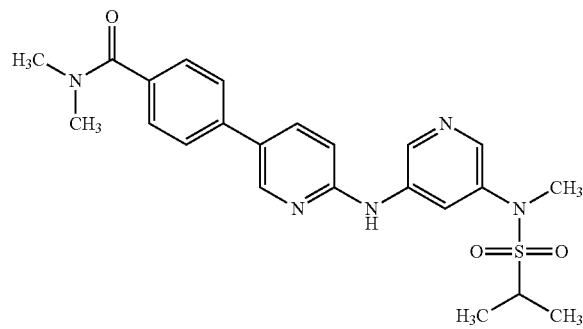 [SMILES: CC(C)S(=O)(=O)N(C)c1cncc(Nc2ccc(-c3ccc(C(=O)N(C)C)cc3)cn2)c1]

Step 1: Intermediate 22—N-(5-bromo-3-pyridyl)-N-methyl-propane-2-sulfonamide

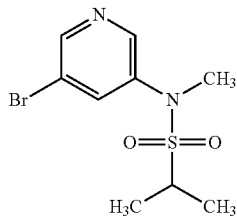

To a solution of N-(5-bromo-3-pyridyl)propane-2-sulfonamide (175 mg, 0.63 mmol) in THF (2 mL) at 0° C. were added MeOH (0.12 mL, 3.14 mmol) and PPh$_3$ (197 mg, 0.75 mmol). After stirring for 10 min, DIAD (0.15 mL, 0.75 mmol) was added and the resulting mixture was stirred at rt overnight. The reaction mixture was poured into water (10 mL) and extracted with EtOAc (2×25 mL). The combined organics were washed with brine, dried over Na$_2$SO$_4$, filtered, concentrated and purified on a silica gel column eluted with 40-50% EtOAc in heptane to give the product as a solid (200 mg, 38%). MS ES+m/z 293 [M+H]$^+$.

Step 2: N,N-dimethyl-4-(6-((5-(N-methylpropan-2-ylsulfonamido)pyridin-3-yl)amino)pyridin-3-yl)benzamide The title compound was prepared as described in Example 25 to give the product as a solid (50 mg, 36%). $^1$H NMR (400 MHz, DMSO-d$_6$) δ 9.57 (s, 1H), 8.80 (d, J=2.4 Hz, 1H), 8.59 (d, J=2.4 Hz, 1H), 8.34 (t, J=2.2 Hz, 1H), 8.21 (d, J=2.4 Hz, 1H), 8.01 (dd, J=2.6, 8.6 Hz, 1H), 7.73 (d, J=8.0 Hz, 2H), 7.48 (d, J=8.4 Hz, 2H), 6.98 (d, J=8.8 Hz, 1H), 3.59-3.52 (m, 1H), 3.48 (s, 3H), 2.97 (bs, 6H), 1.28 (d, J=6.8 Hz, 6H). MS ES+m/z 454 [M+H]$^+$.

Example 27: 4-(6-((5-(N-isopropylmethylsulfonamido)pyridin-3-yl)amino)pyridin-3-yl)-N,N-dimethylbenzamide

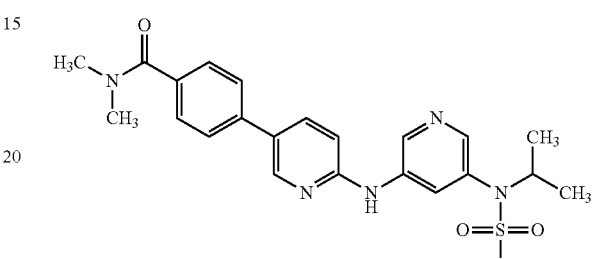

Step 1: Intermediate 23—N-(5-bromo-3-pyridyl)-N-isopropyl-methanesulfonamide

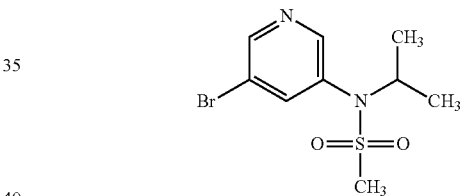

To a solution of 5-bromo-N-isopropyl-pyridin-3-amine (1 g, 4.65 mmol) in pyridine (10 mL) was added DMAP (113 mg, 0.93 mmol) and methanesulfonyl chloride (1.14 mL, 13.95 mmol) at rt and the resulting mixture was stirred at 60° C. overnight. When cooled to rt, the mixture was poured into water (10 mL) and extracted with EtOAc (2×25 mL). The combined organics were washed with brine, dried over Na$_2$SO$_4$, filtered, concentrated and purified by preparative HPLC to give the product (300 mg, 19%). MS ES+m/z 293 [M+H]$^+$.

Step 2: 4-(6-((5-(N-isopropylmethylsulfonamido)pyridin-3-yl)amino)pyridin-3-yl)-N,N-dimethylbenzamide The title compound was prepared as described in Example 25 to give the product as a solid (160 mg, 34%). $^1$H NMR (400 MHz, DMSO-d$_6$) δ 9.59 (s, 1H), 8.91 (d, J=2.0 Hz, 1H), 8.59 (d, J=2.4 Hz, 1H), 8.22 (d, J=2.0 Hz, 1H), 8.05-8.01 (m, 2H), 7.73 (d, J=8.4 Hz, 2H), 7.48 (d, J=8.4 Hz, 2H), 6.98 (d, J=8.4 Hz, 1H), 4.39-4.36 (m, 1H), 3.15 (s, 3H), 2.98 (s, 6H), 1.14 (d, J=6.8 Hz, 6H). MS ES+m/z 454 [M+H]$^+$.

Example 28: 4-(6-((5-(N-cyclopropylmethylsulfonamido)pyridin-3-yl)amino)pyridin-3-yl)-N,N-dimethylbenzamide

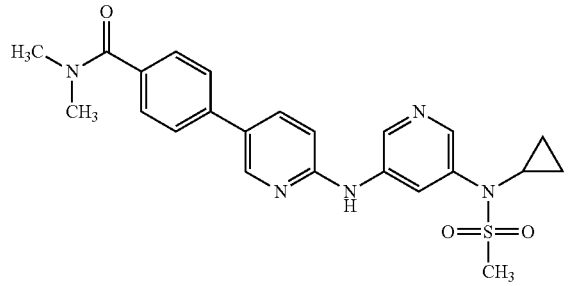 [SMILES: CN(C)C(=O)c1ccc(-c2ccc(Nc3cncc(N(C4CC4)S(C)(=O)=O)c3)nc2)cc1]

Step 1: Intermediate 24—N-(5-bromo-3-pyridyl)-N-cyclopropyl-methanesulfonamide

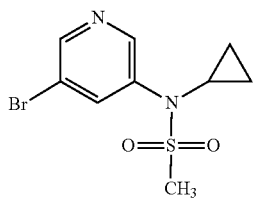

The title compound was prepared as described in Intermediate 23, starting from 5-bromo-N-cyclopropyl-pyridin-3-amine, to give the product (400 mg, 58%). MS ES+m/z 291 [M+H]+.

Step 2: 4-(6-((5-(N-cyclopropylmethylsulfonamido)pyridin-3-yl)amino)pyridin-3-yl)-N,N-dimethylbenzamide The title compound was prepared as described in Example 25 to give the product as a solid (180 mg, 38%). ¹H NMR (400 MHz, DMSO-d₆) δ 9.56 (s, 1H), 8.81 (d, J=2.0 Hz, 1H), 8.60 (d, J=2.4 Hz, 1H), 8.24 (s, 1H), 8.16 (d, J=2.0 Hz, 1H), 8.01 (dd, J=8.8, 2.4 Hz, 1H), 7.73 (d, J=7.6 Hz, 2H), 7.48 (d, J=7.6 Hz, 2H), 6.98 (d, J=8.4 Hz, 1H), 3.23-3.20 (m, 1H), 3.12 (s, 3H), 2.98 (bs, 6H), 0.89-0.84 (m, 2H), 0.68-0.66 (m, 2H). MS ES+m/z 452 [M+H]+.

Example 29: N,N-dimethyl-2-(6-(pyridin-3-ylamino)pyridin-3-yl)pyrimidine-5-carboxamide

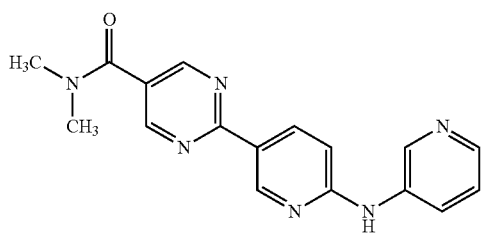

Step 1: Intermediate 25—6-(3-Pyridylamino)pyridine-3-carbonitrile

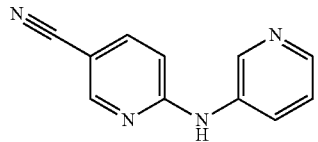 [SMILES: N#Cc1ccc(Nc2cccnc2)nc1]

The title compound was prepared as described in Intermediate 9, starting from 6-chloropyridine-3-carbonitrile and pyridine-3-amine, to give the product as a solid (1.05 g, 74%). MS ES+m/z 197 [M+H]+.

Step 2: Intermediate 26—N-hydroxy-6-(3-pyridylamino)pyridine-3-carboxamidine

6-(3-Pyridylamino)pyridine-3-carbonitrile (500 mg, 2.55 mmol) was taken up in MeOH (10 mL) at rt and NaH (60%,146 mg, 3.82 mmol) was added portion wise. The resulting mixture was stirred at rt overnight. The mixture was then stirred at 50° C. for 1 h, ammonium chloride (300 mg, 5.6 mmol) was added and stirring continued at 65° C. for 4 h. When cooled to rt 7M NH₃ in MeOH (3 mL) was added followed by hydroxylamine HCl (1.77 g, 25.5 mmol) and EtOH (5 mL). The resulting mixture was stirred at 80° C. for 1 h. When cooled to rt the mixture was concentrated and the resulting residue was suspended in half-saturated NaHCO₃ and the precipitate was filtered off, washed sequentially with water (1.5 mL), 2-propanol (2 mL), pentane (3 mL) and dried to give the product as a solid (360 mg, 62%). MS ES+m/z 230 [M+H]+.

Step 3: Intermediate 27—[[6-(3-Pyridylamino)pyridine-3-carboximidoyl]amino]acetate

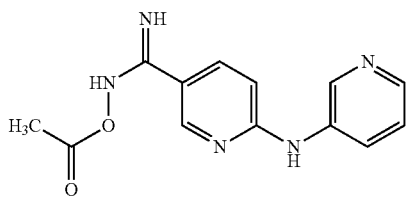 [SMILES: CC(=O)ONC(=N)c1ccc(Nc2cccnc2)nc1]

Acetic anhydride (371 μL) 3.93 mmol) was added to a solution of N-hydroxy-6-(3-pyridylamino)pyridine-3-carboxamidine (360 mg, 1.57 mmol) in AcOH (5 mL) at rt and the resulting mixture was stirred at rt for 30 min. The mixture was concentrated and the resulting residue was taken up in sat. aq. NaHCO₃ (15 mL) and EtOAc (15 mL) and stirred at rt for 10 min. The pH was checked to be above 7 and the formed precipitate was filtered off, washed with water and EtOAc and dried to give the product as a solid (280 mg, 66%). MS ES+m/z 272 [M+H]+.

Step 4: Intermediate 28—Ethyl-2-(diethoxymethyl)-3-hydroxy-prop-2-enoate sodium salt

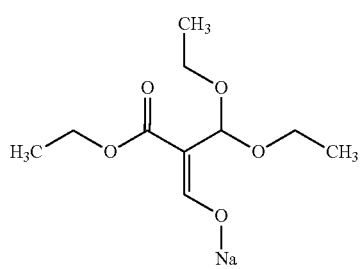

NaH (60%, 500 mg, 13.0 mmol) was added to a solution of ethyl 3,3-diethoxypropanoate (2 mL, 10.3 mmol) and ethyl formate (2 mL, 24.8 mmol) in DME (10 mL) at rt under a nitrogen atmosphere. The resulting mixture was stirred at 50° C. for 10-15 min until hydrogen gas evolution commenced. The mixture was cooled with an ice/water bath and stirred on the thawing cooling bath overnight. The mixture was concentrated and the resulting gum was triturated with Et₂O (3 mL) to give the product as a gum (2.1 g, 85%), which was used in the next step.

Step 5: Intermediate 29—Ethyl 2-[6-(3-pyridylamino)-3-pyridyl]pyrimidine-5-carboxylate

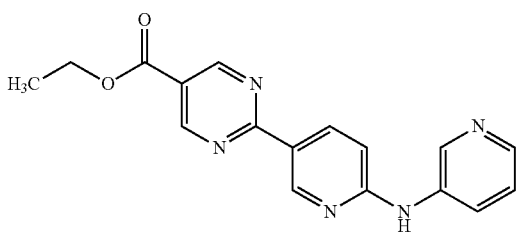 [SMILES: CCOC(=O)c1cnc(-c2ccc(Nc3cccnc3)nc2)nc1]

Zn (203 mg, 3.10 mmol) was added to a solution of [[6-(3-pyridylamino)pyridine-3-carboximidoyl]amino] acetate (280 mg, 1.03 mmol) in AcOH (2 mL) at rt and the resulting mixture was stirred at rt for 5 h to give a thick suspension. More AcOH (3 mL) and Zn (203 mg, 3.10 mmol) were added and stirring continued overnight. The mixture was filtered through celite and the filter cake rinsed with AcOH (1.5 mL). The filtrate was concentrated and the resulting residue (100 mg) was taken up in DMF (2 mL). Ethyl-2-(diethoxymethyl)-3-hydroxy-prop-2-enoate sodium salt (135 mg, 0.563 mmol) was added and the resulting mixture was stirred at 100° C. overnight. When cooled to rt water (6 mL) was added and the mixture stirred for 30 min. The formed precipitate was filtered off, washed sequentially with water, 2-propanol, pentane and dried to give the product as a solid (25 mg, 17%). MS ES+m/z 322 [M+H]+.

Step 6: N,N-dimethyl-2-(6-(pyridin-3-ylamino)pyridin-3-yl)pyrimidine-5-carboxamide Ethyl 2-[6-(3-pyridylamino)-3-pyridyl]pyrimidine-5-carboxylate (25 mg, 0.08 mmol) was taken up in THF (1 mL), MeOH (2 mL) and water (0.5 mL). LiOH hydrate (5 mg, 0.12 mmol) was added and the resulting mixture was stirred at 50° C. for 2 h. When cooled the rt the mixture was concentrated and the resulting residue was taken up in SOCl₂ (1 mL, 13.7 mmol) and THF (2 mL) and refluxed for 1 h. The mixture was concentrated and the residue taken up in THF (3 mL). Dimethylamine HCl (20 mg, 0.25 mmol) and TEA (250 µL, 1.8 mmol) were added and the resulting mixture was stirred at rt for 2 h. The mixture was concentrated and purified by preparative HPLC to give the product as a solid (2.5 mg, 10%). ¹H NMR (500 MHz, METHANOL-d4) δ ppm 3.14 (br d, J=4.41 Hz, 6H), 6.94 (dd, J=8.83, 0.63 Hz, 1H), 7.35-7.41 (m, 1H), 8.14 (dd, J=4.89, 1.42 Hz, 1H), 8.33 (ddd, J=8.35, 2.68, 1.58 Hz, 1H), 8.58 (dd, J=8.83, 2.21 Hz, 1H), 8.85 (dd, J=2.52, 0.63 Hz, 1H), 8.88 (s, 2H), 9.27 (dd, J=2.21, 0.63 Hz, 1H). MS ES+m/z 321 [M+H]+.

Example 30: 4-(6-((5-cyanopyridin-3-yl)amino)pyridin-3-yl)-N,N-dimethylbenzamide

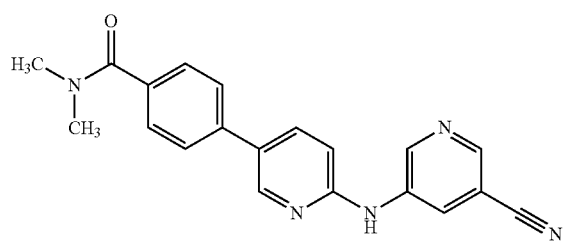 [SMILES: CN(C)C(=O)c1ccc(-c2ccc(Nc3cncc(C#N)c3)nc2)cc1]

Step 1: Intermediate 30—4-(6-Chloro-3-pyridyl)-N,N-dimethyl-benzamide

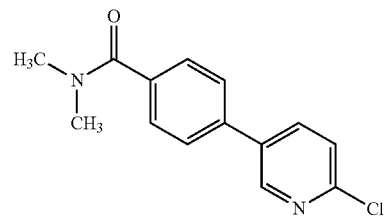 [SMILES: CN(C)C(=O)c1ccc(-c2ccc(Cl)nc2)cc1]

The title compound was prepared as described in Intermediate 3, starting from 4-iodo-N,N-dimethyl-benzamide and (6-chloro-3-pyridyl)boronic acid and stirring the mixture at 70° C. for 3 h, to give the product as a solid (475 mg, 67%). MS ES+m/z 261 [M+H]+.

Step 2: 4-(6-((5-cyanopyridin-3-yl)amino)pyridin-3-yl)-N,N-dimethylbenzamide 4-(6-Chloro-3-pyridyl)-N,N-dimethyl-benzamide (120 mg, 0.46 mmol), 5-aminopyridine-3-carbonitrile (55 mg, 0.46 mmol), Cs₂CO₃ (375 mg, 1.15 mmol), Pd(OAc)₂ (10 mg, 0.05 mmol) and Xphos (44 mg, 0.09 mmol) were dissolved in DMF (3 mL) and the mixture was stirred at 120° C. for 1 h. When cooled to rt the mixture was filtered and the filtrate purified by preparative HPLC to give the product as a solid (25 mg, 16%). ¹H NMR (500 MHz, DMSO-d₆) δ ppm 2.98 (br s, 3H) 3.01 (s, 3H) 7.04 (d, 1H) 7.51 (d, 2H)

7.76 (d, 2H) 8.07 (dd, 1H) 8.52 (s, 1H) 8.64-8.74 (m, 1H) 8.87 (s, 1H) 8.97 (d, 1H) 9.91 (s, 1H). MS ES+m/z 344 [M+H]⁺.

Example 31: 4-(6-((5-acetamidopyridin-3-yl)amino)pyridin-3-yl)-N,N-dimethylbenzamide

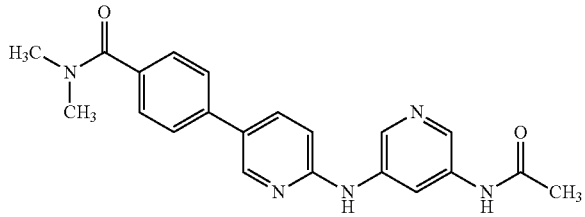 [SMILES: CC(=O)Nc1cncc(Nc2ccc(-c3ccc(C(=O)N(C)C)cc3)cn2)c1]

Step 1: Intermediate 31—N-[5-[(5-bromo-2-pyridyl)amino]-3-pyridyl]acetamide

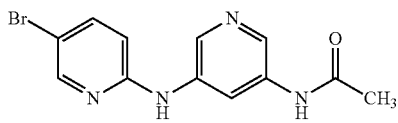 [SMILES: CC(=O)Nc1cncc(Nc2ccc(Br)cn2)c1]

The title compound was prepared as described in Example 9, starting from 5-bromo-2-fluoro-pyridine and N-(5-amino-3-pyridyl)acetamide, to give the product as a solid (467 mg, 59%). MS ES+m/z 307 [M+H]⁺.

Step 2: 4-(6-((5-acetamidopyridin-3-yl)amino)pyridin-3-yl)-N,N-dimethylbenzamide The title compound was prepared as described in Example 10, starting from N-[5-[(5-bromo-2-pyridyl)amino]-3-pyridyl]acetamide and [4-(dimethylcarbamoyl)phenyl]boronic acid, to give the product as a solid (5 mg, 3%). ¹H NMR (500 MHz, DMSO-d₆+Methanol-d₄) δ ppm 2.08 (s, 3H), 2.98 (m, J=12.00 Hz, 6H), 6.98 (d, J=8.83 Hz, 1H), 7.48 (d, J=8.51 Hz, 2H), 7.72 (m, J=8.20 Hz, 2H), 7.98 (dd, J=8.83, 2.52 Hz, 1H), 8.31 (d, J=2.21 Hz, 1H), 8.49 (t, J=2.21 Hz, 1H), 8.56 (d, J=2.21 Hz, 1H), 8.68 (d, J=2.21 Hz, 1H). MS ES+m/z 376 [M+H]⁺.

Example 32: N,N-dimethyl-4-(6-(pyrimidin-5-ylamino)pyridin-3-yl)benzamide

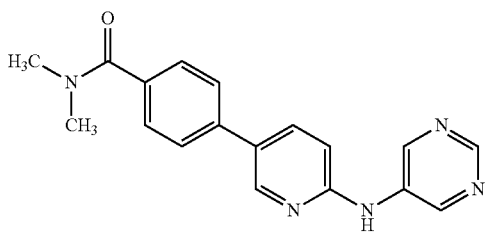 [SMILES: CN(C)C(=O)c1ccc(-c2ccc(Nc3cncnc3)nc2)cc1]

Step 1: Intermediate 32—4-(6-Fluoro-3-pyridyl)-N,N-dimethyl-benzamide

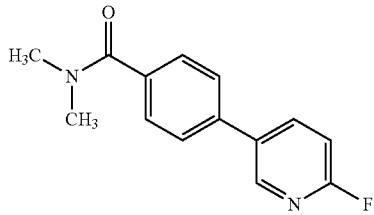 [SMILES: CN(C)C(=O)c1ccc(-c2ccc(F)nc2)cc1]

The title compound was prepared as described in Example 10, starting from 5-bromo-2-fluoro-pyridine and [4-(dimethylcarbamoyl)phenyl]boronic acid, to give the product as a solid (1.17 g, 68%). MS ES+m/z 245 [M+H]⁺.

Step 2: N,N-dimethyl-4-(6-(pyrimidin-5-ylamino)pyridin-3-yl)benzamide

The title compound was prepared as described in Example 9, starting from 4-(6-fluoro-3-pyridyl)-N,N-dimethyl-benzamide and pyrimidin-5-amine, to give the product as a solid (15 mg, 9%). ¹H NMR (500 MHz, DMSO-d₆) δ ppm 2.92-3.04 (m, 6H), 7.01 (d, J=8.51 Hz, 1H), 7.49 (m, J=8.20 Hz, 2H), 7.74 (m, J=8.20 Hz, 2H), 8.04 (dd, J=8.51, 2.52 Hz, 1H), 8.62 (d, J=2.52 Hz, 1H), 8.73 (s, 1H), 9.19 (s, 2H), 9.64 (s, 1H). MS ES+m/z 320 [M+H]⁺.

Example 33: N,N-dimethyl-4-(6-((2-methylpyrimidin-5-yl)amino)pyridin-3-yl)benzamide

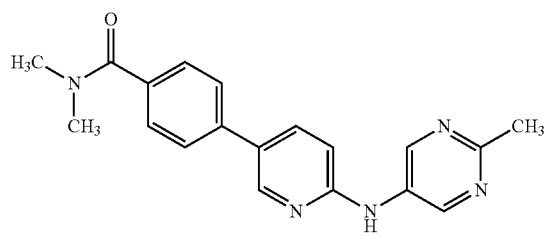

The title compound was prepared as described in Example 9, starting from 4-(6-fluoro-3-pyridyl)-N,N-dimethyl-benzamide and 2-methylpyrimidin-5-amine, to give the product as a solid (20 mg, 11%). ¹H NMR (500 MHz, DMSO-d₆) δ ppm 2.55 (s, 3H), 2.96 (br s, 3H), 2.99 (br s, 3H), 6.96 (d, J=8.51 Hz, 1H), 7.48 (m, J=8.20 Hz, 2H), 7.72 (m, J=8.20 Hz, 2H), 8.00 (dd, J=8.83, 2.52 Hz, 1H), 8.58 (d, J=2.21 Hz, 1H), 9.05 (s, 2H), 9.50 (s, 1H). MS ES+m/z 320 [M+H]⁺.

Example 34: 4-(6-((2-methoxypyrimidin-5-yl)amino)pyridin-3-yl)-N,N-dimethylbenzamide

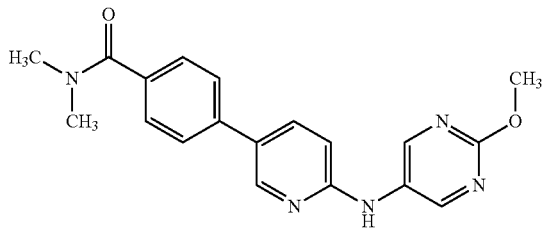

The title compound was prepared as described in Example 9, starting from 4-(6-fluoro-3-pyridyl)-N,N-dimethyl-benzamide and 2-methoxypyrimidin-5-amine, to give the product as a solid (45 mg, 23%). $^1$H NMR (500 MHz, DMSO-$d_6$) δ ppm 2.96 (br s, 3H), 2.99 (br s, 3H), 3.89 (s, 3H), 6.90 (d, J=8.83 Hz, 1H), 7.47 (d, J=8.51 Hz, 2H), 7.71 (d, J=8.20 Hz, 2H), 7.97 (dd, J=8.83, 2.52 Hz, 1H), 8.52 (d, J=2.52 Hz, 1H), 8.92 (s, 2H), 9.32 (s, 1H). MS ES+m/z 350 [M+H]$^+$.

Example 35: N,N-dimethyl-4-(6-((2-methylpyridin-3-yl)amino)pyridin-3-yl)benzamide

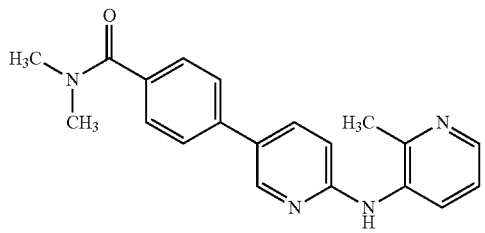 [SMILES: Cc1ncccc1Nc1ccc(-c2ccc(C(=O)N(C)C)cc2)cn1]

The title compound was prepared as described in Example 9, starting from 4-(6-fluoro-3-pyridyl)-N,N-dimethyl-benzamide and 2-methylpyridin-3-amine, to give the product as a solid (33 mg, 18%). $^1$H NMR (500 MHz, DMSO-$d_6$) δ ppm 2.47 (s, 3H), 2.96 (br s, 3H), 2.99 (br s, 3H), 6.97 (d, J=8.83 Hz, 1H), 7.20 (dd, J=8.20, 4.73 Hz, 1H), 7.47 (m, J=8.20 Hz, 2H), 7.69 (m, J=8.20 Hz, 2H), 7.95 (dd, J=8.67, 2.36 Hz, 1H), 8.09-8.12 (m, 1H), 8.14-8.16 (m, 1H), 8.46 (d, J=2.21 Hz, 1H), 8.51 (s, 1H). MS ES+m/z 333 [M+H]$^+$.

Example 36: N,N-dimethyl-4-(6-(pyrazin-2-ylamino)pyridin-3-yl)benzamide

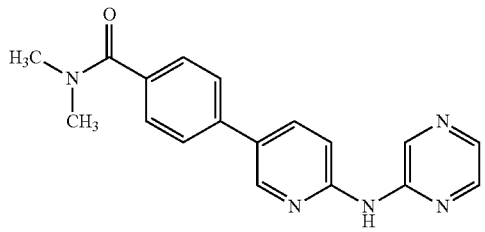

The title compound was prepared as described in Example 25, starting from 4-(6-amino-3-pyridyl)-N,N-dimethyl-benzamide and 2-chloropyrazine, replacing NaOtBu with Cs$_2$CO$_3$ and heating at 160° C., to give the product as a solid (89 mg, 22%). $^1$H NMR (500 MHz, CDCl$_3$) δ ppm 8.97 (s, 1H), 8.47 (d, J=1.89 Hz, 1H), 8.24 (s, 2H), 8.11 (br d, J=8.51 Hz, 1H), 7.99-8.05 (m, 1H), 7.57-7.62 (m, 2H), 7.53-7.57 (m, 2H), 3.15 (br s, 3H), 3.05 (br s, 3H). MS ES+m/z 320 [M+H]$^+$.

Example 37: 5-((5-(4-(dimethylcarbamoyl)phenyl)pyridin-2-yl)amino)-N,N-dimethylnicotinamide

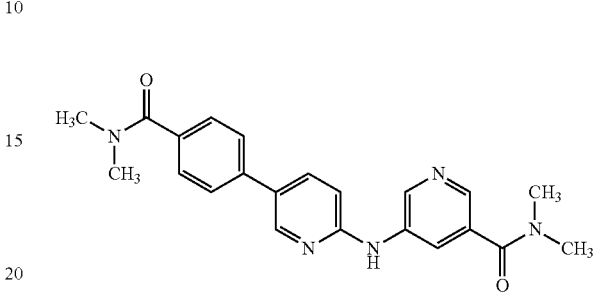

Step 1 Intermediate 33—Ethyl 5-[[5-[4-(dimethylcarbamoyl)phenyl]-2-pyridyl]amino]pyridine-3-carboxylate

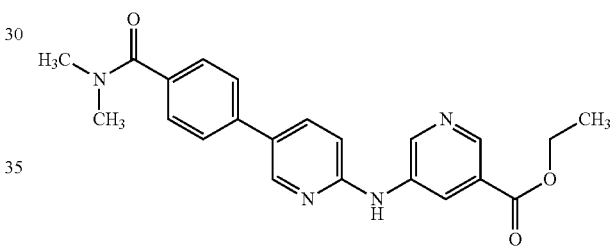

The title compound was prepared as described in Example 25, starting from 4-(6-amino-3-pyridyl)-N,N-dimethyl-benzamide and ethyl 5-bromopyridine-3-carboxylate, replacing NaOtBu with Cs$_2$CO$_3$ and heating at 160° C., to give the product as a solid (472 mg, 41%). MS ES+m/z 391 [M+H]$^+$.

Step 2: 5-((5-(4-(dimethylcarbamoyl)phenyl)pyridin-2-yl)amino)-N,N-dimethylnicotinamide Ethyl 5-[[5-[4-(dimethylcarbamoyl)phenyl]-2-pyridyl]amino]pyridine-3-carboxylate (400 mg, 1.02 mmol) was taken up in MeOH (5 mL). Conc. HCl (4 mL) was added and the mixture refluxed overnight. When cooled to rt the mixture was concentrated. An amount of the resulting residue, 5-[[5-[4-(dimethylcarbamoyl)phenyl]-2-pyridyl]amino]pyridine-3-carboxylic acid (100 mg, 0.28 mmol) was taken up in DMF (3 mL), together with dimethylamine HCl (51 mg, 0.63 mmol) and HATU (240 mg, 0.63 mmol). Triethylamine (0.25 mL, 1.79 mmol) was added and the mixture was heated in a microwave reactor at 60° C. for 1 h. The mixture was diluted with EtOAc (10 mL) and washed with sat. aq. NaHCO$_3$ (2×10 mL), brine, dried over MgSO$_4$, filtered, concentrated and purified by preparative HPLC to give the product as a solid (9 mg, 8%). $^1$H NMR (500 MHz, CDCl$_3$) δ ppm 9.01 (s, 1H), 8.71 (br s, 1H), 8.45 (d, J=2.21 Hz, 1H), 8.22 (s, 1H), 7.76 (dd, J=8.67, 2.36 Hz, 1H), 7.48-7.57 (m, 4H), 7.05 (d, J=8.83 Hz, 1H), 3.16 (br s, 6H), 3.08 (br s, 3H), 3.05 (br s, 3H). MS ES+m/z 390 [M+H]$^+$.

Example 38: N,N-dimethyl-4-(6-((5-(2-oxopyrrolidin-1-yl)pyridin-3-yl)amino)pyridin-3-yl)benzamide

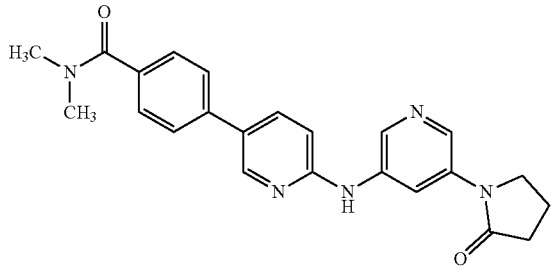 [SMILES: CN(C)C(=O)c1ccc(-c2ccc(Nc3cncc(N4CCCC4=O)c3)nc2)cc1]

The title compound was prepared as described in Example 25, starting from 4-(6-amino-3-pyridyl)-N,N-dimethyl-benzamide and 1-(5-bromo-3-pyridyl)pyrrolidin-2-one, replacing NaOtBu with Cs$_2$CO$_3$ and heating at 160° C., to give the product as a solid (43 mg, 25%). $^1$H NMR (500 MHz, DMSO-d$_6$) δ ppm 2.06-2.17 (m, 2H), 2.52-2.56 (m, 2H), 2.94-3.04 (m, 6H), 3.89 (t, J=7.09 Hz, 2H), 7.49 (d, J=8.51 Hz, 1H), 7.49 (d, J=7.88 Hz, 2H), 7.74 (d, J=8.20 Hz, 2H), 7.94-8.06 (m, 1H), 8.30-8.42 (m, 1H), 8.55-8.62 (m, 2H), 8.77-8.84 (m, 1H), 9.52 (s, 1H). MS ES+m/z 402 [M+H]$^+$.

Example 39: 4-(6-((5-methoxypyridin-3-yl)amino)pyridin-3-yl)-N,N-dimethylbenzamide

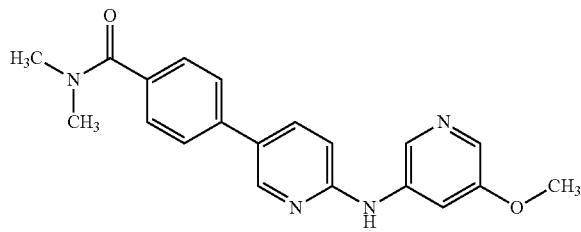

The title compound was prepared as described in Example 25, starting from 4-(6-amino-3-pyridyl)-N,N-dimethyl-benzamide and 3-bromo-5-methoxy-pyridine, replacing NaOtBu with Cs$_2$CO$_3$ and heating at 160° C., to give the product as a solid (21 mg, 6%). $^1$H NMR (500 MHz, CDCl$_3$) δ ppm 3.02-3.10 (m, 3H), 3.15 (br s, 3H), 3.91 (s, 3H), 7.05 (br d, J=8.83 Hz, 1H), 7.48-7.52 (m, 2H), 7.53-7.59 (m, 2H), 7.73-7.79 (m, 1H), 7.87 (s, 1H), 8.23-8.31 (m, 1H), 8.48 (d, J=1.89 Hz, 1H), 8.51 (br s, 1H). MS ES+m/z 349 [M+H]$^+$.

Example 40: 4-(6-((5-(1-cyanocyclopropyl)pyridin-3-yl)amino)pyridin-3-yl)-N,N-dimethylbenzamide

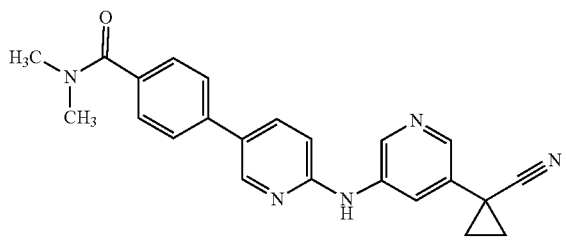 [SMILES: CN(C)C(=O)c1ccc(-c2ccc(Nc3cncc(C4(C#N)CC4)c3)nc2)cc1]

The title compound was prepared as described in Example 25, starting from 4-(6-amino-3-pyridyl)-N,N-dimethyl-benzamide and 1-(5-bromo-3-pyridyl)cyclopropane-1-carbonitrile, to give the product as a solid (240 mg, 84%). $^1$H NMR (500 MHz, DMSO-d$_6$) δ ppm 1.57-1.61 (m, 2H), 1.80-1.84 (m, 2H), 2.98 (br s, 6H), 6.99 (d, J=8.83 Hz, 1H), 7.48 (m, J=8.20 Hz, 2H), 7.74 (m, J=8.20 Hz, 2H), 8.01 (dd, J=8.83, 2.52 Hz, 1H), 8.07 (d, J=2.21 Hz, 1H), 8.27 (t, J=2.21 Hz, 1H), 8.61 (d, J=2.21 Hz, 1H), 8.87 (d, J=2.52 Hz, 1H), 9.58 (s, 1H). MS ES+m/z 384 [M+H]$^+$.

Example 41: 4-(6-((5-(1-carbamoylcyclopropyl)pyridin-3-yl)amino)pyridin-3-yl)-N,N-dimethylbenzamide

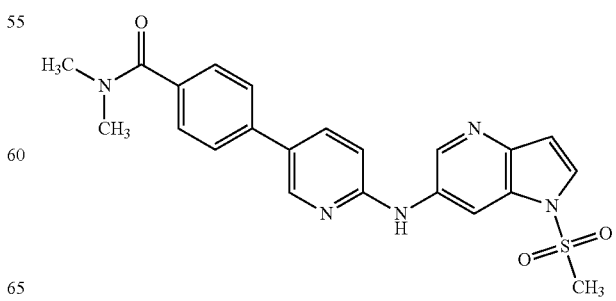

4-[6-[[5-(1-Cyanocyclopropyl)-3-pyridyl]amino]-3-pyridyl]-N,N-dimethyl-benzamide (150 mg, 0.39 mmol) and K$_2$CO$_3$ (270 mg, 1.96 mmol) were taken up in DMSO (3 mL). 30% aq. H$_2$O$_2$ (400 μL, 3.92 mmol) was added and the resulting mixture was stirred at 50° C. for 3 h. MeOH (5 mL) was added and the mixture allowed to cool to rt. The mixture was filtered and the filtrate purified by preparative HPLC to give the product as solid (21 mg, 13%). $^1$H NMR (500 MHz, DMSO-d$_6$) δ ppm 1.00-1.05 (m, 2H), 1.36-1.42 (m, 2H), 2.98 (br s, 6H), 6.50 (br s, 1H), 6.98 (d, J=8.55 Hz, 1H), 7.05 (br s, 1H), 7.46-7.50 (m, 2H), 7.72-7.76 (m, 2H), 7.99 (dd, J=8.67, 2.68 Hz, 1H), 8.09 (d, J=1.89 Hz, 1H), 8.20 (t, J=2.21 Hz, 1H), 8.61-8.65 (m, 1H), 8.82 (d, J=2.52 Hz, 1H), 9.48 (s, 1H). MS ES+m/z 402 [M+H]$^+$.

Example 42: N,N-dimethyl-4-(6-((1-(methylsulfonyl)-1H-pyrrolo[3,2-b]pyridin-6-yl)amino)pyridin-3-yl)benzamide

Step 1 Intermediate 34—6-Bromo-1-methylsulfonyl-pyrrolo[3,2-b]pyridine

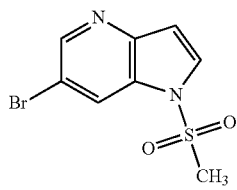

Triethylamine (0.42 mL, 3.05 mmol) was added to a solution of 6-bromo-1H-pyrrolo[3,2-b]pyridine (300 mg, 1.52 mmol) and methanesulfonyl chloride (0.18 mL, 2.28 mmol) in DCM at rt and the resulting mixture was stirred for 2 h. The mixture was concentrated and the resulting residue was dissolved in EtOAc, washed with sat. aq. NaHCO$_3$, water, brine, dried over MgSO$_4$, filtered and concentrated to give the product as a solid (210 mg, 50%). MS ES+m/z 275 [M+H]$^+$.

Step 2: N,N-dimethyl-4-(6-((1-(methylsulfonyl)-1H-pyrrolo[3,2-b]pyridin-6-yl)amino)pyridin-3-yl)benzamide The title compound was prepared as described in Example 25, starting from 4-(6-amino-3-pyridyl)-N,N-dimethyl-benzamide and 6-bromo-1-methylsulfonyl-pyrrolo[3,2-b]pyridine, replacing NaOtBu with Cs$_2$CO$_3$ and heating at 120° C. for 2 h, to give the product as a solid (20 mg, 11%). $^1$H NMR (500 MHz, DMSO-d$_6$) δ ppm 2.99 (br s, 6H), 3.47 (s, 3H), 6.89 (d, J=3.78 Hz, 1H), 7.01 (d, J=8.51 Hz, 1H), 7.49 (d, J=8.20 Hz, 2H), 7.72-7.78 (m, 3H), 8.02 (dd, J=8.83, 2.52 Hz, 1H), 8.60 (d, J=2.21 Hz, 1H), 8.81 (s, 1H), 8.88 (d, J=2.21 Hz, 1H), 9.63 (s, 1H). MS ES+m/z 436 [M+H]$^+$.

Example 43: 4-(6-((1-acetyl-2,3-dihydro-1H-pyrido[2,3-b][1,4]oxazin-7-yl)amino)pyridin-3-yl)-N,N-dimethylbenzamide

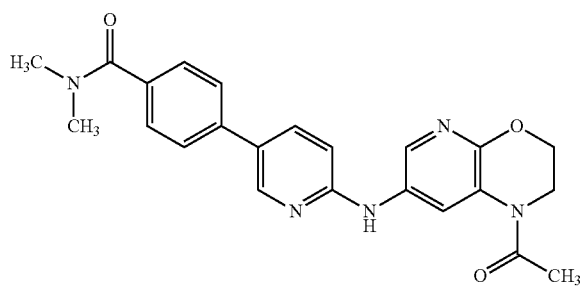 [SMILES: CC(=O)N1CCOc2ncc(Nc3ccc(-c4ccc(C(=O)N(C)C)cc4)cn3)cc21]

Step 1: Intermediate 35—1-(7-Bromo-2,3-dihydro-pyrido[2,3-b][1,4]oxazin-1-yl)ethanone

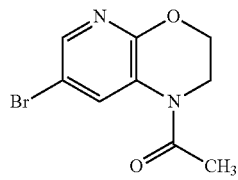

7-Bromo-2,3-dihydro-H-pyrido[2,3-b][1,4]oxazine (1 g, 4.65 mmol) and TEA (971 µL, 6.98 mmol) were taken up in 2-MeTHF (5 mL) and cooled to 0° C. Acetyl chloride (398 µL, 5.58 mmol) was added and the resulting mixture was stirred at rt for 1 h. DCM (10 mL) was added followed by acetyl chloride (398 µL, 5.58 mmol) and the mixture was stirred at rt for 1 h. EtOAc (20 mL) and water (10 mL) were added and the organic layer separated. To the aqueous layer was added 2M aq. NaOH (5 mL) and EtOAc (10 mL) and the organic layer separated. The combined organics were washed with sat. aq. NaHCO$_3$, brine, dried over Na$_2$SO$_4$, filtered and concentrated. Recrystallization from 2-propanol gave the product as a white solid (875 mg, 73%). MS ES+m/z 257 [M+H]$^+$.

Step 2: 4-(6-((1-acetyl-2,3-dihydro-1H-pyrido[2,3-b][1,4]oxazin-7-yl)amino)pyridin-3-yl)-N,N-dimethylbenzamide The title compound was prepared as described in Example 25, starting from 4-(6-amino-3-pyridyl)-N,N-dimethyl-benzamide and 1-(7-bromo-2,3-dihydropyrido[2,3-b][1,4]oxazin-1-yl)ethanone, replacing NaOtBu with Cs$_2$CO$_3$ and heating at 100° C. overnight, to give the product as a solid (3 mg, 2%). $^1$H NMR (500 MHz, DMSO-d$_6$) δ ppm 2.31 (s, 3H), 2.94-3.04 (s, 6H), 3.86-3.93 (m, 2H), 4.29-4.42 (m, 2H), 6.89 (d, J=8.83 Hz, 1H), 7.48 (d, J=8.20 Hz, 2H), 7.71 (d, J=8.51 Hz, 2H), 7.94 (dd, J=8.83, 2.52 Hz, 1H), 8.33 (br s, 1H), 8.51 (d, J=2.21 Hz, 1H), 9.22 (br s, 1H). MS ES+m/z 418 [M+H]$^+$.

Example 44: N,N-dimethyl-4-(6-((1-(methylsulfonyl)-2,3-dihydro-1H-pyrido[2,3-b][1,4]oxazin-7-yl)amino)pyridin-3-yl)benzamide

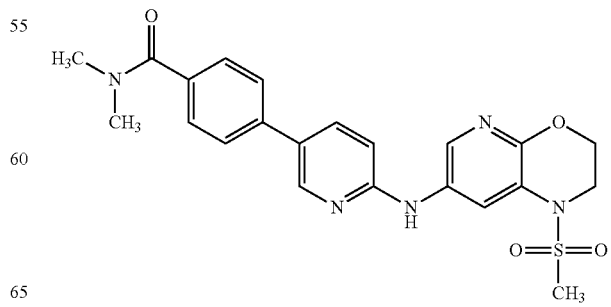

109

Step 1: Intermediate 36—7-Bromo-1-methylsulfonyl-2,3-dihydropyrido[2,3-b][1,4]oxazine

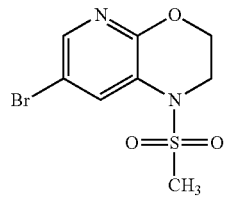

Methanesulfonyl chloride (94 µL, 1.21 mmol) was added to a solution of 7-bromo-2,3-dihydro-1H-pyrido[2,3-b][1,4]oxazine (130 mg, 0.6 mmol) and TEA (126 µL, 0.91 mmol) in 1,4-dioxane (2 mL) at rt and the mixture was stirred for 5 h. Additional methanesulfonyl chloride (94 µL, 1.21 mmol) was added and the mixture was stirred at 60° C. overnight. The mixture was concentrated and the residue was dissolved in EtOAc (60 mL), washed with sat. aq. NaHCO$_3$ (20 mL), sat. aq. NH$_4$Cl (20 mL), brine, dried over MgSO$_4$, filtered and concentrated. Purification on a silica gel column, eluted with 20-60% EtOAc in heptane, gave the product as a solid (92 mg, 52%). MS ES+m/z 293 [M+H]$^+$.

Step 2: N,N-dimethyl-4-(6-((1-(methylsulfonyl)-2,3-dihydro-1H-pyrido[2,3-b][1,4]oxazin-7-yl)amino)pyridin-3-yl)benzamide The title compound was prepared as described in Example 25, starting from 4-(6-amino-3-pyridyl)-N,N-dimethyl-benzamide and 7-bromo-1-methylsulfonyl-2,3-dihydropyrido[2,3-b][1,4]oxazine, replacing NaOtBu with Cs$_2$CO$_3$ and heating at 100° C. overnight, to give the product as a solid (16 mg, 12%). $^1$H NMR (500 MHz, DMSO-d$_6$) δ ppm 2.99 (br s, 6H), 3.22 (s, 3H), 3.82-3.86 (m, 2H), 4.36-4.40 (m, 2H), 6.90 (d, J=8.83 Hz, 1H), 7.48 (d, J=8.51 Hz, 2H), 7.72 (d, J=8.20 Hz, 2H), 7.96 (dd, J=8.67, 2.36 Hz, 1H), 8.38 (d, J=2.52 Hz, 1H), 8.40 (d, J=2.52 Hz, 1H), 8.51 (d, J=2.52 Hz, 1H), 9.29 (s, 1H). MS ES+m/z 454 [M+H]$^+$.

Example 45: tert-butyl 7-((5-(4-(dimethylcarbamoyl)phenyl)pyridin-2-yl)amino)-2,3-dihydro-1H-pyrido[2,3-b][1,4]oxazine-1-carboxylate

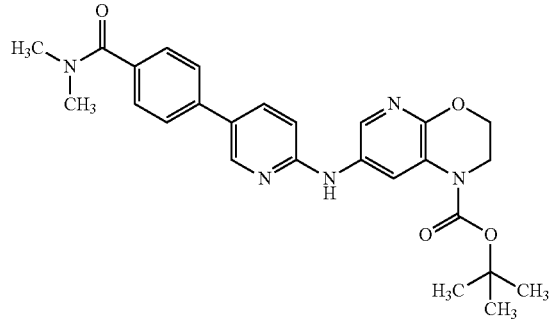 [SMILES: CN(C)C(=O)c1ccc(-c2ccc(Nc3cnc4c(c3)N(C(=O)OC(C)(C)C)CCO4)nc2)cc1]

110

Step 1: Intermediate 37—tert-Butyl 7-bromo-2,3-dihydropyrido[2,3-b][1,4]oxazine-1-carboxylate

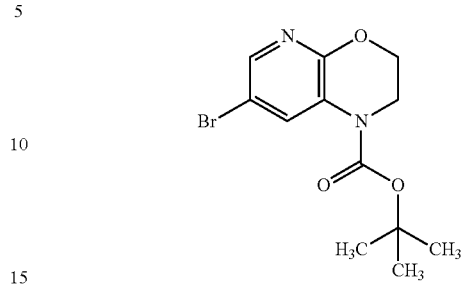

7-Bromo-2,3-dihydro-1H-pyrido[2,3-b][1,4]oxazine (0.6 g, 2.79 mmol) and TEA (583 µL, 4.19 mmol) were taken up in 2-MeTHF (5 mL) and cooled to 0¹° C. tert-Butoxycarbonyl tert-butyl carbonate (1.22 g, 5.58 mmol) was added and the resulting mixture was stirred at rt overnight. EtOAc (20 mL) and water (10 mL) were added and the organic layer separated. The combined organics were washed with sat. aq. NaHCO$_3$, brine, dried over Na$_2$SO$_4$, filtered and concentrated to give the product as a solid. (875 mg, 99%). MS ES+m/z 315 [M+H]$^+$.

Step 2: tert-butyl 7-((5-(4-(dimethylcarbamoyl)phenyl)pyridin-2-yl)amino)-2,3-dihydro-1H-pyrido[2,3-b][1,4]oxazine-1-carboxylate The title compound was prepared as described in Example 25, starting from 4-(6-amino-3-pyridyl)-N,N-dimethyl-benzamide and tert-butyl 7-bromo-2,3-dihydropyrido[2,3-b][1,4]oxazine-1-carboxylate and heating at 100° C. for 3.5 h, to give the product as a solid (200 mg, 45%). $^1$H NMR (500 MHz, DMSO-d$_6$) δ ppm 1.53 (s, 9H), 2.96-3.04 (m, 6H), 3.77-3.86 (m, 2H), 4.24-4.35 (m, 2H), 6.85-6.93 (m, 1H), 7.46-7.51 (m, 2H), 7.68-7.73 (m, 2H), 7.89-8.01 (m, 1H), 8.23-8.34 (m, 1H), 8.44-8.54 (m, 1H), 8.58-8.72 (m, 1H), 9.12-9.27 (m, 1H). MS ES+m/z 476 [M+H]$^+$.

Example 46: 4-(6-((2,3-dihydro-1H-pyrido[2,3-b][1,4]oxazin-7-yl)amino)pyridin-3-yl)-N,N-dimethylbenzamide

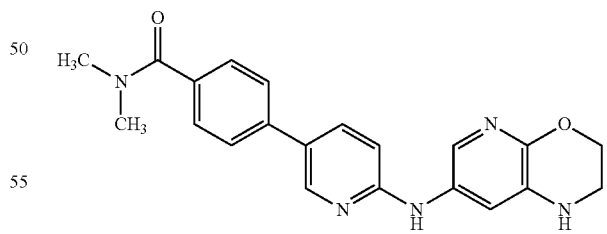

tert-Butyl 7-[[5-[4-(dimethylcarbamoyl)phenyl]-2-pyridyl]amino]-2,3-dihydropyrido[2,3-b][1,4]oxazine-1-carboxylate (200 mg, 0.42 mmol) was dissolved in DCM (5 mL). TFA (240 mg, 2.1 mmol) was added and the mixture stirred at rt overnight. The mixture was concentrated and purified by preparative HPLC to give the product as a solid (14 mg, 8%). $^1$H NMR (500 MHz, DMSO-d$_6$) δ ppm 2.98 (br s, 6H), 3.22-3.29 (m, 2H), 4.19-4.25 (m, 2H), 6.09 (s, 1H), 6.84 (d, J=8.50 Hz, 1H), 7.39 (d, J=2.21 Hz, 1H), 7.42-7.51 (m, 2H), 7.60 (d, J=2.21 Hz, 1H), 7.67-7.71 (m, 2H), 7.89 (dd, J=8.83, 2.52 Hz, 1H), 8.45-8.52 (m, 1H), 8.92 (s, 1H). MS ES+m/z 376 [M+H]+.

Example 47: N,N-dimethyl-4-(6-((5-(3-oxomorpholino)pyridin-3-yl)amino)pyridin-3-yl)benzamide

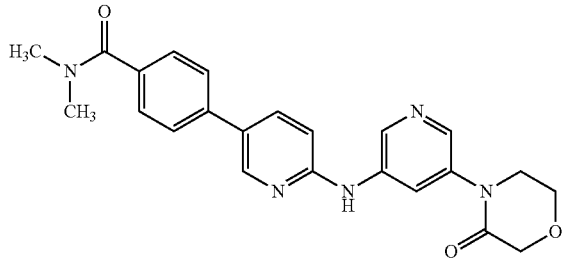 [SMILES: CN(C)C(=O)c1ccc(-c2ccc(Nc3cncc(N4CCOCC4=O)c3)nc2)cc1]

Step 1: Intermediate 38—4-(5-Bromo-3-pyridyl)morpholin-3-one

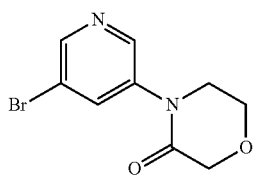 [SMILES: O=C1COCCN1c1cncc(Br)c1]

The title compound was prepared as described in Intermediate 14, starting from 3,5-dibromopyridine and morpholin-3-one to give the product as a solid (204 mg, 38%). MS ES+m/z 257 [M+H]+.

Step 2: N,N-dimethyl-4-(6-((5-(3-oxomorpholino)pyridin-3-yl)amino)pyridin-3-yl)benzamide The title compound was prepared as described in Example 25, starting from 4-(6-amino-3-pyridyl)-N,N-dimethyl-benzamide and 4-(5-bromo-3-pyridyl)morpholin-3-one, replacing NaOtBu with Cs₂CO₃ and heating at 100° C. overnight, to give the product as a solid (17 mg, 21%). ¹H NMR (500 MHz, CDCl₃) δ ppm 3.05 (br s, 3H), 3.15 (br s, 3H), 3.94 (br t, J=4.73 Hz, 2H), 4.11 (br t, J=4.73 Hz, 2H), 4.38 (s, 2H), 7.30-7.36 (m, 1H), 7.48-7.60 (m, 4H), 7.82 (br dd, J=8.67, 2.05 Hz, 1H), 8.42 (br s, 1H), 8.62 (s, 1H), 9.17 (br s, 1H), 9.34 (br s, 1H), 10.56 (br s, 1H). MS ES+m/z 418 [M+H]+.

Example 48: N,N-dimethyl-4-(6-((5-(2-morpholinoethyl)pyridin-3-yl)amino)pyridin-3-yl)benzamide

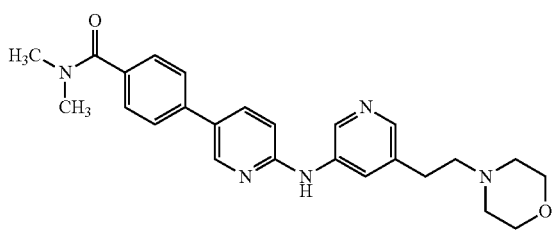 [SMILES: CN(C)C(=O)c1ccc(-c2ccc(Nc3cncc(CCN4CCOCC4)c3)nc2)cc1]

Step 1: Intermediate 39—2-(5-Bromo-3-pyridyl)-1-morpholino-ethanone

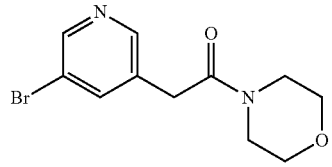 [SMILES: O=C(Cc1cncc(Br)c1)N1CCOCC1]

Trimethylacetyl chloride (900 μL, 7.31 mmol) was added to a mixture of 2-(5-bromo-3-pyridyl)acetic acid (1.5 g, 6.94 mmol) and diisopropylamine (1 mL, 7.14 mmol) in DCM (20 mL) at 0° C. The resulting mixture was stirred at 0° C. for 30 min. Morpholine (750 μL) 8.57 mmol) was added and the reaction mixture was stirred at rt for 2 h. The mixture was washed with sat. aq. NH₄Cl (15 mL), sat. aq. NaHCO₃ (15 mL), dried over Na₂SO₄, filtered and concentrated to give the product as a brown oil which solidified upon standing (1.9 g, 96%). MS ES+m/z 285 [M+H]+.

Step 2: Intermediate 40—4-[2-(5-Bromo-3-pyridyl)ethyl]morpholine

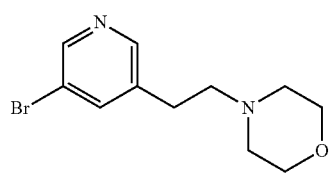 [SMILES: Brc1cncc(CCN2CCOCC2)c1]

Triethoxysilane (3.69 mL, 20 mmol) was added to suspension of zinc acetate (245 mg, 1.33 mmol) in THF (10 mL) at rt and the resulting mixture was stirred at rt for 30 min. A solution of 2-(5-bromo-3-pyridyl)-1-morpholino-ethanone (1.9 g, 6.66 mmol) in THF (15 mL) was added and the mixture was stirred at rt for 3 h. The mixture was heated and stirred at 40° C. overnight. Aq. 1M NaOH (20 mL) was added, the mixture stirred vigorously for 3 h and extracted with EtOAc (3×10 mL). The combined organics were washed with brine, dried over Na₂SO₄, filtered and concentrated. The resulting residue was taken up in MeOH (20 mL) and sodium cyanoborohydride (837 mg, 13.3 mmol) was added, followed by acetic acid (0.5 mL) and the resulting mixture was stirred at rt overnight. The mixture was concentrated and the residue was taken up in 1M aq. HCl (10 mL) and EtOAc (5 mL). The aqueous layer was separated and the organic layer extracted with 1M aq. HCl (5 mL). To the combined aqueous layers was added 2M aq. NaOH (10 mL) (pH checked to be above 7) and EtOAc (5 mL). The organic layer was separated and the aqueous layer extracted with EtOAc (2×5 mL). The combined organics were washed with brine, dried over Na₂SO₄, filtered and concentrated to give the product as an oil (930 mg, 52%). MS ES+m/z 271 [M+H]+.

Step 3: N,N-dimethyl-4-(6-((5-(2-morpholinoethyl)pyridin-3-yl)amino)pyridin-3-yl)benzamide The title compound was prepared as described in Example 25, starting from 4-(6-amino-3-pyridyl)-N,N-dimethyl-benzamide and 4-[2-(5-bromo-3-pyridyl)ethyl]morpholine, to give the product as a solid (60 mg, 34%). ¹H NMR (500 MHz, DMSO-d₆) δ ppm 2.37-2.48 (m, 4H), 2.54 (t, J=7.72 Hz, 2H), 2.74 (t, J=7.57 Hz, 2H), 2.94-3.04 (m, 6H), 3.58 (t, J=4.57 Hz, 4H), 6.97 (d, J=8.51 Hz, 1H), 7.48 (d, J=7.60 Hz, 2H), 7.72 (d, J=7.58 Hz, 2H), 7.96-7.99 (m, 1H), 8.00-8.02 (m, 1H), 8.10 (t, J=2.05 Hz, 1H), 8.58 (d, J=2.21 Hz, 1H), 8.71 (d, J=2.52 Hz, 1H), 9.38 (s, 1H). MS ES+m/z 432 [M+H]⁺.

Example 49: 4-(6-((5-(difluoromethoxy)pyridin-3-yl)amino)pyridin-3-yl)-N,N-dimethylbenzamide

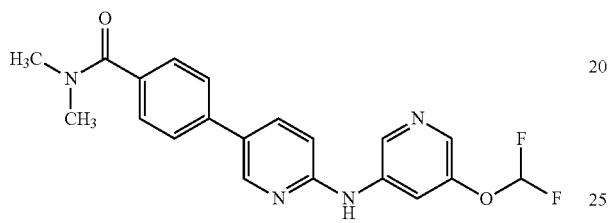

The title compound was prepared as described in Example 25, starting from 4-(6-amino-3-pyridyl)-N,N-dimethyl-benzamide and 3-bromo-5-(difluoromethoxy)pyridine and heating at 90° C. for 4 h, to give the product as a solid (39 mg, 31%). ¹H NMR (500 MHz, DMSO-d₆) δ ppm 2.98 (br d, J=10.09 Hz, 6H), 7.01 (d, J=8.74 Hz, 1H), 7.16-7.46 (m, 1H), 7.47-7.51 (m, 2H), 7.72-7.76 (m, 2H), 8.01-8.05 (m, 2H), 8.34 (t, J=2.36 Hz, 1H), 8.62-8.68 (m, 2H), 9.72 (s, 1H). MS ES+m/z 385 [M+H]⁺.

Example 50: 4-(6-((2,3-dihydro-[1,4]dioxino[2,3-b]pyridin-7-yl)amino)pyridin-3-yl)-N,N-dimethylbenzamide

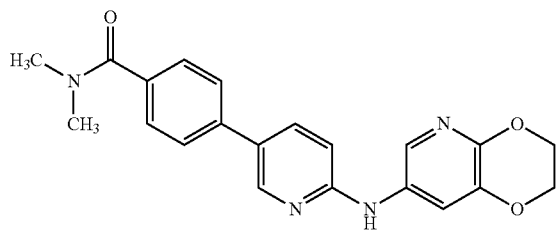

The title compound was prepared as described in Example 25, starting from 4-(6-amino-3-pyridyl)-N,N-dimethyl-benzamide and 7-bromo-2,3-dihydro-[1,4]dioxino[2,3-b]pyridine and heating at 80° C. for 2 days, to give the product as a solid (29 mg, 23%). ¹H NMR (500 MHz, DMSO-d₆) δ ppm 2.93-3.02 (m, 6H), 4.24 (dt, J=3.78, 2.21 Hz, 2H), 4.35 (dt, J=3.78, 2.21 Hz, 2H), 6.87 (d, J=8.57 Hz, 1H), 7.46-7.48 (m, 2H), 7.68-7.71 (m, 2H), 7.87 (d, J=2.52 Hz, 1H), 7.92-7.96 (m, 2H), 8.52 (d, J=2.21 Hz, 1H), 9.21 (s, 1H). MS ES+m/z 377 [M+H]⁺.

Example 51: N,N-dimethyl-4-(6-((6-(2-morpholino-ethyl)pyridin-3-yl)amino)pyridin-3-yl)benzamide

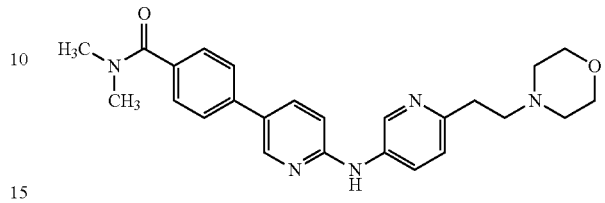

Step 1 Intermediate 41—4-[2-(5-Bromo-2-pyridyl)ethyl]morpholine

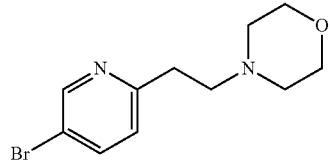 [SMILES: Brc1ccc(CCN2CCOCC2)nc1]

5-Bromo-2-vinyl-pyridine (500 mg, 2.72 mmol), NaOtBu (522 mg, 5.434 mmol) and morpholine (476 μL, 5.43 mmol) were taken up in THF (2.5 mL) and the mixture was stirred at 80° C. overnight. Additional morpholine (1.2 mL, 13.68 mmol) was added and stirring continued at 80° C. overnight. Water and DCM were added, the organic layer was separated and the aqueous layer extracted with DCM. The combined organics were dried over MgSO₄, filtered, concentrated and purified on a silica gel column eluted with 0-100% EtOAc in heptane to give the product as an oil (423 mg, 57%). MS ES+m/z 271 [M+H]⁺.

Step 2: N,N-dimethyl-4-(6-((6-(2-morpholinoethyl)pyridin-3-yl)amino)pyridin-3-yl)benzamide The title compound was prepared as described in Example 25, starting from 4-(6-amino-3-pyridyl)-N,N-dimethyl-benzamide and 4-[2-(5-bromo-2-pyridyl)ethyl]morpholine and heating at 90° C. overnight, to give the product as a solid (35 mg, 25%). ¹H NMR (500 MHz, DMSO-d₆) δ ppm 2.42 (br s, 4H), 2.59-2.67 (m, 2H), 2.77-2.88 (m, 2H), 2.97 (br s, 6H), 3.57 (t, J=4.57 Hz, 4H), 6.93 (d, J=8.56 Hz, 1H), 7.21 (d, J=8.51 Hz, 1H), 7.46-7.49 (m, 2H), 7.69-7.73 (m, 2H), 7.96 (dd, J=8.67, 2.68 Hz, 1H), 8.15 (dd, J=8.51, 2.84 Hz, 1H), 8.54 (d, J=2.21 Hz, 1H), 8.70 (d, J=2.21 Hz, 1H), 9.32 (s, 1H). MS ES+m/z 432 [M+H]⁺.

Example 52: N,N-dimethyl-4-(6-((5-(N-methyl-2-phenylcyclopropane-1-carboxamido)pyridin-3-yl)amino)pyridin-3-yl)benzamide

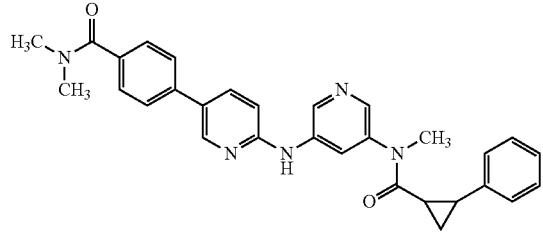 [SMILES: CN(C)C(=O)c1ccc(-c2ccc(Nc3cncc(N(C)C(=O)C4CC4c4ccccc4)c3)nc2)cc1]

Step 1: Intermediate 42—Trans-N-(5-bromo-3-pyridyl)-N-methyl-2-phenyl-cyclopropanecarboxamide

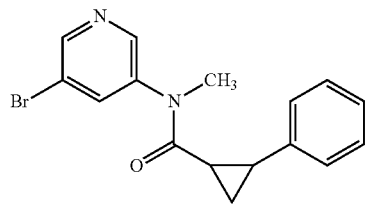 [SMILES: CN(C(=O)C1CC1c1ccccc1)c1cncc(Br)c1]

Trans-2-phenylcyclopropanecarboxylic acid (260 mg, 1.6 mmol) was taken up in SOCl₂ (1 mL, 13.7 mmol) and the resulting mixture was stirred at 70° C. for 3 h. When cooled to rt the mixture was concentrated and the resulting residue was dissolved in 2-MeTHF (3 mL) and cooled to 0° C. 5-bromo-N-methyl-pyridin-3-amine (200 mg, 1.07 mmol) was added followed by DIPEA (0.5 mL, 2.87 mmol) and the resulting mixture was stirred at rt for 1.5 h. Water (5 mL) and EtOAc (5 mL) were added and the organic layer separated. The aqueous layer was extracted with EtOAc (5 mL) and the combined organics were washed with 0.4M aq. HCl (5 mL), sat. aq. NaHCO₃, brine, dried over Na₂SO₄, filtered and concentrated to give the product as an oil (385 mg, quant.). MS ES+m/z 331 [M+H]⁺.

Step 2: N,N-dimethyl-4-(6-((5-(N-methyl-2-phenyl-cyclopropane-1-carboxamido)pyridin-3-yl)amino)pyridin-3-yl)benzamide The title compound was prepared as described in Example 25, starting from 4-(6-amino-3-pyridyl)-N,N-dimethyl-benzamide and trans-N-(5-bromo-3-pyridyl)-N-methyl-2-phenyl-cyclopropanecarboxamide and heating at 95° C. overnight, to give the product as a solid (110 mg, 36%). ¹H NMR (500 MHz, DMSO-d₆) δ ppm 1.23 (br s, 1H), 1.47-1.53 (m, 1H), 1.58-1.79 (m, 1H), 2.38-2.43 (m, 1H), 2.98 (br s, 6H), 3.27 (br s, 3H), 6.95 (d, J=8.51 Hz, 1H), 6.99-7.17 (m, 5H), 7.49 (d, J=8.20 Hz, 2H), 7.72 (d, J=8.51 Hz, 2H), 7.99 (dd, J=8.83, 2.52 Hz, 1H), 8.08 (d, J=1.89 Hz, 1H), 8.43 (br s, 1H), 8.54 (d, J=2.21 Hz, 1H), 8.64 (d, J=2.21 Hz, 1H), 9.58 (s, 1H). MS ES+m/z 492 [M+H]⁺.

Example 53: N,N-dimethyl-4-(6-((5-(1-oxoisoindolin-2-yl)pyridin-3-yl)amino)pyridin-3-yl)benzamide

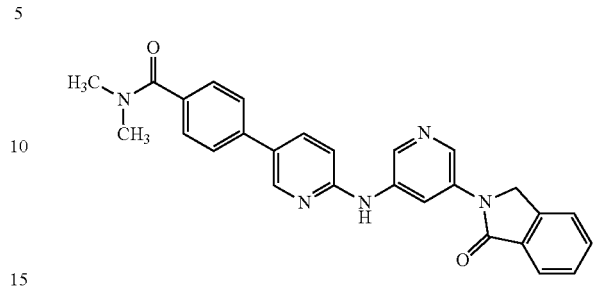

Step 1: Intermediate 43—4-[6-[(5-Bromo-3-pyridyl)amino]-3-pyridyl]-N,N-dimethyl-benzamide

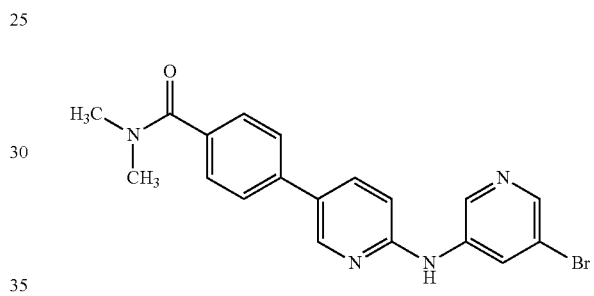

The title compound was prepared as described in Example 25, starting from 4-(6-amino-3-pyridyl)-N,N-dimethyl-benzamide and 3,5-dibromopyridine and heating at 90° C. for 2 h, to give the product as a solid (180 mg, 27%). MS ES+m/z 397 [M+H]⁺.

Step 2: N,N-dimethyl-4-(6-((5-(1-oxoisoindolin-2-yl)pyridin-3-yl)amino)pyridin-3-yl)benzamide 4-[6-[(5-Bromo-3-pyridyl)amino]-3-pyridyl]-N,N-dimethyl-benzamide (105 mg, 0.26 mmol), isoindolin-1-one (60 mg, 0.45 mmol), CuI (10 mg, 0.05 mmol), DMEDA (0.02 mL, 0.16 mmol) and K₂CO₃ (73 mg, 0.53 mmol) were suspended in 1,4-dioxane (3 mL) and stirred at 100° C. overnight. The reaction mixture was filtered, the solid washed with EtOAc and MeOH, and the filtrate concentrated. The resulting residue was washed with aqueous ammonia (25%) and triturated with acetone to give the product as a solid (4 mg, 3%). ¹H NMR (500 MHz, DMSO-d₆) δ ppm 3.00 (br s, 6H), 5.11 (s, 2H), 7.04 (d, J=8.51 Hz, 1H), 7.48-7.52 (m, 2H), 7.56-7.62 (m, 1H), 7.71-7.74 (m, 2H), 7.76 (d, J=8.51 Hz, 2H), 7.84 (d, J=7.57 Hz, 1H), 8.03 (dd, J=8.67, 2.68 Hz, 1H), 8.63 (d, J=2.52 Hz, 2H), 8.82 (d, J=2.21 Hz, 1H), 8.90 (t, J=2.36 Hz, 1H), 9.58 (s, 1H). MS ES+m/z 450 [M+H]⁺.

Example 54: 4-(6-((1-benzyl-6-oxo-1,6-dihydropyridin-3-yl)amino)pyridin-3-yl)-N,N-dimethylbenzamide

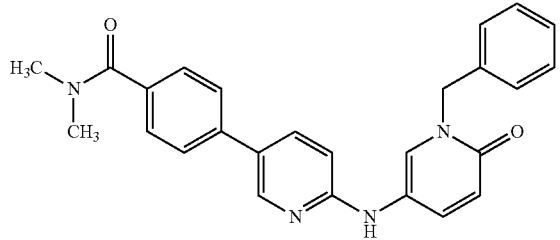 [SMILES: CN(C)C(=O)c1ccc(-c2ccc(Nc3ccc(=O)n(Cc4ccccc4)c3)nc2)cc1]

A solution of Brettphos (33 mg, 0.06 mmol) and Pd₂(dba)₃ (19 mg, 0.02 mmol) in toluene (1 mL) was degassed with nitrogen and stirred at 50° C. for 30 min. It was then transferred to a mixture of 4-(6-amino-3-pyridyl)-N,N-dimethyl-benzamide (100 mg, 0.41 mmol), 1-benzyl-5-bromo-pyridin-2-one (109 mg, 0.41 mmol) and NaOtBu (80 mg, 0.83 mmol) in toluene (4 mL) and DMF (1 mL) and the resulting mixture was stirred at 90° C. overnight. When cooled to rt the mixture was diluted with EtOAc, washed with sat. aq. NH₄Cl, concentrated and purified by preparative HPLC to give the product as a solid (35 mg, 20%). ¹H NMR (500 MHz, DMSO-d₆) δ ppm 2.98 (br s, 6H), 5.13 (s, 2H), 6.49 (d, J=9.77 Hz, 1H), 6.77 (d, J=8.83 Hz, 1H), 7.29-7.39 (m, 5H), 7.46 (m, J=8.20 Hz, 2H), 7.55 (dd, J=9.77, 2.84 Hz, 1H), 7.68 (m, J=8.20 Hz, 2H), 7.89 (dd, J=8.83, 2.52 Hz, 1H), 8.23 (d, J=2.84 Hz, 1H), 8.44 (d, J=2.52 Hz, 1H), 8.80 (s, 1H). MS ES+m/z 450 [M+H]⁺.

Example 55: 4'-((5-(2-(dimethylamino)-2-oxoethyl)pyridin-3-yl)amino)-N,N-dimethyl-[1,1'-biphenyl]-4-carboxamide

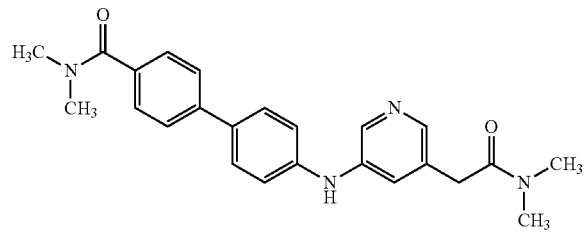

Step 1: Intermediate 44—2-(5-Bromo-3-pyridyl)-N,N-dimethyl-acetamide

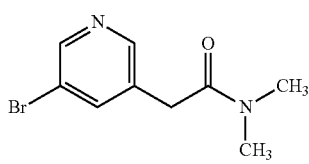

The title compound was prepared as described in Intermediate 39, using dimethylamine instead of morpholine, to give the product as an oil (335 mg, 85%). MS ES+m/z 243 [M+H]⁺.

Step 2: 4'-((5-(2-(dimethylamino)-2-oxoethyl)pyridin-3-yl)amino)-N,N-dimethyl-[1,1'-biphenyl]-4-carboxamide Brettphos (22 mg, 0.04 mmol), Pd₂(dba)₃ (19 mg, 0.02 mmol) and K₂CO₃ (86 mg, 0.62 mmol) were taken up in tBuOH (2 mL) and stirred at 50° C. for 15 min. 4-(6-amino-3-pyridyl)-N,N-dimethyl-benzamide (100 mg, 0.41 mmol) and a solution of 2-(5-bromo-3-pyridyl)-N,N-dimethyl-acetamide (131 mg, 0.54 mmol) in tBuOH (1 mL) were added and the resulting mixture was refluxed overnight. When cooled to rt the mixture was filtered, concentrated and purified by preparative HPLC to give the product as a solid (86 mg, 51%). ¹H NMR (500 MHz, DMSO-d₆) δ ppm 2.86 (s, 3H), 2.98 (br s, 6H), 3.06 (s, 3H), 3.72 (s, 2H), 6.96 (d, J=8.83 Hz, 1H), 7.48 (m, J=8.20 Hz, 2H), 7.72 (m, J=8.20 Hz, 2H), 7.96-8.01 (m, 2H), 8.01-8.05 (m, 1H), 8.57 (d, J=2.52 Hz, 1H), 8.79 (d, J=2.52 Hz, 1H), 9.39 (s, 1H). MS ES+m/z 404 [M+H]⁺.

Example 56: N,N-dimethyl-4-(6-((5-(2-oxo-2-((pyridin-3-ylmethyl)amino)ethyl)pyridin-3-yl)amino)pyridin-3-yl)benzamide

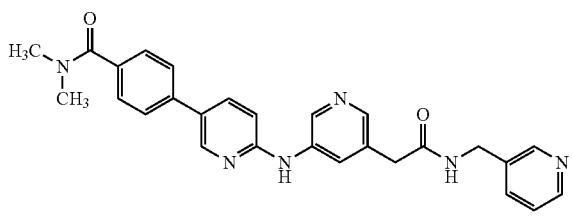 [SMILES: CN(C)C(=O)c1ccc(-c2ccc(Nc3cncc(CC(=O)NCc4cccnc4)c3)nc2)cc1]

Step 1: Intermediate 45—2-(5-Bromo-3-pyridyl)-N-(3-pyridylmethyl)acetamide

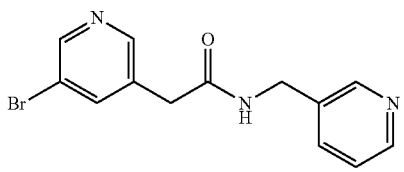 [SMILES: O=C(Cc1cncc(Br)c1)NCc1cccnc1]

The title compound was prepared as described in Intermediate 39, using 3-pyridylmethanamine instead of morpholine, to give the product as an oil (213 mg, 73%). MS ES+m/z 306 [M+H]⁺.

Step 2: N,N-dimethyl-4-(6-((5-(2-oxo-2-((pyridin-3-ylmethyl)amino)ethyl)pyridin-3-yl)amino)pyridin-3-yl)benzamide The title compound was prepared as described in Example 55, starting from 4-(6-amino-3-pyridyl)-N,N-dimethyl-benzamide and 2-(5-bromo-3-pyridyl)-N-(3-pyridylmethyl)acetamide, to give the product as a solid (58 mg, 30%). ¹H NMR (500 MHz, DMSO-d₆) δ ppm 2.98 (br s, 6H), 3.52 (s, 2H), 4.32 (d, J=5.67 Hz, 2H), 6.97 (d, J=8.83 Hz, 1H), 7.32 (dd, J=7.88, 4.73 Hz, 1H), 7.49 (m, J=8.20 Hz, 2H), 7.66 (br d, J=7.88 Hz, 1H), 7.73 (m, J=8.20 Hz, 2H), 7.97-8.01 (m, 1H), 8.01-8.04 (m, 1H), 8.15 (s, 1H), 8.44 (d, J=5.23 Hz, 1H), 8.50 (s, 1H), 8.57 (d, J=2.52 Hz, 1H), 8.69 (br t, J=5.83 Hz, 1H), 8.77 (d, J=2.21 Hz, 1H), 9.41 (s, 1H). MS ES+m/z 467 [M+H]+.

Example 57: (S)-4-(6-((5-(4-isopropyl-2,5-dioxo-imidazolidin-1-yl)pyridin-3-yl)amino)pyridin-3-yl)-N,N-dimethylbenzamide

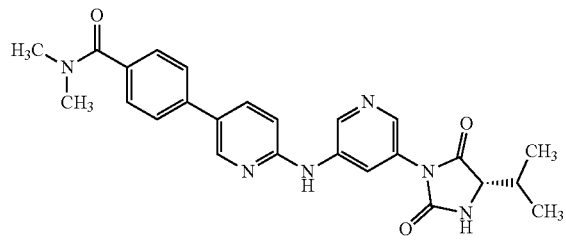 [SMILES: CC(C)[C@@H]1NC(=O)N(c2cncc(Nc3ccc(-c4ccc(C(=O)N(C)C)cc4)cn3)c2)C1=O]

Step 2: Intermediate 46—(5S)-3-(5-bromo-3-pyridyl)-5-isopropyl-imidazolidine-2,4-dione

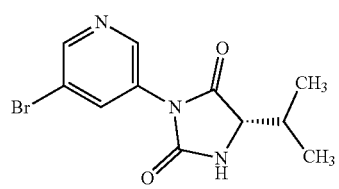 [SMILES: CC(C)[C@@H]1NC(=O)N(c2cncc(Br)c2)C1=O]

Methyl (2S)-2-isocyanato-3-methyl-butanoate (350 μL, 2.36 mmol) was added to a suspension of 5-bromopyridin-3-amine (350 mg, 2.02 mmol) in toluene (3 mL) at 0° C. The resulting mixture was stirred at rt for 2 days. The mixture was placed in refrigerator for 2 h, pentane (3 mL) was added and the precipitate was filtered off, washed with pentane (3 mL) and dried to give the product as a solid. MS ES+m/z 298 [M+H]+.

Step 2: (S)-4-(6-((5-(4-isopropyl-2,5-dioxoimidazo-lidin-1-yl)pyridin-3-yl)amino)pyridin-3-yl)-N,N-dimethylbenzamide The title compound was prepared as described in Example 55, starting from 4-(6-amino-3-pyridyl)-N,N-dimethyl-benzamide and (5S)-3-(5-bromo-3-pyridyl)-5-isopropyl-imidazolidine-2,4-dione, to give the product as a solid (11 mg, 6%). 1H NMR (500 MHz, DMSO-d6) δ ppm 0.92 (d, J=6.94 Hz, 3H), 1.04 (d, J=6.94 Hz, 3H), 2.16 (m, 1H), 2.98 (br s, 6H), 4.20 (d, J=3.15 Hz, 1H), 7.00 (d, J=8.51 Hz, 1H), 7.48 (d, J=8.20 Hz, 2H), 7.74 (d, J=8.20 Hz, 2H), 8.02 (dd, J=8.51, 2.52 Hz, 1H), 8.10 (d, J=1.89 Hz, 1H), 8.26 (t, J=2.21 Hz, 1H), 8.58 (d, J=2.21 Hz, 1H), 8.63 (s, 1H), 8.91 (d, J=2.52 Hz, 1H), 9.64 (s, 1H). MS ES+m/z 459 [M+H]+.

Example 58: 4-(6-((3,4-dihydro-2H-pyrano[2,3-b]pyridin-6-yl)amino)pyridin-3-yl)-N,N-dimethylbenzamide

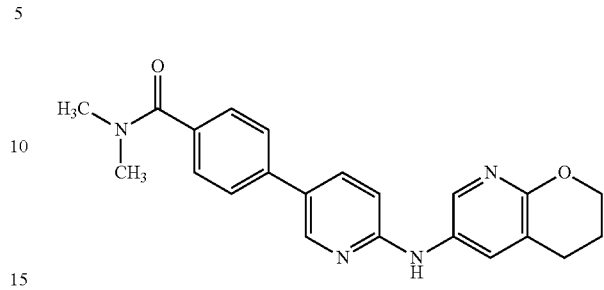

The title compound was prepared as described in Example 55, starting from 4-(6-amino-3-pyridyl)-N,N-dimethyl-benzamide and 6-bromo-3,4-dihydro-2H-pyrano[2,3-b]pyridine, and replacing tBuOH for 1,4-dioxane and K2CO3 for Cs2CO3, to give the product as a solid (99 mg, 64%). 1H NMR (500 MHz, DMSO-d6) δ ppm 1.87-1.97 (m, 2H), 2.80 (t, J=6.46 Hz, 2H), 2.99 (br s, 6H), 4.18-4.28 (m, 2H), 6.83-6.89 (m, 1H), 7.45-7.49 (m, 2H), 7.68-7.73 (m, 2H), 7.93 (td, J=4.33, 2.68 Hz, 2H), 8.20 (d, J=2.84 Hz, 1H), 8.50-8.52 (m, 1H), 9.10 (s, 1H). MS ES+m/z 375 [M+H]+.

Example 59: 4-(6-((1-acetyl-4-methyl-1,2,3,4-tetra-hydropyrido[2,3-b]pyrazin-7-yl)amino)pyridin-3-yl)-N,N-dimethylbenzamide

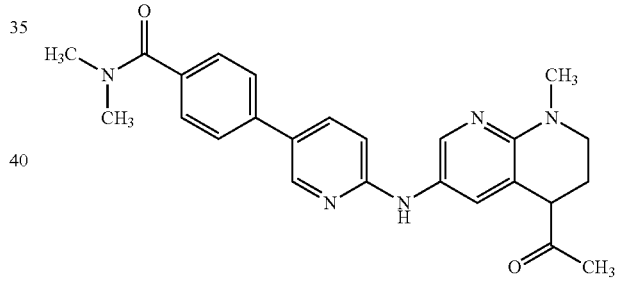

Step 1: Intermediate 47—N-[5-bromo-2-[2-hydroxyethyl(methyl)amino]-3-pyridyl]acetamide

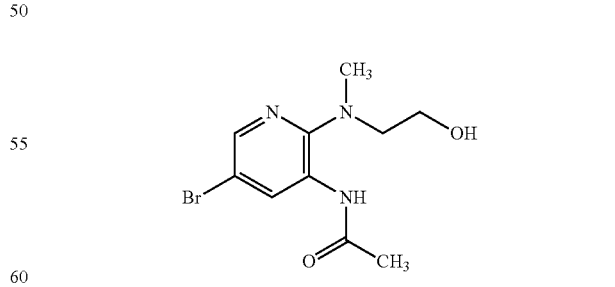

2-(Methylamino)ethanol (840 μL, 10.5 mmol) was added to a suspension of 5-bromo-2-chloro-3-nitro-pyridine (2.37 g, 10 mmol) and K2CO3 (2.07 g, 15 mmol) in EtOH (20 mL) at rt. The resulting mixture was stirred at 70° C. for 30 min. The temperature was lowered to 40° C. and a solution of sodium dithionite (7 g, 40.2 mmol) in water (20 mL) was added slowly. The mixture was stirred at 40° C. for 30 min and then at 50° C. for 15 min. More sodium dithionite (2.5 g, 14.36 mmol) dissolved in water (10 mL) was added and the mixture was stirred at 50° C. for 1 h. Sodium dithionite (5 g, 28.72 mmol) was added and the mixture was stirred at 50° C. for 30 min. The mixture was concentrated to about half the volume and a minimal amount of water was added to give a clear solution. The mixture was extracted with EtOAc (3×10 mL) and the combined organics were washed with brine, dried over Na$_2$SO$_4$, filtered and concentrated. The resulting residue (1 g) was taken up in DCM (15 mL) and pyridine (1 mL, 12.4 mmol). Acetic anhydride (400 µL, 4.23 mmol) was added and the resulting mixture was stirred at 40° C. for 2 days. The mixture was diluted with toluene (5 mL), concentrated and purified on a silica gel column eluted with 0-100% EtOAc in Heptane to give the product as a gum (580 mg, 20%). $^1$H NMR (500 MHz, CDCl$_3$) δ ppm 1.56 (br s, 1H), 2.21 (s, 3H), 2.85 (s, 3H), 3.07-3.17 (m, 2H), 3.89-3.97 (m, 2H), 8.06 (d, J=2.52 Hz, 1H), 8.89 (d, J=2.21 Hz, 1H), 8.95 (br s, 1H). MS ES+m/z 288 [M+H]$^+$.

Step 2: Intermediate 48—1-(7-Bromo-4-methyl-2,3-dihydropyrido[2,3-b]pyrazin-1-yl)ethenone

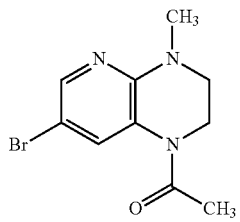

DIAD (436 µL, 2.21 mmol) was added dropwise to a solution of N-[5-bromo-2-[2-hydroxyethyl(methyl)amino]-3-pyridyl]acetamide (580 mg, 2.01 mmol) and triphenylphosphine (581 mg, 2.21 mmol) in THF (20 mL) at rt. The resulting mixture was stirred at rt for 30 min. The mixture was concentrated and purified on a silica gel column eluted with 0-60% EtOAc in heptane to give the product as a gum (485 mg, 89%). MS ES+m/z 270 [M+H]$^+$.

Step 3: 4-(6-((1-acetyl-4-methyl-1,2,3,4-tetrahydropyrido[2,3-b]pyrazin-7-yl)amino)pyridin-3-yl)-N,N-dimethylbenzamide 4-(6-Amino-3-pyridyl)-N,N-dimethyl-benzamide (120 mg, 0.5 mmol), 1-(7-bromo-4-methyl-2,3-dihydropyrido[2,3-b]pyrazin-1-yl)ethanone (134 mg, 0.5 mmol), Brettphos Pd G3 (22 mg, 0.03 mmol) and Cs$_2$CO$_3$ (450 mg, 1.38 mmol) were taken up in tBuOH (5 mL) and stirred at 90° C. for 5 h. The mixture was concentrated and the resulting residue was taken up in EtOAc (5 mL) and water (3 mL). The organic layer was separated and the aqueous layer extracted with EtOAc (2×5 mL). The combined organics were washed with brine, dried over Na$_2$SO$_4$, filtered, concentrated and purified by preparative HPLC to give the product as a solid (65 mg, 30%). $^1$H NMR (500 MHz, DMSO-d$_6$) δ ppm 2.23 (s, 3H), 2.98 (br s, 6H), 3.05 (s, 3H), 3.40 (br t, J=4.89 Hz, 2H), 3.80-3.85 (m, 2H), 6.78 (d, J=8.43 Hz, 1H), 7.44-7.49 (m, 2H), 7.66-7.70 (m, 2H), 7.87 (dd, J=8.67, 2.68 Hz, 1H), 8.12 (br s, 1H), 8.42-8.46 (m, 1H), 8.87 (s, 1H). MS ES+m/z 431 [M+H]$^+$.

Example 60: N,N-dimethyl-4-(6-((6-morpholino-pyridin-3-yl)amino)pyridin-3-yl)benzamide

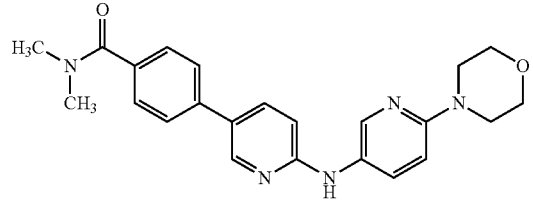 [SMILES: CN(C)C(=O)c1ccc(-c2ccc(Nc3ccc(N4CCOCC4)nc3)nc2)cc1]

The title compound was prepared as described in Example 59, starting from 4-(6-amino-3-pyridyl)-N,N-dimethyl-benzamide and 4-(5-iodo-2-pyridyl)morpholine, to give the product as a solid (38 mg, 23%). $^1$H NMR (500 MHz, DMSO-d$_6$) δ ppm 2.98 (br s, 6H), 3.33-3.38 (m, 4H), 3.70-3.74 (m, 4H), 6.80-6.87 (m, 2H), 7.44-7.48 (m, 2H), 7.66-7.71 (m, 2H), 7.89 (dd, J=8.67, 2.68 Hz, 1H), 7.94 (dd, J=8.98, 2.68 Hz, 1H), 8.40 (d, J=2.21 Hz, 1H), 8.46 (dd, J=2.52, 0.63 Hz, 1H), 8.96 (s, 1H). MS ES+m/z 403 [M+H]$^+$.

Example 61: N,N-dimethyl-4-(6-((2-methyloxazolo[4,5-b]pyridin-6-yl)amino)pyridin-3-yl)benzamide

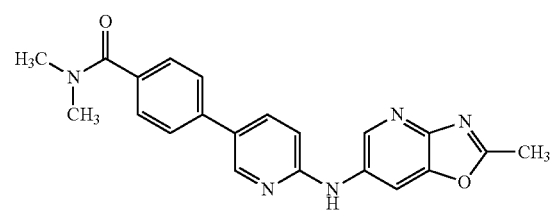

The title compound was prepared as described in Example 59, starting from 4-(6-amino-3-pyridyl)-N,N-dimethyl-benzamide and 6-bromo-2-methyl-oxazolo[4,5-b]pyridine, replacing tBuOH for 1,4-dioxane and stirring at 100° C. for 2 days, to give the product as a solid (16 mg, 4%). $^1$H NMR (500 MHz, DMSO-d$_6$) δ ppm 2.65 (s, 3H), 2.97-3.02 (m, 6H), 6.97-7.03 (m, 1H), 7.49 (s, 1H), 7.51 (s, 1H), 7.73 (s, 1H), 7.75 (s, 1H), 8.00-8.05 (m, 1H), 8.54 (s, 1H), 8.60-8.62 (m, 1H), 8.82 (d, J=2.52 Hz, 1H), 9.71 (s, 1H). MS ES+m/z 374 [M+H]$^+$.

Example 62: 4-(6-([1,3]dioxolo[4,5-b]pyridin-6-ylamino)pyridin-3-yl)-N,N-dimethylbenzamide

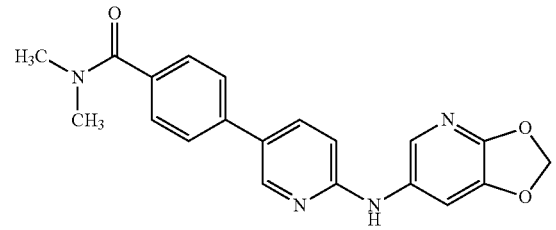 [SMILES: CN(C)C(=O)c1ccc(-c2ccc(Nc3cnc4c(c3)OCO4)nc2)cc1]

The title compound was prepared as described in Example 59, starting from 4-(6-amino-3-pyridyl)-N,N-dimethyl-benzamide and 6-bromo-[1,3]dioxolo[4,5-b]pyridine, replacing tBuOH for 1,4-dioxane and stirring at 100° C. overnight, to give the product as a solid (19 mg, 23%). ¹H NMR (500 MHz, DMSO-d₆) δ ppm 2.98 (br s, 6H) 6.13 (s, 2H) 6.88 (d, J=8.83 Hz, 1H) 7.48 (d, J=7.61 Hz, 2H) 7.70 (s, 1H) 7.71 (s, 1H) 7.77 (d, J=2.21 Hz, 1H) 7.83 (d, J=1.89 Hz, 1H) 7.95 (dd, J=8.67, 2.68 Hz, 1H) 8.52 (d, J=2.52 Hz, 1H) 9.21 (s, 1H). MS ES+m/z 363 [M+H]⁺.

Example 63: N,N-dimethyl-4-(6-(pyridin-3-ylamino)pyridin-3-yl)benzenesulfonamide

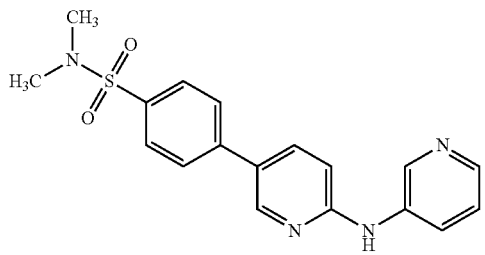 [SMILES: CN(C)S(=O)(=O)c1ccc(-c2ccc(Nc3cccnc3)nc2)cc1]

Step 1: Intermediate 49—4-(6-Chloro-3-pyridyl)-N,N-dimethyl-benzenesulfonamide

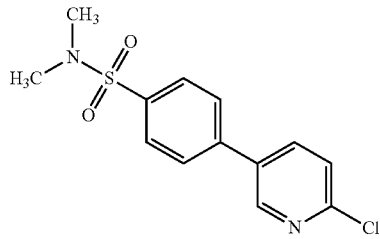 [SMILES: CN(C)S(=O)(=O)c1ccc(-c2ccc(Cl)nc2)cc1]

2-Chloro-5-(4,4,5,5-tetramethyl-1,3,2-dioxaborolan-2-yl)pyridine (1.39 g, 5.82 mmol), 4-iodo-N,N-dimethyl-benzenesulfonamide (1.51 g, 4.85 mmol), K₂CO₃ (1.68 g, 12.13 mmol) and PdCl₂(Amphos) (0.14 g, 0.2 mmol) were dissolved in 1,4-dioxane (5 mL) and water (2 mL) and the mixture was stirred at 95° C. for 2 h. Water and EtOAc was added and the mixture was extracted. The organic layer was concentrated and the residue was recrystallized from EtOH to give the product as a solid (0.25 g, 17%). MS ES+m/z 297 [M+H]⁺.

Step 2: N,N-dimethyl-4-(6-(pyridin-3-ylamino)pyridin-3-yl)benzenesulfonamide

The title compound was prepared as described in Example 30, starting from 4-(6-chloro-3-pyridyl)-N,N-dimethyl-benzenesulfonamide and pyridine-3-amine, to give the product as a solid (26 mg, 11%). ¹H NMR (500 MHz, DMSO-d₆) δ ppm 2.66 (s, 6H) 7.00 (d, 1H) 7.33 (dd, 1H) 7.81 (m, 2H) 7.96 (m, 2H) 8.06 (dd, 1H) 8.15 (dd, 1H) 8.27 (br d, 1H) 8.65 (d, 1H) 8.86 (d, 1H) 9.53 (s, 1H). MS ES+m/z 355 [M+H]⁺.

Example 64: N-methyl-N-(4-(6-(pyridin-3-ylamino)pyridin-3-yl)phenyl)acetamide

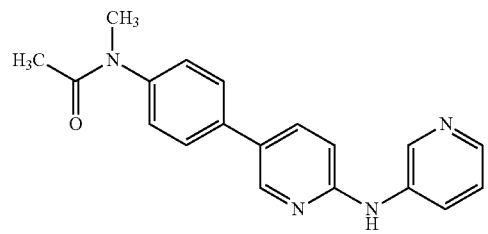 [SMILES: CC(=O)N(C)c1ccc(-c2ccc(Nc3cccnc3)nc2)cc1]

Step 1: Intermediate 50—N-[4-(6-chloro-3-pyridyl)phenyl]-N-methyl-acetamide

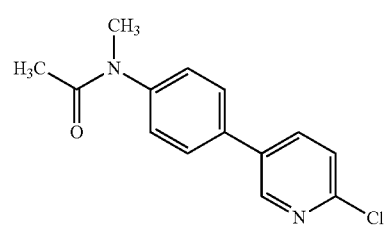 [SMILES: CC(=O)N(C)c1ccc(-c2ccc(Cl)nc2)cc1]

The title compound was prepared as described in Intermediate 3, starting from N-(4-bromophenyl)-N-methyl-acetamide and (6-chloro-3-pyridyl)boronic acid, to give the product as a solid (1.33 g, 58%). MS ES+m/z 261 [M+H]⁺.

Step 2: N-methyl-N-(4-(6-(pyridin-3-ylamino)pyridin-3-yl)phenyl)acetamide

N-[4-(6-chloro-3-pyridyl)phenyl]-N-methyl-acetamide (730 mg, 2.8 mmol), Cs₂CO₃ (1.4 g, 4.2 mmol), 2-(2'-Di-tert-butylphosphine)biphenylpalladium(II) acetate (65 mg, 0.14 mmol), pyridin-3-amine (350 mg, 3.72 mmol) and TEA (0.19 mL, 1.4 mmol) were taken up in 1,4-dioxane (15 mL), the resulting mixture was degassed with nitrogen for 5 min and stirred at 90° C. overnight. NaOtBu (538 mg, 5.6 mmol) and 2-(2'-Di-tert-butylphosphine)biphenylpalladium(II) acetate (65 mg, 0.14 mmol) were added and stirring continued at 90° C. for 4 h. When cooled to rt the mixture was diluted with EtOAc (10 mL), brine (10 mL) and water (5 mL). The organic layer was separated and the aqueous layer extracted with EtOAc (2×10 mL). The combined organics were washed with brine, filtered, concentrated and purified by preparative HPLC to give the product as a solid (36 mg, 4%). ¹H NMR (500 MHz, DMSO-d₆) δ=9.42 (br s, 1H), 8.84 (d, J=2.5 Hz, 1H), 8.61-8.51 (m, 1H), 8.31-8.22 (m, 1H), 8.11 (dd, J=1.3, 4.4 Hz, 1H), 7.97 (dd, J=2.2, 8.5 Hz, 1H), 7.72 (br d, J=7.3 Hz, 2H), 7.40 (br d, J=7.9 Hz, 2H), 7.36-7.27 (m, 1H), 6.96 (d, J=8.8 Hz, 1H), 3.17 (s, 3H), 1.82 (br s, 3H). MS ES+m/z 319 [M+H]⁺.

Example 65: 5-(4-(4-methyl-4H-1,2,4-triazol-3-yl)phenyl)-N-(pyridin-3-yl)pyridin-2-amine

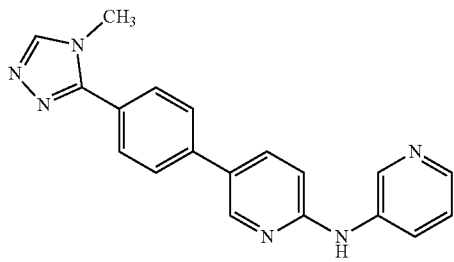 [SMILES: Cn1cnnc1-c1ccc(-c2ccc(Nc3cccnc3)nc2)cc1]

Step 1: Intermediate 51—3-(4-Bromophenyl)-4-methyl-1,2,4-triazole

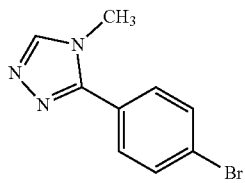

4-Bromobenzohydrazide 650 mg, 3.02 mmol) and DMFDMA (0.5 mL, 3.76 mmol) were taken up in DMF (1.5 mL) and the resulting mixture was heated in a microwave reactor at 130° C. for 1 h. When cooled to rt33% MeNH$_2$ (1.5 mL, 12.05 mmol) in EtOH was added followed by careful addition of AcOH (1 mL, 17.48 mmol). The resulting mixture was heated in a microwave reactor at 130° C. for 30 min. When cooled to rt the mixture was poured into water (15 mL) and kept in refrigerator overnight. The formed precipitate was filtered off and discarded. The pH of the filtrate was adjusted >7 using 2M aq. NaOH and then extracted with EtOAc (3×10 m). The combined organics were washed with brine, dried over Na$_2$SO$_4$, filtered and concentrated to give the product as a solid (440 mg, 61%). MS ES+ m/z 238 [M+H]$^+$.

Step 2: Intermediate 52—2-Chloro-5-[4-(4-methyl-1,2,4-triazol-3-yl)phenyl]pyridine

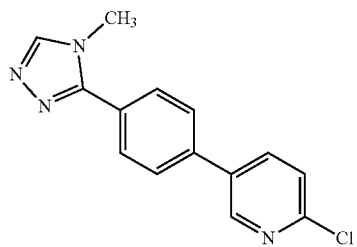 [SMILES: Cn1cnnc1-c1ccc(-c2ccc(Cl)nc2)cc1]

The title compound was prepared as described in Intermediate 4, starting from 3-(4-bromophenyl)-4-methyl-1,2,4-triazole and (6-chloro-3-pyridyl)boronic acid, replacing 1,4-dioxane for n-BuOH and stirring the mixture at 90° C. for 2.5 h, to give the product as a solid (250 mg, 55%). MS ES+m/z 271 [M+H]$^+$.

Step 3: 5-(4-(4-methyl-4H-1,2,4-triazol-3-yl)phenyl)-N-(pyridin-3-yl)pyridin-2-amine The title compound was prepared as described in Example 18, starting from 2-chloro-5-[4-(4-methyl-1,2,4-triazol-3-yl)phenyl]pyridine and pyridine-3-amine and replacing 1,4-dioxane for DMF, to give the product as a solid (15 mg, 10%). $^1$H NMR (500 MHz, DMSO-d$_6$) δ=9.47 (s, 1H), 8.86 (d, J=2.5 Hz, 1H), 8.64-8.63 (m, 1H), 8.60 (s, 1H), 8.28 (br d, J=8.5 Hz, 1H), 8.14 (dd, J=1.1, 4.6 Hz, 1H), 8.05 (dd, J=2.5, 8.8 Hz, 1H), 7.89-7.83 (m, 4H), 7.33 (dd, J=4.7, 8.2 Hz, 1H), 7.00 (d, J=8.5 Hz, 1H), 3.80 (s, 3H). MS ES+m/z 329 [M+H]$^+$.

Example 66: (4-(6-(pyridin-3-ylamino)pyridin-3-yl)phenyl)(pyrrolidin-1-yl)methanone

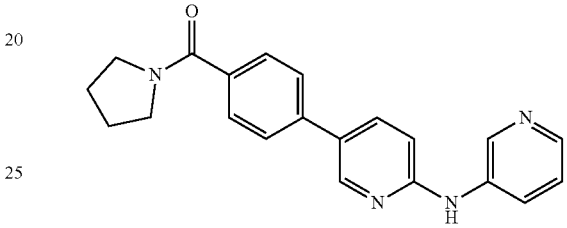

The title compound was prepared as described in Example 10, starting from 5-bromo-N-(3-pyridyl)pyridin-2-amine and [4-(pyrrolidine-1-carbonyl)phenyl]boronic acid, to give the product as a solid (42 mg, 30%). $^1$H NMR (500 MHz, DMSO-d$_6$) δ ppm 1.82-1.94 (m, 4H), 3.44-3.54 (m, 4H), 6.95-7.02 (m, 1H), 7.29-7.34 (m, 1H), 7.59-7.63 (m, 2H), 7.71-7.75 (m, 2H), 7.97-8.03 (m, 1H), 8.10-8.15 (m, 1H), 8.24-8.31 (m, 1H), 8.48-8.63 (m, 1H), 8.75-8.93 (m, 1H), 9.40-9.52 (m, 1H). MS ES+m/z 345 [M+H]$^+$.

Example 67: N-benzyl-N-methyl-4-(6-(pyridin-3-ylamino)pyridin-3-yl)benzamide

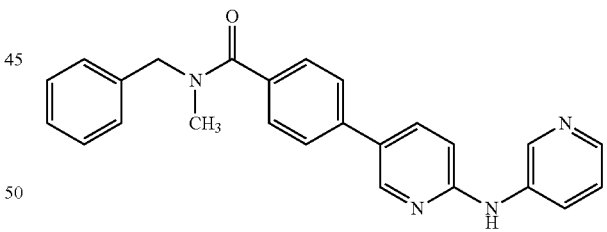

Step 1: Intermediate 53 —: [4-[Benzyl(methyl)carbamoyl]phenyl]boronic acid

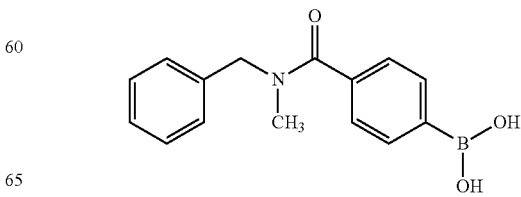

4-Boronobenzoic acid (1 g, 6.03 mmol) was dissolved in DMF (5 mL). HATU (2.8 g, 7.41 mmol) and DIPEA (5.38 mL, 30.88 mmol) were added and the resulting mixture was stirred at rt for 10 min. N-methyl-1-phenyl-methanamine (1.59 mL, 12.4 mmol) was added and the mixture was stirred at rt for 2.5 h. Water (50 mL) and EtOAc (50 mL) were added, the organic layer separated and washed with half sat. aq. NH$_4$Cl (2×50 mL), water (2×50 mL), brine, dried over Na$_2$SO$_4$ and concentrated to give the product as a solid (1.49 g, 90%). MS ES+m/z 270 [M+H]$^+$.

Step 2: N-benzyl-N-methyl-4-(6-(pyridin-3-ylamino)pyridin-3-yl)benzamide

The title compound was prepared as described in Example 10, starting from 5-bromo-N-(3-pyridyl)pyridin-2-amine and [4-[benzyl(methyl)carbamoyl]phenyl]boronic acid, to give the product as a solid (55 mg, 34%). $^1$H NMR (500 MHz, DMSO-d$_6$) δ ppm 9.44 (1H, br s) 8.83 (1H, br s) 8.57 (1H, br s) 8.26 (1H, br d) 8.11 (1H, m) 7.98 (1H, br s) 7.74 (2H, br s) 7.53 (2H, br s) 7.35-7.42 (3H, m) 7.30 (2H, dd) 7.22 (1H, br s) 6.92-7.01 (1H, m) 4.69 (1H, br s) 4.55 (1H, br s) 2.89 (3H, br s). MS ES+m/z 395 [M+H]$^+$.

Example 68: N-ethyl-N-methyl-4-(6-(pyridin-3-ylamino)pyridin-3-yl)benzamide

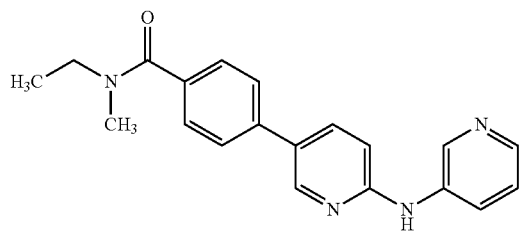 [SMILES: CCN(C)C(=O)c1ccc(-c2ccc(Nc3cccnc3)nc2)cc1]

Step 1: Intermediate 54—Methyl 4-[6-(3-pyridylamino)-3-pyridyl]benzoate

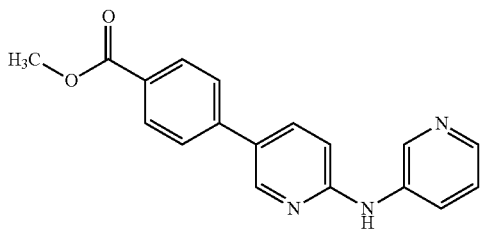 [SMILES: COC(=O)c1ccc(-c2ccc(Nc3cccnc3)nc2)cc1]

The title compound was prepared as described in Example 10, starting from 5-bromo-N-(3-pyridyl)pyridin-2-amine and (4-methoxycarbonylphenyl)boronic acid, to give the product as a solid (412 mg, 70%). MS ES+m/z 306 [M+H]$^+$.

Step 2: Intermediate 55—4-[6-(3-Pyridylamino)-3-pyridyl]benzoic acid

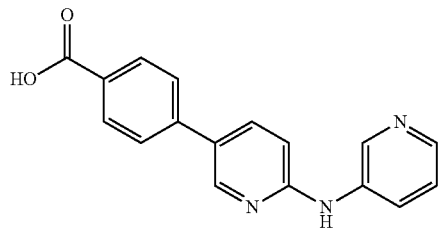 [SMILES: O=C(O)c1ccc(-c2ccc(Nc3cccnc3)nc2)cc1]

Methyl 4-[6-(3-pyridylamino)-3-pyridyl]benzoate (412 mg, 1.35 mmol) was taken up in MeOH (20 mL) and water (2 mL). LiOH hydrate (283 mg, 6.75 mmol) was added and the reaction mixture was refluxed overnight. When cooled to rt the mixture was concentrated and 1M aq. HCl (50 mL) was added. The formed precipitate was filtered off and dried to give the product as a solid (342 mg, 87%). MS ES+m/z 292 [M+H]$^+$.

Step 3: N-ethyl-N-methyl-4-(6-(pyridin-3-ylamino)pyridin-3-yl)benzamide

The title compound was prepared as described in Intermediate 53, starting from 4-[6-(3-pyridylamino)-3-pyridyl]benzoic acid and N-methylethylamine. Purification by preparative HPLC gave the product as a solid (63 mg, 55%). $^1$H NMR (500 MHz, DMSO-d$_6$) δ ppm 1.11 (br s, 3H), 2.95 (br s, 3H), 3.22-3.32 (m, 1H), 3.35-3.54 (m, 1H), 6.98 (dd, J=8.83, 0.63 Hz, 1H), 7.32 (dd, J=8.35, 4.57 Hz, 1H), 7.46 (br s, 2H), 7.73 (m, J=7.60 Hz, 2H), 8.00 (dd, J=8.51, 2.52 Hz, 1H), 8.13 (dd, J=4.57, 1.42 Hz, 1H), 8.27 (m, J=8.40, 2.70, 1.60 Hz, 1H), 8.58 (d, J=2.21 Hz, 1H), 8.85 (d, J=2.21 Hz, 1H), 9.45 (s, 1H). MS ES+m/z 333 [M+H]$^+$.

Example 69: N-(furan-2-ylmethyl)-N-methyl-4-(6-(pyridin-3-ylamino)pyridin-3-yl)benzamide

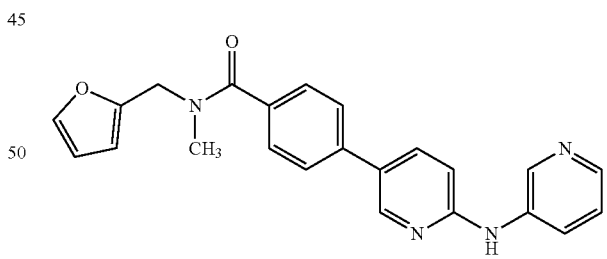

The title compound was prepared as described in Intermediate 53, starting from 4-[6-(3-pyridylamino)-3-pyridyl]benzoic acid and 1-(2-furyl)-N-methyl-methanamine. Purification by preparative HPLC gave the product as a solid (70 mg, 40%). $^1$H NMR (500 MHz, DMSO-d$_6$) δ ppm 2.92 (s, 3H), 4.48 (br s, 1H), 4.68 (br s, 1H), 6.40 (br s, 1H), 6.43-6.47 (m, 1H), 6.97 (d, J=8.51 Hz, 1H), 7.31 (dd, J=8.35, 4.57 Hz, 1H), 7.53 (br s, 2H), 7.64-7.68 (m, 1H), 7.74 (br s, 1H), 7.75 (br s, 1H), 8.00 (dd, J=8.67, 2.36 Hz, 1H), 8.12 (dd, J=4.57, 1.42 Hz, 1H), 8.26 (m, J=8.30 Hz, 1H), 8.58 (d, J=2.21 Hz, 1H), 8.84 (d, J=2.21 Hz, 1H), 9.44 (s, 1H). MS ES+m/z 385 [M+H]$^+$.

Example 70: N-methyl-4-(6-(pyridin-3-ylamino)pyridin-3-yl)-N-(pyridin-3-ylmethyl)benzamide

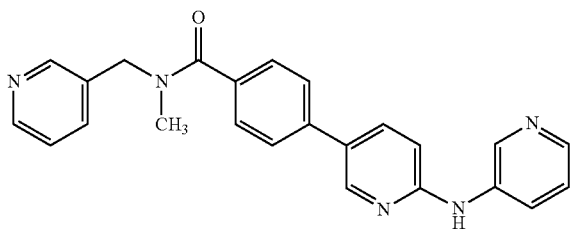 [SMILES: CN(Cc1cccnc1)C(=O)c1ccc(-c2ccc(Nc3cccnc3)nc2)cc1]

The title compound was prepared as described in Intermediate 53, starting from 4-[6-(3-pyridylamino)-3-pyridyl]benzoic acid and N-methyl-1-(3-pyridyl)methanamine. Purification by preparative HPLC gave the product as a solid (45 mg, 33%). $^1$H NMR (500 MHz, DMSO-$d_6$) δ ppm 2.93 (s, 3H), 4.51-4.77 (m, 2H), 6.97 (br d, J=8.83 Hz, 1H), 7.31 (dd, J=8.20, 4.73 Hz, 1H), 7.42 (m, J=7.40, 4.90 Hz, 1H), 7.55 (br s, 2H), 7.74 (m, J=7.90 Hz, 3H), 7.99 (br d, J=7.57 Hz, 1H), 8.12 (dd, J=4.41, 1.26 Hz, 1H), 8.26 (m, J=8.50 Hz, 1H), 8.37-8.66 (m, 3H), 8.84 (d, J=2.21 Hz, 1H), 9.44 (s, 1H). MS ES+m/z 396 [M+H]$^+$.

Example 71: N-methyl-4-(6-(pyridin-3-ylamino)pyridin-3-yl)-N-(thiazol-5-ylmethyl)benzamide

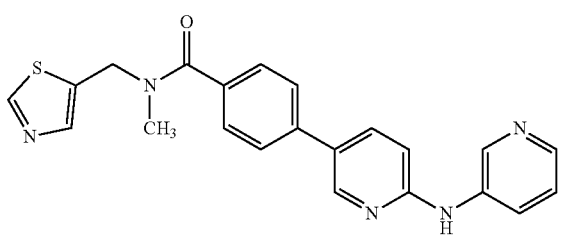 [SMILES: CN(Cc1cncs1)C(=O)c1ccc(-c2ccc(Nc3cccnc3)nc2)cc1]

The title compound was prepared as described in Intermediate 53, starting from 4-[6-(3-pyridylamino)-3-pyridyl]benzoic acid and N-methyl-1-thiazol-5-yl-methanamine. Purification by preparative HPLC gave the product as a solid (48 mg, 27%). $^1$H NMR (500 MHz, DMSO-$d_6$) δ ppm 2.94 (s, 3H), 4.85 (br s, 2H), 6.97 (dd, J=8.83, 0.63 Hz, 1H), 7.29-7.32 (m, 1H), 7.51 (d, J=7.62 Hz, 2H), 7.75 (br d, J=8.20 Hz, 2H), 7.90 (br s, 1H), 7.99 (dd, J=8.67, 2.68 Hz, 1H), 8.12 (dd, J=4.57, 1.42 Hz, 1H), 8.26 (ddd, J=8.35, 2.68, 1.26 Hz, 1H), 8.58 (d, J=2.21 Hz, 1H), 8.84 (d, J=2.21 Hz, 1H), 9.07 (d, J=0.63 Hz, 1H), 9.46 (br s, 1H). MS ES+m/z 402 [M+H]$^+$.

Example 72: N,N-dimethyl-4-(6-((5-(3-methyl-2-oxoimidazolidin-1-yl)pyridin-3-yl)amino)pyridin-3-yl)benzamide

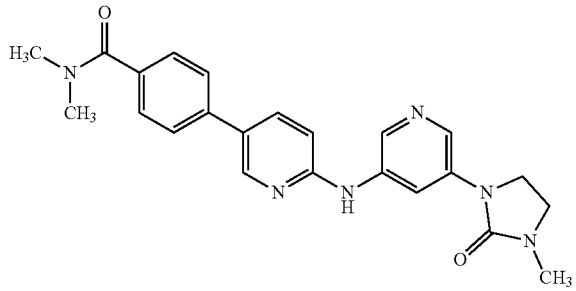 [SMILES: CN(C)C(=O)c1ccc(-c2ccc(Nc3cncc(N4CCN(C)C4=O)c3)nc2)cc1]

Step 1: Intermediate 56—1-(5-Bromo-3-pyridyl)-3-methyl-imidazolidin-2-one

60% NaH (62 mg, 1.61 mmol) was added to a suspension of 1-(5-bromo-3-pyridyl)imidazolidin-2-one (300 mg, 1.24 mmol) in THF (5 mL) at 0° C. The resulting mixture was stirred at rt for 1 h. MeI (85 μL, 1.37 mmol) was added and the reaction mixture was stirred at rt overnight. More MeI (85 μL, 1.37 mmol) was added followed by DMF (1 mL) and the mixture was stirred for 2 h. Sat. aq. NH$_4$Cl (4 mL) was added and the mixture extracted with EtOAc (3×5 mL). The combined organics were washed with brine, dried over Na$_2$SO$_4$, filtered and concentrated to give the product as a solid (280 mg, 89%). MS ES+m/z 256 [M+H]$^+$.

Step 2: N,N-dimethyl-4-(6-((5-(3-methyl-2-oxoimidazolidin-1-yl)pyridin-3-yl)amino)pyridin-3-yl)benzamide The title compound was prepared as described in Example 25, starting from 4-(6-amino-3-pyridyl)-N,N-dimethyl-benzamide and 1-(5-bromo-3-pyridyl)-3-methyl-imidazolidin-2-one and heating at 100° C. for 1 h, to give the product as a solid (20 mg, 12%). $^1$H NMR (500 MHz, DMSO-$d_6$) δ ppm 2.79 (s, 3H), 2.94-3.12 (m, 6H), 3.41-3.58 (m, 2H), 3.79-3.94 (m, 2H), 6.98 (d, 1H), 7.48 (d, 2H), 7.73 (d, 2H), 7.98 (dd, 1H), 8.31 (br s, 1H), 8.42-8.49 (m, 1H), 8.54-8.60 (m, 1H), 8.67 (br s, 1H), 9.42 (s, 1H). MS ES+m/z 417 [M+H]$^+$.

Example 73: 4-(6-((5-(3-benzyl-2-oxoimidazolidin-1-yl)pyridin-3-yl)amino)pyridin-3-yl)-N,N-dimethylbenzamide

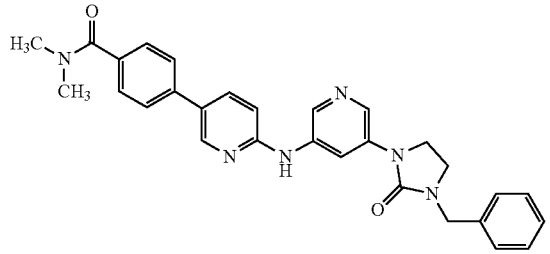 [SMILES: CN(C)C(=O)c1ccc(-c2ccc(Nc3cncc(N4CCN(Cc5ccccc5)C4=O)c3)nc2)cc1]

The title compound was prepared as described in Example 25, starting from 4-(6-amino-3-pyridyl)-N,N-dimethyl-benzamide and 1-benzyl-3-(5-bromo-3-pyridyl)imidazolidin-2-one and heating at 90° C. for 6 h in toluene, to give the product as a solid (166 mg, 81%). ¹H NMR (500 MHz, METHANOL-d4) δ ppm 3.08 (s, 3H), 3.15 (s, 3H), 3.58 (dd, J=9.30, 7.09 Hz, 3H), 3.96-4.02 (m, 2H), 4.53-4.56 (m, 2H), 7.07-7.12 (m, 1H), 7.37-7.41 (m, 5H), 7.56 (d, J=8.51 Hz, 2H), 7.73-7.78 (m, 3H), 8.06-8.10 (m, 1H), 8.57-8.60 (m, 1H), 8.65-8.69 (m, 1H), 8.92-8.95 (m, 1H), 9.36-9.40 (m, 1H). MS ES+m/z 493 [M+H]⁺.

Example 74: 4-(6-((5-(3-(4-methoxybenzyl)-2-oxoimidazolidin-1-yl)pyridin-3-yl)amino)pyridin-3-yl)-N,N-dimethylbenzamide

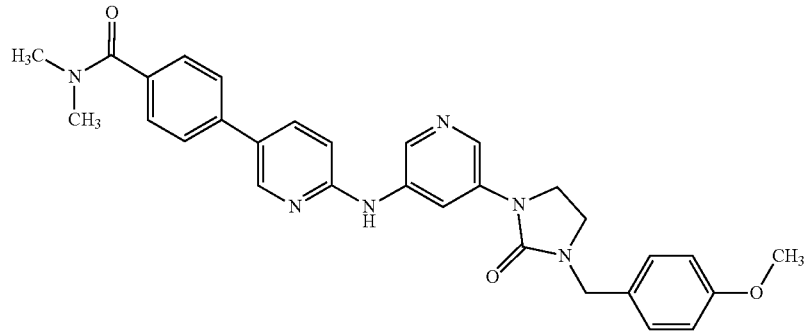

Step 1: Intermediate 57—1-(5-Bromo-3-pyridyl)-3-[(4-methoxyphenyl)methyl]imidazolidin-2-one

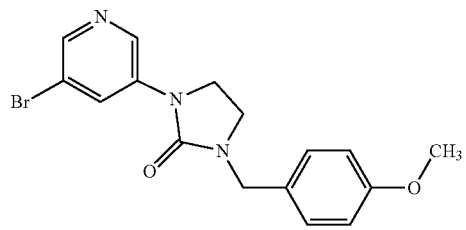 [SMILES: COc1ccc(CN2CCN(c3cncc(Br)c3)C2=O)cc1]

The title compound was prepared as described in Intermediate 56, starting from 1-(5-bromo-3-pyridyl)imidazolidin-2-one and 1-(chloromethyl)-4-methoxy-benzene, replacing THF for DMF, to give the product as a solid (289 mg, quant.). MS ES+m/z 362 [M+H]⁺.

Step 2: 4-(6-((5-(3-(4-methoxybenzyl)-2-oxoimidazolidin-1-yl)pyridin-3-yl)amino)pyridin-3-yl)-N,N-dimethylbenzamide The title compound was prepared as described in Example 25, starting from 4-(6-amino-3-pyridyl)-N,N-dimethyl-benzamide and 1-(5-bromo-3-pyridyl)-3-[(4-methoxyphenyl)methyl]imidazolidin-2-one and heating at 90° C. overnight, to give the product as a solid (250 mg, 77%). ¹H NMR (500 MHz, DMSO-d₆) δ ppm 2.99 (br s, 6H), 3.34-3.42 (m, 2H), 3.76 (s, 3H), 3.86 (br t, J=7.88 Hz, 2H), 4.36 (s, 2H), 6.93-7.01 (m, 3H), 7.26 (d, J=8.51 Hz, 2H), 7.49 (d, J=8.20 Hz, 2H), 7.74 (d, J=8.20 Hz, 2H), 8.00 (dd, J=8.83, 2.52 Hz, 1H), 8.34 (d, J=2.21 Hz, 1H), 8.47-8.49 (m, 1H), 8.58 (d, J=2.21 Hz, 1H), 8.71 (d, J=1.89 Hz, 1H), 9.44 (s, 1H). MS ES+m/z 523 [M+H]⁺.

Example 75: N,N-dimethyl-4-(6-((5-(2-oxoimidazolidin-1-yl)pyridin-3-yl)amino)pyridin-3-yl)benzamide

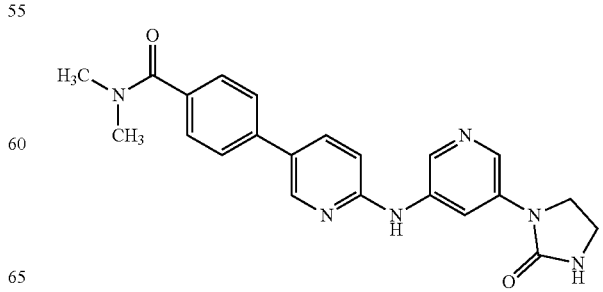

The title compound was prepared as described in Example 55, starting from 4-(6-amino-3-pyridyl)-N,N-dimethyl-benzamide and 1-(5-bromo-3-pyridyl)imidazolidin-2-one, to give the product as a solid (15 mg, 9%). ¹H NMR (500 MHz, DMSO-d₆) δ ppm 2.99 (br s, 6H), 3.46 (t, J=7.88 Hz, 2H), 3.88-3.94 (m, 2H), 6.99 (d, J=8.83 Hz, 1H), 7.10 (s, 1H), 7.49 (m, J=8.20 Hz, 2H), 7.73 (m, J=8.20 Hz, 2H), 7.99 (dd, J=8.83, 2.52 Hz, 1H), 8.29 (d, J=2.21 Hz, 1H), 8.41 (t, J=2.21 Hz, 1H), 8.57 (d, J=2.52 Hz, 1H), 8.73 (d, J=2.21 Hz, 1H), 9.41 (s, 1H). MS ES+m/z 403 [M+H]⁺.

Example 76: N,N-dimethyl-4-(6-((5-(2-oxo-3-(pyridin-3-ylmethyl)imidazolidin-1-yl)pyridin-3-yl)amino)pyridin-3-yl)benzamide

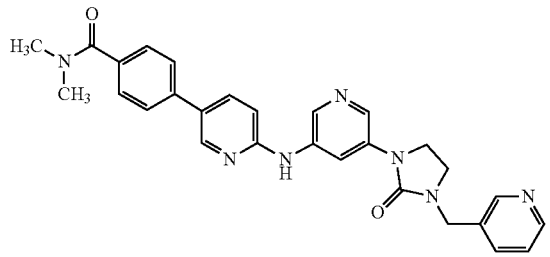 [SMILES: CN(C)C(=O)c1ccc(-c2ccc(Nc3cncc(N4CCN(Cc5cccnc5)C4=O)c3)nc2)cc1]

Step 1: Intermediate 58—1-(5-Bromo-3-pyridyl)-3-(3-pyridylmethyl)imidazolidin-2-one

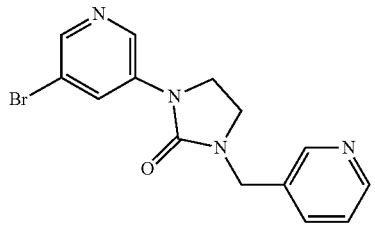

The title compound was prepared as described in Intermediate 56, starting from 1-(5-bromo-3-pyridyl)imidazolidin-2-one and 3-(bromomethyl)pyridine HBr, replacing THF for DMF, to give the product as a solid (206 mg, quant.). MS ES+m/z 333 [M+H]⁺.

Step 2: N,N-dimethyl-4-(6-((5-(2-oxo-3-(pyridin-3-ylmethyl)imidazolidin-1-yl)pyridin-3-yl)amino)pyridin-3-yl)benzamide The title compound was prepared as described in Example 25, starting from 4-(6-amino-3-pyridyl)-N,N-dimethyl-benzamide and 1-(5-bromo-3-pyridyl)-3-(3-pyridylmethyl)imidazolidin-2-one and heating at 90° C. overnight, to give the product as a solid (46 mg, 15%). ¹H NMR (500 MHz, DMSO-d₆) δ ppm 2.99 (br s, 6H), 3.43-3.50 (m, 2H), 3.85-3.93 (m, 2H), 4.47 (s, 2H), 6.99 (d, J=8.51 Hz, 1H), 7.42 (dd, J=7.72, 4.89 Hz, 1H), 7.49 (d, J=8.20 Hz, 2H), 7.72-7.78 (m, 3H), 8.00 (dd, J=8.51, 2.52 Hz, 1H), 8.34 (d, J=2.21 Hz, 1H), 8.49 (s, 1H), 8.53 (d, J=5.13 Hz, 1H), 8.58 (s, 2H), 8.71 (d, J=2.21 Hz, 1H), 9.45 (s, 1H). MS ES+m/z 494 [M+H]⁺.

Example 77: N,N-dimethyl-4-(6-((5-(2-oxo-3-((tetrahydrofuran-2-yl)methyl)imidazolidin-1-yl)pyridin-3-yl)amino)pyridin-3-yl)benzamide

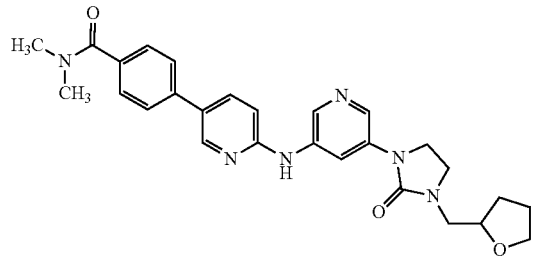 [SMILES: CN(C)C(=O)c1ccc(-c2ccc(Nc3cncc(N4CCN(CC5CCCO5)C4=O)c3)nc2)cc1]

Step 1: Intermediate 59—1-(5-bromo-3-pyridyl)-3-(tetrahydrofuran-2-ylmethyl)imidazolidin-2-one

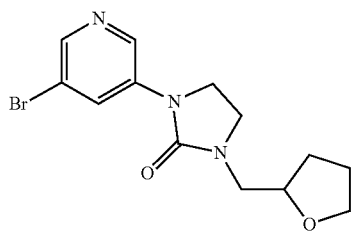

The title compound was prepared as described in Intermediate 56, starting from 1-(5-bromo-3-pyridyl)imidazolidin-2-one and 2-(bromomethyl)tetrahydrofuran, replacing THF for DMF, to give the product as a solid (359 mg, 89%). MS ES+m/z 326 [M+H]⁺.

Step 2: N,N-dimethyl-4-(6-((5-(2-oxo-3-((tetrahydrofuran-2-yl)methyl)imidazolidin-1-yl)pyridin-3-yl)amino)pyridin-3-yl)benzamide The title compound was prepared as described in Example 25, starting from 4-(6-amino-3-pyridyl)-N,N-dimethyl-benzamide and 1-(5-bromo-3-pyridyl)-3-(tetrahydrofuran-2-ylmethyl)imidazolidin-2-one and heating at 90° C. for 1.5 h, to give the product as a solid (31 mg, 19%). ¹H NMR (500 MHz, CDCl₃) δ ppm 1.59-1.67 (m, 1H), 1.89-1.96 (m, 2H), 1.99-2.08 (m, 1H), 3.01-3.18 (m, 6H), 3.25 (dd, J=14.50, 7.25 Hz, 1H), 3.56 (dd, J=14.50, 3.15 Hz, 1H), 3.63-3.70 (m, 1H), 3.75-3.83 (m, 2H), 3.87-3.93 (m, 3H), 4.10 (br dd, J=6.94, 2.84 Hz, 1H), 7.05 (br d, J=8.51 Hz, 1H), 7.51 (d, J=8.20 Hz, 2H), 7.58 (br d, J=8.20 Hz, 2H), 7.80 (dd, J=8.51, 2.21 Hz, 1H), 8.34 (br s, 1H), 8.48-8.58 (m, 2H), 8.68 (br s, 1H). MS ES+m/z 487 [M+H]⁺.

Example 78: N,N-dimethyl-4-(6-((5-(2-oxo-3-(thiazol-4-ylmethyl)imidazolidin-1-yl)pyridin-3-yl)amino)pyridin-3-yl)benzamide

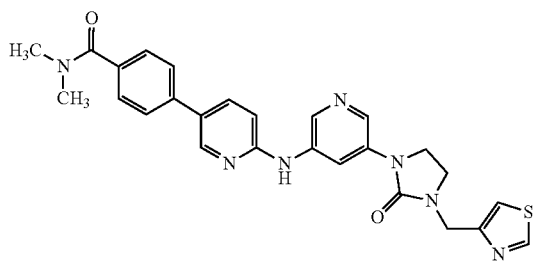 [SMILES: CN(C)C(=O)c1ccc(-c2ccc(Nc3cncc(N4CCN(Cc5cscn5)C4=O)c3)nc2)cc1]

Step 1: Intermediate 60—1-(5-Bromo-3-pyridyl)-3-(thiazol-4-ylmethyl)imidazolidin-2-one

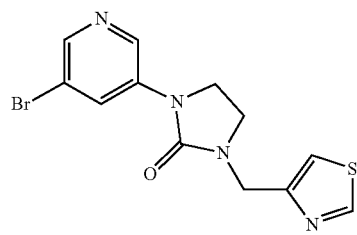 [SMILES: O=C1N(Cc2cscn2)CCN1c1cncc(Br)c1]

The title compound was prepared as described in Intermediate 56, starting from 1-(5-bromo-3-pyridyl)imidazolidin-2-one and 4-(chloromethyl)thiazole HCl, replacing THF for DMF, to give the product as a solid (360 mg, 86%). MS ES+m/z 339 [M+H]+.

Step 2: N,N-dimethyl-4-(6-((5-(2-oxo-3-(thiazol-4-ylmethyl)imidazolidin-1-yl)pyridin-3-yl)amino)pyridin-3-yl)benzamide The title compound was prepared as described in Example 25, starting from 4-(6-amino-3-pyridyl)-N,N-dimethyl-benzamide and 1-(5-bromo-3-pyridyl)-3-(tetrahydrofuran-2-ylmethyl)imidazolidin-2-one and heating at 90° C. for 1.5 h, to give the product as a solid (16 mg, 10%). $^1$H NMR (500 MHz, DMSO-d$_6$) δ ppm 2.98 (br s, 6H), 3.52 (br t, J=8.04 Hz, 2H), 3.88 (br t, J=7.88 Hz, 2H), 4.57 (s, 2H), 6.98 (d, J=8.83 Hz, 1H), 7.48 (m, J=8.20 Hz, 2H), 7.63 (s, 1H), 7.73 (m, J=8.20 Hz, 2H), 7.99 (dd, J=8.67, 2.36 Hz, 1H), 8.33 (d, J=2.21 Hz, 1H), 8.48 (s, 1H), 8.57 (d, J=2.21 Hz, 1H), 8.68 (d, J=1.89 Hz, 1H), 9.11 (d, J=1.89 Hz, 1H), 9.43 (s, 1H). MS ES+m/z 500 [M+H]+.

Example 79: 4-(6-((5-(3-(cyclopropylmethyl)-2-oxoimidazolidin-1-yl)pyridin-3-yl)amino)pyridin-3-yl)-N,N-dimethylbenzamide

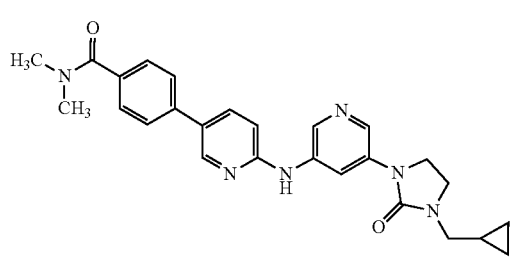 [SMILES: CN(C)C(=O)c1ccc(-c2ccc(Nc3cncc(N4CCN(CC5CC5)C4=O)c3)nc2)cc1]

Step 1: Intermediate 61—1-(5-Bromo-3-pyridyl)-3-(cyclopropylmethyl)imidazolidin-2-one

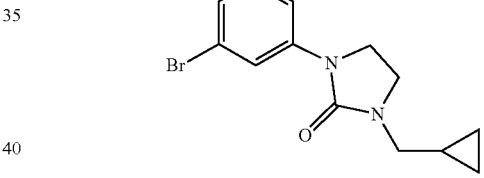

The title compound was prepared as described in Intermediate 56, starting from 1-(5-bromo-3-pyridyl)imidazolidin-2-one and bromomethyl cyclopropane, replacing THF for DMF, to give the product as a solid (308 mg, 84%). MS ES+m/z 296 [M+H]+.

Step 2: 4-(6-((5-(3-(cyclopropylmethyl)-2-oxoimidazolidin-1-yl)pyridin-3-yl)amino)pyridin-3-yl)-N,N-dimethylbenzamide The title compound was prepared as described in Example 25, starting from 4-(6-amino-3-pyridyl)-N,N-dimethyl-benzamide and 1-(5-bromo-3-pyridyl)-3-(tetrahydrofuran-2-ylmethyl)imidazolidin-2-one and heating at 90° C. overnight, to give the product as a solid (4 mg, 2%). $^1$H NMR (500 MHz, CDCl$_3$) δ ppm 0.24-0.28 (m, 2H), 0.58 (dd, J=7.88, 1.26 Hz, 2H), 0.91-1.03 (m, 1H), 3.01-3.17 (m, 6H), 3.20 (d, J=6.94 Hz, 2H), 3.65-3.70 (m, 2H), 3.91 (dd, J=9.14, 6.94 Hz, 2H), 6.71 (s, 1H), 6.99 (d, J=8.51 Hz, 1H), 7.49-7.53 (m, 2H), 7.56-7.60 (m, 2H), 7.80 (dd, J=8.67, 2.36 Hz, 1H), 8.21 (d, J=2.52 Hz, 1H), 8.41 (d, J=2.21 Hz, 1H), 8.51 (d, J=1.89 Hz, 1H), 8.57 (t, J=2.36 Hz, 1H). MS ES+m/z 457 [M+H]+.

Example 80: (S)—N,N-dimethyl-4-(6-((5-(2-oxo-3-(1-phenylethyl)imidazolidin-1-yl)pyridin-3-yl)amino)pyridin-3-yl)benzamide

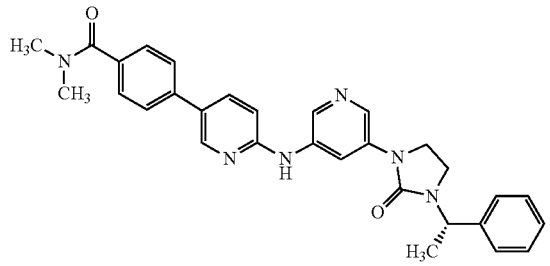 [SMILES: C[C@@H](c1ccccc1)N1CCN(c2cncc(Nc3ccc(-c4ccc(C(=O)N(C)C)cc4)cn3)c2)C1=O]

Step 1: Intermediate 62—1-[(1S)-1-phenylethyl]imidazolidin-2-one

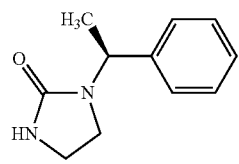

2-Chloroethyl isocyanate (700 μL, 8.21 mmol) was added slowly to a solution of (1S)-1-phenylethanamine (1 mL, 7.82 mmol) in THF (5 mL) at 0° C. and the resulting mixture was stirred at rt for 1 h. More 2-chloroethyl isocyanate (250 μL, 2.93 mmol) was added and the mixture stirred at rt for 1 h. The mixture was cooled to 0° C. and KOtBu (1.32 g, 11.7 mmol) was added slowly. The resulting mixture was stirred at rt for 1 h and then extracted with EtOAc (3×10 mL). The combined organics were washed with brine, dried over Na$_2$SO$_4$, filtered, concentrated and purified on a silica gel column eluted with 0-100% EtOAc in heptane to give the product as an oil (780 mg, 52%). MS ES+m/z 191 [M+H]$^+$.

Step 2: Intermediate 63—1-(5-Bromo-3-pyridyl)-3-[(1S)-1-phenylethyl]imidazolidin-2-one

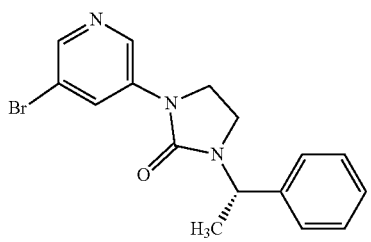 [SMILES: C[C@@H](c1ccccc1)N1CCN(c2cncc(Br)c2)C1=O]

The title compound was prepared as described in Intermediate 14, starting from 3,5-dibromopyridine and 1-[(1S)-1-phenylethyl]imidazolidin-2-one, to give the product as an oil (145 mg, 11%). MS ES+m/z 346 [M+H]$^+$.

Step 3: (S)—N,N-dimethyl-4-(6-((5-(2-oxo-3-(1-phenylethyl)imidazolidin-1-yl)pyridin-3-yl)amino)pyridin-3-yl)benzamide The title compound was prepared as described in Example 25, starting from 4-(6-amino-3-pyridyl)-N,N-dimethyl-benzamide and 1-(5-bromo-3-pyridyl)-3-[(1S)-1-phenylethyl]imidazolidin-2-one and heating at 100° C. for 1 h, to give the product as a solid (15 mg, 8%). $^1$H NMR (500 MHz, DMSO-d$_6$) δ ppm 1.54 (d, J=7.25 Hz, 3H), 2.98 (br s, 6H), 3.11-3.20 (m, 1H), 3.56 (td, J=8.91, 6.78 Hz, 1H), 3.80-3.88 (m, 2H), 5.18 (q, J=7.15 Hz, 1H), 6.98 (d, J=8.55 Hz, 1H), 7.26-7.32 (m, 1H), 7.36-7.40 (m, 4H), 7.46-7.51 (m, 2H), 7.71-7.75 (m, 2H), 7.98 (dd, J=8.67, 2.68 Hz, 1H), 8.31 (d, J=2.21 Hz, 1H), 8.45 (t, J=2.36 Hz, 1H), 8.57 (s, 1H), 8.70 (d, J=2.21 Hz, 1H), 9.43 (s, 1H). MS ES+m/z 507 [M+H]$^+$.

Example 81: (R)—N,N-dimethyl-4-(6-((5-(2-oxo-3-(1-phenylethyl)imidazolidin-1-yl)pyridin-3-yl)amino)pyridin-3-yl)benzamide

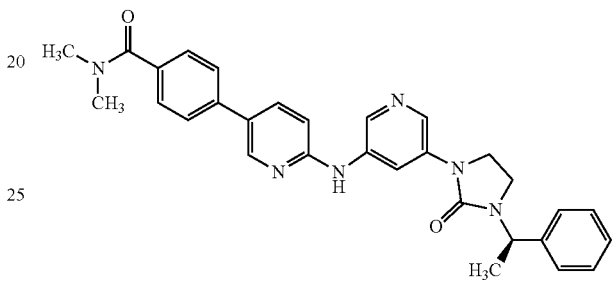

Step 1: Intermediate 64—1-[(1R)-1-phenylethyl]imidazolidin-2-one

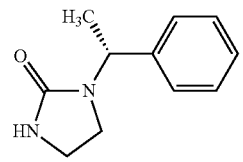

The title compound was prepared as described in Intermediate 62, starting from (1R)-1-phenylethanamine, to give the product as an oil (365 mg, 25%). MS ES+m/z 191 [M+H]$^+$.

Step 2: Intermediate 65—1-(5-Bromo-3-pyridyl)-3-[(1R)-1-phenylethyl]imidazolidin-2-one

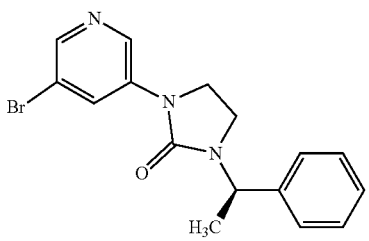 [SMILES: C[C@H](c1ccccc1)N1CCN(c2cncc(Br)c2)C1=O]

The title compound was prepared as described in Intermediate 14, starting from 3,5-dibromopyridine and 1-[(1R)-1-phenylethyl]imidazolidin-2-one, to give the product as an oil (120 mg, 18%). MS ES+m/z 346 [M+H]$^+$.

Step 3: (R)—N,N-dimethyl-4-(6-((5-(2-oxo-3-(1-phenylethyl)imidazolidin-1-yl)pyridin-3-yl)amino)pyridin-3-yl)benzamide The title compound was prepared as described in Example 25, starting from 4-(6-amino-3-pyridyl)-N,N-dimethyl-benzamide and 1-(5-bromo-3-pyridyl)-3-[(1R)-1-phenylethyl]imidazolidin-2-one and heating at 100° C. for 1 h, to give the product as a solid (35 mg, 21%). $^1$H NMR (500 MHz, DMSO-$d_6$) δ ppm 1.54 (d, J=7.25 Hz, 3H), 2.98 (br s, 6H), 3.11-3.21 (m, 1H), 3.56 (td, J=8.91, 6.78 Hz, 1H), 3.80-3.89 (m, 2H), 5.18 (q, J=7.15 Hz, 1H), 6.98 (d, J=8.58 Hz, 1H), 7.27-7.32 (m, 1H), 7.36-7.40 (m, 4H), 7.45-7.51 (m, 2H), 7.71-7.75 (m, 2H), 7.98 (dd, J=8.67, 2.68 Hz, 1H), 8.31 (d, J=2.52 Hz, 1H), 8.45 (t, J=2.36 Hz, 1H), 8.57 (s, 1H), 8.70 (d, J=2.21 Hz, 1H), 9.44 (s, 1H). MS ES+m/z 507 [M+H]$^+$.

Example 82: 1-(4-(6-(pyridin-3-ylamino)pyridin-3-yl)phenyl)pyrrolidin-2-one

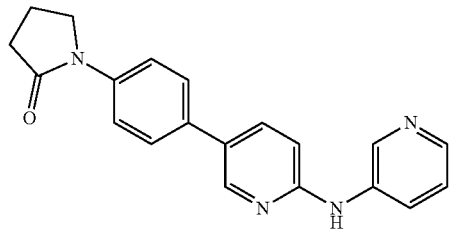 [SMILES: O=C1CCCN1c1ccc(-c2ccc(Nc3cccnc3)nc2)cc1]

Step 1: Intermediate 66—1-[4-(6-Chloro-3-pyridyl)phenyl]pyrrolidin-2-one

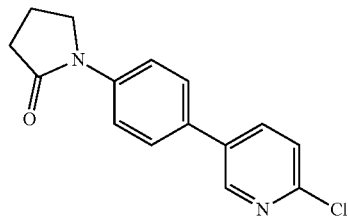 [SMILES: O=C1CCCN1c1ccc(-c2ccc(Cl)nc2)cc1]

The title compound was prepared as described in Intermediate 4, starting from 1-(4-bromophenyl)pyrrolidin-2-one and (6-chloro-3-pyridyl)boronic acid, and stirring the mixture at 75° C. for 3 h, to give the product as a solid (150 mg, 22%). MS ES+m/z 273 [M+H]$^+$.

Step 2: 1-(4-(6-(pyridin-3-ylamino)pyridin-3-yl)phenyl)pyrrolidin-2-one

1-[4-(6-chloro-3-pyridyl)phenyl]pyrrolidin-2-one (75 mg, 0.27 mmol), pyridin-3-amine (40 mg, 0.43 mmol) and NaOtBu (60 mg, 0.62 mmol) were taken up in 1,4-dioxane (5 mL) and the mixture was degassed with nitrogen for 5 min. Pd(OAc)$_2$ (5 mg, 0.02 mmol) and XPhos (25 mg, 0.05 mmol) were added and the resulting mixture was stirred at 90° C. overnight. More pyridin-3-amine (40 mg, 0.43 mmol), NaOtBu (60 mg, 0.62 mmol) and XPhos Pd G1 (10 mg, 0.01 mmol) were added and the mixture stirred at 100° C. overnight. pentanePPSI-Ipr (10 mg, 0.01 mmol) was added and stirring was continued at 90° C. overnight. When cooled to rt EtOAc (10 mL) and brine (10 mL) were added and the mixture filtered. The organic layer was separated and the aqueous layer extracted with EtOAc (2×5 mL). The combined organics were washed with brine, dried over Na$_2$SO$_4$, filtered, concentrated and purified by preparative HPLC to give the product as a solid (15 mg, 17%). $^1$H NMR (500 MHz, DMSO) δ=9.39 (s, 1H), 8.83 (d, J=2.2 Hz, 1H), 8.56-8.51 (m, 1H), 8.30-8.23 (m, 1H), 8.10 (d, J=4.4 Hz, 1H), 7.94 (dd, J=2.4, 8.7 Hz, 1H), 7.74 (d, J=8.8 Hz, 2H), 7.67 (d, J=8.8 Hz, 2H), 7.30 (dd, J=4.6, 8.4 Hz, 1H), 6.95 (d, J=8.5 Hz, 1H), 3.87 (t, J=7.1 Hz, 2H), 2.57-2.51 (m, 2H), 2.13-2.04 (m, 2H). MS ES+m/z 331 [M+H]$^+$.

Example 83: 1-(4-(6-((6-methoxypyridin-3-yl)amino)pyridin-3-yl)phenyl)pyrrolidin-2-one

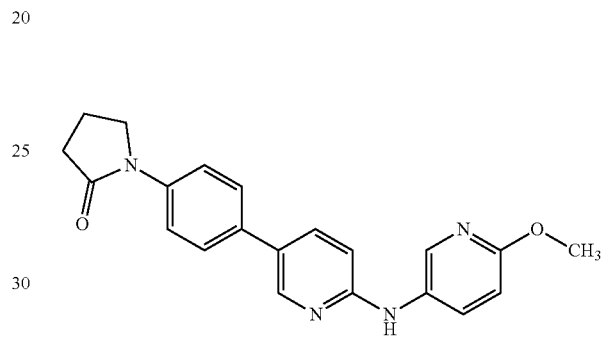

The title compound was prepared as described in Example 55, starting from 1-[4-(6-Chloro-3-pyridyl)phenyl]pyrrolidin-2-one and 5-bromo-2-methoxy-pyridine, and replacing tBuOH for 1,4-dioxane and K$_2$CO$_3$ for Cs$_2$CO$_3$, to give the product as a solid (73 mg, 22%). 1H NMR (500 MHz, DMSO-$d_6$) δ ppm 2.09 (s, 2H) 2.52-2.55 (m, 2H) 3.80-3.85 (s, 3H) 3.87 (t, J=7.09 Hz, 2H) 6.80 (d, J=8.74 Hz, 1H) 6.85 (d, J=8.51 Hz, 1H) 7.65 (d, J=8.83 Hz, 2H) 7.73 (d, J=7.89 Hz, 2H) 7.86-7.91 (m, 1H) 8.04-8.08 (m, 1H) 8.45 (dd, J=5.83, 2.36 Hz, 2H) 9.07 (s, 1H). MS ES+m/z 361 [M+H]$^+$.

Example 84: (S)-2-((5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

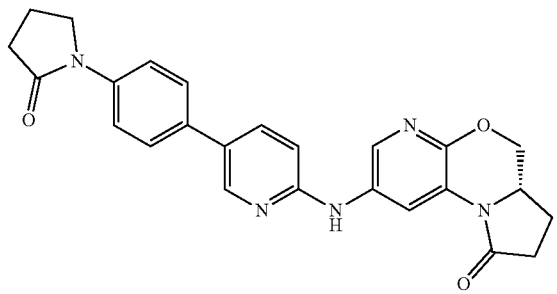 [SMILES: O=C1CCCN1c1ccc(-c2ccc(Nc3cnc4c(c3)N3C(=O)CC[C@H]3CO4)nc2)cc1]

Step 1 Intermediate 67—(5S)-5-[(3-bromo-5-nitro-2-pyridyl)oxymethyl]pyrrolidin-2-one

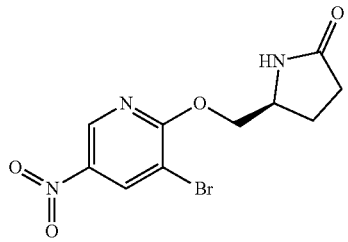 [SMILES: O=C1CC[C@@H](COc2ncc([N+](=O)[O-])cc2Br)N1]

3-Bromo-2-chloro-5-nitro-pyridine (1 g, 4.21 mmol), (5S)-5-(hydroxymethyl)pyrrolidin-2-one (500 mg, 4.34 mmol) and K$_2$CO$_3$ (700 mg, 5.06 mmol) were taken up in MeCN (10 mL) and the resulting mixture was stirred at 70° C. overnight. More (5S)-5-(hydroxymethyl)pyrrolidin-2-one (130 mg, 1.13 mmol) and K$_2$CO$_3$ (300 mg, 2.17 mmol) were added and stirring continued at 70° C. for 5 h. When cooled to rt the mixture was diluted with water (10 mL) and EtOAc (10 mL) and the organic layer separated. The aqueous layer was extracted with EtOAc (2×10 mL) and the combined organics were washed with brine, dried over Na$_2$SO$_4$, filtered and concentrated to give the product as a solid (1.13 g, 85%). MS ES+m/z 316 [M+H]$^+$.

Step 2: Intermediate 68—(6S)-12-nitro-8-oxa-2,10-diazatricyclo[7.4.0.0ˆ{2,6}]trideca-1(9),10,12-trien-3-one

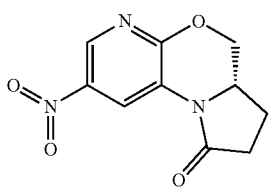 [SMILES: O=C1CC[C@H]2COc3ncc([N+](=O)[O-])cc3N12]

(5S)-5-[(3-bromo-5-nitro-2-pyridyl)oxymethyl]pyrrolidin-2-one (1.13 g, 3.57 mmol), CuI (75 mg, 0.39 mmol), N,N'-dimethylenediamine (85 µL, 0.8 mmol) and K$_2$CO$_3$ (0.99 g, 7.15 mmol) were taken up in EtOAc (20 mL) and the resulting mixture was stirred at 70° C. for 2 h. More CuI (75 mg, 0.39 mmol) and N,N'-dimethylenediamine (85 µL, 0.8 mmol) were added and the mixture was refluxed for 2 h. Cs$_2$CO$_3$ (2 g, 6.14 mmol) and 1,4-dioxane (20 mL) were added and stirring continued at 100° C. overnight. When cooled to rt the mixture was filtered through celite and rinsed with EtOAc (2×5 mL). The filtrate was washed with half-saturated brine (20 mL), dried over Na$_2$SO$_4$, filtered and concentrated to give the product as a solid (720 mg, 86%). MS ES+m/z 236 [M+H]$^+$.

Step 3: Intermediate 69—(6S)-12-amino-8-oxa-2,10-diazatricyclo[7.4.0.0ˆ{2,6}]trideca-1(9),10,12-trien-3-one (6S)-12-nitro-8-oxa-2,10-diazatricyclo[7.4.0.0ˆ{2,6}]trideca-1(9),10,12-trien-3-one (357 mg, 1.52 mmol), Fe (509 mg, 9.11 mmol) and ammonium chloride (244 mg, 4.55 mmol) were taken up in EtOH/H$_2$O (4:1, 12.5 mL) and the resulting mixture was refluxed for 1.5 h. When cooled to rt the mixture was filtered through celite, rinsed with MeOH and the filtrate was concentrated. The resulting residue was suspended in water and pH was adjusted to ~7 by careful addition of a sat. aq. NaHCO$_3$. The mixture was extracted with EtOAc and the combined organics were dried over Na$_2$SO$_4$, filtered and concentrated to give the product as a solid (212 mg, 68%). MS ES+m/z 206 [M+H]$^+$.

Step 4: (S)-2-((5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one The title compound was prepared as described in Example 59, starting from 1-[4-(6-Chloro-3-pyridyl)phenyl]pyrrolidin-2-one and (6S)-12-amino-8-oxa-2,10-diazatricyclo[7.4.0.0ˆ{2,6}]trideca-1(9),10,12-trien-3-one, and stirring at 90° C. overnight, to give the product as a solid (6 mg, 4%). $^1$H NMR (500 MHz, DMSO-d$_6$) δ ppm 1.63-1.77 (m, 1H), 2.05-2.12 (m, 2H), 2.17-2.27 (m, 1H), 2.34-2.44 (m, 1H), 2.51-2.58 (m, 2H), 2.67 (ddd, J=16.87, 11.19, 9.46 Hz, 1H), 3.84-3.94 (m, 3H), 4.07 (tdd, J=9.65, 9.65, 6.86, 3.15 Hz, 1H), 4.58 (dd, J=10.88, 2.99 Hz, 1H), 6.88 (d, J=8.51 Hz, 1H), 7.65 (d, J=7.82 Hz, 2H), 7.72 (d, J=8.55 Hz, 2H), 7.89 (dd, J=8.83, 2.52 Hz, 1H), 8.45 (dd, J=5.83, 2.36 Hz, 2H), 8.97 (d, J=2.52 Hz, 1H), 9.21 (s, 1H). MS ES+m/z 442 [M+H]$^+$.

Example 85: (R)-2-((5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

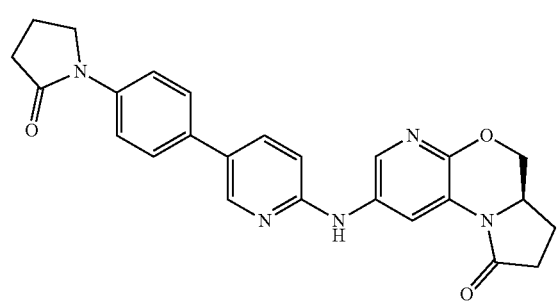 [SMILES: O=C1CCCN1c1ccc(-c2ccc(Nc3cnc4c(c3)N3C(=O)CC[C@@H]3CO4)nc2)cc1]

Step 1: Intermediate 70—(5R)-5-[(3-bromo-5-nitro-2-pyridyl)oxymethyl]pyrrolidin-2-one

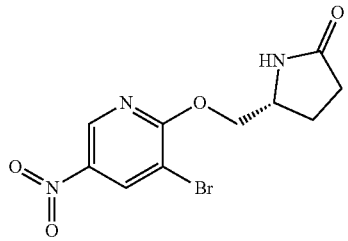 [SMILES: O=C1CC[C@H](COc2ncc([N+](=O)[O-])cc2Br)N1]

The title compound was prepared as described in Intermediate 67, starting from 3-bromo-2-chloro-5-nitro-pyridine and (5R)-5-(hydroxymethyl)pyrrolidin-2-one, to give the product as a solid (1.46 g, 73%). MS ES+m/z 316 [M+H]$^+$.

Step 2: Intermediate 71—: (6R)-12-nitro-8-oxa-2,10-diazatricyclo[7.4.0.0^{2,6}]trideca-1(9),10,12-trien-3-one

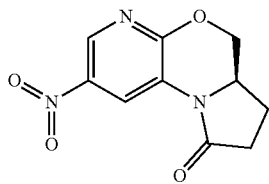 [SMILES: O=C1CC[C@@H]2COc3ncc([N+](=O)[O-])cc3N12]

The title compound was prepared as described in Intermediate 68, starting from (5R)-5-[(3-bromo-5-nitro-2-pyridyl)oxymethyl]pyrrolidin-2-one, to give the product as a solid (609 mg, 56%). MS ES+m/z 236 [M+H]$^+$.

Step 3: Intermediate 72—(R)-2-amino-6,6a,7,8-tetrahydro-9H-pyrido[2,3-b]pyrrolo[1,2-d][1,4]oxazin-9-one

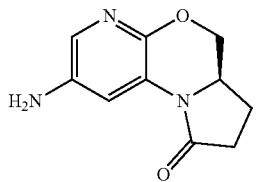 [SMILES: Nc1cnc2c(c1)N1C(=O)CC[C@@H]1CO2]

(6R)-12-nitro-8-oxa-2,10-diazatricyclo[7.4.0.0^{2,6}]trideca-1(9),10,12-trien-3-one (254 mg, 1.08 mmol) was suspended in MeOH (40 mL). Sodium dithionite (752 mg, 4.32 mmol) in water (2 mL) was added and the reaction mixture was stirred at 50° C. for 1 h. When cooled to rt conc. HCl (2 mL) was added and the mixture was stirred at 50° C. for 2 h. The mixture was concentrated and to the resulting residue was added saturated NaHCO$_3$. The mixture was extracted with DCM and the combined organics were dried over MgSO$_4$, filtered and concentrated to give the product as a solid (63 mg, 28%). MS ES+m/z 206 [M+H]$^+$.

Step 4: (R)-2-((5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one The title compound was prepared as described in Example 55, starting from 1-[4-(6-amino-3-pyridyl)phenyl]pyrrolidin-2-one and (R)-2-amino-6,6a,7,8-tetrahydro-9H-pyrido[2,3-b]pyrrolo[1,2-d][1,4]oxazin-9-one, replacing K$_2$CO$_3$ with Cs$_2$CO$_3$ and tBuOH with 1,4-dioxane, to give the product as a solid (56 mg, 58%). $^1$H NMR (500 MHz, DMSO-d$_6$) δ ppm 1.68-1.75 (m, 1H), 2.06-2.12 (m, 2H), 2.24 (s, 1H), 2.40 (s, 1H), 2.61-2.78 (m, 2H), 3.84-3.98 (m, 3H), 4.00-4.17 (m, 1H), 4.59 (dd, J=11.03, 3.15 Hz, 1H), 6.87-6.90 (m, 1H), 7.65-7.69 (m, 2H), 7.72-7.82 (m, 2H), 7.90 (dd, J=8.67, 2.68 Hz, 1H), 8.45-8.48 (m, 2H), 8.97 (d, J=2.52 Hz, 1H), 9.22 (s, 1H). MS ES+m/z 442 [M+H]$^+$.

Example 86: 1-(4-(6-((1-acetyl-2,3-dihydro-1H-pyrido[2,3-b][1,4]oxazin-7-yl)amino)pyridin-3-yl)phenyl)pyrrolidin-2-one

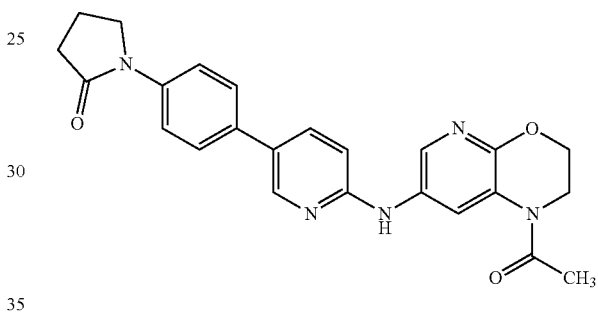

Step 1: Intermediate 73—1-[4-(6-Amino-3-pyridyl)phenyl]pyrrolidin-2-one

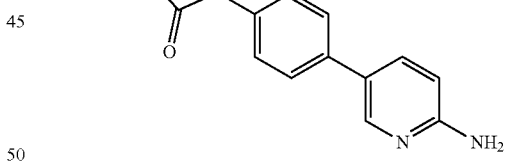

The title compound was prepared as described in Intermediate 3, starting from 1-(4-bromophenyl)pyrrolidin-2-one and 5-(4,4,5,5-tetramethyl-1,3,2-dioxaborolan-2-yl)pyridin-2-amine and stirring the mixture at 75° C. for 3 h, to give the product as a solid (150 mg, 14%). MS ES+m/z 254 [M+H]$^+$.

Step 2: 1-(4-(6-((1-acetyl-2,3-dihydro-1H-pyrido[2,3-b][1,4]oxazin-7-yl)amino)pyridin-3-yl)phenyl)pyrrolidin-2-one The title compound was prepared as described in Example 55, starting from 1-[4-(6-amino-3-pyridyl)phenyl]pyrrolidin-2-one and 1-(7-bromo-2,3-dihydropyrido[2,3-b][1,4]oxazin-1-yl)ethanone, replacing K$_2$CO$_3$ with Cs$_2$CO$_3$ and tBuOH with 1,4-dioxane, to give the product as a solid (29 mg, 18%). $^1$H NMR (500 MHz, DMSO-d$_6$) δ ppm 2.09

(quin, J=7.57 Hz, 2H), 2.31 (s, 3H), 2.53-2.59 (m, 1H), 3.83-3.92 (m, 4H), 4.32-4.38 (m, 2H), 6.87 (d, J=8.51 Hz, 1H), 7.66 (d, J=8.83 Hz, 2H), 7.71-7.75 (m, 2H), 7.90 (dd, J=8.83, 2.52 Hz, 1H), 8.32 (br s, 1H), 8.46 (d, J=2.52 Hz, 1H), 9.15 (s, 1H). MS ES+m/z 430 [M+H]+.

Example 87: 1-(4-(6-((2,3-dihydro-[1,4]dioxino[2,3-b]pyridin-7-yl)amino)pyridin-3-yl)phenyl)pyrrolidin-2-one

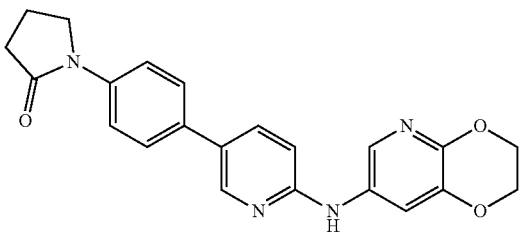 [SMILES: O=C1CCCN1c1ccc(-c2ccc(Nc3cnc4c(c3)OCCO4)nc2)cc1]

The title compound was prepared as described in Example 25, starting from 1-[4-(6-Amino-3-pyridyl)phenyl]pyrrolidin-2-one and 7-bromo-2,3-dihydro-[1,4]dioxino[2,3-b]pyridine and stirring the mixture at 80° C. for 2 days, to give the product as a solid (20 mg, 16%). $^1$H NMR (500 MHz, METHANOL-d4) δ ppm 2.21 (t, J=7.57 Hz, 2H), 2.62 (t, J=8.20 Hz, 2H), 3.97 (t, J=7.09 Hz, 2H), 4.27-4.30 (m, 2H), 4.41 (dt, J=4.02, 2.25 Hz, 2H), 6.84 (dd, J=8.83, 0.63 Hz, 1H), 7.60-7.64 (m, 2H), 7.69 (d, J=7.86 Hz, 2H), 7.80 (d, J=2.21 Hz, 1H), 7.85 (dd, J=8.51, 2.52 Hz, 1H), 7.90 (d, J=2.21 Hz, 1H), 8.39 (dd, J=2.52, 0.63 Hz, 1H). MS ES+m/z 389 [M+H]+.

Example 88: N,N-dimethyl-4-(6-((2-oxo-2,3-dihydro-1H-pyrido[2,3-b][1,4]oxazin-7-yl)amino)pyridin-3-yl)benzamide

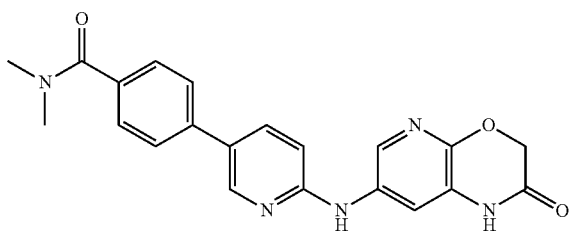 [SMILES: CN(C)C(=O)c1ccc(-c2ccc(Nc3cnc4c(c3)NC(=O)CO4)nc2)cc1]

Step 1 Preparation of ethyl 2-((5-bromo-3-nitropyridin-2-yl)oxy)acetate

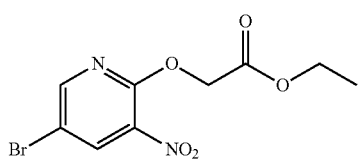 [SMILES: CCOC(=O)COc1ncc(Br)cc1[N+](=O)[O-]]

To a mixture of ethyl 2-hydroxyacetate (14.0 g, 134 mmol) in anhydrous THF (150 mL) was added NaH (4.48 g, 112 mmol, 60% in mineral oil) at 0° C. After stirring for 30 min, 5-bromo-2-chloro-3-nitropyridine (26.6 g, 112 mmol) was added at 0° C., and the reaction mixture was stirred at 25° C. for 15.5 h. TLC showed the reaction was almost completed. The colour of mixture was black. The residue was poured into water (150 mL) at 0° C. and extracted with EtOAc (100 mL×3). The combined organic phase was dried over anhydrous Na$_2$SO$_4$, filtered and concentrated in vacuum. The residue was purified by Combi Flash (6% EtOAc in pentane) to give ethyl 2-((5-bromo-3-nitropyridin-2-yl)oxy)acetate (16.5 g, yield: 48%) as a yellow solid. $^1$H NMR (400 MHz, CDCl$_3$) δ 1.26 (3H, t, J=7.2 Hz), 4.23 (2H, q, J=7.2 Hz), 5.04 (2H, s), 8.39 (1H, d, J=2.4 Hz), 8.46 (1H, d, J=2.4 Hz).

Step 2: Preparation of 7-bromo-1H-pyrido[2,3-b][1,4]oxazin-2(3H)-one

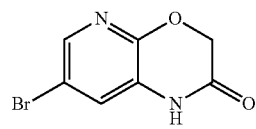

To a mixture of ethyl 2-((5-bromo-3-nitropyridin-2-yl)oxy)acetate (17.5 g, 57.3 mmol) in anhydrous acetic acid (150 mL) was added Fe (48.9 g, 832 mmol) at 25° C. After stirring for 3 h at 60° C., the colour of the mixture was from yellow to black. TLC showed the reaction was almost completed. Acetic acid was removed under reduced pressure; the residue was diluted with DMF (500 mL), filtered and concentrated under reduced pressure. The residue was washed with EtOAc (20 mL) to give 7-bromo-1H-pyrido[2,3-b][1,4]oxazin-2(3H)-one (26.7 g, crude) as a brick-red solid. $^1$H NMR (400 MHz, DMSO-d$_6$) δ 4.82 (2H, s), 7.34 (1H, s), 7.89 (1H, s), 10.96 (1H, s).

Step 3: Preparation of 7-bromo-2,3-dihydro-1H-pyrido[2,3-b][1,4]oxazine

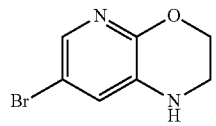

To a solution of 7-bromo-1H-pyrido[2,3-b][1,4]oxazin-2(3H)-one (26.7 g, crude) in THF (100 mL) was added BH$_3$-THF (1 M in THF, 349 mL) at 0° C. The ice bath was removed and the solution was heated at 70° C. for 3 h. The colour of mixture was from red to black. TLC showed the reaction was almost completed. MeOH (120 mL) was added at 0° C., filtered and concentrated. The reaction mixture was purified by Combi Flash (50% EtOAc in pentane) to give 7-bromo-2,3-dihydro-1H-pyrido[2,3-b][1,4]oxazine (4.40 g, yield: 18% via two steps) as a white solid. $^1$H NMR (400 MHz, CDCl$_3$) δ 3.40-3.43 (2H, m), 3.97 (1H, br s), 4.38-4.40 (2H, m), 6.69 (1H, d, J=2.4 Hz), 7.62 (1H, d, J=2.4 Hz).

Step 4: Preparation of 4-bromo-N,N-dimethylbenzamide

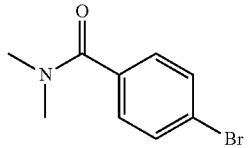

A mixture of 4-bromobenzoic acid (21.0 g, 105 mmol) in $SOCl_2$ (35 mL) was heated at 80° C. for 2 h under $N_2$ atmosphere. After cooling, the reaction mixture was concentrated under reduced pressure. Then to the mixture was added DCM (100 mL), $Me_2NH$ (11.1 g, 136 mmol) and TEA (87 mL), and stirred at 25° C. for 16 h under $N_2$. TLC showed the reaction was completed. The residue was poured into water (50 mL) and extracted with DCM (50 mL×3). The combined organic layer was washed with water (100 mL), dried over anhydrous $Na_2SO_4$, filtered and concentrated in vacuum. The residue was purified by Combi Flash (10% EtOAc in pentane) to afford 4-bromo-N,N-dimethylbenzamide (23.7 g, yield: 99%) as a white solid. $^1H$ NMR (400 MHz, DMSO-$d_6$) δ 2.89 (3H, s), 2.97 (3H, s), 7.36 (2H, d, J=8.8 Hz), 7.63 (2H, d, J=8.4 Hz).

Step 5: Preparation of N,N-dimethyl-4-(4,4,5,5-tetramethyl-1,3,2-dioxaborolan-2-yl)benzamide

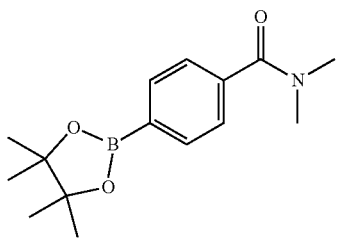

A mixture of 4-bromo-N,N-dimethylbenzamide (23.0 g, 100 mmol), $B_2Pin_2$ (38.4 g, 151 mmol), KOAc (29.7 g, 303 mmol) and $Pd(dppf)Cl_2$ (2.95 g, 4.03 mmol) in dioxane (100 mL) was stirred at 110° C. for 5 h under $N_2$ atmosphere. The red suspension turned to black. Crude LCMS (Rt=0.679 min; MS Calc'd: 275.1; MS Found: 275.8 [M+H]$^+$). The reaction mixture was diluted with EtOAc (200 mL), filtered and concentrated to give crude N,N-dimethyl-4-(4,4,5,5-tetramethyl-1,3,2-dioxaborolan-2-yl)benzamide (35.0 g, crude) as black oil and directly used to next step.

Step 6: Preparation of 4-(6-aminopyridin-3-yl)-N,N-dimethylbenzamide

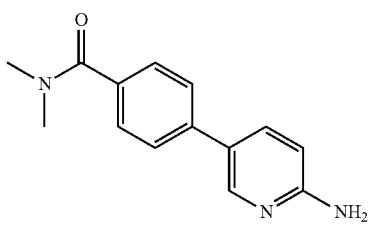 [SMILES: CN(C)C(=O)c1ccc(-c2ccc(N)nc2)cc1]

A mixture of N,N-dimethyl-4-(4,4,5,5-tetramethyl-1,3,2-dioxaborolan-2-yl)benzamide (12.0 g, 43.6 mmol), 5-bromopyridin-2-amine (6.86 g, 39.7 mmol), $Na_2CO_3$ (16.5 g, 198 mmol) in water (30 mL) and $Pd(dppf)Cl_2$ (2.90 g, 3.96 mmol) in DME (100 mL) was stirred at 110° C. for 16 h under $N_2$ atmosphere. Crude LCMS (Rt=0.507 min; MS Calc'd: 241.1; MS Found: 242.1 [M+H]$^+$). The reaction mixture was diluted with ethyl acetate (50 mL), dried over $Na_2SO_4$, filtered and concentrated. The residue was purified by Combi Flash (EtOAc) to afford 4-(6-aminopyridin-3-yl)-N,N-dimethylbenzamide (5.2 g, yield: 54% for two steps) as a white solid. $^1H$ NMR (400 MHz, DMSO-$d_6$) δ 2.97 (6H, s), 6.14 (2H, br s), 6.53 (1H, d, J=8.8 Hz), 7.43 (2H, dd, J=6.8, 2.0 Hz), 7.62 (2H, dd, J=6.4, 1.6 Hz), 7.74 (1H, dd, J=8.4, 2.4 Hz), 8.29 (1H, d, J=2.4 Hz).

Step 7: Preparation of 7-bromo-1-((2-(trimethylsilyl)ethoxy)methyl)-1H-pyrido[2,3-b][1,4]oxazin-2(3H)-one

To a solution of 7-bromo-1H-pyrido[2,3-b][1,4]oxazin-2(3H)-one (500 mg, 2.18 mmol) was added NaH (130 mg, 3.27 mmol, 60% in mineral oil) in DMF (10 mL). The reaction mixture was cooled to 0° C. for 0.5 hour, and SEMCl (726 mg, 4.36 mmol) was added dropwise. The reaction mixture was warmed to 20° C., stirred at 20° C. for 20 h under $N_2$ atmosphere. The colorless solution turned to dark red gradually. LCMS (Rt=0.899 min; MS Calc'd: 358.0; MS Found: 358.9 [M+H]$^+$). The reaction mixture was quenched with MeOH (1 mL), then DMF was removed under reduced pressure. The residue was purified by Combi Flash (70% DCM in pentane) to afford 7-bromo-1-((2-(trimethylsilyl)ethoxy)methyl)-1H-pyrido[2,3-b][1,4]oxazin-2(3H)-one (383 mg, yield: 49%) as a white solid. $^1H$ NMR (400 MHz, CDCl$_3$) δ 0.003 (9H, s), 0.95 (2H, t, J=8.0 Hz), 3.64 (2H, t, J=8.0 Hz), 4.83 (2H, s), 5.29 (2H, s), 7.73 (1H, d, J=2.0 Hz), 8.01 (1H, d, J=2.0 Hz).

Step 8: Preparation of N,N-dimethyl-4-(6-((2-oxo-1-((2-(trimethylsilyl)ethoxy)methyl)-2,3-dihydro-1H-pyrido[2,3-b][1,4]oxazin-7-yl)amino)pyridin-3-yl)benzamide

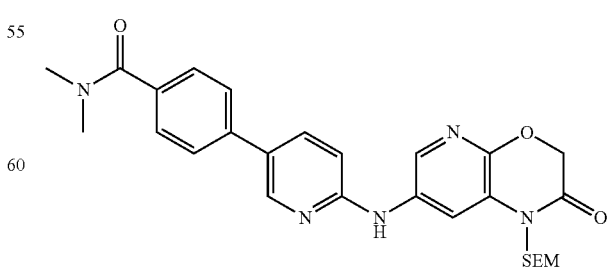

A mixture of $Pd_2(dba)_3$ (35 mg, 0.039 mmol) and Brettphos (42 mg, 0.078 mmol) in dioxane (1 mL) was stirred at 50° C. for 10 min. 4-(6-Aminopyridin-3-yl)-N,N-dimethylbenzamide (188 mg, 0.779 mmol), 7-bromo-1-((2-(trimethylsilyl)ethoxy)methyl)-1H-pyrido[2,3-b][1,4]oxazin-2(3H)-one (280 mg, 0.779 mmol) in dioxane (16 mL) and Cs₂CO₃ (508 mg, 1.56 mmol) were added. The resulting mixture was stirred at 100° C. for 14 h. A black brown mixture was formed. LCMS showed the purity of the desired product (Rt=0.658 min; MS Calc'd: 519.2; MS Found: 519.8 [M+H]⁺). The reaction mixture was diluted with DCM (20 mL), filtered and concentrated. The residue was purified by Combi Flash (EtOAc) to give N,N-dimethyl-4-(6-((2-oxo-1-((2-(trimethylsilyl)ethoxy)methyl)-2,3-dihydro-1H-pyrido[2,3-b][1,4]oxazin-7-yl)amino)pyridin-3-yl)benzamide (450 mg, yield: 82%) as a light yellow solid. ¹H NMR (400 MHz, CDCl₃) δ 0.007 (9H, s), 0.96 (2H, t, J=8.4 Hz), 3.04 (3H, s), 3.14 (3H, s), 3.66 (2H, t, J=8.4 Hz), 4.82 (2H, s), 5.35 (2H, s), 6.56 (1H, br s), 7.78 (1H, d, J=8.8 Hz), 7.47-7.57 (4H, m), 7.74 (1H, dd, J=8.8, 2.4 Hz), 7.97 (1H, d, J=2.0 Hz), 8.01 (1H, d, J=2.4 Hz), 8.45 (1H, d, J=2.4 Hz).

Step 9: Preparation of N,N-dimethyl-4-(6-((2-oxo-2,3-dihydro-1H-pyrido[2,3-b][1,4]oxazin-7-yl)amino)pyridin-3-yl)benzamide

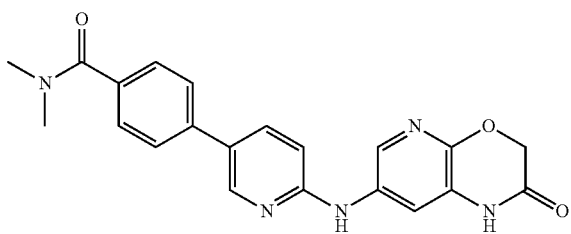 [SMILES: CN(C)C(=O)c1ccc(-c2ccc(Nc3cnc4c(c3)NC(=O)CO4)nc2)cc1]

To a solution of N,N-dimethyl-4-(6-((2-oxo-1-((2-(trimethylsilyl)ethoxy)methyl)-2,3-dihydro-1H-pyrido[2,3-b][1,4]oxazin-7-yl)amino)pyridin-3-yl)benzamide (100 mg, 0.192 mmol) in DCM (3 mL) was added TFA (3 mL, 40.5 mmol) at 10° C., and it was stirred at 10° C. for 1 hour. Then the mixture was concentrated under reduced pressure and the residue was diluted with MeOH (3 mL) and then EDA (439 mg, 3.85 mmol) was added at 10° C. The residue was stirred at 10° C. for 16 h. The yellow solution turned to suspension gradually. Crude LCMS showed the purity of product (Rt=0.501 min, MS Calc'd: 389.2; MS Found: 389.7 [M+H]⁺). The mixture was concentrated under reduced pressure. The residue was purified by prep-HPLC (0.1% NH₃.H₂O as an additive) and lyophilized to give N,N-dimethyl-4-(6-((2-oxo-2,3-dihydro-1H-pyrido[2,3-b][1,4]oxazin-7-yl)amino)pyridin-3-yl)benzamide (32.9 mg, yield: 44%) as a white solid. LCMS (Shimadzu LCMS 2010, mobile phase: from 100% [water+0.05% NH₃.H₂O] and 0% [MeCN] to 5% [water+0.05% NH₃.H₂O] and 95% [MeCN] in 5.8 min, then under this condition for 1.1 min, finally changed to 100% [water+0.05% NH₃.H₂O] and 0% [MeCN] and under this condition for 0.09 min.) purity is 100%, Rt=2.190 min; MS Calc'd.: 389.2, MS Found: 390.2 [M+H]⁺. ¹H NMR (400 MHz, DMSO-d₆) δ 2.97 (6H, s), 4.70 (2H, s), 6.08 (1H, br s), 6.90 (1H, d, J=9.2 Hz), 7.47 (2H, d, J=7.2 Hz), 7.70 (2H, d, J=7.2 Hz), 7.80 (1H, s), 7.95 (1H, d, J=8.8 Hz), 8.08 (1H, s), 8.50 (1H, s), 9.32 (1H, br s).

Example 89: 4-(6-((1-(2-hydroxyacetyl)-2,3-dihydro-1H-pyrido[2,3-b][1,4]oxazin-7-yl)amino)pyridin-3-yl)-N,N-dimethylbenzamide

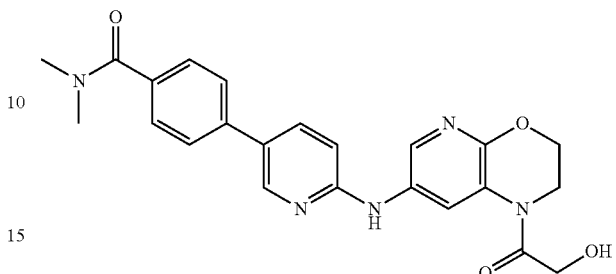

Step 1: Preparation of 2-(7-bromo-2,3-dihydro-1H-pyrido[2,3-b][1,4]oxazin-1-yl)-2-oxoethyl acetate

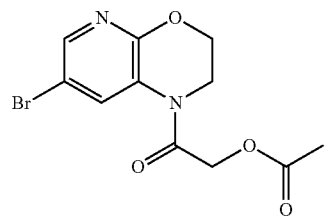 [SMILES: CC(=O)OCC(=O)N1CCOc2ncc(Br)cc21]

A solution of 7-bromo-2,3-dihydro-1H-pyrido[2,3-b][1,4]oxazine (200 mg, 0.930 mmol) in THF (2 mL) was added EtOAc (282 mg, 2.79 mmol) and 2-chloro-2-oxoethyl acetate (508 mg, 3.72 mmol) at 0° C. The ice bath was removed and the mixture was stirred for 2 h at 25° C. The green solution turned to suspension. TLC showed the reaction was completed. The mixture was concentrated under reduced pressure. The residue was purified by Combi Flash (1% MeOH in DCM) to give 2-(7-bromo-2,3-dihydro-1H-pyrido[2,3-b][1,4]oxazin-1-yl)-2-oxoethyl acetate (320 mg, crude) as a yellow solid. ¹H NMR (400 MHz, DMSO-d₆) δ 2.05 (3H, s), 3.86 (2H, t, J=4.8 Hz), 4.40 (2H, t, J=4.8 Hz), 5.01 (2H, s), 8.05 (1H, d, J=2.4 Hz), 8.67 (1H, s).

Step 2: Preparation of 2-(7-((5-(4-(dimethylcarbamoyl)phenyl)pyridin-2-yl)amino)-2,3-dihydro-1H-pyrido[2,3-b][1,4]oxazin-1-yl)-2-oxoethyl acetate

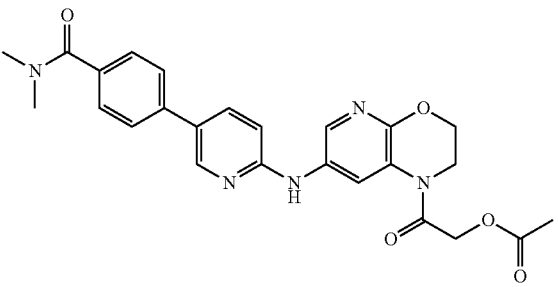 [SMILES: CC(=O)OCC(=O)N1CCOc2ncc(Nc3ccc(-c4ccc(C(=O)N(C)C)cc4)cn3)cc21]

A solution of Pd₂(dba)₃ (85 mg, 0.093 mmol) and Brettphos (100 mg, 0.186 mmol) in dioxane (6 mL) was stirred at 50° C. for 10 min. 2-(7-Bromo-2,3-dihydro-H-pyrido[2,3-b][1,4]oxazin-1-yl)-2-oxoethyl acetate (293 mg, 0.930 mmol), 4-(6-aminopyridin-3-yl)-N,N-dimethylbenzamide (224 mg, 0.930 mmol), dioxane (6 mL) and $Cs_2CO_3$ (606 mg, 1.86 mmol) were added, and the resulting mixture was stirred at 100° C. for 12 h. The red solution turned to dark red. Crude LCMS (Rt=0.623 min; MS Calc'd: 475.2; MS Found: 476.2 [M+H]$^+$). Concentrated in vacuum. The residue was purified by Combi Flash (34% EtOAc in DCM) to give 2-(7-((5-(4-(dimethylcarbamoyl)phenyl)pyridin-2-yl)amino)-2,3-dihydro-1H-pyrido[2,3-b][1,4]oxazin-1-yl)-2-oxoethyl acetate (234 mg, yield: 53%) as a light yellow solid. $^1$H NMR (400 MHz, DMSO-$d_6$) δ 2.12 (3H, s), 2.97 (6H, s), 3.85 (2H, t, J=4.0 Hz), 4.35 (2H, t, J=4.0 Hz), 5.03 (2H, s), 6.87 (1H, d, J=9.2 Hz), 7.47 (2H, dd, J=6.4, 1.6 Hz), 7.71 (2H, dd, J=6.4, 1.6 Hz), 7.94 (1H, dd, J=8.8, 2.4 Hz), 8.43 (1H, s), 8.50 (1H, d, J=2.0 Hz), 8.72 (1H, br s), 9.24 (1H, s).

Step 3: Preparation of 4-(6-((1-(2-hydroxyacetyl)-2,3-dihydro-1H-pyrido[2,3-b][1,4]oxazin-7-yl)amino)pyridin-3-yl)-N,N-dimethylbenzamide To a solution of 2-(7-((5-(4-(dimethylcarbamoyl)phenyl)pyridin-2-yl)amino)-2,3-dihydro-1H-pyrido[2,3-b][1,4]oxazin-1-yl)-2-oxoethyl acetate (80 mg, 0.017 mmol) in dioxane (4 mL) was added MeOH (1.6 mL, 39.4 mmol). Then the colorless solution was added $K_2CO_3$ (70 mg, 0.050 mmol), stirred at 20° C. for 2 h. LCMS (Rt=0.582 min; MS Calc'd: 433.2; MS Found: 434.2 [M+H]$^+$). The reaction mixture was concentrated. The residue was purified by prep-HPLC (0.05% $NH_3.H_2O$ as an additive) and lyophilized to afford 4-(6-((1-(2-hydroxyacetyl)-2,3-dihydro-1H-pyrido[2,3-b][1,4]oxazin-7-yl)amino)pyridin-3-yl)-N,N-dimethylbenzamide (30 mg, yield: 41%) as a white solid. LCMS (Shimadzu LCMS 2010, mobile phase: from 100% [water+0.05% $NH_3.H_2O$] and 0% [MeCN] to 5% [water+0.05% $NH_3.H_2O$] and 95% [MeCN] in 5.8 min, then under this condition for 1.1 min, finally changed to 100% [water+0.05% $NH_3.H_2O$] and 0% [MeCN] and under this condition for 0.09 min.) purity is 96.39%, Rt=2.208 min; MS Calc'd.: 433.2, MS Found: 434.2 [M+H]$^+$. $^1$H NMR (400 MHz, DMSO-$d_6$) δ 2.99 (6H, s), 3.83 (2H, t, J=3.6 Hz), 4.30-4.41 (4H, m), 5.08 (1H, t, J=6.0 Hz), 6.90 (1H, d, J=8.8 Hz), 7.48 (2H, d, J=8.0 Hz), 7.71 (2H, d, J=8.0 Hz), 7.95 (1H, dd, J=8.0, 2.0 Hz), 8.34 (1H, d, J=2.4 Hz), 8.51 (1H, d, J=2.0 Hz), 8.81 (1H, br s), 9.25 (1H, s).

Example 90: 4-(6-((1-(cyclopropanecarbonyl)-2,3-dihydro-1H-pyrido[2,3-b][1,4]oxazin-7-yl)amino)pyridin-3-yl)-N,N-dimethylbenzamide

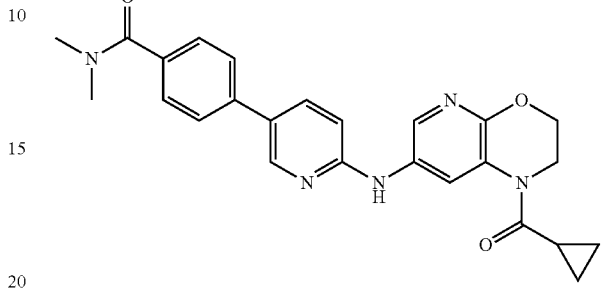

Step 1: Preparation of (7-bromo-2,3-dihydro-1H-pyrido[2,3-b][1,4]oxazin-1-yl)(cyclopropyl)methanone

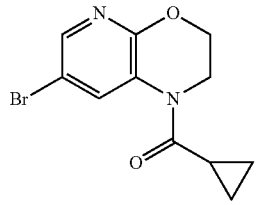 [SMILES: O=C(C1CC1)N1CCOc2ncc(Br)cc21]

In a separate vial, to a solution of cyclopropanecarboxylic acid (240 mg, 2.79 mmol) in DCM (2 mL), DMF (25 mg, 0.349 mmol) was added oxalyl chloride (0.3 mL, 3.49 mmol). The reaction mixture was stirred at 20° C. for 0.5 hour. A light yellow solution was formed. The mixture was concentrated to give crude cyclopropanecarbonyl chloride as a yellow oil. To a solution of 7-bromo-2,3-dihydro-1H-pyrido[2,3-b][1,4]oxazine in DCM (6 mL) was added TEA (0.5 mL, 3.49 mmol). The reaction mixture was cooled to 0° C. and then added cyclopropanecarbonyl chloride in DCM (2 mL) dropwise. The reaction mixture was then warmed to 20° C., stirred at 20° C. for 2 h under $N_2$ atmosphere. The colorless solution turned to yellow gradually. LCMS showed the purity of the desired product (Rt=0.601 min; MS Calc'd: 282.0; MS Found: 282.6 [M+H]$^+$). The reaction mixture was concentrated together with the last reaction (es6012-100). The residue was purified by Combi Flash (1% TEA in DCM) to afford (7-bromo-2,3-dihydro-1H-pyrido[2,3-b][1,4]oxazin-1-yl)(cyclopropyl)methanone (240 mg, yield: 92%) as a yellow gum. $^1$H NMR (400 MHz, CDCl$_3$) δ 0.95-1.01 (2H, m), 1.17-1.23 (2H, m), 1.89-1.20 (1H, m), 4.02 (2H, t, J=4.8 Hz), 4.46 (2H, t, J=4.8 Hz), 8.06 (1H, d, J=2.4 Hz), 8.20 (1H, br s).

Step 2: Preparation of 4-(6-((1-(cyclopropanecarbonyl)-2,3-dihydro-1H-pyrido[2,3-b][1,4]oxazin-7-yl)amino)pyridin-3-yl)-N,N-dimethylbenzamide

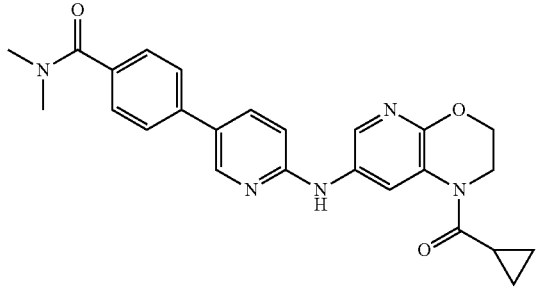 [SMILES: CN(C)C(=O)c1ccc(-c2ccc(Nc3cnc4c(c3)N(C(=O)C3CC3)CCO4)nc2)cc1]

A mixture of Pd$_2$(dba)$_3$ (19 mg, 0.021 mmol) and Brettphos (23 mg, 0.042 mmol) in 1,4-dioxane (1 mL) was stirred at 50° C. for 10 min. 4-(6-Aminopyridin-3-yl)-N,N-dimethylbenzamide (102 mg, 0.424 mmol), (7-bromo-2,3-dihydro-1H-pyrido[2,3-b][1,4]oxazin-1-yl)(cyclopropyl)methanone (120 mg, 0.424 mmol) in dioxane (8 mL) and Cs$_2$CO$_3$ (276 mg, 0.848 mmol) were added, and the resulting mixture was stirred at 100° C. for 6 h. A black brown mixture was formed. LCMS (Rt=0.542 min; MS Calc'd: 443.2; MS Found: 443.8 [M+H]$^+$). The reaction mixture was filtered. The mixture was purified by prep-HPLC (normal phase, Hexane-EtOH (5-70% B)) and lyophilized to give impure product (85 mg) as an off-white solid, then purified by prep-HPLC (0.05% NH$_3$.H$_2$O as an additive) and lyophilized to give 4-(6-((1-(cyclopropanecarbonyl)-2,3-dihydro-1H-pyrido[2,3-b][1,4]oxazin-7-yl)amino)pyridin-3-yl)-N,N-dimethylbenzamide (65.2 mg, yield: 35%) as a white solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 95.84%, Rt=1.193 min; MS Calc'd.: 443.2; MS Found: 444.1 [M+H]$^+$. $^1$H NMR (400 MHz, DMSO-d$_6$) δ 0.85-1.06 (4H, m), 2.12-2.29 (1H, m), 2.98 (6H, s), 3.94-4.02 (2H, m), 4.37 (2H, t, J=4.4 Hz), 6.88 (1H, d, J=8.8 Hz), 7.47 (2H, d, J=8.0 Hz), 7.70 (2H, d, J=8.4 Hz), 7.93 (1H, dd, J=8.8, 2.4 Hz), 8.21 (1H, br s), 8.47 (1H, d, J=2.4 Hz), 8.67 (1H, d, J=2.4 Hz), 9.27 (1H, br s).

Example 91: 1-(7-(((5-(4-(dimethylcarbamoyl)phenyl)pyridin-2-yl)amino)-2,3-dihydro-1H-pyrido[2,3-b][1,4]oxazin-1-yl)-1-oxopropan-2-yl acetate

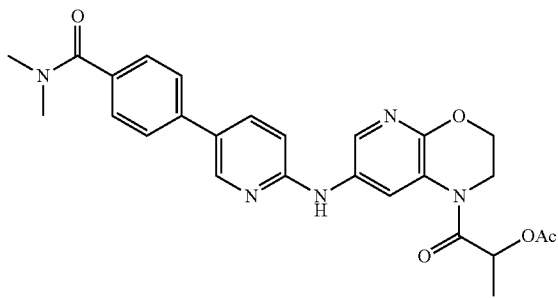 [SMILES: CC(=O)OC(C)C(=O)N1CCOc2ncc(Nc3ccc(-c4ccc(C(=O)N(C)C)cc4)cn3)cc21]

Step 1: Preparation of 2-acetoxypropanoic acid

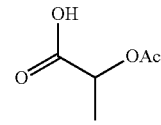

2-Hydroxypropanoic acid (900 mg, 9.99 mmol) was slowly added acetyl chloride (1.4 mL, 20.0 mmol) at 0° C. Then the reaction mixture was warmed to 20° C., stirred at 20° C. for 16 h under N$_2$ atmosphere. A yellow solution was formed gradually. TLC showed the reaction was completed nearly. Acetyl chloride was removed under reduced pressure to afford 2-acetoxypropanoic acid (1.20 g, yield: 90%) as yellow oil. $^1$H NMR (400 MHz, CDCl$_3$) δ 1.53 (3H, d, J=7.2 Hz), 2.14 (3H, s), 5.11 (1H, q, J=7.2 Hz).

Step 2: Preparation of 1-(7-bromo-2,3-dihydro-1H-pyrido[2,3-b][1,4]oxazin-1-yl)-1-oxopropan-2-ylacetate

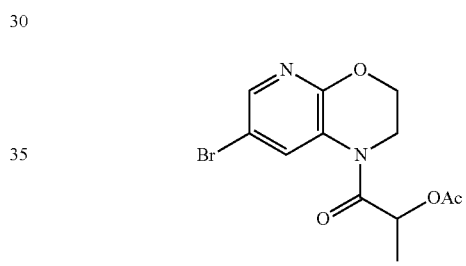

In a separate vial, to a solution of 2-acetoxypropanoic acid (245 mg, 1.86 mmol) in DCM (2 mL), DMF (17 mg, 0.23 mmol) was added oxalyl chloride (0.2 mL, 2.33 mmol). The reaction mixture was stirred at 20° C. for 0.5 hour. A light yellow solution was formed. The mixture was concentrated to give yellow oil. To a solution of 7-bromo-2,3-dihydro-1H-pyrido[2,3-b][1,4]oxazine (100 mg, 0.465 mmol) in DCM (5 mL) was added TEA (0.3 mL, 2.33 mmol). The reaction mixture was cooled to 0° C. and then added 1-chloro-1-oxopropan-2-yl acetate in DCM (2 mL) dropwise. The reaction mixture was then warmed to 20° C., stirred at 20° C. for 2 h under N$_2$ atmosphere. The colorless solution turned to dark red gradually. LCMS showed the purity of the desired product (Rt=0.583 min; MS Calc'd: 328.0; MS Found: 329.3 [M+H]$^+$). The reaction mixture was concentrated. The residue was purified by Combi Flash (1% TEA in DCM) to afford 1-(7-bromo-2,3-dihydro-H-pyrido[2,3-b][1,4]oxazin-1-yl)-1-oxopropan-2-yl acetate (180 mg, yield: 94%). $^1$H NMR (400 MHz, CDCl$_3$) δ 1.51 (3H, d, J=6.4 Hz), 2.13 (3H, s), 3.73-3.84 (1H, m), 4.00-4.10 (1H, m), 4.40-4.52 (2H, m), 5.43 (1H, q, J=6.8 Hz), 8.08 (1H, d, J=2.0 Hz), 8.45 (1H, br s).

Step 3: Preparation of 1-(7-((5-(4-(dimethylcarbamoyl)phenyl)pyridin-2-yl)amino)-2,3-dihydro-1H-pyrido[2,3-b][1,4]oxazin-1-yl)-1-oxopropan-2-yl acetate

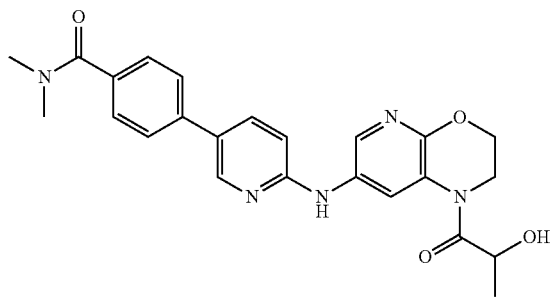 [SMILES: CC(O)C(=O)N1CCOc2ncc(Nc3ccc(-c4ccc(C(=O)N(C)C)cc4)cn3)cc21]

A mixture of Pd$_2$(dba)$_3$ (20 mg, 0.022 mmol) and Brettphos (23 mg, 0.044 mmol) in 1,4-dioxane (1 mL) was stirred at 50° C. for 10 min. 4-(6-aminopyridin-3-yl)-N,N-dimethylbenzamide (105 mg, 0.437 mmol), 1-(7-bromo-2,3-dihydro-1H-pyrido[2,3-b][1,4]oxazin-1-yl)-1-oxopropan-2-yl acetate (180 mg, 0.437 mmol) in dioxane (8 mL) and Cs$_2$CO$_3$ (285 mg, 0.875 mmol) were added, and the resulting mixture was stirred at 100° C. for 6 h. A black brown mixture was formed. LCMS showed the purity of the desired product (Rt=0.642 min; MS Calc'd: 489.2; MS Found: 490.3 [M+H]$^+$). The reaction mixture was diluted with dioxane (10 mL), filtered and concentrated. The residue was purified by Combi Flash (40% EtOAc in DCM (1% TEA as an additive)) to give 1-(7-((5-(4-(dimethylcarbamoyl)phenyl)pyridin-2-yl)amino)-2,3-dihydro-1H-pyrido[2,3-b][1,4]oxazin-1-yl)-1-oxopropan-2-yl acetate (75 mg) as an off-white solid. The impure product (15 mg) was purified by prep-HPLC (0.05% NH$_3$.H$_2$O as an additive) and lyophilized to give 1-(7-((5-(4-(dimethylcarbamoyl)phenyl)pyridin-2-yl)amino)-2,3-dihydro-1H-pyrido[2,3-b][1,4]oxazin-1-yl)-1-oxopropan-2-yl acetate (2.61 mg) as a white solid. LCMS (Shimadzu LCMS 2010, mobile phase: from 100% [water+0.05% NH$_3$.H$_2$O] and 0% [MeCN] to 5% [water+0.05% NH$_3$.H$_2$O] and 95% [MeCN] in 5.8 min, then under this condition for 1.1 min, finally changed to 100% [water+0.05% NH$_3$.H$_2$O] and 0% [MeCN] and under this condition for 0.09 min.) purity is 99.32%, Rt=2.603 min; MS Calc'd.: 489.2, MS Found: 490.2 [M+H]$^+$. $^1$H NMR (400 MHz, CDCl$_3$) δ 1.57 (3H, d, J=6.8 Hz), 2.12 (3H, s), 3.04 (3H, s), 3.13 (3H, s), 3.85-4.09 (2H, m), 4.39-4.58 (2H, m), 5.50-5.68 (1H, m), 6.42 (1H, s), 6.79 (1H, d, J=8.0 Hz), 7.50 (2H, d, J=8.4 Hz), 7.56 (2H, d, J=8.4 Hz), 7.75 (1H, dd, J=8.4, 2.4 Hz), 8.06 (1H, s), 8.42 (1H, d, J=2.0 Hz), 8.52 (1H, br s).

Example 92: 4-(6-((1-(2-hydroxypropanoyl)-2,3-dihydro-1H-pyrido[2,3-b][1,4]oxazin-7-yl)amino)pyridin-3-yl)-N,N-dimethylbenzamide

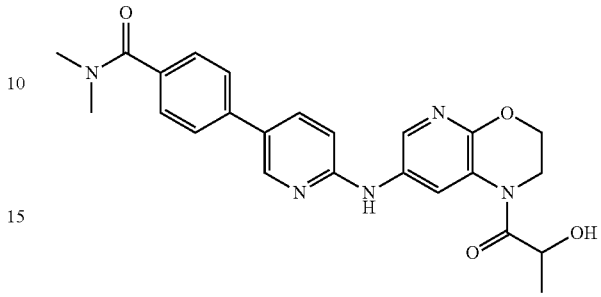

To a solution of 1-(7-((5-(4-(dimethylcarbamoyl)phenyl)pyridin-2-yl)amino)-2,3-dihydro-H-pyrido[2,3-b][1,4]oxazin-1-yl)-1-oxopropan-2-yl acetate (60 mg, 0.12 mmol) in dioxane (4 mL) was added MeOH (0.5 mL). Then the red solution was added K$_2$CO$_3$ (51 mg, 0.37 mmol), stirred at 20° C. for 2 h. The mixture was added MeOH (0.5 mL), stirred at 20° C. for another 2 h. LCMS (Rt=0.614 min; MS Calc'd: 447.2; MS Found: 448.3 [M+H]$^+$). The reaction mixture was concentrated. The residue was purified by prep-HPLC (0.05% NH$_3$.H$_2$O as an additive) and lyophilized to afford 4-(6-((1-(2-hydroxypropanoyl)-2,3-dihydro-1H-pyrido[2,3-b][1,4]oxazin-7-yl)amino)pyridin-3-yl)-N,N-dimethylbenzamide (9.4 mg, yield: 17%) as a white solid. LCMS (Shimadzu LCMS 2010, mobile phase: from 100% [water+0.05% NH$_3$.H$_2$O] and 0% [MeCN] to 5% [water+0.05% NH$_3$.H$_2$O] and 95% [MeCN] in 5.8 min, then under this condition for 1.1 min, finally changed to 100% [water+0.05% NH$_3$.H$_2$O] and 0% [MeCN] and under this condition for 0.09 min.) purity is 96.79%, Rt=2.309 min; MS Calc'd.: 447.2, MS Found: 448.2 [M+H]$^+$. $^1$H NMR (400 MHz, CDCl$_3$) δ 1.44 (3H, d, J=6.4 Hz), 3.04 (3H, s), 3.14 (3H, s), 3.58 (1H, br s), 3.73-4.18 (2H, m), 4.34-4.57 (2H, m), 4.61-4.88 (1H, m), 6.52 (1H, s), 6.81 (1H, d, J=8.0 Hz), 7.50 (2H, d, J=8.0 Hz), 7.56 (2H, d, J=7.6 Hz), 7.77 (1H, dd, J=8.4, 2.4 Hz), 8.08 (1H, s), 8.45 (1H, d, J=2.4 Hz), 8.68 (1H, br s).

Example 93: methyl 7-((5-(4-(dimethylcarbamoyl)phenyl)pyridin-2-yl)amino)-2,3-dihydro-1H-pyrido[2,3-b][1,4]oxazine-1-carboxylate

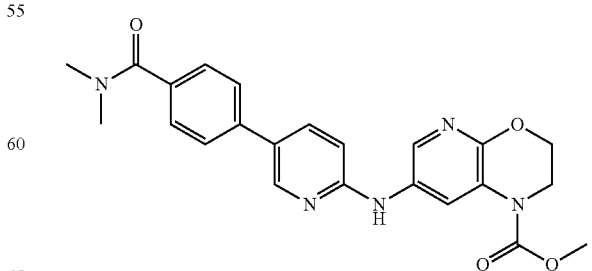

Step 1: Preparation of methyl 7-bromo-2,3-dihydro-1H-pyrido[2,3-b][1,4]oxazine-1-carboxylate

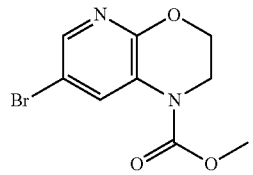

To a solution of 7-bromo-2,3-dihydro-H-pyrido[2,3-b][1,4]oxazine (100 mg, 0.465 mmol) in DCM (5 mL) was added TEA (212 mg, 2.09 mmol). The reaction mixture was cooled to 0° C. and then added methyl carbonochloridate (1.31 g, 13.86 mmol) dropwise. The reaction mixture was then warmed to 20° C., stirred at 20° C. for 18 h under $N_2$ atmosphere. The colorless solution turned to yellow gradually. LCMS showed the purity of the desired product is 33% (Rt=0.692 min; MS Calc'd: 272.0; MS Found: 272.9 [M+H]+). The reaction mixture was concentrated. The residue was purified by Combi Flash (50% DCM in pentane (1% TEA as an additive)) to afford methyl 7-bromo-2,3-dihydro-1H-pyrido[2,3-b][1,4]oxazine-1-carboxylate (65 mg, yield: 51%) as a yellow gum.

$^1$H NMR (400 MHz, CDCl$_3$) δ 3.87 (3H, s), 3.93 (2H, t, J=4.4 Hz), 4.39 (2H, t, J=4.8 Hz), 7.99 (1H, d, J=2.4 Hz), 8.52 (1H, br s).

Step 2: Preparation of methyl 7-((5-(4-(dimethylcarbamoyl)phenyl)pyridin-2-yl)amino)-2,3-dihydro-1H-pyrido[2,3-b][1,4]oxazine-1-carboxylate

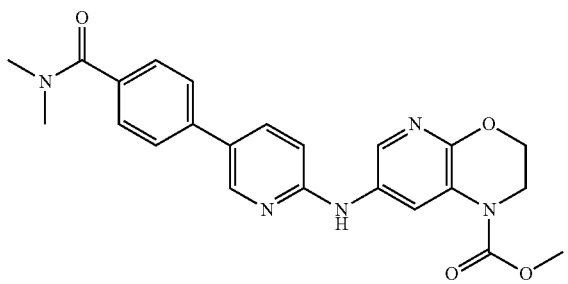

A mixture of Pd$_2$(dba)$_3$ (11 mg, 0.012 mmol) and Brettphos (13 mg, 0.024 mmol) in 1,4-dioxane (1 mL) was stirred at 50° C. for 10 min. 4-(6-aminopyridin-3-yl)-N,N-dimethylbenzamide (57 mg, 0.24 mmol), methyl 7-bromo-2,3-dihydro-1H-pyrido[2,3-b][1,4]oxazine-1-carboxylate (65 mg, 0.238 mmol) in dioxane (3 mL) and Cs$_2$CO$_3$ (155 mg, 0.476 mmol) were added, and the resulting mixture was stirred at 100° C. for 6 h. A black brown mixture was formed. LCMS (Rt=0.648 min; MS Calc'd: 433.2; MS Found: 434.2 [M+H]+). The reaction mixture was filtered. The mixture was purified by prep-HPLC (normal phase, hexane-IPA (15-100% B)) and lyophilized to give methyl 7-((5-(4-(dimethylcarbamoyl)phenyl)pyridin-2-yl)amino)-2,3-dihydro-1H-pyrido[2,3-b][1,4]oxazine-1-carboxylate (8.1 mg, yield: 8%) as a white solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 98.90%, Rt=1.156 min; MS Calc'd.: 433.2; MS Found: 434.0 [M+H]+. $^1$H NMR (400 MHz, CDCl$_3$) δ 3.04 (3H, s), 3.13 (3H, s), 3.86 (3H, s), 3.96 (2H, t, J=4.8 Hz), 4.41 (2H, t, J=4.8 Hz), 6.52 (1H, br s), 6.81 (1H, d, J=8.8 Hz), 7.49 (2H, d, J=8.0 Hz), 7.56 (2H, d, J=8.0 Hz), 7.75 (1H, dd, J=8.4, 2.4 Hz), 8.01 (1H, d, J=2.4 Hz), 8.44 (1H, d, J=2.0 Hz), 8.54 (1H, br s).

Example 94: 4-(6-((1-benzoyl-2,3-dihydro-1H-pyrido[2,3-b][1,4]oxazin-7-yl)amino)pyridin-3-yl)-N,N-dimethylbenzamide

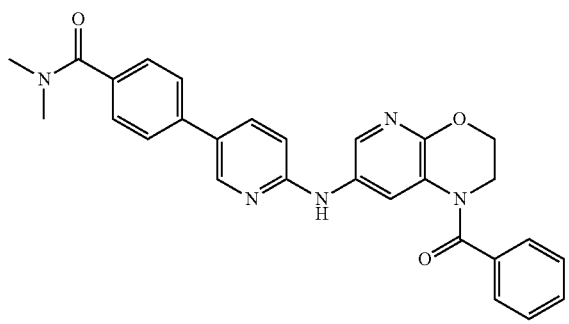

Step 1: Preparation of (7-bromo-2,3-dihydro-1H-pyrido[2,3-b][1,4]oxazin-1-yl)(phenyl)methanone

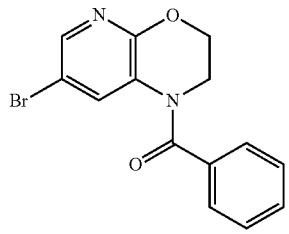 [SMILES: O=C(c1ccccc1)N1CCOc2ncc(Br)cc21]

To a solution of 7-bromo-2,3-dihydro-1H-pyrido[2,3-b][1,4]oxazine (500 mg, 2.33 mmol) in DCM (5 mL) was added TEA (1 mL, 7 mmol) and benzoyl chloride (983 mg, 6.99 mmol) at 0° C., the mixture was stirred at 25° C. for 2 h. TLC showed the starting material was consumed completely. The solution was yellow. The reaction mixture was concentrated and purified by Combi Flash (50% EtOAc in pentane) to give (7-bromo-2,3-dihydro-1H-pyrido[2,3-b][1,4]oxazin-1-yl)(phenyl)methanone (500 mg, yield: 67%) as a white solid. $^1$H NMR (400 MHz, CDCl$_3$) δ 3.94 (2H, t, J=4.8 Hz), 4.30 (2H, t, J=4.8 Hz), 7.40-7.60 (5H, m), 7.90-8.15 (2H, m).

Step 2: Preparation of 4-(6-((1-benzoyl-2,3-dihydro-1H-pyrido[2,3-b][1,4]oxazin-7-yl)amino)pyridin-3-yl)-N,N-dimethylbenzamide

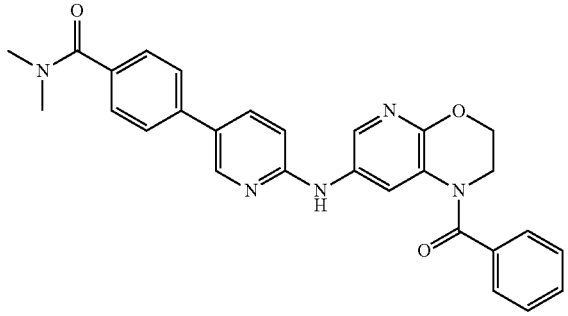 [SMILES: CN(C)C(=O)c1ccc(-c2ccc(Nc3cnc4c(c3)N(C(=O)c3ccccn3)CCO4)nc2)cc1]

A mixture of (7-bromo-2,3-dihydro-1H-pyrido[2,3-b][1,4]oxazin-1-yl)(phenyl)methanone (100 mg, 0.313 mmol), 4-(6-aminopyridin-3-yl)-N,N-dimethylbenzamide (76 mg, 0.31 mmol), Pd$_2$(dba)$_3$ (14 mg, 0.016 mmol), Brettphos (17 mg, 0.031 mmol) and Cs$_2$CO$_3$ (306 mg, 0.940 mmol) in dioxane (3 mL) was stirred at 100° C. for 16 h. LCMS (Rt=0.694 min; MS Calc'd: 479.2; MS Found: 480.1 [M+H]$^+$). A black suspension was formed. The mixture was filtered and concentrated to give an orange gum. The residue was purified by prep-HPLC (Welch diol; DCM-MeCN) to give 4-(6-((1-benzoyl-2,3-dihydro-1H-pyrido[2,3-b][1,4]oxazin-7-yl)amino)pyridin-3-yl)-N,N-dimethylbenzamide (28.0 mg, yield: 19%) as a white solid.

LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 98.94%, Rt=1.337 min; MS Calc'd.: 479.2; MS Found: 480.1 [M+H]$^+$. $^1$H NMR (400 MHz, CDCl$_3$) δ 2.98 (6H, s), 3.87 (2H, t, J=4.8 Hz), 4.38 (2H, t, J=4.4 Hz), 6.76 (1H, d, J=8.8 Hz), 7.40-7.55 (5H, m), 7.60 (2H, d, J=2.4 Hz), 7.90 (2H, d, J=8.4 Hz), 7.89 (1H, d, J=8.8 Hz), 8.25 (1H, s), 8.41 (2H, d, J=2.4 Hz), 9.17 (1H, br s).

Example 95: N,N-dimethyl-4-(6-((1-picolinoyl-2,3-dihydro-1H-pyrido[2,3-b][1,4]oxazin-7-yl)amino)pyridin-3-yl)benzamide

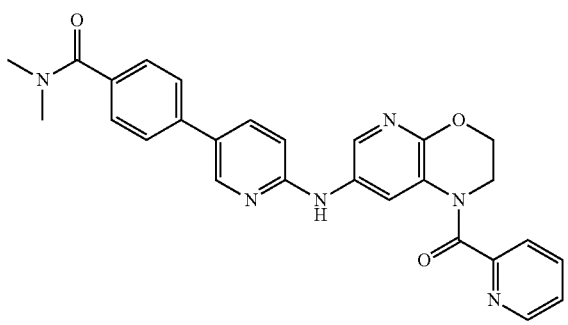 [SMILES: CN(C)C(=O)c1ccc(-c2ccc(Nc3cnc4c(c3)N(C(=O)c3ccccn3)CCO4)nc2)cc1]

Step 1: Preparation of (7-bromo-2,3-dihydro-H-pyrido[2,3-b][1,4]oxazin-1-yl)(pyridin-2-yl)methanone

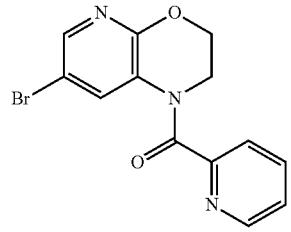

To a mixture of picolinic acid (172 mg, 1.40 mmol) in SOCl$_2$ (3 mL) was stirred at 80° C. for 2 h. The orange solution turned to blue gradually. SOCl$_2$ was removed under reduced pressure to give crude picolinoyl chloride as a green solid. To a solution of 7-bromo-2,3-dihydro-1H-pyrido[2,3-b][1,4]oxazine (100 mg, 0.465 mmol) in THF (3 mL) was added TEA (235 mg, 2.33 mmol). The reaction mixture was cooled to 0° C. and then added picolinoyl chloride in THF (1 mL) dropwise. The reaction mixture was then warmed to 20° C., stirred at 20° C. for 2 h under N$_2$ atmosphere. The blue mixture turned to brown gradually. LCMS is 94% (Rt=0.681 min; MS Calc'd: 319.0; MS Found: 319.9 [M+H]$^+$). The mixture was concentrated. The residue was purified by Combi Flash (1% TEA in DCM) to give (7-bromo-2,3-dihydro-1H-pyrido[2,3-b][1,4]oxazin-1-yl)(pyridin-2-yl)methanone (160 mg, yield: 98%) as a red gum. $^1$H NMR (400 MHz, CDCl$_3$) δ 4.09 (2H, t, J=4.8 Hz), 4.47 (2H, t, J=4.8 Hz), 7.42-7.47 (1H, m), 7.84 (1H, d, J=8.0 Hz), 7.86-7.93 (1H, m), 8.06 (1H, d, J=2.0 Hz), 8.37 (1H, br s), 8.62 (1H, d, J=4.4 Hz).

Step 2: Preparation of N,N-dimethyl-4-(6-((1-picolinoyl-2,3-dihydro-1H-pyrido[2,3-b][1,4]oxazin-7-yl)amino)pyridin-3-yl)benzamide

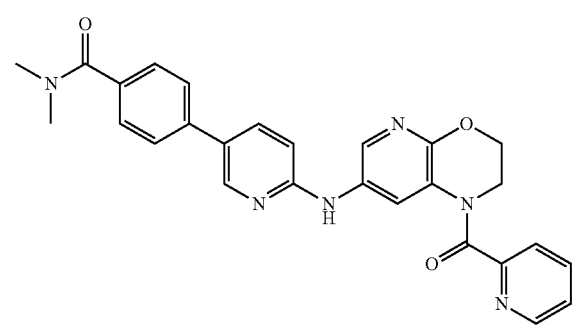

A mixture of Pd$_2$(dba)$_3$ (11 mg, 0.012 mmol) and Brettphos (13 mg, 0.025 mmol) in 1,4-dioxane (1 mL) was stirred at 50° C. for 10 min. 4-(6-aminopyridin-3-yl)-N,N-dimethylbenzamide (60 mg, 0.25 mmol), (7-bromo-2,3-dihydro-1H-pyrido[2,3-b][1,4]oxazin-1-yl)(pyridin-2-yl)methanone (80 mg, 0.25 mmol) in dioxane (5 mL) and Cs$_2$CO$_3$ (163 mg, 0.500 mmol) were added, and the resulting mixture was stirred at 100° C. for 6 h. A black brown mixture was formed. LCMS (Rt=0.634 min; MS Calc'd: 480.2; MS Found: 481.3 [M+H]$^+$). The reaction mixture was filtered.

The mixture was purified by prep-HPLC (normal phase, hexane-IPA (40-100% B)) and lyophilized to give N,N-dimethyl-4-(6-((1-picolinoyl-2,3-dihydro-1H-pyrido[2,3-b][1,4]oxazin-7-yl)amino)pyridin-3-yl)benzamide (10.3 mg, yield: 9%) as an off-white solid. LCMS (Shimadzu LCMS 2010, mobile phase: from 100% [water+0.05% NH$_3$.H$_2$O] and 0% [MeCN] to 5% [water+0.05% NH$_3$.H$_2$O] and 95% [MeCN] in 5.8 min, then under this condition for 1.1 min, finally changed to 100% [water+0.05% NH$_3$.H$_2$O] and 0% [MeCN] and under this condition for 0.09 min.) purity is 95.63%, Rt=2.629 min; MS Calc'd.: 480.2, MS Found: 481.2 [M+H]$^+$. $^1$H NMR (400 MHz, DMSO-d$_6$) δ 2.98 (6H, s), 3.81-3.99 (2H, m), 4.29-4.45 (2H, m), 6.69-6.89 (1H, m), 7.47 (2H, d, J=6.8 Hz), 7.48-7.59 (1H, m), 7.70 (2H, d, J=6.8 Hz), 7.79 (1H, d, J=6.8 Hz), 7.90 (1H, d, J=6.8 Hz), 8.02 (1H, t, J=6.4 Hz), 8.26 (1H, br s), 8.42 (1H, s), 8.62 (1H, s), 9.21 (1H, br s). $^1$H NMR (400 MHz, DMSO-d$_6$+D$_2$O) δ 2.92 (3H, s), 2.96 (3H, s), 3.79-3.91 (2H, m), 4.29-4.43 (2H, m), 6.66-6.87 (1H, m), 7.44 (2H, d, J=7.6 Hz), 7.47-7.55 (1H, m), 7.65 (2H, d, J=7.6 Hz), 7.74 (1H, d, J=7.2 Hz), 7.85 (1H, d, J=8.0 Hz), 7.97 (1H, t, J=6.8 Hz), 8.07 (1H, br s), 8.33 (1H, s), 8.54 (1H, s). $^1$H NMR (400 MHz, DMSO-d$_6$+D$_2$O, t=80° C.) δ 2.95 (6H, s), 4.38 (2H, t, J=4.0 Hz), 3.76-3.85 (2H, m, overlapped with H$_2$O), 6.75 (1H, d, J=8.4 Hz), 7.40-7.49 (3H, m), 7.59-7.64 (2H, m), 7.69 (1H, dd, J=8.0, 1.2 Hz), 7.79-7.83 (1H, m), 7.90-7.97 (1H, m), 8.01 (1H, s), 8.24, 8.60 (0.8H+0.2H, s), 8.30 (1H, s), 8.50-8.53 (1H, m).

Example 96: 4-(6-((1-(3-hydroxy-2,2-dimethylpropanoyl)-2,3-dihydro-1H-pyrido[2,3-b][1,4]oxazin-7-yl)amino)pyridin-3-yl)-N,N-dimethylbenzamide

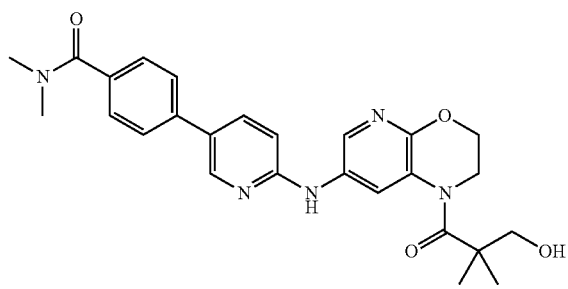 [SMILES: CN(C)C(=O)c1ccc(-c2ccc(Nc3cnc4c(c3)N(C(=O)C(C)(C)CO)CCO4)nc2)cc1]

Step 1: Preparation of 3-acetoxy-2,2-dimethylpropanoic acid

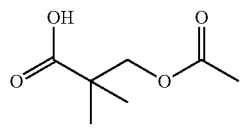

3-Hydroxy-2,2-dimethylpropanoic acid (1.00 g, 8.47 mmol) was slowly added acetyl chloride (1.33 g, 16.9 mmol) at 0° C. The reaction mixture was then warmed to 20° C., stirred at 20° C. for 16 h under N$_2$ atmosphere. The colorless solution was formed gradually. Acetyl chloride was removed under reduced pressure to afford 3-acetoxy-2,2-dimethylpropanoic acid (1.30 g, yield: 96%) as a white gum. $^1$H NMR (400 MHz, CDCl$_3$) δ 1.26 (6H, s), 2.06 (3H, s), 4.12 (2H, s).

Step 2: Preparation of 3-(7-bromo-2,3-dihydro-1H-pyrido[2,3-b][1,4]oxazin-1-yl)-2,2-dimethyl-3-oxopropyl acetate

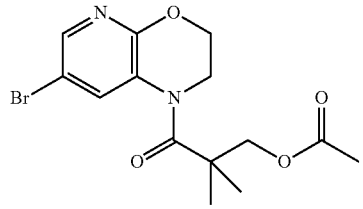 [SMILES: CC(=O)OCC(C)(C)C(=O)N1CCOc2ncc(Br)cc21]

In a separate vial, to a solution of 3-acetoxy-2,2-dimethylpropanoic acid (447 mg, 2.79 mmol), DMF (25 mg, 0.35 mmol) in DCM (6 mL) was added oxalyl chloride (443 mg, 3.49 mmol). The reaction mixture was stirred at 20° C. for 0.5 hour. A light yellow solution was formed. The mixture was concentrated to give crude 3-chloro-2,2-dimethyl-3-oxopropyl acetate as a yellow oil. To a solution of 7-bromo-2,3-dihydro-1H-pyrido[2,3-b][1,4]oxazine (150 mg, 0.698 mmol) in DCM (6 mL) was added TEA (353 mg, 3.49 mmol). The reaction mixture was cooled to 0° C. and then added 3-chloro-2,2-dimethyl-3-oxopropyl acetate in DCM (6 mL) dropwise. The reaction mixture was then warmed to 20° C., stirred at 20° C. for 2 h under N$_2$ atmosphere. The colorless solution turned to orange gradually. LCMS (Rt=0.636 min, MS Calc'd.: 356.0; MS Found: 356.8 [M+H]$^+$). The reaction mixture was concentrated. The residue was purified by Combi Flash (80% DCM in pentane (1% TEA as an additive)) to afford the product 3-(7-bromo-2,3-dihydro-1H-pyrido[2,3-b][1,4]oxazin-1-yl)-2,2-dimethyl-3-oxopropyl acetate (330 mg, yield: 74%) as a red gum. $^1$H NMR (400 MHz, CDCl$_3$) δ 1.41 (6H, s), 2.09 (3H, s), 3.99 (2H, t, J=4.4 Hz), 4.24 (2H, s), 4.46 (2H, t, J=4.4 Hz), 8.04 (1H, d, J=2.0 Hz), 8.28 (1H, d, J=2.0 Hz).

Step 3: Preparation of 3-(7-((5-(4-(dimethylcarbamoyl)phenyl)pyridin-2-yl)amino)-2,3-dihydro-1H-pyrido[2,3-b][1,4]oxazin-1-yl)-2,2-dimethyl-3-oxopropyl acetate

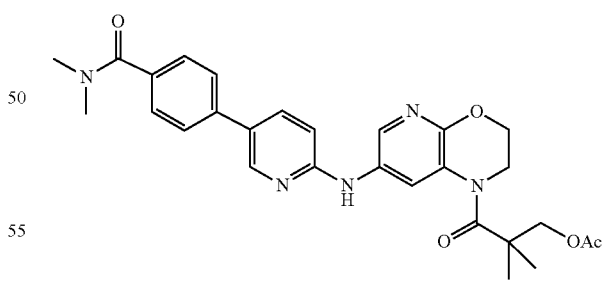

A mixture of Pd$_2$(dba)$_3$ (24 mg, 0.026 mmol) and Brettphos (28 mg, 0.052 mmol) in 1,4-dioxane (1 mL) was stirred at 50° C. for 10 min. 4-(6-Aminopyridin-3-yl)-N,N-dimethylbenzamide (170 mg, 0.704 mmol), 3-(7-bromo-2,3-dihydro-1H-pyrido[2,3-b][1,4]oxazin-1-yl)-2,2-dimethyl-3-oxopropyl acetate (330 mg, 0.517 mmol) in dioxane (8 mL) and Cs$_2$CO$_3$ (337 mg, 1.03 mmol) were added and the resulting mixture was stirred at 100° C. for 10 h. A black brown mixture was formed. LCMS showed the purity of the desired product (Rt=0.557 min; MS Calc'd: 517.2; MS Found: 518.2 [M+H]⁺). The reaction mixture was diluted with DCM (10 mL), filtered and concentrated. The residue was purified by Combi Flash (1% TEA in EtOAc) to give 3-(7-((5-(4-(dimethylcarbamoyl)phenyl)pyridin-2-yl)amino)-2,3-dihydro-1H-pyrido[2,3-b][1,4]oxazin-1-yl)-2,2-dimethyl-3-oxopropyl acetate (100 mg, yield: 37%) as a red gum. ¹H NMR (400 MHz, CDCl₃) δ 1.43 (6H, s), 2.06 (3H, s), 3.04 (3H, s), 3.13 (3H, s), 4.02 (2H, t, J=4.0 Hz), 4.24 (2H, s), 4.47 (2H, t, J=4.4 Hz), 6.58 (1H, br s), 6.79 (1H, d, J=8.8 Hz), 7.47-7.54 (4H, m), 7.74 (1H, dd, J=8.8, 2.0 Hz), 8.07 (1H, d, J=2.8 Hz), 8.28 (1H, d, J=2.8 Hz), 8.41 (1H, d, J=2.0 Hz).

Step 4: Preparation of 4-(6-((1-(3-hydroxy-2,2-dimethylpropanoyl)-2,3-dihydro-1H-pyrido[2,3-b][1,4]oxazin-7-yl)amino)pyridin-3-yl)-N,N-dimethylbenzamide

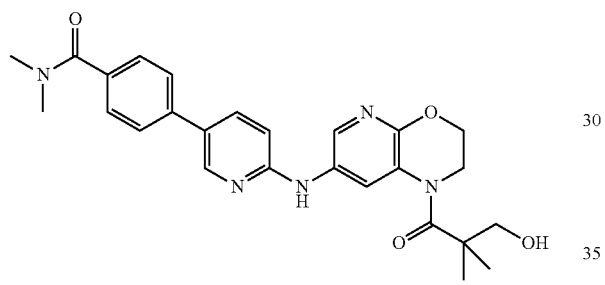

To a solution of 3-(7-((5-(4-(dimethylcarbamoyl)phenyl)pyridin-2-yl)amino)-2,3-dihydro-1H-pyrido[2,3-b][1,4]oxazin-1-yl)-2,2-dimethyl-3-oxopropyl acetate (70 mg, 0.14 mmol) in dioxane (4 mL) was added MeOH (635 mg, 19.8 mmol). Then the yellow solution was added K₂CO₃ (56 mg, 0.41 mmol), stirred at 20° C. for 4 h. LCMS (Rt=0.505 min; MS Calc'd: 475.2; MS Found: 476.2 [M+H]⁺). The reaction mixture was concentrated. The residue was purified by prep-HPLC (0.05% NH₃.H₂O as an additive) and lyophilized to afford 4-(6-((1-(3-hydroxy-2,2-dimethylpropanoyl)-2,3-dihydro-1H-pyrido[2,3-b][1,4]oxazin-7-yl)amino)pyridin-3-yl)-N,N-dimethylbenzamide (22.7 mg, yield: 35%) as a white solid.

LCMS (Shimadzu LCMS 2010, Mobile phase: from 100% [water+0.04% TFA] to 40% [water+0.04% TFA] and 60% [MeCN+0.02% TFA] in 1.35 min, then under this condition for 0.9 min, finally changed to 100% [water+0.04% TFA] and under this condition for 0.75 min.) purity is 98.68%, Rt=1.403 min; MS Calc'd.: 475.2; MS Found: 476.1 [M+H]⁺. ¹H NMR (400 MHz, DMSO-d₆) δ 1.28 (6H, s), 2.98 (6H, s), 3.54 (2H, d, J=5.6 Hz), 4.04 (2H, t, J=4.0 Hz), 4.35 (2H, t, J=3.6 Hz), 4.97 (1H, t, J=5.6 Hz), 6.86 (1H, d, J=8.4 Hz), 7.47 (2H, d, J=8.4 Hz), 7.71 (2H, d, J=8.4 Hz), 7.93 (1H, dd, J=8.8, 2.4 Hz), 8.24 (1H, d, J=2.4 Hz), 8.43 (1H, d, J=2.8 Hz), 8.49 (1H, d, J=2.0 Hz), 9.16 (1H, br s).

Example 97: N,N-dimethyl-4-(6-((1-pivaloyl-2,3-dihydro-1H-pyrido[2,3-b][1,4]oxazin-7-yl)amino)pyridin-3-yl)benzamide

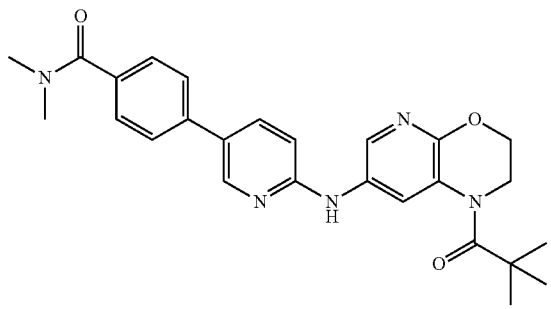 [SMILES: CN(C)C(=O)c1ccc(-c2ccc(Nc3cnc4c(c3)N(C(=O)C(C)(C)C)CCO4)nc2)cc1]

Step 1: Preparation of 1-(7-bromo-2,3-dihydro-1H-pyrido[2,3-b][1,4]oxazin-1-yl)-2,2-dimethylpropan-1-one

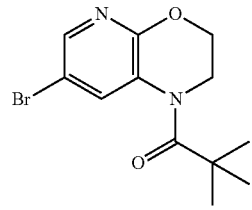 [SMILES: CC(C)(C)C(=O)N1CCOc2ncc(Br)cc21]

To a solution of 7-bromo-2,3-dihydro-1H-pyrido[2,3-b][1,4]oxazine (100 mg, 0.465 mmol) in DCM (5 mL) was added TEA (235 mg, 2.33 mmol). The reaction mixture was cooled to 0° C. and then added pivaloyl chloride (2.3 mL, 18 mmol) dropwise. The reaction mixture was then warmed to 20° C., stirred at 20° C. for 18 h under N₂ atmosphere. The colorless solution turned to suspension. LCMS showed the purity of the desired product (Rt=0.656 min; MS Calc'd: 298.0; MS Found: 299.6 [M+H]⁺). The reaction mixture was concentrated. The residue was purified by Combi Flash (40% DCM in pentane (1% TEA as an additive)), then the impure product was purified by prep-TLC (1% TEA in DCM) to afford 1-(7-bromo-2,3-dihydro-1H-pyrido[2,3-b][1,4]oxazin-1-yl)-2,2-dimethylpropan-1-one (30 mg, yield: 22%) as a yellow gum. ¹H NMR (400 MHz, CDCl₃) δ 1.39 (9H, s), 4.02 (2H, t, J=4.8 Hz), 4.45 (2H, t, J=4.8 Hz), 8.02 (1H, d, J=2.4 Hz), 8.37 (1H, d, J=2.0 Hz).

Step 2: Preparation of N,N-dimethyl-4-(6-((1-pivaloyl-2,3-dihydro-1H-pyrido[2,3-b][1,4]oxazin-7-yl)amino)pyridin-3-yl)benzamide

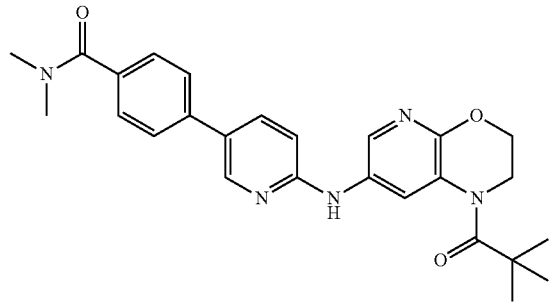 [SMILES: CN(C)C(=O)c1ccc(-c2ccc(Nc3cnc4c(c3)N(C(=O)C(C)(C)C)CCO4)nc2)cc1]

A mixture of Pd₂(dba)₃ (5 mg, 0.005 mmol) and Brettphos (5 mg, 0.01 mmol) in 1,4-dioxane (1 mL) was stirred at 50° C. for 10 min. 4-(6-Aminopyridin-3-yl)-N,N-dimethylbenzamide (24 mg, 0.10 mmol), 1-(7-bromo-2,3-dihydro-1H-pyrido[2,3-b][1,4]oxazin-1-yl)-2,2-dimethylpropan-1-one (30 mg, 0.10 mmol) in dioxane (2 mL) and Cs₂CO₃ (65 mg, 0.20 mmol) were added and the resulting mixture was stirred at 100° C. for 6 h. A black brown mixture was formed. LCMS (Rt=0.677 min; MS Calc'd: 459.2; MS Found: 460.3 [M+H]⁺). The reaction mixture was filtered. The mixture was purified by prep-HPLC (normal phase, hexane-IPA (10-100% B)) and lyophilized to give impure product (25 mg), then purified by prep-HPLC (0.05% NH₃.H₂O as an additive) and lyophilized to give N,N-dimethyl-4-(6-((1-pivaloyl-2,3-dihydro-1H-pyrido[2,3-b][1,4]oxazin-7-yl)amino)pyridin-3-yl)benzamide (11.2 mg, yield: 24%) as a white solid. LCMS (Shimadzu LCMS 2010, mobile phase: from 100% [water+0.05% NH₃.H₂O] and 0% [MeCN] to 5% [water+0.05% NH₃.H₂O] and 95% [MeCN] in 5.8 min, then under this condition for 1.1 min, finally changed to 100% [water+0.05% NH₃.H₂O] and 0% [MeCN] and under this condition for 0.09 min.) purity is 97.48%, Rt=2.902 min; MS Calc'd: 459.2, MS Found: 460.2 [M+H]⁺. ¹H NMR (400 MHz, CDCl₃) δ 1.39 (9H, s), 3.04 (3H, s), 3.13 (3H, s), 4.05 (2H, t, J=4.0 Hz), 4.47 (2H, t, J=4.4 Hz), 6.41 (1H, br s), 6.80 (1H, d, J=8.8 Hz), 7.49 (2H, d, J=8.4 Hz), 7.55 (2H, d, J=8.4 Hz), 7.75 (1H, dd, J=8.4, 2.4 Hz), 8.07 (1H, d, J=2.4 Hz), 8.30 (1H, d, J=2.8 Hz), 8.42 (1H, d, J=1.6 Hz).

Example 98: tert-butyl (3-((5-((5-(4-(dimethylcarbamoyl)phenyl)pyridin-2-yl)amino)pyridin-3-yl)carbamoyl)phenyl)carbamate Step 1: Preparation of 3-((tert-butoxycarbonyl)amino)benzoic acid

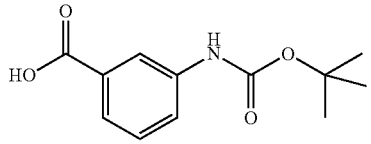 [SMILES: CC(C)(C)OC(=O)Nc1cccc(C(=O)O)c1]

To a solution of 3-aminobenzoic acid (5.00 g, 36.5 mmol), TEA (10 mL, 72.9 mmol), H₂O (42 mL) in dioxane (84 mL) was added Boc₂O (12.6 mL, 54.7 mmol) at 20° C. Reaction mixture was allowed to stir at 20° C. for 18 h. The solution became colorless to light yellow. TLC showed absence of starting material. 1,4-Dioxane was removed under reduced pressure and HCl (60 mL, 3M) was added drop-wise. The white precipitate was filtered out, washed with hexane (50 mL×3) and dried to afford 3-((tert-butoxycarbonyl)amino)benzoic acid (8.64 g, yield: 100%) as a white solid. ¹H NMR (400 MHz, CDCl₃) δ 1.53 (9H, s), 6.64 (1H, br s), 7.40 (1H, t, J=8.0 Hz), 7.66-7.81 (2H, m), 7.97-8.02 (1H, s), 11.99 (1H, br s).

Step 2: Preparation of tert-butyl (3-((5-bromopyridin-3-yl)carbamoyl)phenyl)carbamate

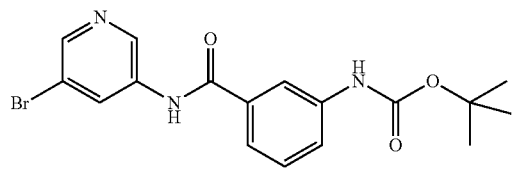 [SMILES: CC(C)(C)OC(=O)Nc1cccc(C(=O)Nc2cncc(Br)c2)c1]

3-((Tert-butoxycarbonyl)amino)benzoic acid (500 mg, 2.11 mmol) and 5-bromopyridin-3-amine (365 mg, 2.11 mmol) in pyridine (8 mL) was added EDCI (607 mg, 3.17 mmol). The mixture was stirred at 20° C. for 18 h. The color of solution became tangerine gradually. Crude LCMS showed the purity of desired product (Rt=0.813 min; MS Calc'd: 391.0; MS Found: 394.1 [M+H]⁺). Pyridine was removed under reduced pressure. After addition of sat-.NaHCO₃ (30 mL) to the residue, the mixture was extracted with DCM (20 mL×3). The organic layer was dried over anhydrous Na₂SO₄, and concentrated in vacuum. The residue was purified by Combi Flash (1% TEA in DCM) to give tert-butyl (3-((5-bromopyridin-3-yl)carbamoyl)phenyl)carbamate (750 mg, yield: 91%) as an off-white solid. ¹H NMR (400 MHz, CDCl₃) δ 1.54 (9H, s), 6.67 (1H, br s), 7.38-7.51 (2H, m), 7.57 (1H, d, J=7.8 Hz), 8.02 (1H, s), 8.14 (1H, br s), 8.45 (1H, d, J=2.0 Hz), 8.57 (1H, t, J=2.0 Hz), 8.62 (1H, d, J=2.0 Hz).

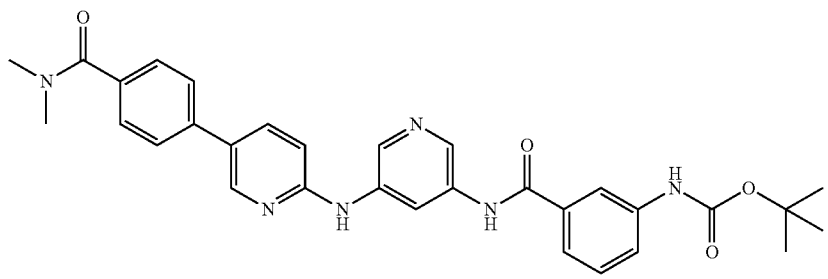

Step 3: Preparation of tert-butyl (3-((5-((5-(4-(dimethylcarbamoyl)phenyl)pyridin-2-yl)amino)pyridin-3-yl)carbamoyl)phenyl)carbamate

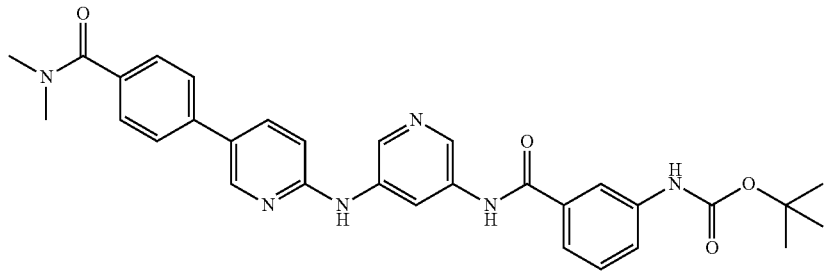 [SMILES: CN(C)C(=O)c1ccc(-c2ccc(Nc3cncc(NC(=O)c4cccc(NC(=O)OC(C)(C)C)c4)c3)nc2)cc1]

A mixture of Pd$_2$(dba)$_3$ (13 mg, 0.015 mmol, 3 mol %) and Brettphos (16 mg, 0.029 mmol, 6 mol %) in 1,4-dioxane (1 mL) was stirred at 50° C. for 10 min. Tert-butyl (3-((5-bromopyridin-3-yl)carbamoyl)phenyl)carbamate (190 mg, 0.484 mmol), 4-(6-aminopyridin-3-yl)-N,N-dimethylbenzamide (117 mg, 0.484 mmol) in dioxane (3 mL) and Cs$_2$CO$_3$ (316 mg, 0.969 mmol) were added and the resulting mixture was stirred at 100° C. for 16 h. The color of mixture was black brown. LCMS is 66% (Rt=0.670 min; MS Calc'd: 552.2; MS Found: 553.0 [M+H]$^+$). The reaction mixture was diluted with EtOAc (20 mL), filtered and concentrated to give crude product tert-butyl (3-((5-((5-(4-(dimethylcarbamoyl)phenyl)pyridin-2-yl)amino)pyridin-3-yl)carbamoyl)phenyl)carbamate as an orange gum and directly used to next step. Crude product (50 mg) was purified by prep-HPLC (0.05% NH$_3$.H$_2$O as an additive) and lyophilized to afford tert-butyl (3-((5-((5-(4-(dimethylcarbamoyl)phenyl)pyridin-2-yl)amino)pyridin-3-yl)carbamoyl)phenyl)carbamate (2.40 mg) as a white solid. LCMS (Shimadzu LCMS 2010, mobile phase: from 100% [water+0.05% NH$_3$.H$_2$O] and 0% [MeCN] to 5% [water+0.05% NH$_3$.H$_2$O] and 95% [MeCN] in 5.8 min, then under this condition for 1.1 min, finally changed to 100% [water+0.05% NH$_3$.H$_2$O] and 0% [MeCN] and under this condition for 0.09 min.) purity is 98.48%, Rt=3.319 min; MS Calc'd.: 552.2, MS Found: 553.2 [M+H]$^+$. $^1$H NMR (400 MHz, DMSO-d$_6$) δ 1.50 (9H, s), 7.01 (1H, d, J=8.8 Hz), 7.43 (1H, t, J=8.0 Hz), 7.48 (2H, d, J=8.0 Hz), 7.57 (1H, d, J=7.8 Hz), 7.62 (1H, d, J=8.8 Hz), 7.73 (2H, d, J=8.0 Hz), 8.01 (1H, dd, J=8.8, 3.2 Hz), 8.04-8.07 (1H, m), 8.47 (1H, d, J=2.0 Hz), 8.59 (1H, d, J=2.4 Hz), 8.67 (1H, t, J=2.0 Hz), 8.70 (1H, d, J=2.0 Hz), 9.50 (1H, br s), 9.58 (1H, br s), 10.41 (1H, br s). $^1$H NMR (400 MHz, DMSO-d$_6$+D$_2$O) δ 1.43 (9H, s), 2.92 (3H, s), 2.95 (3H, s), 6.96 (1H, d, J=9.2 Hz), 7.39 (1H, t, J=7.6 Hz), 7.44 (2H, d, J=8.0 Hz), 7.49-7.58 (2H, m), 7.69 (2H, d, J=8.4 Hz), 7.93-7.99 (2H, m), 8.39 (1H, d, J=2.4 Hz), 8.52 (1H, d, J=2.4 Hz), 8.58 (1H, d, J=2.4 Hz), 8.67 (1H, t, J=2.0 Hz).

Example 99: 4-(6-((5-(3-aminobenzamido)pyridin-3-yl)amino)pyridin-3-yl)-N,N-dimethylbenzamide

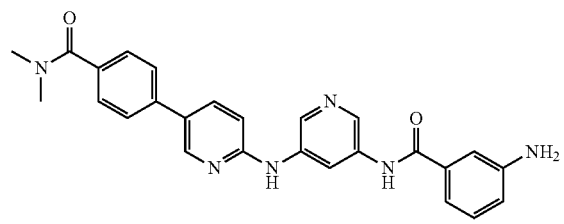 [SMILES: CN(C)C(=O)c1ccc(-c2ccc(Nc3cncc(NC(=O)c4cccc(N)c4)c3)nc2)cc1]

To a stirred solution of tert-butyl (3-((5-((5-(4-(dimethylcarbamoyl)phenyl)pyridin-2-yl)amino)pyridin-3-yl)carbamoyl)phenyl)carbamate (267 mg, 0.483 mmol) in DCM (6 mL) was added TFA (4 M, 10 mL) at 20° C. The red solution precipitated. Then reaction mixture was stirred for 2 h. LCMS (Rt=0.563 min; MS Calc'd: 452.2; MS Found: 452.9 [M+H]$^+$). The mixture was concentrated. The residue was purified by Combi Flash (8% MeOH in DCM (1% TEA as an additive)) to afford 4-(6-((5-(3-aminobenzamido)pyridin-3-yl)amino)pyridin-3-yl)-N,N-dimethylbenzamide (210 mg, yield: 96%) as an off-white solid. Crude product (50 mg) was purified by prep-HPLC (0.05% NH$_3$.H$_2$O as an additive) and lyophilized to afford 4-(6-((5-(3-aminobenzamido)pyridin-3-yl)amino)pyridin-3-yl)-N,N-dimethylbenzamide (2.88 mg) as a white solid. LCMS (Shimadzu LCMS 2010, mobile phase: from 100% [water+0.05% NH$_3$.H$_2$O] and 0% [MeCN] to 5% [water+0.05% NH$_3$.H$_2$O] and 95% [MeCN] in 5.8 min, then under this condition for 1.1 min, finally changed to 100% [water+0.05% NH$_3$.H$_2$O] and 0% [MeCN] and under this condition for 0.09 min.) purity is 99.55%, Rt=2.547 min; MS Calc'd.: 452.2, MS Found: 453.2 [M+H]$^+$. $^1$H NMR (400 MHz, DMSO-d$_6$) δ 2.96 (3H, s), 2.99 (3H, s), 5.35 (2H, br s), 6.77 (1H, d, J=8.8 Hz), 6.99 (1H, d, J=8.8 Hz), 7.07-7.13 (2H, m), 7.14 (1H, t, J=8.4 Hz), 7.48 (2H, d, J=8.0 Hz), 7.73 (2H, d, J=8.0 Hz), 8.00 (1H, dd, J=8.4, 1.6 Hz), 8.44-8.47 (1H, m), 8.57-8.60 (1H, m), 9.62-8.67 (1H, m), 8.71-8.73 (1H, m), 9.48 (1H, br s), 10.26 (1H, br s).

Example 100: (E)-4-(6-((5-(3-(4-(dimethylamino)but-2-enamido)benzamido)pyridin-3-yl)amino)pyridin-3-yl)-N,N-dimethylbenzamide

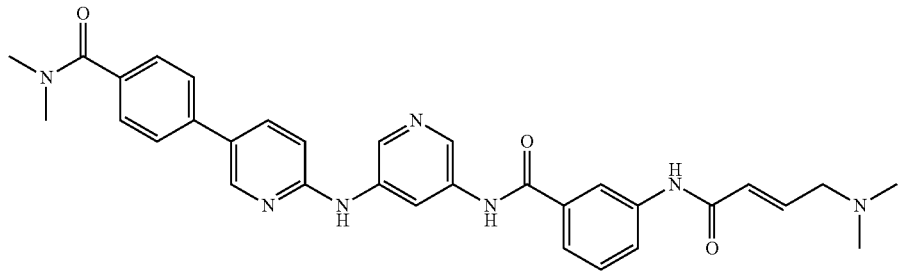

4-(6-((5-(3-aminobenzamido)pyridin-3-yl)amino)pyridin-3-yl)-N,N-dimethylbenzamide (80 mg, 0.177 mmol) and (E)-4-(dimethylamino)but-2-enoic acid (25 mg, 0.194 mmol) in pyridine (2 mL) was added EDCI (51 mg, 0.265 mmol). The mixture was stirred at 25° C. for 16 h. A dark red solution was formed gradually. LCMS showed the purity of desired product (Rt=0.568 min; MS Calc'd: 563.3; MS Found: 564.0 [M+H]$^+$). Pyridine was removed under reduced pressure. The crude product was purified by prep-HPLC (0.05% NH$_3$.H$_2$O as an additive) and lyophilized to give impure product (15 mg), then purified by prep-HPLC (0.225% FA as an additive) again and lyophilized to give (E)-4-(6-((5-(3-(4-(dimethylamino)but-2-enamido)benzamido)pyridin-3-yl)amino)pyridin-3-yl)-N,N-dimethylbenzamide (12.4 mg, yield: 12%) as a light yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 97.29%, Rt=1.303 min; MS Calc'd.: 563.3; MS Found: 564.1 [M+H]$^+$. $^1$H NMR (400 MHz, DMSO-d$_6$) δ 2.19 (6H, s), 2.97 (6H, s), 3.07 (2H, dd, J=8.4, 1.6 Hz), 6.25-6.33 (1H, m), 6.73-6.82 (1H, m), 7.00 (1H, d, J=8.0 Hz), 7.45-7.52 (3H, m), 7.67 (1H, d, J=7.6 Hz), 7.73 (2H, d, J=8.8 Hz), 7.87-7.93 (1H, m), 8.00 (1H, dd, J=8.4, 2.4 Hz), 8.16 (1H, s), 8.20 (1H, t, J=2.0 Hz), 8.48 (1H, d, J=2.4 Hz), 8.58 (1H, d, J=2.8 Hz), 8.67 (1H, t, J=2.0 Hz), 8.72 (1H, d, J=2.0 Hz), 9.50 (1H, br s), 10.28 (1H, br s), 10.45 (1H, br s). $^1$H NMR (400 MHz, DMSO-d$_6$+D$_2$O) δ 2.36 (6H, s), 2.94 (3H, s), 2.97 (3H, s), 3.34 (2H, dd, J=6.0), 6.33 (1H, d, J=15.6 Hz), 6.70-6.81 (1H, m), 6.98 (1H, d, J=9.2 Hz), 7.43-7.54 (3H, m), 7.66 (1H, d, J=8.0 Hz), 7.71 (2H, d, J=8.4 Hz), 7.82 (1H, dd, J=7.8, 1.6 Hz), 7.98 (1H, dd, J=8.8, 2.4 Hz), 8.15-8.23 (2H, m), 8.43 (1H, d, J=2.0 Hz), 8.55 (1H, d, J=2.4 Hz), 8.62 (1H, d, J=2.4 Hz), 8.70 (1H, t, J=2.4 Hz).

Example 101: tert-butyl (3-(3-((5-((5-(4-(dimethylcarbamoyl)phenyl)pyridin-2-yl)amino)pyridin-3-yl)amino)-3-oxopropyl)phenyl)carbamate

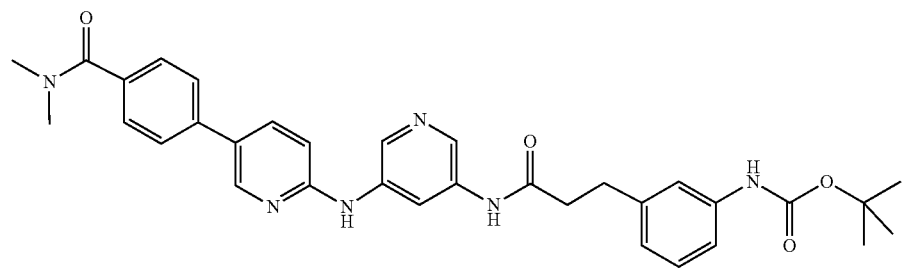 [SMILES: CN(C)C(=O)c1ccc(-c2ccc(Nc3cncc(NC(=O)CCc4cccc(NC(=O)OC(C)(C)C)c4)c3)nc2)cc1]

Step 1: Preparation of 3-(3-((tert-butoxycarbonyl)amino)phenyl)propanoic acid

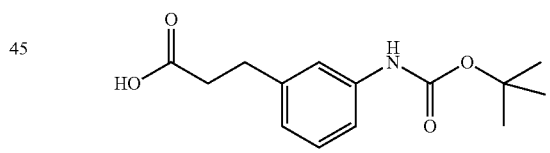

To a solution of 3-(3-aminophenyl)propanoic acid (850 mg, 5.15 mmol), TEA (1.4 mL, 10.3 mmol), H$_2$O (7 mL) in dioxane (14 mL) was added Boc$_2$O (1.8 mL, 7.72 mmol) at 20° C. Reaction mixture was allowed to stir for 18 h. The colorless solution became yellow gradually. LCMS is 95% (RT=0.759 min; MS Calc'd: 265.1; MS Found: 288.1 [M+Na]+). 1,4-dioxane was removed under reduced pressure and HCl solution (5 mL, 2 M) was added drop-wise. After addition of H$_2$O (40 mL), the mixture was extracted with DCM (20 mL×3). The organic layer was dried over anhydrous Na$_2$SO$_4$, and concentrated to afford 3-(3-((tert-butoxycarbonyl)amino)phenyl)propanoic acid (1.36 g, yield: 99%) as an off-white solid. $^1$H NMR (400 MHz, CDCl$_3$) δ 1.52 (9H, s), 2.68 (2H, t, J=8.0 Hz), 2.93 (2H, t, J=8.0 Hz), 6.57 (1H, s), 6.89 (1H, d, J=7.6 Hz), 7.12-7.24 (2H, m), 7.28 (1H, br s).

Step 2: Preparation of tert-butyl (3-(3-((5-bromopyridin-3-yl)amino)-3-oxopropyl)phenyl)carbamate

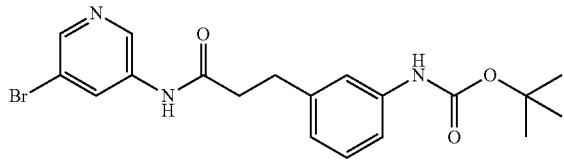 [SMILES: CC(C)(C)OC(=O)Nc1cccc(CCC(=O)Nc2cncc(Br)c2)c1]

3-(3-((Tert-butoxycarbonyl)amino)phenyl)propanoic acid (182 mg, 0.688 mmol) and 5-bromopyridin-3-amine (100 mg, 0.578 mmol) in pyridine (4 mL) was added EDCI (166 mg, 0.867 mmol). The mixture was stirred at 20° C. for 20 h. The color of solution became dark red gradually. Crude LCMS showed the purity of desired product (Rt=0.825 min; MS Calc'd: 419.1; MS Found: 442.2 [M+Na]$^+$). Pyridine was removed under reduced pressure. The residue was purified by Combi Flash (1% TEA in DCM) to give tert-butyl (3-(3-((5-bromopyridin-3-yl)amino)-3-oxopropyl) phenyl)carbamate (175 mg, yield: 72%) as an off-white solid. $^1$H NMR (400 MHz, CDCl$_3$) δ 1.51 (9H, s), 2.66 (2H, t, J=7.6 Hz), 2.98 (2H, t, J=8.0 Hz), 6.67 (1H, s), 6.87 (1H, d, J=7.6 Hz), 7.03 (1H, d, J=8.4 Hz), 7.17 (1H, t, J=7.6 Hz), 7.42 (1H, br s), 7.87 (1H, br s), 8.35 (2H, t, J=2.4 Hz), 8.39 (1H, t, J=2.0 Hz).

Step 3: Preparation of tert-butyl (3-(3-((5-((5-(4-(dimethylcarbamoyl)phenyl)pyridin-2-yl)amino) pyridin-3-yl)amino)-3-oxopropyl)phenyl)carbamate

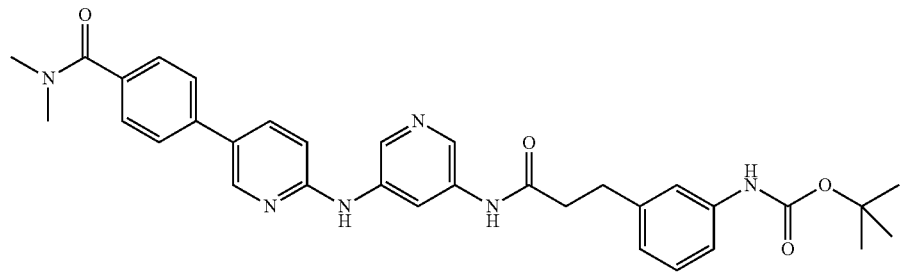 [SMILES: CN(C)C(=O)c1ccc(-c2ccc(Nc3cncc(NC(=O)CCc4cccc(NC(=O)OC(C)(C)C)c4)c3)nc2)cc1]

A mixture of Pd$_2$(dba)$_3$ (15 mg, 0.017 mmol, 4 mol %) and Brettphos (18 mg, 0.033 mmol, 8 mol %) in 1,4-dioxane (1 mL) was stirred at 50° C. for 10 min. Tert-butyl (3-(3-((5-bromopyridin-3-yl)amino)-3-oxopropyl)phenyl)carbamate (175 mg, 0.416 mmol), 4-(6-aminopyridin-3-yl)-N,N-dimethylbenzamide (100 mg, 0.416 mmol) in dioxane (6 mL) and Cs$_2$CO$_3$ (271 mg, 0.833 mmol) were added and the resulting mixture was stirred at 100° C. for 18 h. A black brown mixture was formed. LCMS (Rt=0.661 min; MS Calc'd: 580.3; MS Found: 581.0 [M+H]$^+$). The reaction mixture was diluted with ethyl acetate (20 mL), filtered and concentrated to give an orange gum. Crude product (50 mg) was purified by prep-HPLC (0.05% NH$_3$.H$_2$O as an additive) and lyophilized to afford tert-butyl (3-(3-((5-((5-(4-(dimethylcarbamoyl)phenyl)pyridin-2-yl)amino)pyridin-3-yl)amino)-3-oxopropyl)phenyl)carbamate (2.40 mg) as a white solid. Another crude product did not purify, and directly used to next step. LCMS (Shimadzu LCMS 2010, mobile phase: from 100% [water+0.05% NH$_3$.H$_2$O] and 0% [MeCN] to 5% [water+0.05% NH$_3$.H$_2$O] and 95% [MeCN] in 5.8 min, then under this condition for 1.1 min, finally changed to 100% [water+0.05% NH$_3$.H$_2$O] and 0% [MeCN] and under this condition for 0.09 min.) purity is 97.29%, Rt=3.363 min; MS Calc'd.: 580.3, MS Found: 581.3 [M+H]$^+$. $^1$H NMR (400 MHz, DMSO-d$_6$) δ 1.44 (9H, s), 2.60-2.65 (2H, m, overlapped with DMSO-d$_6$), 2.84 (2H, t, J=8.0 Hz), 2.95 (6H, s), 6.83 (1H, d, J=7.2 Hz), 6.95 (1H, d, J=8.4 Hz), 7.13 (1H, t, J=7.6 Hz), 7.20 (1H, d, J=8.8 Hz), 7.41 (1H, s), 7.46 (2H, d, J=8.0 Hz), 7.70 (2H, d, J=8.4 Hz), 7.96 (1H, dd, J=8.8, 2.4 Hz), 8.30 (1H, d, J=2.4 Hz), 8.48 (1H, t, J=2.0 Hz), 8.54 (1H, d, J=2.8 Hz), 8.62 (1H, d, J=2.4 Hz), 9.26 (1H, br s), 9.43 (1H, br s), 10.09 (1H, br s).

Example 102: 4-(6-((5-(3-(3-aminophenyl)propanamido)pyridin-3-yl)amino)pyridin-3-yl)-N,N-dimethylbenzamide

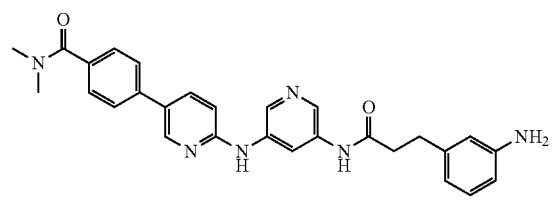 [SMILES: CN(C)C(=O)c1ccc(-c2ccc(Nc3cncc(NC(=O)CCc4cccc(N)c4)c3)nc2)cc1]

To a stirred solution of tert-butyl (3-(3-((5-((5-(4-(dimethylcarbamoyl)phenyl)pyridin-2-yl)amino)pyridin-3-yl)amino)-3-oxopropyl)phenyl)carbamate (248 mg, 0.427 mmol) in DCM (4 mL) was added HCl/EtOAc (4 M, 8.5 mL) at 20° C. The red solution precipitated. Then the reaction mixture was stirred for 16 h. LCMS the purity of the desired product (Rt=0.627 min; MS Calc'd: 480.2; MS Found: 481.1 [M+H]$^+$). The mixture was concentrated. The residue (100 mg) was purified by prep-TLC (MeOH:DCM (1% TEtOAc as an additive)=1:9) to give impure product (60 mg) as an off-white solid, then purified by prep-HPLC (0.05% NH$_3$.H$_2$O as an additive) again and lyophilized to afford 4-(6-((5-(3-(3-aminophenyl)propanamido)pyridin-3-yl)amino)pyridin-3-yl)-N,N-dimethylbenzamide (2.23 mg) as a white solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 96.20%, Rt=1.343 min; MS Calc'd.: 480.3; MS Found: 481.1 [M+H]+. 1H NMR (400 MHz, DMSO-d6) δ 2.58 (2H, t, J=8.8 Hz, overlapped with DMSO-d6), 2.74 (2H, t, J=8.0 Hz), 2.96 (6H, s), 4.93 (2H, br s), 6.33-6.44 (3H, m), 6.89 (1H, t, J=7.6 Hz), 6.96 (1H, d, J=8.8 Hz), 7.46 (2H, d, J=8.4 Hz), 7.70 (2H, d, J=8.4 Hz), 7.96 (1H, dd, J=8.8, 2.4 Hz), 8.31 (1H, d, J=2.0 Hz), 8.48 (1H, t, J=2.0 Hz), 8.54 (1H, d, J=2.8 Hz), 8.62 (1H, d, J=2.4 Hz), 9.41 (1H, br s), 10.05 (1H, br s).

Example 103: (E)-4-(6-((5-(3-(3-(4-(dimethylamino) but-2-enamido)phenyl)propanamido)pyridin-3-yl) amino)pyridin-3-yl)-N,N-dimethylbenzamide

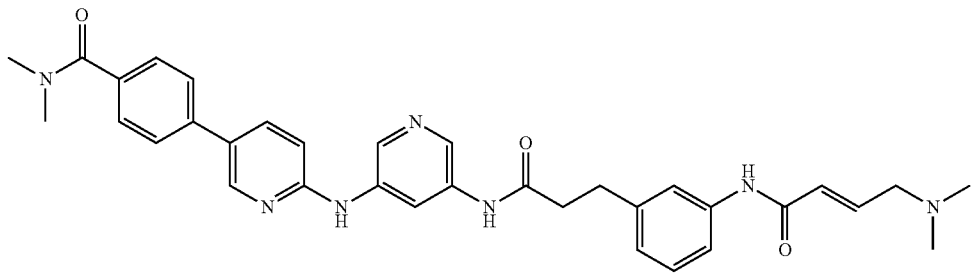

4-(6-((5-(3-(3-aminophenyl)propanamido)pyridin-3-yl) amino)pyridin-3-yl)-N,N-dimethylbenzamide (50 mg, 0.104 mmol) and (E)-4-(dimethylamino)but-2-enoic acid (16 mg, 0.12 mmol) in pyridine (2 mL) was added EDCI (30 mg, 0.156 mmol). The mixture was stirred at 20° C. for 16 h. A dark red solution was formed gradually. LCMS showed the purity of desired product (Rt=0.666 min; MS Calc'd: 591.3; MS Found: 614.4 [M+Na]+). Pyridine was removed under reduced pressure. The crude product was purified by prep-TLC (MeOH:DCM (1% TEA as an additive)=1:10) to give impure product (50 mg), then purified by prep-HPLC (0.225% formic acid as an additive) again and lyophilized to give (E)-4-(6-((5-(3-(3-(4-(dimethylamino)but-2-enamido) phenyl)propanamido)pyridin-3-yl)amino)pyridin-3-yl)-N, N-dimethylbenzamide (5.0 mg, yield: 8%) as an off-white solid. LCMS (Shimadzu LCMS 2010, mobile phase: from 100% [water+0.05% NH3.H2O] and 0% [MeCN] to 5% [water+0.05% NH3.H2O] and 95% [MeCN] in 5.8 min, then under this condition for 1.1 min, finally changed to 100% [water+0.05% NH3.H2O] and 0% [MeCN] and under this condition for 0.09 min.) purity is 100%, Rt=2.838 min; MS Calc'd.: 591.3, MS Found: 592.3 [M+H]+. 1H NMR (400 MHz, DMSO-d6) δ 2.19 (6H, s), 2.66 (2H, t, J=8.0 Hz), 2.90 (2H, t, J=7.2 Hz), 2.97 (6H, s), 3.08 (2H, d, J=5.6 Hz), 6.27 (1H, d, J=15.2 Hz), 6.63-6.78 (1H, m), 6.97 (1H, t, J=8.4 Hz), 7.23 (1H, t, J=8.0 Hz), 7.41-7.52 (3H, m), 7.59 (1H, s), 7.72 (2H, d, J=8.0 Hz), 7.99 (1H, dd, J=8.4, 2.4 Hz), 8.16 (1H, s), 8.25-8.38 (1H, m), 8.43-8.69 (3H, m), 9.45 (1H, br s), 10.02 (1H, br s), 10.11 (1H, br s).

Example 104: tert-butyl (3-(((5-((5-(4-(dimethylcarbamoyl)phenyl)pyridin-2-yl)amino)pyridin-2-yl) methyl)carbamoyl)phenyl)carbamate

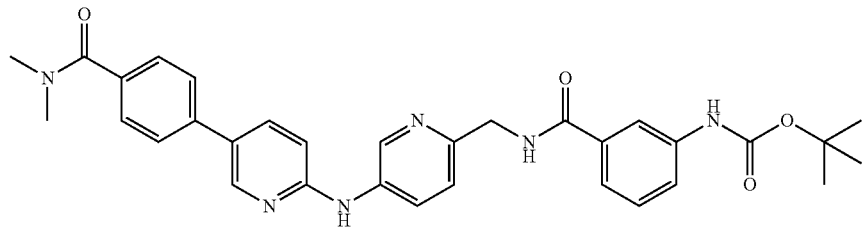 [SMILES: CN(C)C(=O)c1ccc(-c2ccc(Nc3ccc(CNC(=O)c4cccc(NC(=O)OC(C)(C)C)c4)nc3)nc2)cc1]

Step 1: Preparation of tert-butyl ((5-bromopyridin-2-yl)methyl)carbamate

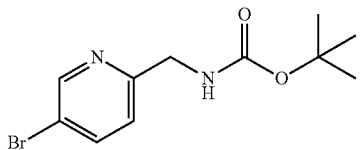 [SMILES: CC(C)(C)OC(=O)NCc1ccc(Br)cn1]

To a solution of 5-bromopicolinonitrile (5.00 g, 27.3 mmol), CoCl$_2$.6H$_2$O (9.75 g, 40.9 mmol) in MeOH (65 mL) was added NaBH$_4$ (3.10 g, 81.9 mmol) at 0° C., and the mixture was stirred at 0° C. for 1 h under N$_2$ atmosphere. TLC showed the reaction was completed. To the mixture was added H$_2$O (8 mL) and Boc$_2$O (11.9 g, 54.6 mmol). The mixture was stirred at 70° C. for 15 h. The dark red mixture turned to black, and produced a purple solid. TLC indicated the reaction was completed. The resulting mixture was concentrated. The residue was diluted with H$_2$O (130 mL) and DCM (130 mL) then filtered. The aqueous layer was extracted with DCM (120 mL×2). The combined organic layer was dried over anhydrous Na$_2$SO$_4$ and concentrated under reduced pressure. The residue was purified by Combi Flash (25% EtOAc in pentane) to give tert-butyl ((5-bromopyridin-2-yl)methyl)carbamate (4.11 g, yield: 52%) as a yellow solid. $^1$H NMR (400 MHz, CDCl$_3$) δ 1.45 (9H, s), 4.39 (2H, d, J=5.6 Hz), 5.47 (1H, br s), 7.19 (1H, d, J=8.0 Hz), 7.77 (1H, dd, J=8.4, 2.4 Hz), 8.59 (1H, d, J=2.0 Hz).

Step 2: Preparation of (5-bromopyridin-2-yl)methanamine

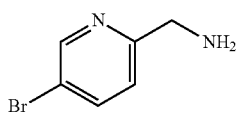

A mixture of tert-butyl ((5-bromopyridin-2-yl)methyl)carbamate (4.10 g, 14.3 mmol) in EtOAc (10 mL) was added HCl/EtOAc (1 M in EtOAc, 70 mL) and the reaction was stirred at 25° C. for 15 h. The yellow solution produced a light yellow suspension. TLC showed the reaction was completed. Concentrated in vacuum to give (5-bromopyridin-2-yl)methanamine (3.63 g, crude) as a light yellow solid. $^1$H NMR (400 MHz, d$_6$-DMSO) δ 4.67 (2H, q, J=5.6 Hz), 8.04 (1H, d, J=8.8 Hz), 8.66 (1H, dd, J=8.4, 2.4 Hz), 9.06 (2H, br s), 9.27 (1H, d, J=2.0 Hz).

Step 3: Preparation of tert-butyl (3-(((5-bromopyridin-2-yl)methyl)carbamoyl)phenyl)carbamate

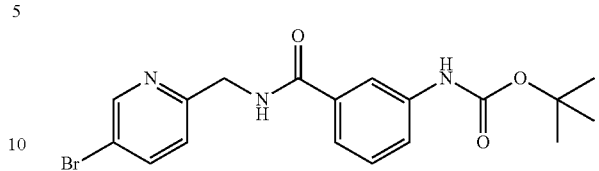

A solution of 3-((tert-butoxycarbonyl)amino)benzoic acid (696 mg, 2.94 mmol) in pyridine (8 mL) was added (5-bromopyridin-2-yl)methanamine (500 mg, 2.67 mmol) and EDCI (1.02 g, 5.34 mmol) and the reaction was stirred at 50° C. for 15 h. The yellow solution turned to black. Crude LCMS (Rt=0.696 min; MS Calc'd: 405.1; MS Found: 405.7 [M+H]$^+$). The mixture was concentrated in vacuum. The residue was purified by Combi Flash (86% DCM in pentane) to give tert-butyl (3-(((5-bromopyridin-2-yl)methyl)carbamoyl)phenyl)carbamate (218 mg, yield: 20%) as a yellow solid. $^1$H NMR (400 MHz, CDCl$_3$) δ 1.56 (9H, s), 4.71 (2H, d, J=5.2 Hz), 6.57 (1H, s), 7.30 (1H, s), 7.38 (1H, t, J=8.0 Hz), 7.51 (1H, d, J=8.0 Hz), 7.59 (1H, d, J=7.6 Hz), 7.79-7.82 (2H, m), 8.63 (1H, d, J=2.4 Hz).

Step 4: Preparation of tert-butyl (3-(((5-((5-(4-(dimethylcarbamoyl)phenyl)pyridin-2-yl)amino)pyridin-2-yl)methyl)carbamoyl)phenyl)carbamate

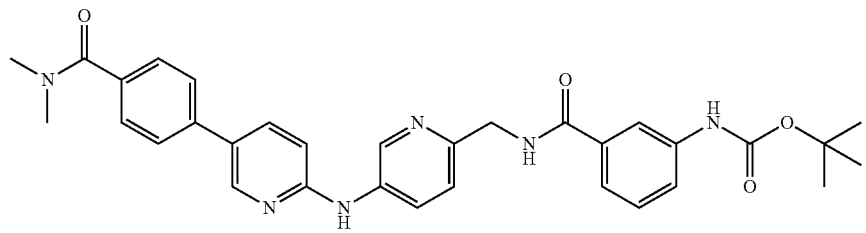 [SMILES: CN(C)C(=O)c1ccc(-c2ccc(Nc3ccc(CNC(=O)c4cccc(NC(=O)OC(C)(C)C)c4)nc3)nc2)cc1]

A mixture of Pd$_2$(dba)$_3$ (15 mg, 0.016 mmol, 3 mol %) and Brettphos (17 mg, 0.032 mmol, 6 mol %) in dioxane (8 mL) was stirred at 50° C. for 10 min. Tert-butyl (3-(((5-bromopyridin-2-yl)methyl)carbamoyl)phenyl)carbamate (218 mg, 0.536 mmol), 4-(6-aminopyridin-3-yl)-N,N-dimethylbenzamide (129 mg, 0.537 mmol) in dioxane (8 mL) and Cs$_2$CO$_3$ (350 mg, 1.07 mmol) were added and the resulting mixture was stirred at 100° C. for 15 h. The dark red solution turned to brown mixture. Crude LCMS (Rt=0.736 min; MS Calc'd: 566.3; MS Found: 567.3 [M+H]$^+$). The reaction mixture was diluted with EtOAc (30 mL), dried over Na$_2$SO$_4$, filtered and concentrated. The residue was purified by Combi Flash (5% MeOH in DCM) and lyophilized to give tert-butyl (3-(((5-((5-(4-(dimethylcarbamoyl)phenyl)pyridin-2-yl)amino)pyridin-2-yl)methyl)carbamoyl)phenyl)carbamate (145 mg, yield: 48%) as a light yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.)

purity is 98.09%, Rt=1.845 min; MS Calc'd.: 566.3; MS Found: 567.1 [M+H]$^+$. $^1$H NMR (400 MHz, DMSO-d$_6$) δ 1.48 (9H, s), 2.97 (6H, s), 4.50 (2H, d, J=5.2 Hz), 6.95 (1H, d, J=8.4 Hz), 7.26 (1H, d, J=8.8 Hz), 7.34 (1H, t, J=8.0 Hz), 7.46-7.57 (4H, m), 7.71 (2H, d, J=8.0 Hz), 7.97 (1H, dd, J=9.2, 2.8 Hz), 8.02 (1H, s), 8.18 (1H, dd, J=8.8, 2.8 Hz), 8.55 (1H, s), 8.81 (1H, s), 8.95-8.98 (1H, m), 9.44 (1H, s), 9.50 (1H, s).

Example 105: 4-(6-((6-((3-aminobenzamido)methyl) pyridin-3-yl)amino)pyridin-3-yl)-N,N-dimethylbenzamide

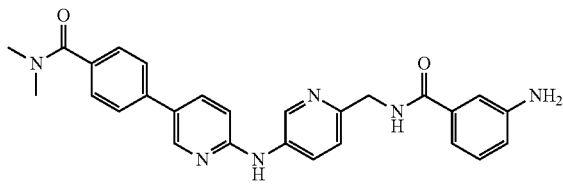 [SMILES: CN(C)C(=O)c1ccc(-c2ccc(Nc3ccc(CNC(=O)c4cccc(N)c4)nc3)nc2)cc1]

A mixture of tert-butyl (3-(((5-((5-(4-(dimethylcarbamoyl)phenyl)pyridin-2-yl)amino)pyridin-2-yl)methyl)carbamoyl)phenyl)carbamate (140 mg, 0.247 mmol) in EtOAc (3 mL) was added HCl/EtOAc (1 M in EtOAc, 5 mL) and the reaction was stirred at 25° C. for 2 h. The yellow solution produced a light yellow solid. TLC showed the reaction was completed. The mixture was concentrated in vacuum. The residue was lyophilized to give 4-(6-((6-((3-aminobenzamido)methyl)pyridin-3-yl)amino)pyridin-3-yl)-N,N-dimethylbenzamide (151 mg, yield: 99%) as a yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 97.02%, Rt=1.592 min; MS Calc'd.: 466.2; MS Found: 467.1 [M+H]$^+$. $^1$H NMR (400 MHz, DMSO-d$_6$) δ 2.95 (3H, s), 2.98 (3H, s), 4.78 (2H, d, J=6.0 Hz), 7.16 (1H, d, J=8.8 Hz), 7.48-7.51 (3H, m), 7.59 (1H, t, J=8.0 Hz), 7.76 (2H, d, J=8.4 Hz), 7.81 (1H, s), 7.88 (1H, d, J=9.2 Hz), 7.94 (1H, d, J=8.0 Hz), 8.11 (1H, dd, J=8.8, 2.8 Hz), 8.54 (1H, dd, J=9.2, 2.8 Hz), 8.67 (1H, d, J=2.4 Hz), 9.48 (1H, d, J=3.2 Hz), 9.58 (1H, t, J=4.8 Hz).

Example 106: (E)-4-(6-((6-((3-(4-(dimethylamino) but-2-enamido)benzamido)methyl)pyridin-3-yl) amino)pyridin-3-yl)-N,N-dimethylbenzamide

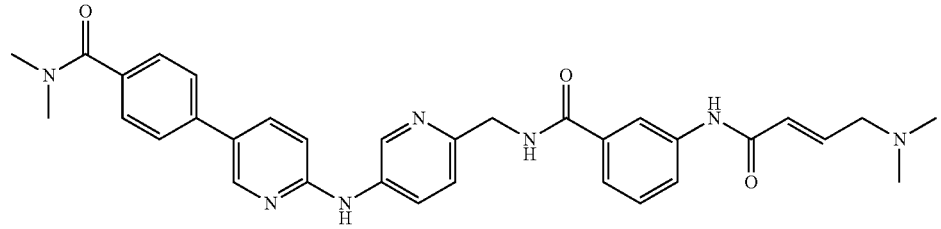

A solution of 4-(6-((6-((3-aminobenzamido)methyl)pyridin-3-yl)amino)pyridin-3-yl)-N,N-dimethylbenzamide (151 mg, 0.246 mmol) in pyridine (4 mL), was added (E)-4-(dimethylamino)but-2-enoic acid (49 mg, 0.30 mmol) and EDCI (95 mg, 0.49 mmol). And the reaction was stirred at 20° C. for 16 h. The light yellow solution turned to dark red. Crude LCMS (Rt=0.626 min; MS Calc'd: 577.3; MS Found: 578.3 [M+H]$^+$). Filtered and concentrated in vacuum. The residue was purified by prep-HPLC (0.05% NH$_3$.H$_2$O as an additive) and lyophilized to give (E)-4-(6-((6-((3-(4-(dimethylamino)but-2-enamido)benzamido)methyl)pyridin-3-yl)amino)pyridin-3-yl)-N,N-dimethylbenzamide (53.1 mg, yield: 37%) as a light yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 97.02%, Rt=1.418 min; MS Calc'd.: 577.3; MS Found: 578.4 [M+H]$^+$. $^1$H NMR (400 MHz, d$_6$-DMSO) δ 2.18 (6H, s), 2.98 (6H, s), 3.06 (2H, d, J=6.4 Hz), 4.52 (2H, d, J=5.2 Hz), 6.28 (1H, d, J=15.6 Hz), 6.76 (1H, d, J=15.2 Hz), 6.96 (1H, d, J=8.4 Hz), 7.27 (1H, d, J=8.8 Hz), 7.42 (1H, t, J=8.0 Hz), 7.47 (1H, s), 7.49 (1H, s), 7.60 (1H, d, J=8.0 Hz), 7.70 (1H, s), 7.73 (1H, s), 7.86 (1H, d, J=9.2 Hz), 7.97 (1H, dd, J=8.8, 2.8 Hz), 8.14 (1H, s), 8.18 (1H, dd, J=8.4, 2.4 Hz), 8.55 (1H, d, J=2.8 Hz), 8.80 (1H, d, J=3.2 Hz), 9.01 (1H, s), 9.40 (1H, s).

Example 107: 4-(6-((5-(3-(3-(2-aminoacetamido)
phenyl)propanamido)pyridin-3-yl)amino)pyridin-3-
yl)-N,N-dimethylbenzamide

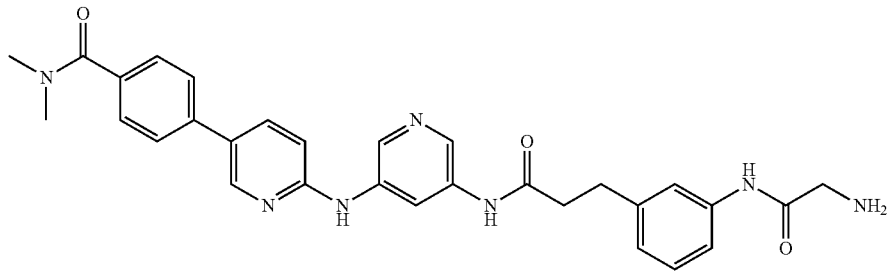 [SMILES: CN(C)C(=O)c1ccc(-c2ccc(Nc3cncc(NC(=O)CCc4cccc(NC(=O)CN)c4)c3)nc2)cc1]

Step 1: Preparation of tert-butyl (2-((3-(3-((5-((5-
(4-(dimethylcarbamoyl)phenyl)pyridin-2-yl)amino)
pyridin-3-yl)amino)-3-oxopropyl)phenyl)amino)-2-
oxoethyl)carbamate

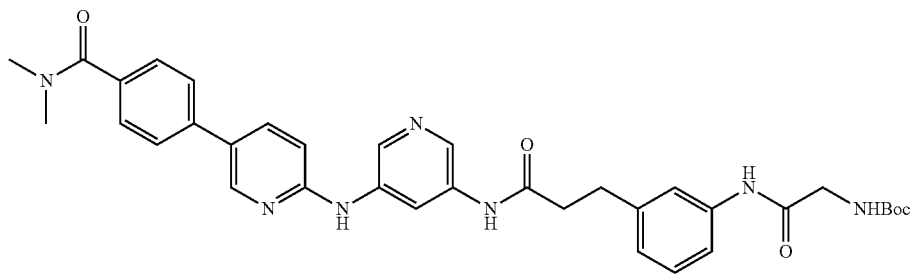 [SMILES: CN(C)C(=O)c1ccc(-c2ccc(Nc3cncc(NC(=O)CCc4cccc(NC(=O)CNC(=O)OC(C)(C)C)c4)c3)nc2)cc1]

To a suspension of 4-(6-((5-(3-(3-aminophenyl)propana-mido)pyridin-3-yl)amino)pyridin-3-yl)-N,N-dimethylbenz-amide (328 mg, 0.523 mmol) in pyridine (5 mL) was added EDCI (100 mg, 0.523 mmol). And the resulting mixture was stirred at 20° C. for 18 h. A red solution was formed. LCMS (Rt=0.611 min; MS Calc'd: 637.6; MS Found: 638.2 [M+H]⁺). The reaction solution was concentrated to afford a red solid. DCM (30 mL) and water (10 mL) was added to the solid. The water layer was washed by DCM (30 mL×2). The organic layer was collected and concentrated to give tert-butyl (2-((3-(3-((5-((5-(4-(dimethylcarbamoyl)phenyl)pyri-din-2-yl)amino)pyridin-3-yl)amino)-3-oxopropyl)phenyl)amino)-2-oxoethyl)carbamate (260 mg, yield: 69%) as a red solid. Used in the next step without purification.

Step 2: Preparation of 4-(6-((5-(3-(3-(2-aminoacet-
amido)phenyl)propanamido)pyridin-3-yl)amino)
pyridin-3-yl)-N,N-dimethylbenzamide

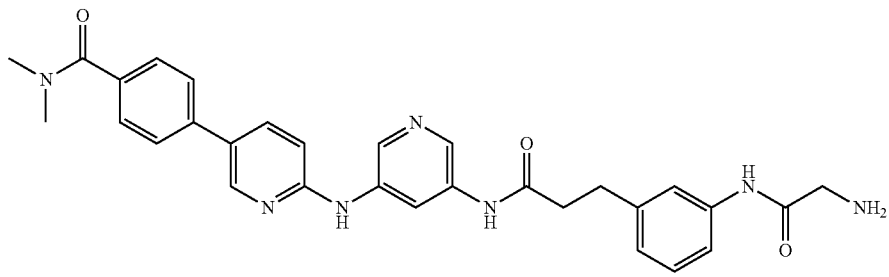 [SMILES: CN(C)C(=O)c1ccc(-c2ccc(Nc3cncc(NC(=O)CCc4cccc(NC(=O)CN)c4)c3)nc2)cc1]

A mixture of tert-butyl (2-((3-(3-((5-((5-(4-(dimethylcarbamoyl)phenyl)pyridin-2-yl)amino)pyridin-3-yl)amino)-3-oxopropyl)phenyl)amino)-2-oxoethyl)carbamate (260 mg, 0.483 mmol) and aq. HCl (4 M, 20 mL) was stirred at 10° C. for 4 h. A red solution was formed. LCMS is 90% (Rt=0.533 min; MS Calc'd: 537.6; MS Found: 538.1 [M+H]⁺). The reaction solution was concentrated to afford 4-(6-((5-(3-(3-(2-aminoacetamido)phenyl)propanamido)pyridin-3-yl)amino)pyridin-3-yl)-N,N-dimethylbenzamide (201 mg, yield: 51%) as a red solid. Used in the next step without purification. Crude product (105 mg) was purified by prep-HPLC (0.05% NH$_3$.H$_2$O as an additive) and lyophilized to afford 4-(6-((5-(3-(3-(2-aminoacetamido)phenyl)propanamido)pyridin-3-yl)amino)pyridin-3-yl)-N,N-dimethylbenzamide (3.21 mg) as a white solid. LCMS (Shimadzu LCMS 2010, mobile phase: from 100% [water+0.05% NH$_3$.H$_2$O] and 0% [MeCN] to 5% [water+0.05% NH$_3$.H$_2$O] and 95% [MeCN] in 5.8 min, then under this condition for 1.1 min, finally changed to 100% [water+0.05% NH$_3$.H$_2$O] and 0% [MeCN] and under this condition for 0.09 min.) purity is 100%, Rt=2.717 min; MS Calc'd.: 537.2, MS Found: 538.3 [M+H]⁺. ¹H NMR (400 MHz, DMSO-d$_6$) δ 2.43-2.45 (2H, overlap with DMSO), 2.66-2.68 (2H, m), 2.87 (2H, t, J=7.6 Hz), 2.97 (3H, s), 2.98 (3H, s), 6.91 (1H, d, J=8.0 Hz), 6.95 (1H, d, J=7.6 Hz), 7.22 (1H, t, J=8.8 Hz), 7.46-7.48 (4H, m), 7.71 (2H, d, J=8.4 Hz), 7.96 (1H, dd, J=8.8, 2.4 Hz), 8.03 (1H, d, J=8.4 Hz), 8.09 (1H, dd, J=9.2, 2.8 Hz), 8.25 (1H, br s), 8.54 (1H, d, J=2.8 Hz), 8.65 (1H, dd, J=9.2, 2.8 Hz), 9.32 (1H, br s), 10.35 (1H, br s).

Example 108: (E)-4-(6-((5-(3-(3-(2-(4-(dimethylamino)but-2-enamido)acetamido)phenyl)propanamido)pyridin-3-yl)amino)pyridin-3-yl)-N,N-dimethylbenzamide

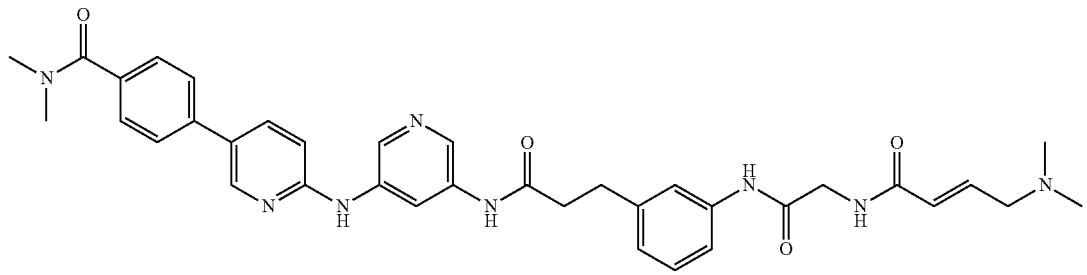

To a mixture of 4-(6-((5-(3-(3-(2-aminoacetamido)phenyl)propanamido)pyridin-3-yl)amino)pyridin-3-yl)-N,N-dimethylbenzamide (80 mg, 0.12 mmol), (E)-4-(dimethylamino)but-2-enoic acid (23 mg, 0.17 mmol) and EDCI (45 mg, 0.23 mmol) was added pyridine (5 mL). And the resulting mixture was stirred at 20° C. for 20 h. A red solution was formed. LCMS is 8% (Rt=2.971 min; MS Calc'd: 648.7; MS Found: 649.3 [M+H]⁺). Solvent was removed under reduced pressure to afford a red solid. Crude product was purified by prep-HPLC (0.05% NH$_3$.H$_2$O as an additive) and lyophilized to give impure product as a brown solid. Then the solid was purified by prep-HPLC (0.05% HCl as an additive) and lyophilized to give (E)-4-(6-((5-(3-(3-(2-(4-(dimethylamino)but-2-enamido)acetamido)phenyl)propanamido)pyridin-3-yl)amino)pyridin-3-yl)-N,N-dimethylbenzamide (5.53 mg, yield: 7%) as a yellow solid. LCMS (Shimadzu LCMS 2010, mobile phase: C) 10 mM NH$_4$HCO$_3$ in Water; D) MeCN. Gradient: 1% D increase to 5% D within 0.6 min; 5% D increase to 100% D within 3.4 min; then back to 1% D within 0.3 min. Flow rate 0.8 mL/min) purity is 100%, Rt=2.439 min; MS Calc'd.: 648.3, MS Found: 649.3 [M+H]⁺. ¹H NMR (400 MHz, DMSO-d$_6$) δ 2.73 (3H, s), 2.74 (3H, s), 2.89 (2H, t, J=7.6 Hz), 2.75-2.79 (2H, m), 2.95 (3H, s), 2.98 (3H, s), 3.96 (2H, d, J=6.0 Hz), 4.30 (2H, t, J=5.8 Hz), 6.19-6.25 (1H, m), 6.30 (1H, d, J=11.6 Hz), 6.96 (1H, d, J=7.6 Hz), 7.08 (1H, d, J=9.6 Hz), 7.22 (1H, t, J=7.6 Hz), 7.43 (1H, d, J=8.0 Hz), 7.48-7.50 (3H, m), 7.73 (2H, d, J=8.0 Hz), 7.92 (1H, d, J=8.8 Hz), 8.10 (1H, dd, J=8.8, 2.0 Hz), 8.23 (1H, d, J=8.4 Hz), 8.51 (1H, d, J=1.6 Hz), 8.75 (1H, t, J=4.8 Hz), 8.86 (1H, br s), 10.13 (2H, br s), 10.50 (1H, br s), 11.28 (1H, br s).

Example 109: N-(3-(3-((5-((5-(4-(dimethylcarbamoyl)phenyl)pyridin-2-yl)amino)pyridin-3-yl)amino)-3-oxopropyl)phenyl)piperidine-4-carboxamide

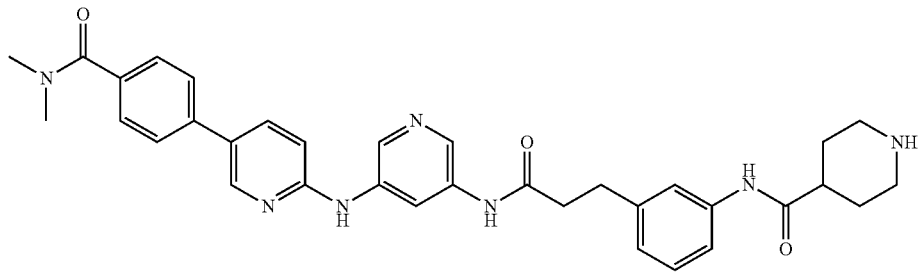 [SMILES: CN(C)C(=O)c1ccc(-c2ccc(Nc3cncc(NC(=O)CCc4cccc(NC(=O)C5CCNCC5)c4)c3)nc2)cc1]

Step 1: Preparation of tert-butyl 4-((3-(3-((5-((5-(4-(dimethylcarbamoyl)phenyl)pyridin-2-yl)amino)pyridin-3-yl)amino)-3-oxopropyl)phenyl)carbamoyl)piperidine-1-carboxylate

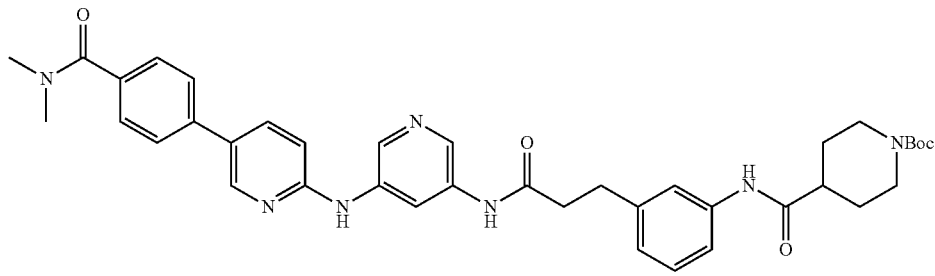 [SMILES: CN(C)C(=O)c1ccc(-c2ccc(Nc3cncc(NC(=O)CCc4cccc(NC(=O)C5CCN(C(=O)OC(C)(C)C)CC5)c4)c3)nc2)cc1]

To a mixture of 4-(6-((5-(3-(3-aminophenyl)propanamido)pyridin-3-yl)amino)pyridin-3-yl)-N,N-dimethylbenzamide (209 mg, 0.333 mmol) 1-(tert-butoxycarbonyl)piperidine-4-carboxylic acid (76 mg, 0.33 mmol) and EDCI (96 mg, 0.50 mmol) was added pyridine (10 mL), and then stirred 20° C. for 20 h. A red mixture was formed. LCMS (Rt=0.657 min; MS Calc'd: 691.3; MS Found: 692.5 [M+H]$^+$). Solvent was removed under reduced pressure to give a red solid. DCM (15 mL) and water (15 mL) was added to the solid. The water layer was washed by DCM (30 mL×4). The organic layer was collected and concentrated to give tert-butyl 4-((3-(3-((5-((5-(4-(dimethylcarbamoyl)phenyl)pyridin-2-yl)amino)pyridin-3-yl)amino)-3-oxopropyl)phenyl)carbamoyl)piperidine-1-carboxylate (235 g, yield: 73%) as a red solid.

Step 2: Preparation of N-(3-(3-((5-((5-(4-(dimethylcarbamoyl)phenyl)pyridin-2-yl)amino)pyridin-3-yl)amino)-3-oxopropyl)phenyl)piperidine-4-carboxamide

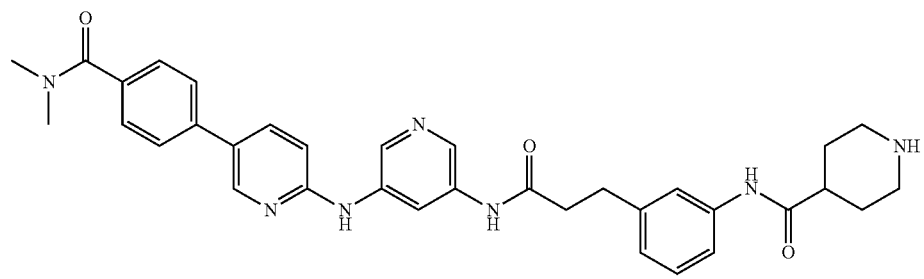 [SMILES: CN(C)C(=O)c1ccc(-c2ccc(Nc3cncc(NC(=O)CCc4cccc(NC(=O)C5CCNCC5)c4)c3)nc2)cc1]

A mixture of tert-butyl 4-((3-(3-((5-((5-(4-(dimethylcarbamoyl)phenyl)pyridin-2-yl)amino)pyridin-3-yl)amino)-3-oxopropyl)phenyl)carbamoyl)piperidine-1-carboxylate (235 mg, 0.339 mmol) and aq. HCl (4 M, 20 mL) was stirred at 20° C. for 2 h. A red solution was formed. LCMS (Rt=0.540 min; MS Calc'd: 591.3; MS Found: 592.2 [M+H]$^+$). The reaction solution was concentrated to give N-(3-(3-((5-((5-(4-(dimethylcarbamoyl)phenyl)pyridin-2-yl)amino)pyridin-3-yl)amino)-3-oxopropyl)phenyl)piperidine-4-carboxamide (250 mg, yield: 99%) as a red solid. Used in the next step without purification. Crude product (50 mg) was purified by prep-HPLC (0.05% HCl as an additive) and lyophilized to afford N-(3-(3-((5-((5-(4-(dimethylcarbamoyl)phenyl)pyridin-2-yl)amino)pyridin-3-yl)amino)-3-oxopropyl)phenyl)piperidine-4-carboxamide (2.15 mg) as a yellow solid. LCMS (Shimadzu LCMS 2010, mobile phase: C) 10 mM NH$_4$HCO$_3$ in Water; D) MeCN. Gradient: 1% D increase to 5% D within 0.6 min; 5% DB increase to 100% D within 3.4 min; then back to 1% D within 0.3 min. Flow rate 0.8 mL/min) purity is 96.71%, Rt=2.324 min; MS Calc'd.: 591.3, MS Found: 592.3 [M+H]$^+$. $^1$H NMR (400 MHz, DMSO-d$_6$) δ 1.75-1.85 (2H, m), 1.90-1.95 (2H, m), 2.61-2.66 (1H, m), 2.73 (2H, t, J=7.2 Hz), 2.88 (4H t, J=7.2 Hz), 2.95 (3H, s), 2.99 (3H, s), 3.28-3.33 (2H, m), 6.95 (1H, d, J=8.0 Hz), 7.05 (1H, d, J=8.8 Hz), 7.20 (1H, t, J=8.0 Hz), 7.40 (1H, d, J=7.6 Hz), 7.49 (2H, d, J=8.8 Hz), 7.55 (1H, s), 7.73 (2H, d, J=8.0 Hz), 7.93 (1H, d, J=8.4 Hz), 8.07 (1H, dd, J=9.2, 2.0 Hz), 8.20 (1H, dd, J=8.8, 1.6 Hz), 8.51 (1H, d, J=1.6 Hz), 8.61 (1H, br s), 8.83 (1H, s), 8.91 (1H, br s), 9.97 (1H, br s), 10.08 (1H, br s), 11.08 (1H, br s).

Example 110: (E)-1-(4-(dimethylamino)but-2-enoyl)-N-(3-(3-((5-((5-(4-(dimethylcarbamoyl)phenyl)pyridin-2-yl)amino)pyridin-3-yl)amino)-3-oxopropyl)phenyl)piperidine-4-carboxamide

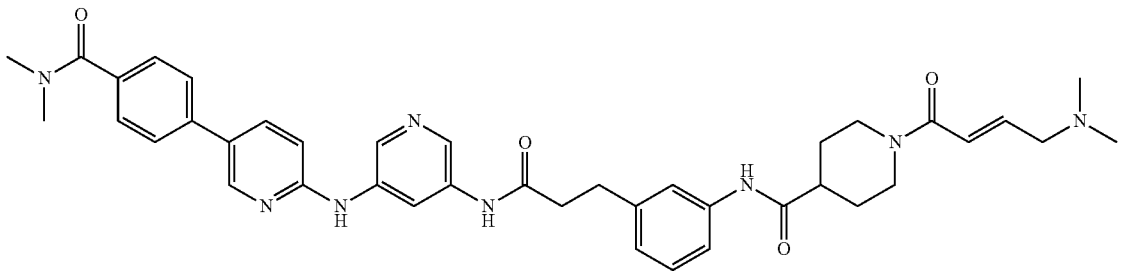

To a mixture of N-(3-(3-((5-((5-(4-(dimethylcarbamoyl)phenyl)pyridin-2-yl)amino)pyridin-3-yl)amino)-3-oxopropyl)phenyl)piperidine-4-carboxamide (200 mg, 0.271 mmol), (E)-4-(dimethylamino)but-2-enoic acid (53 mg, 0.41 mmol) and EDCI (103 mg, 0.542 mmol) was added pyridine (15 mL). And the resulting mixture was stirred at 20° C. for 20 h. A red solution was formed. LCMS (Rt=3.011 min; MS Calc'd: 702.84; MS Found: 703.3 [M+H]$^+$). The reaction mixture was concentrated under reduced pressure to afford a red solid. The crude product was purified by prep-HPLC (0.05% NH$_3$.H$_2$O as an additive) and lyophilized to afford a yellow solid. Then the solid was purified by prep-HPLC (0.05% HCl as an additive) and lyophilized to give (E)-1-(4-(dimethylamino)but-2-enoyl)-N-(3-(3-((5-((5-(4-(dimethylcarbamoyl)phenyl)pyridin-2-yl)amino)pyridin-3-yl)amino)-3-oxopropyl)phenyl)piperidine-4-carboxamide (5.71 mg, yield: 3%) as a yellow solid.

LCMS (Shimadzu LCMS 2010, mobile phase: C) 10 mM NH$_4$HCO$_3$ in Water; D) MeCN. Gradient: 1% D increase to 5% D within 0.6 min; 5% DB increase to 100% D within 3.4 min; then back to 1% D within 0.3 min. Flow rate 0.8 mL/min) purity is 100%, Rt=2.499 min; MS Calc'd.: 702.3, MS Found: 703.5 [M+H]$^+$. $^1$H NMR (400 MHz, DMSO-d$_6$) δ 1.46-1.56 (2H, m), 1.81-1.84 (2H, m), 2.63-2.67 (1H, m), 2.73 (3H, s) 2.74 (3H, s), 2.77 (2H, t, J=7.6 Hz), 2.90 (2H, t, J=7.2 Hz), 2.95 (3H, s), 2.99 (3H, s), 3.10 (2H, t, J=11.6 Hz), 3.93 (1H, d, J=12.4 Hz), 4.00 (2H, t, J=5.6 Hz), 4.40 (1H, d, J=12.4 Hz), 6.12-6.18 (1H, m), 6.70 (1H, d, J=12 Hz), 6.94 (1H, d, J=6.8 Hz), 7.14 (1H, d, J=2.2 Hz), 7.20 (1H, t, J=8 Hz), 7.42 (1H, d, J=8.8 Hz), 7.49 (2H, d, J=8 Hz), 7.57 (1H, s), 7.74 (2H, d, J=7.6 Hz), 7.89 (1H, d, J=8.8 Hz), 8.13 (1H, dd, J=8.8, 2 Hz), 8.28 (1H, dd, J=8.8, 2.4 Hz), 8.51 (1H, d, J=2.4 Hz), 8.93 (1H, d, J=1.6 Hz), 10.07 (1H, s), 10.39 (1H, br s), 10.74 (1H, br s), 11.57 (1H, br s).

Example 111: 4-(6-((5-(3-(3-(6-aminohexanamido)phenyl)propanamido)pyridin-3-yl)amino)pyridin-3-yl)-N,N-dimethylbenzamide

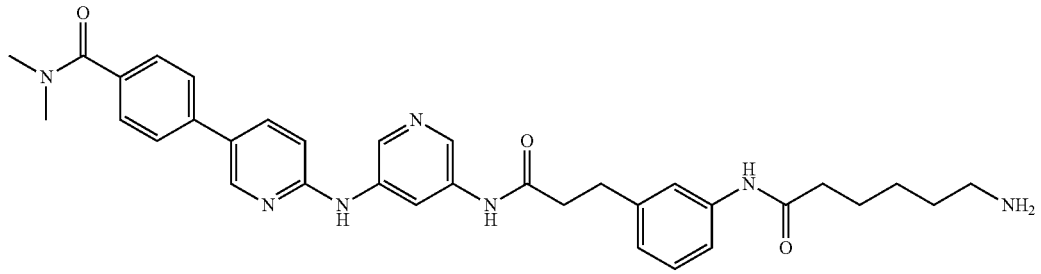 [SMILES: CN(C)C(=O)c1ccc(-c2ccc(Nc3cncc(NC(=O)CCc4cccc(NC(=O)CCCCCN)c4)c3)nc2)cc1]

Step 1: Preparation of tert-butyl (6-((3-(3-((5-((5-(4-(dimethylcarbamoyl)phenyl)pyridin-2-yl)amino)pyridin-3-yl)amino)-3-oxopropyl)phenyl)amino)-6-oxohexyl)carbamate

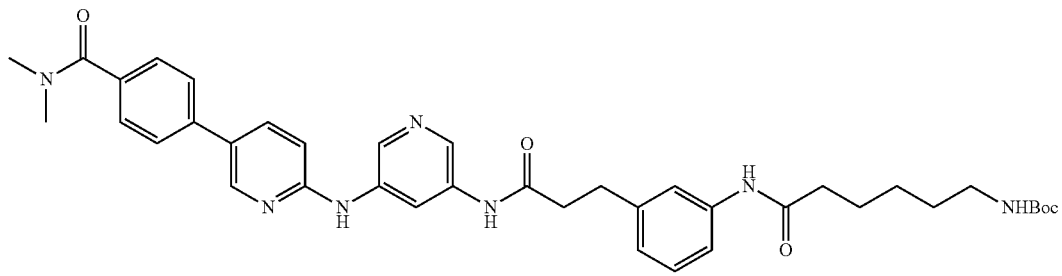 [SMILES: CN(C)C(=O)c1ccc(-c2ccc(Nc3cncc(NC(=O)CCc4cccc(NC(=O)CCCCCNC(=O)OC(C)(C)C)c4)c3)nc2)cc1]

To a mixture of 4-(6-((5-(3-(3-aminophenyl)propanamido)pyridin-3-yl)amino)pyridin-3-yl)-N,N-dimethylbenzamide (209 mg, 0.333 mmol) 6-((tert-butoxycarbonyl)amino)hexanoic acid (77 mg, 0.33 mmol) and EDCI (96 mg, 0.50 mmol) was added pyridine (10 mL), and then stirred at 20° C. for 20 h. A red mixture was formed. LCMS (Rt=0.659 min; MS Calc'd: 693.8; MS Found: 694.6[M+H]$^+$). The solvent was removed under reduced pressure to afford a red solid. DCM (15 mL) and water (15 mL) was added to the solid. The water layer was washed by DCM (30 mL×4). The organic layer was collected and concentrated to give tert-butyl (6-((3-(3-((5-((5-(4-(dimethylcarbamoyl)phenyl)pyridin-2-yl)amino)pyridin-3-yl)amino)-3-oxopropyl)phenyl)amino)-6-oxohexyl)carbamate (245 mg, yield: 79%) as a red solid. Used in the next step without purification.

Step 2: Preparation of 4-(6-((5-(3-(3-(6-aminohexanamido)phenyl)propanamido)pyridin-3-yl)amino)pyridin-3-yl)-N,N-dimethylbenzamide

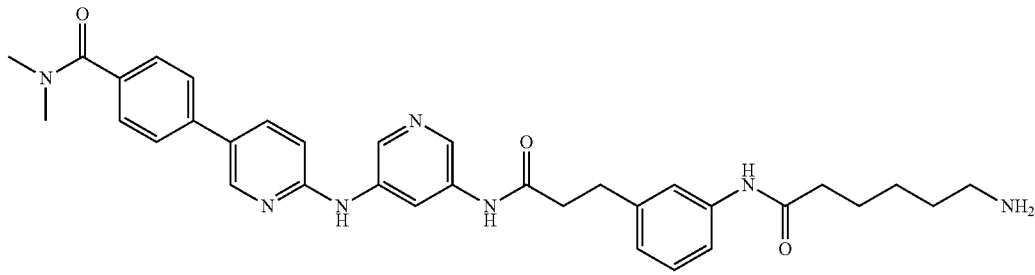 [SMILES: CN(C)C(=O)c1ccc(-c2ccc(Nc3cncc(NC(=O)CCc4cccc(NC(=O)CCCCCN)c4)c3)nc2)cc1]

A mixture of tert-butyl (6-((3-(3-((5-((5-(4-(dimethylcarbamoyl)phenyl)pyridin-2-yl)amino)pyridin-3-yl)amino)-3-oxopropyl)phenyl)amino)-6-oxohexyl)carbamate (245 mg, 0.353 mmol) and aq. HCl (4 M, 20 mL) was stirred at 20° C. for 2 h. And the red solution was formed. LCMS (Rt=0.548 min; MS Calc'd: 593.3; MS Found: 594.3 [M+H]⁺). The reaction solution was concentrated to give 4-(6-((5-(3-(3-(6-aminohexanamido)phenyl)propanamido)pyridin-3-yl)amino)pyridin-3-yl)-N,N-dimethylbenzamide (243 mg, yield: 93%) as a red solid. Used in the next step without purification. The crude product (43 mg) was purified by prep-HPLC (0.05% HCl as an additive) and lyophilized to give 4-(6-((5-(3-(3-(6-aminohexanamido)phenyl)propanamido)pyridin-3-yl)amino)pyridin-3-yl)-N,N-dimethylbenzamide (2.22 mg) as a yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 96.80%, Rt=1.214 min; MS Calc'd.: 593.3; MS Found: 594.1 [M+H]⁺. ¹H NMR (400 MHz, DMSO-$d_6$) δ 1.29-1.36 (2H, m), 1.52-1.62 (4H, m), 2.66-2.79 (8H, m), 2.96 (3H, s), 2.96 (3H, s), 6.93 (1H, d, J=7.2 Hz), 7.04 (1H, d, J=8.0 Hz), 7.19 (1H, t, J=7.6 Hz), 7.42 (1H, d, J=2.2 Hz), 7.49 (2H, d, J=8.4 Hz), 7.52 (1H, br s), 7.74 (2H, d, J=8.4 Hz), 7.83 (3H, br s), 7.94 (1H, d, J=9.2 Hz), 8.07 (1H, d, J=11.6 Hz), 8.20 (1H, d, J=8.8 Hz), 8.22 (1H, d, J=1.6 Hz), 8.81 (1H, br s), 9.92 (2H, br s), 11.03 (1H, br s).

Example 112: (E)-4-(6-((5-(3-(3-(6-(4-(dimethylamino)but-2-enamido)hexanamido)phenyl)propanamido)pyridin-3-yl)amino)pyridin-3-yl)-N,N-dimethylbenzamide

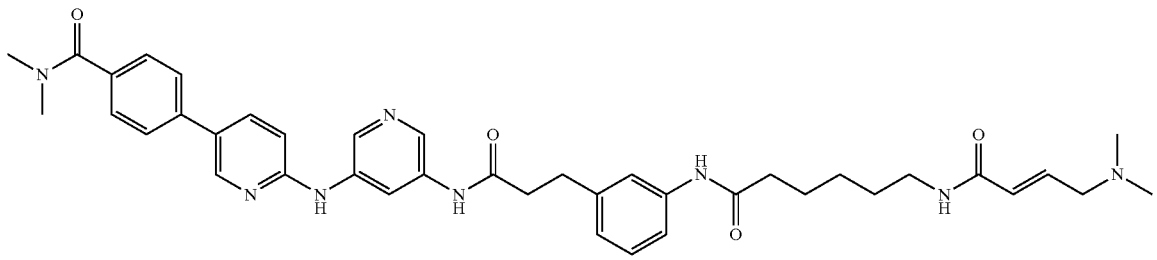

To a mixture of 4-(6-((5-(3-(3-(6-aminohexanamido)phenyl)propanamido)pyridin-3-yl)amino)pyridin-3-yl)-N,N-dimethylbenzamide (200 mg, 0.270 mmol) (E)-4-(dimethylamino)but-2-enoic acid (52 mg, 0.41 mmol) and EDCI (104 mg, 0.540 mmol) was added pyridine (4 mL). And the resulting mixture was stirred at 20° C. for 20 h. A red solution was formed. LCMS (Rt=3.162 min; MS Calc'd: 704.3; MS Found: 705.2 [M+H]⁺). The solvent was concentrated to give a red solid. The crude product was purified by prep-HPLC (0.05% NH₃.H₂O as an additive) and lyophilized to give (E)-4-(6-((5-(3-(3-(6-(4-(dimethylamino)but-2-enamido)hexanamido)phenyl)propanamido)pyridin-3-yl)amino)pyridin-3-yl)-N,N-dimethylbenzamide (22.96 mg, yield: 12%) as a brown solid. LCMS (Shimadzu LCMS 2010, mobile phase: C) 10 mM NH₄HCO₃ in Water; D) MeCN. Gradient: 1% D increase to 5% D within 0.6 min; 5% DB increase to 100% D within 3.4 min; then back to 1% D within 0.3 min. Flow rate 0.8 mL/min) purity is 100%, Rt=2.531 min; MS Calc'd.: 704.4, MS Found: 705.5 [M+H]⁺. ¹H NMR (400 MHz, DMSO-$d_6$) δ 1.26-1.33 (2H, m), 1.40-1.47 (2H, m), 1.55-1.62 (2H, m), 2.12 (6H, s), 2.29 (2H, t, J=7.6 Hz), 2.66 (2H, d, J=7.6 Hz), 2.86 (2H, t, J=7.6 Hz), 2.98 (6H, s), 3.04-3.44 (2H, m), 3.37-3.40 (2H, m), 5.84 (1H, dt, J=12.0, 1.6 Hz), 5.93-5.99 (1H, m), 6.92-6.92 (2H, m), 7.19 (1H, t, J=8.0 Hz), 7.42 (1H, d, J=8.0 Hz), 7.47-7.49 (3H, m), 7.71 (2H, d, J=2.1 Hz), 7.96 (1H, dd, J=8.4, 2.4 Hz), 8.02-8.08 (2H, m), 8.10 (1H, dd, J=6.4, 2.8 Hz), 8.55 (1H, J=2.8 Hz), 8.6 (1H, J=2.8 Hz), 9.32 (1H, br s), 9.82 (1H, br s), 10.35 (1H, br s).

Example 113: 4-(6-((5-(3-(3-(2-(2-aminoethoxy)ethoxy)propanamido)benzamido)pyridin-3-yl)amino)pyridin-3-yl)-N,N-dimethylbenzamide

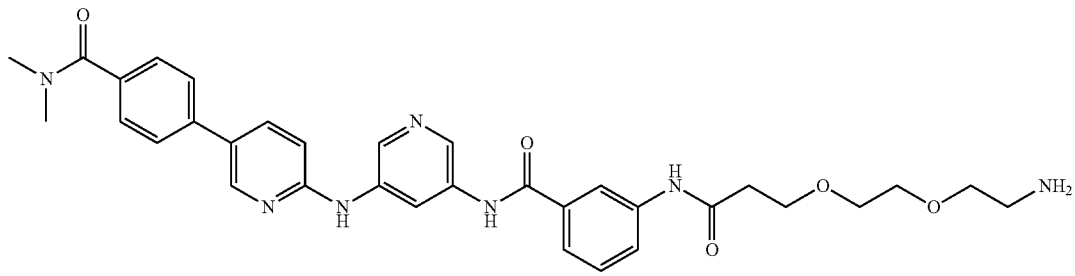 [SMILES: CN(C)C(=O)c1ccc(-c2ccc(Nc3cncc(NC(=O)c4cccc(NC(=O)CCOCCOCCN)c4)c3)nc2)cc1]

Step 1: Preparation of tert-butyl (2-(2-(3-((3-((5-((5-(4-(dimethylcarbamoyl)phenyl)pyridin-2-yl)amino)pyridin-3-yl)carbamoyl)phenyl)amino)-3-oxopropoxy)ethoxy)ethyl)carbamate

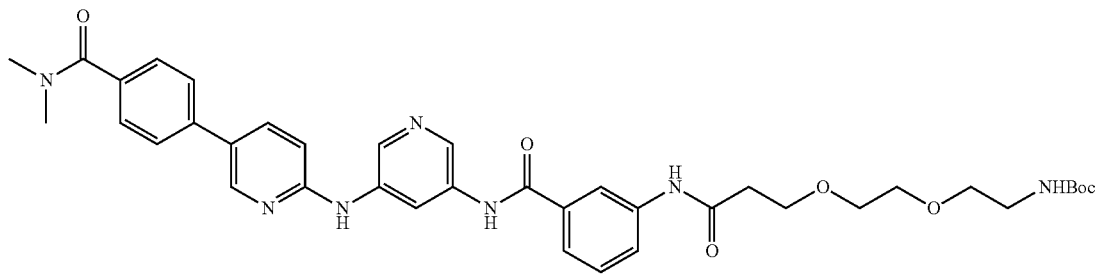 [SMILES: CN(C)C(=O)c1ccc(-c2ccc(Nc3cncc(NC(=O)c4cccc(NC(=O)CCOCCOCCNC(=O)OC(C)(C)C)c4)c3)nc2)cc1]

2,2-Dimethyl-4-oxo-3,8,11-trioxa-5-azatetradecan-14-oic acid (100 mg, 0.361 mmol) and 4-(6-((5-(3-aminobenzamido)pyridin-3-yl)amino)pyridin-3-yl)-N,N-dimethylbenzamide (163 mg, 361 μmol) in pyridine (6 mL) was added EDCI (104 mg, 0.541 mmol). The mixture was stirred at 20° C. for 18 h. The color of solution became tangerine gradually. Crude LCMS showed the purity of desired product (Rt=0.628 min; MS Calc'd: 711.3; MS Found: 712.6 [M+H]+). Pyridine was removed under reduced pressure. After addition of DCM (30 mL) to the residue, the mixture was washed with H₂O (10 mL×3). The organic layer was dried over Na₂SO₄, filtered and concentrated to give tert-butyl (2-(2-(3-((3-((5-((5-(4-(dimethylcarbamoyl)phenyl)pyridin-2-yl)amino)pyridin-3-yl)carbamoyl)phenyl)amino)-3-oxopropoxy)ethoxy)ethyl)carbamate (250 mg, yield: 97%) as a yellow solid. Used in the next step without further purification.

Step 2: Preparation of 4-(6-((5-(3-(3-(2-(2-aminoethoxy)ethoxy)propanamido)benzamido)pyridin-3-yl)amino)pyridin-3-yl)-N,N-dimethylbenzamide

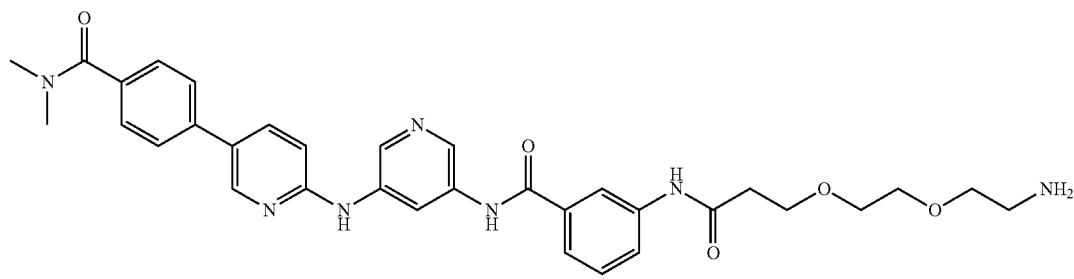 [SMILES: CN(C)C(=O)c1ccc(-c2ccc(Nc3cncc(NC(=O)c4cccc(NC(=O)CCOCCOCCN)c4)c3)nc2)cc1]

To a stirred solution of tert-butyl (2-(2-(3-((3-((5-((5-(4-(dimethylcarbamoyl)phenyl)pyridin-2-yl)amino)pyridin-3-yl)carbamoyl)phenyl)amino)-3-oxopropoxy)ethoxy)ethyl)carbamate (250 mg, 0.351 mmol) in DCM (4 mL) was added HCl/EtOAc (4 M, 4 mL) at 20° C. A red solution turned to suspension, the reaction mixture was stirred for 1 hour. LCMS is 49% (Rt=0.661 min; MS Calc'd: 611.3; MS Found: 612.6 [M+H]+). The mixture was concentrated to give 4-(6-((5-(3-(3-(2-(2-aminoethoxy)ethoxy)propanamido)benzamido)pyridin-3-yl)amino)pyridin-3-yl)-N,N-dimethylbenzamide (227 mg, yield: 100%) as an off-white solid. Used in the next step without further purification. This product (10 mg) was purified by prep-HPLC (0.05% NH$_3$.H$_2$O as an additive) and lyophilized to give 4-(6-((5-(3-(3-(2-(2-aminoethoxy)ethoxy)propanamido)benzamido)pyridin-3-yl)amino)pyridin-3-yl)-N,N-dimethylbenzamide (2.75 mg) as a white solid. LCMS (Shimadzu LCMS 2010, mobile phase: from 100% [water+0.05% NH$_3$.H$_2$O] and 0% [MeCN] to 5% [water+0.05% NH$_3$.H$_2$O] and 95% [MeCN] in 5.8 min, then under this condition for 1.1 min, finally changed to 100% [water+0.05% NH$_3$.H$_2$O] and 0% [MeCN] and under this condition for 0.09 min.) purity is 98.23%, Rt=3.091 min; MS Calc'd.: 611.3, MS Found: 612.3 [M+H]+. $^1$H NMR (400 MHz, DMSO-d$_6$) δ 2.59 (4H, t, J=6.0 Hz), 2.64-2.69 (2H, m), 2.97 (3H, s), 3.01 (3H, s), 3.45-3.57 (4H, m), 3.72 (2H, t, J=6.0 Hz), 7.01 (1H, d, J=8.4 Hz), 7.44-7.51 (3H, m), 7.66 (1H, d, J=7.2 Hz), 7.73 (2H, d, J=8.0 Hz), 7.84 (1H, d, J=7.6 Hz), 8.01 (1H, dd, J=8.4, 2.4 Hz), 8.16 (1H, s), 8.48 (1H, t, J=2.0 Hz), 8.58 (1H, d, J=2.0 Hz), 8.68 (1H, t, J=2.0 Hz), 8.72 (1H, d, J=2.0 Hz), 9.52 (1H, br s), 10.21 (1H, br s), 10.48 (1H, br s).

Example 114: (E)-N,N-dimethyl-4-(6-((5-(3-(2-methyl-6-oxo-10,13-dioxa-2,7-diazahexadec-4-en-16-amido)benzamido)pyridin-3-yl)amino)pyridin-3-yl)benzamide

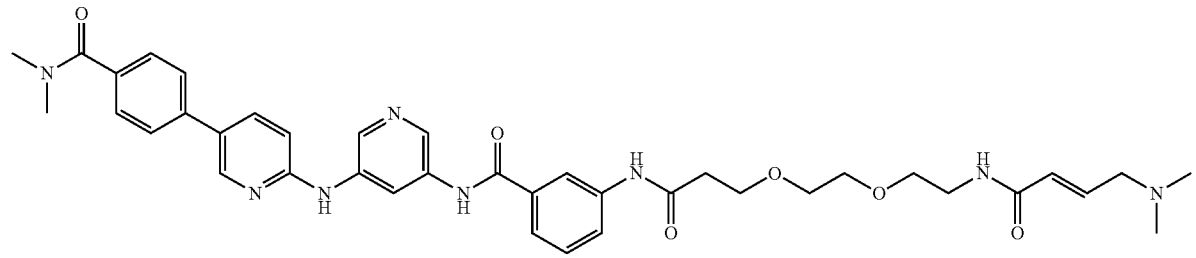

4-(6-((5-(3-(3-(2-(2-Aminoethoxy)ethoxy)propanamido)benzamido)pyridin-3-yl)amino)pyridin-3-yl)-N,N-dimethylbenzamide (100 mg, 0.154 mmol) and (E)-4-(dimethylamino)but-2-enoic acid (20 mg, 0.15 mmol) in pyridine (4 mL) was added EDCI (44 mg, 0.23 mmol). The mixture was stirred at 20° C. for 18 h. A tangerine solution was formed gradually. Crude LCMS showed the purity of desired product (Rt=0.661 min; MS Calc'd: 722.4; MS Found: 723.5 [M+H]+). Pyridine was removed under reduced pressure. The residue was purified by prep-HPLC (0.05% NH$_3$.H$_2$O as an additive) and lyophilized to give (E)-N,N-dimethyl-4-(6-((5-(3-(2-methyl-6-oxo-10,13-dioxa-2,7-diazahexadec-4-en-16-amido)benzamido)pyridin-3-yl)amino)pyridin-3-yl)benzamide (24.8 mg, yield: 22%) as an off-white solid. LCMS (Shimadzu LCMS 2010, mobile phase: from 100% [water+0.05% NH$_3$.H$_2$O] and 0% [MeCN] to 5% [water+ 0.05% NH$_3$.H$_2$O] and 95% [MeCN] in 5.8 min, then under this condition for 1.1 min, finally changed to 100% [water+ 0.05% NH$_3$.H$_2$O] and 0% [MeCN] and under this condition for 0.09 min.) purity is 96.31%, Rt=1.205 min; MS Calc'd.: 722.3, MS Found: 723.1 [M+H]+. $^1$H NMR (400 MHz, DMSO-d$_6$) δ 2.10 (6H, s), 2.59 (2H, t, J=6.0 Hz), 2.97 (3H, s), 2.99 (3H, s), 3.17-3.25 (2H, m), 3.38-3.45 (4H, m), 3.49-3.55 (4H, m), 3.72 (2H, t, J=6.0 Hz), 5.85 (1H, d, J=12.0 Hz), 5.92-5.99 (1H, m), 7.01 (1H, d, J=8.0 Hz), 7.45-7.51 (3H, m), 7.66 (1H, d, J=8.0 Hz), 7.73 (2H, d, J=8.4 Hz), 7.85 (1H, d, J=7.2 Hz), 8.01 (1H, dd, J=8.8, 2.8 Hz), 8.14-8.21 (2H, m), 8.48 (1H, d, J=2.0 Hz), 8.59 (1H, d, J=2.4 Hz), 8.68 (1H, t, J=2.0 Hz), 8.72 (1H, d, J=2.4 Hz), 8.51 (1H, br s), 10.19 (1H, br s), 10.46 (1H, br s).

Example 115: 4-(6-((5-aminopyridin-3-yl)amino)pyridin-3-yl)-N,N-dimethylbenzamide

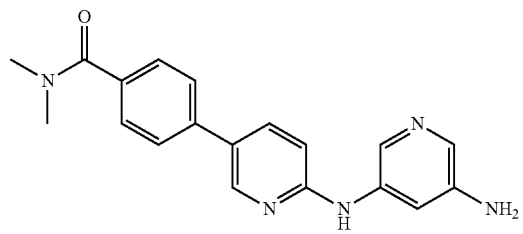 [SMILES: CN(C)C(=O)c1ccc(-c2ccc(Nc3cncc(N)c3)nc2)cc1]

Step 1: Preparation of 4-bromo-N,N-dimethylbenzamide

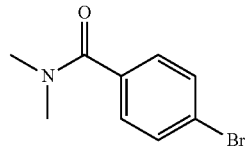

A mixture of 4-bromobenzoic acid (50.0 g, 249 mmol) in SOCl$_2$ (220 mL) was heated at 80° C. for 12 h under N$_2$ atmosphere. A yellow solution was formed. After cooling, the reaction mixture was concentrated under reduced pressure. Then to the mixture was added DCM (500 mL), dimethylamine hydrochloride (36.0 g, 444 mmol) and TEA (207 mL), and stirred at 25° C. for 24 h under N₂. A yellow suspension was formed. TLC showed the reaction was completed. The residue was poured into water (20 mL) and extracted with DCM (20 mL×3). The combined organic layer was washed with water (100 mL), dried over anhydrous Na$_2$SO$_4$, filtered and concentrated in vacuum. The residue was recrystallization by MTBE to afford 4-bromo-N,N-dimethylbenzamide (50 g, yield: 88%) as alight red solid. $^1$H NMR (400 MHz, CDCl$_3$) δ 2.96 (3H, s), 3.09 (3H, s), 7.29 (2H, d, J=8.4 Hz), 7.53 (2H, d, J=8.4 Hz).

Step 2: Preparation of N,N-dimethyl-4-(4,4,5,5-tetramethyl-1,3,2-dioxaborolan-2-yl)benzamide

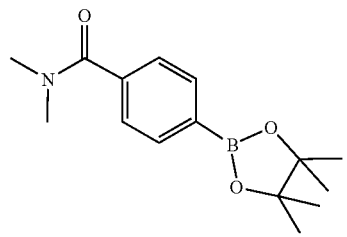

A mixture of 4-bromo-N,N-dimethylbenzamide (25.0 g, 110 mmol), B$_2$Pin$_2$ (36.2 g, 142 mmol), KOAc (32.3 g, 329 mmol) and Pd(dppf)Cl$_2$ (2.00 g, 2.73 mmol) in dioxane (200 mL) was stirred at 110° C. for 14 h under N$_2$ atmosphere. The red suspension turned to black. Crude LCMS (Rt=0.657 min; MS Calc'd: 275.1; MS Found: 275.9 [M+H]$^+$). The reaction mixture was diluted with EtOAc (200 mL), filtered and concentrated to give crude N,N-dimethyl-4-(4,4,5,5-tetramethyl-1,3,2-dioxaborolan-2-yl)benzamide (50.0 g, crude) as black oil and directly used to next step.

Step 3: Preparation of 4-(6-aminopyridin-3-yl)-N,N-dimethylbenzamide

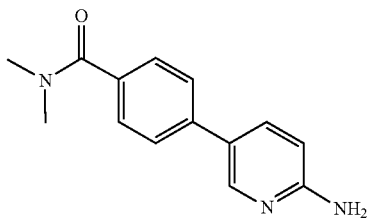 [SMILES: CN(C)C(=O)c1ccc(-c2ccc(N)nc2)cc1]

A mixture of N,N-dimethyl-4-(4,4,5,5-tetramethyl-1,3,2-dioxaborolan-2-yl)benzamide (15.0 g, 54.5 mmol), 5-bromopyridin-2-amine (7.86 g, 45.4 mmol), Na$_2$CO$_3$ (2 M, 68 mL) in water and Pd(dppf)Cl$_2$ (1.33 g, 1.82 mmol) in DME (200 mL) was stirred at 100° C. for 16 h under N$_2$ atmosphere. A black suspension was formed. Crude LCMS (Rt=0.427 min; MS Calc'd: 241.1; MS Found: 242.0 [M+H]$^+$). The reaction mixture was diluted with ethyl acetate (100 mL), dried over Na$_2$SO$_4$, filtered and concentrated. The residue was purified by Combi Flash (EtOAc) to afford 4-(6-aminopyridin-3-yl)-N,N-dimethylbenzamide (5.0 g, yield: 46% over two steps) as an off white solid. $^1$H NMR (400 MHz, CDCl$_3$) δ 3.03 (3H, s), δ 3.12 (3H, s), 4.58 (2H, br s), 6.58 (1H, dd, J=8.4, 0.8 Hz), 7.47 (2H, d, J=8.8 Hz), 7.53 (2H, d, J=8.0 Hz), 7.66 (1H, dd, J=8.4, 2.4 Hz), 8.29 (1H, dd, J=2.4, 0.8 Hz).

Step 4: Preparation of 4-(6-((5-aminopyridin-3-yl)amino)pyridin-3-yl)-N,N-dimethylbenzamide

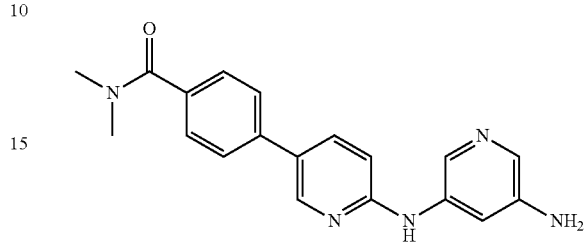

A mixture of Pd$_2$(dba)$_3$ (19 mg, 0.021 mmol) and Brettphos (22 mg, 0.041 mmol) in 1,4-dioxane (1 mL) was stirred at 50° C. for 10 min. 4-(6-Aminopyridin-3-yl)-N,N-dimethylbenzamide (100 mg, 0.414 mmol), 5-bromopyridin-3-amine (72 mg, 0.414 mmol) in dioxane (8 mL) and Cs$_2$CO$_3$ (270 mg, 0.829 mmol) were added and the resulting mixture was stirred at 100° C. for 16 h. A black brown mixture was formed. LCMS showed the purity of the desired product (Rt=0.529 min; MS Calc'd: 333.2; MS Found: 333.7 [M+H]$^+$). The reaction mixture was diluted with DCM (10 mL), filtered and concentrated. The residue was purified by prep-HPLC (0.05% NH$_3$.H$_2$O as an additive) and lyophilized to give 4-(6-((5-aminopyridin-3-yl)amino)pyridin-3-yl)-N,N-dimethylbenzamide (26.4 mg, yield: 19%) as an off-white solid. LCMS (Shimadzu LCMS 2010, mobile phase: from 100% [water+0.05% NH$_3$.H$_2$O] and 0% [MeCN] to 5% [water+0.05% NH$_3$.H$_2$O] and 95% [MeCN] in 5.8 min, then under this condition for 1.1 min, finally changed to 100% [water+0.05% NH$_3$.H$_2$O] and 0% [MeCN] and under this condition for 0.09 min.) purity is 99.71%, Rt=2.089 min; MS Calc'd.: 333.2, MS Found: 334.1 [M+H]$^+$. $^1$H NMR (400 MHz, DMSO-d$_6$) δ 2.96 (3H, s), 2.97 (3H, s), 5.22 (2H, br s), 6.92 (1H, d, J=8.8 Hz), 7.46 (2H, d, J=8.4 Hz), 7.48-7.60 (2H, m), 7.69 (2H, d, J=8.0 Hz), 7.92 (1H, dd, J=8.8, 2.4 Hz), 7.96 (1H, d, J=2.8 Hz), 8.50 (1H, d, J=2.4 Hz), 9.10 (1H, br s).

Example 116: 4-(6-((5-(4-aminobenzamido)pyridin-3-yl)amino)pyridin-3-yl)-N,N-dimethylbenzamide

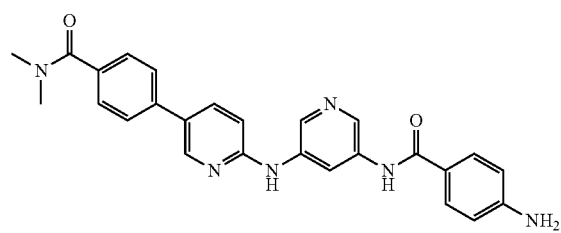 [SMILES: CN(C)C(=O)c1ccc(-c2ccc(Nc3cncc(NC(=O)c4ccc(N)cc4)c3)nc2)cc1]

Step 1: Preparation of 4-((tert-butoxycarbonyl)amino)benzoic acid

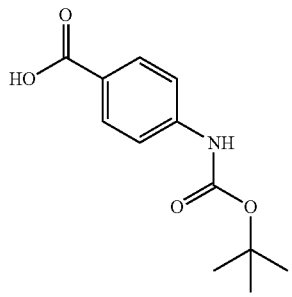 [SMILES: CC(C)(C)OC(=O)Nc1ccc(C(=O)O)cc1]

To a solution of 4-aminobenzoic acid (8.00 g, 58.3 mmol), TEA (16 mL, 117 mmol), H$_2$O (60 mL) in dioxane (120 mL) was added Boc$_2$O (20.1 mL, 87.5 mmol) at 10° C. Reaction mixture was allowed to stir at 10° C. for 18 h. The solution became colorless to light yellow. TLC showed absence of starting material. 1-4-dioxane was removed under reduced pressure and HCl (60 mL, 3 M) was added dropwise. White precipitate was filtered out, washed with hexane (50 mL×3) and dried to afford 4-((tert-butoxycarbonyl)amino)benzoic acid (13.0 g, crude) as a white solid. $^1$H NMR (400 MHz, CDCl$_3$) δ 1.53 (9H, s), 6.84 (1H, br s), 7.46 (2H, d, J=8.4 Hz), 8.03 (2H, d, J=8.4 Hz).

Step 2: Preparation of tert-butyl (4-((5-((5-(4-(dimethylcarbamoyl)phenyl)pyridin-2-yl)amino)pyridin-3-yl)carbamoyl)phenyl)carbamate

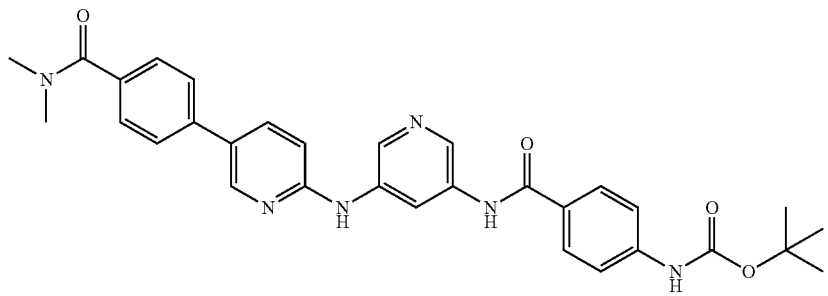 [SMILES: CN(C)C(=O)c1ccc(-c2ccc(Nc3cncc(NC(=O)c4ccc(NC(=O)OC(C)(C)C)cc4)c3)nc2)cc1]

4-((Tert-butoxycarbonyl)amino)benzoic acid (178 mg, 0.750 mmol) and 4-(6-((5-aminopyridin-3-yl)amino)pyridin-3-yl)-N,N-dimethylbenzamide (250 mg, 0.750 mmol) in pyridine (4 mL) was added EDCI (216 mg, 1.12 mmol). The mixture was stirred at 20° C. for 18 h. The color of solution became orange gradually. Crude LCMS showed the purity of desired product (Rt=0.630 min; MS Calc'd: 552.3; MS Found: 553.4 [M+H]$^+$). Pyridine was removed under reduced pressure. The mixture was concentrated in vacuum. The residue was purified by Combi Flash (1% TEtOAc in DCM) to give tert-butyl (4-((5-((5-(4-(dimethylcarbamoyl)phenyl)pyridin-2-yl)amino)pyridin-3-yl)carbamoyl)phenyl)carbamate (260 mg, yield: 63%) as an off-white solid.

Step 3: Preparation of 4-(6-((5-(4-aminobenzamido)pyridin-3-yl)amino)pyridin-3-yl)-N,N-dimethylbenzamide

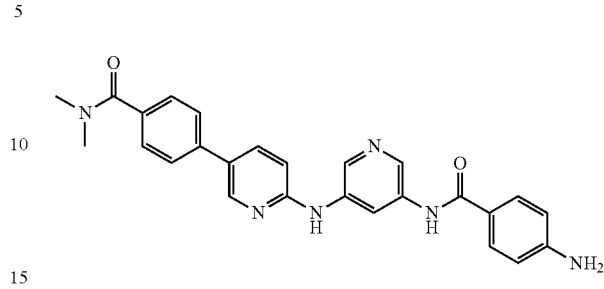

To a stirred solution of tert-butyl (4-((5-((5-(4-(dimethylcarbamoyl)phenyl)pyridin-2-yl)amino)pyridin-3-yl)carbamoyl)phenyl)carbamate (260 mg, 0.470 mmol) in dioxane (4 mL) was added HCl/dioxane (4 M, 9.4 mL) at 10° C. Then the reaction mixture was stirred at 10° C. for 16 h. A yellow solution was formed. LCMS the purity of the desired product (Rt=0.558 min; MS Calc'd: 452.2; MS Found: 453.1 [M+H]$^+$). The mixture was concentrated to afford 4-(6-((5-(4-aminobenzamido)pyridin-3-yl)amino)pyridin-3-yl)-N,N-dimethylbenzamide (400 mg, crude) as an off-white solid. The residue (200 mg, crude) was purified by prep-HPLC (0.05% NH$_3$.H$_2$O as an additive) and lyophilized to afford 4-(6-((5-(4-aminobenzamido)pyridin-3-yl)amino)pyridin-3-yl)-N,N-dimethylbenzamide (2.16 mg yield: 2%) as a white solid. LCMS (Shimadzu LCMS 2010, mobile phase: from 100% [water+0.05% NH$_3$.H$_2$O] and 0% [MeCN] to 5% [water+0.05% NH$_3$.H$_2$O] and 95% [MeCN] in 5.8 min, then under this condition for 1.1 min, finally changed to 100% [water+0.05% NH$_3$.H$_2$O] and 0% [MeCN] and under this condition for 0.09 min.) purity is 100%, Rt=2.526 min; MS Calc'd.: 452.2, MS Found: 453.2 [M+H]$^+$. $^1$H NMR (400 MHz, DMSO-d$_6$) δ 2.97 (3H, s), 2.99 (3H, s), 5.81 (2H, br s), 6.61 (2H, d, J=8.8 Hz), 6.99 (1H, d, J=9.2 Hz), 7.48 (2H, d, J=8.4 Hz), 7.73 (2H, d, J=8.4 Hz), 7.75 (2H, d, J=8.4 Hz), 7.99 (1H, dd, J=8.8, 2.8 Hz), 8.46 (1H, d, J=2.4 Hz), 8.58 (1H, d, J=2.4 Hz), 8.62 (1H, t, J=2.4 Hz), 8.67 (1H, d, J=2.4 Hz), 9.44 (1H, br s), 9.93 (1H, br s).

Example 117: (E)-4-(6-((5-(4-(4-(dimethylamino)but-2-enamido)benzamido)pyridin-3-yl)amino)pyridin-3-yl)-N,N-dimethylbenzamide

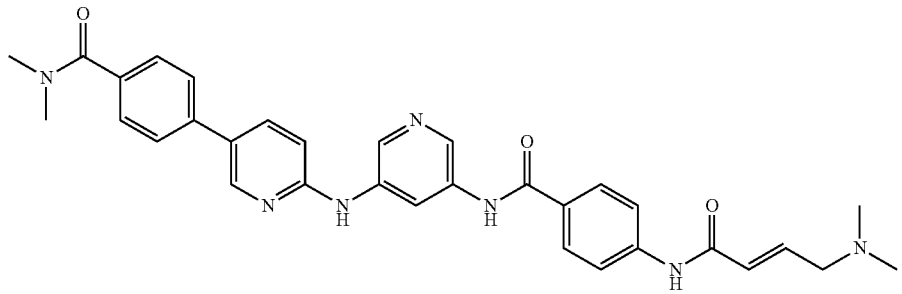

4-(6-((5-(4-Aminobenzamido)pyridin-3-yl)amino)pyridin-3-yl)-N,N-dimethylbenzamide (200 mg, 0.442 mmol) and (E)-4-(dimethylamino)but-2-enoic acid (86 mg, 0.66 mmol) in pyridine (4 mL) was added EDCI (127 mg, 0.663 mmol). The mixture was stirred at 10° C. for 18 h. A dark red solution was formed gradually. LCMS showed the purity of desired product (Rt=0.545 min; MS Calc'd: 563.3; MS Found: 564.4 [M+H]$^+$). Pyridine was removed under reduced pressure. The crude product was purified by prep-HPLC (0.05% NH$_3$H$_2$O as an additive) and lyophilized to give (E)-4-(6-((5-(4-(4-(dimethylamino)but-2-enamido)benzamido)pyridin-3-yl)amino)pyridin-3-yl)-N,N-dimethylbenzamide (12.2 mg, yield: 5%) as an off-white solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 98.29%, Rt=1.464 min; MS Calc'd.: 563.3; MS Found: 564.1 [M+H]$^+$. $^1$H NMR (400 MHz, DMSO-d$_6$) δ 2.20 (6H, s), 2.98 (3H, s), 3.00 (3H, s), 3.09 (2H, d, J=5.2 Hz), 6.33 (1H, d, J=15.6 Hz), 6.80 (1H, d, J=15.6 Hz), 7.01 (1H, d, J=8.8 Hz), 7.49 (2H, d, J=8.0 Hz), 7.74 (2H, d, J=8.0 Hz), 7.82 (2H, d, J=8.0 Hz), 7.99 (2H, d, J=8.0 Hz), 8.03 (1H, d, J=2.8 Hz), 8.50 (1H, d, J=2.0 Hz), 8.60 (1H, d, J=2.0 Hz), 8.69 (1H, t, J=2.0 Hz), 8.71 (1H, d, J=2.4 Hz), 9.51 (1H, br s), 10.33 (1H, br s), 10.39 (1H, br s).

Example 118: 4-(6-((5-(3-(4-aminophenyl)propanamido)pyridin-3-yl)amino)pyridin-3-yl)-N,N-dimethylbenzamide

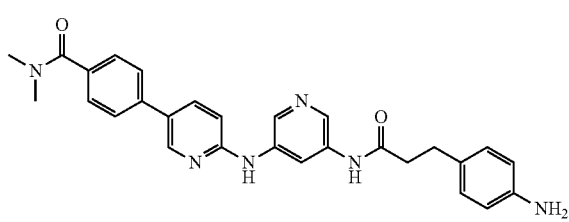 [SMILES: CN(C)C(=O)c1ccc(-c2ccc(Nc3cncc(NC(=O)CCc4ccc(N)cc4)c3)nc2)cc1]

Step 1: Preparation of 3-(4-((tert-butoxycarbonyl)amino)phenyl)propanoic acid

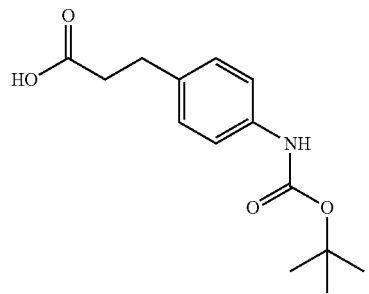 [SMILES: CC(C)(C)OC(=O)Nc1ccc(CCC(=O)O)cc1]

To a solution of 3-(4-aminophenyl)propanoic acid (1.00 g, 6.05 mmol), TEA (1.68 mL, 12.1 mmol), H$_2$O (7 mL) in dioxane (14 mL) was added Boc$_2$O (2.08 mL, 9.07 mmol) at 10° C. Reaction mixture was allowed to stir at 10° C. for 18 h. The solution turned colorless to light yellow. LCMS showed the purity of desired product (Rt=0.641 min; MS Calc'd: 265.1; MS Found: 287.9 [M+Na]$^+$). 1-4-dioxane was removed under reduced pressure. HCl (3 M) was added to adjust PH to 5. The residue was washed with pentane (50 mL×3) and dried to afford 3-(4-((tert-butoxycarbonyl)amino)phenyl)propanoic acid (1.5 g, yield: 93%) as an off white solid. $^1$H NMR (400 MHz, CDCl$_3$) δ 1.51 (9H, s), 2.64 (2H, t, J=8.0 Hz), 2.91 (2H, t, J=7.6 Hz), 6.50 (1H, br s), 7.12 (2H, d, J=8.0 Hz), 7.27 (2H, d, J=8.0 Hz).

Step 2: Preparation of tert-butyl (4-(3-((5-((5-(4-(dimethylcarbamoyl)phenyl)pyridin-2-yl)amino)pyridin-3-yl)amino)-3-oxopropyl)phenyl)carbamate

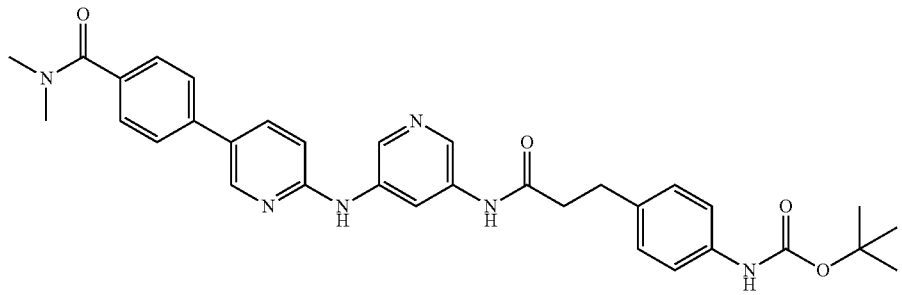 [SMILES: CN(C)C(=O)c1ccc(-c2ccc(Nc3cncc(NC(=O)CCc4ccc(NC(=O)OC(C)(C)C)cc4)c3)nc2)cc1]

3-(4-((Tert-butoxycarbonyl)amino)phenyl)propanoic acid (199 mg, 0.750 mmol) and 4-(6-((5-aminopyridin-3-yl)amino)pyridin-3-yl)-N,N-dimethylbenzamide (250 mg, 0.750 mmol) in pyridine (4 mL) was added EDCI (216 mg, 1.12 mmol). The mixture was stirred at 20° C. for 18 h. The color of solution became orange gradually. Crude LCMS showed the purity of desired product (Rt=0.630 min; MS Calc'd: 580.3; MS Found: 581.4 [M+H]$^+$). Pyridine was removed under reduced pressure. The mixture was concentrated in vacuum. The residue was purified by Combi Flash (1% TEtOAc in EtOAc) to give tert-butyl (4-(3-((5-((5-(4-(dimethylcarbamoyl)phenyl)pyridin-2-yl)amino)pyridin-3-yl)amino)-3-oxopropyl)phenyl)carbamate (250 mg, yield: 57%) as an off-white solid. $^1$H NMR (400 MHz, DMSO-d$_6$) δ 1.45 (9H, s), 2.62 (2H, t, J=8.0 Hz), 2.85 (2H, t, J=8.0 Hz), 3.05 (3H, s), 3.07 (3H, s), 6.99 (1H, d, J=8.8 Hz), 7.13 (2H, d, J=8.4 Hz), 7.35 (2H, d, J=8.4 Hz), 7.48 (2H, d, J=8.4 Hz), 7.72 (2H, d, J=8.4 Hz), 7.98 (1H, dd, J=8.8, 2.8 Hz), 8.32 (1H, d, J=2.0 Hz), 8.48 (1H, t, J=2.0 Hz), 8.56 (1H, d, J=2.0 Hz), 8.66 (1H, d, J=2.0 Hz), 9.23 (1H, br s), 9.49 (1H, br s), 10.12 (1H, br s).

Step 3: Preparation of 4-(6-((5-(3-(4-aminophenyl)propanamido)pyridin-3-yl)amino)pyridin-3-yl)-N,N-dimethylbenzamide

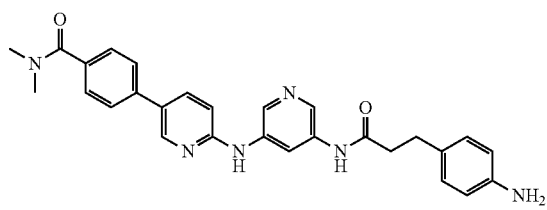 [SMILES: CN(C)C(=O)c1ccc(-c2ccc(Nc3cncc(NC(=O)CCc4ccc(N)cc4)c3)nc2)cc1]

To a stirred solution of tert-butyl (4-(3-((5-((5-(4-(dimethylcarbamoyl)phenyl)pyridin-2-yl)amino)pyridin-3-yl)amino)-3-oxopropyl)phenyl)carbamate (250 mg, 0.431 mmol) in dioxane (4 mL) was added HCl/dioxane (4 M, 8.6 mL) at 15° C. Then the reaction mixture was stirred at 15° C. for 16 h. A yellow solution was formed. LCMS (Rt=0.539 min; MS Calc'd: 480.2; MS Found: 481.3 [M+H]$^+$). The mixture was concentrated to afford 4-(6-((5-(3-(4-aminophenyl)propanamido)pyridin-3-yl)amino)pyridin-3-yl)-N,N-dimethylbenzamide (350 mg, crude) as an off-white solid. The residue (200 mg, crude) was purified by prep-HPLC (0.225% FA as an additive) and lyophilized to afford 4-(6-((5-(3-(4-aminophenyl)propanamido)pyridin-3-yl)amino)pyridin-3-yl)-N,N-dimethylbenzamide (2.05 mg yield: 2%) as a white solid. LCMS (Shimadzu LCMS 2010, mobile phase: from 100% [water+0.05% NH$_3$.H$_2$O] and 0% [MeCN] to 5% [water+0.05% NH$_3$.H$_2$O] and 95% [MeCN] in 5.8 min, then under this condition for 1.1 min, finally changed to 100% [water+0.05% NH$_3$.H$_2$O] and 0% [MeCN] and under this condition for 0.09 min.) purity is 99.11%, Rt=2.610 min; MS Calc'd: 480.2, MS Found: 481.3 [M+H]$^+$. $^1$H NMR (400 MHz, DMSO-d$_6$) δ 2.69 (2H, t, J=7.6 Hz), 2.91 (2H, t, J=7.6 Hz), 2.97 (3H, s), 2.99 (3H, s), 7.02 (2H, d, J=8.8 Hz), 7.06 (1H, s), 7.25 (2H, d, J=7.6 Hz), 7.49 (2H, d, J=8.4 Hz), 7.73 (2H, d, J=8.4 Hz), 8.05 (1H, dd, J=8.4, 2.0 Hz), 8.46 (1H, s), 8.58-8.61 (2H, m), 8.85 (1H, s), 9.81 (1H, br s), 10.40 (1H, br s).

Example 119: (E)-4-(6-((5-(3-(4-(4-(dimethylamino)but-2-enamido)phenyl)propanamido)pyridin-3-yl)amino)pyridin-3-yl)-N,N-dimethylbenzamide

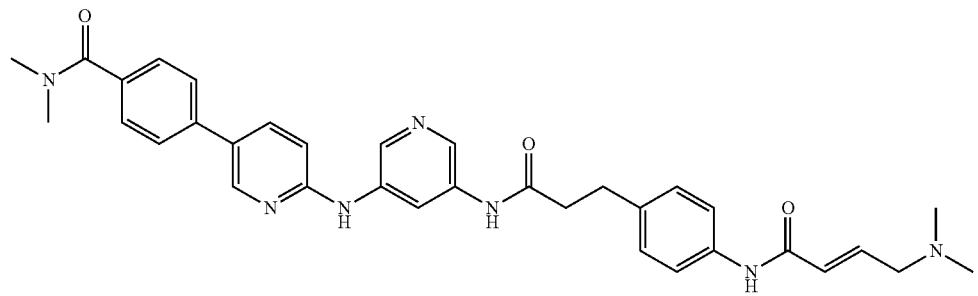

4-(6-((5-(3-(4-aminophenyl)propanamido)pyridin-3-yl)amino)pyridin-3-yl)-N,N-dimethylbenzamide (150 mg, 0.312 mmol) and (E)-4-(dimethylamino)but-2-enoic acid (60 mg, 0.66 mmol) in pyridine (4 mL) was added EDCI (90 mg, 0.468 mmol). The mixture was stirred at 10° C. for 18 h. A dark red solution was formed gradually. LCMS showed the purity of desired product (Rt=0.546 min; MS Calc'd: 591.3; MS Found: 592.5 [M+H]$^+$). Pyridine was removed under reduced pressure. The crude product was purified by prep-HPLC (0.05% NH$_3$H$_2$O as an additive) and lyophilized to give (E)-4-(6-((5-(3-(4-(4-(dimethylamino)but-2-enamido)phenyl)propanamido)pyridin-3-yl)amino)pyridin-3-yl)-N,N-dimethylbenzamide (10.0 mg, yield: 5%) as a red solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 98.49%, Rt=1.472 min; MS Calc'd: 591.3; MS Found: 592.1 [M+H]$^+$. $^1$H NMR (400 MHz, DMSO-d$_6$) δ 2.17 (6H, s), 2.61-2.68 (2H, m), 2.89 (2H, t, J=7.6 Hz), 2.98 (3H, s), 3.00 (3H, s), 3.04 (2H, d, J=4.8 Hz), 6.25 (1H, d, J=15.2 Hz), 6.66-6.74 (1H, m), 6.98 (1H, d, J=8.4 Hz), 7.21 (2H, d, J=8.8 Hz), 7.49 (2H, d, J=8.8 Hz), 7.57 (2H, d, J=8.4 Hz), 7.74 (2H, d, J=8.4 Hz), 8.00 (1H, dd, J=8.8, 2.4 Hz), 8.32 (1H, d, J=2.0 Hz), 8.50 (1H, t, J=2.4 Hz), 8.57 (1H, d, J=2.8 Hz), 8.66 (1H, d, J=2.0 Hz), 9.47 (1H, br s), 10.00 (1H, br s), 10.10 (1H, br s).

Example 120: methyl(5-((5-(4-(dimethylcarbamoyl)phenyl)pyridin-2-yl)amino)pyridin-3-yl)carbamate

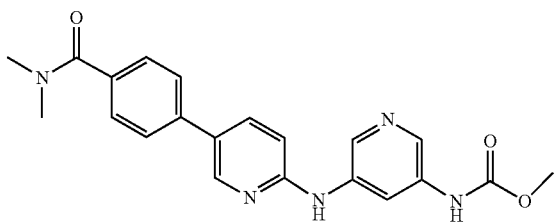

To a suspension of 4-(6-((5-aminopyridin-3-yl)amino)pyridin-3-yl)-N,N-dimethylbenzamide (50 mg, 0.15 mmol) in anhydrous DCM (2 mL) was added a solution of methyl carbonochloridate (16 mg, 0.16 mmol) in DCM (1 mL) from 10-15° C. Then the reaction mixture was stirred at 10-15° C. for 1 hr. The reaction mixture turned into brown solution from suspension. LCMS is (Rt=0.661 min; MS Calc'd: 391.2; MS Found: 392.0 [M+H]$^+$). To the reaction mixture was added saturated aqueous NaHCO$_3$ (20 mL), then extracted with DCM (20 mL×2). The combined organic layer was washed with brine (20 mL), dried over anhydrous Na$_2$SO$_4$ and concentrated. The crude product was purified by prep-HPLC (0.225% FA as an additive). Most of the solvent was removed under reduced pressure and the remaining part was lyophilized to give methyl (5-((5-(4-(dimethylcarbamoyl)phenyl)pyridin-2-yl)amino)pyridin-3-yl)carbamate (20.6 mg, yield: 35%) as a yellow solid. LCMS (Agilent LCMS 1200-6140A, mobile phase: from 99% [water+0.1% FA] and 1% [MeCN+0.1% FA] to 95% [water+0.1% FA] and 5% [MeCN+0.1% FA] in 0.6 min, then changed to 100% [MeCN+0.1% FA] under this condition for 3.4 min, finally back to 99% [water+0.1% FA] and 1% [MeCN+0.1% FA] and under this condition for 0.5 min.) purity is 98.27%, Rt=2.072 min; MS Calc'd.: 391.2, MS Found: 392.3 [M+H]$^+$. $^1$H NMR (400 MHz, DMSO-d$_6$) δ 2.95-3.05 (6H, m), 3.73 (3H, s), 7.03 (1H, d, J=8.8 Hz), 7.50 (2H, d, J=7.6 Hz), 7.75 (2H, d, J=8.4 Hz), 8.05 (1H, d, J=7.6 Hz), 8.33 (1H, s), 8.46 (1H, s), 8.61 (1H, s), 8.90 (1H, s), 9.84 (1H, br s), 10.19 (1H, br s).

Example 121: 4-(6-((5-benzamidopyridin-3-yl)amino)pyridin-3-yl)-N,N-dimethylbenzamide

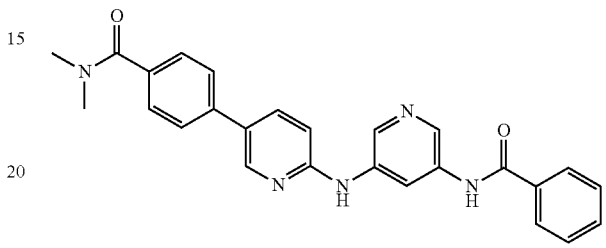

A mixture of 4-(6-((5-aminopyridin-3-yl)amino)pyridin-3-yl)-N,N-dimethylbenzamide (50 mg, 0.15 mmol), benzoic acid (27 mg, 0.22 mmol) and EDC.HCl (58 mg, 0.30 mmol) in pyridine (2 mL) was stirred at 50° C. for 2 h. A brown suspension was obtained. LCMS (Rt=0.813 min; MS Calc'd: 437.2; MS Found: 438.0 [M+H]$^+$). The reaction mixture was concentrated and the crude product was triturated with MeOH (5 mL) and filtered. The solid was lyophilized to give 4-(6-((5-benzamidopyridin-3-yl)amino)pyridin-3-yl)-N,N-dimethylbenzamide (34.2 mg, yield: 52%) as a pale yellow solid. LCMS (Agilent LCMS 1200-6140A, mobile phase: from 100% [water+0.05% NH$_3$.H$_2$O] and 0% [MeCN] to 5% [water+0.05% NH$_3$.H$_2$O] and 95% [MeCN] in 5.8 min, then under this condition for 1.1 min, finally changed to 100% [water+0.05% NH$_3$.H$_2$O] and 0% [MeCN] and under this condition for 0.09 min.) purity is 97.22%, Rt=2.849 min; MS Calc'd.: 437.2, MS Found: 438.2 [M+H]$^+$. $^1$H NMR (400 MHz, DMSO-d$_6$) δ 2.95-3.05 (6H, m), 7.01 (1H, d, J=8.8 Hz), 7.49 (2H, d, J=8.4 Hz), 7.55-7.65 (3H, m), 7.74 (2H, d, J=8.4 Hz), 7.90-8.05 (3H, m), 8.51 (1H, d, J=2.0 Hz), 8.59 (1H, s), 8.70 (1H, s), 8.73 (1H, d, J=2.4 Hz), 9.51 (1H, br s), 10.45 (1H, br s).

Example 122: 4-(6-((5-(2-cyanoacetamido)pyridin-3-yl)amino)pyridin-3-yl)-N,N-dimethylbenzamide

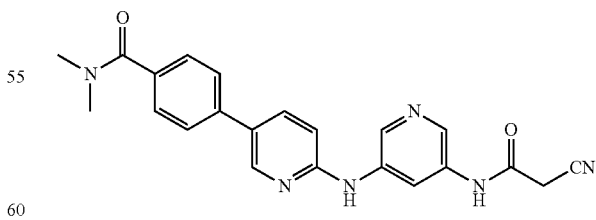

A solution of 4-(6-((5-aminopyridin-3-yl)amino)pyridin-3-yl)-N,N-dimethylbenzamide (50 mg, 0.15 mmol), 2-cyanoacetic acid (19 mg, 0.22 mmol) and EDC.HCl (58 mg, 0.30 mmol) in pyridine (2 mL) was stirred at 50° C. for 2 h. A brown suspension was formed. LCMS (Rt=0.668 min; MS Calc'd: 400.2; MS Found: 401.0 [M+H]$^+$). The reaction mixture was filtered and the solid was washed with MeOH (2 mL×2), then lyophilized to give 4-(6-((5-(2-cyanoacetamido)pyridin-3-yl)amino)pyridin-3-yl)-N,N-dimethylbenzamide (10.3 mg, yield: 17%) as a yellow solid. LCMS (Agilent LCMS 1200-6140A, mobile phase: from 99% [water+0.1% FA] and 1% [MeCN+0.1% FA] to 95% [water+0.1% FA] and 5% [MeCN+0.1% FA] in 0.6 min, then changed to 100% [MeCN+0.1% FA] under this condition for 3.4 min, finally back to 99% [water+0.1% FA] and 1% [MeCN+0.1% FA] and under this condition for 0.5 min.) purity is 100%, Rt=2.051 min; MS Calc'd.: 400.2, MS Found: 401.3 [M+H]$^+$. $^1$H NMR (400 MHz, DMSO-d$_6$) δ 2.95-3.05 (6H, m), 3.97 (2H, s), 7.00 (1H, d, J=8.8 Hz), 7.49 (2H, d, J=8.4 Hz), 7.74 (2H, d, J=8.4 Hz), 8.01 (1H, dd, J=8.8, 2.8 Hz), 8.32 (1H, s), 8.54 (1H, d, J=2.0 Hz), 8.58 (1H, d, J=2.4 Hz), 8.66 (1H, d, J=2.4 Hz), 9.54 (1H, br s), 10.50 (1H, br s).

Example 123: N,N-dimethyl-4-(6-((5-(2-phenylacetamido)pyridin-3-yl)amino)pyridin-3-yl)benzamide

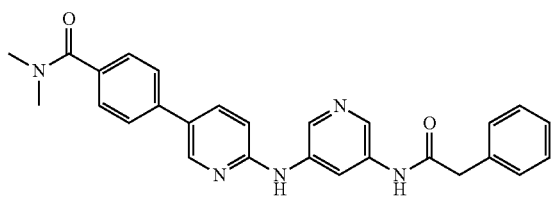 [SMILES: CN(C)C(=O)c1ccc(-c2ccc(Nc3cncc(NC(=O)Cc4ccccc4)c3)nc2)cc1]

A mixture of 4-(6-((5-aminopyridin-3-yl)amino)pyridin-3-yl)-N,N-dimethylbenzamide (50 mg, 0.15 mmol), 2-phenylacetic acid (31 mg, 0.22 mmol) and EDC.HCl (58 mg, 0.30 mmol) in pyridine (2 mL) was stirred at 50° C. for 2 h. LCMS (Rt=0.832 min; MS Calc'd: 451.2; MS Found: 452.1 [M+H]$^+$). The reaction mixture was concentrated to give the crude product, which was triturated with MeOH (3 mL) and filtered. LCMS indicated it still contains some impurity. Then it was combined with the filtrate and further purified by prep-HPLC (0.225% FA as an additive). Most of MeCN was removed under reduced pressure and the remaining part was lyophilized to give N,N-dimethyl-4-(6-((5-(2-phenylacetamido)pyridin-3-yl)amino)pyridin-3-yl)benzamide (22.3 mg, yield: 33%) as a pale yellow solid. LCMS (Agilent LCMS 1200-6140A, mobile phase: from 99% [water+0.1% FA] and 1% [MeCN+0.1% FA] to 95% [water+0.1% FA] and 5% [MeCN+0.1% FA] in 0.6 min, then changed to 100% [MeCN+0.1% FA] under this condition for 3.4 min, finally back to 99% [water+0.1% FA] and 1% [MeCN+0.1% FA] and under this condition for 0.5 min.) purity is 99.00%, Rt=2.376 min; MS Calc'd.: 451.2, MS Found: 452.3 [M+H]$^+$. $^1$H NMR (400 MHz, DMSO-d$_6$) δ 2.95-3.05 (6H, m), 3.72 (2H, s), 7.01 (1H, d, J=8.8 Hz), 7.25-7.40 (5H, m), 7.49 (2H, d, J=8.0 Hz), 7.74 (2H, d, J=8.4 Hz), 8.02 (1H, dd, J=8.4, 2.0 Hz), 8.44 (1H, s), 8.55-8.60 (2H, m), 8.74 (1H, s), 9.65 (1H, br s), 10.53 (1H, br s).

Example 124: N,N-dimethyl-4-(6-((5-(3-methylureido)pyridin-3-yl)amino)pyridin-3-yl)benzamide

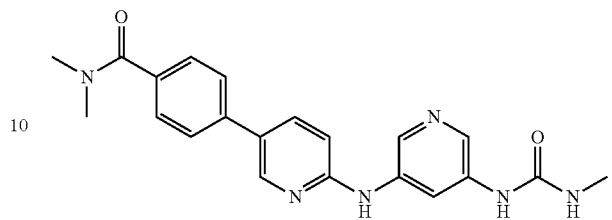

Step 1: Preparation of 1-(5-bromopyridin-3-yl)-3-methylurea

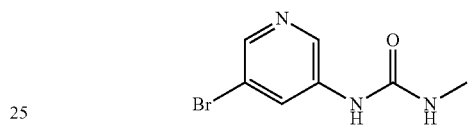

To a solution of 5-bromopyridin-3-amine (1.00 g, 5.78 mmol) in pyridine (10 mL) was added methylcarbamic chloride (649 mg, 6.94 mmol) between 10-15° C. Then the reaction mixture was stirred at 10-15° C. for 3 h. The reaction mixture turned into red from yellow solution. LCMS (Rt=0.555 min; MS Calc'd: 229.0; MS Found: 230.0 [M+H]$^+$). The reaction mixture was diluted with EtOAc (100 mL), then washed with 1N aqueous HCl (25 mL×2), saturated aqueous NaHCO$_3$ (50 mL), brine (25 mL) and concentrated. The crude product was triturated with MTBE (5 mL) and washed with MTBE (2 mL×2) to give 1-(5-bromopyridin-3-yl)-3-methylurea (520 mg, yield: 39%) as a pale yellow solid. $^1$H NMR (400 MHz, DMSO-d$_6$) δ 2.60-2.70 (3H, m), 6.29 (1H, br s), 8.20 (1H, t, J=2.4 Hz), 8.26 (1H, t, J=2.4 Hz), 8.43 (1H, d, J=2.4 Hz), 8.96 (1H, br s).

Step 2: Preparation of N,N-dimethyl-4-(6-((5-(3-methylureido)pyridin-3-yl)amino)pyridin-3-yl)benzamide

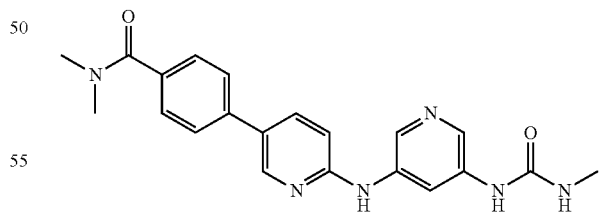

A mixture of 4-(6-aminopyridin-3-yl)-N,N-dimethylbenzamide (100 mg, 0.41 mmol), 1-(5-bromopyridin-3-yl)-3-methylurea (114 mg, 0.50 mmol), Pd$_2$(dba)$_3$ (19 mg, 0.021 mmol), Brettphos (22 mg, 0.041 mmol) and Cs$_2$CO$_3$ (270 mg, 0.83 mmol) in anhydrous dioxane (3 mL) was degassed and purged with N$_2$ for 3 times. Then the resulting reaction mixture was heated at 100° C. for 16 h under N$_2$ atmosphere. The reaction mixture turned into yellow suspension from red. Crude LCMS showed the purity of desired product is 63% (Rt=0.630 min; MS Calc'd: 390.2; MS Found: 391.1 [M+H]+). To the mixture was added water (25 mL), then extracted with EtOAc/THF (25 mL×3, 1/1). The combined organic layer was washed with brine (25 mL), dried over anhydrous Na$_2$SO$_4$ and concentrated. The residue was purified by prep-HPLC (0.225% FA as an additive). Most of MeCN was removed under reduced pressure and the remaining part was lyophilized to give N,N-dimethyl-4-(6-((5-(3-methylureido)pyridin-3-yl)amino)pyridin-3-yl)benzamide (51.0 mg, yield: 32%) as a yellow solid. LCMS (Agilent LCMS 1200-6140A, mobile phase: from 99% [water+0.1% FA] and 1% [MeCN+0.1% FA] to 95% [water+0.1% FA] and 5% [MeCN+0.1% FA] in 0.6 min, then changed to 100% [MeCN+0.1% FA] under this condition for 3.4 min, finally back to 99% [water+0.1% FA] and 1% [MeCN+0.1% FA] and under this condition for 0.5 min.) purity is 100%, Rt=1.974 min; MS Calc'd.: 390.2, MS Found: 391.4 [M+H]+. $^1$H NMR (400 MHz, DMSO-d$_6$) δ 2.68 (3H, d, J=4.8 Hz), 2.95-3.05 (6H, m), 6.34 (1H, q, J=4.8 Hz), 7.01 (1H, d, J=8.8 Hz), 7.49 (2H, d, J=8.0 Hz), 7.74 (2H, d, J=8.4 Hz), 8.02 (1H, dd, J=8.8, 2.0 Hz), 8.32 (1H, s), 8.37 (1H, s), 8.58 (1H, d, J=2.0 Hz), 8.70 (1H, s), 9.04 (1H, br s), 9.65 (1H, br s).

Example 125: 4-(6-((5-(2-(dimethylamino)acetamido)pyridin-3-yl)amino)pyridin-3-yl)-N,N-dimethylbenzamide

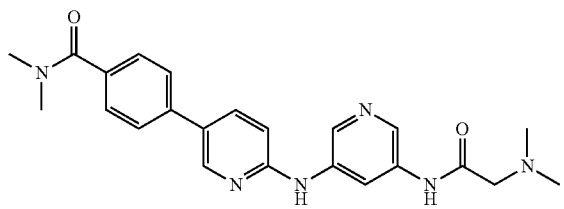

A mixture of 4-(6-((5-aminopyridin-3-yl)amino)pyridin-3-yl)-N,N-dimethylbenzamide (50 mg, 0.15 mmol), N,N-dimethylglycine (23 mg, 0.22 mmol) and EDC.HCl (58 mg, 0.30 mmol) in pyridine (2 mL) was heated at 50° C. for 2 h. Crude LCMS showed the purity of desired product (Rt=0.816 min; MS Calc'd: 418.2; MS Found: 419.0 [M+H]+). The reaction mixture was concentrated and the residue was purified by prep-HPLC (0.225% FA as an additive). Most of MeCN was removed under reduced pressure and the remaining part was lyophilized to give the product (42.6 mg, still contains some impurity). The product was then further purified by pre-HPLC (hexane/IPA as eluent) and lyophilized to give 4-(6-((5-(2-(dimethylamino)acetamido)pyridin-3-yl)amino)pyridin-3-yl)-N,N-dimethylbenzamide (9.9 mg, yield: 16%) as a white solid. LCMS (Agilent LCMS 1200-6140A, mobile phase: from 99% [water+0.1% FA] and 1% [MeCN+0.1% FA] to 95% [water+0.1% FA] and 5% [MeCN+0.1% FA] in 0.6 min, then changed to 100% [MeCN+0.1% FA] under this condition for 3.4 min, finally back to 99% [water+0.1% FA] and 1% [MeCN+0.1% FA] and under this condition for 0.5 min.) purity is 100%, Rt=1.776 min; MS Calc'd: 418.2, MS Found: 419.3 [M+H]+. $^1$H NMR (400 MHz, DMSO-d$_6$) δ 2.30 (6H, s), 2.95-3.05 (6H, m), 3.12 (2H, s), 6.99 (1H, d, J=8.8 Hz), 7.49 (2H, d, J=8.4 Hz), 7.74 (2H, d, J=8.0 Hz), 7.99 (1H, dd, J=8.8, 2.0 Hz), 8.37 (1H, d, J=1.6 Hz), 8.55 (1H, s), 8.58 (1H, d, J=1.6 Hz), 8.70 (1H, s), 9.48 (1H, br s), 9.93 (1H, br s).

Example 126: N-(5-((5-(4-(dimethylcarbamoyl)phenyl)pyridin-2-yl)amino)pyridin-3-yl)tetrahydro-2H-pyran-4-carboxamide

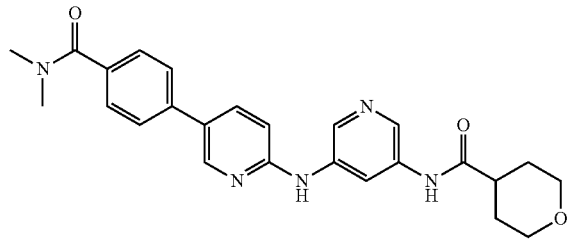 [SMILES: CN(C)C(=O)c1ccc(-c2ccc(Nc3cncc(NC(=O)C4CCOCC4)c3)nc2)cc1]

A mixture of 4-(6-((5-aminopyridin-3-yl)amino)pyridin-3-yl)-N,N-dimethylbenzamide (50 mg, 0.15 mmol), tetrahydro-2H-pyran-4-carboxylic acid (29 mg, 0.22 mmol) and EDC.HCl (58 mg, 0.30 mmol) in pyridine (2 mL) was stirred at 50° C. for 2 h. Crude LCMS showed the purity of desired product (Rt=0.800 min; MS Calc'd: 445.2; MS Found: 446.0 [M+H]+). The reaction mixture was concentrated and the residue was purified by prep-HPLC (0.225% FA as an additive). Most of MeCN was removed under reduced pressure and the remaining part was lyophilized to give N-(5-((5-(4-(dimethylcarbamoyl)phenyl)pyridin-2-yl)amino)pyridin-3-yl)tetrahydro-2H-pyran-4-carboxamide (20.9 mg, yield: 28%) as a yellow solid. LCMS (Agilent LCMS 1200-6140A, mobile phase: from 99% [water+0.1% FA] and 1% [MeCN+0.1% FA] to 95% [water+0.1% FA] and 5% [MeCN+0.1% FA] in 0.6 min, then changed to 100% [MeCN+0.1% FA] under this condition for 3.4 min, finally back to 99% [water+0.1% FA] and 1% [MeCN+0.1% FA] and under this condition for 0.5 min.) purity is 97.71%, Rt=2.082 min; MS Calc'd.: 445.2, MS Found: 446.3 [M+H]+. $^1$H NMR (400 MHz, DMSO-d$_6$) δ 1.65-1.80 (4H, m), 2.60-2.70 (1H, m), 2.95-3.05 (6H, m), 3.30-3.40 (2H, m), 3.90-3.95 (2H, m), 6.99 (1H, d, J=8.8 Hz), 7.49 (2H, d, J=8.4 Hz), 7.74 (2H, d, J=8.4 Hz), 8.01 (1H, dd, J=8.8, 2.0 Hz), 8.40 (1H, s), 8.55-8.60 (2H, m), 8.69 (1H, s), 9.53 (1H, br s), 10.15 (1H, br s).

Example 127: N,N-dimethyl-4-(6-((5-(methylsulfonamido)pyridin-3-yl)amino)pyridin-3-yl)benzamide

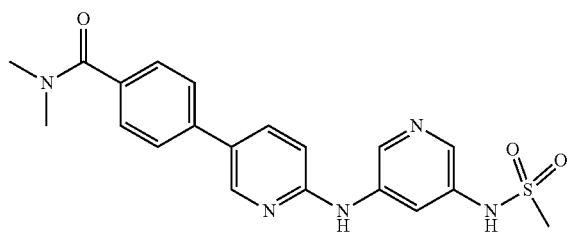 [SMILES: CN(C)C(=O)c1ccc(-c2ccc(Nc3cncc(NS(C)(=O)=O)c3)nc2)cc1]

To a mixture of 4-(6-((5-aminopyridin-3-yl)amino)pyridin-3-yl)-N,N-dimethylbenzamide (160 mg, 0.48 mmol) in DCM (8 mL) was added TEA (121 mg, 1.20 mmol) and MsCl (110 mg, 0.96 mmol, 0.7 mL) dropwise and stirred at 25° C. for 20 h to give a brown solution. LCMS showed the reaction was incomplete. MsCl (110 mg, 0.7 mL) was added into the above mixture and stirred for another 16 h to give a brown suspension. LCMS (Rt=0.692 min; MS Calc'd:

411.1; MS Found: 412.1 [M+H]⁺). The mixture was concentrated under reduced pressure to give a residue. The residue was purified by prep-HPLC (0.05% NH$_3$.H$_2$O as an additive) to give N,N-dimethyl-4-(6-((5-(methylsulfonamido)pyridin-3-yl)amino)pyridin-3-yl)benzamide (15.8 mg, yield: 8%) as an off-white solid. LCMS (Shimadzu LCMS 2010, Mobile phase: from 100% [water+0.04% TFA] to 40% [water+0.04% TFA] and 60% [MeCN+0.02% TFA] in 1.35 min, then under this condition for 0.9 min, finally changed to 100% [water+0.04% TFA] and under this condition for 0.75 min) purity is 98.73%, Rt=1.486 min; MS Calc'd.: 411.1; MS Found: 412.0 [M+H]⁺. ¹H NMR (400 MHz, DMSO-d$_6$) δ 2.90-3.04 (9H, m), 7.48 (2H, d, J=8.4 Hz), 7.73 (2H, d, J=8.4 Hz), 7.94 (1H, d, J=2.0 Hz), 7.99 (1H, dd, J=8.8, 2.4 Hz), 8.04 (1H, t, J=2.4 Hz), 8.56 (1H, d, J=2.4 Hz), 8.67 (1H, d, J=2.4 Hz), 9.47 (1H, br s).

Example 128: N-(5-((5-(4-(dimethylcarbamoyl)phenyl)pyridin-2-yl)amino)pyridin-3-yl)picolinamide

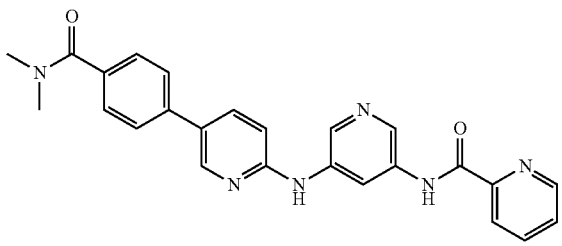 [SMILES: CN(C)C(=O)c1ccc(-c2ccc(Nc3cncc(NC(=O)c4ccccn4)c3)nc2)cc1]

To a mixture of picolinic acid (28 mg, 0.23 mmol) in pyridine (2 mL) was added EDC.HCl (43 mg, 0.225 mmol) and 4-(6-((5-aminopyridin-3-yl)amino)pyridin-3-yl)-N,N-dimethylbenzamide (50 mg, 0.15 mmol), the reaction mixture was stirred at 50° C. for 2 h to give a brown solution. LCMS (Rt=1.163 min; MS Calc'd: 438.2; MS Found: 439.2 [M+H]⁺). The mixture was concentrated under reduced pressure to give a residue. The residue was purified by washing with MeOH (5 mL) to give a crude product. The crude product was further purified by prep-HPLC (0.05% NH$_3$.H$_2$O as an additive) to give an impure product (25 mg, LCMS purity is 94.6%). The impure product was further purified by washing with MeOH (5 mL) to give N-(5-((5-(4-(dimethylcarbamoyl)phenyl)pyridin-2-yl)amino)pyridin-3-yl)picolinamide (9.7 mg, yield: 15%) as a pale yellow solid. LCMS (Shimadzu LCMS 2010, Mobile phase: from 100% [water+0.04% TFA] to 40% [water+0.04% TFA] and 60% [MeCN+0.02% TFA] in 1.35 min, then under this condition for 0.9 min, finally changed to 100% [water+0.04% TFA] and under this condition for 0.75 min) purity is 100%, Rt=1.575 min; MS Calc'd.: 438.2; MS Found: 439.1 [M+H]⁺. ¹H NMR (400 MHz, DMSO-d$_6$) δ 2.98 (6H, s), 7.01 (1H, d, J=8.4 Hz), 7.49 (2H, d, J=8.0 Hz), 7.69-7.80 (3H, m), 8.01 (1H, dd, J=8.4, 2.4 Hz), 8.10 (1H, t, J=1.2 Hz), 8.19 (1H, d, J=7.6 Hz), 8.60 (2H, d, J=2.8 Hz), 8.71-8.85 (3H, m), 9.51 (1H, br s), 10.82 (1H, br s).

Example 129: N-(5-((5-(4-(dimethylcarbamoyl)phenyl)pyridin-2-yl)amino)pyridin-3-yl)nicotinamide

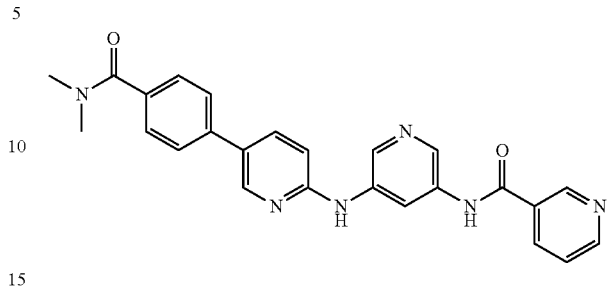

To a mixture of nicotinic acid (33 mg, 0.27 mmol) in pyridine (2 mL) was added EDC.HCl (52 mg, 0.27 mmol) and 4-(6-((5-aminopyridin-3-yl)amino)pyridin-3-yl)-N,N-dimethylbenzamide (60 mg, 0.18 mmol), the resulting mixture was stirred at 50° C. for 2 h to give a brown solution. LCMS (Rt=0.690 min; MS Calc'd: 438.2; MS Found: 439.1 [M+H]⁺). The mixture was concentrated under reduced pressure to give a residue. The residue was purified by washing with MeOH (5 mL). The filter cake was further purified by prep-HPLC (0.225% FA as an additive) and lyophilized to give N-(5-((5-(4-(dimethylcarbamoyl)phenyl)pyridin-2-yl)amino)pyridin-3-yl)nicotinamide (20.6 mg, yield: 26%) as a white solid. LCMS (Shimadzu LCMS 2010, Mobile phase: from 100% [water+0.04% TFA] to 40% [water+0.04% TFA] and 60% [MeCN+0.02% TFA] in 1.35 min, then under this condition for 0.9 min, finally changed to 100% [water+0.04% TFA] and under this condition for 0.75 min) purity is 100%, Rt=1.452 min; MS Calc'd.: 438.2; MS Found: 439.1 [M+H]⁺. ¹H NMR (400 MHz, DMSO-d$_6$) δ 2.91-3.05 (6H, m), 7.03 (1H, d, J=8.4 Hz), 7.49 (2H, d, J=8.8 Hz), 7.60-7.64 (1H, m), 7.74 (2H, d, J=8.8 Hz), 8.04 (1H, dd, J=8.4, 2.4 Hz), 8.33-8.37 (1H, m), 8.60 (2H, dd, J=8.0, 2.4 Hz), 8.76-8.78 (1H, m), 8.80 (1H, dd, J=4.8, 1.6 Hz), 8.85-8.88 (1H, m), 9.13-9.17 (1H, m), 9.74 (1H, br s), 10.79 (1H, br s).

Example 130: N-(5-((5-(4-(dimethylcarbamoyl)phenyl)pyridin-2-yl)amino)pyridin-3-yl)isonicotinamide

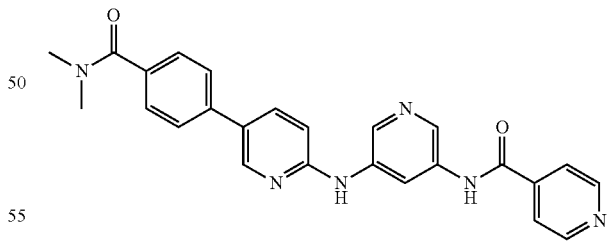

To a mixture of isonicotinic acid (28 mg, 0.23 mmol) in DMF (5 mL) was added TEA (38 mg, 0.37 mmol) and HATU (143 mg, 0.375 mmol), the reaction mixture was stirred at 25° C. for 0.5 hour, then added 4-(6-((5-aminopyridin-3-yl)amino)pyridin-3-yl)-N,N-dimethylbenzamide (50 mg, 0.15 mmol), the resulting mixture was stirred at 25° C. for 16 h to give a saffron solution. LCMS (Rt=0.706 min; MS Calc'd: 438.2; MS Found: 439.2 [M+H]⁺). The mixture was diluted with water (10 mL), then extracted with DCM (10 mL×2), the combined extracts were washed with brine (15 mL×2), dried over Na₂SO₄, filtered and concentrated under reduced pressure to give a residue. The residue was purified by washing with MeOH (5 mL). The filter cake was further purified by prep-HPLC (0.05% NH₃.H₂O as an additive) and lyophilized to give N-(5-((5-(4-(dimethylcarbamoyl)phenyl)pyridin-2-yl)amino)pyridin-3-yl)isonicotinamide (12.5 mg, yield: 18%) as a white solid. LCMS (Shimadzu LCMS 2010, Mobile phase: from 100% [water+0.04% TFA] to 40% [water+0.04% TFA] and 60% [MeCN+0.02% TFA] in 1.35 min, then under this condition for 0.9 min, finally changed to 100% [water+0.04% TFA] and under this condition for 0.75 min) purity is 96.50%, Rt=1.466 min; MS Calc'd.: 438.2; MS Found: 439.1 [M+H]⁺. ¹H NMR (400 MHz, DMSO-d₆) δ 2.91-3.05 (6H, m), 7.01 (1H, d, J=8.8 Hz), 7.49 (2H, d, J=8.4 Hz), 7.73 (2H, d, J=8.4 Hz), 7.85-7.96 (2H, m), 8.01 (1H, dd, J=8.4, 2.4 Hz), 8.51 (1H, d, J=2.0 Hz), 8.59 (1H, d, J=2.4 Hz), 8.67-8.75 (2H, m), 8.78-8.83 (2H, m), 9.54 (1H, br s), 10.69 (1H, br s).

Example 131: 2-amino-N-(5-((5-(4-(dimethylcarbamoyl)phenyl)pyridin-2-yl)amino)pyridin-3-yl)isonicotinamide

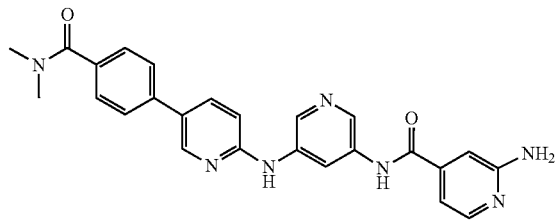 [SMILES: CN(C)C(=O)c1ccc(-c2ccc(Nc3cncc(NC(=O)c4ccnc(N)c4)c3)nc2)cc1]

To a mixture of 2-aminoisonicotinic acid (37 mg, 0.27 mmol) in pyridine (2 mL) was added EDC.HCl (69 mg, 0.36 mmol) and 4-(6-((5-aminopyridin-3-yl)amino)pyridin-3-yl)-N,N-dimethylbenzamide (60 mg, 0.18 mmol), the resulting mixture was stirred at 50° C. for 2 h to give a saffron solution. LCMS (Rt=0.685 min; MS Calc'd: 453.2; MS Found: 489.2 [M+Na]+). The mixture was concentrated under reduced pressure to give a residue. The residue was purified by washing with MeOH/water (5 mL/1 mL) to give a crude product. Then further purified by prep-HPLC (0.225% FA as an additive) and lyophilized to give 2-amino-N-(5-((5-(4-(dimethylcarbamoyl)phenyl)pyridin-2-yl)amino)pyridin-3-yl)isonicotinamide (16.2 mg, yield: 20%) as a pale yellow powder. LCMS (Shimadzu LCMS 2010, Mobile phase: from 100% [water+0.04% TFA] to 40% [water+0.04% TFA] and 60% [MeCN+0.02% TFA] in 1.35 min, then under this condition for 0.9 min, finally changed to 100% [water+0.04% TFA] and under this condition for 0.75 min) purity is 99.45%, Rt=1.386 min; MS Calc'd.: 453.2; MS Found: 454.1 [M+H]⁺. ¹H NMR (400 MHz, DMSO-d₆) δ 2.91-3.04 (6H, m), 6.25 (2H, br s), 6.86-6.89 (1H, m), 6.95 (1H, dd, J=5.6, 1.6 Hz), 7.00 (1H, d, J=8.8 Hz), 7.48 (2H, d, J=8.4 Hz), 7.73 (2H, d, J=8.4 Hz), 8.00 (1H, dd, J=8.8, 2.4 Hz), 8.08 (1H, d, J=5.2 Hz), 8.46 (1H, d, J=2.0 Hz), 8.58 (1H, d, J=2.4 Hz), 8.66 (1H, t, J=2.0 Hz), 8.73 (1H, d, J=2.4 Hz), 9.52 (1H, br s), 10.48 (1H, br s).

Example 132: N-(5-((5-(4-(dimethylcarbamoyl)phenyl)pyridin-2-yl)amino)pyridin-3-yl)-1-hydroxy-1,3-dihydrobenzo[c][1,2]oxaborole-5-carboxamide

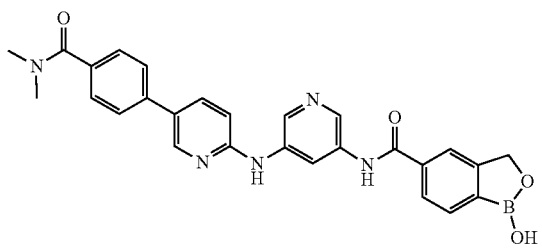 [SMILES: CN(C)C(=O)c1ccc(-c2ccc(Nc3cncc(NC(=O)c4ccc5c(c4)COB5O)c3)nc2)cc1]

Step 1: Preparation of 3-(acetoxymethyl)-4-bromobenzoic acid

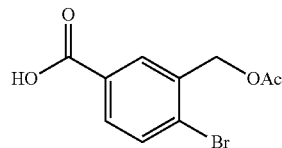 [SMILES: CC(=O)OCc1cc(C(=O)O)ccc1Br]

To a mixture of 4-bromo-3-(hydroxymethyl)benzoic acid (300 mg, 1.30 mmol) in pyridine (10 mL) was added Ac₂O (132 mg, 1.30 mmol), the reaction mixture was stirred at 25° C. for 2 h to give a yellow solution. LCMS showed the reaction was completed. The mixture was concentrated under reduced pressure to remove pyridine. The mixture was diluted with water (10 mL). The mixture was adjust to pH=2 with HCl (2M). The mixture was extracted with EtOAc (20 mL×2). The combined extracts were washed with brine (30 mL×2), dried over Na₂SO₄, filtered and concentrated under reduced pressure to give 3-(acetoxymethyl)-4-bromobenzoic acid (320 mg, yield: 90%) as a white solid. ¹H NMR (400 MHz, DMSO-d₆) δ 2.11 (3H, s), 5.16 (2H, s), 7.81-7.84 (2H, m), 8.00-8.03 (1H, m).

Step 2: Preparation of 2-bromo-5-((5-((5-(4-(dimethylcarbamoyl)phenyl)pyridin-2-yl)amino)pyridin-3-yl)carbamoyl)benzylacetate

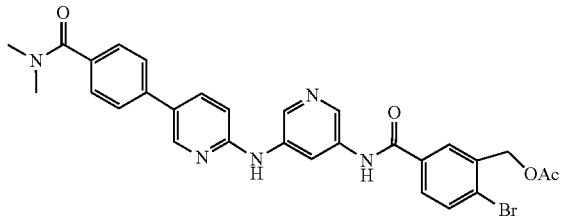 [SMILES: CC(=O)OCc1cc(C(=O)Nc2cncc(Nc3ccc(-c4ccc(C(=O)N(C)C)cc4)cn3)c2)ccc1Br]

To a mixture of 4-(6-((5-aminopyridin-3-yl)amino)pyridin-3-yl)-N,N-dimethylbenzamide (100 mg, 0.30 mmol) in pyridine (2 mL) was added 3-(acetoxymethyl)-4-bromobenzoic acid (164 mg, 0.60 mmol) and EDC.HCl (115 mg, 0.60 mmol), the reaction mixture was stirred at 50° C. for 2 h to give a brown suspension. LCMS (Rt=0.626 min; MS Calc'd: 589.1; MS Found: 589.9 [M+H]⁺). The mixture was concentrated under reduced pressure to give a residue. The residue was purified by washing with MeCN/pentane (2 mL/6 mL) to give 2-bromo-5-((5-((5-(4-(dimethylcarbamoyl)phenyl)pyridin-2-yl)amino)pyridin-3-yl)carbamoyl)benzyl acetate (120 mg, yield: 68%) as an off-white solid. ¹H NMR (400 MHz, DMSO-d₆) δ 2.13 (3H, s), 2.90-3.08 (6H, m), 5.20 (2H, s), 7.00 (1H, d, J=8.4 Hz), 7.48 (2H, d, J=8.4 Hz), 7.73 (2H, d, J=8.4 Hz), 7.87 (1H, d, J=8.4 Hz), 7.90-7.94 (1H, m), 8.01 (1H, dd, J=8.8, 2.8 Hz), 8.06 (1H, d, J=2.0 Hz), 8.49 (1H, d, J=2.0 Hz), 8.58 (1H, d, J=2.8 Hz), 8.67-8.73 (2H, m), 9.53 (1H, br s), 10.57 (1H, br s).

Step 3: Preparation of 5-((5-((5-(4-(dimethylcarbamoyl)phenyl)pyridin-2-yl)amino)pyridin-3-yl)carbamoyl)-2-(4,4,5,5-tetramethyl-1,3,2-dioxaborolan-2-yl)benzyl acetate

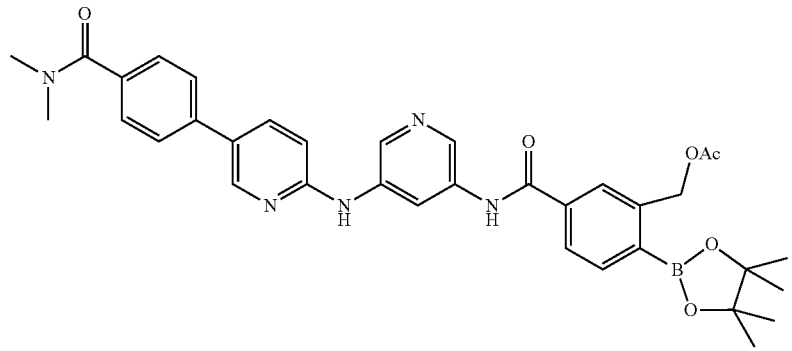

To a mixture of 2-bromo-5-((5-((5-(4-(dimethylcarbamoyl)phenyl)pyridin-2-yl)amino)pyridin-3-yl)carbamoyl)benzyl acetate (120 mg, 0.20 mmol) in dioxane (10 mL) was added B₂Pin₂ (78 mg, 0.30 mmol), Pd(dppf)Cl₂ (15 mg, 0.02 mmol) and KOAc (60 mg, 0.61 mmol), the reaction mixture was stirred at 100° C. under N₂ atmosphere for 16 h to give a brown suspension. LCMS (Rt=0.825 min; MS Calc'd: 635.3; MS Found: 636.3 [M+H]⁺). The mixture was diluted with water (20 mL) and extracted with EtOAc (25 mL×2). The combined extracts were washed with brine (30 mL×2), dried over Na₂SO₄, filtered and concentrated under reduced pressure to give a residue. The residue was purified by Combi FlashCombi Flash (DCM:MeOH=100:1 to 95:5) to give 5-((5-((5-(4-(dimethylcarbamoyl)phenyl)pyridin-2-yl)amino)pyridin-3-yl)carbamoyl)-2-(4,4,5,5-tetramethyl-1,3,2-dioxaborolan-2-yl)benzyl acetate (100 mg, yield: 35%) as an off-white solid.

LCMS purity is 45%, Rt=0.846 min; MS Calc'd: 635.3; MS Found: 636.3 [M+H]⁺).

Step 4: Preparation of N-(5-((5-(4-(dimethylcarbamoyl)phenyl)pyridin-2-yl)amino)pyridin-3-yl)-1-hydroxy-1,3-dihydrobenzo[c][1,2]oxaborole-5-carboxamide

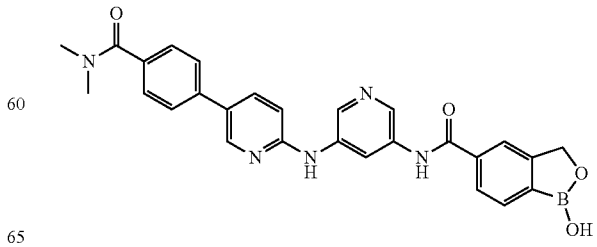

To a mixture of 5-((5-((5-(4-(dimethylcarbamoyl)phenyl)pyridin-2-yl)amino)pyridin-3-yl)carbamoyl)-2-(4,4,5,5-tetramethyl-1,3,2-dioxaborolan-2-yl)benzyl acetate (100 mg, crude) in MeOH (5 mL) was added NaOH (12 mg, 0.31 mmol) in MeOH (1 mL) dropwise. The reaction mixture was stirred at 40° C. for 6 h to give a brown solution. LCMS (Rt=0.677 min; MS Calc'd: 493.2; MS Found: 494.1 [M+H]$^+$). The mixture was concentrated under reduced pressure to give a residue. The residue was purified by prep-HPLC (0.05% NH$_3$.H$_2$O as an additive) purification to give an impure product. Then further purified by washing with MeOH/MeCN (1 mL/4 mL) to give N-(5-((5-(4-(dimethylcarbamoyl)phenyl)pyridin-2-yl)amino)pyridin-3-yl)-1-hydroxy-1,3-dihydrobenzo[c][1,2]oxaborole-5-carboxamide (8.0 mg, yield: 10%) as a white solid. LCMS (Shimadzu LCMS 2010, Mobile phase: from 100% [water+0.04% TFA] to 40% [water+0.04% TFA] and 60% [MeCN+0.02% TFA] in 1.35 min, then under this condition for 0.9 min, finally changed to 100% [water+0.04% TFA] and under this condition for 0.75 min) purity is 98.92%, Rt=1.594 min; MS Calc'd.: 493.2, MS Found: 494.0 [M+H]$^+$. $^1$H NMR (400 MHz, DMSO-d$_6$) δ 2.92-3.06 (6H, m), 5.10 (2H, s), 7.00 (1H, d, J=8.8 Hz), 7.48 (2H, d, J=8.4 Hz), 7.73 (2H, d, J=8.4 Hz), 7.88 (1H, d, J=8.0 Hz), 7.94 (1H, d, J=7.6 Hz), 7.97-8.05 (2H, m), 8.50 (1H, d, J=2.0 Hz), 8.58 (1H, d, J=2.4 Hz), 8.70 (1H, t, J=2.4 Hz), 8.73 (1H, d, J=2.4 Hz), 9.40 (1H, br s), 9.51 (1H, br s), 10.52 (1H, br s).

Example 133: N-(5-((5-(4-(dimethylcarbamoyl)phenyl)pyridin-2-yl)amino)pyridin-3-yl)-1-hydroxy-1,3-dihydrobenzo[c][1,2]oxaborole-6-carboxamide

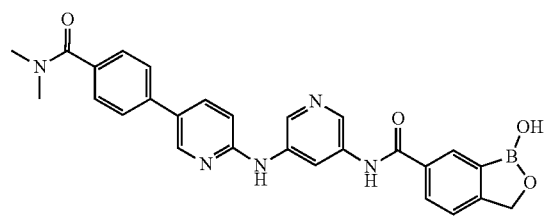 [SMILES: CN(C)C(=O)c1ccc(-c2ccc(Nc3cncc(NC(=O)c4ccc5c(c4)B(O)OC5)c3)nc2)cc1]

Step 1: Preparation of 3-bromo-4-(hydroxymethyl)benzoic acid

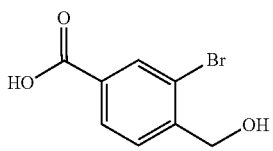 [SMILES: O=C(O)c1ccc(CO)c(Br)c1]

To a mixture of 3-bromo-4-formylbenzoic acid (300 mg, 1.31 mmol) in THF (15 mL) was added NaBH$_4$ (50 mg, 1.3 mmol) in portions at 0° C., then warmed to 20° C. and stirred for 3 h to give a black suspension. LCMS showed the reaction was completed. The mixture was quenched with water (15 mL), then adjust to pH=1 with HCl (1M). The mixture was extracted with EtOAc (15 mL×2). The combined extracts were washed with brine (20 mL×2), dried over Na$_2$SO$_4$, filtered and concentrated under reduced pressure to give 3-bromo-4-(hydroxymethyl)benzoic acid (280 mg, yield: 92%) as a white solid. $^1$H NMR (400 MHz, DMSO-d$_6$) δ 4.55 (2H, d, J=5.2 Hz), 5.62 (1H, t, J=5.2 Hz), 7.67 (1H, d, J=7.6 Hz), 7.96 (1H, dd, J=8.0, 1.2 Hz), 8.03 (1H, d, J=1.2 Hz).

Step 2: Preparation of 4-(acetoxymethyl)-3-bromobenzoic acid

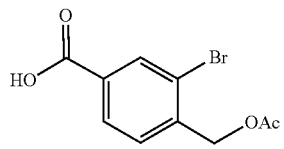

To a mixture of 3-bromo-4-(hydroxymethyl)benzoic acid (280 mg, 1.21 mmol) in pyridine (10 mL) was added Ac$_2$O (124 mg, 1.21 mmol), the reaction mixture was stirred at 25° C. for 2 h to give a yellow solution. LCMS showed the reaction was completed. The mixture was concentrated under reduced pressure to remove pyridine and then diluted with water (20 mL). The mixture was adjust to pH=1 with HCl (2M). The mixture was extracted with DCM (20 mL×2). The combined extracts were washed with brine (25 mL×2), dried over Na$_2$SO$_4$, filtered and concentrated under reduced pressure to give 4-(acetoxymethyl)-3-bromobenzoic acid (300 mg, yield: 91%) as a white solid. $^1$H NMR (400 MHz, DMSO-d$_6$) δ 2.13 (3H, s), 5.16 (2H, s), 7.60 (1H, d, J=8.0 Hz), 7.95 (1H, dd, J=8.0, 1.6 Hz), 8.10 (1H, d, J=1.6 Hz).

Step 3: Preparation of 2-bromo-4-((5-((5-(4-(dimethylcarbamoyl)phenyl)pyridin-2-yl)amino)pyridin-3-yl)carbamoyl)benzylacetate

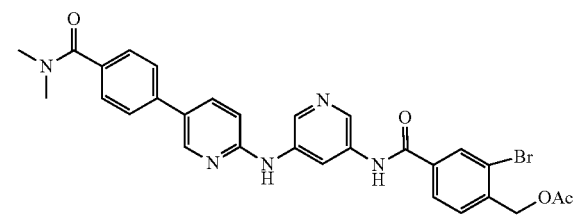 [SMILES: CC(=O)OCc1ccc(C(=O)Nc2cncc(Nc3ccc(-c4ccc(C(=O)N(C)C)cc4)cn3)c2)cc1Br]

To a mixture of 4-(6-((5-aminopyridin-3-yl)amino)pyridin-3-yl)-N,N-dimethylbenzamide (50 mg, 0.15 mmol) in pyridine (2 mL) was added 4-(acetoxymethyl)-3-bromobenzoic acid (82 mg, 0.30 mmol) and EDC.HCl (57 mg, 0.30 mmol), the reaction mixture was stirred at 50° C. for 2 h to give a brown suspension. LCMS (Rt=0.725 min; MS Calc'd: 589.1; MS Found: 590.0 [M+H]$^+$). The mixture was concentrated under reduced pressure to give a residue. The residue was purified by washing with MeOH (3 mL) twice to give 2-bromo-4-((5-((5-(4-(dimethylcarbamoyl)phenyl)pyridin-2-yl)amino)pyridin-3-yl)carbamoyl)benzyl acetate (75 mg, yield: 82%) as an off-white solid. $^1$H NMR (400 MHz, DMSO-d$_6$) δ 2.14 (3H, s), 2.92-3.08 (6H, m), 5.20 (2H, s), 7.01 (1H, d, J=8.4 Hz), 7.48 (2H, d, J=8.4 Hz), 7.65 (1H, d, J=8.0 Hz), 7.73 (2H, d, J=8.4 Hz), 7.94-8.04 (2H, m), 8.27 (1H, d, J=2.0 Hz), 8.50 (1H, d, J=2.0 Hz), 8.59 (1H, d, J=2.4 Hz), 8.65-8.74 (2H, m), 9.52 (1H, br s), 10.54 (1H, br s).

Step 4: Preparation of 4-((5-((5-(4-(dimethylcarbamoyl)phenyl)pyridin-2-yl)amino)pyridin-3-yl)carbamoyl)-2-(4,4,5,5-tetramethyl-1,3,2-dioxaborolan-2-yl)benzyl acetate

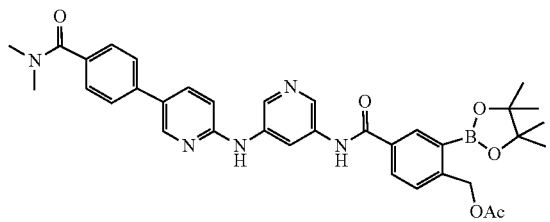

To a mixture of 2-bromo-4-((5-((5-(4-(dimethylcarbamoyl)phenyl)pyridin-2-yl)amino)pyridin-3-yl)carbamoyl)benzyl acetate (130 mg, 0.221 mmol) in dioxane (10 mL) was added B$_2$Pin$_2$ (84 mg, 0.33 mmol), Pd(dppf)Cl$_2$ (16 mg, 0.022 mmol) and KOAc (65 mg, 0.66 mmol), the reaction mixture was stirred at 100° C. under N$_2$ atmosphere for 16 h to give a brown suspension. LCMS is 63% (Rt=0.677 min; MS Calc'd: 635.3; MS Found: 636.0 [M+H]$^+$). The mixture was diluted with water (15 mL) and extracted with EtOAc (20 mL×2). The combined extracts were washed with brine (20 mL×2), dried over Na$_2$SO$_4$, filtered and concentrated under reduced pressure to give 4-((5-((5-(4-(dimethylcarbamoyl)phenyl)pyridin-2-yl)amino)pyridin-3-yl)carbamoyl)-2-(4,4,5,5-tetramethyl-1,3,2-dioxaborolan-2-yl)benzyl acetate (120 mg, yield: 85%) as a black gum.

Step 5: Preparation of N-(5-((5-(4-(dimethylcarbamoyl)phenyl)pyridin-2-yl)amino)pyridin-3-yl)-1-hydroxy-1,3-dihydrobenzo[c][1,2]oxaborole-6-carboxamide

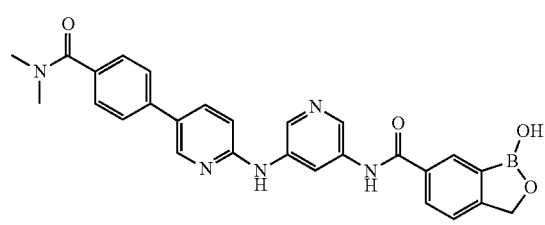 [SMILES: CN(C)C(=O)c1ccc(-c2ccc(Nc3cncc(NC(=O)c4ccc5c(c4)B(O)OC5)c3)nc2)cc1]

To a mixture of 4-((5-((5-(4-(dimethylcarbamoyl)phenyl)pyridin-2-yl)amino)pyridin-3-yl)carbamoyl)-2-(4,4,5,5-tetramethyl-1,3,2-dioxaborolan-2-yl)benzyl acetate (60 mg, 0.09 mmol) in MeOH (5 mL) was added NaOH (8 mg, 0.2 mmol) in MeOH (1 mL) dropwise. The reaction mixture was stirred at 40° C. for 6 h to give a brown suspension. The reaction was repeated once. LCMS (batch 1) (Rt=0.786 min; MS Calc'd: 493.2; MS Found: 494.0 [M+H]$^+$). LCMS (batch 2) (Rt=0.782 min; MS Calc'd: 493.2; MS Found: 494.3 [M+H]$^+$). The two batches were combined and concentrated under reduced pressure respective to give a residue. The residue was purified by prep-HPLC (0.01% NH$_4$HCO$_3$ as an additive) to give N-(5-((5-(4-(dimethylcarbamoyl)phenyl)pyridin-2-yl)amino)pyridin-3-yl)-1-hydroxy-1,3-dihydrobenzo[c][1,2]oxaborole-6-carboxamide (30.7 mg, yield: 32%) as a white solid. LCMS (Shimadzu LCMS 2010, Mobile phase: from 100% [water+0.04% TFA] to 40% [water+0.04% TFA] and 60% [MeCN+0.02% TFA] in 1.35 min, then under this condition for 0.9 min, finally changed to 100% [water+0.04% TFA] and under this condition for 0.75 min) purity is 97.81%, Rt=1.569 min; MS Calc'd.: 493.2, MS Found: 494.2 [M+H]$^+$. $^1$H NMR (400 MHz, DMSO-d$_6$) δ 2.93-3.04 (6H, m), 5.09 (2H, s), 7.01 (1H, d, J=8.8 Hz), 7.48 (2H, d, J=8.4 Hz), 7.58 (1H, d, J=8.0 Hz), 7.73 (2H, d, J=8.4 Hz), 8.01 (1H, dd, J=8.4, 2.4 Hz), 8.08 (1H, dd, J=8.0, 1.6 Hz), 8.36 (1H, d, J=2.0 Hz), 8.51 (1H, d, J=2.0 Hz), 8.59 (1H, d, J=2.8 Hz), 8.68-8.75 (2H, m), 9.39 (1H, br s), 9.51 (1H, br s), 10.51 (1H, br s).

Example 134: 4-(6-((5-(3-(3-aminobenzyl)-2-oxopyrrolidin-1-yl)pyridin-3-yl)amino)pyridin-3-yl)-N,N-dimethylbenzamide

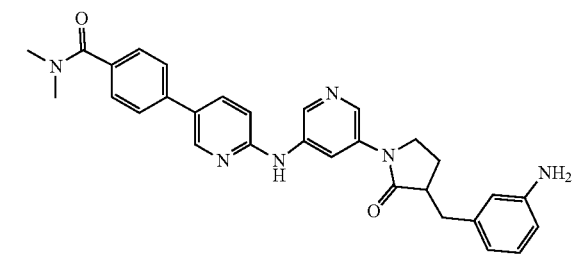 [SMILES: CN(C)C(=O)c1ccc(-c2ccc(Nc3cncc(N4CCC(Cc5cccc(N)c5)C4=O)c3)nc2)cc1]

Step 1: Preparation of 1-(5-bromopyridin-3-yl)pyrrolidin-2-one

To a mixture of pyrrolidin-2-one (4.00 g, 47.0 mmol), 3,5-dibromopyridine (11.1 g, 47.0 mmol) in dioxane (120 mL) was added CuI (895 mg, 4.70 mmol), TMEDA (546 mg, 4.70 mmol) and K$_2$CO$_3$ (9.74 g, 70.50 mmol). The reaction mixture was stirred at 110° C. under N$_2$ atmosphere for 16 h to give a blue suspension. LCMS (Rt=0.800 min; MS Calc'd: 242.0; MS Found: 242.7 [M+H]$^+$). The mixture was cooled to room temperature. Then diluted with water (40 mL) and extracted with EtOAc (50 mL×2). The combined extracts were washed with brine (50 mL×2), dried over Na$_2$SO$_4$, filtered and concentrated under reduced pressure to give a residue. The residue was purified by Combi Flash (pentane:EtOAc=4:1 to 1:1 to 1:3) to give 1-(5-bromopyridin-3-yl)pyrrolidin-2-one (0.8 g, yield: 7%) as an off-white solid. $^1$H NMR (400 MHz, DMSO-d$_6$) δ 2.02-2.13 (2H, m), 2.50-2.56 (2H, m), 3.88 (2H, t, J=7.2 Hz), 8.43 (1H, t, J=2.0 Hz), 8.46 (1H, d, J=1.6 Hz), 8.84 (1H, d, J=2.0 Hz).

Step 2: Preparation of 1-(5-bromopyridin-3-yl)-3-(3-nitrobenzyl)pyrrolidin-2-one

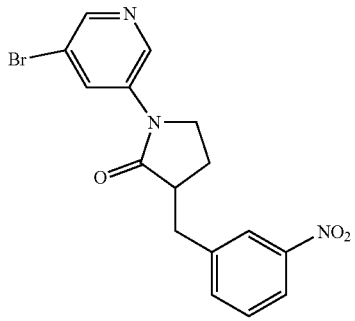 [SMILES: O=C1C(Cc2cccc([N+](=O)[O-])c2)CCN1c1cncc(Br)c1]

To a mixture of LHMDS (1 M, 2.05 mL) in THF (8 mL) was added 1-(5-bromopyridin-3-yl)pyrrolidin-2-one (0.45 g, 1.9 mmol) in THF (8 mL) dropwise at −78° C. and stirred for 0.5 hour, then added 1-(bromomethyl)-3-nitrobenzene (484 mg, 2.24 mmol) in THF (8 mL) dropwise at −78° C., then warmed to room temperature (20° C.) and stirred for another 16 h to give a yellow solution. LCMS (Rt=0.667 min; MS Calc'd: 375.0; MS Found: 375.8 [M+H]$^+$). The mixture was quenched saturated NH$_4$Cl solution (30 mL), then extracted with EtOAc (40 mL×2), the combined extracts were washed with brine (40 mL×2), dried over Na$_2$SO$_4$, filtered and concentrated under reduced pressure to give a residue. The residue was purified by Combi Flash (pentane:EtOAc=3:1 to 1:1 to 1:3) to give 1-(5-bromopyridin-3-yl)-3-(3-nitrobenzyl)pyrrolidin-2-one (200 mg, yield: 26%) as a white solid. $^1$H NMR (400 MHz, DMSO-d$_6$) δ 1.72-1.85 (1H, m), 2.04-2.13 (1H, m), 2.85-2.94 (1H, m), 3.03-3.14 (1H, m), 3.20-3.29 (1H, m), 3.69-3.82 (2H, m), 7.62 (1H, t, J=8.0 Hz), 7.77 (1H, d, J=7.6 Hz), 8.10 (1H, dd, J=8.0, 1.6 Hz), 8.15-8.18 (1H, m), 8.43 (1H, t, J=2.0 Hz), 8.48 (1H, d, J=2.0 Hz), 8.86 (1H, d, J=2.0 Hz).

Step 3: Preparation of N,N-dimethyl-4-(6-((5-(3-(3-nitrobenzyl)-2-oxopyrrolidin-1-yl)pyridin-3-yl)amino)pyridin-3-yl)benzamide

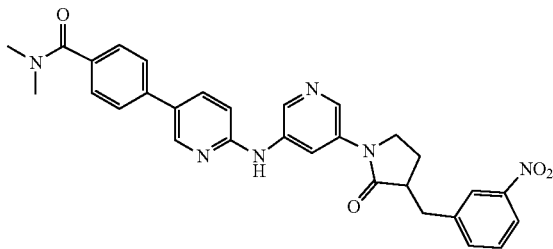 [SMILES: CN(C)C(=O)c1ccc(-c2ccc(Nc3cncc(N4CCC(Cc5cccc(N)c5)C4=O)c3)nc2)cc1]

A mixture of Pd$_2$(dba)$_3$ (24 mg, 0.026 mmol), Brettphos (14 mg, 0.026 mmol) in dioxane (2 mL) was stirred at 50° C. for 10 min. Then added 1-(5-bromopyridin-3-yl)-3-(3-nitrobenzyl)pyrrolidin-2-one (100 mg, 0.27 mmol), 4-(6-aminopyridin-3-yl)-N,N-dimethylbenzamide (96 mg, 0.40 mmol) and Cs$_2$CO$_3$ (173 mg, 0.53 mmol) in dioxane (3 mL). The reaction mixture was stirred at 100° C. under N$_2$ atmosphere for 16 h to give a brown suspension. LCMS (Rt=0.749 min; MS Calc'd: 536.2; MS Found: 537.1 [M+H]$^+$). The mixture was cooled to room temperature and filtered. The filter cake was washed with DCM (8 mL×2). The filtrate was concentrated under reduced pressure to give a residue. The residue was purified by Combi Flash (DCM:MeOH=100:1 to 95:5 to 10:1) to give N,N-dimethyl-4-(6-((5-(3-(3-nitrobenzyl)-2-oxopyrrolidin-1-yl)pyridin-3-yl)amino)pyridin-3-yl)benzamide (120 mg, yield: 43%) as a yellow solid. Crude LCMS is 51% (Rt=1.732 min; MS Calc'd: 536.2; MS Found: 537.2 [M+H]$^+$).

Step 4: Preparation of 4-(6-((5-(3-(3-aminobenzyl)-2-oxopyrrolidin-1-yl)pyridin-3-yl)amino)pyridin-3-yl)-N,N-dimethylbenzamide

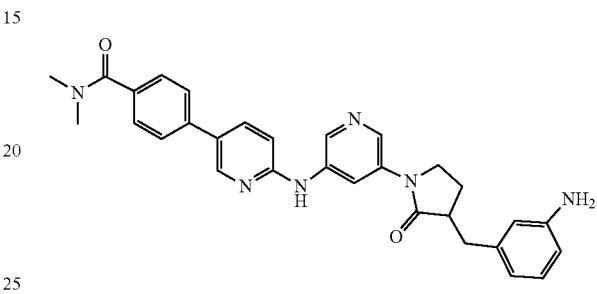

First Batch:

To a mixture of N,N-dimethyl-4-(6-((5-(3-(3-nitrobenzyl)-2-oxopyrrolidin-1-yl)pyridin-3-yl)amino)pyridin-3-yl)benzamide (30 mg, 0.056 mmol) in MeOH (10 mL) was added Pd/C (100 mg, 10% purity, 50% wet), the resulting mixture was purged in H$_2$ atmosphere for 3 times, then stirred at 20° C. under H$_2$ atmosphere (15 Psi) for 3 h to give a black suspension. LCMS (Rt=0.553 min; MS Calc'd: 506.2; MS Found: 507.1 [M+H]$^+$). The mixture was diluted with DMF (3 mL) and filtered. The filter cake was washed with hot MeOH (5 mL×2). The filtrate was concentrated under reduced pressure to give a residue. The residue was purified on next batch.

Second Batch: ES6958-73

To a mixture of N,N-dimethyl-4-(6-((5-(3-(3-nitrobenzyl)-2-oxopyrrolidin-1-yl)pyridin-3-yl)amino)pyridin-3-yl)benzamide (90 mg, 0.17 mmol) in MeOH (10 mL) was added Pd/C (100 mg, 10% purity, 50% wet), the resulting mixture was purged in H$_2$ atmosphere for 3 times, then stirred at 20° C. under H$_2$ atmosphere (15 Psi) for 3 h to give a black suspension. LCMS is 64% (Rt=0.687 min; MS Calc'd: 506.2; MS Found: 507.3 [M+H]$^+$). The mixture was diluted with DMF (5 mL) and filtered. The filter cake was washed with hot MeOH (10 mL×2). The filtrate was concentrated under reduced pressure to give a residue. The residue and first batch were combined and purified by prep-HPLC (0.05% NH$_3$.H$_2$O as an additive) and to give 4-(6-((5-(3-(3-aminobenzyl)-2-oxopyrrolidin-1-yl)pyridin-3-yl)amino)pyridin-3-yl)-N,N-dimethylbenzamide (14.1 mg, average yield: 12%) as a white solid. LCMS (Shimadzu LCMS 2010, Mobile phase: from 100% [water+0.04% TFA] to 40% [water+0.04% TFA] and 60% [MeCN+0.02% TFA] in 1.35 min, then under this condition for 0.9 min, finally changed to 100% [water+0.04% TFA] and under this condition for 0.75 min) purity is 100%, Rt=1.514 min; MS Calc'd: 506.2; MS Found: 507.1 [M+H]$^+$. $^1$H NMR (400 MHz, DMSO-d$_6$) δ 1.68-1.77 (1H, m), 2.06-2.18 (1H, m), 2.81-2.92 (1H, m), 2.92-3.06 (7H, m), 3.28-3.31 (1H, m), 3.65-3.78 (2H, m), 4.98 (2H, br s), 6.35-6.43 (2H, m), 6.43-6.49 (1H, m), 6.93 (1H, t, J=7.6 Hz), 6.99 (1H, d, J=8.4 Hz), 7.48 (2H, d, J=8.0 Hz), 7.74 (2H, d, J=8.4 Hz), 8.00

(1H, dd, J=8.4, 2.4 Hz), 8.40 (1H, d, J=2.0 Hz), 8.56-8.63 (2H, m), 8.78 (1H, d, J=2.0 Hz), 9.52 (1H, br s).

Example 135: N-(5-((5-(4-(dimethylcarbamoyl)phenyl)pyridin-2-yl)amino)pyridin-3-yl)-1H-indole-6-carboxamide

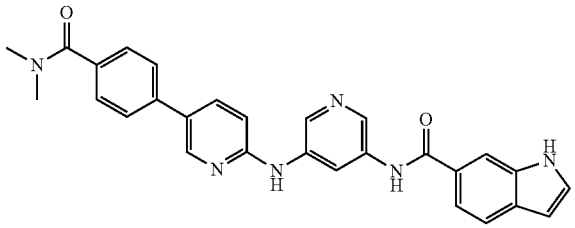 [SMILES: CN(C)C(=O)c1ccc(-c2ccc(Nc3cncc(NC(=O)c4ccc5cc[nH]c5c4)c3)nc2)cc1]

To a mixture of 4-(6-((5-aminopyridin-3-yl)amino)pyridin-3-yl)-N,N-dimethylbenzamide (50 mg, 0.15 mmol) in pyridine (2 mL) was added 1H-indole-6-carboxylic acid (36 mg, 0.22 mmol) and EDC.HCl (43 mg, 0.22 mmol), the reaction mixture was stirred at 50° C. for 2 h to give a brown solution. LCMS (Rt=1.189 min; MS Calc'd: 476.2; MS Found: 477.2 [M+H]$^+$). The mixture was concentrated under reduced pressure to give a residue. The residue was purified by washing with MeOH/water (5 mL/1 mL) to give a crude product. Then further purified by prep-HPLC (0.05% NH$_3$.H$_2$O as an additive) give a product (MeCN was confirmed by HNMR), then further purified by washing with MeOH (2 mL) to give N-(5-((5-(4-(dimethylcarbamoyl)phenyl)pyridin-2-yl)amino)pyridin-3-yl)-1H-indole-6-carboxamide (8.3 mg, yield: 11%) as a pale yellow solid. LCMS (Shimadzu LCMS 2010, Mobile phase: from 100% [water+0.04% TFA] to 40% [water+0.04% TFA] and 60% [MeCN+0.02% TFA] in 1.35 min, then under this condition for 0.9 min, finally changed to 100% [water+0.04% TFA] and under this condition for 0.75 min) purity is 98.28%, Rt=1.637 min; MS Calc'd.: 476.2; MS Found: 477.1 [M+H]$^+$. $^1$H NMR (400 MHz, DMSO-d$_6$) δ 2.95-3.04 (6H, m), 6.50-6.54 (1H, m), 7.01 (1H, d, J=8.4 Hz), 7.48 (2H, d, J=8.4 Hz), 7.57 (1H, t, J=2.8 Hz), 7.65-7.68 (2H, m), 7.74 (2H, d, J=8.0 Hz), 8.01 (1H, dd, J=8.4, 2.4 Hz), 8.09-8.13 (1H, m), 8.52 (1H, d, J=2.0 Hz), 8.59 (1H, d, J=2.8 Hz), 8.69-8.72 (2H, m), 9.49 (1H, br s), 10.35 (1H, br s), 11.50 (1H, br s).

Example 136: N-(5-((5-(4-(dimethylcarbamoyl)phenyl)pyridin-2-yl)amino)pyridin-3-yl)benzo[d]oxazole-6-carboxamide

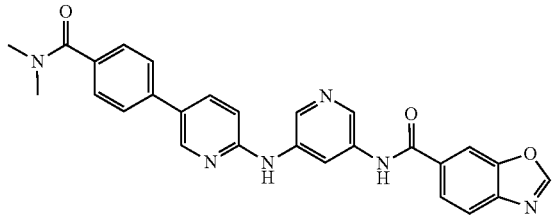 [SMILES: CN(C)C(=O)c1ccc(-c2ccc(Nc3cncc(NC(=O)c4ccc5ncoc5c4)c3)nc2)cc1]

To a mixture of 4-(6-((5-aminopyridin-3-yl)amino)pyridin-3-yl)-N,N-dimethylbenzamide (50 mg, 0.15 mmol) in pyridine (2 mL) was added benzo[d]oxazole-6-carboxylic acid (37 mg, 0.22 mmol) and EDC.HCl (43 mg, 0.22 mmol), the reaction mixture was stirred at 50° C. for 2 h to give a brown suspension. LCMS (Rt=1.152 min; MS Calc'd: 478.2; MS Found: 479.2 [M+H]$^+$). The mixture was concentrated under reduced pressure to give a residue. The residue was purified by washing with MeOH/water (5 mL/1 mL) to give a crude product. The impure product was further purified by prep-HPLC (0.05% NH$_3$.H$_2$O as an additive) to give an impure product. Then further purified by washing with MeOH (2 mL) to give N-(5-((5-(4-(dimethylcarbamoyl)phenyl)pyridin-2-yl)amino)pyridin-3-yl)benzo[d]oxazole-6-carboxamide (5.2 mg, yield: 7%) as a white solid. LCMS (Agilent LCMS 1200-6140A, mobile phase: from 99% [water+0.1% FA] and 1% [MeCN+0.1% FA] to 95% [water+0.1% FA] and 5% [MeCN+0.1% FA] in 0.6 min, then changed to 100% [MeCN+0.1% FA] under this condition for 3.4 min, finally back to 99% [water+0.1% FA] and 1% [MeCN+0.1% FA] and under this condition for 0.5 min.) purity is 98.01%, Rt=2.231 min; MS Calc'd.: 478.2; MS Found: 479.3 [M+H]$^+$. $^1$H NMR (400 MHz, DMSO-d$_6$) δ 2.94-3.06 (6H, m), 7.01 (1H, d, J=8.4 Hz), 7.49 (2H, d, J=8.4 Hz), 7.73 (2H, d, J=8.4 Hz), 7.97 (1H, d, J=8.4 Hz), 8.01 (1H, dd, J=8.4, 2.4 Hz), 8.07 (1H, dd, J=8.0, 2.0 Hz), 8.44 (1H, d, J=1.2 Hz), 8.53 (1H, d, J=2.0 Hz), 8.59 (1H, d, J=2.4 Hz), 8.70-8.75 (2H, m), 8.95 (1H, s), 9.53 (1H, br s), 10.55 (1H, br s), Example 137: N,N-dimethyl-4-(6-((5-(3-phenylpropanamido)pyridin-3-yl)amino)pyridin-3-yl)benzamide

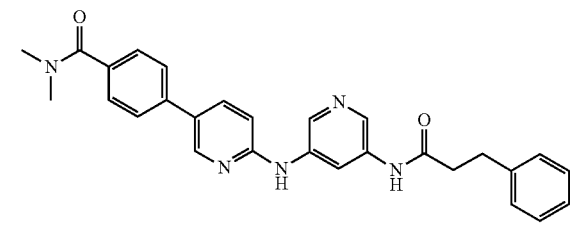 [SMILES: CN(C)C(=O)c1ccc(-c2ccc(Nc3cncc(NC(=O)CCc4ccccc4)c3)nc2)cc1]

To a mixture of 4-(6-((5-aminopyridin-3-yl)amino)pyridin-3-yl)-N,N-dimethylbenzamide (50 mg, 0.15 mmol) in pyridine (2 mL) was added 3-phenylpropanoic acid (34 mg, 0.22 mmol) and EDC.HCl (43 mg, 0.22 mmol), the reaction mixture was stirred at 50° C. for 2 h to give a brown solution. LCMS (Rt=0.783 min; MS Calc'd: 465.2; MS Found: 466.1 [M+H]$^+$). The mixture was concentrated under reduced pressure to give a residue. The residue was purified by washing with MeOH/water (5 mL/1 mL) to give a crude product. Then further purified by prep-HPLC (0.05% NH$_3$.H$_2$O as an additive) to give N,N-dimethyl-4-(6-((5-(3-phenylpropanamido)pyridin-3-yl)amino)pyridin-3-yl)benzamide (33.9 mg, yield: 49%) as a white solid. LCMS (Shimadzu LCMS 2010, Mobile phase: from 100% [water+0.04% TFA] to 40% [water+0.04% TFA] and 60% [MeCN+0.02% TFA] in 1.35 min, then under this condition for 0.9 min, finally changed to 100% [water+0.04% TFA] and under this condition for 0.75 min) purity is 100%, Rt=1.681 min; MS Calc'd: 465.2; MS Found: 466.1 [M+H]$^+$. $^1$H NMR (400 MHz, DMSO-d$_6$) δ 2.67 (2H, t, J=7.2 Hz), 2.91-3.05 (8H, m), 6.98 (1H, d, J=8.8 Hz), 7.12-7.20 (1H, m), 7.21-7.35 (4H, m), 7.48 (2H, d, J=8.0 Hz), 7.73 (2H, d, J=8.4 Hz), 7.99 (1H, dd, J=8.4, 2.4 Hz), 8.32 (1H, d, J=1.6 Hz), 8.50 (1H, d, J=2.0 Hz), 8.56 (1H, d, J=2.4 Hz), 8.65 (1H, d, J=2.4 Hz), 9.45 (1H, br s), 10.09 (1H, br s).

Example 138: N,N-dimethyl-4-(6-((5-(2-phenylcyclopropane-1-carboxamido)pyridin-3-yl)amino)pyridin-3-yl)benzamide

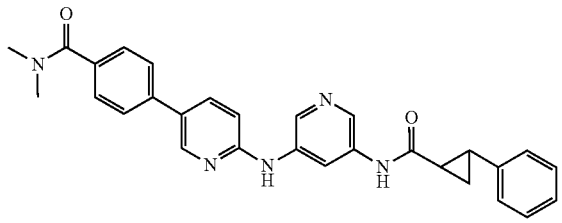 [SMILES: CN(C)C(=O)c1ccc(-c2ccc(Nc3cncc(NC(=O)C4CC4c4ccccc4)c3)nc2)cc1]

To a mixture of 4-(6-((5-aminopyridin-3-yl)amino)pyridin-3-yl)-N,N-dimethylbenzamide (50 mg, 0.15 mmol) in pyridine (2 mL) was added 2-phenylcyclopropane-1-carboxylic acid (36 mg, 0.22 mmol) and EDC.HCl (43 mg, 0.22 mmol), the reaction mixture was stirred at 50° C. for 2 h to give a brown solution. LCMS (Rt=0.848 min; MS Calc'd: 477.2; MS Found: 478.1 [M+H]$^+$). The mixture was concentrated under reduced pressure to give a residue. The residue was purified by washing with MeOH/water (5 mL/1 mL) to give a crude product. Then further purified by prep-HPLC (0.05% NH$_3$.H$_2$O as an additive) to give an impure product (30 mg, purity: 89.8%). Then further purified by prep-HPLC (0.225% FA as an additive) to give N,N-dimethyl-4-(6-((5-(2-phenylcyclopropane-1-carboxamido)pyridin-3-yl)amino)pyridin-3-yl)benzamide (23.9 mg, yield: 33%) as a white solid. LCMS (Agilent LCMS 1200-6140A, mobile phase: from 99% [water+0.1% FA] and 1% [MeCN+0.1% FA] to 95% [water+0.1% FA] and 5% [MeCN+0.1% FA] in 0.6 min, then changed to 100% [MeCN+0.1% FA] under this condition for 3.4 min, finally back to 99% [water+0.1% FA] and 1% [MeCN+0.1% FA] and under this condition for 0.5 min.) purity is 100%, Rt=2.568 min; MS Calc'd: 477.2; MS Found: 478.3 [M+H]$^+$. $^1$H NMR (400 MHz, DMSO-d$_6$) δ 1.38-1.47 (1H, m), 1.48-1.59 (1H, m), 2.11-2.22 (1H, m), 2.40-2.55 (1H, m), 2.90-3.06 (6H, m), 7.00 (1H, d, J=8.8 Hz), 7.16-7.23 (3H, m), 7.25-7.33 (2H, m), 7.49 (2H, d, J=8.4 Hz), 7.73 (2H, d, J=8.4 Hz), 7.95-8.04 (1H, m), 8.39-8.45 (1H, m), 8.52-8.60 (2H, m), 8.70-8.76 (1H, m), 9.61 (1H, br s), 10.55 (1H, br s).

Example 139: 4-(6-((5-(4-fluorobenzamido)pyridin-3-yl)amino)pyridin-3-yl)-N,N-dimethylbenzamide

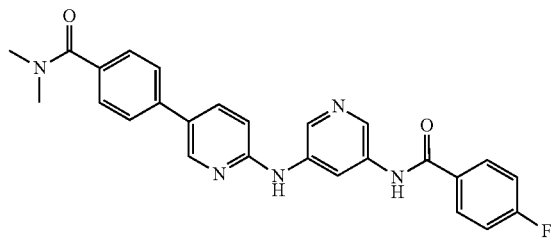 [SMILES: CN(C)C(=O)c1ccc(-c2ccc(Nc3cncc(NC(=O)c4ccc(F)cc4)c3)nc2)cc1]

To a mixture of 4-fluorobenzoic acid (32 mg, 0.22 mmol) in DMF (5 mL) was added HATU (142 mg, 0.37 mmol) and TEA (38 mg, 0.37 mmol), the reaction mixture was stirred at 25° C. for 0.5 hour, then added 4-(6-((5-aminopyridin-3-yl)amino)pyridin-3-yl)-N,N-dimethylbenzamide (50 mg, 0.15 mmol), the resulting mixture was stirred at 25° C. for 16 h to give a saffron solution. LCMS (Rt=0.752 min; MS Calc'd: 455.2; MS Found: 470.2 [M+H]$^+$). The mixture was diluted with water (10 mL), then extracted with DCM (10 mL×2). The combined extracts were washed with brine (15 mL×2), dried over Na$_2$SO$_4$, filtered and concentrated under reduced pressure to give a residue. The residue was purified by washing with MeOH (5 mL). The filter cake was further purified by prep-HPLC (0.05% NH$_3$.H$_2$O as an additive) purification to give 4-(6-((5-(4-fluorobenzamido)pyridin-3-yl)amino)pyridin-3-yl)-N,N-dimethylbenzamide (8.7 mg, yield: 13%) as a white solid. LCMS (Shimadzu LCMS 2010, Mobile phase: from 100% [water+0.04% TFA] to 40% [water+0.04% TFA] and 60% [MeCN+0.02% TFA] in 1.35 min, then under this condition for 0.9 min, finally changed to 100% [water+0.04% TFA] and under this condition for 0.75 min) purity is 100%, Rt=1.642 min; MS Calc'd: 455.2; MS Found: 456.1 [M+H]$^+$. $^1$H NMR (400 MHz, DMSO-d$_6$) δ 2.95-3.04 (6H, m), 7.00 (1H, d, J=8.8 Hz), 7.40 (2H, t, J=8.8 Hz), 7.48 (2H, d, J=8.4 Hz), 7.73 (2H, d, J=8.4 Hz), 7.98-8.03 (1H, m), 8.04-8.10 (2H, m), 8.49 (1H, d, J=2.4 Hz), 8.58 (1H, d, J=2.0 Hz), 8.68 (1H, t, J=2.4 Hz), 8.71 (1H, t, J=2.8 Hz), 9.52 (1H, br s), 10.45 (1H, br s).

Example 140: 4-(6-((5-(3-fluorobenzamido)pyridin-3-yl)amino)pyridin-3-yl)-N,N-dimethylbenzamide

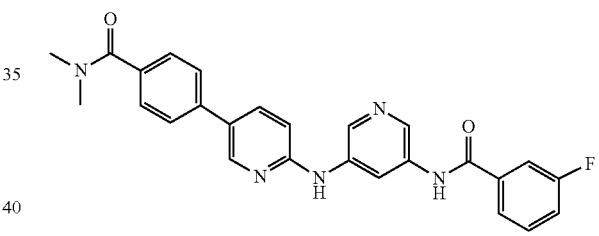

To a mixture of 3-fluorobenzoic acid (32 mg, 0.22 mmol) in DMF (5 mL) was added TEA (38 mg, 0.37 mmol) and HATU (142 mg, 0.37 mmol), the reaction mixture was stirred at 25° C. for 0.5 hour, then added 4-(6-((5-aminopyridin-3-yl)amino)pyridin-3-yl)-N,N-dimethylbenzamide (50 mg, 0.15 mmol). The resulting mixture was stirred at 25° C. for 16 h to give a saffron solution. LCMS (Rt=0.761 min; MS Calc'd: 455.2; MS Found: 478.2 [M+Na]+). The mixture was diluted with water (10 mL), then extracted with DCM (10 mL×2), the combined extracts were washed with brine (15 mL×2), dried over Na$_2$SO$_4$, filtered and concentrated under reduced pressure to give a residue. The residue was purified by washing with MeOH (5 mL). The filter cake was further purified by prep-HPLC (0.05% NH$_3$.H$_2$O as an additive) to give 4-(6-((5-(3-fluorobenzamido)pyridin-3-yl)amino)pyridin-3-yl)-N,N-dimethylbenzamide (11.4 mg, yield: 17%) as a white solid. LCMS (Shimadzu LCMS 2010, Mobile phase: from 100% [water+0.04% TFA] to 40% [water+0.04% TFA] and 60% [MeCN+0.02% TFA] in 1.35 min, then under this condition for 0.9 min, finally changed to 100% [water+0.04% TFA] and under this condition for 0.75 min) purity is 100%, Rt=1.639 min; MS Calc'd: 455.2; MS Found: 456.1 [M+H]$^+$. $^1$H NMR (400 MHz, DMSO-d$_6$) δ 2.91-3.04 (6H, m), 7.00 (1H, d, J=8.8 Hz), 7.46-7.52 (3H, m), 7.58-7.65 (1H, m), 7.73 (2H, d, J=8.4 Hz), 7.78-7.83

(1H, m), 7.83-7.87 (1H, m), 8.01 (1H, dd, J=8.8, 2.4 Hz), 8.50 (1H, d, J=2.0 Hz), 8.59 (1H, d, J=2.4 Hz), 8.70 (1H, d, J=2.4 Hz), 8.72 (1H, d, J=2.4 Hz), 9.53 (1H, br s), 10.51 (1H, br s).

Example 141: 4-(6-((5-(3-methoxybenzamido)pyridin-3-yl)amino)pyridin-3-yl)-N,N-dimethylbenzamide

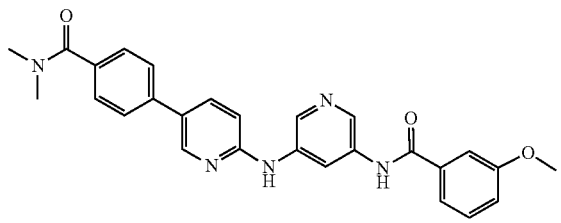

To a mixture of 4-(6-((5-aminopyridin-3-yl)amino)pyridin-3-yl)-N,N-dimethylbenzamide (50 mg, 0.15 mmol) in pyridine (2 mL) was added 3-methoxybenzoic acid (34 mg, 0.22 mmol) and EDC.HCl (43 mg, 0.22 mmol), the reaction mixture was stirred at 50° C. for 2 h to give a brown solution. LCMS (Rt=0.770 min; MS Calc'd: 467.2; MS Found: 468.1 [M+H]$^+$). The mixture was concentrated under reduced pressure to give a residue. The residue was purified by washing with MeOH/water (5 mL/1 mL) to give a crude product. Then further purified by prep-HPLC (0.05% NH$_3$.H$_2$O as an additive) to give 4-(6-((5-(3-methoxybenzamido)pyridin-3-yl)amino)pyridin-3-yl)-N,N-dimethylbenzamide (23.6 mg, yield: 34%) as a white solid. LCMS (Shimadzu LCMS 2010, Mobile phase: from 100% [water+0.04% TFA] to 40% [water+0.04% TFA] and 60% [MeCN+0.02% TFA] in 1.35 min, then under this condition for 0.9 min, finally changed to 100% [water+0.04% TFA] and under this condition for 0.75 min) purity is 100%, Rt=1.636 min; MS Calc'd: 467.2; MS Found: 468.1 [M+H]$^+$. $^1$H NMR (400 MHz, DMSO-d$_6$) δ 2.98 (6H, s), 3.85 (3H, s), 7.00 (1H, d, J=8.8 Hz), 7.19 (1H, dd, J=8.4, 2.4 Hz), 7.45-7.53 (4H, m), 7.58 (1H, d, J=8.0 Hz), 7.73 (2H, d, J=8.4 Hz), 8.00 (1H, dd, J=8.8, 2.4 Hz), 8.49 (1H, d, J=2.0 Hz), 8.59 (1H, d, J=2.4 Hz), 8.65-8.73 (2H, m), 9.50 (1H, br s), 10.39 (1H, br s).

Example 142: 4-(6-((5-(4-methoxybenzamido)pyridin-3-yl)amino)pyridin-3-yl)-N,N-dimethylbenzamide

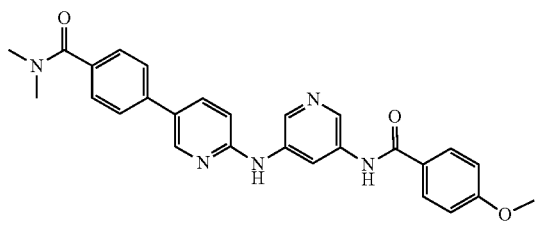

To a mixture of 4-(6-((5-aminopyridin-3-yl)amino)pyridin-3-yl)-N,N-dimethylbenzamide (50 mg, 0.15 mmol) in pyridine (2 mL) was added 3-methoxybenzoic acid (34 mg, 0.22 mmol) and EDC.HCl (43 mg, 0.22 mmol), the reaction mixture was stirred at 50° C. for 2 h to give a brown suspension. LCMS (Rt=0.778 min; MS Calc'd: 467.2; MS Found: 468.1 [M+H]$^+$). The mixture was concentrated under reduced pressure to give a residue. The residue was purified by washing with MeOH (5 mL) to give a crude product. Then further purified by prep-HPLC (0.05% NH$_3$.H$_2$O as an additive) to give 4-(6-((5-(4-methoxybenzamido)pyridin-3-yl)amino)pyridin-3-yl)-N,N-dimethylbenzamide (20.3 mg, yield: 29%) as a pale yellow powder. LCMS (Shimadzu LCMS 2010, Mobile phase: from 100% [water+0.04% TFA] to 40% [water+0.04% TFA] and 60% [MeCN+0.02% TFA] in 1.35 min, then under this condition for 0.9 min, finally changed to 100% [water+0.04% TFA] and under this condition for 0.75 min) purity is 100%, Rt=1.645 min; MS Calc'd: 467.2; MS Found: 468.1 [M+H]$^+$. $^1$H NMR (400 MHz, DMSO-d$_6$) δ 2.96-3.05 (6H, m), 3.85 (3H, s), 7.00 (1H, d, J=8.8 Hz), 7.09 (2H, d, J=8.4 Hz), 7.48 (2H, d, J=8.0 Hz), 7.73 (2H, d, J=8.0 Hz), 7.95-8.04 (3H, m), 8.49 (1H, d, J=2.0 Hz), 8.58 (1H, d, J=2.8 Hz), 8.65-8.70 (2H, m), 9.48 (1H, br s), 10.27 (1H, br s).

Example 143: N-(5-((5-(4-(dimethylcarbamoyl)phenyl)pyridin-2-yl)amino)pyridin-3-yl)-1H-indole-4-carboxamide

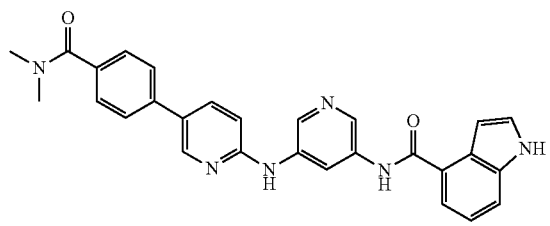 [SMILES: CN(C)C(=O)c1ccc(-c2ccc(Nc3cncc(NC(=O)c4cccc5[nH]ccc45)c3)nc2)cc1]

To a mixture of 4-(6-((5-aminopyridin-3-yl)amino)pyridin-3-yl)-N,N-dimethylbenzamide (50 mg, 0.15 mmol) in pyridine (2 mL) was added 1H-indole-4-carboxylic acid (36 mg, 0.22 mmol) and EDC.HCl (43 mg, 0.22 mmol), the reaction mixture was stirred at 50° C. for 2 h to give a brown solution. LCMS (Rt=0.757 min; MS Calc'd: 476.2; MS Found: 477.0 [M+H]$^+$). The mixture was concentrated under reduced pressure to give a residue. The residue was purified by washing with MeOH/water (5 mL/1 mL) to give a crude product. Then further purified by prep-HPLC (0.05% NH$_3$.H$_2$O as an additive) to give N-(5-((5-(4-(dimethylcarbamoyl)phenyl)pyridin-2-yl)amino)pyridin-3-yl)-1H-indole-4-carboxamide (27.2 mg, yield: 38%) as a white solid. LCMS (Shimadzu LCMS 2010, Mobile phase: from 100% [water+0.04% TFA] to 40% [water+0.04% TFA] and 60% [MeCN+0.02% TFA] in 1.35 min, then under this condition for 0.9 min, finally changed to 100% [water+0.04% TFA] and under this condition for 0.75 min) purity is 99.23%, Rt=1.598 min; MS Calc'd: 476.2; MS Found: 477.1 [M+H]$^+$. $^1$H NMR (400 MHz, DMSO-d$_6$) δ 2.91-3.09 (6H, m), 6.85-6.89 (1H, m), 7.01 (1H, d, J=8.4 Hz), 7.23 (1H, t, J=7.6 Hz), 7.45-7.56 (3H, m), 7.57-7.65 (2H, m), 7.73 (2H, d, J=8.0 Hz), 8.00 (1H, dd, J=8.8, 2.8 Hz), 8.50 (1H, d, J=2.0 Hz), 8.59 (1H, d, J=2.8 Hz), 8.70 (1H, d, J=2.4 Hz), 8.77 (1H, d, J=2.0 Hz), 9.48 (1H, br s), 10.35 (1H, br s), 11.39 (1H, br s).

227

Example 144: N-(5-((5-(4-(dimethylcarbamoyl)phenyl)pyridin-2-yl)amino)pyridin-3-yl)-1H-benzo[d]imidazole-4-carboxamide

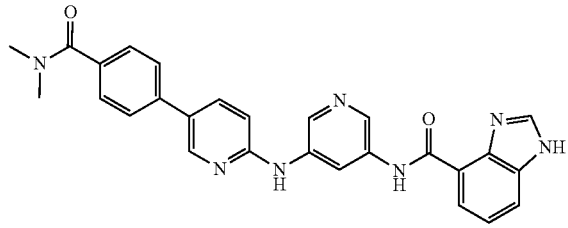 [SMILES: CN(C)C(=O)c1ccc(-c2ccc(Nc3cncc(NC(=O)c4cccc5[nH]cnc45)c3)nc2)cc1]

To a mixture of 4-(6-((5-aminopyridin-3-yl)amino)pyridin-3-yl)-N,N-dimethylbenzamide (80 mg, 0.24 mmol) in pyridine (2 mL) was added 1H-benzo[d]imidazole-4-carboxylic acid (58 mg, 0.36 mmol) and EDC.HCl (92 mg, 0.48 mmol), the reaction mixture was stirred at 50° C. for 2 h to give a brown suspension. LCMS (Rt=0.660 min; MS Calc'd: 477.2; MS Found: 478.1 [M+H]$^+$). The mixture was concentrated under reduced pressure to give a residue. The residue was purified by washing with MeOH (5 mL) to give a crude product. Then further purified by prep-HPLC (0.225% FA as an additive) to give N-(5-((5-(4-(dimethylcarbamoyl)phenyl)pyridin-2-yl)amino)pyridin-3-yl)-1H-benzo[d]imidazole-4-carboxamide (7.9 mg, yield: 7%) as a white solid. LCMS (Agilent LCMS 1200-6140A, mobile phase: from 99% [water+0.1% FA] and 1% [MeCN+0.1% FA] to 95% [water+0.1% FA] and 5% [MeCN+0.1% FA] in 0.6 min, then changed to 100% [MeCN+0.1% FA] under this condition for 3.4 min, finally back to 99% [water+0.1% FA] and 1% [MeCN+0.1% FA] and under this condition for 0.5 min.) purity is 97.48%, Rt=2.126 min; MS Calc'd: 477.2; MS Found: 478.3 [M+H]$^+$. $^1$H NMR (400 MHz, DMSO-d$_6$) δ 2.91-3.05 (6H, m), 7.04 (1H, d, J=8.8 Hz), 7.45-7.53 (3H, m), 7.76 (2H, d, J=8.4 Hz), 7.85-7.94 (1H, m), 8.00-8.07 (2H, m), 8.61-8.72 (3H, m), 8.74-8.80 (1H, m), 8.83-8.92 (1H, m), 9.75 (1H, br s).

Example 145: 3-((5-(4-(2-oxopyrrolidin-1-yl)phenyl)pyridin-2-yl)amino)quinoline-5-carboxamide

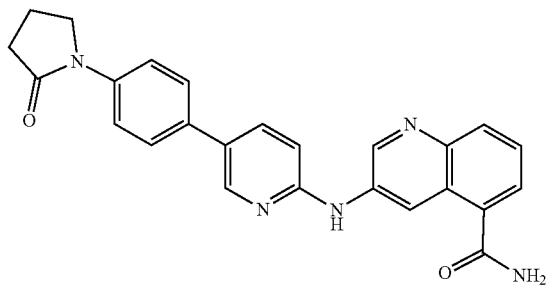 [SMILES: NC(=O)c1cccc2ncc(Nc3ccc(-c4ccc(N5CCCC5=O)cc4)cn3)cc12]

228

Step 1: Preparation of 3-bromoquinoline-5-carboxamide

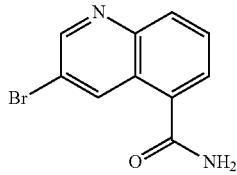

To a solution of 3-bromoquinoline-5-carboxylic acid (50 mg, 0.20 mmol) and NH$_4$Cl (21 mg, 0.40 mmol) in pyridine (1 mL) was added EDCI (114 mg, 0.595 mmol) under N$_2$ atmosphere. The mixture was stirred at 18-20° C. for 16 h under N$_2$ atmosphere. A white suspension was formed. LCMS (Rt=0.630 min; MS Calc'd: 250.0; MS Found: 250.8 [M+H]$^+$). The mixture was concentrated under reduced pressure. The residue was poured into water (10 mL) and extracted with DCM (10 mL×3). The combined organic layer was dried over Na$_2$SO$_4$, filtered and concentrated in vacuum to give 3-bromoquinoline-5-carboxamide (60 mg, crude) as a white solid. LCMS is 40% (Rt=0.629 min; MS Calc'd: 250.0; MS Found: 250.8 [M+H]$^+$).

Step 2: Preparation of 3-((5-(4-(2-oxopyrrolidin-1-yl)phenyl)pyridin-2-yl)amino)quinoline-5-carboxamide

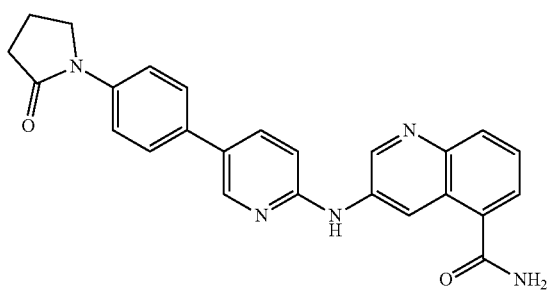 [SMILES: NC(=O)c1cccc2ncc(Nc3ccc(-c4ccc(N5CCCC5=O)cc4)cn3)cc12]

A mixture of 1-(4-(6-aminopyridin-3-yl)phenyl)pyrrolidin-2-one (50 mg, 0.20 mmol), 3-bromoquinoline-5-carboxamide (50 mg, crude), Pd$_2$(dba)$_3$ (9 mg, 0.010 mmol), Brettphos (11 mg, 0.020 mmol) and Cs$_2$CO$_3$ (193 mg, 0.592 mmol) in dioxane (3 mL) was stirred at 100° C. for 16 h.

Example 146: N-methyl-3-((5-(4-(2-oxopyrrolidin-1-yl)phenyl)pyridin-2-yl)amino)quinoline-5-carboxamide

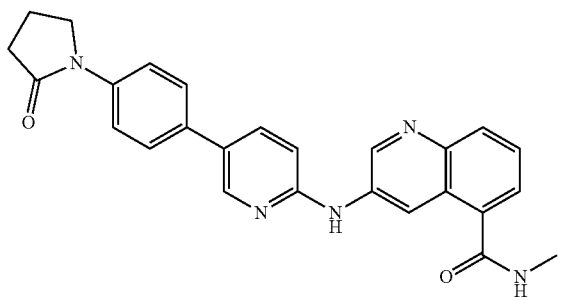 [SMILES: CNC(=O)c1cccc2ncc(Nc3ccc(-c4ccc(N5CCCC5=O)cc4)cn3)cc12]

Step 1: Preparation of 3-bromo-N-methylquinoline-5-carboxamide

To a solution of 3-bromoquinoline-5-carboxylic acid (50 mg, 0.20 mmol) and MeNH$_2$—HCl (12 mg, 0.40 mmol) in pyridine (1 mL) was added EDCI (114 mg, 0.595 mmol) under N$_2$ atmosphere. The mixture was stirred at 18-20° C. for 16 h under N$_2$ atmosphere. A white suspension was formed. LCMS (Rt=0.683 min; MS Calc'd: 264.0; MS Found: 264.6 [M+H]$^+$). The mixture was concentrated under reduced pressure. The residue was poured into water (10 mL) and extracted with DCM (10 mL×3). The combined organic layer was washed with water (10 mL), dried over Na$_2$SO$_4$, filtered and concentrated in vacuum to give 3-bromo-N-methylquinoline-5-carboxamide (55 mg, crude) as a white solid. LCMS is 21% (Rt=0.788 min; MS Calc'd: 264.0; MS Found: 265.7 [M+H]$^+$).

Step 2: Preparation of N-methyl-3-((5-(4-(2-oxopyrrolidin-1-yl)phenyl)pyridin-2-yl)amino)quinoline-5-carboxamide

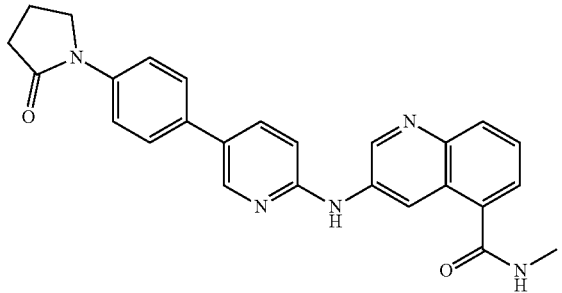 [SMILES: CNC(=O)c1cccc2ncc(Nc3ccc(-c4ccc(N5CCCC5=O)cc4)cn3)cc12]

A mixture of 1-(4-(6-aminopyridin-3-yl)phenyl)pyrrolidin-2-one (50 mg, 0.20 mmol), 3-bromo-N-methylquinoline-5-carboxamide (52 mg, crude), Pd$_2$(dba)$_3$ (9 mg, 0.01 mmol), Brettphos (11 mg, 0.02 mmol) and Cs$_2$CO$_3$ (193 mg, 0.592 mmol) in dioxane (3 mL) was stirred at 100° C. for 16 h. A black suspension was formed. LCMS (Rt=0.685 min; MS Calc'd: 437.2; MS Found: 438.0 [M+H]$^+$). The mixture was filtered and concentrated to give an orange gum. The residue was purified by prep-HPLC (0.05% HCl as an additive) and lyophilized to give N-methyl-3-((5-(4-(2-oxopyrrolidin-1-yl)phenyl)pyridin-2-yl)amino)quinoline-5-carboxamide (4.6 mg, yield for 2 steps: 5%) as a yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 98.83%, Rt=1.244 min; MS Calc'd.: 437.2; MS Found: 438.1 [M+H]$^+$. $^1$H NMR (400 MHz, DMSO-d$_6$) δ 2.09 (2H, t, J=7.2 Hz), 2.50-2.56 (2H, m, overlapped with DMSO signal), 2.89 (3H, d, J=4.4 Hz), 3.88 (2H, t, J=6.8 Hz), 7.09 (1H, d, J=8.4 Hz), 7.65-7.85 (6H, m), 8.06 (1H, d, J=2.0 Hz), 8.15 (1H, d, J=8.4 Hz), 8.59 (1H, s), 8.67 (1H, d, J=4.8 Hz), 9.20 (1H, s), 9.60 (1H, s), 10.22 (1H, br s).

Example 147: N,N-dimethyl-3-((5-(4-(2-oxopyrrolidin-1-yl)phenyl)pyridin-2-yl)amino)quinoline-5-carboxamide

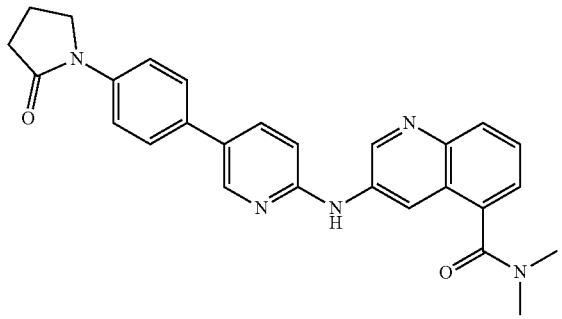 [SMILES: CN(C)C(=O)c1cccc2ncc(Nc3ccc(-c4ccc(N5CCCC5=O)cc4)cn3)cc12]

Step 1: Preparation of 3-bromo-N,N-dimethylquinoline-5-carboxamide

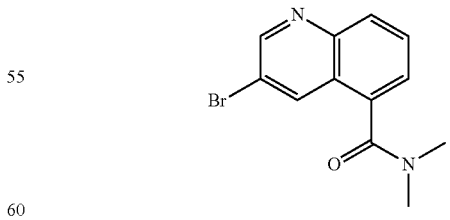

To a mixture of 3-bromoquinoline-5-carboxylic acid (50 mg, 0.20 mmol) in pyridine (2 mL) was added EDCI (76 mg, 0.40 mmol) and N-methylmethanamine (65 mg, 0.79 mmol, HCl salt). The reaction mixture was stirred at 50° C. for 2 h to give a brown suspension. LCMS (Rt=0.661 min; MS Calc'd: 278.0; MS Found: 278.8 [M+H]$^+$). The mixture was concentrated under reduced pressure to give a residue. 20 mL water was added. The mixture was extracted with EtOAc (15 mL×2). The combined extract was washed with brine (20 mL×2), dried over Na$_2$SO$_4$, filtered and concentrated under reduced pressure to give 3-bromo-N,N-dimethylquinoline-5-carboxamide (48 mg, yield: 86%) as a yellow solid. $^1$H NMR (400 MHz, CDCl$_3$) δ 2.79 (3H, s), 3.13 (3H, s), 7.64 (1H, dd, J=7.6, 1.6 Hz), 7.82-7.88 (1H, m), 8.11 (1H, dt, J=8.4, 0.8 Hz), 8.36 (1H, dd, J=2.4, 0.8 Hz), 9.03 (1H, d, J=2.4 Hz).

Step 2: Preparation of N,N-dimethyl-3-((5-(4-(2-oxopyrrolidin-1-yl)phenyl)pyridin-2-yl)amino)quinoline-5-carboxamide

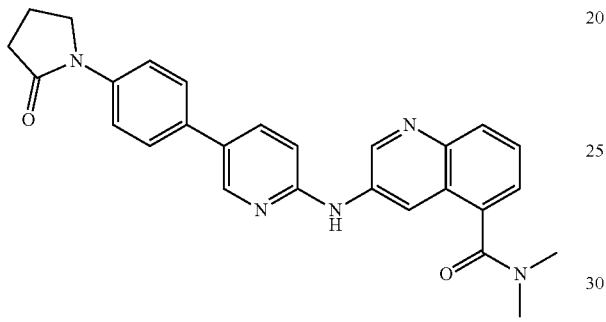

A mixture of Pd$_2$(dba)$_3$ (16 mg, 0.020 mmol) and Brettphos (9 mg, 0.02 mmol) in dioxane (3 mL) was stirred at 50° C. under N$_2$ atmosphere for 10 min. Then added into a mixture of 1-(4-(6-aminopyridin-3-yl)phenyl)pyrrolidin-2-one (50 mg, 0.20 mmol), 3-bromo-N,N-dimethylquinoline-5-carboxamide (48 mg, 0.17 mmol) and Cs$_2$CO$_3$ (112 mg, 0.344 mmol) in dioxane (5 mL). The reaction mixture was stirred at 100° C. under N$_2$ atmosphere for 16 h to give a brown suspension. LCMS (Rt=0.689 min; MS Calc'd: 451.2; MS Found: 452.1 [M+H]$^+$). The mixture was filtered. The filter cake was washed with DCM (5 mL×2). The filtrate was concentrated under reduced pressure to give a residue. The residue was purified by prep-HPLC (0.05% NH$_3$H$_2$O as an additive) purification to give 40 mg of product. But it contained n-BuOH (confirmed by HNMR). The impure product was further purified by prep-HPLC (normal phase, [Hexane-IPA]) and lyophilized to give N,N-dimethyl-3-((5-(4-(2-oxopyrrolidin-1-yl)phenyl)pyridin-2-yl)amino)quinoline-5-carboxamide (20.7 mg, yield: 27%) as a yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 99.88%, Rt=1.591 min; MS Calc'd.: 451.2; MS Found: 452.1 [M+H]$^+$. $^1$H NMR (400 MHz, DMSO-d$_6$) δ 2.01-2.16 (2H, m), 2.50-2.56 (2H, m, overlapped with DMSO signal), 2.80 (3H, s), 3.19 (3H, s), 3.87 (2H, t, J=7.2 Hz), 7.03 (1H, d, J=8.8 Hz), 7.46 (1H, d, J=7.2 Hz), 7.56 (1H, t, J=7.2 Hz), 7.65-7.80 (4H, m), 7.95 (1H, d, J=8.4 Hz), 8.00 (1H, dd, J=8.8, 2.8 Hz), 8.57 (1H, d, J=2.4 Hz), 8.75 (1H, d, J=2.0 Hz), 9.12 (1H, d, J=2.4 Hz), 9.83 (1H, br s).

Example 148: 1-(4-(6-((5-(pyrrolidine-1-carbonyl)quinolin-3-yl)amino)pyridin-3-yl)phenyl)pyrrolidin-2-one

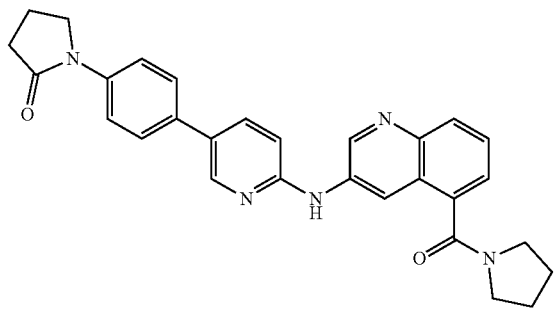 [SMILES: O=C(c1cccc2ncc(Nc3ccc(-c4ccc(N5CCCC5=O)cc4)cn3)cc12)N1CCCC1]

Step 1: Preparation of (3-bromoquinolin-5-yl)(pyrrolidin-1-yl)methanone

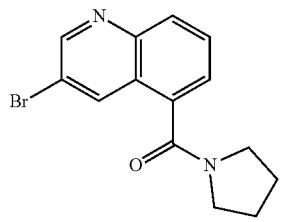 [SMILES: O=C(c1cccc2ncc(Br)cc12)N1CCCC1]

A mixture of 3-bromoquinoline-5-carboxylic acid (50 mg, 0.20 mmol) in SOCl$_2$ (1.64 g, 13.8 mmol) was stirred at 80° C. for 1 hour. The mixture was concentrated and dissolved in DCM (3 mL). To above solution was added pyrrolidine (28 mg, 0.40 mmol) and TEA (60 mg, 0.60 mmol). The mixture was stirred at 25° C. for 1 hour. A white suspension was formed. LCMS (Rt=0.759 min; MS Calc'd: 304.0; MS Found: 304.7 [M+H]$^+$). The mixture was concentrated under reduced pressure. The residue was poured into water (10 mL) and extracted with DCM (10 mL×3). The combined organic layer was dried over Na$_2$SO$_4$, filtered and concentrated in vacuum to give (3-bromoquinolin-5-yl)(pyrrolidin-1-yl)methanone (50 mg, crude) as a white solid.

Step 2: Preparation of 1-(4-(6-((5-(pyrrolidine-1-carbonyl)quinolin-3-yl)amino)pyridin-3-yl)phenyl)pyrrolidin-2-one

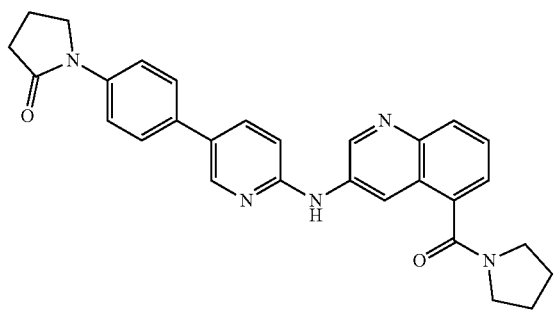 [SMILES: O=C(c1cccc2ncc(Nc3ccc(-c4ccc(N5CCCC5=O)cc4)cn3)cc12)N1CCCC1]

A mixture of 1-(4-(6-aminopyridin-3-yl)phenyl)pyrrolidin-2-one (50 mg, 0.20 mmol), (3-bromoquinolin-5-yl)(pyrrolidin-1-yl)methanone (60 mg, 0.20 mmol), $Pd_2(dba)_3$ (9 mg, 0.01 mmol), Brettphos (11 mg, 0.020 mmol) and $Cs_2CO_3$ (193 mg, 0.592 mmol) in dioxane (3 mL) was stirred at 100° C. for 16 h. A black suspension was formed. LCMS (Rt=0.741 min; MS Calc'd: 477.2; MS Found: 478.0 [M+H]+). The mixture was filtered and concentrated to give an orange gum. The residue was purified by prep-HPLC (0.05% HCl as an additive) and lyophilized to give 1-(4-(6-((5-(pyrrolidine-1-carbonyl)quinolin-3-yl)amino)pyridin-3-yl)phenyl)pyrrolidin-2-one (5.8 mg, yield for 2 steps: 6%) as a yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 98.49%, Rt=1.347 min; MS Calc'd.: 477.2; MS Found: 478.1 [M+H]+. $^1$H NMR (400 MHz, DMSO-$d_6$) δ 1.74-1.89 (2H, m), 1.89-2.04 (2H, m), 2.04-2.17 (2H, m), 2.50-2.56 (2H, m, overlapped with DMSO signal), 3.14 (2H, t, J=6.8 Hz), 3.68 (2H, t, J=6.8 Hz), 3.88 (2H, t, J=7.2 Hz), 7.07 (1H, d, J=8.4 Hz), 7.55-7.61 (1H, m), 7.61-7.69 (1H, m), 7.69-7.80 (4H, m), 7.95-8.09 (2H, m), 8.54 (1H, d, J=2.4 Hz), 8.90 (1H, d, J=2.4 Hz), 9.28 (1H, d, J=2.0 Hz), 10.07 (1H, br s).

Example 149: 1-(4-(6-((5-(3-hydroxypyrrolidine-1-carbonyl)quinolin-3-yl)amino)pyridin-3-yl)phenyl)pyrrolidin-2-one

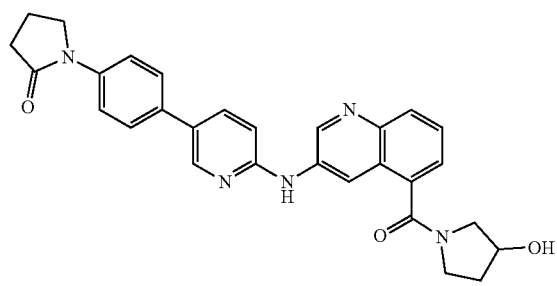 [SMILES: O=C(c1cccc2ncc(Nc3ccc(-c4ccc(N5CCCC5=O)cc4)cn3)cc12)N1CCC(O)C1]

Step 1: Preparation of (3-bromoquinolin-5-yl)(3-hydroxypyrrolidin-1-yl)methanone

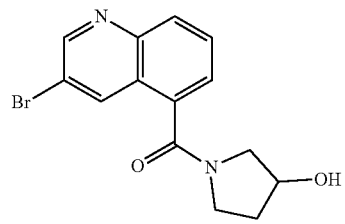 [SMILES: O=C(c1cccc2ncc(Br)cc12)N1CCC(O)C1]

A mixture of 3-bromoquinoline-5-carboxylic acid (50 mg, 0.20 mmol) in $SOCl_2$ (1.64 g, 13.8 mmol) was stirred at 80° C. for 1 hour. The mixture was concentrated and dissolved in DCM (3 mL). To the solution was added pyrrolidin-3-ol (35 mg, 0.40 mmol) and TEA (60 mg, 0.60 mmol). The mixture was stirred at 25° C. for 1 hour. A white suspension was formed. LCMS (Rt=0.792 min; MS Calc'd: 320.0; MS Found: 322.9 [M+H]+). The mixture was concentrated under reduced pressure. The residue was poured into water (10 mL) and extracted with DCM (10 mL×3). The combined organic layer was dried over $Na_2SO_4$, filtered and concentrated in vacuum to give (3-bromoquinolin-5-yl)(3-hydroxypyrrolidin-1-yl)methanone (50 mg, crude) as a white solid. LCMS is 99% (Rt=0.658 min; MS Calc'd: 320.0; MS Found: 320.7 [M+H]+).

Step 2: Preparation of 1-(4-(6-((5-(3-hydroxypyrrolidine-1-carbonyl)quinolin-3-yl)amino)pyridin-3-yl)phenyl)pyrrolidin-2-one

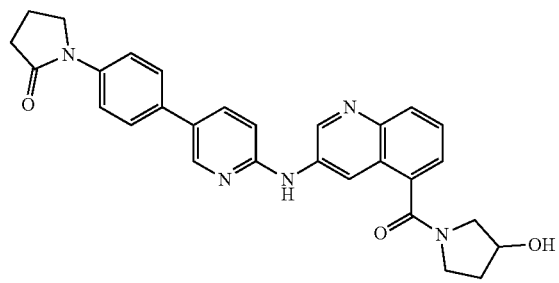 [SMILES: O=C(c1cccc2ncc(Nc3ccc(-c4ccc(N5CCCC5=O)cc4)cn3)cc12)N1CCC(O)C1]

A mixture of 1-(4-(6-aminopyridin-3-yl)phenyl)pyrrolidin-2-one (50 mg, 0.20 mmol), (3-bromoquinolin-5-yl)(3-hydroxypyrrolidin-1-yl)methanone (63 mg, 0.20 mmol), $Pd_2(dba)_3$ (9 mg, 0.01 mmol), Brettphos (11 mg, 0.02 mmol) and $Cs_2CO_3$ (193 mg, 0.592 mmol) in dioxane (3 mL) was stirred at 100° C. for 16 h. A black suspension was formed. LCMS (Rt=1.203 min; MS Calc'd: 493.2; MS Found: 494.2 [M+H]+). The mixture was filtered and concentrated to give an orange gum. The residue was purified by prep-HPLC (0.05% HCl as an additive) and lyophilized to give 1-(4-(6-((5-(3-hydroxypyrrolidine-1-carbonyl)quinolin-3-yl)amino)pyridin-3-yl)phenyl)pyrrolidin-2-one (21.3 mg, yield for 2 steps: 22%) as a yellow solid. LCMS (Shimadzu LCMS 2010, Mobile phase: from 90% [water+0.04% TFA] and 10% [MeCN+0.02% TFA] to 20% [water+0.04% TFA] and 80% [MeCN+0.02% TFA] in 1.35 min, then under this condition for 0.9 min, finally changed to 90% [water+0.04% TFA] and 10% [MeCN+0.02% TFA] and under this condition for 0.75 min.) purity is 98.43%, Rt=1.210 min; MS Calc'd.: 493.2; MS Found: 494.2 [M+H]+. $^1$H NMR (400 MHz, DMSO-$d_6$) δ 1.70-2.15 (4H, m), 2.50-2.56 (2H, m, overlapped with DMSO signal), 2.91-3.25 (1H, m), 3.30-3.45 (1H, m), 3.52-3.80 (2H, m), 3.82-3.92 (2H, m), 3.30-4.50 (1H, m, overlapped with $H_2O$ signal), 7.06-7.16 (1H, m), 7.65-7.84 (6H, m), 8.04-8.11 (1H, m), 8.15-8.25 (1H, m), 8.58 (0.5H, d, J=2.4 Hz), 8.63 (0.5H, d, J=2.0 Hz), 8.98 (0.5H, d, J=2.0 Hz), 9.07 (0.5H, s), 9.55 (0.5H, d, J=2.0 Hz), 9.64 (0.5H, d, J=2.0 Hz), 10.57 (1H, br s).

Example 150: 1-(4-(6-((1-(cyclopropanecarbonyl)-2,3-dihydro-1H-pyrido[2,3-b][1,4]oxazin-7-yl)amino)pyridin-3-yl)phenyl)pyrrolidin-2-one

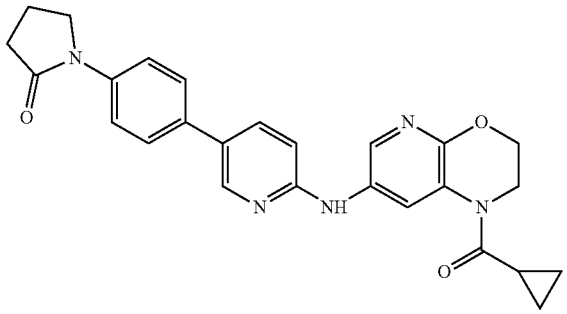 [SMILES: O=C1CCCN1c1ccc(-c2ccc(Nc3cnc4c(c3)N(C(=O)C3CC3)CCO4)nc2)cc1]

A mixture of Pd$_2$(dba)$_3$ (36 mg, 0.039 mmol) and Brettphos (42 mg, 0.079 mmol) in 1,4-dioxane (1 mL) was stirred at 50° C. for 10 min. 1-(4-(6-Aminopyridin-3-yl)phenyl)pyrrolidin-2-one (100 mg, 0.395 mmol), (7-bromo-2,3-dihydro-1H-pyrido[2,3-b][1,4]oxazin-1-yl)(cyclopropyl)methanone (112 mg, 0.395 mmol) in dioxane (5 mL) and Cs$_2$CO$_3$ (386 mg, 1.18 mmol) were added and the resulting mixture was stirred at 100° C. for 18 h. A black brown mixture was formed. LCMS showed the purity of the desired product (Rt=0.555 min; MS Calc'd: 455.2; MS Found: 456.1 [M+H]$^+$). The reaction mixture was diluted with DCM (10 mL), filtered and concentrated. The residue was purified by prep-HPLC (0.05% NH$_3$.H$_2$O as an additive) and lyophilized to give 1-(4-(6-((1-(cyclopropanecarbonyl)-2,3-dihydro-1H-pyrido[2,3-b][1,4]oxazin-7-yl)amino)pyridin-3-yl)phenyl)pyrrolidin-2-one (24.0 mg, yield: 13%) as a white solid. $^1$H NMR (400 MHz, DMSO-d$_6$) δ 0.92-1.00 (4H, m), 2.03-2.12 (2H, m), 2.17-2.26 (1H, m), 2.55 (2H, overlaped with DMSO), 3.86 (2H, t, J=6.8 Hz), 3.94-4.03 (2H, m), 4.36 (2H, t, J=4.0 Hz), 6.86 (1H, d, J=8.4 Hz), 7.64 (2H, d, J=8.0 Hz), 7.72 (2H, d, J=8.4 Hz), 7.89 (1H, d, J=8.4 Hz), 8.21 (1H, br s), 8.43 (1H, s), 8.65 (1H, s), 9.21 (1H, s).

Example 151: methyl 7-((5-(4-(2-oxopyrrolidin-1-yl)phenyl)pyridin-2-yl)amino)-2,3-dihydro-1H-pyrido[2,3-b][1,4]oxazine-1-carboxylate

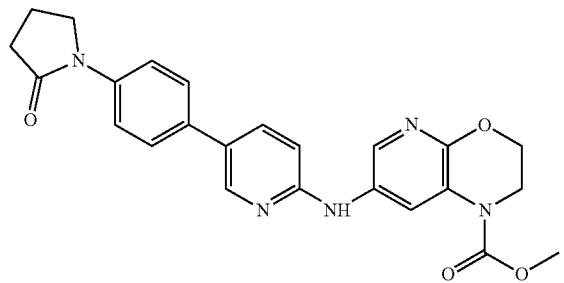 [SMILES: COC(=O)N1CCOc2ncc(Nc3ccc(-c4ccc(N5CCCC5=O)cc4)cn3)cc21]

A mixture of Pd$_2$(dba)$_3$ (36 mg, 0.039 mmol) and Brettphos (42 mg, 0.079 mmol) in 1,4-dioxane (1 mL) was stirred at 50° C. for 10 min. 1-(4-(6-aminopyridin-3-yl)phenyl)pyrrolidin-2-one (100 mg, 0.395 mmol), methyl 7-bromo-2,3-dihydro-1H-pyrido[2,3-b][1,4]oxazine-1-carboxylate (108 mg, 0.395 mmol) in dioxane (5 mL) and Cs$_2$CO$_3$ (386 mg, 1.18 mmol) were added and the resulting mixture was stirred at 100° C. for 18 h. A black brown mixture was formed. LCMS showed the purity of the desired product (Rt=0.549 min; MS Calc'd: 445.2; MS Found: 446.0 [M+H]$^+$). The reaction mixture was diluted with DCM (10 mL), filtered and concentrated. The residue was purified by prep-HPLC (normal, hexane-EtOH) and triturated with EtOAc (1 mL) to give methyl 7-((5-(4-(2-oxopyrrolidin-1-yl)phenyl)pyridin-2-yl)amino)-2,3-dihydro-1H-pyrido[2,3-b][1,4]oxazine-1-carboxylate (15.7 mg, yield: 9%) as a white solid. $^1$H NMR (400 MHz, DMSO-d$_6$) δ 2.03-2.12 (2H, m), 2.55 (2H, overlaped with DMSO), 3.78 (3H, s), 3.83-3.89 (4H, m), 4.30 (2H, t, J=4.4 Hz), 6.87 (1H, d, J=9.2 Hz), 7.65 (2H, d, J=8.8 Hz), 7.73 (2H, d, J=8.8 Hz), 7.89 (1H, dd, J=8.4, 2.4 Hz), 8.29 (1H, d, J=2.0 Hz), 8.46 (1H, d, J=2.4 Hz), 8.66 (1H, br s), 9.15 (1H, s).

Example 152: 1-(4-(6-((1-isobutyryl-2,3-dihydro-1H-pyrido[2,3-b][1,4]oxazin-7-yl)amino)pyridin-3-yl)phenyl)pyrrolidin-2-one

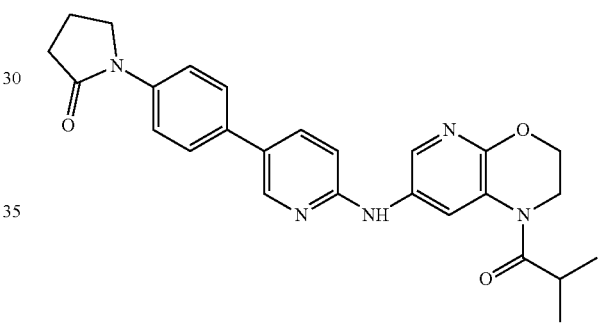

A mixture of Pd$_2$(dba)$_3$ (36 mg, 0.039 mmol) and Brettphos (42 mg, 0.079 mmol) in 1,4-dioxane (1 mL) was stirred at 50° C. for 10 min. 1-(4-(6-Aminopyridin-3-yl)phenyl)pyrrolidin-2-one (100 mg, 0.395 mmol), 1-(7-bromo-2,3-dihydro-1H-pyrido[2,3-b][1,4]oxazin-1-yl)-2-methylpropan-1-one (112 mg, 0.395 mmol) in dioxane (4 mL) and Cs$_2$CO$_3$ (386 mg, 1.18 mmol) were added and the resulting mixture was stirred at 100° C. for 18 h. A black brown mixture was formed. LCMS showed the purity of the desired product (Rt=0.569 min; MS Calc'd: 457.2; MS Found: 458.1 [M+H]$^+$). The reaction mixture was diluted with DCM (10 mL), filtered and concentrated. The residue was purified by prep-HPLC (0.225% FA as an additive) to give 1-(4-(6-((1-isobutyryl-2,3-dihydro-1H-pyrido[2,3-b][1,4]oxazin-7-yl)amino)pyridin-3-yl)phenyl)pyrrolidin-2-one (25.6 mg, yield: 14%) as a yellow solid. $^1$H NMR (400 MHz, DMSO-d$_6$) δ 1.12 (6H, d, J=6.4 Hz), 2.02-2.12 (2H, m), 2.52 (2H, overlaped with DMSO), 3.16-3.26 (1H, m), 3.86 (2H, t, J=6.8 Hz), 3.92 (2H, t, J=4.4 Hz), 4.35 (2H, t, J=4.0 Hz), 6.86 (1H, d, J=8.8 Hz), 7.65 (2H, d, J=8.8 Hz), 7.72 (2H, d, J=8.8 Hz), 7.89 (1H, dd, J=8.4, 2.4 Hz), 8.30 (1H, br s), 8.44 (1H, d, J=2.4 Hz), 8.58 (1H, s), 9.18 (1H, s).

Example 153: 1-(4-(6-((1-(isopropylsulfonyl)-2,3-dihydro-1H-pyrido[2,3-b][1,4]oxazin-7-yl)amino)pyridin-3-yl)phenyl)pyrrolidin-2-one

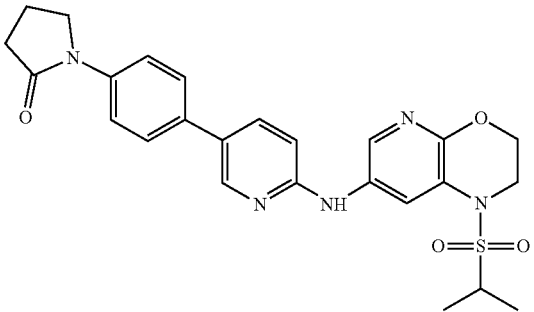 [SMILES: CC(C)S(=O)(=O)N1CCOc2ncc(Nc3ccc(-c4ccc(N5CCCC5=O)cc4)cn3)cc21]

A mixture of Pd₂(dba)₃ (30 mg, 0.034 mmol) and Brettphos (36 mg, 0.067 mmol) in 1,4-dioxane (1 mL) was stirred at 50° C. for 10 min. 1-(4-(6-Aminopyridin-3-yl)phenyl)pyrrolidin-2-one (85 mg, 0.34 mmol), 7-bromo-1-(isopropylsulfonyl)-2,3-dihydro-1H-pyrido[2,3-b][1,4]oxazine (108 mg, 0.336 mmol) in dioxane (4 mL) and Cs₂CO₃ (328 mg, 1.01 mmol) were added and the resulting mixture was stirred at 100° C. for 16 h. A black brown mixture was formed. LCMS showed the purity of the desired (Rt=0.588 min; MS Calc'd: 493.1; MS Found: 494.0 [M+H]⁺). The reaction mixture was diluted with DCM (10 mL), filtered and concentrated. The residue was purified by prep-HPLC (0.05% NH₃.H₂O as an additive) to give 1-(4-(6-((1-(isopropylsulfonyl)-2,3-dihydro-1H-pyrido[2,3-b][1,4]oxazin-7-yl)amino)pyridin-3-yl)phenyl)pyrrolidin-2-one (33.3 mg, yield: 20%) as a white solid. ¹H NMR (400 MHz, DMSO-d₆) δ 1.33 (6H, d, J=6.8 Hz), 2.03-2.11 (2H, m), 2.52 (2H, overlaped with DMSO), 3.70-3.78 (1H, m), 3.81 (2H, t, J=4.0 Hz), 3.85 (2H, t, J=6.8 Hz), 4.34 (2H, t, J=4.0 Hz), 6.86 (1H, d, J=8.4 Hz), 7.65 (2H, d, J=8.8 Hz), 7.72 (2H, d, J=8.8 Hz), 7.90 (1H, dd, J=8.8, 2.4 Hz), 8.30 (1H, d, J=2.0 Hz), 8.35 (1H, d, J=2.0 Hz), 8.43 (1H, d, J=2.4 Hz), 9.23 (1H, s).

Example 154: 1-(4-(6-((1-(cyclopropylsulfonyl)-2,3-dihydro-1H-pyrido[2,3-b][1,4]oxazin-7-yl)amino)pyridin-3-yl)phenyl)pyrrolidin-2-one

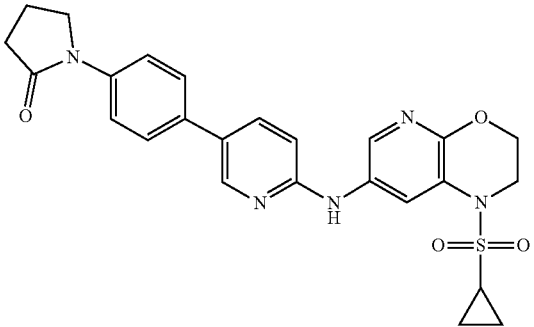 [SMILES: O=C1CCCN1c1ccc(-c2ccc(Nc3cnc4c(c3)N(S(=O)(=O)C3CC3)CCO4)nc2)cc1]

A mixture of Pd₂(dba)₃ (54 mg, 0.059 mmol) and Brettphos (64 mg, 0.118 mmol) in 1,4-dioxane (1 mL) was stirred at 50° C. for 10 min. 1-(4-(6-aminopyridin-3-yl)phenyl)pyrrolidin-2-one (150 mg, 0.592 mmol), 7-bromo-1-(cyclopropylsulfonyl)-2,3-dihydro-1H-pyrido[2,3-b][1,4]oxazine (284 mg, 0.888 mmol) in dioxane (9 mL) and Cs₂CO₃ (579 mg, 1.01 mmol) were added and the resulting mixture was stirred at 100° C. for 18 h. A black brown mixture was formed. LCMS showed the purity of the desired product (Rt=0.575 min; MS Calc'd: 491.2; MS Found: 492.1 [M+H]⁺). The reaction mixture was diluted with DCM (10 mL), filtered and concentrated. The residue was purified by prep-HPLC (0.225% FA as an additive) to give 1-(4-(6-((1-(cyclopropylsulfonyl)-2,3-dihydro-1H-pyrido[2,3-b][1,4]oxazin-7-yl)amino)pyridin-3-yl)phenyl)pyrrolidin-2-one (5.0 mg, yield: 2%) as a white solid. ¹H NMR (400 MHz, DMSO-d₆) δ 1.02-1.11 (4H, m), 2.03-2.13 (2H, m), 2.56 (2H, overlaped with DMSO), 2.85-2.94 (1H, m), 3.81-3.92 (4H, m), 4.39 (2H, t, J=4.0 Hz), 6.86 (1H, d, J=8.8 Hz), 7.65 (2H, d, J=8.8 Hz), 7.72 (2H, d, J=9.2 Hz), 7.90 (1H, dd, J=9.2, 2.4 Hz), 8.38 (1H, s), 8.41 (1H, d, J=2.4 Hz), 8.45 (1H, d, J=1.6 Hz), 9.25 (1H, s).

Example 155: 1-(4-(6-((1-pivaloyl-2,3-dihydro-1H-pyrido[2,3-b][1,4]oxazin-7-yl)amino)pyridin-3-yl)phenyl)pyrrolidin-2-one

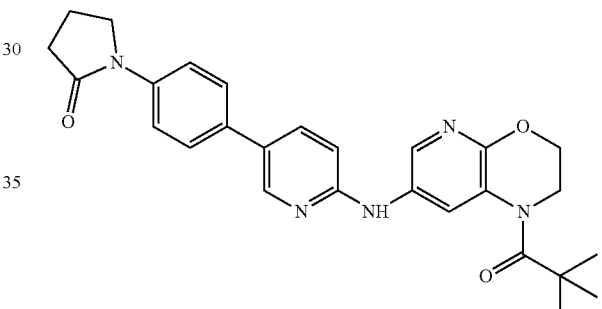

A mixture of Pd₂(dba)₃ (18 mg, 0.020 mmol) and Brettphos (21 mg, 0.039 mmol) in 1,4-dioxane (1 mL) was stirred at 50° C. for 10 min. 1-(4-(6-Aminopyridin-3-yl)phenyl)pyrrolidin-2-one (100 mg, 0.395 mmol), 1-(7-bromo-2,3-dihydro-1H-pyrido[2,3-b][1,4]oxazin-1-yl)-2,2-dimethylpropan-1-one (118 mg, 0.395 mmol) in dioxane (4 mL) and Cs₂CO₃ (257 mg, 0.790 mmol) were added and the resulting mixture was stirred at 100° C. for 12 h. A black brown mixture was formed. LCMS showed the purity of the desired product (Rt=0.599 min; MS Calc'd: 471.2; MS Found: 472.0 [M+H]⁺). The reaction mixture was diluted with DCM (10 mL), filtered and concentrated. The residue was purified by Combi Flash (DCM) and triturated with EtOAc (2 mL) to give 1-(4-(6-((1-pivaloyl-2,3-dihydro-1H-pyrido[2,3-b][1,4]oxazin-7-yl)amino)pyridin-3-yl)phenyl)pyrrolidin-2-one (14.8 mg, yield: 8%) as a white solid. ¹H NMR (400 MHz, DMSO-d₆) δ 1.32 (9H, s), 2.03-2.13 (2H, m), 2.56 (2H, overlaped with DMSO), 3.86 (2H, t, J=6.8 Hz), 4.02 (2H, t, J=4.8 Hz), 4.36 (2H, t, J=4.8 Hz), 6.84 (1H, d, J=8.8 Hz), 7.65 (2H, d, J=8.8 Hz), 7.72 (2H, d, J=8.8 Hz), 7.88 (1H, dd, J=8.4, 2.4 Hz), 8.28 (1H, d, J=2.4 Hz), 8.43 (1H, d, J=2.8 Hz), 8.45 (1H, d, J=2.4 Hz), 9.10 (1H, s).

Example 156: 1-(4-(6-((1-(methylsulfonyl)-2,3-dihydro-1H-pyrido[2,3-b][1,4]oxazin-7-yl)amino)pyridin-3-yl)phenyl)pyrrolidin-2-one

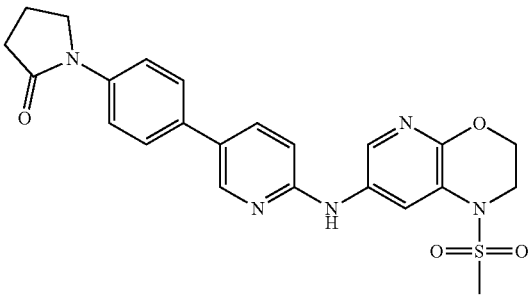 [SMILES: CS(=O)(=O)N1CCOc2ncc(Nc3ccc(-c4ccc(N5CCCC5=O)cc4)cn3)cc21]

A mixture of Pd$_2$(dba)$_3$ (36 mg, 0.039 mmol) and Brettphos (42 mg, 0.080 mmol) in 1,4-dioxane (1 mL) was stirred at 50° C. for 10 min. 1-(4-(6-Aminopyridin-3-yl)phenyl)pyrrolidin-2-one (100 mg, 0.395 mmol), 7-bromo-1-(methylsulfonyl)-2,3-dihydro-1H-pyrido[2,3-b][1,4]oxazine (115 mg, 0.395 mmol) in dioxane (4 mL) and Cs$_2$CO$_3$ (386 mg, 1.18 mmol) were added and the resulting mixture was stirred at 100° C. for 12 h. A black brown mixture was formed. LCMS showed the purity of the desired product (Rt=0.553 min; MS Calc'd: 465.1; MS Found: 465.9 [M+H]$^+$). The reaction mixture was diluted with DCM (10 mL), filtered and concentrated. The residue was purified by prep-HPLC (0.05% NH$_3$.H$_2$O as an additive) to give (13.7 mg, yield: 7%) as a white solid. $^1$H NMR (400 MHz, DMSO-d$_6$) δ 2.03-2.15 (2H, m), 2.56 (2H, overlaped with DMSO), 3.22 (3H, s), 3.83 (2H, t, J=4.4 Hz), 3.87 (2H, t, J=6.4 Hz), 4.37 (2H, t, J=4.0 Hz), 6.87 (1H, d, J=9.2 Hz), 7.66 (2H, d, J=8.8 Hz), 7.74 (2H, d, J=8.8 Hz), 7.91 (1H, dd, J=8.8, 2.8 Hz), 8.37 (1H, d, J=2.4 Hz), 8.40 (1H, d, J=2.4 Hz), 8.47 (1H, d, J=2.0 Hz), 9.24 (1H, s).

Example 157: N-methyl-N-(5-((5-(4-(2-oxopyrrolidin-1-yl)phenyl)pyridin-2-yl)amino)pyridin-3-yl)methanesulfonamide

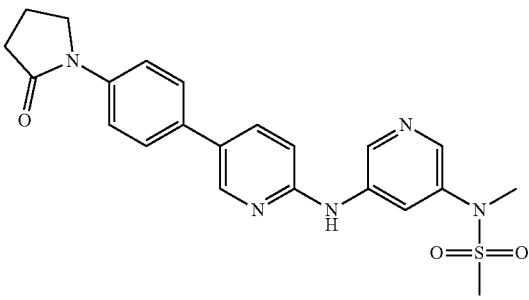 [SMILES: CN(c1cncc(Nc2ccc(-c3ccc(N4CCCC4=O)cc3)cn2)c1)S(C)(=O)=O]

A mixture of Pd$_2$(dba)$_3$ (18 mg, 0.020 mmol) and Brettphos (21 mg, 0.039 mmol) in 1,4-dioxane (1 mL) was stirred at 50° C. for 10 min. 1-(4-(6-Aminopyridin-3-yl)phenyl)pyrrolidin-2-one (100 mg, 0.395 mmol), N-(5-bromopyridin-3-yl)-N-methylmethanesulfonamide (105 mg, 0.395 mmol) in dioxane (5 mL) and Cs$_2$CO$_3$ (257 mg, 0.790 mmol) were added and the resulting mixture was stirred at 100° C. for 12 h. A black brown mixture was formed. LCMS showed the purity of the desired product (Rt=0.574 min; MS Calc'd: 437.1; MS Found: 437.9 [M+H]$^+$). The reaction mixture was diluted with DCM (10 mL), filtered and concentrated. The residue was purified by prep-HPLC (0.05% NH$_3$.H$_2$O as an additive) to give N-methyl-N-(5-((5-(4-(2-oxopyrrolidin-1-yl)phenyl)pyridin-2-yl)amino)pyridin-3-yl)methanesulfonamide (15.0 mg, yield: 9%) as a white solid. $^1$H NMR (400 MHz, CDCl$_3$) δ 2.15-2.25 (2H, m), 2.65 (2H, t, J=8.0 Hz), 2.94 (3H, s), 3.41 (3H, s), 3.92 (2H, t, J=6.8 Hz), 6.63 (1H, s), 6.88 (1H, d, J=8.4 Hz), 7.55 (2H, d, J=8.8 Hz), 7.71 (2H, d, J=8.8 Hz), 7.79 (1H, dd, J=8.8, 2.8 Hz), 8.24-8.27 (2H, m), 8.49 (1H, d, J=2.0 Hz), 8.56 (1H, d, J=2.4 Hz).

Example 158: N-(2-methoxy-5-((5-(4-(2-oxopyrrolidin-1-yl)phenyl)pyridin-2-yl)amino)pyridin-3-yl)acetamide

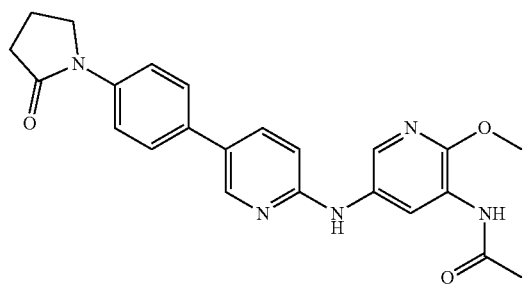 [SMILES: COc1ncc(Nc2ccc(-c3ccc(N4CCCC4=O)cc3)cn2)cc1NC(C)=O]

A mixture of Pd$_2$(dba)$_3$ (29 mg, 0.032 mmol) and Brettphos (34 mg, 0.063 mmol) in 1,4-dioxane (1 mL) was stirred at 50° C. for 10 min. 1-(4-(6-Aminopyridin-3-yl)phenyl)pyrrolidin-2-one (80 mg, 0.316 mmol), N-(5-bromo-2-methoxypyridin-3-yl)acetamide (77 mg, 0.316 mmol) in dioxane (4 mL) and Cs$_2$CO$_3$ (309 mg, 0.947 mmol) were added and the resulting mixture was stirred at 100° C. for 12 h. A black brown mixture was formed. LCMS showed the purity of the desired product (Rt=0.543 min; MS Calc'd: 417.1; MS Found: 418.0 [M+H]$^+$). The reaction mixture was diluted with DCM (10 mL), filtered and concentrated. The residue was purified by prep-HPLC (0.225% FA as an additive) to give N-(2-methoxy-5-((5-(4-(2-oxopyrrolidin-1-yl)phenyl)pyridin-2-yl)amino)pyridin-3-yl)acetamide (26.2 mg, yield: 20%) as a white solid. $^1$H NMR (400 MHz, DMSO-d$_6$) δ 2.03-2.10 (2H, m), 2.12 (3H, s), 2.56 (2H, overlaped with DMSO), 3.86 (2H, t, J=6.8 Hz), 3.90 (3H, s), 6.85 (1H, d, J=8.8 Hz), 7.64 (2H, d, J=8.8 Hz), 7.72 (2H, d, J=8.8 Hz), 7.87 (1H, dd, J=8.8, 2.4 Hz), 8.38 (1H, d, J=2.4 Hz), 8.44 (1H, d, J=2.4 Hz), 8.57 (1H, d, J=2.4 Hz), 9.08 (1H, s), 9.33 (1H, s).

Example 159: N-(2-methoxy-5-((5-(4-(2-oxopyrrolidin-1-yl)phenyl)pyridin-2-yl)amino)pyridin-3-yl)methanesulfonamide

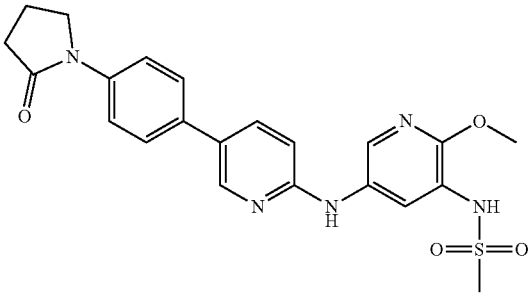 [SMILES: COc1ncc(Nc2ccc(-c3ccc(N4CCCC4=O)cc3)cn2)cc1NS(C)(=O)=O]

A mixture of Pd$_2$(dba)$_3$ (36 mg, 0.039 mmol) and Brettphos (42 mg, 0.079 mmol) in 1,4-dioxane (1 mL) was stirred at 50° C. for 10 min. 1-(4-(6-Aminopyridin-3-yl)phenyl)pyrrolidin-2-one (100 mg, 0.395 mmol), N-(5-bromo-2-methoxypyridin-3-yl)methanesulfonamide (111 mg, 0.395 mmol) in dioxane (4 mL) and Cs$_2$CO$_3$ (386 mg, 1.18 mmol) were added and the resulting mixture was stirred at 100° C. for 12 h. A black brown mixture was formed. LCMS showed the purity of the desired product (Rt=0.537 min; MS Calc'd: 453.1; MS Found: 454.1 [M+H]$^+$). The reaction mixture was diluted with DCM (10 mL), filtered and concentrated. The residue was purified by prep-HPLC (0.225% FA as an additive) and triturated (1 mL) to give N-(2-methoxy-5-((5-(4-(2-oxopyrrolidin-1-yl)phenyl)pyridin-2-yl)amino)pyridin-3-yl)methanesulfonamide (19.1 mg, yield: 11%) as a white solid. $^1$H NMR (400 MHz, DMSO-d$_6$) δ 2.03-2.10 (2H, m), 2.56 (2H, overlaped with DMSO), 3.04 (3H, s), 3.86 (2H, t, J=6.8 Hz), 3.88 (3H, s), 6.86 (1H, d, J=8.8 Hz), 7.65 (2H, d, J=8.8 Hz), 7.73 (2H, d, J=8.8 Hz), 7.89 (1H, dd, J=8.8, 2.4 Hz), 8.01 (1H, d, J=2.4 Hz), 8.40 (1H, d, J=2.4 Hz), 8.46 (1H, d, J=2.0 Hz), 9.17 (1H, s), 9.19 (1H, s).

Example 160: N-(2-methoxy-5-((5-(4-(2-oxopyrrolidin-1-yl)phenyl)pyridin-2-yl)amino)pyridin-3-yl)-N-methylacetamide

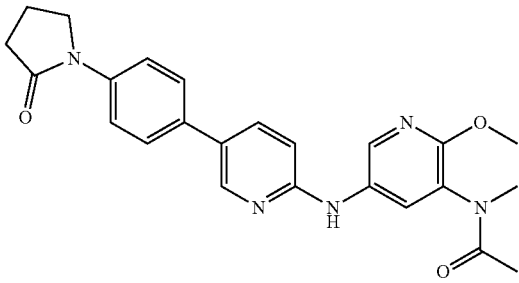 [SMILES: COc1ncc(Nc2ccc(-c3ccc(N4CCCC4=O)cc3)cn2)cc1N(C)C(C)=O]

A mixture of Pd$_2$(dba)$_3$ (36 mg, 0.039 mmol) and Brettphos (42 mg, 0.079 mmol) in 1,4-dioxane (1 mL) was stirred at 50° C. for 10 min. 1-(4-(6-Aminopyridin-3-yl)phenyl)pyrrolidin-2-one (100 mg, 0.395 mmol), N-(5-bromo-2-methoxypyridin-3-yl)-N-methylacetamide (102 mg, 0.395 mmol) in dioxane (4 mL) and Cs$_2$CO$_3$ (386 mg, 1.18 mmol) were added and the resulting mixture was stirred at 100° C. for 12 h. A black brown mixture was formed. LCMS showed the purity of the desired product (Rt=0.553 min; MS Calc'd: 431.2; MS Found: 432.0 [M+H]$^+$). The reaction mixture was diluted with DCM (10 mL), filtered and concentrated. The residue was purified by prep-HPLC (0.225% FA as an additive) to give N-(2-methoxy-5-((5-(4-(2-oxopyrrolidin-1-yl)phenyl)pyridin-2-yl)amino)pyridin-3-yl)-N-methylacetamide (17.4 mg, yield: 10%) as a white solid. $^1$H NMR (400 MHz, DMSO-d$_6$) δ 1.75 (3H, s), 2.04-2.12 (2H, m), 2.44 (2H, overlaped with DMSO), 3.06 (3H, s), 3.86 (2H, t, J=6.8 Hz), 3.89 (3H, s), 6.88 (1H, d, J=8.4 Hz), 7.66 (2H, d, J=8.4 Hz), 7.73 (2H, d, J=8.8 Hz), 7.92 (1H, dd, J=8.0, 1.2 Hz), 8.21 (1H, s), 8.42 (1H, s), 8.49 (1H, s), 9.27 (1H, s).

Example 161: N-(2-methoxy-5-((5-(4-(2-oxopyrrolidin-1-yl)phenyl)pyridin-2-yl)amino)pyridin-3-yl)-N-methylmethanesulfonamide

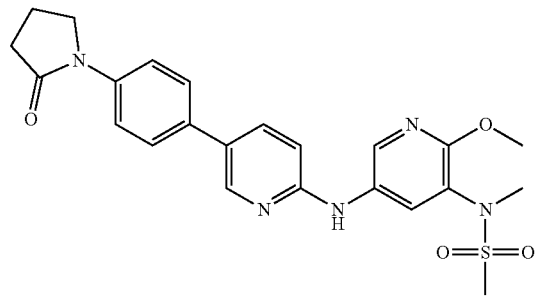 [SMILES: COc1ncc(Nc2ccc(-c3ccc(N4CCCC4=O)cc3)cn2)cc1N(C)S(C)(=O)=O]

A mixture of Pd$_2$(dba)$_3$ (29 mg, 0.032 mmol) and Brettphos (34 mg, 0.063 mmol) in 1,4-dioxane (1 mL) was stirred at 50° C. for 10 min. 1-(4-(6-Aminopyridin-3-yl)phenyl)pyrrolidin-2-one (80 mg, 0.316 mmol), N-(5-bromo-2-methoxypyridin-3-yl)-N-methylmethanesulfonamide (93 mg, 0.316 mmol) in dioxane (5 mL) and Cs$_2$CO$_3$ (309 mg, 0.947 mmol) were added and the resulting mixture was stirred at 100° C. for 12 h. A black brown mixture was formed. LCMS showed the purity of the desired product (Rt=0.573 min; MS Calc'd: 467.1; MS Found: 468.0 [M+H]$^+$). The reaction mixture was diluted with DCM (10 mL), filtered and concentrated. The residue was purified by prep-HPLC (0.225% FA as an additive) to give N-(2-methoxy-5-((5-(4-(2-oxopyrrolidin-1-yl)phenyl)pyridin-2-yl)amino)pyridin-3-yl)-N-methylmethanesulfonamide (20.3 mg, yield: 14%) as a yellow solid. $^1$H NMR (400 MHz, DMSO-d$_6$) δ 2.03-2.10 (2H, m), 2.56 (2H, overlaped with DMSO), 3.05 (3H, s), 3.17 (3H, s), 3.86 (2H, t, J=7.2 Hz), 3.91 (3H, s), 6.86 (1H, d, J=8.4 Hz), 7.66 (2H, d, J=8.8 Hz), 7.73 (2H, d, J=9.2 Hz), 7.91 (1H, dd, J=8.8, 2.4 Hz), 8.16 (1H, d, J=2.8 Hz), 8.47 (1H, d, J=2.4 Hz), 8.50 (1H, d, J=2.4 Hz), 9.24 (1H, s).

Example 162: (S)-2-((5-(4-(2-oxopyrrolidin-1-yl)phenyl)pyrazin-2-yl)amino)-6,6a,7,8-tetrahydro-9H-pyrido[2,3-b]pyrrolo[1,2-d][1,4]oxazin-9-one

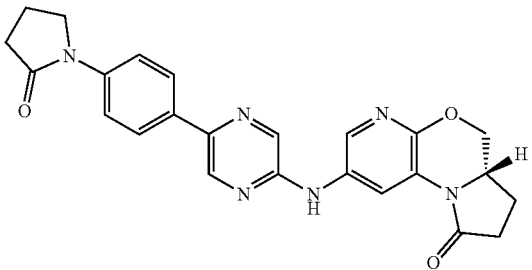 [SMILES: O=C1CCCN1c1ccc(-c2cnc(Nc3cnc4c(c3)N3C(=O)CC[C@H]3CO4)cn2)cc1]

Step 1: Preparation of 1-(4-(5-bromopyrazin-2-yl)phenyl)pyrrolidin-2-one

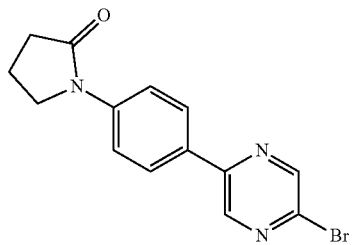 [SMILES: O=C1CCCN1c1ccc(-c2cnc(Br)cn2)cc1]

1-(4-(4,4,5,5-Tetramethyl-1,3,2-dioxaborolan-2-yl)phenyl)pyrrolidin-2-one (300 mg, 1.04 mmol), 2,5-dibromopyrazine (621 mg, 2.61 mmol), Pd(dppf)Cl₂ (76.4 mg, 0.104 mmol) and K₂CO₃ (433 mg, 3.13 mmol) were taken up in dioxane (20 mL) and H₂O (4 mL) and the resulting mixture was stirred at 80° C. for 16 h. A black solution was formed. LCMS (Rt=0.651 min; MS Calc'd: 317.0; MS Found: 317.7 [M+H]⁺). The mixture was concentrated in vacuum. The residue was purified by Combi Flash (50% EtOAc in pentane) to give 1-(4-(5-bromopyrazin-2-yl)phenyl)pyrrolidin-2-one (270 mg, yield: 81%) as a yellow solid. ¹H NMR (400 MHz, CDCl₃) δ 2.17-2.60 (2H, m), 2.66 (2H, t, J=8.0 Hz), 3.93 (2H, t, J=6.8 Hz), 7.80 (2H, d, J=8.8 Hz), 8.01 (2H, d, J=9.2 Hz), 8.69 (1H, d, J=1.6 Hz), 8.76 (1H, d, J=1.6 Hz).

Step 2: Preparation of 1-(5-Amino-3-pyridyl)pyrrolidin-2-one

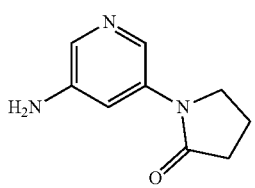 [SMILES: Nc1cncc(N2CCCC2=O)c1]

5-Bromopyridin-3-amine (10 g, 57.8 mmol), pyrrolidin-2-one (9 ml, 63.2 mmol), K₂CO₃ (15 g, 115.6 mmol), CuI (1.1 g, 5.78 mmol) and DMEDA (1.3 ml, 8.42 mmol) were taken up in 1,4-dioxane (100 ml) and the resulting mixture was refluxed overnight. After cooling to rt, EtOAc was added and the mixture filtered through celite. The filtrate was concentrated and purified on a silica gel column to give the product as a solid (6 g, 59%). MS ES+m/z 178 [M+H]⁺.

Step 3: Preparation of (5S)-5-[(3-bromo-5-nitro-2-pyridyl)oxymethyl]pyrrolidin-2-one

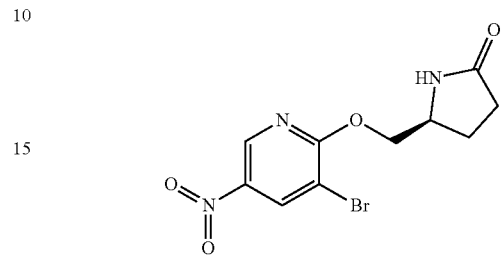

3-Bromo-2-chloro-5-nitro-pyridine (1 g, 4.21 mmol), (5S)-5-(hydroxymethyl)pyrrolidin-2-one (500 mg, 4.34 mmol) and K₂CO₃ (700 mg, 5.06 mmol) were taken up in MeCN (10 ml) and the resulting mixture was stirred at 70° C. overnight. More (5S)-5-(hydroxymethyl)pyrrolidin-2-one (130 mg, 1.13 mmol) and K₂CO₃ (300 mg, 2.17 mmol) were added and stirring continued at 70° C. for 5 h. After cooling to rt, the mixture was diluted with water (10 ml) and EtOAc (10 ml) and the organic layer separated. The remaining aqueous layer was further extracted with EtOAc (2×10 ml) and the combined organics were washed with brine, dried over Na₂SO₄, filtered and concentrated to give the product as a solid (1.13 g, 85%). MS ES+m/z 316 [M+H]⁺.

Step 4: Preparation of (6S)-12-nitro-8-oxa-2,10-diazatricyclo[7.4.0.02,6]trideca-1(9),10,12-trien-3-one

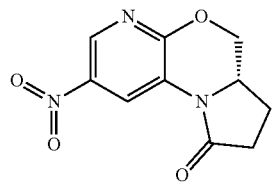 [SMILES: O=C1CC[C@H]2COc3ncc([N+](=O)[O-])cc3N12]

(5S)-5-[(3-bromo-5-nitro-2-pyridyl)oxymethyl]pyrrolidin-2-one (1.13 g, 3.57 mmol), CuI (75 mg, 0.39 mmol), N,N'-dimethylethylenediamine (85 μl, 0.8 mmol) and K₂CO₃ (0.99 g, 7.15 mmol) were taken up in EtOAc (20 ml) and the resulting mixture was stirred at 70° C. for 2 h. More CuI (75 mg, 0.39 mmol) and N,N'-dimethylethylenediamine (85 μl, 0.8 mmol) were added and the mixture was refluxed for 2 h. Cs₂CO₃ (2 g, 6.14 mmol) and 1,4-dioxane (20 ml) were added and stirring continued at 100° C. overnight. When cooled to rt the mixture was filtered through celite and rinsed with EtOAc (2×5 ml). The filtrate was washed with half-saturated brine (20 ml), dried over Na₂SO₄, filtered and concentrated to give the product as a solid (720 mg, 86%). MS ES+m/z 236 [M+H]⁺.

Step 5: Preparation of (S)-2-amino-6,6a,7,8-tetra-hydro-9H-pyrido[2,3-b]pyrrolo[1,2-d][1,4]oxazin-9-one

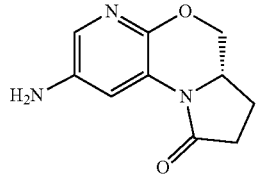 [SMILES: Nc1cnc2c(c1)N1C(=O)CC[C@H]1CO2]

(6S)-12-nitro-8-oxa-2,10-diazatricyclo[7.4.0.02,6]tri-deca-1(9),10,12-trien-3-one (357 mg, 1.52 mmol), Fe (509 mg, 9.11 mmol) and ammonium chloride (244 mg, 4.55 mmol) were taken up in EtOH/H$_2$O (4:1, 12.5 ml) and the resulting mixture was refluxed for 1.5 h. After cooling to rt the mixture was filtered through celite, rinsed with MeOH and the filtrate was concentrated. The resulting residue was suspended in water and pH was adjusted to about ~7 by careful addition of a sat. aq. NaHCO$_3$. The mixture was extracted with EtOAc and the combined organics were dried over Na$_2$SO$_4$, filtered and concentrated to give the product as a solid (212 mg, 68%). MS ES+m/z 206 [M+H]$^+$.

Step 6: Preparation of (S)-2-((5-(4-(2-oxopyrroli-din-1-yl)phenyl)pyrazin-2-yl)amino)-6,6a,7,8-tetra-hydro-9H-pyrido[2,3-b]pyrrolo[1,2-d][1,4]oxazin-9-one

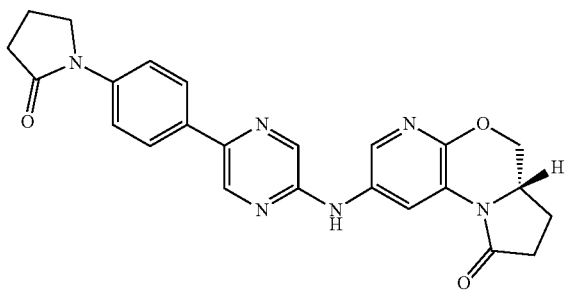 [SMILES: O=C1CCCN1c1ccc(-c2cnc(Nc3cnc4c(c3)N3C(=O)CC[C@H]3CO4)cn2)cc1]

A mixture of Pd$_2$(dba)$_3$ (37 mg, 0.041 mmol) and Brett-phos (44 mg, 0.082 mmol) in 1,4-dioxane (1 mL) was stirred at 50° C. for 10 min. 1-(4-(5-Bromopyrazin-2-yl)phenyl) pyrrolidin-2-one (130 mg, 0.409 mmol), (S)-2-amino-6,6a,7,8-tetrahydro-9H-pyrido[2,3-b]pyrrolo[1,2-d][1,4]oxazin-9-one (84 mg, 0.409 mmol) in dioxane (5 mL) and Cs$_2$CO$_3$ (400 mg, 1.23 mmol) were added and the resulting mixture was stirred at 100° C. for 12 h. A black brown mixture was formed. LCMS showed the purity of the desired product (Rt=0.696 min; MS Calc'd: 442.2; MS Found: 443.1 [M+H]$^+$). The reaction mixture was diluted with DCM (10 mL), filtered and concentrated. The residue was purified by prep-HPLC (0.05% NH$_3$.H$_2$O as an additive) and lyophilized to give (S)-2-((5-(4-(2-oxopyrrolidin-1-yl)phenyl) pyrazin-2-yl)amino)-6,6a,7,8-tetrahydro-9H-pyrido[2,3-b] pyrrolo[1,2-d][1,4]oxazin-9-one (13.8 mg, yield: 8%) as a white solid. $^1$H NMR (400 MHz, DMSO-d$_6$) δ 1.62-1.76 (1H, m), 2.04-2.13 (2H, m), 2.17-2.27 (1H, m), 2.32-2.42 (1H, m), 2.54 (2H, overlap with DMSO), 2.63-2.73 (1H, m), 3.84-3.95 (3H, m), 4.04-4.11 (1H, m), 4.60 (1H, dd, J=10.8, 2.8 Hz), 7.76 (2H, d, J=8.8 Hz), 8.01 (2H, d, J=8.4 Hz), 8.27 (1H, s), 8.44 (1H, d, J=2.8 Hz), 8.70 (1H, s), 9.00 (1H, d, J=2.4 Hz), 9.70 (1H, s).

Example 163: 1-(5-((5-(4-(2-oxopyrrolidin-1-yl) phenyl)pyridin-2-yl)amino)pyridin-3-yl)-3-(thiazol-4-ylmethyl)imidazolidin-2-one

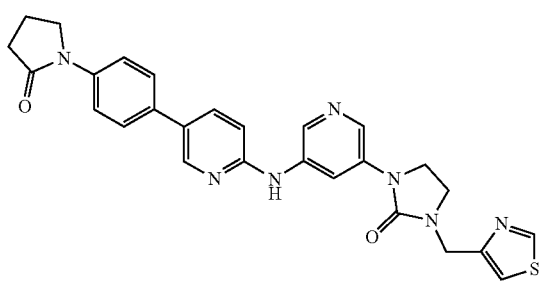 [SMILES: O=C1CCCN1c1ccc(-c2ccc(Nc3cncc(N4CCN(Cc5cscn5)C4=O)c3)nc2)cc1]

Step 1: Preparation of 1-(5-bromopyridin-3-yl)-3-(thiazol-4-ylmethyl)imidazolidin-2-one

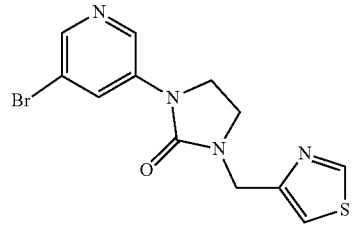 [SMILES: O=C1N(Cc2cscn2)CCN1c1cncc(Br)c1]

To a solution of 1-(5-bromopyridin-3-yl)imidazolidin-2-one (100 mg, 0.413 mmol) in DMF (2 mL) was added NaH (66 mg, 1.7 mmol, 60% purity) and then the mixture was stirred at 25° C. for 30 min. To the mixture was added 4-(chloromethyl)thiazole (105 mg, 0.620 mmol, HCl salt) at 0° C. and the mixture was stirred at 25° C. for 3 h. A gray suspension was formed. LCMS showed 1-(5-bromopyridin-3-yl)imidazolidin-2-one was consumed completely and desired product (Rt=0.560 min; MS Calc'd: 338.0; MS Found: 338.7[M+H]$^+$) was detected. Amounts of crude 1-(5-bromopyridin-3-yl)imidazolidin-2-one were increased using the same synthetic procedure as above and poured into sat. aq. NH$_4$Cl (50 mL), extracted with EtOAc (50 mL×3). The combined organic layer was washed with brine (50 mL×6), dried over Na$_2$SO$_4$ and concentrated to dryness. The residue was purified by Combi Flash (EtOAc) to give 1-(5-bromopyridin-3-yl)-3-(thiazol-4-ylmethyl)imidazoli-din-2-one (288 mg, 92% yield) as a yellow gum. $^1$H NMR (400 MHz, CDCl$_3$) δ 3.60-3.70 (2H, m), 3.80-3.90 (2H, m), 4.66 (2H, s), 7.31 (1H, d, J=2.0 Hz), 8.34 (1H, d, J=2.0 Hz), 8.47 (1H, t, J=2.4 Hz), 8.52 (1H, d, J=2.8 Hz), 8.81 (1H, d, J=2.0 Hz).

Step 2: Preparation of 1-(5-((5-(4-(2-oxopyrrolidin-1-yl)phenyl)pyridin-2-yl)amino)pyridin-3-yl)-3-(thiazol-4-ylmethyl)imidazolidin-2-one

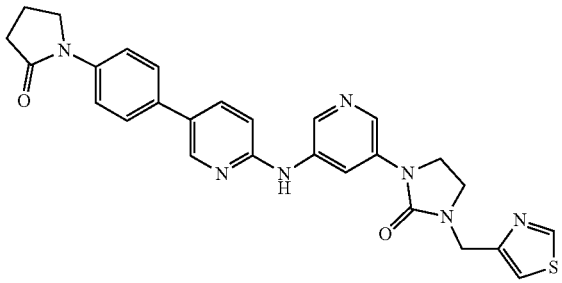 [SMILES: O=C1CCCN1c1ccc(-c2ccc(Nc3cncc(N4CCN(Cc5cscn5)C4=O)c3)nc2)cc1]

To a suspension of 1-(4-(6-aminopyridin-3-yl)phenyl)pyrrolidin-2-one (70 mg, 0.028 mmol), 1-(5-bromopyridin-3-yl)-3-(thiazol-4-ylmethyl)imidazolidin-2-one (105 mg, 0.310 mmol) and Cs$_2$CO$_3$ (270 mg, 0.829 mmol) in dioxane (2 mL) was added Pd$_2$(dba)$_3$ (25 mg, 0.028 mmol) and Brettphos (30 mg, 0.055 mmol) under N$_2$ atmosphere. Then the mixture was stirred at about 100° C. for 16 h. A brown suspension was formed. LCMS showed 1-(4-(6-aminopyridin-3-yl)phenyl)pyrrolidin-2-one was consumed completely and the purity of desired product (Rt=0.720 min; MS Calc'd: 511.2; MS Found: 512.1 [M+H]$^+$). The mixture was filtered and the cake was washed with DCM/MeOH (10:1, 5 mL×3). The combined filtrate was concentrated to dryness. The residue was purified by prep-HPLC (0.225% FA as an additive). After lyophilization, the product was triturated with EtOAc (2 mL) and filtered. The cake was lyophilized for 16 h to give 1-(5-((5-(4-(2-oxopyrrolidin-1-yl)phenyl)pyridin-2-yl)amino)pyridin-3-yl)-3-(thiazol-4-ylmethyl)imidazolidin-2-one (13.06 mg, 8% yield) as an off-white solid. $^1$H NMR (400 MHz, DMSO-d$_6$) δ 2.04-2.14 (2H, m), 2.53-2.54 (2H, m), 3.49-3.57 (2H, m), 3.85-3.92 (4H, m), 4.57 (2H, s), 6.97 (1H, d, J=8.4 Hz), 7.60-7.80 (5H, m), 7.93-7.98 (1H, m), 8.30-8.35 (1H, m), 8.50 (1H, t, J=2.4 Hz), 8.54 (1H, d, J=2.4 Hz), 8.66 (1H, d, J=1.2 Hz), 9.12 (1H, d, J=2.0 Hz), 9.41 (1H, br s).

Example 164: 1-(5-((5-(4-(2-oxopyrrolidin-1-yl)phenyl)pyrazin-2-yl)amino)pyridin-3-yl)-3-(thiazol-4-ylmethyl)imidazolidin-2-one

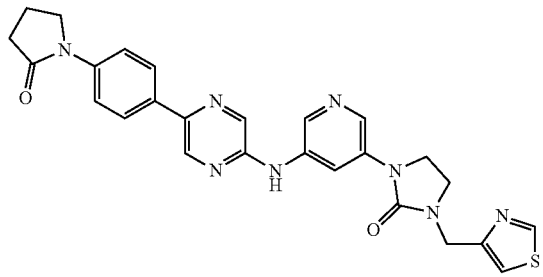 [SMILES: O=C1CCCN1c1ccc(-c2cnc(Nc3cncc(N4CCN(Cc5cscn5)C4=O)c3)cn2)cc1]

To a suspension of 1-(4-(5-aminopyrazin-2-yl)phenyl)pyrrolidin-2-one (70 mg, 0.28 mmol), 1-(5-bromopyridin-3-yl)-3-(thiazol-4-ylmethyl)imidazolidin-2-one (105 mg, 0.310 mmol) and Cs$_2$CO$_3$ (269 mg, 0.826 mmol) in dioxane (2 mL) was added Pd$_2$(dba)$^3$ (25 mg, 0.028 mmol) Brettphos (30 mg, 0.055 mmol) under N$_2$ atmosphere. Then the mixture was stirred at about 100° C. for 16 h. A brown suspension was formed. LCMS showed desired product purity (Rt=0.716 min; MS Calc'd: 512.2; MS Found: 513.1 [M+H]$^+$). The mixture was filtered and the cake was washed with DCM/MeOH (10:1, 5 mL×3). The combined filtrate was concentrated to dryness. The residue was purified by prep-HPLC (0.225% FA as an additive). After lyophilization, the product was triturated with EtOAc (2 mL) and filtered. The cake was lyophilized for 16 h to give 1-(5-((5-(4-(2-oxopyrrolidin-1-yl)phenyl)pyrazin-2-yl)amino)pyridin-3-yl)-3-(thiazol-4-ylmethyl)imidazolidin-2-one (8.46 mg, 5% yield) as an off-white solid. $^1$H NMR (400 MHz, DMSO-d$_6$) δ 2.04-2.14 (2H, m), 2.53-2.54 (2H, m), 3.49-3.57 (2H, m), 3.85-3.94 (4H, m), 4.58 (2H, s), 7.85 (1H, d, J=2.0 Hz), 7.78 (2H, d, J=8.8 Hz), 8.04 (2H, d, J=8.8 Hz), 8.34-8.38 (2H, m), 8.55 (1H, t, J=2.4 Hz), 8.69 (1H, d, J=2.0 Hz), 8.79 (1H, d, J=1.2 Hz), 9.12 (1H, d, J=2.0 Hz), 9.87 (1H, br s).

Example 165: 1-(oxazol-4-ylmethyl)-3-(5-((5-(4-(2-oxopyrrolidin-1-yl)phenyl)pyridin-2-yl)amino)pyridin-3-yl)imidazolidin-2-one

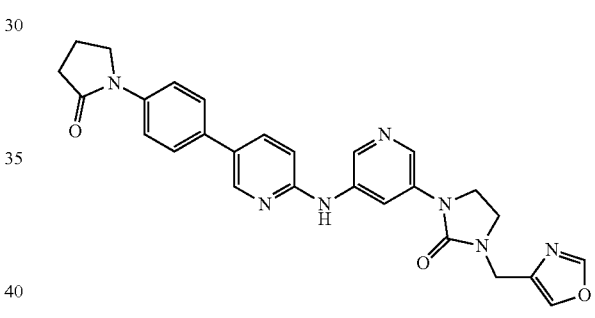

Step 1: Preparation of oxazol-4-ylmethanol

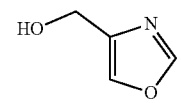

To a solution of ethyl oxazole-4-carboxylate (2.00 g, 14.2 mmol in THF (20 mL)/H$_2$O (3 mL) was added NaBH$_4$ (1.07 g, 28.3 mmol) at 0° C. and then the mixture was stirred at 25° C. for 72 h. A white cloudy was formed. To the mixture was added anhydrous Na$_2$SO$_4$ (20 g) and the mixture was stirred at 25° C. for 1 hour. The mixture was filtered and the cake was washed with MTBE (20 mL). The combined organic layer was concentrated to dryness. The residue was purified by Combi Flash (EtOAc in pentane from 10% to 100%) to give oxazol-4-ylmethanol (800 mg, 56% yield) as colorless oil. $^1$H NMR (400 MHz, CDCl$_3$) δ 2.52 (1H, brt, J=5.6 Hz), 4.64 (2H, d, J=5.6 Hz), 7.64 (1H, d, J=0.8 Hz), 7.89 (1H, s).

Step 2: Preparation of oxazol-4-ylmethyl 4-methylbenzenesulfonate

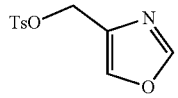 [SMILES: Cc1ccc(S(=O)(=O)OCc2cocn2)cc1]

To a solution of oxazol-4-ylmethanol (150 mg, 1.51 mmol) and Ts$_2$O (544 mg, 1.67 mmol) in DCM (5 mL) was added TEA (383 mg, 3.78 mmol) at 0° C. and then the mixture was stirred at 0° C. for 1 hour. A yellow solution was formed. TLC (EtOAc, by KMnO$_4$) showed oxazol-4-yl-methanol was consumed completely and a new spot (Rf~0.8) was formed. The mixture was poured into water (10 mL) and extracted with DCM (5 mL×2). The combined organic layer was washed with brine (10 mL), dried over Na$_2$SO$_4$ and concentrated to dryness to give oxazol-4-ylm-ethyl 4-methylbenzenesulfonate (400 mg, crude) as yellow oil, which was used to next step directly.

Step 3: Preparation of 1-(5-bromopyridin-3-yl)-3-(oxazol-4-ylmethyl)imidazolidin-2-one

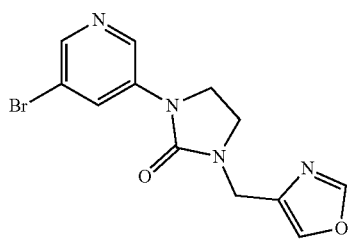 [SMILES: O=C1N(Cc2cocn2)CCN1c1cncc(Br)c1]

To a solution of 1-(5-bromopyridin-3-yl)imidazolidin-2-one (130 mg, 0.537 mmol) in DMF (2 mL) was added NaH (64 mg, 1.6 mmol, 60% purity) at 0° C. and then the mixture was stirred at 25° C. for 30 min. To the mixture was added oxazol-4-ylmethyl 4-methylbenzenesulfonate (400 mg, crude) at 0° C. and the mixture was stirred at 25° C. for 1 hour. A yellow suspension was formed. LCMS showed 1-(5-bromopyridin-3-yl)imidazolidin-2-one was consumed completely and the purity of desired product (Rt=0.680 min; MS Calc'd: 322.0; MS Found: 324.6 [M+H]$^+$). The mixture was poured into sat.aq.NH$_4$Cl (50 mL) and extracted with EtOAc (50 mL×3). The combined organic layer was washed with brine (50 mL×6), dried over Na$_2$SO$_4$ and concentrated to dryness. The residue was purified by Combi Flash (eluting with EtOAc in pentane from 10% to 100%). to give 1-(5-bromopyridin-3-yl)-3-(oxazol-4-ylmethyl)imidazolidin-2-one (150 mg, 86% yield) as a yellow gum. $^1$H NMR (400 MHz, CDCl$_3$) δ 3.60-3.70 (2H, m), 3.80-3.90 (2H, m), 4.44 (2H, s), 7.70 (1H, s), 7.88 (1H, s), 8.32-8.36 (1H, m), 8.43-8.47 (1H, m), 8.49-8.54 (1H, m).

Step 4: Preparation of 1-(oxazol-4-ylmethyl)-3-(5-((5-(4-(2-oxopyrrolidin-1-yl)phenyl)pyridin-2-yl)amino)pyridin-3-yl)imidazolidin-2-one

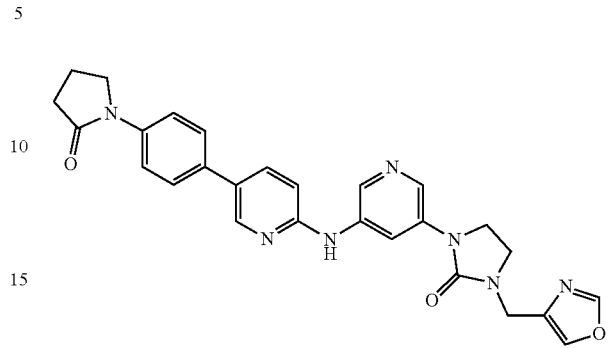

To a suspension of 1-(4-(6-aminopyridin-3-yl)phenyl)pyrrolidin-2-one (70 mg, 0.28 mmol), 1-(5-bromopyridin-3-yl)-3-(oxazol-4-ylmethyl)imidazolidin-2-one (100 mg, 0.310 mmol) and Cs$_2$CO$_3$ (270 mg, 0.829 mmol) in dioxane (2 mL) was added Pd$_2$(dba)$_3$ (25 mg, 0.028 mmol) and Brettphos (30 mg, 0.055 mmol) under N$_2$ atmosphere. Then the mixture was stirred at about 100° C. for 16 h. A brown suspension was formed. LCMS showed purity of desired product (Rt=0.683 min; MS Calc'd: 495.2; MS Found: 496.1[M+H]$^+$). The mixture was filtered and the cake was washed with DCM/MeOH (10:1, 10 mL×3). The combined filtrate was concentrated to dryness. The residue was purified by prep-HPLC (0.05% ammonia hydroxide as an additive) and then lyophilization to give 1-(oxazol-4-ylmethyl)-3-(5-((5-(4-(2-oxopyrrolidin-1-yl)phenyl)pyridin-2-yl)amino)pyridin-3-yl)imidazolidin-2-one (33.6 mg, 24% yield) as an off-white solid.

$^1$H NMR (400 MHz, DMSO-d$_6$) δ 2.00-2.14 (2H, m), 2.53-2.54 (2H, m), 3.45-3.53 (2H, m), 3.80-3.90 (4H, m), 4.33 (2H, s), 6.97 (1H, d, J=8.8 Hz), 7.66 (2H, d, J=8.8 Hz), 7.72 (2H, d, J=8.8 Hz), 7.94 (1H, dd, J=8.8, 2.8 Hz), 8.06 (1H, d, J=0.8 Hz), 8.29 (1H, d, J=2.4 Hz), 8.33 (1H, d, J=0.8 Hz), 8.49 (1H, d, J=2.4 Hz), 8.51 (1H, d, J=2.4 Hz), 8.58 (1H, d, J=2.4 Hz).

Example 166: 1-(oxazol-5-ylmethyl)-3-(5-((5-(4-(2-oxopyrrolidin-1-yl)phenyl)pyridin-2-yl)amino)pyridin-3-yl)imidazolidin-2-one

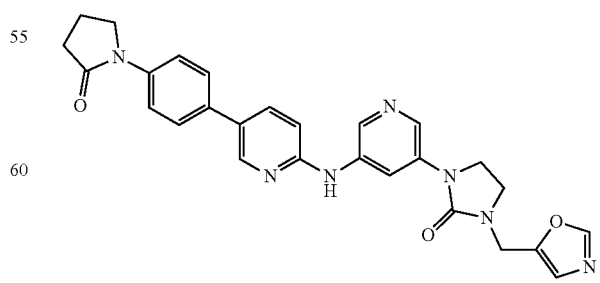

Step 1: Preparation of oxazol-5-ylmethanol

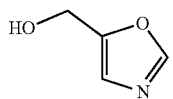

To a solution of ethyl oxazole-5-carboxylate (2.00 g, 14.2 mmol) in THF (20 mL) was added NaBH$_4$ (1.07 g, 28.3 mmol) at 0° C. and then the mixture was stirred at 25° C. for 48 h. A white cloudy was formed. To the mixture was added anhydrous Na$_2$SO$_4$ (20 g) and the mixture was stirred at 25° C. for 1 hour. The mixture was filtered and the cake was washed with MTBE (20 mL). The combined organic layer was concentrated to dryness. The residue was purified by Combi Flash (EtOAc in pentane from 10% to 100%) to give oxazol-5-ylmethanol (900 mg, 64% yield) as colorless oil. $^1$H NMR (400 MHz, CDCl$_3$) δ 2.02 (1H, brt, J=6.0 Hz), 4.74 (2H, d, J=6.0 Hz), 7.06 (1H, s), 7.89 (1H, s).

Step 2: Preparation of oxazol-5-ylmethyl 4-methylbenzenesulfonate

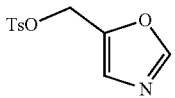

To a solution of oxazol-5-ylmethanol (150 mg, 1.51 mmol) and Ts$_2$O (519 mg, 1.59 mmol) in DCM (5 mL) was added TEA (383 mg, 3.78 mmol) at 0° C. and then the mixture was stirred at 0° C. for 1 hour. A yellow solution was formed. TLC (EtOAc, by KMnO$_4$) showed oxazol-5-ylmethanol was consumed completely and a new spot (Rf~0.8) was formed. The mixture was poured into water (10 mL) and extracted with DCM (5 mL×2). The combined organic layer was washed with brine (10 mL), dried over Na$_2$SO$_4$ and concentrated to dryness to give oxazol-5-ylmethyl 4-methylbenzenesulfonate (400 mg, crude) as yellow oil, which was used to next step directly.

Step 3: Preparation of 1-(5-bromopyridin-3-yl)-3-(oxazol-5-ylmethyl)imidazolidin-2-one

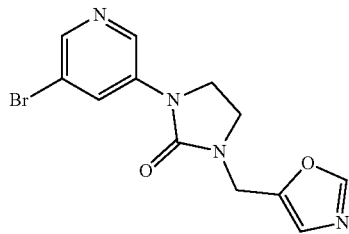 [SMILES: O=C1N(Cc2cnco2)CCN1c1cncc(Br)c1]

To a solution of 1-(5-bromopyridin-3-yl)imidazolidin-2-one (150 mg, 0.620 mmol) in DMF (5 mL) was added NaH (75 mg, 1.9 mmol, 60% purity) at 0° C. and then the mixture was stirred at 25° C. for 30 min. To the mixture was added oxazol-5-ylmethyl 4-methylbenzenesulfonate (400 mg, crude) at 0° C. and the mixture was stirred at 25° C. for 1 hour. A brown suspension was formed. LCMS showed about 14% of 1-(5-bromopyridin-3-yl)imidazolidin-2-one (Rt=0.585 min; MS Calc'd: 241.0; MS Found: 241.8 [M+H]$^+$) was remained and purity of desired product was 46% (Rt=0.683 min; MS Calc'd: 322.0; MS Found: 324.8 [M+H]$^+$). To the mixture was added oxazol-5-ylmethyl 4-methylbenzenesulfonate (200 mg crude) at 0° C. and then the mixture was stirred at 25° C. for 1 hour. A brown suspension was formed. LCMS showed desired product purity (Rt=0.693 min; MS Calc'd: 322.0; MS Found: 322.7 [M+H]$^+$). The mixture was poured into sat.aq.NH$_4$Cl (10 mL) and extracted with EtOAc (10 mL×3). The combined organic layer was washed with brine (10 mL×6), dried over Na$_2$SO$_4$ and concentrated to dryness. The residue was purified by Combi Flash (EtOAc=100%) to give 1-(5-bromopyridin-3-yl)-3-(oxazol-5-ylmethyl)imidazolidin-2-one (150 mg, 74% yield) as an off-white solid. $^1$H NMR (400 MHz, CDCl$_3$) δ 3.54-3.61 (2H, m), 3.84-3.93 (2H, m), 4.59 (2H, s), 7.10 (1H, s), 7.90 (1H, s), 8.38 (1H, d, J=1.6 Hz), 8.47 (1H, t, J=2.4 Hz), 8.54 (1H, d, J=2.4 Hz).

Step 4: Preparation of 1-(oxazol-5-ylmethyl)-3-(5-((5-(4-(2-oxopyrrolidin-1-yl)phenyl)pyridin-2-yl)amino)pyridin-3-yl)imidazolidin-2-one

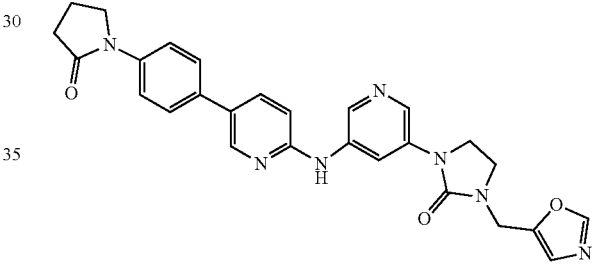

To a suspension of 1-(4-(6-aminopyridin-3-yl)phenyl)pyrrolidin-2-one (80 mg, 0.32 mmol), 1-(5-bromopyridin-3-yl)-3-(oxazol-5-ylmethyl)imidazolidin-2-one (114 mg, 0.354 mmol) and Cs$_2$CO$_3$ (309 mg, 0.948 mmol) in dioxane (2 mL) was added Pd$_2$(dba)$_3$ (29 mg, 0.032 mmol) and Brettphos (34 mg, 0.063 mmol) under N$_2$ atmosphere. Then the mixture was stirred at about 100° C. for 16 h. A brown suspension was formed. LCMS showed desired purity of product (Rt=0.683 min; MS Calc'd: 495.2; MS Found: 496.1[M+H]$^+$). The mixture was filtered and the cake was washed with DCM/MeOH (10:1, 10 mL×3). The combined filtrate was concentrated to dryness. The residue was purified by prep-HPLC (0.05% ammonia hydroxide as an additive) and then lyophilized to give 1-(oxazol-5-ylmethyl)-3-(5-((5-(4-(2-oxopyrrolidin-1-yl)phenyl)pyridin-2-yl)amino) pyridin-3-yl)imidazolidin-2-one (8.1 mg, 5% yield) as a white solid. $^1$H NMR (400 MHz, DMSO-d$_6$) δ 2.04-2.14 (2H, m), 2.53-2.54 (2H, m), 3.44-3.51 (2H, m), 3.80-3.91 (4H, m), 4.53 (2H, s), 6.97 (1H, d, J=8.8 Hz), 7.19 (1H, s), 7.68 (2H, d, J=8.8 Hz), 7.75 (2H, d, J=8.8 Hz), 7.94 (1H, dd, J=8.8, 2.8 Hz), 8.31 (1H, d, J=2.4 Hz), 8.37 (1H, s), 8.49 (1H, d, J=2.4 Hz), 8.53 (1H, d, J=2.8 Hz), 8.67 (1H, d, J=2.4 Hz), 9.41 (1H, br s).

Example 167: (E)-4-(4-(dimethylamino)but-2-enamido)-N-(5-((5-(4-(2-oxopyrrolidin-1-yl)phenyl)pyridin-2-yl)amino)pyridin-3-yl)benzamide

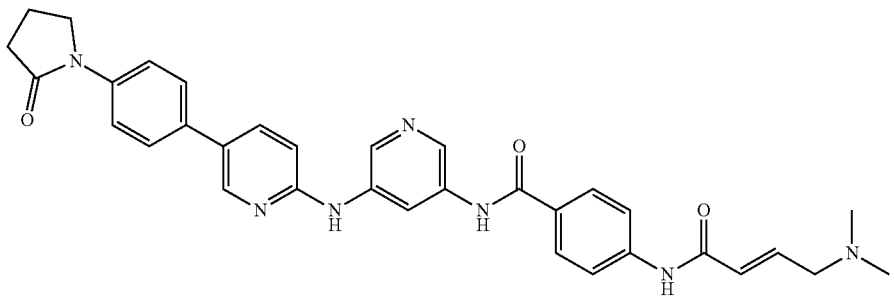 [SMILES: CN(C)C/C=C/C(=O)Nc1ccc(C(=O)Nc2cncc(Nc3ccc(-c4ccc(N5CCCC5=O)cc4)cn3)c2)cc1]

A solution of 1-(4-(6-((5-aminopyridin-3-yl)amino)pyridin-3-yl)phenyl)pyrrolidin-2-one (100 mg, 0.290 mmol), (E)-4-(4-(dimethylamino)but-2-enamido)benzoic acid (143 mg, 0.579 mmol) and EDCI (138 mg, 0.724 mmol) in pyridine (5 mL) was stirred at 25° C. under $N_2$ for 3 hours. LCMS showed that the purity of desired product is 68.9%. The reaction mixture was stirred at 25° C. under $N_2$ for 30 min. A yellow suspension was formed. LCMS showed that the starting material was consumed completely. The purity of desired product is 93% (Rt=0.591 min; MS Calcd: 575.3; MS Found: 576.1 [M+H]$^+$). The reaction mixture was concentrated to dryness. The residue was triturated with MeCN/MeOH (1/1, 10 mL) and filtered to give an impure product (84 mg). The impure product was triturated with MeCN (10 mL) to give (E)-4-(4-(dimethylamino)but-2-enamido)-N-(5-((5-(4-(2-oxopyrrolidin-1-yl)phenyl)pyridin-2-yl)amino)pyridin-3-yl)benzamide (71.3 mg, yield: 42.8%) as a yellow solid.

$^1$H NMR (400 MHz, DMSO-d$_6$) δ 2.10-2.27 (2H, m), 2.56-2.59 (2H, m), 2.79 (6H, brs), 3.89 (2H, t, J=6.6 Hz), 3.96 (2H, brs), 6.56 (1H, d, J=14.4 Hz), 6.81-6.93 (1H, m), 7.12 (1H, d, J=8.4 Hz), 7.69-7.74 (2H, m), 7.75-7.80 (2H, m), 7.90 (2H, d, J=8.4 Hz), 8.07 (2H, d, J=8.4 Hz), 8.63 (1H, brs), 8.79 (1H, brs), 8.96 (1H, brs), 9.13 (1H, brs), 10.25 (1H, brs), 10.59 (1H, brs), 10.86 (1H, brs), 10.92 (1H, brs).

Example 168: 4-(4-(dimethylamino)butanamido)-N-(5-((5-(4-(2-oxopyrrolidin-1-yl)phenyl)pyridin-2-yl)amino)pyridin-3-yl)benzamide

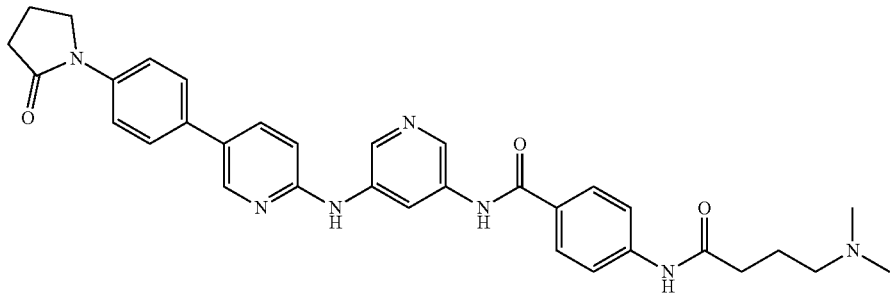 [SMILES: CN(C)CCCC(=O)Nc1ccc(C(=O)Nc2cncc(Nc3ccc(-c4ccc(N5CCCC5=O)cc4)cn3)c2)cc1]

A mixture of 1-(4-(6-((5-aminopyridin-3-yl)amino)pyridin-3-yl)phenyl)pyrrolidin-2-one (50 mg, 0.15 mmol, HCl salt) and 4-(4-(dimethylamino)butanamido)benzoic acid (72 mg, 0.29 mmol) in pyridine (3 mL) was added EDCI (56 mg, 0.29 mmol) at 28° C., then the reaction mixture was stirred at 28° C. for 5.5 hours. A yellow solution was formed. LCMS showed that the purity of desired product is 94.8% (Rt=0.562; MS Calcd: 577.2; MS Found: 578.1 [M+H]$^+$). The reaction mixture was concentrated to dryness. Then the residue was purified by prep-HPLC (0.1% TFA as an additive) and lyophilized to give 4-(4-(dimethylamino)butanamido)-N-(5-((5-(4-(2-oxopyrrolidin-1-yl)phenyl)pyridin-2-yl)amino)pyridin-3-yl)benzamide (7.7 mg, yield: 8.9%) as a yellow solid.

$^1$H NMR (400 MHz, DMSO-d$_6$) δ 1.90-2.01 (2H, m), 2.05-2.15 (2H, m), 2.53-2.56 (4H, m), 2.82 (6H, d, J=5.2 Hz), 3.08-3.16 (2H, m), 3.85-3.91 (2H, t, J=7.2 Hz), 7.02-7.07 (1H, m), 7.68-7.73 (2H, m), 7.75-7.79 (4H, m), 7.99-8.05 (3H, m), 8.59 (1H, d, J=2.0 Hz), 8.65 (1H, d, J=16.8 Hz), 8.85 (1H, s), 8.93 (1H, brs), 9.86 (1H, brs), 10.38 (1H, brs), 10.61 (1H, brs).

Example 169: (E)-4-(dimethylamino)-N-(3-(3-oxo-3-((5-((5-(4-(2-oxopyrrolidin-1-yl)phenyl)pyridin-2-yl)amino)pyridin-3-yl)amino)propyl)phenyl)but-2-enamide

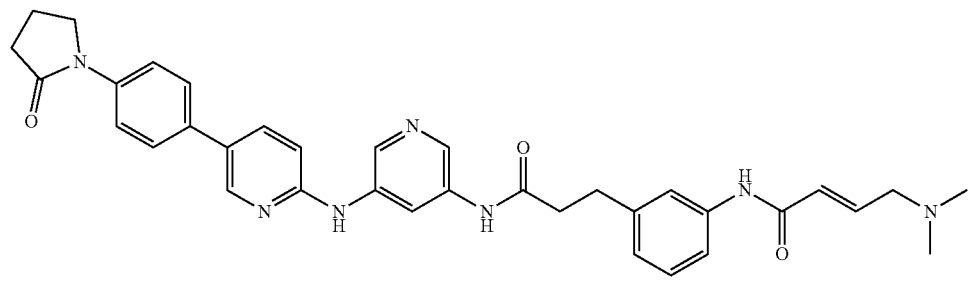 [SMILES: CN(C)C/C=C/C(=O)Nc1cccc(CCC(=O)Nc2cncc(Nc3ccc(-c4ccc(N5CCCC5=O)cc4)cn3)c2)c1]

Step 1: Preparation of tert-butyl (3-(3-oxo-3-((5-((5-(4-(2-oxopyrrolidin-1-yl)phenyl)pyridin-2-yl)amino)pyridin-3-yl)amino)propyl)phenyl)carbamate

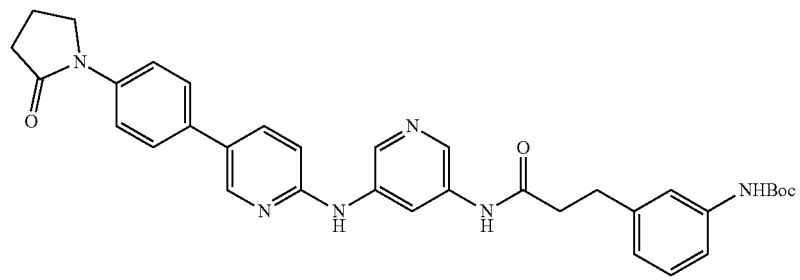 [SMILES: CC(C)(C)OC(=O)Nc1cccc(CCC(=O)Nc2cncc(Nc3ccc(-c4ccc(N5CCCC5=O)cc4)cn3)c2)c1]

To a mixture of 1-(4-(6-((5-aminopyridin-3-yl)amino)pyridin-3-yl)phenyl)pyrrolidin-2-one (300 mg, 0.717 mmol, HCl salt) and 3-(3-((tert-butoxycarbonyl)amino)phenyl)propanoic acid (209 mg, 0.789 mmol) in pyridine (10 mL) was added EDCI (275 mg, 1.43 mmol) at 28° C. and then the reaction mixture was stirred at 50° C. for 2 hours. A yellow suspension was formed. LCMS showed that purity of product is 82% (Rt=0.784 min; MS Calcd: 592.2; MS Found: 593.3 [M+H]$^+$). The mixture was added water (20 mL) and extracted with EtOAc (50 mL×3). Then organic layer was concentrated to dryness. The aqueous layer was extracted with DCM/MeOH (10/1, 50 mL×3). The combined organic layer was concentrated under reduced pressure to give tert-butyl (3-(3-oxo-3-((5-((5-(4-(2-oxopyrrolidin-1-yl)phenyl)pyridin-2-yl)amino)pyridin-3-yl)amino)propyl)phenyl)carbamate (500 mg, crude) as a yellow solid.

Step 2: Preparation of 3-(3-aminophenyl)-N-(5-((5-(4-(2-oxopyrrolidin-1-yl)phenyl)pyridin-2-yl)amino)pyridin-3-yl)propanamide

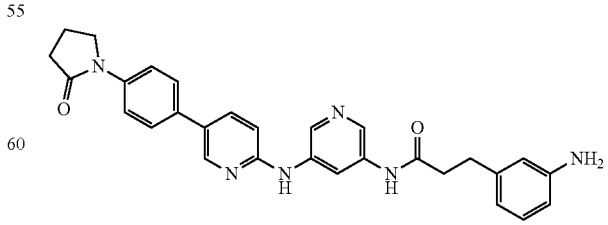

A suspension of tert-butyl (3-(3-oxo-3-((5-((5-(4-(2-oxopyrrolidin-1-yl)phenyl)pyridin-2-yl)amino)pyridin-3-yl)amino)propyl)phenyl)carbamate (500 mg, 0.844 mmol, crude) in HCl/EtOAc (35 mL, 4 M in EtOAc) was stirred at 28° C. for 1 hour. A yellow suspension was formed. LCMS showed that the purity of desired product is 98.8% (Rt=0.672 min; MS Calcd: 492.2; MS Found: 493.3 [M+H]$^+$). The mixture was concentrated to dryness. The residue was triturated with sat.NaHCO$_3$ (10 mL)/MeCN (5 mL) and filtered. The filter cake was triturated with MeCN (5 mL) to give 3-(3-aminophenyl)-N-(5-((5-(4-(2-oxopyrrolidin-1-yl)phenyl)pyridin-2-yl)amino)pyridin-3-yl)propanamide (230 mg, yield for two steps: 65%) as a light red solid.
$^1$H NMR (400 MHz, DMSO-d$_6$) δ 2.06-2.13 (2H, m), 2.64-2.65 (2H, m), 2.74-2.85 (2H, m), 2.93-2.98 (2H, m), 3.89 (2H, t, J=6.8 Hz), 6.95-7.15 (4H, m), 7.24-7.41 (1H, m), 7.67-7.84 (4H, m), 8.06 (1H, d, J=7.2 Hz), 8.61 (2H, d, J=8.4 Hz), 8.69 (1H, s), 9.04 (1H, s), 10.16 (1H, brs), 10.80 (1H, brs).

Step 3: Preparation of (E)-4-(dimethylamino)-N-(3-(3-oxo-3-((5-((5-(4-(2-oxopyrrolidin-1-yl)phenyl)pyridin-2-yl)amino)pyridin-3-yl)amino)propyl)phenyl)but-2-enamide

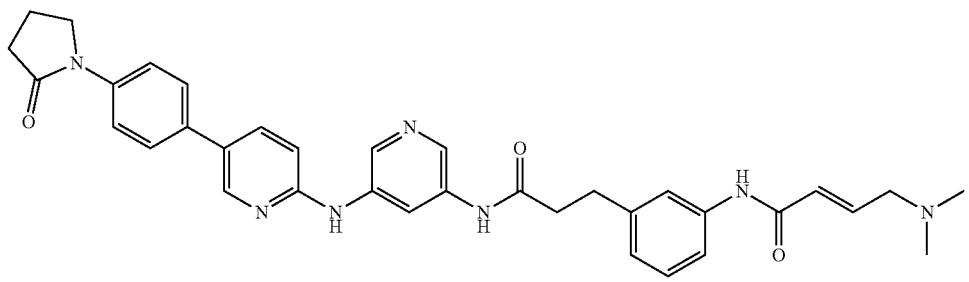 [SMILES: CN(C)C/C=C/C(=O)Nc1cccc(CCC(=O)Nc2cncc(Nc3ccc(-c4ccc(N5CCCC5=O)cc4)cn3)c2)c1]

To a mixture of 3-(4-aminophenyl)-N-(5-((5-(4-(2-oxopyrrolidin-1-yl)phenyl)pyridin-2-yl)amino)pyridin-3-yl)propanamide (50 mg, 0.10 mmol) and (E)-4-(dimethylamino)but-2-enoic acid (26 mg, 0.20 mmol) in pyridine (2 mL) was added EDCI (39 mg, 0.20 mmol) at 28° C. and then the reaction mixture was stirred at 28° C. for 3 hours. A red suspension was formed. LCMS showed that the purity of desired product is 69% (Rt=1.254 min; MS Calcd: 603.3; MS Found: 604.2 [M+H]$^+$). The reaction mixture was concentrated to dryness. Then the residue was purified by prep-HPLC (0.225% FA as an additive) and lyophilized to give (E)-4-(dimethylamino)-N-(3-(3-oxo-3-((5-((5-(4-(2-oxopyrrolidin-1-yl)phenyl)pyridin-2-yl)amino)pyridin-3-yl)amino)propyl)phenyl)but-2-enamide (15.5 mg, yield: 24%) as a brown solid.
$^1$H NMR (400 MHz, DMSO-d$_6$) δ 2.03-2.11 (2H, m), 2.49 (6H, s), 2.48-2.51 (2H, m), 2.65-2.70 (2H, m), 2.84-2.95 (2H, m), 3.54-3.62 (2H, m), 3.87 (2H, t, J=6.8 Hz), 6.36 (1H, d, J=15.6 Hz), 6.63-6.78 (1H, m), 6.97 (1H, t, J=8.8 Hz), 7.25 (1H, t, J=7.6 Hz), 7.49 (1H, d, J=8.0 Hz), 7.59 (1H, s), 7.65-7.71 (2H, m), 7.73-7.76 (2H, m), 7.95 (1H, dd, J=8.4 Hz, 2.4 Hz), 8.14 (1H, s), 8.33 (1H, d, J=2.0 Hz), 8.48-8.55 (2H, m), 8.61 (1H, d, J=2.0 Hz), 9.4 (1H, s), 10.11 (1H, s), 10.15 (1H, s).

Example 170: 4-(dimethylamino)-N-(3-(3-oxo-3-((5-((5-(4-(2-oxopyrrolidin-1-yl)phenyl)pyridin-2-yl)amino)pyridin-3-yl)amino)propyl)phenyl)butanamide

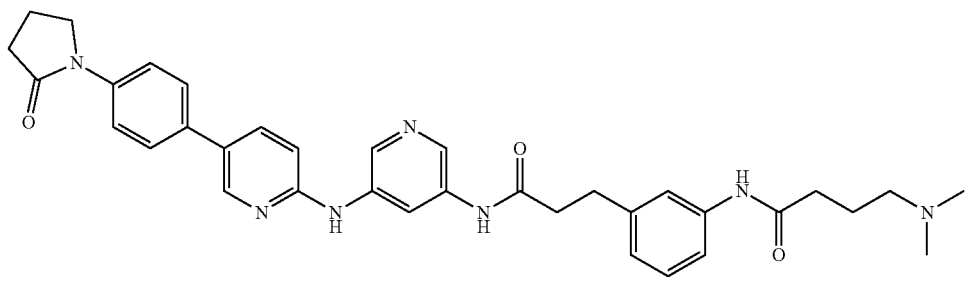 [SMILES: CN(C)CCCC(=O)Nc1cccc(CCC(=O)Nc2cncc(Nc3ccc(-c4ccc(N5CCCC5=O)cc4)cn3)c2)c1]

To a mixture of 3-(4-aminophenyl)-N-(5-((5-(4-(2-oxopyrrolidin-1-yl)phenyl)pyridin-2-yl)amino)pyridin-3-yl)propanamide (50 mg, 0.10 mmol) and 4-(dimethylamino)butanoic acid (27 mg, 0.20 mmol) in pyridine (2 mL) was added EDCI (39 mg, 0.20 mmol) at 28° C. and then the reaction mixture was stirred at 28° C. for 16 hours. A red suspension was formed. LCMS showed that the purity of desired product is 92% (Rt=1.244 min; MS Calcd: 605.3; MS Found: 606.3[M+H]$^+$). The reaction mixture was concentrated to dryness. Then the residue was purified by prep-HPLC (0.225% FA as an additive) and lyophilized to give 4-(dimethylamino)-N-(3-(3-oxo-3-((5-((5-(4-(2-oxopyrrolidin-1-yl)phenyl)pyridin-2-yl)amino)pyridin-3-yl)amino)propyl)phenyl)butanamide (7.0 mg, yield: 11%) as a yellow solid.

$^1$H NMR (400 MHz, DMSO-d$_6$) δ 1.85-1.95 (2H, m), 2.03-2.15 (2H, m), 2.37-2.42 (2H, in), 2.46-2.50 (2H, m), 2.65-2.71 (4H, m), 2.79 (6H, s), 2.85-2.95 (2H, m), 3.87 (2H, t, J=7.2 Hz), 6.94-7.00 (2H, m), 7.22 (1H, t, J=9.6 Hz), 7.40 (1H, d, J=8.0 Hz), 7.52 (1H, s), 7.65-7.71 (2H, m), 7.72-7.78 (2H, m), 7.98 (1H, dd, J=8.8, 2.4 Hz), 8.43 (1H, s), 8.54 (1H, d, J=2.4 Hz), 8.57 (1H, brs), 8.74 (1H, s), 9.64 (1H, brs), 9.96 (1H, s), 10.3 (1H, brs).

Example 171: (E)-4-(dimethylamino)-N-(2-oxo-2-((3-((2-oxo-3-(5-((5-(4-(2-oxopyrrolidin-1-yl)phenyl)pyridin-2-yl)amino)pyridin-3-yl)imidazolidin-1-yl)methyl)phenyl)amino)ethyl)but-2-enamide nopyridin-3-yl)phenyl)pyrrolidin-2-one (615 mg, 2.43 mmol), Pd$_2$(dba)$_3$ (202 mg, 0.220 mmol), Brettphos (236 mg, 0.440 mmol) and Cs$_2$CO$_3$ (2.15 g, 6.60 mmol) in dioxane (20 mL) was stirred at 100° C. for 16 hours under N$_2$ atmosphere. A black suspension was formed. LCMS showed the purity of the desired product is 28% (Rt=0.799 min; MS Calcd: 549.1; MS Found: 550.1 [M+H]$^+$). The reaction mixture was diluted with water (10 mL) and EtOAc/THF (40 mL, 1/1) then separated. The aqueous was extracted with EtOAc/THF (50 mL×3, 1/1) and then extracted with DCM (50 mL×3). The combined organic phase was concentrated. The residue was purified by Combi Flash (4% MeOH in DCM) and triturated with PE/EtOAc (15 mL, 1/1) to give 1-(3-nitrobenzyl)-3-(5-((5-(4-(2-oxopyrrolidin-1-yl)phenyl)pyridin-2-yl)amino)pyridin-3-yl)imidazolidin-2-one (500 mg, yield: 41%) as a yellow solid.

$^1$H NMR (400 MHz, DMSO-d$_6$) δ 2.03-2.15 (2H, m), 2.55-2.63 (2H, overlapped with DMSO), 3.48 (2H, t, J=7.6 Hz), 3.81-3.97 (4H, m), 4.58 (2H, s), 6.98 (1H, d, J=7.8 Hz), 7.64-7.78 (5H, m), 7.82 (1H, d, J=10.8 Hz), 7.95 (1H, d, J=7.2 Hz), 8.13-8.27 (2H, m), 8.35 (1H, s), 8.53 (2H, d, J=6.4 Hz), 8.70 (1H, s), 9.44 (1H, brs).

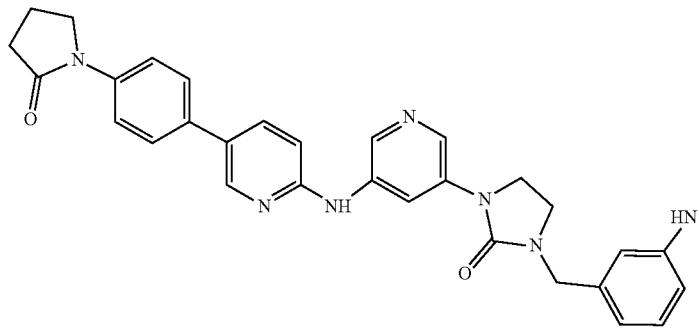

Step 1: Preparation of 1-(3-nitrobenzyl)-3-(5-((5-(4-(2-oxopyrrolidin-1-yl)phenyl)pyridin-2-yl)amino)pyridin-3-yl)imidazolidin-2-one Step 2: Preparation of 1-(3-aminobenzyl)-3-(5-((5-(4-(2-oxopyrrolidin-1-yl)phenyl)pyridin-2-yl)amino)pyridin-3-yl)imidazolidin-2-one

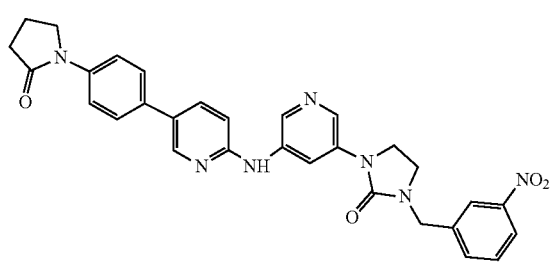 [SMILES: O=C1CCCN1c1ccc(-c2ccc(Nc3cncc(N4CCN(Cc5cccc([N+](=O)[O-])c5)C4=O)c3)nc2)cc1]

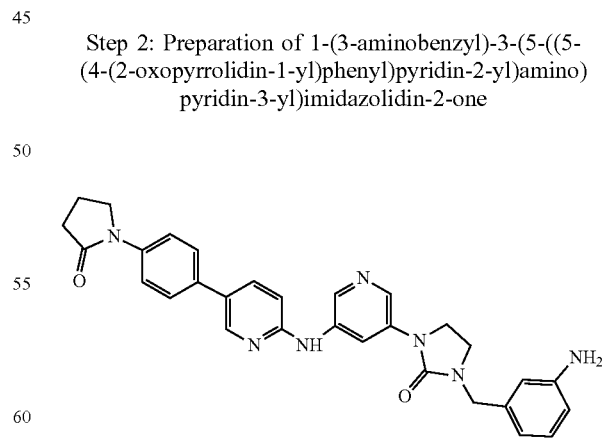

A suspension of 1-(5-bromopyridin-3-yl)-3-(3-nitrobenzyl)imidazolidin-2-one (830 mg, 2.20 mmol), 1-(4-(6-ami- A mixture of 1-(3-nitrobenzyl)-3-(5-((5-(4-(2-oxopyrrolidin-1-yl)phenyl)pyridin-2-yl)amino)pyridin-3-yl)imidazolidin-2-one (450 mg, 0.819 mol) and Pd/C (300 mg, 10% purity, 50% wet) in THF (500 mL) was stirred at 25° C. for 16 hours under H$_2$ balloon (15 Psi). A black suspension was formed. LCMS showed the purity of the desired product is 59% (Rt=0.659 min; MS Calcd: 519.2; MS Found: 520.3 [M+H]$^+$). The reaction mixture was filtered and the filter cake was washed with THF/DCM (50 mL×6, 1/1). The combined organic phase was concentrated. The residue was purified by Combi Flash (10% MeOH in DCM) to give 1-(3-aminobenzyl)-3-(5-((5-(4-(2-oxopyrrolidin-1-yl)phenyl)pyridin-2-yl)amino)pyridin-3-yl)imidazolidin-2-one (250 mg, yield: 59%) as an off-white solid.

$^1$H NMR (400 MHz, DMSO-d$_6$) δ 2.03-2.12 (2H, m), 2.52-2.55 (2H, overlapped with DMSO), 3.39 (2H, t, J=7.4 Hz), 3.83-3.89 (4H, m), 4.26 (2H, s), 5.10 (2H, brs), 6.42-6.50 (3H, m), 6.94-7.02 (2H, m), 7.64-7.78 (4H, m), 7.94 (1H, dd, J=8.8 Hz, 2.8 Hz), 8.34 (1H, d, J=2.4 Hz), 8.48 (1H, t, J=2.4 Hz), 8.53 (1H, d, J=2.4 Hz), 8.67 (1H, d, J=2.4 Hz), 9.39 (1H, brs).

Step 3: Preparation of tert-butyl (2-oxo-2-((3-((2-oxo-3-(5-((5-(4-(2-oxopyrrolidin-1-yl)phenyl)pyridin-2-yl)amino)pyridin-3-yl)imidazolidin-1-yl)methyl)phenyl)amino)ethyl)carbamate

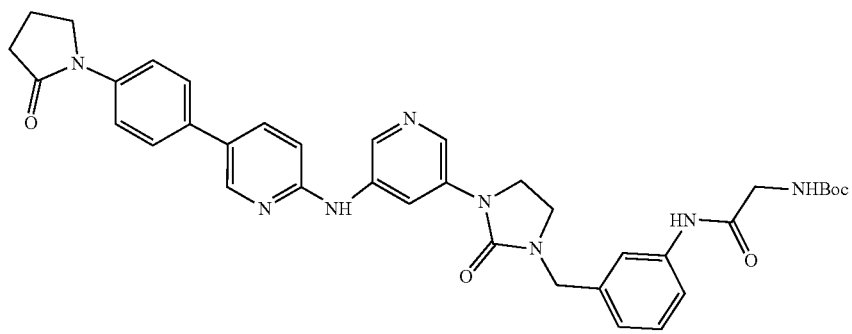 [SMILES: CC(C)(C)OC(=O)NCC(=O)Nc1cccc(CN2CCN(c3cncc(Nc4ccc(-c5ccc(N6CCCC6=O)cc5)cn4)c3)C2=O)c1]

A mixture of 1-(3-aminobenzyl)-3-(5-((5-(4-(2-oxopyrrolidin-1-yl)phenyl)pyridin-2-yl)amino)pyridin-3-yl)imidazolidin-2-one (250 mg, 0.481 mmol), Boc-gly-OH (126 mg, 0.722 mol) and EDCI (190 mg, 0.991 mmol) in pyridine (4 mL) was stirred at 20° C. for 2 hours. A brown solution was formed. LCMS showed the purity of the desired product is 84% (Rt=1.084 min; MS Calcd: 676.3; MS Found: 677.3 [M+H]$^+$). The reaction mixture was diluted with DCM (20 mL) and water (10 mL) then separated. The aqueous was extracted with DCM (20 mL×3). The combined organic phase was concentrated to give tert-butyl (2-oxo-2-((3-((2-oxo-3-(5-((5-(4-(2-oxopyrrolidin-1-yl)phenyl)pyridin-2-yl)amino)pyridin-3-yl)imidazolidin-1-yl)methyl)phenyl)amino)ethyl)carbamate (380 mg, crude) as a yellow solid, which used for next step without purification.

Step 4: Preparation of 2-amino-N-(3-((2-oxo-3-(5-((5-(4-(2-oxopyrrolidin-1-yl)phenyl)pyridin-2-yl)amino)pyridin-3-yl)imidazolidin-1-yl)methyl)phenyl)acetamide

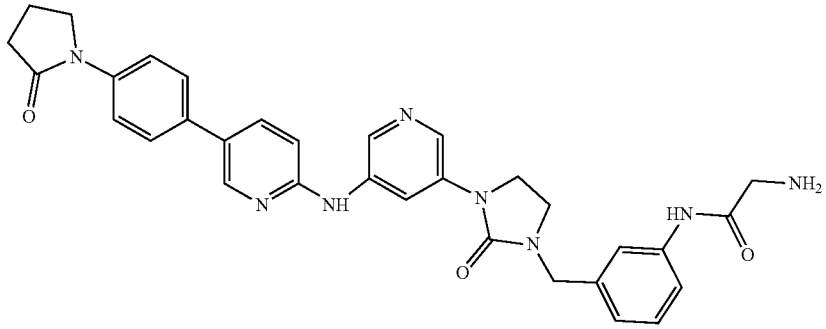 [SMILES: NCC(=O)Nc1cccc(CN2CCN(c3cncc(Nc4ccc(-c5ccc(N6CCCC6=O)cc5)cn4)c3)C2=O)c1]

A mixture of tert-butyl (2-oxo-2-((3-((2-oxo-3-(5-((5-(4-(2-oxopyrrolidin-1-yl)phenyl)pyridin-2-yl)amino)pyridin-3-yl)imidazolidin-1-yl)methyl)phenyl)amino)ethyl)carbamate (380 mg, 0.562 mol) in HCl/dioxane (40 mL, 4M in dioxane) was stirred at 20° C. for 2 hours. The reaction mixture turned into white suspension from yellow solution. LCMS showed the purity of the desired product is 100% (Rt=0.928 min; MS Calcd: 576.1; MS Found: 577.1 [M+H]$^+$). The reaction mixture was concentrated. The residue was washed with saturated aqueous NaHCO$_3$ (15 mL) and filtered to give 2-amino-N-(3-((2-oxo-3-(5-((5-(4-(2-oxopyrrolidin-1-yl)phenyl)pyridin-2-yl)amino)pyridin-3-yl)imidazolidin-1-yl)methyl)phenyl)acetamide (400 mg, crude) as a brown solid.

$^1$H NMR (400 MHz, DMSO-d$_6$) δ 2.03-2.12 (2H, m), 2.55-2.58 (2H, overlapped with DMSO), 3.22-3.30 (2H, m), 3.41-3.44 (2H, overlapped with H$_2$O), 3.81-3.92 (4H, m), 4.39 (2H, s), 6.92-7.04 (2H, m), 7.30 (1H, t, J=7.6 Hz), 7.53-7.63 (2H, m), 7.64-7.78 (4H, m), 7.94 (1H, d, J=8.4 Hz), 8.30-8.37 (1H, m), 8.43-8.51 (1H, m), 8.52-8.54 (1H, m), 8.66 (1H, s), 9.39 (1H, brs).

Step 5: Preparation of (E)-4-(dimethylamino)-N-(2-oxo-2-((3-((2-oxo-3-(5-((5-(4-(2-oxopyrrolidin-1-yl)phenyl)pyridin-2-yl)amino)pyridin-3-yl)imidazolidin-1-yl)methyl)phenyl)amino)ethyl)but-2-enamide

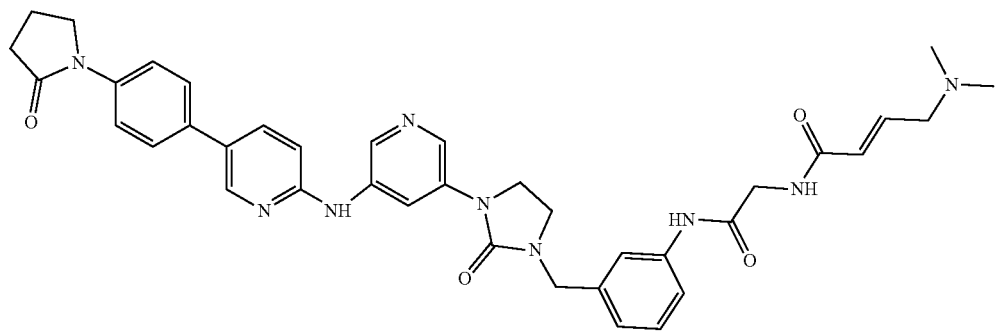 [SMILES: CN(C)C/C=C/C(=O)NCC(=O)Nc1cccc(CN2CCN(c3cncc(Nc4ccc(-c5ccc(N6CCCC6=O)cc5)cn4)c3)C2=O)c1]

A mixture of 2-amino-N-(3-((2-oxo-3-(5-((5-(4-(2-oxopyrrolidin-1-yl)phenyl)pyridin-2-yl)amino)pyridin-3-yl)imidazolidin-1-yl)methyl)phenyl)acetamide (100 mg, 0.173 mmol), (E)-4-(dimethylamino)but-2-enoic acid (27 mg, 0.209 mmol), EDCI (55 mg, 0.285 mmol), HOBt (36 mg, 0.269 mmol) and TEA (53 mg, 0.520 mmol) in DMF (3 mL) was stirred at 25° C. for 16 hours under N$_2$ atmosphere. A black suspension was formed. LCMS showed the purity of the desired product is 100% (Rt=1.607 min; MS Calcd: 687.3; MS Found: 688.3 [M+H]$^+$). The reaction mixture was filtered. The filtrated was purified by prep-HPLC (0.04% NH$_3$H$_2$O+10 mM NH$_4$HCO$_3$ as additives), lyophilized and triturated with MeCN/PE (0.5 mL, 1/1) to give (E)-4-(dimethylamino)-N-(2-oxo-2-((3-((2-oxo-3-(5-((5-(4-(2-oxopyrrolidin-1-yl)phenyl)pyridin-2-yl)amino)pyridin-3-yl)imidazolidin-1-yl)methyl)phenyl)amino)ethyl)but-2-enamide (5.3 mg, yield: 4%) as a gray brown solid.

$^1$H NMR (400 MHz, DMSO-d$_6$) δ 2.03-2.12 (2H, m), 2.26 (6H, s), 2.52-2.55 (2H, overlapped with DMSO), 3.03-3.25 (2H, m), 3.41 (2H, t, J=7.6 Hz), 3.83-3.90 (4H, m), 3.95 (2H, d, J=5.6 Hz), 4.39 (2H, s), 6.18 (1H, d, J=15.6 Hz), 6.54-6.61 (1H, m), 6.94-7.03 (2H, m), 7.31 (1H, t, J=8.0 Hz), 7.52-7.59 (2H, m), 7.65-7.77 (4H, m), 7.95 (1H, dd, J=8.4 Hz, 2.4 Hz), 8.34 (1H, d, J=2.4 Hz), 8.38-8.45 (1H, m), 8.47-8.52 (1H, m), 8.53-8.55 (1H, m), 8.65-8.69 (1H, m), 9.39 (1H, brs), 10.08 (1H, s).

Example 172: (E)-4-(dimethylamino)-N-(2-oxo-2-((4-((2-oxo-3-(5-((5-(4-(2-oxopyrrolidin-1-yl)phenyl)pyridin-2-yl)amino)pyridin-3-yl)imidazolidin-1-yl)methyl)phenyl)amino)ethyl)but-2-enamide

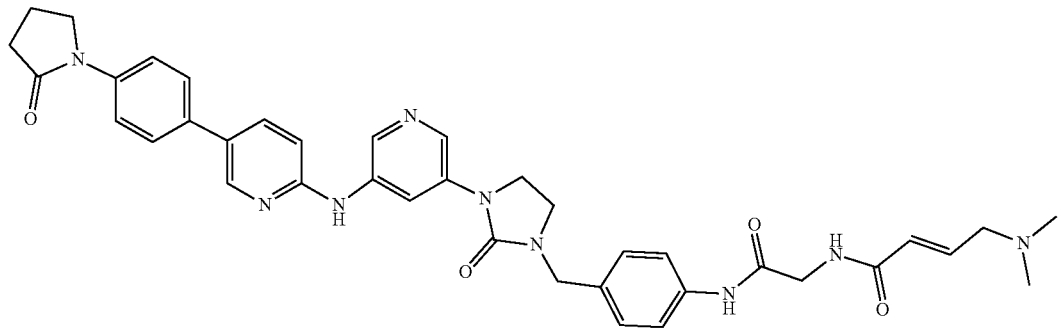 [SMILES: CN(C)C/C=C/C(=O)NCC(=O)Nc1ccc(CN2CCN(c3cncc(Nc4ccc(-c5ccc(N6CCCC6=O)cc5)cn4)c3)C2=O)cc1]

Step 1: Preparation of tert-butyl (4-((2-oxo-3-(5-((5-(4-(2-oxopyrrolidin-1-yl)phenyl)pyridin-2-yl)amino)pyridin-3-yl)imidazolidin-1-yl)methyl)phenyl)carbamate

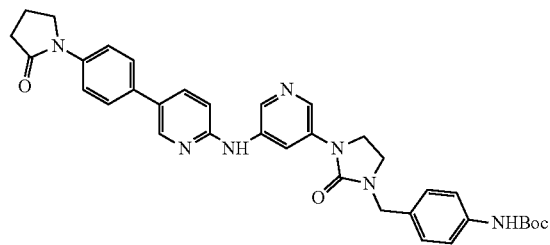 [SMILES: CC(C)(C)OC(=O)Nc1ccc(CN2CCN(c3cncc(Nc4ccc(-c5ccc(N6CCCC6=O)cc5)cn4)c3)C2=O)cc1]

To a mixture of 1-(4-(6-aminopyridin-3-yl)phenyl)pyrrolidin-2-one (200 mg, 0.790 mmol) in dioxane (6 mL) was added tert-butyl (4-((3-(5-bromopyridin-3-yl)-2-oxoimidazolidin-1-yl)methyl)phenyl)carbamate (424 mg, 0.948 mmol), Pd(dba)$_2$ (45 mg, 0.079 mmol), Brettphos (42 mg, 0.079 mmol) and Cs$_2$CO$_3$ (514 mg, 1.58 mmol), the reaction mixture was purged in N$_2$ atmosphere for 3 times and stirred at 50° C. for 1 hour, then heated to 100° C. under N$_2$ atmosphere and stirred for another 5 hours to give a yellow suspension. LCMS showed the purity of the desired product is 50% (Rt=0.816 min; MS Calcd: 619.3; MS Found: 620.2 [M+H]$^+$). The mixture was cooled to room temperature and diluted with water (40 mL). Some yellow solid was precipitated out and filtered. The filter cake was dried in high vacuum to give a residue. The residue was washed with EtOAc (30 mL) twice to give tert-butyl (4-((2-oxo-3-(5-((5-(4-(2-oxopyrrolidin-1-yl)phenyl)pyridin-2-yl)amino)pyridin-3-yl)imidazolidin-1-yl)methyl)phenyl)carbamate (400 mg, yield: 82%) as a red solid.

$^1$H NMR (400 MHz, DMSO-d$_6$) δ 1.47 (9H, s), 2.02-2.13 (2H, m), 2.49-2.53 (2H, m), 3.34-3.40 (2H, m), 3.82-3.91 (4H, m), 4.34 (2H, s), 6.97 (1H, d, J=8.4 Hz), 7.20 (2H, d, J=8.4 Hz), 7.44 (2H, d, J=8.4 Hz), 7.69 (2H, d, J=8.8 Hz), 7.75 (2H, d, J=8.8 Hz), 7.95 (1H, dd, J=8.8, 2.4 Hz), 8.33 (1H, d, J=2.0 Hz), 8.48 (1H, t, J=2.4 Hz), 8.54 (1H, d, J=2.4 Hz), 8.68 (1H, d, J=2.0 Hz), 9.36 (1H, brs), 9.39 (1H, brs).

Step 2: Preparation of 1-(4-aminobenzyl)-3-(5-((5-(4-(2-oxopyrrolidin-1-yl)phenyl)pyridin-2-yl)amino)pyridin-3-yl)imidazolidin-2-one

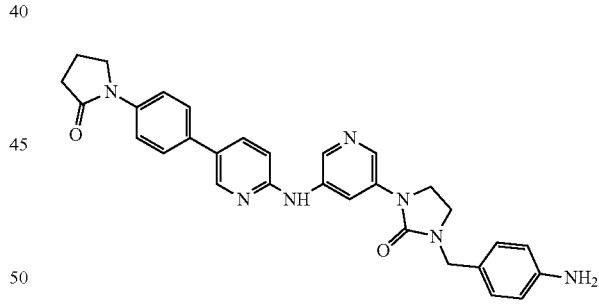

To a mixture of tert-butyl (4-((2-oxo-3-(5-((5-(4-(2-oxopyrrolidin-1-yl)phenyl)pyridin-2-yl)amino)pyridin-3-yl)imidazolidin-1-yl)methyl)phenyl)carbamate (400 mg, 0.645 mmol) in EtOAc (5 mL) was added HCl/EtOAc (20 mL, 4M in EtOAc), the resulting mixture was stirred at 25° C. for 3 hours to give an off-white suspension. LCMS showed the purity of product is 95% (Rt=0.688 min; MS Calcd: 519.2; MS Found: 520.1 [M+H]$^+$). The mixture was concentrated under reduced pressure to give 1-(4-aminobenzyl)-3-(5-((5-(2-methyl-4-(2-oxopyrrolidin-1-yl)phenyl)pyridin-2-yl)amino)pyridin-3-yl)imidazolidin-2-one (350 mg, crude, HCl salt) as an off-white solid.

Step 3: Preparation of tert-butyl (2-oxo-2-((4-((2-oxo-3-(5-((5-(4-(2-oxopyrrolidin-1-yl)phenyl)pyridin-2-yl)amino)pyridin-3-yl)imidazolidin-1-yl)methyl)phenyl)amino)ethyl)carbamate

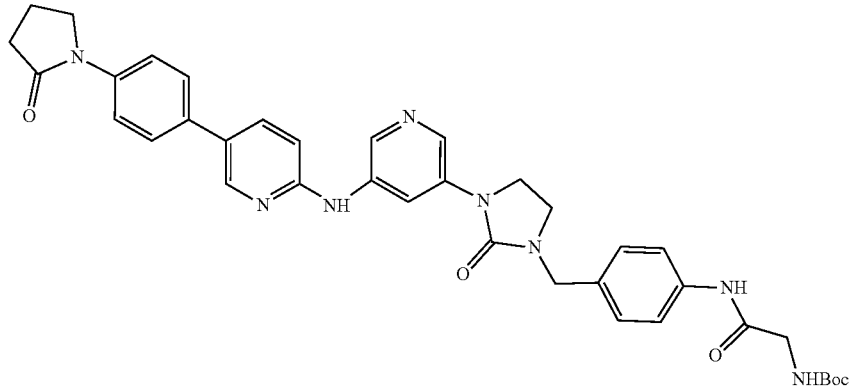 [SMILES: CC(C)(C)OC(=O)NCC(=O)Nc1ccc(CN2CCN(c3cncc(Nc4ccc(-c5ccc(N6CCCC6=O)cc5)cn4)c3)C2=O)cc1]

To a mixture of 1-(4-aminobenzyl)-3-(5-((5-(4-(2-oxopyrrolidin-1-yl)phenyl)pyridin-2-yl)amino)pyridin-3-yl)imidazolidin-2-one (150 mg, 0.270 mmol, HCl salt) in DMF (8 mL) was added Boc-gly-OH (236 mg, 1.35 mmol), and HOBt (73 mg, 0.54 mmol), EDCI (103 mg, 0.540 mmol) and TEA (82 mg, 0.81 mmol), the reaction mixture was stirred at 100° C. and stirred for 6 hours to give a brown suspension. LCMS showed the purity of the desired product is 52% (Rt=0.797 min; MS Calcd: 676.3; MS Found: 677.1 [M+H]$^+$). The mixture was diluted with water (30 mL) and extracted with DCM (35 mL×3). The combined organic layer was washed with brine (50 mL×2), dried over anhydrous Na$_2$SO$_4$ and concentrated under reduced pressure to give a residue. The residue was washed with EtOAc (20 mL) twice to give (180 mg, yield for two steps: 96%) as an off-white solid.

Step 4: Preparation of 2-amino-N-(4-((2-oxo-3-(5-((5-(4-(2-oxopyrrolidin-1-yl)phenyl)pyridin-2-yl)amino)pyridin-3-yl)imidazolidin-1-yl)methyl)phenyl)acetamide

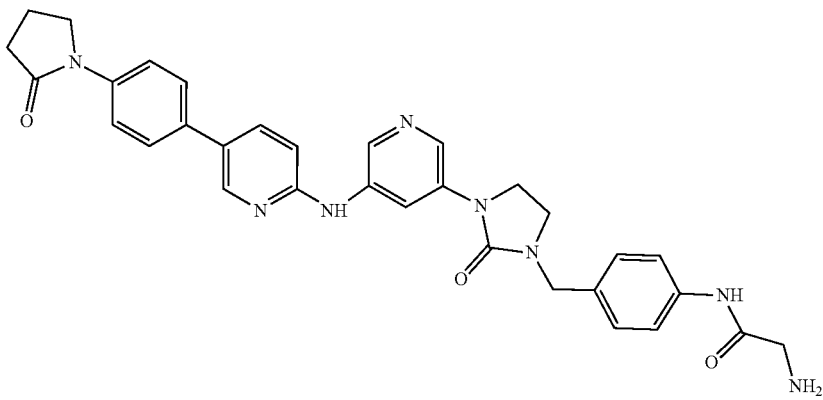 [SMILES: NCC(=O)Nc1ccc(CN2CCN(c3cncc(Nc4ccc(-c5ccc(N6CCCC6=O)cc5)cn4)c3)C2=O)cc1]

To a mixture of tert-butyl (2-oxo-2-((4-((2-oxo-3-(5-((5-(4-(2-oxopyrrolidin-1-yl)phenyl)pyridin-2-yl)amino)pyridin-3-yl)imidazolidin-1-yl)methyl)phenyl)amino)ethyl)carbamate (180 mg, 0.266 mmol) in EtOAc (10 mL) was added HCl/EtOAc (20 mL, 4 M in EtOAc), the reaction mixture was stirred at 25° C. for 2 hours to give an off-white suspension. LCMS showed the purity of product is 48% (Rt=0.710 min; MS Calcd: 576.3; MS Found: 577.1 [M+H]$^+$). The mixture was concentrated under reduced pressure to give 2-amino-N-(4-((2-oxo-3-(5-((5-(4-(2-oxopyrrolidin-1-yl)phenyl)pyridin-2-yl)amino)pyridin-3-yl)imidazolidin-1-yl)methyl)phenyl)acetamide (160 mg, crude, HCl salt) as an off-white solid.

¹H NMR (400 MHz, DMSO-d₆) δ 2.02-2.13 (2H, m), 2.49-2.53 (2H, m), 3.49 (2H, t, J=8.0 Hz), 3.75-3.84 (2H, m), 3.85-3.96 (4H, m), 4.43 (2H, s), 7.15 (1H, d, J=8.4 Hz), 7.32 (2H, d, J=8.4 Hz), 7.63 (2H, d, J=8.4 Hz), 7.72 (2H, d, J=8.8 Hz), 7.77 (2H, d, J=8.8 Hz), 8.08 (1H, dd, J=8.4, 2.4 Hz), 8.27 (2H, brs), 8.65 (1H, d, J=2.4 Hz), 8.69 (1H, d, J=2.0 Hz), 8.74 (1H, d, J=2.0 Hz), 9.25 (1H, d, J=1.6 Hz), 10.72 (1H, brs), 10.81 (1H, brs).

Step 4: Preparation of (E)-4-(dimethylamino)-N-(2-oxo-2-((4-((2-oxo-3-(5-((5-(4-(2-oxopyrrolidin-1-yl)phenyl)pyridin-2-yl)amino)pyridin-3-yl)imidazolidin-1-yl)methyl)phenyl)amino)ethyl)but-2-enamide

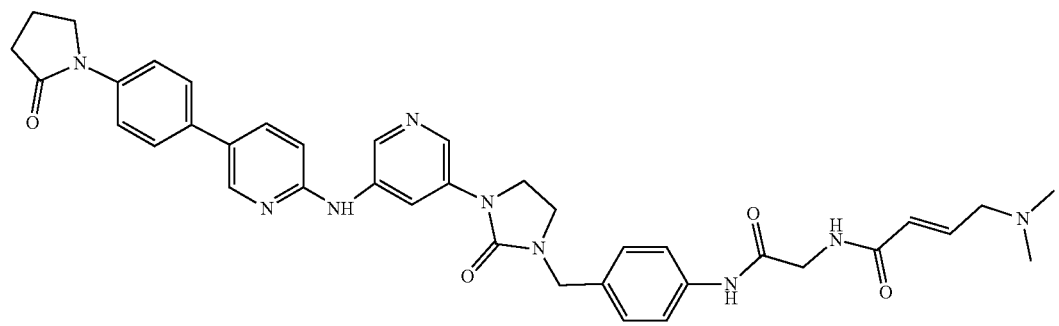 [SMILES: CN(C)C/C=C/C(=O)NCC(=O)Nc1ccc(CN2CCN(c3cncc(Nc4ccc(-c5ccc(N6CCCC6=O)cc5)cn4)c3)C2=O)cc1]

To a mixture of 2-amino-N-(4-((2-oxo-3-(5-((5-(4-(2-oxopyrrolidin-1-yl)phenyl)pyridin-2-yl)amino)pyridin-3-yl)imidazolidin-1-yl)methyl)phenyl)acetamide (150 mg, 0.245 mmol, HCl salt) in DMF (5 mL) was added (E)-4-(dimethylamino)but-2-enoic acid (122 mg, 0.734 mmol, HCl salt), EDCI (141 mg, 0.734 mmol), HOBt (99 mg, 0.73 mmol) and TEA (99 mg, 0.98 mmol), the reaction mixture was stirred at 25° C. for 2 hours to give a brown suspension. LCMS showed the purity of the desired product is 63% (Rt=1.621 min; MS Calcd: 687.3; MS Found: 688.1 [M+H]⁺). The mixture was diluted with water (30 mL) and DCM (30 mL) and then filtered. The filter cake was washed with DCM/MeOH (10:1, 11 mL×2). The filtrate was extracted with DCM (40 mL×2), the combined extracts were washed with brine (50 mL×2), dried over Na₂SO₄, filtered and concentrated under reduced pressure to give a residue. The residue was washed with DMF to give an impure product (60 mg). Then further purified by prep-HPLC (0.225% FA as anadditive) purification to give (E)-4-(dimethylamino)-N-(2-oxo-2-((4-((2-oxo-3-(5-((5-(4-(2-oxopyrrolidin-1-yl)phenyl)pyridin-2-yl)amino)pyridin-3-yl)imidazolidin-1-yl)methyl)phenyl)amino)ethyl)but-2-enamide (5.4 mg, yield for two steps: 3%) as a yellow solid.

¹H NMR (400 MHz, DMSO-d₆) δ 2.02-2.13 (2H, m), 2.36 (6H, s), 2.49-2.53 (2H, m), 3.31-3.42 (2H, m), 3.42-3.48 (2H, m), 3.82-3.90 (4H, m), 3.94-4.02 (2H, m), 4.36 (2H, s), 6.23 (1H, d, J=15.6 Hz), 6.52-6.65 (1H, m), 6.96 (1H, d, J=8.8 Hz), 7.26 (2H, d, J=8.0 Hz), 7.58 (2H, d, J=8.0 Hz), 7.67 (2H, d, J=8.8 Hz), 7.73 (2H, d, J=8.8 Hz), 7.94 (1H, dd, J=8.4, 2.4 Hz), 8.32 (1H, s), 8.42-8.49 (2H, m), 8.52 (1H, d, J=2.0 Hz), 8.66 (1H, brs), 9.40 (1H, brs), 10.08 (1H, brs).

Example 173: (R)-2-((5-(3-fluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

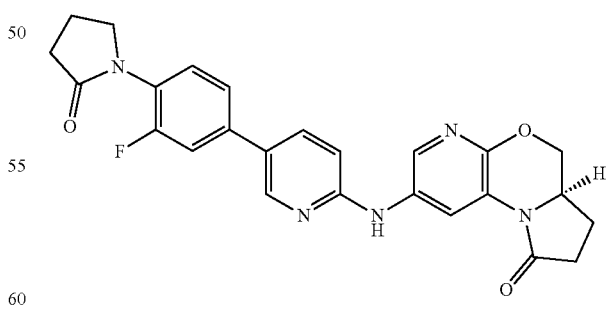

A mixture of 1-(4-(6-chloropyridin-3-yl)-2-fluorophenyl)pyrrolidin-2-one (150 mg, 0.516 mmol), (R)-2-amino-6,6a,7,8-tetrahydro-9H-pyrido[2,3-b]pyrrolo[1,2-d][1,4]oxazin-9-one (138 mg, 0.670 mmol), Pd₂(dba)₃ (47 mg, 0.051 mmol), Brettphos (55 mg, 0.10 mmol) and Cs₂CO₃ (336 mg, 1.03 mmol) in anhydrous dioxane (3 mL) was degassed and purged with N₂ for 3 times. Then the resulting reaction mixture was heated at 90° C. for 15 hours under N₂ atmosphere. The reaction mixture turned into yellow suspension from red. Crude LCMS showed the purity of the desired product is 22% (Rt=0.569 min; MS Calcd: 459.4; MS Found: 460.0 [M+H]⁺). The reaction mixture was diluted with water (20 mL) and EtOAc (20 mL). The aqueous layer was extracted with EtOAc/THF (20 mL×3, 1/1). The combined organic layer was washed with brine (25 mL), dried over anhydrous Na₂SO₄ and concentrated. The residue was purified by Combi Flash (2% to 5% MeOH in DCM) and triturated with CH₃CN (5 mL) to give a impure product and lyophilized to give (R)-2-((5-(3-fluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one (39.3 mg, yield: 17%) as an off-white solid.

¹H NMR (400 MHz, DMSO-d₆) δ 1.71 (1H, t, J=6.0 Hz), 2.14 (2H, t, J=7.2 Hz), 2.21-2.25 (1H, m), 2.35-2.42 (1H, m), 2.44-2.47 (2H, m), 2.64-2.74 (1H, m), 3.79 (2H, t, J=6.8 Hz), 3.91 (1H, t, J=10.8 Hz), 4.03-4.12 (1H, m), 4.59 (1H, dd, J=10.8, 2.8 Hz), 6.88 (1H, d, J=8.8 Hz), 7.46-7.56 (2H, m), 7.60 (1H, d, J=10.8 Hz), 7.94 (1H, dd, J=8.8, 2.4 Hz), 8.44 (1H, d, J=2.4 Hz), 8.51 (1H, d, J=2.4 Hz), 8.97 (1H, d, J=2.8 Hz), 9.29 (1H, brs).

Example 174: 1-(4-(6-((5-(5-methyl-1,1-dioxido-1,2,5-thiadiazolidin-2-yl)pyridin-3-yl)amino)pyridin-3-yl)phenyl)pyrrolidin-2-one

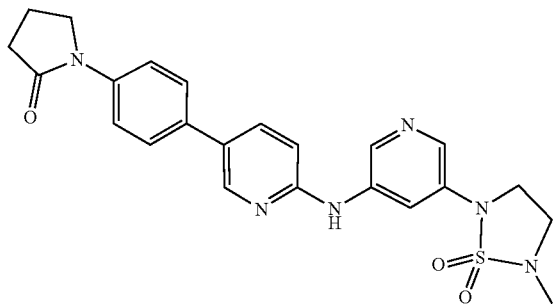 [SMILES: CN1CCN(c2cncc(Nc3ccc(-c4ccc(N5CCCC5=O)cc4)cn3)c2)S1(=O)=O]

Step 1: Preparation of tert-butyl (N-(2-chloroethyl)-N-methylsulfamoyl)carbamate

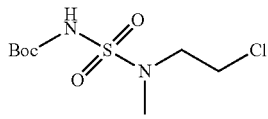 [SMILES: CN(CCCl)S(=O)(=O)NC(=O)OC(C)(C)C]

To a solution of chlorosulfonyl isocyanate (2.50 g, 17.7 mmol) in anhydrous DCM (25 mL) was added t-BuOH (1.69 mL, 17.7 mmol) dropwise at 0° C. After stirring at 0° C. for 0.5 hour, the resulting N-Boc-sulfamoyl chloride and TEA (5.36 g, 53.0 mmol) solution was added dropwise to a solution of 2-chloro-N-methylethan-1-amine-HCl (2.30 g, 17.7 mmol) in DCM (60 mL) at 0-5° C. After the completion of the addition, the reaction mixture was stirred at 0-5° C. for 0.5 hour, then further stirred at 20-25° C. for 2 hours. The reaction mixture turned into yellow suspension from solution. The reaction mixture was diluted with DCM (250 mL), then washed with 1N aqueous HCl (100 mL), brine (100 mL), dried over anhydrous Na₂SO₄ and concentrated. The residue was purified by Combi Flash (10% to 25% EtOAc in PE) to give tert-butyl (N-(2-chloroethyl)-N-methylsulfamoyl)carbamate (4.50 g, yield: 93%) as yellow oil.

¹H NMR (400 MHz, CDCl₃) δ 1.50 (9H, s), 3.05 (3H, s), 3.68 (4H, s), 7.12 (1H, brs).

Step 2: Preparation of tert-butyl 5-methyl-1,2,5-thiadiazolidine-2-carboxylate 1,1-dioxide

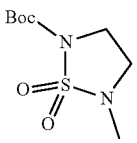

A mixture of tert-butyl (N-(2-chloroethyl)-N-methylsulfamoyl)carbamate (4.00 g, 14.7 mmol) and K₂CO₃ (3.04 g, 22.0 mmol) in DMSO (40 mL) was stirred at 15-20° C. for 16 hours. The reaction mixture turned into white suspension from colorless solution. To the reaction mixture was added water (100 mL), then extracted with EtOAc (100 mL×3). The combined organic layer was washed with water (100 mL×2), brine (100 mL), dried over anhydrous Na₂SO₄ and concentrated. The residue was purified by Combi Flash (10% to 25% EtOAc in PE) to give tert-butyl 5-methyl-1,2,5-thiadiazolidine-2-carboxylate 1,1-dioxide (2.80 g, yield: 81%) as a white solid.

¹H NMR (400 MHz, CDCl₃) δ 1.55 (9H, s), 2.78 (3H, s), 3.31 (2H, t, J=6.4 Hz), 3.81 (2H, t, J=6.4 Hz).

Step 3: Preparation of 2-methyl-1,2,5-thiadiazolidine 1,1-dioxide

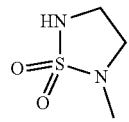

To a solution of tert-butyl 5-methyl-1,2,5-thiadiazolidine-2-carboxylate 1,1-dioxide (2.30 g, 9.73 mmol) in anhydrous DCM (25 mL) was added TFA (25 mL) at 15-20° C. Then the reaction mixture was stirred at 15-20° C. for 1 hour. The reaction turned into pale yellow solution from colorless. The reaction mixture was concentrated and the residue was diluted with DCM (50 mL) and basified with DIPEA to pH=8 and concentrated. The residue was purified by Combi Flash (10% to 50% EtOAc in PE) to give 2-methyl-1,2,5-thiadiazolidine 1,1-dioxide (1.15 g, yield: 87%) as colorless oil.

¹H NMR (400 MHz, CDCl₃) δ 2.75 (3H, s), 3.36-341 (2H, m), 3.48-3.53 (2H, m), 4.47 (1H, brs).

Step 4: Preparation of 2-(5-bromopyridin-3-yl)-5-methyl-1,2,5-thiadiazolidine 1,1-dioxide

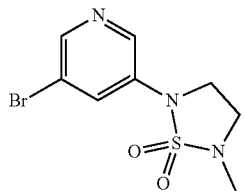

A mixture of 2-methyl-1,2,5-thiadiazolidine 1,1-dioxide (50 mg, 0.37 mmol), 3, 5-dibromopyridine (261 mg, 1.10 mmol), CuI (21 mg, 0.11 mmol), Cs$_2$CO$_3$ (179 mg, 0.550 mmol) and DMEDA (19 mg, 0.22 mmol) in anhydrous dioxane (4 mL) was degassed and purged with N$_2$ for 3 times. Then the resulting reaction mixture was heated at 100° C. for 16 hours under N$_2$ atmosphere. The reaction mixture turned into blue suspension from yellow. LCMS showed the purity of the desired product is 31% (Rt=0.692 min; MS Calcd: 291.0; MS Found: 291.6 [M+H]$^+$). The reaction mixture was filtered and the filtrate was concentrated. The residue was purified by Combi Flash (20% to 60% EtOAc in PE) to give 2-(5-bromopyridin-3-yl)-5-methyl-1,2,5-thiadiazolidine 1,1-dioxide (58 mg, yield: 54%) as a white solid.

$^1$H NMR (400 MHz, CDCl$_3$) δ 2.88 (3H, s), 3.53-3.58 (2H, m), 3.87 (2H, t, J=6.4 Hz), 7.81 (1H, t, J=2.4 Hz), 8.39 (1H, d, J=2.4 Hz), 8.46 (1H, d, J=2.0 Hz).

Step 5: Preparation of 1-(4-(6-((5-(5-methyl-1,1-dioxido-1,2,5-thiadiazolidin-2-yl)pyridin-3-yl)amino)pyridin-3-yl)phenyl)pyrrolidin-2-one

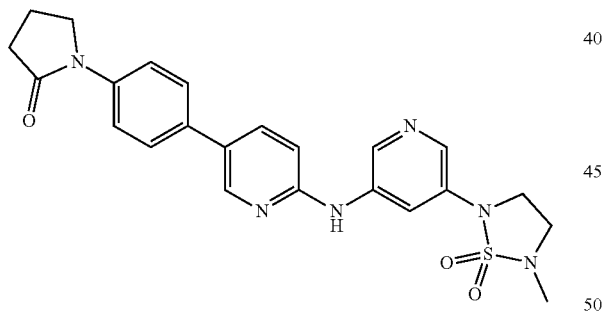

A mixture of 2-(5-bromopyridin-3-yl)-5-methyl-1,2,5-thiadiazolidine 1,1-dioxide (58 mg, 0.20 mmol), 1-(4-(6-aminopyridin-3-yl)phenyl)pyrrolidin-2-one (50 mg, 0.20 mmol), Pd$_2$(dba)$_3$ (9 mg, 0.01 mmol), Brettphos (11 mg, 0.020 mmol) and Cs$_2$CO$_3$ (129 mg, 0.395 mmol) in anhydrous dioxane (3 mL) was degassed and purged with N$_2$ for 3 times. Then the reaction mixture was heated at 100° C. for 16 hours under N$_2$ atmosphere. The reaction mixture turned into brown suspension from red. LCMS showed the purity of the desired product is 75% (Rt=0.744 min; MS Calcd: 464.2; MS Found: 465.0 [M+H]$^+$). To the reaction mixture was added water (20 mL), then extracted with EtOAc/THF (20 mL×3, 1/1). The combined organic layer was washed with brine (20 mL), dried over anhydrous Na$_2$SO$_4$ and concentrated. The residue was triturated with EtOAc (5 mL), then further purified by prep-HPLC (0.225% FA as an additive). Most of the CH$_3$CN was removed under reduced pressure and the remaining part was lyophilized to give 1-(4-(6-((5-(5-methyl-1,1-dioxido-1,2,5-thiadiazolidin-2-yl)pyridin-3-yl)amino)pyridin-3-yl)phenyl)pyrrolidin-2-one (12.6 mg, yield: 14%) as a white solid.

$^1$H NMR (400 MHz, DMSO-d$_6$) δ 2.00-2.15 (2H, m), 2.52-2.55 (2H, m), 2.76 (3H, s), 3.54 (2H, t, J=6.4 Hz), 3.88 (2H, t, J=7.2 Hz), 3.93 (2H, t, J=6.4 Hz), 6.98 (1H, d, J=8.4 Hz), 7.69 (2H, d, J=9.2 Hz), 7.75 (2H, d, J=8.8 Hz), 7.95-8.05 (1H, m), 8.21 (1H, t, J=2.0 Hz), 8.54 (1H, d, J=2.4 Hz), 8.76 (1H, s), 9.59 (1H, brs).

Example 175: (S)-1-(4-(6-((2-methyl-1,1-dioxido-2,3,3a,4-tetrahydropyrido[2,3-b][1,2,5]thiadiazolo[2,3-d][1,4]oxazin-8-yl)amino)pyridin-3-yl)phenyl)pyrrolidin-2-one

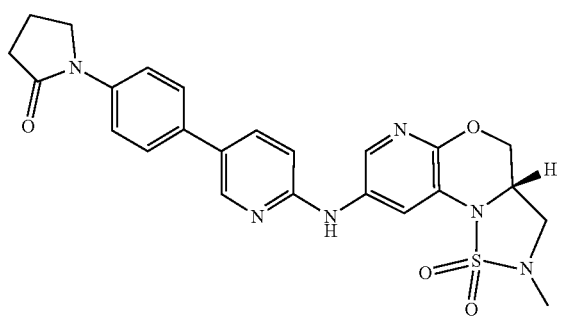 [SMILES: CN1C[C@H]2COc3ncc(Nc4ccc(-c5ccc(N6CCCC6=O)cc5)cn4)cc3N2S1(=O)=O]

Step 1: Preparation of (R)-1-(benzyloxy)-3-(methylamino)propan-2-ol

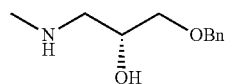

A solution of (S)-2-((benzyloxy)methyl)oxirane (6.00 g, 36.5 mmol) in DCM (25 mL) was added dropwise to MeNH$_2$ (130 mL, 40% purity in MeOH) at 0° C. After the addition, the reaction mixture was stirred at 10-15° C. for 16 hours. The reaction mixture turned into suspension from solution. The reaction mixture was concentrated and the remaining part was extracted with DCM (100 mL×3). The combined organic layer was washed with brine (50 mL), dried over anhydrous Na$_2$SO$_4$ and concentrated to give (R)-1-(benzyloxy)-3-(methylamino)propan-2-ol (6.10 g, yield: 86%) as yellow oil.

$^1$H NMR (400 MHz, CDCl$_3$) δ 2.44 (3H, s), 2.65-2.70 (2H, m), 3.45-3.55 (2H, m), 3.90-3.95 (1H, m), 4.55 (2H, s), 7.25-7.40 (5H, m).

Step 2: Preparation of methyl (S)-3-((benzyloxy)methyl)-5-methyl-1,2,5-thiadiazolidine-2-carboxylate 1,1-dioxide

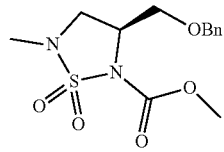

To a solution of (R)-1-(benzyloxy)-3-(methylamino)propan-2-ol (6.10 g, 31.2 mmol) in anhydrous THF (200 mL) was added Burgess reagent (18.6 g, 78.1 mmol) at 10-15° C. Then the reaction mixture was stirred at 75° C. for 16 hours. The reaction mixture turned into yellow solution from colorless. To the reaction mixture was added saturated aqueous NH$_4$Cl (100 mL), then extracted with EtOAc (200 mL×2). The combined organic layer was washed with brine (100 mL), dried over anhydrous Na$_2$SO$_4$ and concentrated. The residue was purified by Combi Flash (10% to 30% EtOAc in PE) to give methyl (S)-3-((benzyloxy)methyl)-5-methyl-1,2,5-thiadiazolidine-2-carboxylate 1,1-dioxide (5.92 g, yield: 60%) as yellow gum.

$^1$H NMR (400 MHz, CDCl$_3$) δ 2.77 (3H, s), 3.33-3.39 (1H, m), 3.41-3.45 (1H, m), 3.64-3.69 (1H, m), 3.74-3.79 (1H, m), 3.90 (3H, s), 4.24-4.31 (1H, m), 4.52-4.60 (2H, m), 7.29-7.40 (5H, m).

Step 3: Preparation of methyl (S)-3-(hydroxymethyl)-5-methyl-1,2,5-thiadiazolidine-2-carboxylate 1,1-dioxide

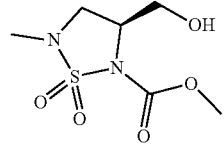

To a solution of methyl (S)-3-((benzyloxy)methyl)-5-methyl-1,2,5-thiadiazolidine-2-carboxylate 1,1-dioxide (5.92 g, 18.8 mmol) in absolute MeOH (200 mL) was added 10% Pd(OH)$_2$/C (1.00 g) under N$_2$ atmosphere. The reaction mixture was degassed and purged with H$_2$ for 3 times and the resulting reaction mixture was hydrogenated (50 psi) at 50° C. for 24 hours. The reaction mixture turned into colorless from yellow solution. The reaction mixture was filtered and the solid was washed with MeOH (10 mL×3). The filtrate was concentrated and the residue was dissolved in EtOH (25 mL) and concentrated to give methyl (S)-3-(hydroxymethyl)-5-methyl-1,2,5-thiadiazolidine-2-carboxylate 1,1-dioxide (3.50 g, yield: 83%) as colorless gum.

$^1$H NMR (400 MHz, CDCl$_3$) δ 2.80 (3H, s), 3.35-3.45 (2H, m), 3.75-3.85 (2H, m), 3.93 (3H, s), 4.20-4.30 (1H, m).

Step 4: Preparation of methyl (S)-3-(((3-bromo-5-nitropyridin-2-yl)oxy)methyl)-5-methyl-1,2,5-thiadiazolidine-2-carboxylate 1,1-dioxide

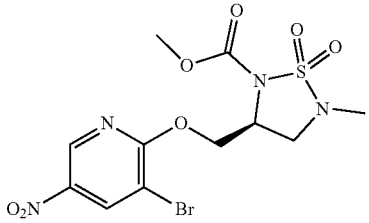 [SMILES: COC(=O)N1[C@H](COc2ncc([N+](=O)[O-])cc2Br)CN(C)S1(=O)=O]

A mixture of methyl (S)-3-(hydroxymethyl)-5-methyl-1,2,5-thiadiazolidine-2-carboxylate 1,1-dioxide (3.30 g, 14.7 mmol), 3-bromo-2-chloro-5-nitro-pyridine (4.19 g, 17.7 mmol) and K$_2$CO$_3$ (4.07 g, 29.4 mmol) in CH$_3$CN (60 mL) was heated at 90° C. for 2 hours under N$_2$ atmosphere. The reaction mixture turned into brown suspension from yellow. The reaction mixture was filtered and the solid was washed with EtOAc (20 mL×3). The filtrate was concentrated and the residue was purified by Combi Flash (20% to 40% EtOAc in PE) to give methyl (S)-3-(((3-bromo-5-nitropyridin-2-yl)oxy)methyl)-5-methyl-1,2,5-thiadiazolidine-2-carboxylate 1,1-dioxide (4.20 g, yield: 67%) as yellow gum.

Step 5: Preparation of methyl (S)-3-(((5-amino-3-bromopyridin-2-yl)oxy)methyl)-5-methyl-1,2,5-thiadiazolidine-2-carboxylate 1,1-dioxide and (S)-3-(((5-amino-3-bromopyridin-2-yl)oxy)methyl)-1,2,512-thiadiazolidine 1,1-dioxide

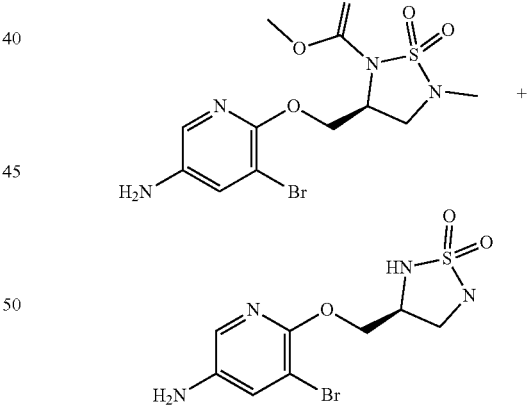

A mixture of methyl (S)-3-(((3-bromo-5-nitropyridin-2-yl)oxy)methyl)-5-methyl-1,2,5-thiadiazolidine-2-carboxylate 1,1-dioxide (4.20 g, 9.88 mmol) and Fe powder (2.21 g, 39.5 mmol), NH$_4$Cl (5.28 g, 98.8 mmol) in EtOH (45 mL) and H$_2$O (15 mL) was heated at 90° C. for 16 hours. The reaction mixture turned into black suspension from gray. The reaction mixture was filtered through a pad of celite and the solid was washed with EtOH (20 mL×3). The filtrate was concentrated and the residue was diluted with water (50 mL) and extracted with EtOAc (50 mL×3). The combined organic layer was washed with brine (50 mL), dried over anhydrous Na$_2$SO$_4$ and concentrated. The residue was purified by Combi Flash (50% to 100% EtOAc in PE) to give methyl (S)-3-(((5-amino-3-bromopyridin-2-yl)oxy)methyl)-5-methyl-1,2,5-thiadiazolidine-2-carboxylate 1,1-dioxide (2.40 g, yield: 61%) as a yellow solid and (S)-3-(((5-amino-3-bromopyridin-2-yl)oxy)methyl)-1,2,512-thiadiazolidine 1,1-dioxide (860 mg, yield: 26%) as a gray solid.

Step 6: Preparation of methyl (S)-3-(((3-bromo-5-((di-tert-butoxycarbonyl)amino)pyridin-2-yl)oxy)methyl)-5-methyl-1,2,5-thiadiazolidine-2-carboxylate-1,1-dioxide

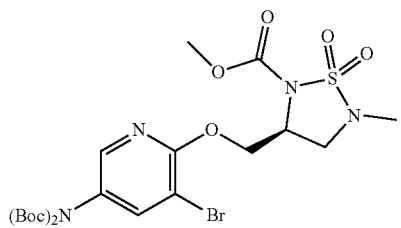

To a solution of methyl (S)-3-(((5-amino-3-bromopyridin-2-yl)oxy)methyl)-5-methyl-1,2,5-thiadiazolidine-2-carboxylate 1,1-dioxide (3.20 g, 8.10 mmol), DIPEA (4.19 g, 32.4 mmol) and DMAP (198 mg, 1.62 mmol) in DCM (80 mL) was added Boc₂O (7.07 g, 32.4 mmol) at 15-20° C. Then the reaction mixture was stirred at 15-20° C. for 16 hours under N₂ atmosphere. The reaction mixture turned into yellow solution from colorless. The reaction mixture was concentrated and the residue was purified by Combi Flash (30% to 80% EtOAc in PE) to give (S)-3-(((3-bromo-5-((di-tert-butoxycarbonyl)amino)pyridin-2-yl)oxy)methyl)-5-methyl-1,2,5-thiadiazolidine-2-carboxylate-1,1-dioxide (2.20 g, yield: 46%) as yellow gum.

¹H NMR (400 MHz, CDCl₃) δ 1.45 (18H, s), 2.80 (3H, s), 3.15-3.25 (1H, m), 3.70-3.80 (4H, m), 4.25-4.35 (2H, m), 5.30-5.35 (1H, m), 7.84 (1H, d, J=2.0 Hz), 8.21 (1H, d, J=2.4 Hz).

Step 7: Preparation of tert-butyl (S)-3-(((3-bromo-5-((di-tert-butoxycarbonyl)amino)pyridin-2-yl)oxy)methyl)-5-methyl-1,2,5-thiadiazolidine-2-carboxylate 1,1-dioxide

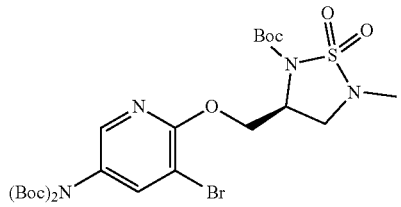

To a solution of (S)-4-(((5-amino-3-bromopyridin-2-yl)oxy)methyl)-2-methyl-1,2,5-thiadiazolidine 1,1-dioxide (860 mg, 2.55 mmol), DIPEA (1.32 g, 10.2 mmol) and DMAP (62 mg, 0.51 mmol) in DCM (25 mL) was added Boc₂O (2.23 g, 10.2 mmol) at 15-20° C. Then the reaction mixture was stirred at 15-20° C. for 16 hours under N₂ atmosphere. The reaction mixture turned into yellow solution from colorless. The reaction mixture was concentrated and the residue was purified by Combi Flash (20% to 50% EtOAc in PE) to give tert-butyl (S)-3-(((3-bromo-5-((di-tert-butoxycarbonyl)amino)pyridin-2-yl)oxy)methyl)-5-methyl-1,2,5-thiadiazolidine-2-carboxylate 1,1-dioxide (1.50 g, yield: 92%) as colorless gum.

¹H NMR (400 MHz, CDCl₃) δ 1.45 (27H, s), 2.79 (3H, s), 3.20-3.25 (1H, m), 3.75-3.80 (1H, m), 4.20-4.25 (2H, m), 5.25-5.30 (1H, m), 7.84 (1H, d, J=2.4 Hz), 8.22 (1H, d, J=2.0 Hz).

Step 8: Preparation of tert-butyl (S)-(5-bromo-6-((5-methyl-1,1-dioxido-1,2,5-thiadiazolidin-3-yl)methoxy)pyridin-3-yl)carbamate

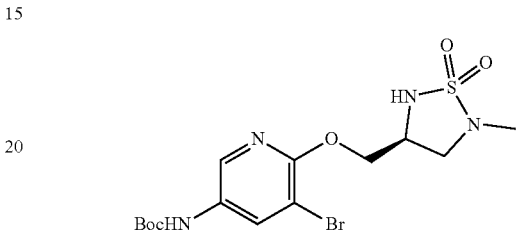

To a solution of tert-butyl (S)-3-(((3-bromo-5-((di-tert-butoxycarbonyl)amino)pyridin-2-yl)oxy)methyl)-5-methyl-1,2,5-thiadiazolidine-2-carboxylate 1,1-dioxide (2.20 g, 3.69 mmol) in MeOH (40 mL) and H₂O (20 mL) was added 10% aqueous NaOH (10 mL) at 15-20° C. Then the reaction mixture was stirred at 15-20° C. for 2 hours. The reaction mixture turned into yellow solution from colorless. The reaction mixture was concentrated. The residue was diluted with water (50 mL), then extracted with EtOAc (50 mL×3). The combined organic layer was washed with brine (50 mL), dried over anhydrous Na₂SO₄ and concentrated. The residue was purified by Combi Flash (30% to 80% EtOAc in PE) to give tert-butyl (S)-(5-bromo-6-((5-methyl-1,1-dioxido-1,2,5-thiadiazolidin-3-yl)methoxy)pyridin-3-yl)carbamate (2.00 g) as colorless gum. The average yield was 46% for 3 steps.

¹H NMR (400 MHz, CDCl₃) δ 1.55 (9H, s), 2.27 (1H, dd, J=7.6, 5.6 Hz), 2.84 (3H, s), 3.34-3.40 (1H, m), 3.62-3.70 (3H, m), 4.82-4.90 (1H, m), 6.68 (1H, s), 8.29 (1H, d, J=2.8 Hz), 8.44 (1H, s).

Step 9: Preparation of tert-butyl (S)-(2-methyl-1,1-dioxido-2,3,3a,4-tetrahydropyrido[2,3-b][1,2,5]thiadiazolo[2,3-d][1,4]oxazin-8-yl)carbamate

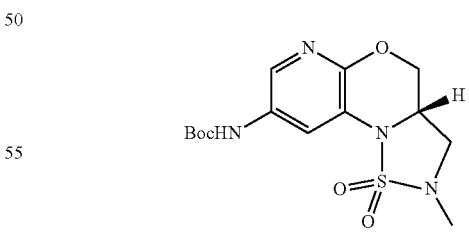

A mixture of tert-butyl (S)-(5-bromo-6-((5-methyl-1,1-dioxido-1,2,5-thiadiazolidin-3-yl)methoxy)pyridin-3-yl)carbamate (2.30 g, 5.26 mmol), CuI (301 mg, 1.58 mmol), Cs₂CO₃ (3.43 g, 10.5 mmol) and DMEDA (278 mg, 3.16 mmol) in anhydrous dioxane (80 mL) was degassed and purged with N₂ for 3 times. Then the resulting reaction mixture was heated at 90° C. for 16 hours under N₂ atmosphere. The reaction mixture turned into brown suspension from yellow. LCMS showed the purity of the desired product is 74% (Rt=0.754 min; MS Calcd: 356.1; MS Found: 379.2 [M+Na]+). The reaction mixture was filtered through a pad of celite and the solid was washed with EtOAc (25 mL×4). The filtrate was concentrated and the residue was purified by Combi Flash (35% to 70% EtOAc in PE), then further purified by YMC-Pack CN (0% to 80% EtOH in PE) to give tert-butyl (S)-(2-methyl-1,1-dioxido-2,3,3a,4-tetrahydropyrido[2,3-b][1,2,5]thiadiazolo[2,3-d][1,4]oxazin-8-yl)carbamate (560 mg, yield: 30%) as a yellow solid.

¹H NMR (400 MHz, CDCl₃) δ 1.51 (9H, s), 2.89 (3H, s), 3.24 (1H, dd, J=10.4, 5.4 Hz), 3.60 (1H, dd, J=10.0, 4.8 Hz), 3.85 (1H, t, J=10.8 Hz), 4.15-4.23 (1H, m), 4.34 (1H, dd, J=10.8, 3.2 Hz), 8.52 (1H, brs), 7.82-7.86 (2H, m).

Step 10: Preparation of (S)-8-amino-2-methyl-2,3,3a,4-tetrahydropyrido[2,3-b][1,2,5]thiadiazolo[2,3-d][1,4]oxazine 1,1-dioxide

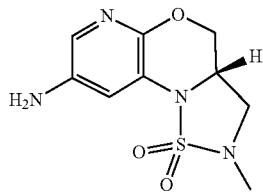 [SMILES: CN1C[C@H]2COc3ncc(N)cc3N2S1(=O)=O]

To a solution of tert-butyl (S)-(2-methyl-1,1-dioxido-2,3,3a,4-tetrahydropyrido[2,3-b][1,2,5]thiadiazolo[2,3-d][1,4]oxazin-8-yl)carbamate (560 mg, 1.57 mmol) in anhydrous DCM (5 mL) was added TFA (5 mL) at 15-20° C. Then the reaction mixture was stirred at 15-20° C. for 2 hours. The reaction mixture turned into yellow solution from colorless. The reaction mixture was concentrated and the residue was basified with saturated aqueous NaHCO₃ to pH=8, then extracted with DCM (15 mL×5). The combined organic layer was dried over anhydrous Na₂SO₄ and concentrated to give (S)-8-amino-2-methyl-2,3,3a,4-tetrahydropyrido[2,3-b][1,2,5]thiadiazolo[2,3-d][1,4]oxazine 1,1-dioxide (339 mg, yield: 84%) as a white solid.

¹H NMR (400 MHz, CDCl₃) δ 2.80 (3H, s), 3.15 (1H, dd, J=10.4, 4.8 Hz), 3.52 (1H, dd, J=10.4, 7.2 Hz), 3.83 (1H, t, J=10.8 Hz), 4.00-4.10 (1H, m), 4.18 (1H, dd, J=10.8, 3.2 Hz), 6.56 (1H, d, J=2.4 Hz), 7.60 (1H, d, J=2.4 Hz).

Note: Two protons of NH₂ were not observed.

Step 11: Preparation of (S)-1-(4-(6-((2-methyl-1,1-dioxido-2,3,3a,4-tetrahydropyrido[2,3-b][1,2,5]thiadiazolo[2,3-d][1,4]oxazin-8-yl)amino)pyridin-3-yl)phenyl)pyrrolidin-2-one

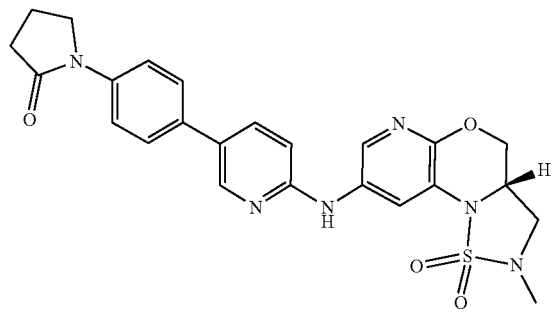 [SMILES: CN1C[C@H]2COc3ncc(Nc4ccc(-c5ccc(N6CCCC6=O)cc5)cn4)cc3N2S1(=O)=O]

A mixture of (S)-8-amino-2-methyl-2,3,3a,4-tetrahydropyrido[2,3-b][1,2,5]thiadiazolo[2,3-d][1,4]oxazine 1,1-dioxide (60 mg, 0.23 mmol), 1-(4-(6-chloropyridin-3-yl)phenyl)pyrrolidin-2-one (77 mg, 0.28 mmol), Pd₂(dba)₃ (21 mg, 0.023 mmol), Brettphos (25 mg, 0.047 mmol) and Cs₂CO₃ (229 mg, 0.702 mmol) in anhydrous dioxane (3 mL) was degassed and purged with N₂ for 3 times. Then the resulting reaction mixture was heated at 90° C. for 16 hours. The reaction mixture turned into brown suspension from red. LCMS showed the purity of the desired product is 70% (Rt=1.079 min; MS Calcd: 492.2; MS Found: 493.1 [M+H]⁺). The mixture was filtered through a pad of celite and the solid was washed with DCM/MeOH (10 mL×4, 10/1) and the filtrate was concentrated. The residue was purified by Combi Flash (2% to 10% MeOH in DCM), then triturated with CH₃CN (5 mL) and lyophilized to give (S)-1-(4-(6-((2-methyl-1,1-dioxido-2,3,3a,4-tetrahydropyrido[2,3-b][1,2,5]thiadiazolo[2,3-d][1,4]oxazin-8-yl)amino)pyridin-3-yl)phenyl)pyrrolidin-2-one (24.9 mg, yield: 22%) as a yellow solid.

¹H NMR (400 MHz, DMSO-d₆) δ 2.03-2.13 (2H, m), 2.55-2.60 (2H, m), 2.74 (3H, s), 3.25-3.30 (1H, m), 3.60 (1H, dd, J=10.8, 6.8 Hz), 3.70 (1H, t, J=6.8 Hz), 3.87 (2H, t, J=6.8 Hz), 4.20-4.30 (1H, m), 4.49 (1H, dd, J=10.8, 2.8 Hz), 6.92 (1H, d, J=8.8 Hz), 7.67 (2H, d, J=8.8 Hz), 7.74 (2H, d, J=8.8 Hz), 7.94 (1H, dd, J=8.8, 2.4 Hz), 8.16 (2H, s), 8.52 (1H, d, J=2.4 Hz), 9.43 (1H, brs).

Example 176: (S)-2-((4-methyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

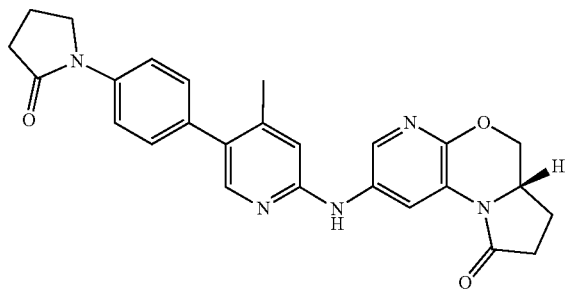 [SMILES: Cc1cc(Nc2cnc3c(c2)N2C(=O)CC[C@H]2CO3)ncc1-c1ccc(N2CCCC2=O)cc1]

Step 1: Preparation of 1-(4-(6-chloro-4-methylpyridin-3-yl)phenyl)pyrrolidin-2-one

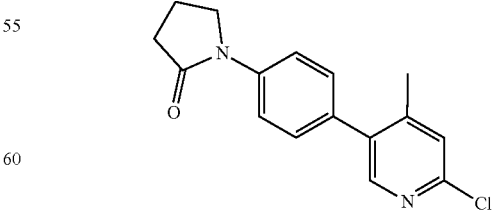

A mixture of 1-(4-(4,4,5,5-tetramethyl-1,3,2-dioxaborolan-2-yl)phenyl)pyrrolidin-2-one (500 mg, 1.74 mmol), 5-bromo-2-chloro-4-methylpyridine (359 mg, 1.74 mmol), Pd(dppf)Cl₂ (127 mg, 0.174 mmol) and Na₂CO₃ (554 mg, 5.22 mmol) in dioxane (6 mL) and water (1.5 mL) was degassed and purged with N₂ for 3 times. And the resulting reaction mixture was stirred at 100° C. for 2 hours under N₂ atmosphere. A black suspension was formed. LCMS showed the purity of the desired product is 52% (Rt=0.858 min; MS Calcd: 286.1; MS Found: 287.0 [M+H]⁺). The reaction mixture was diluted with water (10 mL). The aqueous layer was extracted with EtOAc (30 mL×3). The combined organic layer was washed with water (20 mL×2), brine (40 mL), dried over anhydrous Na₂SO₄, filtered and concentrated under reduced pressure. The residue was purified by Combi Flash (20% to 60% EtOAc in PE) to give 1-(4-(6-chloro-4-methylpyridin-3-yl)phenyl)pyrrolidin-2-one (450 mg, yield: 79%) as a yellow solid.

¹H NMR (400 MHz, CDCl₃) δ 2.16-2.25 (2H, m), 2.28 (3H, s), 2.65 (2H, t, J=8.2 Hz), 3.92 (2H, t, J=7.0 Hz), 7.24 (1H, s), 7.27-7.32 (2H, m), 7.69-7.75 (2H, m), 8.19 (1H, s).

Step 2: Preparation of (S)-2-((4-methyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

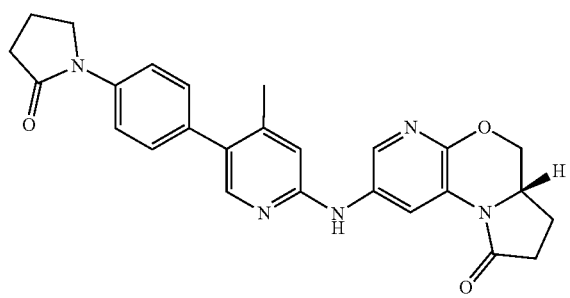 [SMILES: Cc1cc(Nc2cnc3c(c2)N2C(=O)CC[C@H]2CO3)ncc1-c1ccc(N2CCCC2=O)cc1]

A mixture of 1-(4-(6-chloro-4-methylpyridin-3-yl)phenyl)pyrrolidin-2-one (50 mg, 0.17 mmol), (S)-2-amino-6,6a,7,8-tetrahydro-9H-pyrido[2,3-b]pyrrolo[1,2-d][1,4]oxazin-9-one (36 mg, 0.17 mmol), Pd₂(dba)₃ (16 mg, 0.017 mmol), Brettphos (19 mg, 0.034 mmol) and Cs₂CO₃ (114 mg, 0.348 mmol) in anhydrous dioxane (3 mL) was degassed and purged with N₂ for 3 times. And the resulting reaction mixture was stirred at 90° C. for 16 hours under N₂ atmosphere. A gray suspension was formed. LCMS showed the purity of the desired product is 56% (Rt=0.722 min; MS Calcd: 455.2; MS Found: 456.1[M+H]+). The reaction mixture was diluted with water (10 mL). The aqueous layer was extracted with EtOAc (30 mL×3). The combined organic layer was washed with water (20 mL×2), brine (40 mL), dried over anhydrous Na₂SO₄, filtered and concentrated under reduced pressure. The residue was purified by prep-HPLC (0.225% FA as an additive) to give (S)-2-((4-methyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one (15.1 mg, yield: 19%) as an off-white solid.

¹H NMR (400 MHz, DMSO-d₆) δ 1.65-1.76 (1H, m), 2.05-2.10 (2H, m), 2.19-2.26 (4H, m), 2.35-2.43 (1H, m), 2.50-2.56 (2H, m), 2.63-2.74 (1H, m), 3.86-3.94 (3H, m), 4.04-4.10 (1H, m), 4.59 (1H, dd, J=10.8 Hz, 3.0 Hz), 6.74 (1H, s), 7.37 (2H, d, J=8.6 Hz), 7.73 (2H, d, J=8.6 Hz), 7.92 (1H, s), 8.37 (1H, d, J=2.4 Hz), 8.93 (1H, d, J=2.4 Hz), 9.19 (1H, brs).

Example 177: (S)-2-((4-isopropyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

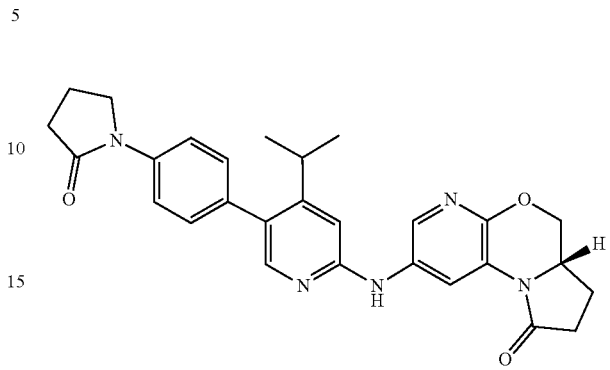

Step 1: Preparation of 2-(5-bromo-2-chloropyridin-4-yl)propan-2-ol

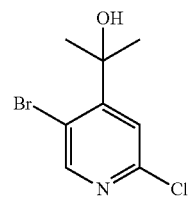

To a solution of methyl 5-bromo-2-chloroisonicotinate (2.00 g, 7.98 mmol) in THF (20 mL) was added MeMgBr (6.6 mL, 3 M in THF) dropwise at −10° C. The resulting reaction mixture was warmed to 0° C. gradually and further stirred for 2 hours under N₂ atmosphere. A yellow suspension was formed. TLC showed the starting material was consumed completely. The reaction mixture was quenched with sat. aq. NH₄Cl (20 mL), and extracted with EtOAc (30 mL×3). The combined organic layer was washed with water (20 mL×2), brine (40 mL), dried over anhydrous Na₂SO₄, filtered and concentrated under reduced pressure. The residue was purified by Combi Flash (20% to 50% EtOAc in PE) to give 2-(5-bromo-2-chloropyridin-4-yl)propan-2-ol (1.60 g, yield: 80%) as a white solid.

¹H NMR (400 MHz, CDCl₃) δ 1.73 (6H, s), 2.49 (1H, brs), 7.75 (1H, s), 8.43 (1H, s).

Step 2: Preparation of 5-bromo-2-chloro-4-isopropylpyridine

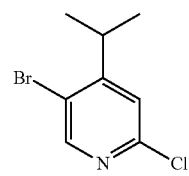

A solution of 2-(5-bromo-2-chloropyridin-4-yl)propan-2-ol (500 mg, 2.00 mmol) in HI (20 mL, 40%) was stirred at 100° C. for 48 hours. A black solution with black deposit was formed. TLC showed the starting material was consumed completely. The reaction mixture was quenched with sat.aq.Na$_2$SO$_3$ (10 mL), and extracted with EtOAc (30 mL×3). The combined organic layer was washed with sat. aq. Na$_2$SO$_3$ (20 mL×2), brine (40 mL), dried over anhydrous Na$_2$SO$_4$, filtered and concentrated under reduced pressure. The residue was purified by Combi Flash (0% to 10% EtOAc in PE) to give 5-bromo-2-chloro-4-isopropylpyridine (468 mg, yield: 61%) as colorless oil.

$^1$H NMR (400 MHz, CDCl$_3$) δ 1.26 (6H, d, J=6.8 Hz), 3.25-3.30 (1H, m), 7.22 (1H, s), 8.42 (1H, s).

Step 3: Preparation of 1-(4-(6-chloro-4-isopropylpyridin-3-yl)phenyl)pyrrolidin-2-one

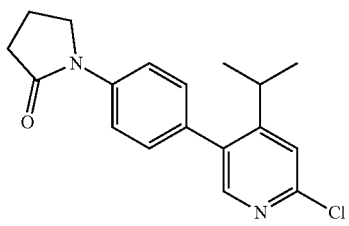 [SMILES: CC(C)c1cc(Cl)ncc1-c1ccc(N2CCCC2=O)cc1]

A mixture of 5-bromo-2-chloro-4-isopropylpyridine (163 mg, 0.696 mmol), 1-(4-(4,4,5,5-tetramethyl-1,3,2-dioxaborolan-2-yl)phenyl)pyrrolidin-2-one (200 mg, 0.696 mmol), Pd(dppf)Cl$_2$ (51 mg, 0.070 mmol) and Na$_2$CO$_3$ (221 mg, 2.09 mmol) in dioxane (4 mL) and water (1 mL) was degassed and purged with N$_2$ for 3 times. And the resulting reaction mixture was stirred at 100° C. for 2 hours under N$_2$ atmosphere. A black suspension was formed. LCMS showed the purity of the desired product is 41% (Rt=0.931 min; MS Calcd: 314.1; MS Found: 315.0 [M+H]$^+$). The reaction mixture was diluted with water (10 mL). The aqueous layer was extracted with EtOAc (30 mL×3). The combined organic layer was washed with water (20 mL×2), brine (40 mL), dried over anhydrous Na$_2$SO$_4$, filtered and concentrated under reduced pressure. The residue was purified by Combi Flash (20% to 60% EtOAc in PE) to give 1-(4-(6-chloro-4-isopropylpyridin-3-yl)phenyl)pyrrolidin-2-one (200 mg, yield: 64%) as a yellow solid.

$^1$H NMR (400 MHz, CDCl$_3$) δ 1.15 (6H, d, J=6.8 Hz), 2.16-2.25 (2H, m), 2.61-2.69 (2H, m), 3.01-3.12 (1H, m), 3.89-3.94 (2H, m), 7.24 (1H, s), 7.27-7.30 (2H, m), 7.69-7.73 (2H, m), 8.16 (1H, s).

Step 4: Preparation of compound (S)-2-((4-isopropyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

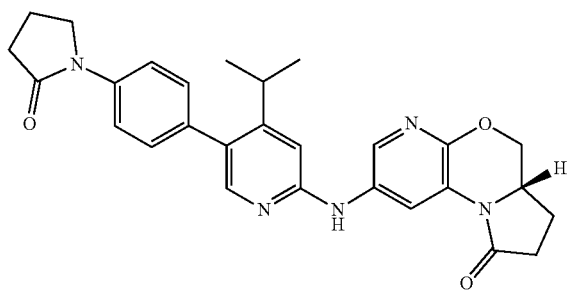 [SMILES: CC(C)c1cc(Nc2cnc3c(c2)N2C(=O)CC[C@H]2CO3)ncc1-c1ccc(N2CCCC2=O)cc1]

A mixture of 1-(4-(6-chloro-4-isopropylpyridin-3-yl)phenyl)pyrrolidin-2-one (200 mg, 0.635 mmol), (S)-2-amino-6,6a,7,8-tetrahydro-9H-pyrido[2,3-b]pyrrolo[1,2-d][1,4]oxazin-9-one (130 mg, 0.635 mmol), Pd$_2$(dba)$_3$ (58 mg, 0.063 mmol), Brettphos (68 mg, 0.127 mmol) and Cs$_2$CO$_3$ (414 mg, 1.27 mmol) in anhydrous dioxane (8 mL) was degassed and purged with N$_2$ for 3 times. And the resulting reaction mixture was stirred at 90° C. for 16 hours under N$_2$ atmosphere. A gray suspension was formed. LCMS showed the purity of the desired product is 39% (Rt=0.757 min; MS Calcd: 483.2; MS Found: 484.2[M+H]$^+$). The reaction mixture was diluted with water (10 mL). The aqueous layer was extracted with EtOAc (30 mL×3). The combined organic layer was washed with water (20 mL×2), brine (40 mL), dried over anhydrous Na$_2$SO$_4$, filtered and concentrated under reduced pressure. The residue was purified by Combi Flash (0% to 10% MeOH in DCM) to give a crude compound (S)-2-((4-isopropyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one (200 mg, crude, contained byproduct (S)-2-((5-(4-(2-oxopyrrolidin-1-yl)phenyl)-4-(prop-1-en-2-yl)pyridin-2-yl)amino)-6,6a,7,8-tetrahydro-9H-pyrido[2,3-b]pyrrolo[1,2-d][1,4]oxazin-9-one) as a yellow solid, which was further treated with H$_2$ (45 psi)/Pd/C. The residue was purified by prep-HPLC (0.225% FA as an additive) to give (S)-2-((4-isopropyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one (52.8 mg, yield: 17% for 2 steps) as a light yellow solid.

$^1$H NMR (400 MHz, DMSO-d$_6$) δ 1.11 (6H, d, J=6.8 Hz), 1.65-1.76 (1H, m), 2.05-2.13 (2H, m), 2.18-2.26 (1H, m), 2.35-2.43 (1H, m), 2.50-2.56 (2H, m), 2.63-2.70 (1H, m), 2.95-3.02 (1H, m), 3.86-3.94 (3H, m), 4.04-4.10 (1H, m), 4.58 (1H, dd, J=10.8 Hz, 3.0 Hz), 6.83 (1H, s), 7.31 (2H, d, J=8.6 Hz), 7.73 (2H, d, J=8.6 Hz), 7.86 (1H, s), 8.36 (1H, d, J=2.4 Hz), 8.95 (1H, d, J=2.4 Hz), 9.18 (1H, brs).

Example 178: (S)-2-((4-cyclopropyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

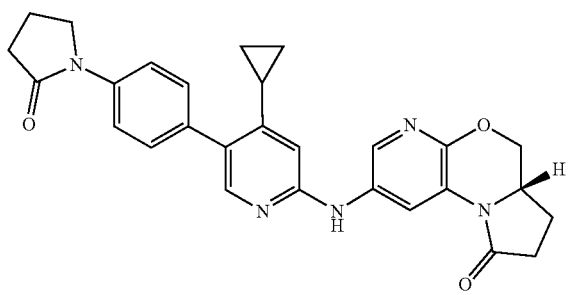 [SMILES: O=C1CCCN1c1ccc(-c2cnc(Nc3cnc4c(c3)N3C(=O)CC[C@H]3CO4)cc2C2CC2)cc1]

Step 1: Preparation of 5-bromo-2-chloro-4-iodopyridine

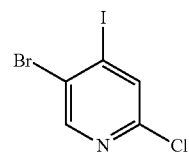

To a solution of 5-bromo-2-chloropyridine (2.00 g, 10.4 mmol) in anhydrous THF (40 mL) was added LDA (6.2 mL, 2 M in THF) dropwise at −60° C. After the addition, the resulting reaction mixture was stirred at −60° C. for 0.5 h. Then NIS (2.34 g, 10.4 mmol) was added into above solution in portions at −60° C. The reaction mixture was warmed to 15° C. gradually and further stirred for 1.5 hours under $N_2$ atmosphere. A yellow solution was formed. TLC showed the starting material was consumed completely. The reaction mixture was quenched with sat. aq. $NH_4Cl$ (20 mL), then extracted with EtOAc (30 mL×3). The combined organic layer was washed with water (20 mL×2), brine (40 mL), dried over anhydrous $Na_2SO_4$, filtered and concentrated under reduced pressure. The residue was purified by Combi Flash (0% to 10% EtOAc in PE) to give 5-bromo-2-chloro-4-iodopyridine (2.00 g, yield: 60%) as a white solid. $^1$H NMR (400 MHz, $CDCl_3$) δ 7.86 (1H, s), 8.47 (1H, s).

Step 2: Preparation of 5-bromo-2-chloro-4-cyclopropylpyridine

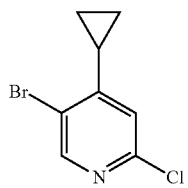 [SMILES: Clc1cc(C2CC2)c(Br)cn1]

A mixture of 5-bromo-2-chloro-4-iodopyridine (200 mg, 0.628 mmol), cyclopropylboronic acid (54 mg, 0.63 mmol), Pd(dppf)$Cl_2$ (46 mg, 0.063 mmol) and $Na_2CO_3$ (200 mg, 1.88 mmol) in dioxane (4 mL) and water (1 mL) was degassed and purged with $N_2$ for 3 times. And the resulting reaction mixture was stirred at 100° C. for 16 hours under $N_2$ atmosphere. A black suspension was formed. LCMS showed the purity of the desired product is 52% (Rt=0.931 min; MS Calcd: 230.9; MS Found: 231.6 [M+H]$^+$). The reaction mixture was diluted with water (10 mL). The aqueous layer was extracted with EtOAc (30 mL×3). The combined organic layer was washed with water (20 mL×2), brine (40 mL), dried over anhydrous $Na_2SO_4$, filtered and concentrated under reduced pressure. The residue was purified by Combi Flash (0% to 10% EtOAc in PE) to give 5-bromo-2-chloro-4-cyclopropylpyridine (122 mg, yield: 64%) as a yellow solid.

Step 3: Preparation of 1-(4-(6-chloro-4-cyclopropylpyridin-3-yl)phenyl)pyrrolidin-2-one

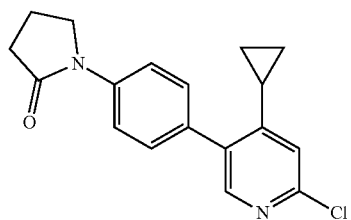 [SMILES: O=C1CCCN1c1ccc(-c2cnc(Cl)cc2C2CC2)cc1]

A mixture of 5-bromo-2-chloro-4-cyclopropylpyridine (81 mg, 0.35 mmol), 1-(4-(4,4,5,5-tetramethyl-1,3,2-dioxaborolan-2-yl)phenyl)pyrrolidin-2-one (100 mg, 0.348 mmol), Pd(dppf)$Cl_2$ (25 mg, 0.035 mmol) and $Na_2CO_3$ (111 mg, 1.04 mmol) in dioxane (4 mL) and water (1 mL) was degassed and purged with $N_2$ for 3 times. And the resulting reaction mixture was stirred at 100° C. for 2 hours under $N_2$ atmosphere. A black suspension was formed. LCMS showed the purity of the desired product is 54% (Rt=0.721 min; MS Calcd: 312.1; MS Found: 312.8 [M+H]$^+$). The reaction mixture was diluted with water (10 mL). The aqueous layer was extracted with EtOAc (30 mL×3). The combined organic layer was washed with water (20 mL×2), brine (40 mL), dried over anhydrous $Na_2SO_4$, filtered and concentrated under reduced pressure. The residue was purified by Combi Flash (20% to 50% EtOAc in PE) to give 1-(4-(6-chloro-4-cyclopropylpyridin-3-yl)phenyl)pyrrolidin-2-one (100 mg, yield: 92%) as a yellow solid.
$^1$H NMR (400 MHz, $CDCl_3$) δ 0.82-0.88 (2H, m), 1.02-1.07 (2H, m), 1.87-1.92 (1H, m), 2.17-2.25 (2H, m), 2.66 (2H, t, J=8.2 Hz), 3.92 (2H, t, J=7.0 Hz), 6.76 (1H, s), 7.40-7.44 (2H, m), 7.71-7.75 (2H, m), 8.16 (1H, s).

Step 4: Preparation of (S)-2-((4-cyclopropyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

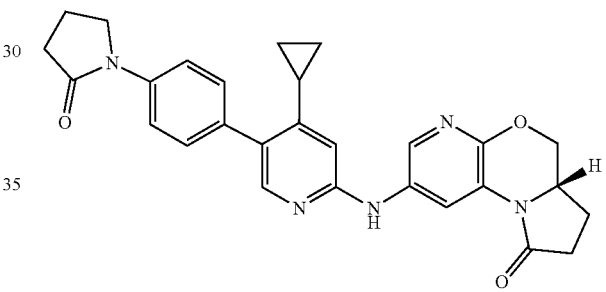

A mixture of 1-(4-(6-chloro-4-cyclopropylpyridin-3-yl)phenyl)pyrrolidin-2-one (100 mg, 0.320 mmol), (S)-2-amino-6,6a,7,8-tetrahydro-9H-pyrido[2,3-b]pyrrolo[1,2-d][1,4]oxazin-9-one (66 mg, 0.32 mmol), $Pd_2(dba)_3$ (29 mg, 0.032 mmol), Brettphos (34 mg, 0.064 mmol) and $Cs_2CO_3$ (208 mg, 0.639 mmol) in anhydrous dioxane (5 mL) was degassed and purged with $N_2$ for 3 times. And the resulting reaction mixture was stirred at 90° C. for 16 hours under $N_2$ atmosphere. A yellow suspension was formed. LCMS showed the purity of the desired product is 58% (Rt=0.747 min; MS Calcd: 481.2; MS Found: 482.1[M+H]$^+$). The reaction mixture was diluted with water (10 mL). The aqueous layer was extracted with DCM/MeOH (30 mL×3, 10/1). The combined organic layer was washed with water (20 mL×2), brine (40 mL), dried over anhydrous $Na_2SO_4$, filtered and concentrated under reduced pressure. The residue was purified by Combi Flash (0% to 10% MeOH in DCM), and further purified by prep-HPLC (0.225% FA as an additive) to give (S)-2-((4-cyclopropyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one (40.0 mg, yield: 26%) as a white solid.
$^1$H NMR (400 MHz, DMSO-$d_6$) δ 0.70-0.79 (2H, m), 0.94-1.01 (2H, m), 1.64-1.75 (1H, m), 1.77-1.84 (1H, m), 2.05-2.11 (2H, m), 2.17-2.24 (1H, m), 2.34-2.43 (1H, m), 2.50-2.56 (2H, m), 2.63-2.73 (1H, m), 3.85-3.93 (3H, m), 4.02-4.10 (1H, m), 4.57 (1H, dd, J=10.8 Hz, 3.0 Hz), 6.35

(1H, s), 7.44 (2H, d, J=8.6 Hz), 7.74 (2H, d, J=8.6 Hz), 7.91 (1H, s), 8.37 (1H, d, J=2.4 Hz), 8.93 (1H, d, J=2.6 Hz), 9.04 (1H, brs).

Example 179: (S)-2-((4-methoxy-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

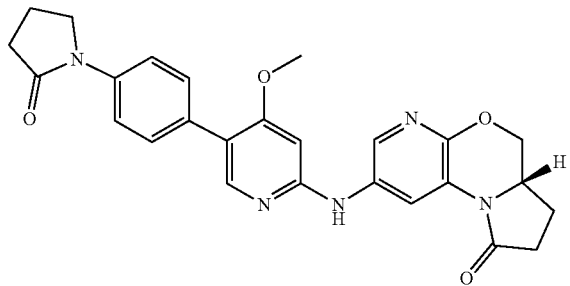 [SMILES: COc1cc(Nc2cnc3c(c2)N2C(=O)CC[C@H]2CO3)ncc1-c1ccc(N2CCCC2=O)cc1]

Step 1: Preparation of 1-(4-(6-chloro-4-methoxypyridin-3-yl)phenyl)pyrrolidin-2-one

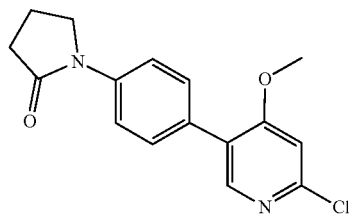 [SMILES: COc1cc(Cl)ncc1-c1ccc(N2CCCC2=O)cc1]

A mixture of 1-(4-(4,4,5,5-tetramethyl-1,3,2-dioxaborolan-2-yl)phenyl)pyrrolidin-2-one (500 mg, 1.74 mmol), 5-bromo-2-chloro-4-methoxypyridine (387 mg, 1.74 mmol), Pd(dppf)Cl$_2$ (127 mg, 0.174 mmol) and Na$_2$CO$_3$ (554 mg, 5.22 mmol) in dioxane (6 mL) and water (1.5 mL) was degassed and purged with N$_2$ for 3 times. And the resulting reaction mixture was stirred at 100° C. for 2 hours under N$_2$ atmosphere. A black suspension was formed. LCMS showed the purity of the desired product is 51% (Rt=0.649 min; MS Calcd: 302.1; MS Found: 302.8 [M+H]$^+$). The reaction mixture was diluted with water (10 mL). The aqueous layer was extracted with EtOAc (30 mL×3). The combined organic layer was washed with water (20 mL×2), brine (40 mL), dried over anhydrous Na$_2$SO$_4$, filtered and concentrated under reduced pressure. The residue was purified by Combi Flash (20% to 60% EtOAc in PE) to give 1-(4-(6-chloro-4-methoxypyridin-3-yl)phenyl)pyrrolidin-2-one (450 mg, yield: 78%) as a yellow solid.

Step 2: Preparation of (S)-2-((4-methoxy-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

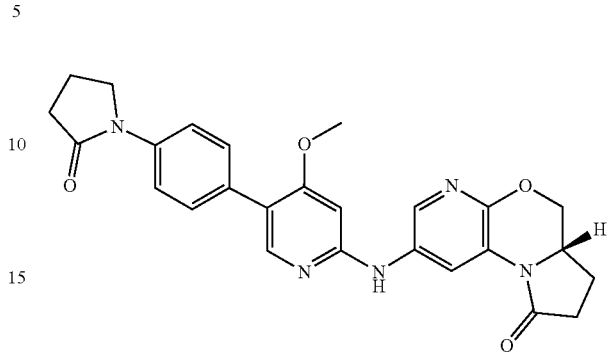

A mixture of 1-(4-(6-chloro-4-methoxypyridin-3-yl)phenyl)pyrrolidin-2-one (50 mg, 0.17 mmol), (S)-2-amino-6,6a,7,8-tetrahydro-9H-pyrido[2,3-b]pyrrolo[1,2-d][1,4]oxazin-9-one (34 mg, 0.17 mmol), Pd$_2$(dba)$_3$ (15 mg, 0.017 mmol), Brettphos (18 mg, 0.033 mmol) and Cs$_2$CO$_3$ (108 mg, 0.330 mmol) in anhydrous dioxane (3 mL) was degassed and purged with N$_2$ for 3 times. And the resulting reaction mixture was stirred at 90° C. for 16 hours under N$_2$ atmosphere. A gray suspension was formed. LCMS showed the purity of the desired product is 60% (Rt=0.721 min; MS Calcd: 471.2; MS Found: 472.1[M+H]$^+$). The reaction mixture was diluted with water (10 mL). The aqueous layer was extracted with EtOAc (30 mL×3). The combined organic layer was washed with water (20 mL×2), brine (40 mL), dried over anhydrous Na$_2$SO$_4$, filtered and concentrated under reduced pressure. The residue was purified by Combi Flash (0% to 10% MeOH in DCM), and further purified by prep-HPLC (0.225% FA as an additive) to give (S)-2-((4-methoxy-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one (57.1 mg, yield: 67%) as a light yellow solid.
$^1$H NMR (400 MHz, DMSO-d$_6$) δ 1.65-1.76 (1H, m), 2.04-2.10 (2H, m), 2.19-2.26 (1H, m), 2.33-2.43 (1H, m), 2.50-2.56 (2H, m), 2.63-2.73 (1H, m), 3.80-3.94 (6H, m), 4.04-4.11 (1H, m), 4.59 (1H, dd, J=10.6 Hz, 3.0 Hz), 6.48 (1H, s), 7.47 (2H, d, J=8.8 Hz), 7.68 (2H, d, J=8.8 Hz), 7.95 (1H, s), 8.39 (1H, d, J=2.4 Hz), 8.94 (1H, d, J=2.4 Hz), 9.26 (1H, brs).

Example 180: (S)-2-((5-(3-fluoro-4-(2-oxopyrrolidin-1-yl)phenyl)-4-methylpyridin-2-yl)amino)-6,6a,7,8-tetrahydro-9H-pyrido[2,3-b]pyrrolo[1,2-d][1,4]oxazin-9-one

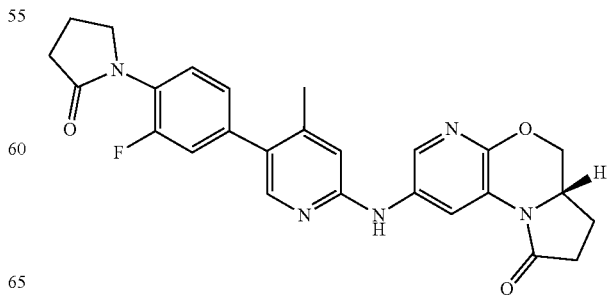

Step 1: Preparation of 1-(4-(6-chloro-4-methylpyridin-3-yl)-2-fluorophenyl)pyrrolidin-2-one

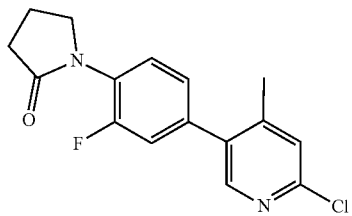 [SMILES: Cc1cc(Cl)ncc1-c1ccc(N2CCCC2=O)c(F)c1]

A mixture of 5-bromo-2-chloro-4-methylpyridine (203 mg, 0.983 mmol), 1-(2-fluoro-4-(4,4,5,5-tetramethyl-1,3,2-dioxaborolan-2-yl)phenyl)pyrrolidin-2-one (300 mg, 0.983 mmol), Pd(dppf)Cl$_2$ (72 mg, 0.098 mmol) and Na$_2$CO$_3$ (313 mg, 2.95 mmol) in dioxane (4 mL) and water (1 mL) was degassed and purged with N$_2$ for 3 times. And the resulting reaction mixture was stirred at 90° C. for 4 hours under N$_2$ atmosphere. A black suspension was formed. LCMS showed the purity of the desired product is 60% (Rt=0.850 min; MS Calcd: 304.1; MS Found: 304.9 [M+H]$^+$). The reaction mixture was diluted with water (10 mL). The aqueous layer was extracted with EtOAc (30 mL×3). The combined organic layer was washed with water (20 mL×2), brine (40 mL), dried over anhydrous Na$_2$SO$_4$, filtered and concentrated under reduced pressure. The residue was purified by Combi Flash (20% to 80% EtOAc in PE) to give 1-(4-(6-chloro-4-methylpyridin-3-yl)-2-fluorophenyl)pyrrolidin-2-one (240 mg, yield: 80%) as a yellow solid.

$^1$H NMR (400 MHz, CDCl$_3$) δ 2.21-2.28 (2H, m), 2.30 (3H, s), 2.61 (2H, t, J=8.0 Hz), 3.89 (2H, t, J=7.0 Hz), 7.07-7.12 (2H, m), 7.24-7.26 (1H, m), 7.52-7.56 (1H, m), 8.19 (1H, s).

Step 2: Preparation of (S)-2-((5-(3-fluoro-4-(2-oxopyrrolidin-1-yl)phenyl)-4-methylpyridin-2-yl)amino)-6,6a,7,8-tetrahydro-9H-pyrido[2,3-b]pyrrolo[1,2-d][1,4]oxazin-9-one

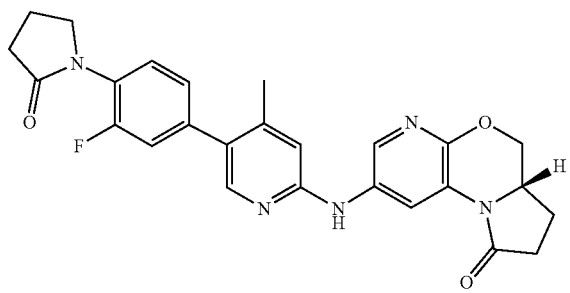 [SMILES: Cc1cc(Nc2cnc3c(c2)N2C(=O)CC[C@H]2CO3)ncc1-c1ccc(N2CCCC2=O)c(F)c1]

A mixture of 1-(4-(6-chloro-4-methylpyridin-3-yl)-2-fluorophenyl)pyrrolidin-2-one (50 mg, 0.16 mmol), (S)-2-amino-6,6a,7,8-tetrahydro-9H-pyrido[2,3-b]pyrrolo[1,2-d][1,4]oxazin-9-one (34 mg, 0.16 mmol), Pd$_2$(dba)$_3$ (15 mg, 0.016 mmol), Brettphos (18 mg, 0.033 mmol) and Cs$_2$CO$_3$ (107 mg, 0.328 mmol) in anhydrous dioxane (3 mL) was degassed and purged with N$_2$ for 3 times. And the resulting reaction mixture was stirred at 90° C. for 16 hours under N$_2$ atmosphere. A yellow suspension was formed. LCMS showed the purity of the desired product is 54% (Rt=0.717 min; MS Calcd: 455.2; MS Found: 456.1[M+H]$^+$). The reaction mixture was diluted with water (10 mL). The aqueous layer was extracted with EtOAc (30 mL×3). The combined organic layer was washed with water (20 mL×2), brine (40 mL), dried over anhydrous Na$_2$SO$_4$, filtered and concentrated under reduced pressure. The residue was purified by prep-HPLC (0.225% FA as an additive) to give (S)-2-((5-(3-fluoro-4-(2-oxopyrrolidin-1-yl)phenyl)-4-methylpyridin-2-yl)amino)-6,6a,7,8-tetrahydro-9H-pyrido[2,3-b]pyrrolo[1,2-d][1,4]oxazin-9-one (41.2 mg, yield: 52%) as a light yellow solid.

$^1$H NMR (400 MHz, DMSO-d$_6$) δ 1.65-1.76 (1H, m), 2.09-2.17 (2H, m), 2.17-2.23 (1H, m), 2.24 (3H, s), 2.35-2.43 (1H, m), 2.43-2.50 (2H, m), 2.62-2.72 (1H, m), 3.80 (2H, t, J=7.0 Hz), 3.88-3.94 (1H, m), 4.04-4.10 (1H, m), 4.59 (1H, dd, J=10.8 Hz, 3.0 Hz), 6.74 (1H, s), 7.21-7.27 (1H, m), 7.32-7.38 (1H, m), 7.50 (1H, t, J=8.2 Hz), 7.96 (1H, s), 8.37 (1H, d, J=2.4 Hz), 8.92 (1H, d, J=2.4 Hz), 9.24 (1H, brs).

Example 181: (S)-2-((5-(3-fluoro-4-(2-oxopyrrolidin-1-yl)phenyl)-4-isopropylpyridin-2-yl)amino)-6,6a,7,8-tetrahydro-9H-pyrido[2,3-b]pyrrolo[1,2-d][1,4]oxazin-9-one

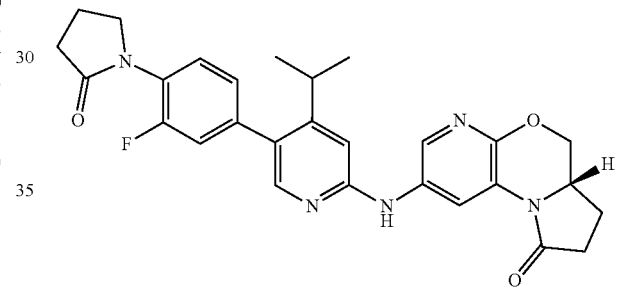

Step 1: Preparation of 1-(4-(6-chloro-4-isopropylpyridin-3-yl)-2-fluorophenyl)pyrrolidin-2-one

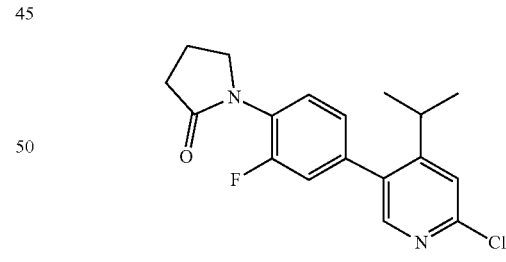

A mixture of 5-bromo-2-chloro-4-isopropylpyridine (154 mg, 0.655 mmol), 1-(2-fluoro-4-(4,4,5,5-tetramethyl-1,3,2-dioxaborolan-2-yl)phenyl)pyrrolidin-2-one (200 mg, 0.655 mmol), Pd(dppf)Cl$_2$ (48 mg, 0.065 mmol) and Na$_2$CO$_3$ (208 mg, 1.97 mmol) in dioxane (4 mL) and water (1 mL) was degassed and purged with N$_2$ for 3 times. And the resulting reaction mixture was stirred at 100° C. for 2 hours under N$_2$ atmosphere. A black suspension was formed. LCMS showed the purity of the desired product is 37% (Rt=0.895 min; MS Calcd: 332.1; MS Found: 332.9 [M+H]$^+$). The reaction mixture was diluted with water (10 mL). The aqueous layer was extracted with EtOAc (30 mL×3). The combined organic layer was washed with water (20 mL×2), brine (40 mL), dried over anhydrous Na₂SO₄, filtered and concentrated under reduced pressure. The residue was purified by Combi Flash (20% to 60% EtOAc in PE) to give 1-(4-(6-chloro-4-isopropylpyridin-3-yl)-2-fluorophenyl)pyrrolidin-2-one (170 mg, yield: 55%) as a yellow solid.

¹H NMR (400 MHz, CDCl₃) δ 1.18 (6H, d, J=6.8 Hz), 2.20-2.29 (2H, m), 2.58-2.63 (2H, m), 3.00-3.10 (1H, m), 3.87-3.94 (2H, m), 7.05-7.10 (1H, m), 7.17-7.21 (1H, m), 7.24-7.26 (1H, m), 7.31 (1H, s), 8.16 (1H, s).

Step 2: Preparation of (S)-2-((5-(3-fluoro-4-(2-oxopyrrolidin-1-yl)phenyl)-4-isopropylpyridin-2-yl)amino)-6,6a,7,8-tetrahydro-9H-pyrido[2,3-b]pyrrolo[1,2-d][1,4]oxazin-9-one

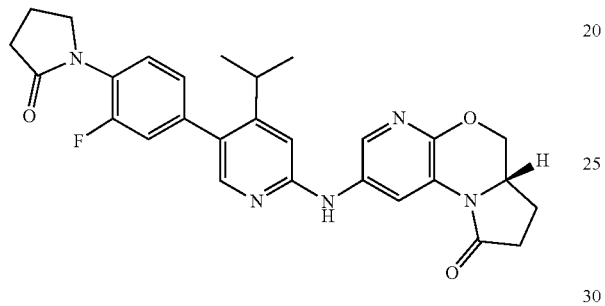

A mixture of 1-(4-(6-chloro-4-isopropylpyridin-3-yl)-2-fluorophenyl)pyrrolidin-2-one (170 mg, 0.511 mmol), (S)-2-amino-6,6a,7,8-tetrahydro-9H-pyrido[2,3-b]pyrrolo[1,2-d][1,4]oxazin-9-one (105 mg, 0.511 mmol), Pd₂(dba)₃ (47 mg, 0.051 mmol), Brettphos (55 mg, 0.102 mmol) and Cs₂CO₃ (326 mg, 1.02 mmol) in dioxane (8 mL) was degassed and purged with N₂ for 3 times. And the resulting reaction mixture was stirred at 90° C. for 16 hours under N₂ atmosphere. A gray suspension was formed. LCMS the purity of the desired product is 30% (Rt=0.761 min; MS Calcd: 501.2; MS Found: 502.1 [M+H]⁺). The reaction mixture was diluted with water (10 mL). The aqueous layer was extracted with EtOAc (30 mL×3). The combined organic layer was washed with water (20 mL×2), brine (40 mL), dried over anhydrous Na₂SO₄, filtered and concentrated under reduced pressure. The residue was purified by Combi Flash (0% to 10% MeOH in DCM) to give a crude compound (S)-2-((5-(3-fluoro-4-(2-oxopyrrolidin-1-yl)phenyl)-4-isopropylpyridin-2-yl)amino)-6,6a,7,8-tetrahydro-9H-pyrido[2,3-b]pyrrolo[1,2-d][1,4]oxazin-9-one (180 mg, crude, contained byproduct (S)-2-((5-(3-fluoro-4-(2-oxopyrrolidin-1-yl)phenyl)-4-(prop-1-en-2-yl)pyridin-2-yl)amino)-6,6a,7,8-tetrahydro-9H-pyrido[2,3-b]pyrrolo[1,2-d][1,4]oxazin-9-one) as a yellow solid, which was further treated with H₂ (45 psi)/Pd/C. The residue was purified by prep-HPLC (0.225% FA as an additive) to give (S)-2-((5-(3-fluoro-4-(2-oxopyrrolidin-1-yl)phenyl)-4-isopropylpyridin-2-yl)amino)-6,6a,7,8-tetrahydro-9H-pyrido[2,3-b]pyrrolo[1,2-d][1,4]oxazin-9-one (28.9 mg, yield: 11% for 2 steps) as a light yellow solid.

¹H NMR (400 MHz, DMSO-d₆) δ 1.13 (6H, d, J=6.8 Hz), 1.64-1.76 (1H, m), 2.10-2.17 (2H, m), 2.18-2.23 (1H, m), 2.35-2.43 (1H, m), 2.46 (2H, t, J=8.0 Hz), 2.62-2.72 (1H, m), 2.93-3.01 (1H, m), 3.81 (2H, t, J=6.8 Hz), 3.86-3.94 (1H, m), 4.04-4.11 (1H, m), 4.58 (1H, dd, J=10.8 Hz, 3.0 Hz), 6.83 (1H, s), 7.15-7.21 (1H, m), 7.25-7.32 (1H, m), 7.51 (1H, t, J=8.2 Hz), 7.91 (1H, s), 8.37 (1H, d, J=2.4 Hz), 8.95 (1H, d, J=2.4 Hz), 9.18 (1H, brs).

Example 182: (S)-2-((4-cyclopropyl-5-(3-fluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

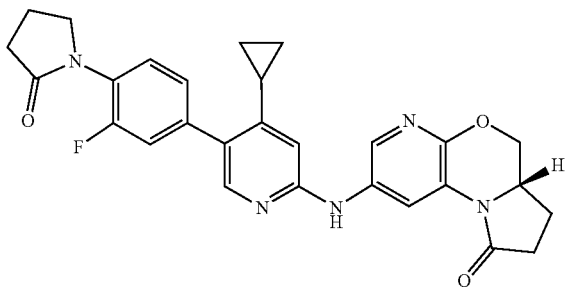 [SMILES: O=C1CCCN1c1ccc(-c2cnc(Nc3cnc4c(c3)N3C(=O)CC[C@H]3CO4)cc2C2CC2)cc1F]

Step 1: Preparation of 1-(4-(6-chloro-4-cyclopropylpyridin-3-yl)-2-fluorophenyl)pyrrolidin-2-one

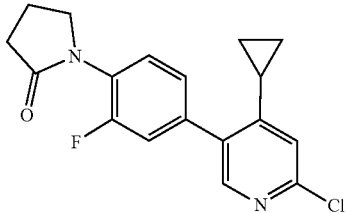 [SMILES: O=C1CCCN1c1ccc(-c2cnc(Cl)cc2C2CC2)cc1F]

A mixture of 5-bromo-2-chloro-4-cyclopropylpyridine (122 mg, 0.524 mmol), 1-(2-fluoro-4-(4,4,5,5-tetramethyl-1,3,2-dioxaborolan-2-yl)phenyl)pyrrolidin-2-one (160 mg, 0.524 mmol), Pd(dppf)Cl₂ (38 mg, 0.052 mmol) and Na₂CO₃ (167 mg, 1.57 mmol) in dioxane (4 mL) and water (1 mL) was degassed and purged with N₂ for 3 times. And the resulting reaction mixture was stirred at 100° C. for 2 hours under N₂ atmosphere. A black suspension was formed. LCMS showed the purity of the desired product is 40% (Rt=0.694 min; MS Calcd: 330.1; MS Found: 330.8 [M+H]⁺). The reaction mixture was diluted with water (10 mL). The aqueous layer was extracted with EtOAc (30 mL×3). The combined organic layer was washed with water (20 mL×2), brine (40 mL), dried over anhydrous Na₂SO₄, filtered and concentrated under reduced pressure. The residue was purified by Combi Flash (20% to 60% EtOAc in PE) to give 1-(4-(6-chloro-4-cyclopropylpyridin-3-yl)-2-fluorophenyl)pyrrolidin-2-one (112 mg, yield: 39%) as a yellow solid.

¹H NMR (400 MHz, CDCl₃) δ 0.83-0.88 (2H, m), 1.06-1.09 (2H, m), 1.87-1.93 (1H, m), 2.20-2.30 (2H, m), 2.58-2.64 (2H, m), 3.90 (2H, t, J=7.0 Hz), 6.77 (1H, s), 7.20-7.24 (1H, m), 7.32-7.43 (1H, m), 7.52-7.60 (1H, m), 8.15 (1H, s).

Step 2: Preparation of (S)-2-((4-cyclopropyl-5-(3-fluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

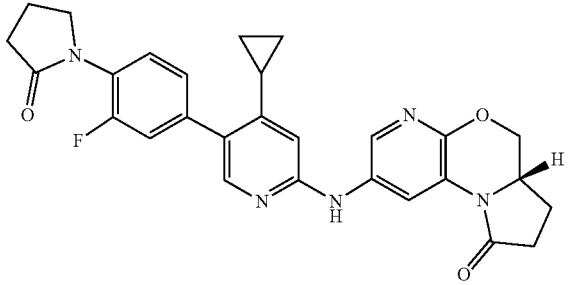 [SMILES: O=C1CCCN1c1ccc(-c2cnc(Nc3cnc4c(c3)N3C(=O)CC[C@H]3CO4)cc2C2CC2)cc1F]

A mixture of 1-(4-(6-chloro-4-cyclopropylpyridin-3-yl)-2-fluorophenyl)pyrrolidin-2-one (100 mg, 0.302 mmol), (S)-2-amino-6,6a,7,8-tetrahydro-9H-pyrido[2,3-b]pyrrolo[1,2-d][1,4]oxazin-9-one (62 mg, 0.30 mmol), $Pd_2(dba)_3$ (28 mg, 0.030 mmol), Brettphos (32 mg, 0.060 mmol) and $Cs_2CO_3$ (197 mg, 0.604 mmol) in anhydrous dioxane (5 mL) was degassed and purged with $N_2$ for 3 times. And the resulting reaction mixture was stirred at 90° C. for 16 hours under $N_2$ atmosphere. A yellow suspension was formed. LCMS showed the purity of the desired product is 42% (Rt=0.750 min; MS Calcd: 499.2; MS Found: 500.2 [M+H]$^+$). The reaction mixture was diluted with water (10 mL). The aqueous layer was extracted with DCM/MeOH (30 mL×3, 10/1). The combined organic layer was washed with water (20 mL×2), brine (40 mL), dried over anhydrous $Na_2SO_4$, filtered and concentrated under reduced pressure. The residue was purified by Combi Flash (0% to 5% MeOH in DCM), and further purified by prep-HPLC (0.225% FA as an additive) and prep-HPLC (0.05% $NH_3 \cdot H_2O$ as an additive) to give (S)-2-((4-cyclopropyl-5-(3-fluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one (12.1 mg, yield: 8%) as a white solid.

$^1$H NMR (400 MHz, DMSO-d$_6$) δ 0.73-0.80 (2H, m), 0.97-1.03 (2H, m), 1.64-1.75 (1H, m), 1.79-1.87 (1H, m), 2.10-2.21 (1H, m), 2.35-2.43 (1H, m), 2.46 (2H, t, J=8.0 Hz), 2.63-2.73 (1H, m), 3.81 (2H, t, J=7.0 Hz), 3.86-3.94 (1H, m), 4.04-4.11 (1H, m), 4.57 (1H, dd, J=10.8 Hz, 3.0 Hz), 6.37 (1H, s), 7.29-7.33 (1H, m), 7.36-7.41 (1H, m), 7.52 (1H, t, J=8.2 Hz), 7.95 (1H, s), 8.37 (1H, d, J=2.4 Hz), 8.92 (1H, d, J=2.6 Hz), 9.09 (1H, brs).

Example 183: (S)-2-((5-(3-fluoro-4-(2-oxopyrrolidin-1-yl)phenyl)-4-methoxypyridin-2-yl)amino)-6,6a,7,8-tetrahydro-9H-pyrido[2,3-b]pyrrolo[1,2-d][1,4]oxazin-9-one

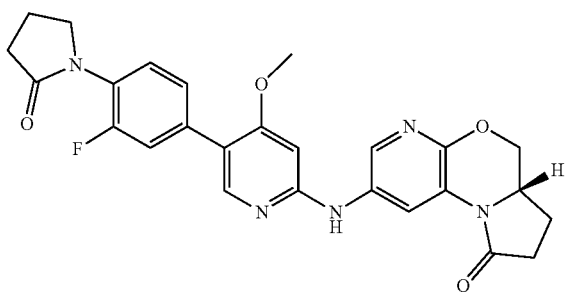 [SMILES: COc1cc(Nc2cnc3c(c2)N2C(=O)CC[C@H]2CO3)ncc1-c1ccc(N2CCCC2=O)c(F)c1]

Step 1: Preparation of 1-(4-(6-chloro-4-methoxypyridin-3-yl)-2-fluorophenyl)pyrrolidin-2-one A mixture of 5-bromo-2-chloro-4-methoxypyridine (219 mg, 0.983 mmol), 1-(2-fluoro-4-(4,4,5,5-tetramethyl-1,3,2-dioxaborolan-2-yl)phenyl)pyrrolidin-2-one (300 mg, 0.983 mmol), Pd(dppf)Cl$_2$ (72 mg, 0.098 mmol) and $Na_2CO_3$ (313 mg, 2.95 mmol) in dioxane (4 mL) and water (1 mL) was degassed and purged with $N_2$ for 3 times. And the resulting reaction mixture was stirred at 90° C. for 4 hours under $N_2$ atmosphere. A black suspension was formed. LCMS showed the purity of the desired product is 63% (Rt=0.823 min; MS Calcd: 320.1; MS Found: 320.9 [M+H]). The reaction mixture was diluted with water (10 mL). The aqueous layer was extracted with EtOAc (30 mL×3). The combined organic layer was washed with water (20 mL×2), brine (40 mL), dried over anhydrous $Na_2SO_4$, filtered and concentrated under reduced pressure. The residue was purified by Combi Flash (20% to 80% EtOAc in PE) to give 1-(4-(6-chloro-4-methoxypyridin-3-yl)-2-fluorophenyl)pyrrolidin-2-one (230 mg, yield: 78%) as a yellow solid.

$^1$H NMR (400 MHz, CDCl$_3$) δ 2.20-2.28 (2H, m), 2.60 (2H, t, J=8.0 Hz), 3.84-3.89 (2H, m), 3.90 (3H, s), 6.92 (1H, s), 7.24-7.33 (2H, m), 7.49 (1H, t, J=8.0 Hz), 8.19 (1H, s).

Step 2: Preparation of (S)-2-((5-(3-fluoro-4-(2-oxopyrrolidin-1-yl)phenyl)-4-methoxypyridin-2-yl)amino)-6,6a,7,8-tetrahydro-9H-pyrido[2,3-b]pyrrolo[1,2-d][1,4]oxazin-9-one A mixture of 1-(4-(6-chloro-4-methoxypyridin-3-yl)-2-fluorophenyl)pyrrolidin-2-one (50 mg, 0.16 mmol), (S)-2-amino-6,6a,7,8-tetrahydro-9H-pyrido[2,3-b]pyrrolo[1,2-d][1,4]oxazin-9-one (32 mg, 0.16 mmol), $Pd_2(dba)_3$ (14 mg, 0.016 mmol), Brettphos (17 mg, 0.032 mmol) and $Cs_2CO_3$ (101 mg, 0.311 mmol) in anhydrous dioxane (3 mL) was degassed and purged with $N_2$ for 3 times. And the resulting reaction mixture was stirred at 90° C. for 16 hours under $N_2$ atmosphere. A yellow suspension was formed. LCMS showed the purity of the desired product is 58% (Rt=0.716 min; MS Calcd: 489.2; MS Found: 490.1[M+H]$^+$). The reaction mixture was diluted with water (10 mL). The aqueous layer was extracted with EtOAc (30 mL×3). The combined organic layer was washed with water (20 mL×2), brine (40 mL), dried over anhydrous Na₂SO₄, filtered and concentrated under reduced pressure. The residue was purified by Combi Flash (0% to 10% MeOH in DCM), and further purified by prep-TLC (DCM/MeOH, 10/1) to give (S)-2-((5-(3-fluoro-4-(2-oxopyrrolidin-1-yl)phenyl)-4-methoxypyridin-2-yl)amino)-6,6a,7,8-tetrahydro-9H-pyrido[2,3-b]pyrrolo[1,2-d][1,4]oxazin-9-one (42.9 mg, yield: 56%) as a light yellow solid.

¹H NMR (400 MHz, DMSO-d₆) δ 1.62-1.77 (1H, m), 2.10-2.18 (2H, m), 2.19-2.27 (1H, m), 2.33-2.43 (1H, m), 2.50-2.56 (2H, m), 2.63-2.73 (1H, m), 3.75-3.82 (2H, m), 3.85 (3H, s), 3.88-3.95 (1H, m), 4.04-4.11 (1H, m), 4.56-4.63 (1H, m), 6.49 (1H, s), 7.32-7.48 (3H, m), 8.00-8.04 (1H, m), 8.40-8.44 (1H, m), 8.96 (1H, s), 9.25 (1H, brs).

Example 184: (S)-2-((5-(3,5-difluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

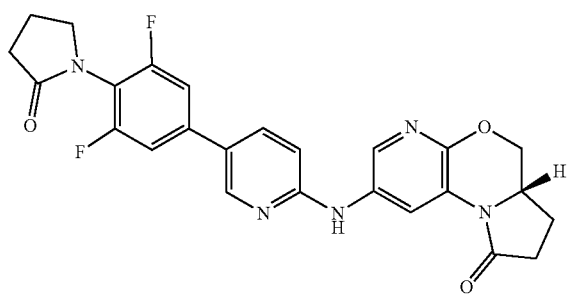 [SMILES: O=C1CCCN1c1c(F)cc(-c2ccc(Nc3cnc4c(c3)N3C(=O)CC[C@H]3CO4)nc2)cc1F]

Step 1: Preparation of N-(4-bromo-2,6-difluorophenyl)-4-chlorobutanamide

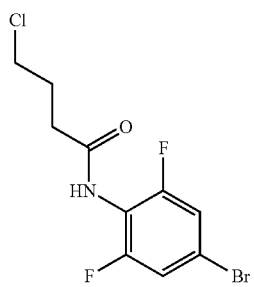 [SMILES: O=C(CCCCl)Nc1c(F)cc(Br)cc1F]

To a solution of 4-bromo-2,6-difluoroaniline (5.00 g, 24.0 mmol) and Et₃N (5.0 mL, 36 mmol) in anhydrous THF (50 mL) was added 4-chlorobutanoyl chloride (3.5 mL, 31 mmol) dropwise at 0° C. over a period of 0.5 hour under N₂ atmosphere. After the addition, the resulting reaction mixture was stirred at 0° C. for 3.5 hours. A yellow suspension was formed. TLC showed the starting material was consumed completely. The reaction mixture was diluted with water (50 mL) and the aqueous layer was extracted with EtOAc (100 mL×2). The combined organic layer was washed with brine (100 mL), dried over anhydrous Na₂SO₄, filtered and concentrated. The residue was triturated with PE/EtOAc (50 mL, 20/1) to give N-(4-bromo-2,6-difluorophenyl)-4-chlorobutanamide (5.7 g, yield: 76%) as a light yellow solid.

¹H NMR (400 MHz, CDCl₃) δ 2.16-2.25 (2H, m), 2.57-2.70 (2H, m), 3.67 (2H, t, J=6.0 Hz), 6.81 (1H, brs), 7.16 (2H, d, J=6.8 Hz).

Step 2: Preparation of 1-(4-bromo-2,6-difluorophenyl)pyrrolidin-2-one

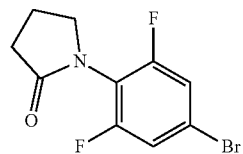 [SMILES: O=C1CCCN1c1c(F)cc(Br)cc1F]

To a mixture of N-(4-bromo-2,6-difluorophenyl)-4-chlorobutanamide (5.70 g, 18.2 mmol) in anhydrous THF (400 mL) was added KOtBu (4.09 g, 36.5 mmol) at −10° C. and then the mixture was stirred at 0° C. for 3 hours. A brown suspension was formed. TLC showed the starting material was consumed completely. The reaction mixture was poured into sat. aq. NH₄Cl (100 mL) and extracted with EtOAc (200 mL×3). The combined organic layer was washed with water (100 mL×2), brine (100 mL), dried over anhydrous Na₂SO₄, filtered and concentrated under reduced pressure. The residue was triturated with PE/EtOAc (30 mL, 3/1) to give 1-(4-bromo-2,6-difluorophenyl)pyrrolidin-2-one (5.00 g, yield: >99%) as a yellow solid.

¹H NMR (400 MHz, CDCl₃) δ 2.21-2.31 (2H, m), 2.56 (2H, t, J=8.0 Hz), 3.73 (2H, t, J=7.0 Hz), 7.14-7.20 (2H, m).

Step 3: Preparation of 1-(2,6-difluoro-4-(4,4,5,5-tetramethyl-1,3,2-dioxaborolan-2-yl)phenyl)pyrrolidin-2-one

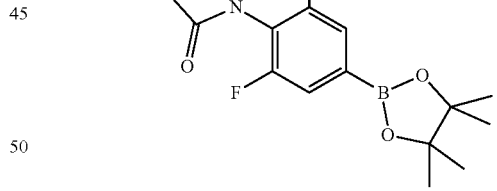

A mixture of 1-(4-bromo-2,6-difluorophenyl)pyrrolidin-2-one (500 mg, 1.81 mmol), Bispin (552 mg, 2.17 mmol), Pd(dppf)Cl₂ (133 mg, 0.181 mmol) and KOAc (533 mg, 5.43 mmol) in anhydrous dioxane (5 mL) was degassed and purged with N₂ for 3 times. And the resulting mixture was stirred at 100° C. for 16 hours under N₂ atmosphere. A black suspension was formed. LCMS showed the purity of the boronic acid of the desired product is 45% (Rt=0.617 min; MS Calcd: 241.1; MS Found: 241.9 [M+H]⁺). The reaction mixture was filtered through a pad of celite, washed with EtOAc (50 mL) and concentrated under reduced pressure to give 1-(2,6-difluoro-4-(4,4,5,5-tetramethyl-1,3,2-dioxaborolan-2-yl)phenyl)pyrrolidin-2-one (crude), which was used for the next step without further purification.

Step 4: Preparation of 1-(4-(6-chloropyridin-3-yl)-2,6-difluorophenyl)pyrrolidin-2-one

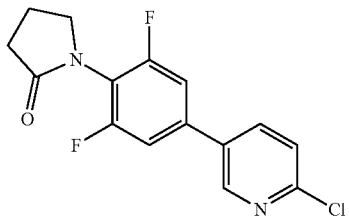 [SMILES: O=C1CCCN1c1c(F)cc(-c2ccc(Cl)nc2)cc1F]

A mixture of 1-(2,6-difluoro-4-(4,4,5,5-tetramethyl-1,3,2-dioxaborolan-2-yl)phenyl)pyrrolidin-2-one (584 mg, 1.81 mmol), 5-bromo-2-chloropyridine (290 mg, 1.51 mmol), Pd(dppf)Cl$_2$ (110 mg, 0.151 mmol) and Na$_2$CO$_3$ (479 mg, 4.52 mmol) in dioxane (4 mL) and water (1 mL) was degassed and purged with N$_2$ for 3 times. And the resulting reaction mixture was stirred at 100° C. for 4 hours under N$_2$ atmosphere. A black suspension was formed. LCMS the purity of the desired product is 34% (Rt=0.896 min; MS Calcd: 308.1; MS Found: 308.9 [M+H]$^+$). The reaction mixture was diluted with water (10 mL). The aqueous layer was extracted with EtOAc (30 mL×3). The combined organic layer was washed with water (20 mL×2), brine (40 mL), dried over anhydrous Na$_2$SO$_4$, filtered and concentrated under reduced pressure. The residue was purified by Combi Flash (20% to 60% EtOAc in PE) to give 1-(4-(6-chloropyridin-3-yl)-2,6-difluorophenyl)pyrrolidin-2-one (300 mg, yield: 64% for 2 steps) as a light yellow solid $^1$H NMR (400 MHz, CDCl$_3$) δ 2.25-2.35 (2H, m), 2.60 (2H, t, J=8.2 Hz), 3.81 (2H, t, J=7.0 Hz), 7.17 (2H, d, J=8.4 Hz), 7.41-7.46 (1H, m), 7.75-7.82 (1H, m), 8.53-8.60 (1H, m).

Step 5: Preparation of (S)-2-((5-(3,5-difluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

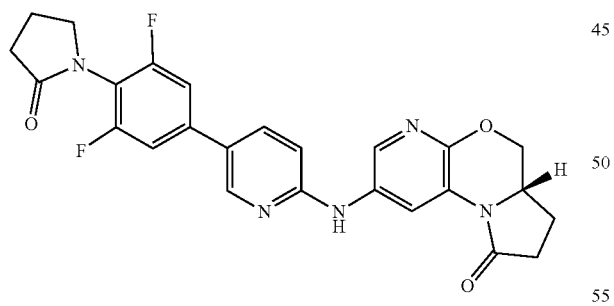

A mixture of 1-(4-(6-chloropyridin-3-yl)-2,6-difluorophenyl)pyrrolidin-2-one (50 mg, 0.16 mmol), (S)-2-amino-6,6a,7,8-tetrahydro-9H-pyrido[2,3-b]pyrrolo[1,2-d][1,4]oxazin-9-one (33 mg, 0.16 mmol), Pd$_2$(dba)$_3$ (15 mg, 0.016 mmol), Brettphos (17 mg, 0.032 mmol) and Cs$_2$CO$_3$ (106 mg, 0.324 mmol) in anhydrous dioxane (3 mL) was degassed and purged with N$_2$ for 3 times. And the resulting mixture was stirred at 90° C. for 16 hours under N$_2$ atmosphere. A yellow suspension was formed. LCMS the purity of the desired product is 37% (Rt=0.744 min; MS Calcd: 477.2; MS Found: 478.0 [M+H]$^+$). The reaction mixture was diluted with water (10 mL). The aqueous layer was extracted with EtOAc (30 mL×3). The combined organic layer was washed with water (20 mL×2), brine (40 mL), dried over anhydrous Na$_2$SO$_4$, filtered and concentrated under reduced pressure. The residue was purified by prep-HPLC (0.225% FA as an additive) and further triturated with MeCN (3 mL) to give (S)-2-((5-(3,5-difluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one (15.1 mg, yield: 19%) as a light yellow solid.
$^1$H NMR (400 MHz, DMSO-d$_6$) δ 1.66-1.77 (1H, m), 2.16-2.27 (3H, m), 2.33-2.43 (1H, m), 2.45-2.50 (2H, m), 2.63-2.73 (1H, m), 3.71 (2H, t, J=7.0 Hz), 3.91 (1H, t, J=10.4 Hz), 4.04-4.11 (1H, m), 4.59 (1H, dd, J=10.8 Hz, 2.4 Hz), 6.88 (1H, d, J=8.8 Hz), 7.59 (2H, d, J=9.4 Hz), 7.99 (1H, dd, J=8.8 Hz, 2.4 Hz), 8.45 (1H, d, J=2.2 Hz), 8.57 (1H, d, J=2.0 Hz), 8.96 (1H, d, J=2.2 Hz), 9.38 (1H, brs).

Example 185: (S)-2-((5-(2,5-difluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

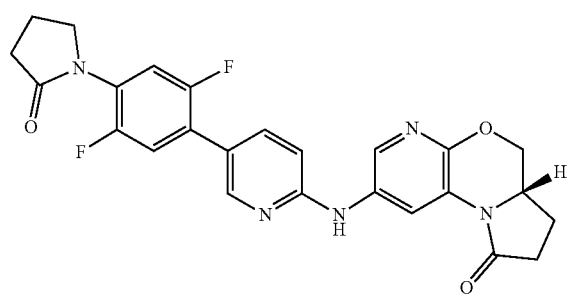 [SMILES: O=C1CCCN1c1cc(F)c(-c2ccc(Nc3cnc4c(c3)N3C(=O)CC[C@H]3CO4)nc2)cc1F]

Step 1: Preparation of 1-(4-(6-chloropyridin-3-yl)-2,5-difluorophenyl)pyrrolidin-2-one

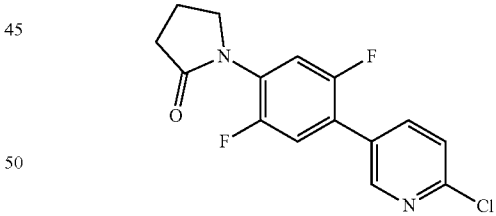

A mixture of 1-(2,5-difluoro-4-(4,4,5,5-tetramethyl-1,3,2-dioxaborolan-2-yl)phenyl)pyrrolidin-2-one (806 mg, 2.49 mmol), 5-bromo-2-chloropyridine (400 mg, 2.08 mmol), Pd(dppf)Cl$_2$ (152 mg, 0.208 mmol) and Na$_2$CO$_3$ (661 mg, 6.24 mmol) in dioxane (4 mL) and water (1 mL) was degassed and purged with N$_2$ for 3 times. And the resulting mixture was stirred at 100° C. for 4 hours under N$_2$ atmosphere. A black suspension was formed. LCMS the purity of the desired product is 51% (Rt=0.840 min; MS Calcd: 308.1; MS Found: 308.9[M+H]$^+$). The reaction mixture was diluted with water (10 mL). The aqueous layer was extracted with EtOAc (30 mL×3). The combined organic layer was washed with water (20 mL×2), brine (40 mL), dried over anhydrous Na$_2$SO$_4$, filtered and concentrated under reduced pressure. The residue was purified by Combi Flash (20% to 60% EtOAc in PE) to give 1-(4-(6-chloropyridin-3-yl)-2,5-difluorophenyl)pyrrolidin-2-one (600 mg, yield: 94%) as a light yellow solid.

$^1$H NMR (400 MHz, CDCl$_3$) δ 2.20-2.29 (2H, m), 2.60 (2H, t, J=8.0 Hz), 3.90 (2H, t, J=7.0 Hz), 7.16-7.25 (1H, m), 7.37-7.47 (2H, m), 7.81 (1H, d, J=8.2 Hz), 8.53 (1H, s).

Step 2: Preparation of (S)-2-((5-(2,5-difluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

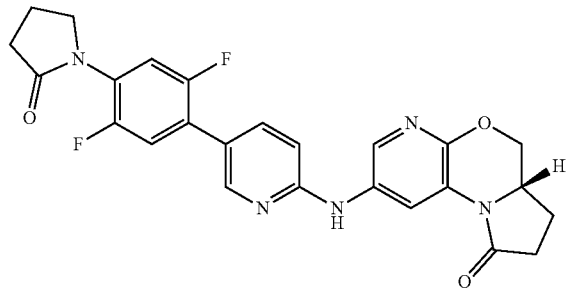 [SMILES: O=C1CCCN1c1cc(F)c(-c2ccc(Nc3cnc4c(c3)N3C(=O)CC[C@H]3CO4)nc2)cc1F]

A mixture of 1-(4-(6-chloropyridin-3-yl)-2,5-difluorophenyl)pyrrolidin-2-one (50 mg, 0.16 mmol), (S)-2-amino-6,6a,7,8-tetrahydro-9H-pyrido[2,3-b]pyrrolo[1,2-d][1,4]oxazin-9-one (33 mg, 0.16 mmol), Pd$_2$(dba)$_3$ (15 mg, 0.016 mmol), Brettphos (17 mg, 0.032 mmol) and Cs$_2$CO$_3$ (106 mg, 0.324 mmol) in anhydrous dioxane (3 mL) was degassed and purged with N$_2$ for 3 times. And the resulting mixture was stirred at 90° C. for 16 hours under N$_2$ atmosphere. A yellow suspension was formed. LCMS the purity of the desired product is 37% (Rt=0.744 min; MS Calcd: 477.2; MS Found: 478.1[M+H]$^+$). The reaction mixture was diluted with water (10 mL). The aqueous layer was extracted with EtOAc (30 mL×3). The combined organic layer was washed with water (20 mL×2), brine (40 mL), dried over anhydrous Na$_2$SO$_4$, filtered and concentrated under reduced pressure. The residue was purified by prep-HPLC (0.225% FA as an additive) and further triturated with MeCN (3 mL) to give (S)-2-((5-(2,5-difluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one (15.1 mg, yield: 19%) as a yellow solid.

$^1$H NMR (400 MHz, DMSO-d$_6$) δ 1.65-1.77 (1H, m), 2.08-2.17 (2H, m), 2.18-2.27 (1H, m), 2.33-2.43 (1H, m), 2.45-2.50 (2H, m), 2.63-2.73 (1H, m), 3.81 (2H, t, J=6.8 Hz), 3.91 (1H, t, J=10.0 Hz), 4.04-4.11 (1H, m), 4.59 (1H, dd, J=10.4 Hz, 2.4 Hz), 6.89 (1H, d, J=8.8 Hz), 7.47-7.60 (2H, m), 7.81 (1H, d, J=8.6 Hz), 8.35 (1H, s), 8.43 (1H, d, J=2.0 Hz), 8.98 (1H, d, J=2.2 Hz), 9.36 (1H, brs).

Example 186: (S)-2-((5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one

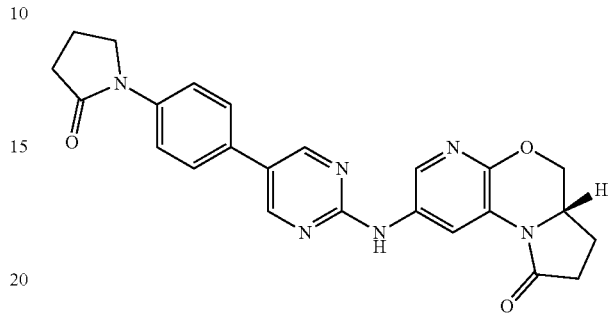

Step 1: Preparation of 1-(4-(2-chloropyrimidin-5-yl)phenyl)pyrrolidin-2-one

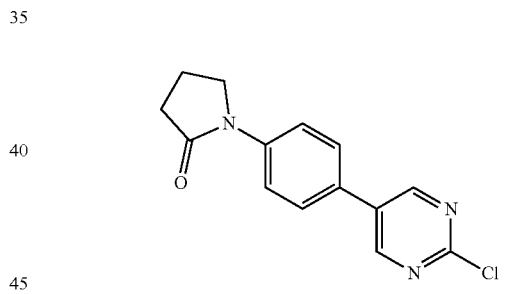

1-(4-(4,4,5,5-tetramethyl-1,3,2-dioxaborolan-2-yl)phenyl)pyrrolidin-2-one (965 mg, 3.36 mmol), 5-bromo-2-chloropyrimidine (500 mg, 2.58 mmol), K$_3$PO$_4$ (1.65 g, 7.75 mmol) and Pd(dppf)Cl$_2$ (75 mg, 0.10 mmol) were taken up in dioxane (15 mL) and H$_2$O (3 mL) and the resulting mixture was stirred at 80° C. for 4 hours. A black solution was formed. LCMS showed the purity of the desired product is 52% (Rt=0.730 min; MS Calcd: 273.1; MS Found: 273.9 [M+H]$^+$). TLC showed the starting material was consumed nearly. The mixture was concentrated under reduced pressure. The residue was purified by Combi Flash (70% EA in PE) to give 1-(4-(2-chloropyrimidin-5-yl)phenyl)pyrrolidin-2-one (500 mg, yield: 71%) as a white solid.

$^1$H NMR (400 MHz, CDCl$_3$) δ 2.18-2.25 (2H, m), 2.66 (2H, t, J=8.0 Hz), 3.92 (2H, t, J=7.2 Hz), 7.56 (2H, d, J=8.8 Hz), 7.81 (2H, d, J=9.2 Hz), 8.81 (2H, s).

Step 2: Preparation of (S)-2-((5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one

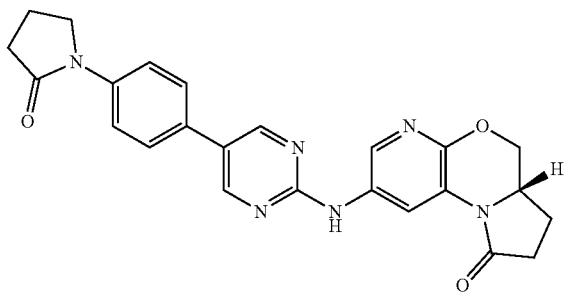 [SMILES: O=C1CCCN1c1ccc(-c2cnc(Nc3cnc4c(c3)N3C(=O)CC[C@H]3CO4)nc2)cc1]

A mixture of (S)-2-amino-6,6a,7,8-tetrahydro-9H-pyrido[2,3-b]pyrrolo[1,2-d][1,4]oxazin-9-one (33 mg, 0.16 mmol), 1-(4-(2-chloropyrimidin-5-yl)phenyl)pyrrolidin-2-one (40 mg, 0.15 mmol) and con. HCl (43 mg, 42 uL) in EtOH (3 mL) was stirred at 80° C. for 16 hours. The yellow solution turned to suspension. LCMS showed that the purity of the desired product is 34% (Rt=0.776 min; MS Calcd: 442.2; MS Found: 443.0 [M+H]+). The reaction mixture was filtered and washed with MeCN (10 mL) to give (S)-2-((5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one (17.4 mg, yield: 27%) as a yellow solid.

$^1$H NMR (400 MHz, DMSO-$d_6$) δ 1.67-1.76 (1H, m), 2.04-2.11 (2H, m), 2.20-2.25 (1H, m), 2.35-2.39 (1H, m), 2.54 (2H, overlapped with DMSO), 2.62-2.72 (1H, m), 3.85-3.96 (3H, m), 4.02-4.10 (1H, m), 4.59 (1H, dd, J=10.4, 3.2 Hz), 7.70-7.78 (4H, m), 8.29 (1H, d, J=2.4 Hz), 8.80 (2H, s), 9.12 (1H, d, J=2.8 Hz), 9.79 (1H, brs).

Example 187: (S)-2-((5-(3-fluoro-4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one

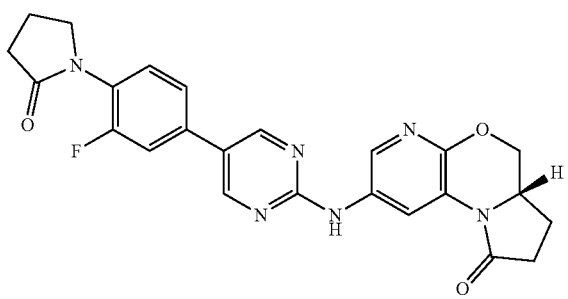 [SMILES: O=C1CCCN1c1ccc(-c2cnc(Nc3cnc4c(c3)N3C(=O)CC[C@H]3CO4)nc2)cc1F]

Step 1: Preparation of 1-(4-(2-chloropyrimidin-5-yl)-2-fluorophenyl)pyrrolidin-2-one 1-(2-fluoro-4-(4,4,5,5-tetramethyl-1,3,2-dioxaborolan-2-yl)phenyl)pyrrolidin-2-one (1.02 g, 3.35 mmol), 5-bromo-2-chloropyrimidine (500 mg, 2.58 mmol), $K_3PO_4$ (1.64 g, 7.74 mmol) and Pd(dppf)$Cl_2$ (75 mg, 0.10 mmol) were taken up in dioxane (15 mL) and $H_2O$ (3 mL) and the resulting mixture was stirred at 80° C. for 4 hours. A black solution was formed. LCMS showed the purity of the desired product is 54% (Rt=0.754 min; MS Calcd: 291.1; MS Found: 291.9 [M+H]+). TLC showed the starting material was consumed nearly. The mixture was concentrated under reduced pressure. The residue was purified by Combi Flash (70% EA in PE) to give 1-(4-(2-chloropyrimidin-5-yl)-2-fluorophenyl)pyrrolidin-2-one (330 mg, yield: 44%) as a light yellow solid.

$^1$H NMR (400 MHz, CDCl$_3$) δ 2.20-2.30 (2H, m), 2.61 (2H, t, J=8.0 Hz), 3.90 (2H, t, J=7.2 Hz), 7.33-7.39 (2H, m), 7.62-7.67 (1H, m), 8.80 (2H, s).

Step 2: Preparation of (S)-2-((5-(3-fluoro-4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one A mixture of (S)-2-amino-6,6a,7,8-tetrahydro-9H-pyrido[2,3-b]pyrrolo[1,2-d][1,4]oxazin-9-one (50 mg, 0.24 mmol), 1-(4-(2-chloropyrimidin-5-yl)-2-fluorophenyl)pyrrolidin-2-one (71 mg, 0.24 mmol) and con. HCl (72 mg, 73 uL) in EtOH (5 mL) was stirred at 80° C. for 16 hours. The yellow solution turned yellow suspension. LCMS showed that the purity of the desired product is 77% (Rt=0.602 min; MS Calcd: 460.2; MS Found: 460.9 [M+H]+). The reaction mixture was added Et$_3$N (1 mL) and concentrated. The residue was diluted with DMF (4 mL) and standing for 2 hours. The mixture was filtered and washed with MeCN (10 mL) to give (S)-2-((5-(3-fluoro-4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one (14.8 mg, yield: 13%) as a yellow solid. The filtrate was purified by prep-HPLC (0.05% NH₃·H₂O as an additive) and lyophilized to give (S)-2-((5-(3-fluoro-4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one (8.4 mg, yield: 7%) as a white solid.

¹H NMR (400 MHz, DMSO-d₆) δ 1.65-1.76 (1H, m), 2.07-2.17 (2H, m), 2.20-2.24 (1H, m), 2.35-2.42 (1H, m), 2.45 (2H, t, J=8.0 Hz), 2.64-2.72 (1H, m), 3.78 (2H, t, J=7.2 Hz), 3.91 (1H, t, J=10.4 Hz), 4.03-4.11 (1H, m), 4.59 (1H, dd, J=10.8, 3.2 Hz), 7.52 (1H, t, J=8.4 Hz), 7.60 (1H, dd, J=8.4, 2.0 Hz), 7.72 (1H, dd, J=12.4, 2.0 Hz), 8.28 (1H, d, J=2.4 Hz), 8.85 (2H, s), 9.11 (1H, d, J=2.8 Hz), 9.86 (1H, brs).

Example 188: (S)-2-((6-amino-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

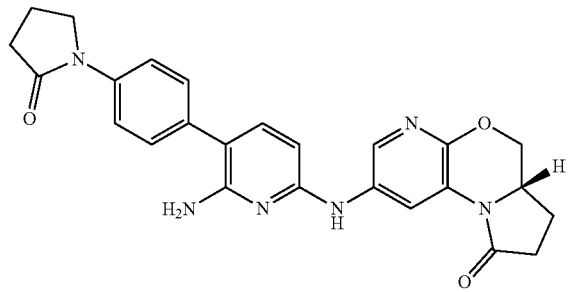 [SMILES: Nc1nc(Nc2cnc3c(c2)N2C(=O)CC[C@H]2CO3)ccc1-c1ccc(N2CCCC2=O)cc1]

Step 1: Preparation of 1-(4-(2-amino-6-chloropyridin-3-yl)phenyl)pyrrolidin-2-one

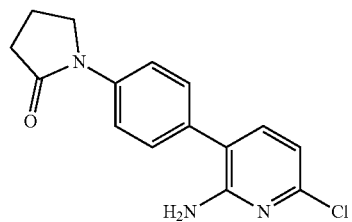 [SMILES: Nc1nc(Cl)ccc1-c1ccc(N2CCCC2=O)cc1]

1-(4-(4,4,5,5-tetramethyl-1,3,2-dioxaborolan-2-yl)phenyl)pyrrolidin-2-one (900 mg, 3.13 mmol), 3-bromo-6-chloropyridin-2-amine (500 mg, 2.41 mmol), K₃PO₄ (1.53 g, 7.23 mmol) and Pd(dppf)Cl₂ (70 mg, 0.096 mmol) were taken up in dioxane (15 mL) and H₂O (3 mL). The resulting mixture was stirred at 80° C. for 4 hours. A black solution was formed. LCMS showed the purity of the desired product is 48% (Rt=0.715 min; MS Calcd: 287.1; MS Found: 287.8 [M+H]⁺). TLC showed the starting material was remained. The mixture was concentrated under reduced pressure. The residue was purified by Combi Flash (90% EA in PE) to give impure product (240 mg) as a yellow solid, then triturated with EA:PE=1:1 (10 mL) for 1 hour to give 1-(4-(2-amino-6-chloropyridin-3-yl)phenyl)pyrrolidin-2-one (121 mg, yield: 17%) as a light yellow solid.

¹H NMR (400 MHz, CDCl₃) δ 2.15-2.23 (2H, m), 2.64 (2H, t, J=8.0 Hz), 3.91 (2H, t, J=7.2 Hz), 4.58 (2H, brs), 6.48 (2H, d, J=8.0 Hz), 7.42 (2H, dd, J=8.8, 2.0 Hz), 7.67 (2H, d, J=8.8 Hz).

Step 2: Preparation of (S)-2-((6-amino-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

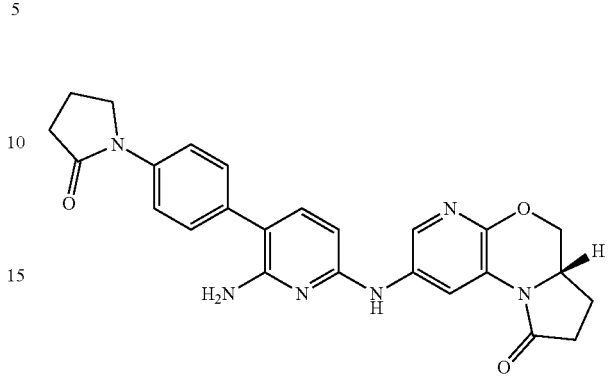

A mixture of Pd₂(dba)₃ (22 mg, 0.024 mmol) and Brettphos (26 mg, 0.048 mmol) in 1,4-dioxane (1 mL) was stirred at 50° C. for 10 min. (S)-2-amino-6,6a,7,8-tetrahydro-9H-pyrido[2,3-b]pyrrolo[1,2-d][1,4]oxazin-9-one (50 mg, 0.243 mmol), 1-(4-(2-amino-6-chloropyridin-3-yl)phenyl)pyrrolidin-2-one (77 mg, 0.27 mmol) in dioxane (5 mL) and Cs₂CO₃ (198 mg, 0.609 mmol) were added and the resulting mixture was stirred at 100° C. for 12 hours. A black brown mixture was formed. LCMS showed that 1-(4-(2-amino-6-chloropyridin-3-yl)phenyl)pyrrolidin-2-one was consumed completely. The reaction mixture was concentrated. The residue was purified by Combi Flash (8% MeOH in DCM) to give impure product (70 mg) as a yellow gum, then purified by prep-HPLC (0.225% FA as an additive) and lyophilized to give (S)-2-((6-amino-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one (2.67 mg, yield: 2%) as a yellow solid.

¹H NMR (400 MHz, DMSO-d₆) δ 1.61-1.70 (1H, m), 2.01-2.13 (2H, m), 2.16-2.25 (1H, m), 2.35-2.40 (1H, m), 2.58-2.63 (3H, m), 3.81-3.88 (3H, m), 3.98-4.03 (1H, m), 4.52-4.57 (1H, m), 5.68 (2H, brs), 6.03 (1H, d, J=7.6 Hz), 7.17 (1H, d, J=8.0 Hz), 7.38 (2H, d, J=8.4 Hz), 7.55 (1H, s), 7.68 (2H, d, J=8.4 Hz), 8.17 (1H, s), 8.81 (1H, brs).

Example 189: (S)-2-((6-(4-(2-oxopyrrolidin-1-yl)phenyl)pyridazin-3-yl)amino)-6,6a,7,8-tetrahydro-9H-pyrido[2,3-b]pyrrolo[1,2-d][1,4]oxazin-9-one

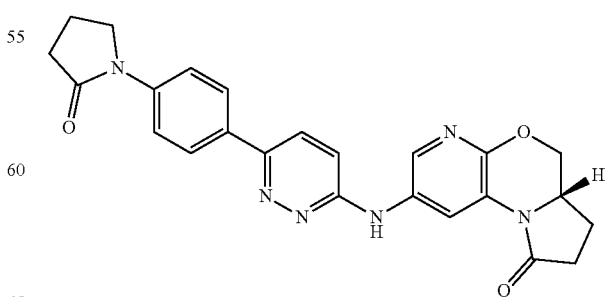

Step 1: Preparation of 1-(4-(6-chloropyridazin-3-yl)phenyl)pyrrolidin-2-one

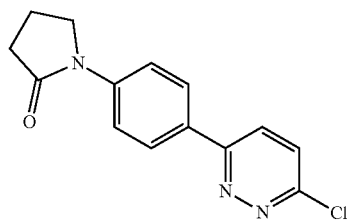 [SMILES: O=C1CCCN1c1ccc(-c2ccc(Cl)nn2)cc1]

1-(4-(4,4,5,5-tetramethyl-1,3,2-dioxaborolan-2-yl)phenyl)pyrrolidin-2-one (1.25 g, 4.36 mmol), 3,6-dichloropyridazine (500 mg, 3.36 mmol), $K_3PO_4$ (2.14 g, 10.1 mmol) and Pd(dppf)Cl$_2$ (98 mg, 0.13 mmol) were taken up in dioxane (15 mL) and H$_2$O (3 mL) and the resulting mixture was stirred at 80° C. for 4 hours. A black solution was formed. LCMS showed the purity of the desired product is 34% (Rt=0.715 min; MS Calcd: 273.1; MS Found: 273.8 [M+H]$^+$). TLC showed the starting material was consumed completely. The mixture was concentrated under reduced pressure. The residue was purified by Combi Flash (EA) to give impure product as a yellow solid, then triturated with CH$_3$CN (4 mL) for 2 hours to give 1-(4-(6-chloropyridazin-3-yl)phenyl)pyrrolidin-2-one (122 mg, yield: 13%) as a white solid.

$^1$H NMR (400 MHz, CDCl$_3$) δ 2.18-2.26 (2H, m), 2.67 (2H, t, J=7.6 Hz), 3.94 (2H, t, J=7.2 Hz), 7.55 (1H, d, J=8.8 Hz), 7.80-7.85 (3H, m), 8.08 (2H, d, J=8.8 Hz).

Step 2: Preparation of (S)-2-((6-(4-(2-oxopyrrolidin-1-yl)phenyl)pyridazin-3-yl)amino)-6,6a,7,8-tetrahydro-9H-pyrido[2,3-b]pyrrolo[1,2-d][1,4]oxazin-9-one

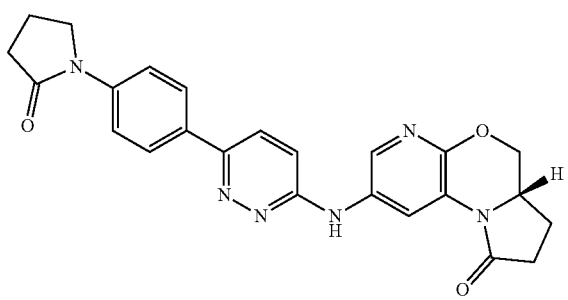 [SMILES: O=C1CCCN1c1ccc(-c2ccc(Nc3cnc4c(c3)N3C(=O)CC[C@H]3CO4)nn2)cc1]

A mixture of (S)-2-amino-6,6a,7,8-tetrahydro-9H-pyrido[2,3-b]pyrrolo[1,2-d][1,4]oxazin-9-one (30 mg, 0.15 mmol) and 1-(4-(6-chloropyridazin-3-yl)phenyl)pyrrolidin-2-one (40 mg, 0.15 mmol) in EtOH (3 mL) was stirred at 80° C. for 16 hours. A red solution was formed. LCMS showed the starting material was not consumed. The red solution was added HCl (43 mg, 44 uL). And the mixture was stirred at 80° C. for 16 hours. LCMS showed that the purity of the desired product is 66% (Rt=0.642 min; MS Calcd: 442.2; MS Found: 442.9 [M+H]). The reaction mixture was filtered and washed with MeCN (10 mL) to give (S)-2-((6-(4-(2-oxopyrrolidin-1-yl)phenyl)pyridazin-3-yl)amino)-6,6a,7,8-tetrahydro-9H-pyrido[2,3-b]pyrrolo[1,2-d][1,4]oxazin-9-one (19.0 mg, yield: 29%) as a yellow solid.

$^1$H NMR (400 MHz, DMSO-d$_6$) δ 1.66-1.75 (1H, m), 2.04-2.13 (2H, m), 2.21-2.25 (1H, m), 2.37-2.45 (1H, m), 2.57 (2H, overlapped with DMSO), 2.67-2.72 (1H, m), 3.87-3.97 (3H, m), 4.05-4.11 (1H, m), 4.63 (1H, dd, J=10.8, 3.2 Hz), 7.41 (1H, d, J=9.6 Hz), 7.84 (2H, d, J=8.8 Hz), 8.04 (2H, d, J=8.8 Hz), 8.19 (1H, d, J=9.2 Hz), 8.42 (1H, d, J=2.8 Hz), 8.96 (1H, d, J=2.4 Hz), 9.97 (1H, brs).

Example 190: (S)-2-((6-methyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

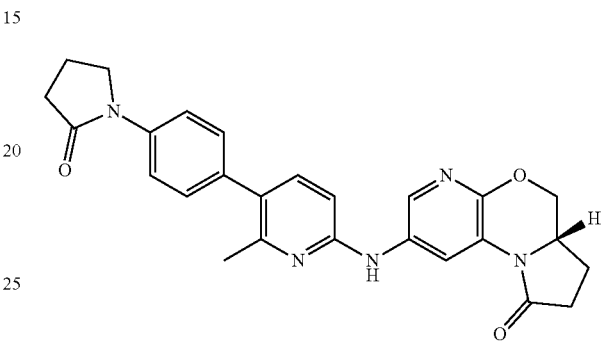

Step 1: Preparation of 1-(4-(6-chloro-2-methylpyridin-3-yl)phenyl)pyrrolidin-2-one

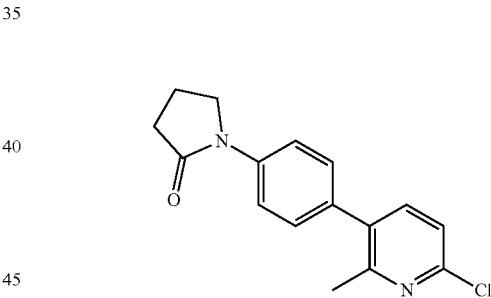

1-(4-(4,4,5,5-tetramethyl-1,3,2-dioxaborolan-2-yl)phenyl)pyrrolidin-2-one (904 mg, 3.15 mmol), 3-bromo-6-chloro-2-methylpyridine (500 mg, 2.42 mmol), $K_3PO_4$ (1.54 g, 7.27 mmol) and Pd(dppf)Cl$_2$ (71 mg, 0.097 mmol) were taken up in dioxane (15 mL) and H$_2$O (3 mL) and the resulting mixture was stirred at 80° C. for 4 hours. A black solution was formed. LCMS showed the purity of the desired product is 78% (Rt=0.792 min; MS Calcd: 286.1; MS Found: 286.8 [M+H]$^+$). TLC showed the starting material was consumed completely. The mixture was concentrated under reduced pressure. The residue was purified by Combi Flash (48% EA in PE) to give 1-(4-(6-chloro-2-methylpyridin-3-yl)phenyl)pyrrolidin-2-one (500 mg, yield: 72%) as a light yellow solid.

$^1$H NMR (400 MHz, CDCl$_3$) δ 2.16-2.25 (2H, m), 2.48 (3H, s), 2.65 (2H, t, J=8.0 Hz), 3.91 (2H, t, J=7.2 Hz), 7.20 (1H, d, J=8.0 Hz), 7.30 (2H, d, J=8.8 Hz), 7.46 (1H, d, J=8.4 Hz), 7.71 (2H, d, J=8.8 Hz).

Step 2: Preparation of (S)-2-((6-methyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

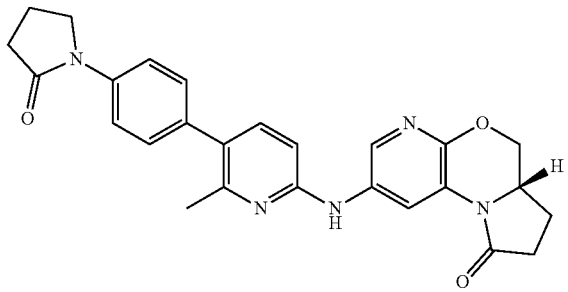 [SMILES: Cc1nc(Nc2cnc3c(c2)N2C(=O)CC[C@H]2CO3)ccc1-c1ccc(N2CCCC2=O)cc1]

A mixture of Pd$_2$(dba)$_3$ (22 mg, 0.024 mmol) and Brettphos (26 mg, 0.048 mmol) in 1,4-dioxane (1 mL) was stirred at 50° C. for 10 min. (S)-2-amino-6,6a,7,8-tetrahydro-9H-pyrido[2,3-b]pyrrolo[1,2-d][1,4]oxazin-9-one (50 mg, 0.24 mmol), 1-(4-(6-chloro-2-methylpyridin-3-yl)phenyl)pyrrolidin-2-one (77 mg, 0.27 mmol) in dioxane (5 mL) and Cs$_2$CO$_3$ (198 mg, 0.609 mmol) were added and the resulting mixture was stirred at 100° C. for 14 hours. A black brown mixture was formed. LCMS showed that the purity of the desired product is 57% (Rt=0.667 min; MS Calcd: 455.2; MS Found: 456.0 [M+H]$^+$). The reaction mixture was diluted with DCM (10 mL), filtered and concentrated. The residue was purified by prep-HPLC (0.05% NH$_3$.H$_2$O as an additive) and lyophilized to give (S)-2-((6-methyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one (24.8 mg, yield: 22%) as a white solid.

$^1$H NMR (400 MHz, DMSO-d$_6$) δ 1.63-1.75 (1H, m), 2.04-2.12 (2H, m), 2.17-2.25 (1H, m), 2.35-2.42 (4H, m), 2.53 (2H, overlapped with DMSO), 2.60-2.73 (1H, m), 3.85-3.91 (3H, m), 4.02-4.10 (1H, m), 4.57 (1H, dd, J=10.8, 2.8 Hz), 6.70 (1H, d, J=8.4 Hz), 7.35 (2H, d, J=8.4 Hz), 7.41 (1H, d, J=8.8 Hz), 7.71 (2H, d, J=8.8 Hz), 8.33 (1H, d, J=2.4 Hz), 9.13 (1H, brs), 9.31 (1H, d, J=2.4 Hz).

Example 191: (S)-2-((5-(2-fluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

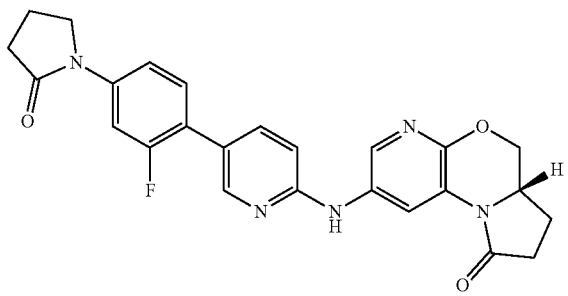 [SMILES: O=C1CCCN1c1ccc(-c2ccc(Nc3cnc4c(c3)N3C(=O)CC[C@H]3CO4)nc2)c(F)c1]

Step 1: Preparation of 1-(4-(6-chloropyridin-3-yl)-3-fluorophenyl)pyrrolidin-2-one

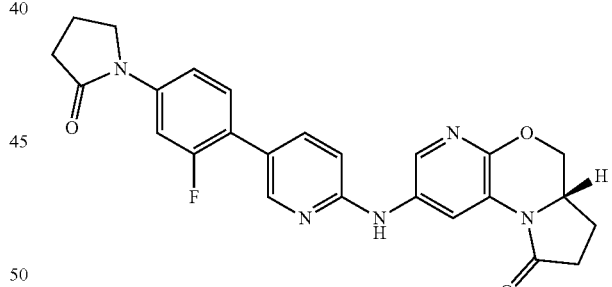

1-(3-fluoro-4-(4,4,5,5-tetramethyl-1,3,2-dioxaborolan-2-yl)phenyl)pyrrolidin-2-one (1.03 g, 3.38 mmol), 5-bromo-2-chloropyridine (500 mg, 2.60 mmol), K$_3$PO$_4$ (1.65 g, 7.79 mmol) and Pd(dppf)Cl$_2$ (76 mg, 0.10 mmol) were taken up in dioxane (15 mL) and H$_2$O (3 mL) and the resulting mixture was stirred at 80° C. for 4 hours. A black solution was formed. LCMS showed the purity of the desired product is 40% (Rt=0.784 min; MS Calcd: 290.1; MS Found: 290.8 [M+H]$^+$). TLC showed the starting material was consumed completely. The mixture was concentrated under reduced pressure. The residue was purified by Combi Flash (59% EA in PE) to give 1-(4-(6-chloropyridin-3-yl)-3-fluorophenyl)pyrrolidin-2-one (240 mg, yield: 32%) as a white solid.

$^1$H NMR (400 MHz, CDCl$_3$) δ 2.15-2.25 (2H, m), 2.66 (2H, t, J=8.0 Hz), 3.89 (2H, t, J=7.6 Hz), 7.38-7.43 (2H, m), 7.46-7.50 (1H, m), 7.69 (1H, d, J=13.6 Hz), 7.83 (1H, d, J=8.8 Hz), 8.55 (1H, s).

Step 2: Preparation of (S)-2-((5-(2-fluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one A mixture of Pd$_2$(dba)$_3$ (22 mg, 0.024 mmol) and Brettphos (26 mg, 0.048 mmol) in 1,4-dioxane (1 mL) was stirred at 50° C. for 10 min. (S)-2-amino-6,6a,7,8-tetrahydro-9H-pyrido[2,3-b]pyrrolo[1,2-d][1,4]oxazin-9-one (50 mg, 0.24 mmol), 1-(4-(6-chloropyridin-3-yl)-3-fluorophenyl)pyrrolidin-2-one (78 mg, 0.27 mmol) in dioxane (5 mL) and Cs$_2$CO$_3$ (198 mg, 0.609 mmol) were added and the resulting mixture was stirred at 100° C. for 14 hours. A black brown mixture was formed. LCMS showed that the purity of the desired product is 53% (Rt=0.673 min; MS Calcd: 459.2; MS Found: 460.0 [M+H]$^+$). The reaction mixture was diluted with DCM (10 mL), filtered and concentrated. The residue was purified by prep-HPLC (0.05% NH$_3$.H$_2$O as an additive) and lyophilized to give (S)-2-((5-(2-fluoro-4-(2-oxopyrrolidin-1-yl)phenyl)pyridin-2-yl)amino)-6,6a,7,8- tetrahydro-9H-pyrido[2,3-b]pyrrolo[1,2-d][1,4]oxazin-9-one (24.8 mg, yield: 22%) as a white solid.

$^1$H NMR (400 MHz, DMSO-$d_6$) δ 1.65-1.72 (1H, m), 2.03-2.11 (2H, m), 2.17-2.22 (1H, m), 2.34-2.42 (1H, m), 2.55 (2H, overlapped with DMSO), 2.63-2.71 (1H, m), 3.84-3.92 (3H, m), 4.02-4.10 (1H, m), 4.58 (1H, dd, J=10.8, 3.2 Hz), 6.87 (1H, d, J=8.8 Hz), 7.48-7.57 (2H, m), 7.72-7.78 (2H, m), 8.30 (1H, s), 8.40 (1H, d, J=2.4 Hz), 8.98 (1H, d, J=2.8 Hz), 9.27 (1H, brs).

Example 192: (S)-2-((5-(2-methyl-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

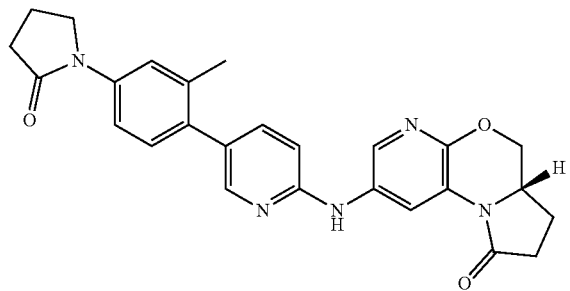 [SMILES: Cc1cc(N2CCCC2=O)ccc1-c1ccc(Nc2cnc3c(c2)N2C(=O)CC[C@H]2CO3)nc1]

Step 1: Preparation of 1-(4-bromo-3-methylphenyl)pyrrolidin-2-one

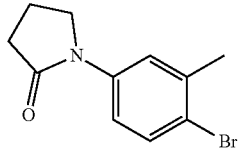

To a mixture of 4-bromo-3-methylaniline (3.20 g, 17.2 mmol), TEA (1.83 g, 18.1 mmol) in THF (50 mL) was added 4-chlorobutanoyl chloride (2.47 g, 17.5 mmol) dropwise at 0° C. and stirred for 0.5 hour, the brown solution was turned into an off-white suspension. TLC (plate 1, PE/EtOAc=5:1) showed the reaction was completed. Then added t-BuOK (4.82 g, 43.0 mmol) in portions at 0° C., then warmed to 15° C. and stirred for another 2.5 hours to give a brown suspension. TLC (plate 2, PE/EtOAc=3/1) showed the reaction was completed. The mixture was quenched with sat.NH$_4$Cl (40 mL) and then extracted with EtOAc (30 mL×2). The combined extracts were washed with brine (35 mL×2), dried over Na$_2$SO$_4$, filtered and concentrated under reduced pressure to give a residue. The residue was washed with PE (40 mL) to give 1-(4-bromo-3-methylphenyl)pyrrolidin-2-one (4.3 g, yield: 98%) as an off-white solid.

$^1$H NMR (400 MHz, DMSO-$d_6$) δ 2.02-2.12 (2H, m), 2.34 (3H, s), 2.48-2.51 (2H, m), 3.81 (2H, t, J=6.8 Hz), 7.50 (1H, dd, J=8.8, 2.4 Hz), 7.55 (1H, d, J=8.8 Hz), 7.62 (1H, d, J=2.4 Hz).

Step 2: Preparation of 1-(3-methyl-4-(4,4,5,5-tetramethyl-1,3,2-dioxaborolan-2-yl)phenyl)pyrrolidin-2-one

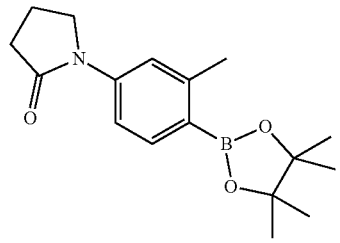 [SMILES: Cc1cc(N2CCCC2=O)ccc1B1OC(C)(C)C(C)(C)O1]

To a mixture of 1-(4-bromo-3-methylphenyl)pyrrolidin-2-one (2.50 g, 9.84 mmol), Bispin (3.75 g, 14.8 mmol), Pd(dppf)Cl$_2$ (720 mg, 0.984 mmol) in dioxane (60 mL) was added KOAc (2.90 g, 29.5 mmol), the resulting mixture was stirred at 90° C. under N$_2$ atmosphere for 4 hours to give a brown suspension. LCMS showed the purity of the desired product is 78% (Rt=1.837 min; MS Calcd: 301.2; MS Found: 301.9 [M+H]$^+$). The mixture was filtered. The filtrate was concentrated under reduced pressure to give 1-(3-methyl-4-(4,4,5,5-tetramethyl-1,3,2-dioxaborolan-2-yl)phenyl)pyrrolidin-2-one (2.96 g, crude) as a brown solid.

Step 3: Preparation of 1-(4-(6-chloropyridin-3-yl)-3-methylphenyl)pyrrolidin-2-one

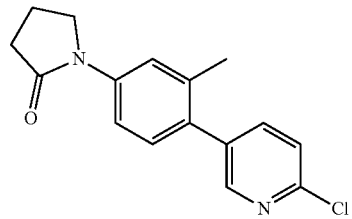 [SMILES: Cc1cc(N2CCCC2=O)ccc1-c1ccc(Cl)nc1]

To a mixture of 1-(3-methyl-4-(4,4,5,5-tetramethyl-1,3,2-dioxaborolan-2-yl)phenyl)pyrrolidin-2-one (689 mg, 2.29 mmol), 5-bromo-2-chloro-pyridine (400 mg, 2.08 mmol), Pd(dppf)Cl$_2$ (152 mg, 0.208 mmol) in dioxane (12 mL) was added Na$_2$CO$_3$ (441 mg, 4.16 mmol) and H$_2$O (2 mL), the resulting mixture was stirred at 90° C. under N$_2$ atmosphere for 4 hours to give a brown suspension. LCMS showed the purity of the desired product is 37% (Rt=0.821 min; MS Calcd: 286.1; MS Found: 286.9 [M+H]$^+$). The mixture was diluted with water (30 mL) and extracted with EtOAc (35 mL×2). The combined extracts were washed with brine (35 mL×2), dried over Na$_2$SO$_4$, filtered and concentrated under reduced pressure to give a residue. The residue was purified by Combi Flash (PE/EtOAc=6/1 to 3/1 to 3/2) to give 1-(4-(6-chloropyridin-3-yl)-3-methylphenyl)pyrrolidin-2-one (300 mg, yield: 41%) as a yellow solid.

$^1$H NMR (400 MHz, DMSO-$d_6$) δ 2.02-2.12 (2H, m), 2.26 (3H, s), 2.48-2.51 (2H, m), 3.87 (2H, t, J=6.8 Hz), 7.28 (1H, d, J=8.0 Hz), 7.58-7.65 (3H, m), 7.89 (1H, dd, J=8.0, 2.4 Hz), 8.41 (1H, d, J=2.4 Hz).

Step 4: Preparation of (S)-2-((5-(2-methyl-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

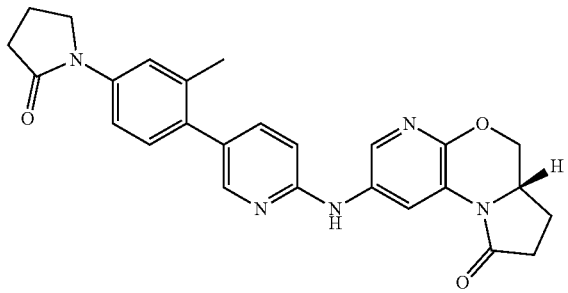 [SMILES: Cc1cc(N2CCCC2=O)ccc1-c1ccc(Nc2cnc3c(c2)N2C(=O)CC[C@H]2CO3)nc1]

To a mixture of 1-(4-(6-chloropyridin-3-yl)-3-methylphenyl)pyrrolidin-2-one (60 mg, 0.21 mmol), (S)-2-amino-6,6a,7,8-tetrahydro-9H-pyrido[2,3-b]pyrrolo[1,2-d][1,4]oxazin-9-one (39 mg, 0.19 mmol) in dioxane (5 mL) was added Brettphos (10 mg, 0.019 mmol), Cs$_2$CO$_3$ (124 mg, 0.38 mmol) and Pd$_2$(dba)$_3$ (17 mg, 0.019 mmol), the resulting mixture was purged with N$_2$ for 3 times and stirred at 50° C. for 0.5 hour, then heated to 95° C. for 15.5 hours under N$_2$ atmosphere to give a brown solution. LCMS showed the purity of desired product is 20% (Rt=1.296 min; MS Calcd: 492.2; MS Found: 456.1 [M+H]$^+$). The mixture was filtered. The filter cake was washed with DCM (10 mL×2). The filtrate was concentrated under reduced pressure to give a residue. The residue was purified by Combi Flash (DCM/MeOH=100/1 to 10/1), then further purified by prep-HPLC (0.225% FA as an additive) purification to give (S)-2-((5-(2-methyl-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one (11.5 mg, yield: 13%) as a white solid.

$^1$H NMR (400 MHz, DMSO-d$_6$) δ 1.65-1.74 (1H, m), 2.02-2.12 (2H, m), 2.18-2.25 (1H, m), 2.28 (3H, s), 2.34-2.44 (1H, m), 2.48-2.51 (2H, m), 2.61-2.72 (1H, m), 3.85 (2H, t, J=6.8 Hz), 3.86-3.92 (1H, m), 4.04-4.10 (1H, m), 4.57-4.61 (1H, m), 6.89 (1H, d, J=8.4 Hz), 7.22 (1H, d, J=8.8 Hz), 7.51-7.59 (2H, m), 7.64 (1H, dd, J=8.4, 0.8 Hz), 8.06 (1H, s), 8.42 (1H, s), 8.93 (1H, s), 9.34 (1H, brs).

Example 193: (S)-2-((4-(methoxymethyl)-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

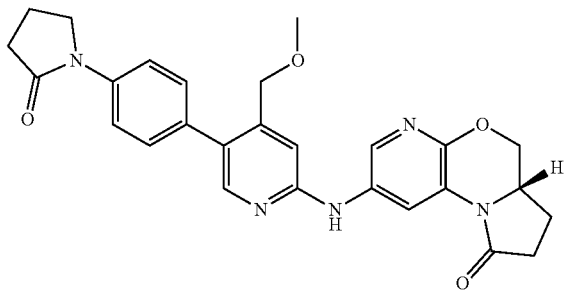 [SMILES: COCc1cc(Nc2cnc3c(c2)N2C(=O)CC[C@H]2CO3)ncc1-c1ccc(N2CCCC2=O)cc1]

Step 1: Preparation of (5-bromo-2-chloropyridin-4-yl)methanol

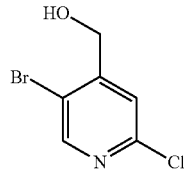

To a mixture of 5-bromo-2-chloroisonicotinaldehyde (1.00 g, 4.54 mmol) in THF (15 mL) was added NaBH$_4$ (172 mg, 4.54 mmol) in portions at 0° C., then warmed to 20° C. and stirred for 2 hours to give a yellow suspension. TLC (PE/EtOAc=3/1) showed the reaction was completed. The mixture was quenched with water (15 mL), then adjusted to pH=3-4 with HCl (1 M). The mixture was extracted with EtOAc (30 mL×2). The combined extracts were washed with brine (30 mL×2), dried over Na$_2$SO$_4$, filtered and concentrated under reduced pressure to give a residue. The residue was purified by Combi Flash (PE/EtOAc=8/1 to 6/1 to 5/1) to give (5-bromo-2-chloropyridin-4-yl)methanol (820 mg, yield: 81%) as a white solid.

$^1$H NMR (400 MHz, DMSO-d$_6$) δ 4.52 (2H, s), 5.80 (1H, brs), 7.54 (1H, s), 8.52 (1H, s).

Step 2: Preparation of 5-bromo-2-chloro-4-(methoxymethyl)pyridine

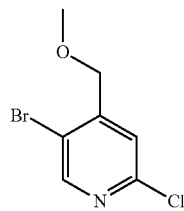

To a mixture of (5-bromo-2-chloropyridin-4-yl)methanol (350 mg, 1.57 mmol) in anhydrous THF (10 mL) was added NaH (94 mg, 2.4 mmol, 60% purity dispersed in mineral oil) in portions at 0° C. and stirred for 0.5 hour, the colorless solution turn to a brown solution, then added MeI (456 mg, 3.21 mmol) dropwise at 0° C., then warmed to 25° C. and stirred for 2.5 hours to give a pale yellow solution. TLC (PE/EtOAc=5/1) showed the reaction was completely. The mixture was quenched with ice water (10 mL), then extracted with EtOAc (20 mL×2), the combined extracts were washed with brine (25 mL×2), dried over Na$_2$SO$_4$, filtered and concentrated under reduced pressure to give a residue. The residue was purified by Combi Flash (PE/EtOAc=10/1 to 8/1) to give 5-bromo-2-chloro-4-(methoxymethyl)pyridine (260 mg, yield: 70%) as a colorless oil.

$^1$H NMR (400 MHz, DMSO-d$_6$) δ 3.43 (3H, s), 4.47 (2H, s), 7.49 (1H, s), 8.57 (1H, s).

Step 3: Preparation of 1-(4-(6-chloro-4-(methoxymethyl)pyridin-3-yl)phenyl)pyrrolidin-2-one

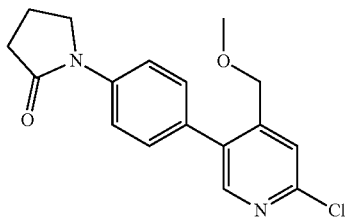 [SMILES: COCc1cc(Cl)ncc1-c1ccc(N2CCCC2=O)cc1]

To a mixture of 1-(4-(4,4,5,5-tetramethyl-1,3,2-dioxaborolan-2-yl)phenyl)pyrrolidin-2-one (300 mg, 1.04 mmol), 5-bromo-2-chloro-4-(methoxymethyl)pyridine (247 mg, 1.04 mmol), Pd(dppf)Cl$_2$ (76 mg, 0.10 mmol) in dioxane (10 mL) was added Na$_2$CO$_3$ (277 mg, 2.61 mmol) and H$_2$O (2 mL), the resulting mixture was stirred at 95° C. under N$_2$ atmosphere for 3 hours to give a brown suspension. LCMS showed the purity of desired product is 81% (Rt=0.835 min; MS Calcd: 316.1; MS Found: 317.1 [M+H]$^+$). The mixture was filtered. The filter cake was washed with EtOAc (10 mL). The filtrate was diluted with water (20 mL), then extracted with EtOAc (30 mL×2). The combined extracts were washed with brine (30 mL×2), dried over Na$_2$SO$_4$, filtered and concentrated under reduced pressure to give a residue. The residue was purified by Combi Flash (PE/EtOAc=3/1 to 1/1 to 1/2) (TLC: PE/EtOAc=1/1) to give 1-(4-(6-chloro-4-(methoxymethyl)pyridin-3-yl)phenyl)pyrrolidin-2-one (300 mg, yield: 91%) as a yellow solid.

$^1$H NMR (400 MHz, DMSO-d$_6$) δ 2.02-2.12 (2H, m), 2.48-2.51 (2H, m), 3.31 (3H, s), 3.89 (2H, t, J=6.8 Hz), 4.41 (2H, s), 7.44 (2H, d, J=8.8 Hz), 7.56 (1H, s), 7.79 (2H, d, J=8.8 Hz), 8.30 (1H, s).

Step 4: Preparation of (S)-2-((4-(methoxymethyl)-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

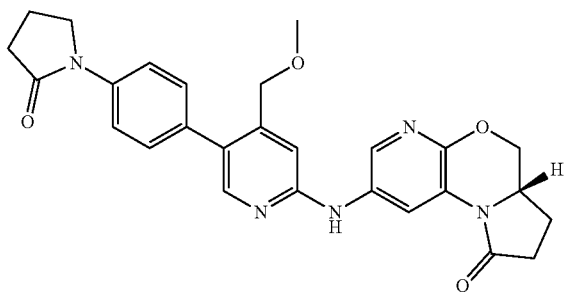 [SMILES: COCc1cc(Nc2cnc3c(c2)N2C(=O)CC[C@H]2CO3)ncc1-c1ccc(N2CCCC2=O)cc1]

To a mixture of 1-(4-(6-chloro-4-(methoxymethyl)pyridin-3-yl)phenyl)pyrrolidin-2-one (85 mg, 0.27 mmol), (S)-2-amino-6,6a,7,8-tetrahydro-9H-pyrido[2,3-b]pyrrolo[1,2-d][1,4]oxazin-9-one (50 mg, 0.24 mmol), Pd$_2$(dba)$_3$ (22 mg, 0.024 mmol), Brettphos (13 mg, 0.024 mmol) in dioxane (6 mL) was added Cs$_2$CO$_3$ (159 mg, 0.487 mmol), the resulting mixture was stirred at 50° C. under N$_2$ atmosphere for 1 hour. Then heated to 95° C. and stirred for another 3 hours under N$_2$ atmosphere to give a brown suspension. LCMS showed the purity of desired product is 33% (Rt=0.742 min; MS Calcd: 485.2; MS Found: 486.2 [M+H]$^+$). The mixture was filtered. The filter cake was washed with DCM (10 mL×2). The filtrate was concentrated under reduced pressure to give a residue. The residue was purified by Combi Flash (DCM/MeOH=100/1 to 10/1) (TLC: DCM/MeOH=15/1), then further purified by prep-HPLC (0.225% FA as an additive) to give (S)-2-((4-(methoxymethyl)-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one (15.0 mg, yield: 12%) as a pale yellow solid.

$^1$H NMR (400 MHz, DMSO-d$_6$) δ 1.65-1.74 (1H, m), 2.02-2.12 (2H, m), 2.15-2.22 (1H, m), 2.31-2.42 (1H, m), 2.48-2.51 (2H, m), 2.65-2.72 (1H, m), 3.31 (3H, s), 3.82-3.90 (3H, m), 4.00-4.10 (1H, m), 4.35 (2H, s), 4.55-4.61 (1H, m), 6.99 (1H, s), 7.36 (2H, d, J=8.8 Hz), 7.73 (2H, d, J=8.8 Hz), 7.95 (1H, s), 8.36 (1H, d, J=2.4 Hz), 8.95 (1H, d, J=2.4 Hz), 9.35 (1H, brs).

Example 194: (S)-2-((3-methyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

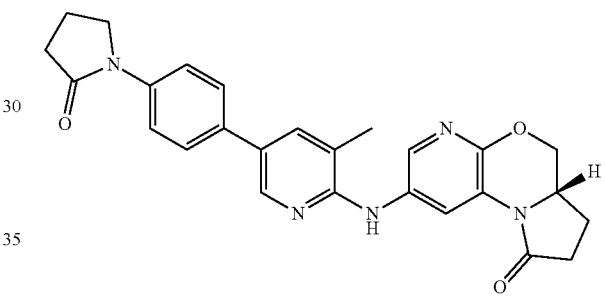

Step 1: Preparation of 1-(4-(6-chloro-5-methylpyridin-3-yl)phenyl)pyrrolidin-2-one

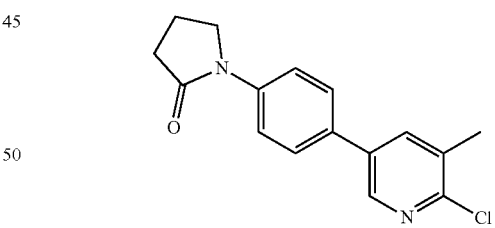

To a mixture of 1-(4-(4,4,5,5-tetramethyl-1,3,2-dioxaborolan-2-yl)phenyl)pyrrolidin-2-one (890 mg, 3.10 mmol), 5-bromo-2-chloro-3-methylpyridine (400 mg, 1.94 mmol), Pd(dppf)Cl$_2$ (85 mg, 0.12 mmol) in dioxane (12 mL) was added Na$_2$CO$_3$ (616 mg, 5.81 mmol) and H$_2$O (2 mL), the resulting mixture was stirred at 80° C. under N$_2$ atmosphere for 5 hours to give a brown suspension. LCMS showed the purity of desired product is 73% (Rt=1.642 min; MS Calcd: 286.1; MS Found: 286.8 [M+H]$^+$). The mixture was diluted with water (30 mL) and extracted with EtOAc (35 mL×2). The combined extracts were washed with brine (35 mL×2), dried over Na$_2$SO$_4$, filtered and concentrated under reduced pressure to give a residue. The residue was washed with EtOAc/PE (5 mL/30 mL) to give 1-(4-(6-chloro-5-methylpyridin-3-yl)phenyl)pyrrolidin-2-one (450 mg, yield: 81%) as a brown solid.

¹H NMR (400 MHz, DMSO-d₆) δ 2.02-2.12 (2H, m), 2.41 (3H, s), 2.48-2.51 (2H, m), 3.89 (2H, t, J=6.8 Hz), 7.72-7.85 (4H, m), 8.15 (1H, d, J=2.0 Hz), 7.79 (1H, d, J=2.0 Hz).

Step 2: Preparation of (S)-2-((3-methyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one

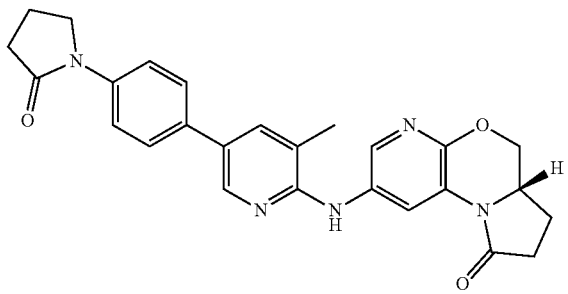 [SMILES: Cc1cc(-c2ccc(N3CCCC3=O)cc2)cnc1Nc1cnc2c(c1)N1C(=O)CC[C@H]1CO2]

To a mixture of 1-(4-(6-chloro-5-methylpyridin-3-yl)phenyl)pyrrolidin-2-one (60 mg, 0.21 mmol), (S)-2-amino-6,6a,7,8-tetrahydro-9H-pyrido[2,3-b]pyrrolo[1,2-d][1,4]oxazin-9-one (39 mg, 0.19 mmol) in dioxane (5 mL) was added Brettphos (10 mg, 0.019 mmol), Cs₂CO₃ (124 mg, 0.380 mmol) and Pd₂(dba)₃ (17 mg, 0.019 mmol), the resulting mixture was purged with N₂ for 3 times and stirred at 50° C. for 0.5 hour, then heated to 95° C. for 15.5 hours under N₂ atmosphere to give a brown solution. LCMS showed the purity of desired product is 13% (Rt=1.288 min; MS Calcd: 455.2; MS Found: 456.0 [M+H]⁺). The mixture was filtered. The filter cake was washed with DCM (10 mL×2). The filtrate was concentrated under reduced pressure to give a residue. The residue was purified by Combi Flash (DCM/MeOH=100:1 to 10:1), then further purified by prep-HPLC (0.225% FA as an additive) purification to give (S)-2-((3-methyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one (7.7 mg, yield: 9%) as a yellow solid.

¹H NMR (400 MHz, DMSO-d₆) δ 1.62-1.74 (1H, m), 2.04-2.11 (2H, m), 2.16-2.27 (1H, m), 2.35 (3H, s), 2.38-2.46 (1H, m), 2.49-2.52 (2H, m), 2.66-2.71 (1H, m), 3.86 (2H, t, J=7.2 Hz), 3.89-3.96 (1H, m), 4.02-4.14 (1H, m), 4.52-4.64 (1H, m), 7.66 (2H, d, J=8.8 Hz), 7.73 (2H, d, J=8.8 Hz), 7.87 (1H, s), 8.16-8.25 (2H, m), 8.31-8.47 (1H, m), 8.96 (1H, brs).

Example 195: (S)-2-((4-methoxy-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one

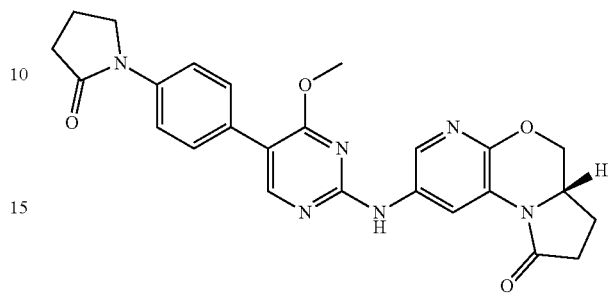

Step 1: Preparation of 1-(4-(4,4,5,5-tetramethyl-1,3,2-dioxaborolan-2-yl)phenyl)pyrrolidin-2-one

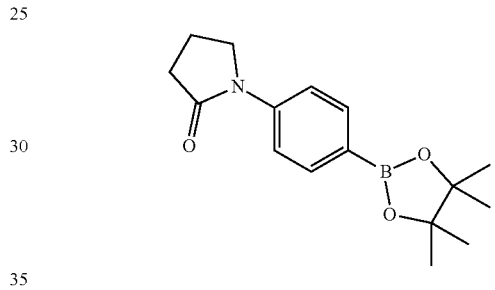

A mixture of 1-(4-bromophenyl)pyrrolidin-2-one (16.0 g, 66.6 mmol), Bispin (20.3 g, 80.0 mmol) and KOAc (14.0 g, 199 mmol) and Pd(dppf)Cl₂ (1.46 g, 2.00 mmol) in dioxane (300 mL) was stirred at 100° C. for 17 hours. The yellow solution turned to suspension. LCMS showed the purity of product is 63% (Rt=0.713 min; MS Calcd: 287.2; MS Found: 288.2 [M+H]⁺). The reaction mixture was cooled to 20° C. and filtered through silica gel then washed with PE/EA (1/1, 2 L). The solvent was evaporated under reduced pressure to give 1-(4-(4,4,5,5-tetramethyl-1,3,2-dioxaborolan-2-yl)phenyl)pyrrolidin-2-one (33.0 g, crude) as a yellow gum.

Step 2: Preparation of 1-(4-(2-chloro-4-methoxypyrimidin-5-yl)phenyl)pyrrolidin-2-one

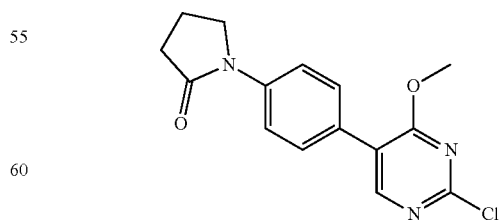

1-(4-(4,4,5,5-tetramethyl-1,3,2-dioxaborolan-2-yl)phenyl)pyrrolidin-2-one (1.41 g, 4.92 mmol), 5-bromo-2-chloro-4-methoxypyrimidine (1.00 g, 4.48 mmol), K₃PO₄ (2.85 g, 13.4 mmol) and Pd(dppf)Cl₂ (140 mg, 0.179 mmol)

were taken up in dioxane (25 mL) and H₂O (5 mL), the mixture was stirred at 80° C. for 4 hours. A black solution was formed. LCMS showed the purity of product is 23% (Rt=0.670 min; MS Calcd: 303.1; MS Found: 303.9 [M+H]⁺). The reaction mixture was diluted EtOAc (10 mL) and extracted with EtOAc (10 mL×2). The mixture was concentrated under reduced pressure. The residue was purified by Combi Flash (50% to 80% EtOAc in PE) to give 1-(4-(2-chloro-4-methoxypyrimidin-5-yl)phenyl)pyrrolidin-2-one (500 mg, yield: 37% for two steps) as a white solid.

¹H NMR (400 MHz, CDCl₃) δ 2.15-2.25 (2H, m), 2.65 (2H, t, J=8.0 Hz), 3.91 (2H, t, J=7.2 Hz), 4.06 (3H, s), 7.55-7.65 (2H, m), 7.69-7.77 (2H, m), 8.34 (1H, s).

Step 3: Preparation of (S)-2-((4-methoxy-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one

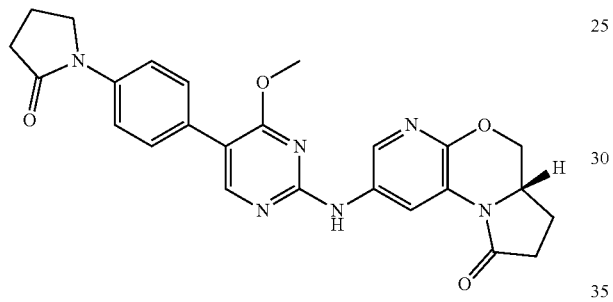

A mixture of 1-(4-(2-chloro-4-methoxypyrimidin-5-yl)phenyl)pyrrolidin-2-one (60 mg, 0.19 mmol), (S)-2-amino-6,6a,7,8-tetrahydro-9H-pyrido[2,3-b]pyrrolo[1,2-d][1,4]oxazin-9-one (40 mg, 0.19 mmol) and con. HCl (15 uL) in DMF (3 mL) was stirred at 80° C. for 16 hours. The yellow solution turned to suspension. LCMS showed that 1-(4-(2-chloro-4-methoxypyrimidin-5-yl)phenyl)pyrrolidin-2-one was remained. Then the (S)-2-amino-6,6a,7,8-tetrahydro-9H-pyrido[2,3-b]pyrrolo[1,2-d][1,4]oxazin-9-one (40 mg, 0.19 mmol) was added to the suspension, and stirred at 80° C. for 12 hours. LCMS-2 showed the purity of product is 50% (Rt=1.386 min; MS Calcd: 472.2; MS Found: 473.0 [M+H]⁺). The reaction mixture was filtered and the solid was washed with CH₃CN (3 mL). The filtrate was purified by HPLC (0.05% NH₃.H₂O as an additive) and lyophilized to give a solid. The solid was triturated with CH₃CN (2 mL) to give (S)-2-((4-methoxy-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one (7.0 mg, yield: 7%) as a white solid.

¹H NMR (400 MHz, DMSO-d₆) δ 1.59-1.75 (1H, m), 2.01-2.13 (2H, m), 2.16-2.26 (1H, m), 2.36-2.43 (1H, m), 2.54 (2H, overlapped with DMSO), 2.65-2.71 (1H, m), 3.84-3.95 (3H, m), 3.98-4.03 (3H, m), 4.04-4.11 (1H, m), 4.57 (1H, dd, J=10.8, 3.2 Hz), 7.55 (2H, d, J=8.8 Hz), 7.69 (2H, d, J=7.2 Hz), 8.17 (1H, d, J=2.4 Hz), 8.30 (1H, s), 9.34 (1H, s), 9.75 (1H, s).

Example 196: (S)-2-((4-methyl-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one

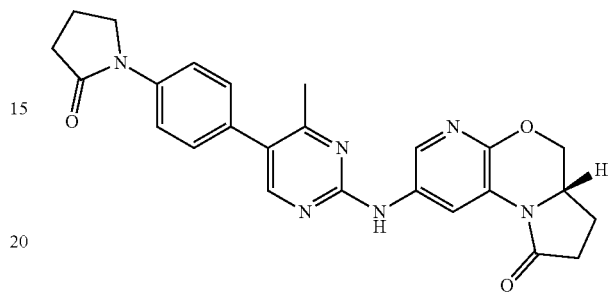

Step 1: Preparation of 1-(4-(2-chloro-4-methylpyrimidin-5-yl)phenyl)pyrrolidin-2-one

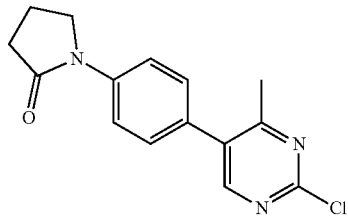 [SMILES: Cc1nc(Cl)ncc1-c1ccc(N2CCCC2=O)cc1]

1-(4-(4,4,5,5-tetramethyl-1,3,2-dioxaborolan-2-yl)phenyl)pyrrolidin-2-one (2.08 g, 7.23 mmol), 5-bromo-2-chloro-4-methylpyrimidine (1.00 g, 4.82 mmol), K₃PO₄ (3.07 g, 14.5 mmol) and Pd(dppf)Cl₂ (141 mg, 0.193 mmol) were taken up in dioxane (25 mL) and H₂O (5 mL). The resulting mixture was stirred at 80° C. for 4 hours. A black solution was formed. LCMS showed the purity of product is 21% (Rt=0.688 min; MS Calcd: 287.1; MS Found: 288.0 [M+H]⁺). The reaction mixture was diluted with EtOAc (10 mL) and extracted with EtOAc (10 mL×2). The mixture was concentrated under reduced pressure. The residue was purified by Combi Flash (10% to 35% EtOAc in PE) to give 1-(4-(2-chloro-4-methylpyrimidin-5-yl)phenyl)pyrrolidin-2-one (320 mg, yield: 23%) as a yellow solid.

¹H NMR (400 MHz, CDCl₃) δ 2.20-2.24 (2H, m), 2.52 (3H, s), 2.66 (2H, t, J=8.0 Hz), 3.92 (2H, t, J=6.8 Hz), 7.29-7.34 (2H, m), 7.74-7.77 (2H, m), 8.40 (1H, s).

Step 2: Preparation of (S)-2-((4-methyl-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one

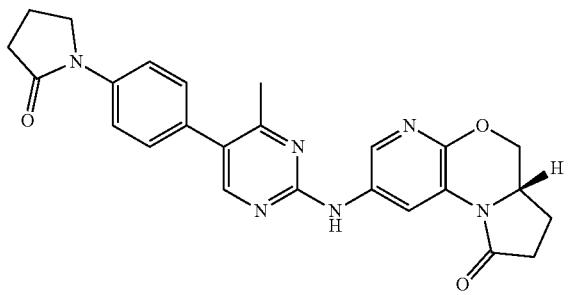 [SMILES: Cc1nc(Nc2cnc3c(c2)N2C(=O)CC[C@H]2CO3)ncc1-c1ccc(N2CCCC2=O)cc1]

A mixture of 1-(4-(2-chloro-4-methylpyrimidin-5-yl)phenyl)pyrrolidin-2-one (77 mg, 0.26 mmol), (S)-2-amino-6,6a,7,8-tetrahydro-9H-pyrido[2,3-b]pyrrolo[1,2-d][1,4]oxazin-9-one (50 mg, 0.24 mmol) and con. HCl (56 uL) in DMF (4 mL) was stirred at 80° C. for 16 hours. The yellow solution turned to suspension. LCMS showed that the 1-(4-(2-chloro-4-methylpyrimidin-5-yl)phenyl)pyrrolidin-2-one was remained. Then added (S)-2-amino-6,6a,7,8-tetrahydro-9H-pyrido[2,3-b]pyrrolo[1,2-d][1,4]oxazin-9-one (15 mg, 0.24 mmol) was stirred at 80° C. for 12 hours. The yellow solution turned to suspension. LCMS showed the purity of product is 23% (Rt=0.798 min; MS Calcd: 456.2; MS Found: 457.1 [M+H]$^+$). The reaction mixture was filtered to give a yellow solid. The yellow solid was purified by HPLC (0.225% FA as additive) and lyophilized to give (S)-2-((4-methyl-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one (12 mg, yield: 11%) as an off-white solid.

$^1$H NMR (400 MHz, DMSO-d$_6$) δ 1.69-1.80 (1H, m), 2.19-2.25 (2H, m), 2.30-2.40 (1H, m), 2.45 (3H, s), 2.55-2.63 (1H, m), 2.64-2.69 (2H, m), 2.70-2.79 (1H, m), 3.86-3.95 (3H, m), 4.08-4.17 (1H, m), 4.63 (1H, dd, J=10.8, 3.2 Hz), 7.08 (1H, s), 7.31 (2H, d, J=8.4 Hz), 7.71 (2H, d, J=8.8 Hz), 8.23-8.28 (2H, m), 9.33 (1H, d, J=2.4 Hz).

Example 197: (S)-2-((4-(methoxymethyl)-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one

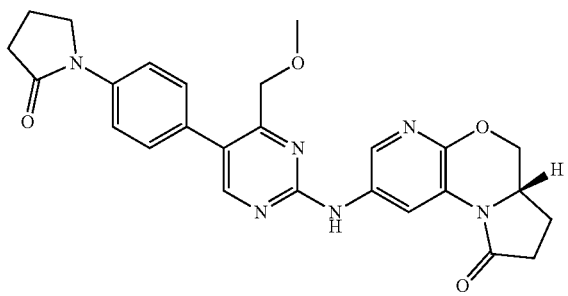 [SMILES: COCc1nc(Nc2cnc3c(c2)N2C(=O)CC[C@H]2CO3)ncc1-c1ccc(N2CCCC2=O)cc1]

Step 1: Preparation of methyl 5-chloro-2-(methylthio)pyrimidine-4-carboxylate

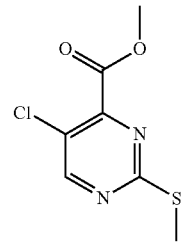

Oxalyl chloride (15.5 g, 122 mmol) was added dropwise to a mixture of 5-chloro-2-(methylthio)pyrimidine-4-carboxylic acid (5.0 g, 24 mmol) in DCM (80 mL) and DMF (357 mg, 4.89 mmol) at 0° C. The mixture was stirred at 15° C. for 2 h. The mixture was concentrated. MeOH (50 mL) was added dropwise to the residue at 0° C. and stirred at 15° C. for 2 h to give a brown solution. TLC showed the starting material was consumed. The mixture was concentrated. The residue was purified by flash silica gel chromatography (ISCO®; 20 g SepaFlash® Silica Flash Column, Eluent of 09% Ethyl acetate/Petroleum ether gradient @40 mL/min) to give methyl 5-chloro-2-(methylthio)pyrimidine-4-carboxylate (5.2 g, yield: 98%) as a white solid.

$^1$H NMR (400 MHz, CDCl$_3$) δ 2.58 (3H, s), 4.00 (3H, s), 8.60 (1H, s).

Step 2: Preparation of (5-chloro-2-(methylthio)pyrimidin-4-yl)methanol

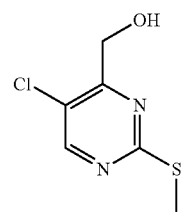

DIBAL-H (1 M in toluene, 48 mL, 48 mmol) in toluene was added dropwise to a solution of methyl 5-chloro-2-(methylthio)pyrimidine-4-carboxylate (5.2 g, 24 mmol) in DCM (100 mL) at −60° C. The mixture was slowly warmed to 15° C., and stirred at 15° C. for 15 h to give a yellow solution. LCMS showed that the purity of the desired product is 64% (Rt=0.648 min; MS Calcd: 190.0; MS Found: 190.8 [M+H]$^+$). TLC showed one main spot with larger polarity was detected. The mixture was quenched with sat.aq.NH$_4$Cl (150 mL), diluted with EtOAc (150 mL) and filtered. The mixture was extracted with EtOAc (150 mL×2). The combined organic layer was dried over anhydrous Na$_2$SO$_4$, filtered and concentrated under reduced pressure. The residue was purified by flash silica gel chromatography (ISCO®; 40 g SepaFlash® Silica Flash Column, Eluent of 08% Ethyl acetate/Petroleum ether gradient @40 mL/min) to give (5-chloro-2-(methylthio)pyrimidin-4-yl)methanol (1.8 g, yield: 40%) as a pale yellow solid.

$^1$H NMR (400 MHz, DMSO-d$_6$) δ 2.54 (3H, s), 4.58 (2H, d, J=6.4 Hz), 5.46 (1H, t, J=6.4 Hz), 8.66 (1H, s).

Step 3: Preparation of 5-chloro-4-(methoxymethyl)-2-(methylthio)pyrimidine

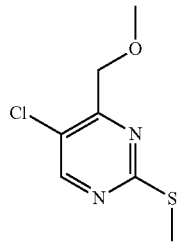

Me₃OBF₄ (698 mg, 4.72 mmol) was added to a mixture of (5-chloro-2-(methylthio)pyrimidin-4-yl)methanol (900 mg, 4.72 mmol) and N1,N1,N8,N8-tetramethylnaphthalene-1,8-diamine (1.5 g, 7.1 mmol) in DCM (20 mL). The mixture was stirred at 20° C. for 1 h to give a brown suspension. LCMS showed that the purity of the desired product is 44% (Rt=0.739 min; MS Calcd: 204.0; MS Found: 204.8 [M+H]⁺). TLC showed one spot with lower polarity was detected. The mixture was diluted with MeOH (10 mL) and concentrated. The residue was purified by flash silica gel chromatography (ISCO®; 12 g SepaFlash® Silica Flash Column, Eluent of 05% Ethyl acetate/Petroleum ether gradient @30 mL/min) to give 5-chloro-4-(methoxymethyl)-2-(methylthio)pyrimidine (650 mg, crude) as yellow oil.

¹H NMR (400 MHz, DMSO-d₆) δ 2.53 (3H, s), 3.37 (3H, s), 4.54 (2H, s), 8.71 (1H, s).

Step 4: Preparation of 1-(4-(4-(methoxymethyl)-2-(methylthio)pyrimidin-5-yl)phenyl)pyrrolidin-2-one

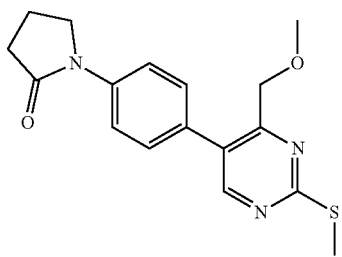 [SMILES: COCc1nc(SC)ncc1-c1ccc(N2CCCC2=O)cc1]

A mixture of 5-chloro-4-(methoxymethyl)-2-(methylthio)pyrimidine (100 mg, 0.489 Mmol), 1-(4-(4,4,5,5-tetramethyl-1,3,2-dioxaborolan-2-yl)phenyl)pyrrolidin-2-one (309 mg, 1.07 mmol), Cs₂CO₃ (318 mg, 0.977 mmol) and Pd(t-Bu₃P)₂ (12 mg, 0.024 mmol) in dioxane (2 mL) and H₂O (0.4 mL) was stirred at 100° C. for 5 h under N₂ to give a black suspension. LCMS showed that the purity of the desired product is 35% (Rt=1.542 min; MS Calcd: 329.1; MS Found: 330.1 [M+H]⁺). TLC showed one main spot with larger polarity was detected. The mixture was combined with ES9451-41 and filtered and concentrated. The residue was purified by flash silica gel chromatography (ISCO®; 20 g SepaFlash® Silica Flash Column, Eluent of 050% Ethyl acetate/Petroleum ether gradient @ 35 mL/min) to give 1-(4-(4-(methoxymethyl)-2-(methylthio)pyrimidin-5-yl)phenyl)pyrrolidin-2-one (49% for two steps) as colorless oil.

¹H NMR (400 MHz, DMSO-d₆) δ 1.07 (3H, s), 2.02-2.14 (2H, m), 2.53 (2H, t, J=8.0 Hz), 3.26 (3H, s), 3.88 (2H, t, J=6.8 Hz), 4.38 (2H, s), 7.48 (2H, d, J=8.8 Hz), 7.78 (2H, d, J=8.8 Hz), 8.59 (1H, s).

Step 5: Preparation of 1-(4-(4-(methoxymethyl)-2-(methylsulfonyl)pyrimidin-5-yl)phenyl)pyrrolidin-2-one

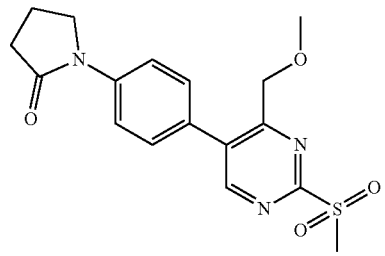 [SMILES: COCc1nc(S(C)(=O)=O)ncc1-c1ccc(N2CCCC2=O)cc1]

The mixture of 1-(4-(4-(methoxymethyl)-2-(methylthio)pyrimidin-5-yl)phenyl)pyrrolidin-2-one (380 mg, 1.15 mmol) and m-CPBA (468 mg, 2.31 mmol, 85% purity) in DCM (20 mL) was stirred at 20° C. for 30 min to give a pale yellow suspension. LCMS showed that the purity of the desired product is 65% (Rt=1.335 min; MS Calcd: 361.1; MS Found: 362.0 [M+H]⁺). TLC showed the starting material was consumed. The mixture was diluted with DCM (50 mL) and quenched with sat.aq.Na₂SO₃ (50 mL). The mixture was washed with sat.aq.NaHCO₃ (50 mL×2). The organic layer was dried over anhydrous Na₂SO₄, filtered and concentrated under reduced pressure to give 1-(4-(4-(methoxymethyl)-2-(methylsulfonyl)pyrimidin-5-yl)phenyl)pyrrolidin-2-one (370 mg, crude) as a yellow solid.

Step 6: Preparation of (S)-2-((4-(methoxymethyl)-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one

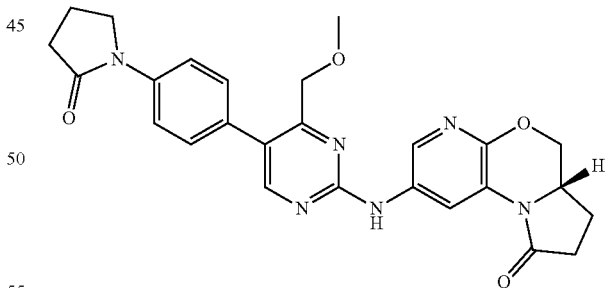

TFA (32 mg, 0.28 mmol) was added to a solution of 1-(4-(4-(methoxymethyl)-2-(methylsulfonyl)pyrimidin-5-yl)phenyl)pyrrolidin-2-one (50 mg, 0.14 mmol) and 2-amino-6,6a,7,8-tetrahydro-9H-pyrido[2,3-b]pyrrolo[1,2-d][1,4]oxazin-9-one (57 mg, 0.28 mmol) in THF (1.5 mL). The mixture was stirred at 70° C. for 15 h under N₂ to give a brown solution. LCMS showed the desired MS was detected and most of 1-(4-(4-(methoxymethyl)-2-(methylsulfonyl)pyrimidin-5-yl)phenyl)pyrrolidin-2-one were remained. The mixture was stirred at 70° C. for 20 h under N₂ to give brown solution. LCMS showed that the purity of the desired product is 49% (Rt=1.403 min; MS Calcd: 486.2; MS Found: 487.2 [M+H]⁺). The mixture was concentrated. The residue was purified by prep-HPLC (0.225% FA as an additive) and lyophilized to give (S)-2-((4-(methoxymethyl)-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one (13.6 mg, yield: 18% for two steps) as a yellow solid.

¹H NMR (400 MHz, DMSO-d₆) δ 1.62-1.77 (1H, m), 2.03-2.14 (2H, m), 2.17-2.26 (1H, m), 2.34-2.43 (1H, m), 2.52 (2H, t, J=8.0 Hz), 2.64-2.74 (1H, m), 3.28 (3H, s), 3.82-3.97 (3H, m), 4.00-4.14 (1H, m), 4.35 (2H, s), 4.58 (1H, dd, J=10.8, 2.8 Hz), 7.46 (2H, d, J=8.4 Hz), 7.75 (2H, d, J=8.4 Hz), 8.30 (1H, d, J=2.4 Hz), 8.40 (1H, s), 9.25 (1H, d, J=2.4 Hz), 9.85 (1H, s).

Example 198: (S)-2-((5-(2-methyl-4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one

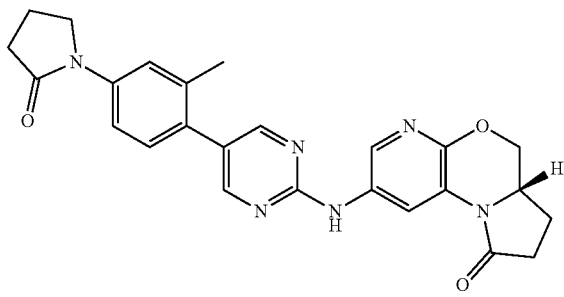 [SMILES: Cc1cc(N2CCCC2=O)ccc1-c1cnc(Nc2cnc3c(c2)N2C(=O)CC[C@H]2CO3)nc1]

Step 1: Preparation of 1-(3-methyl-4-(4,4,5,5-tetramethyl-1,3,2-dioxaborolan-2-yl)phenyl)pyrrolidin-2-one

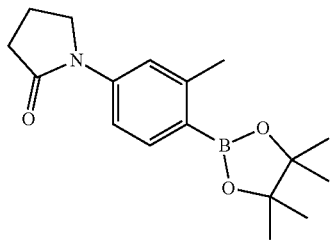 [SMILES: Cc1cc(N2CCCC2=O)ccc1B1OC(C)(C)C(C)(C)O1]

A mixture of 1-(4-bromo-3-methylphenyl)pyrrolidin-2-one (2.90 g, 11.4 mmol), Bispin (3.48 g, 13.7 mmol) and K(OAc) (2.40 g, 34.2 mmol) and Pd(dppf)Cl₂ (250 mg, 0.342 mmol) in dioxane (60 mL) was stirred at 100° C. for 17 hours. The yellow solution turned to suspension. LCMS showed the purity of product is 67% (Rt=0.950 min; MS Calcd: 301.2; MS Found: 301.9 [M+H]⁺). The reaction mixture was cooled to 20° C. and filtered through silica gel then washed with PE/EA (1/1, 300 mL). The solvent was evaporated under reduced pressure to give 1-(3-methyl-4-(4,4,5,5-tetramethyl-1,3,2-dioxaborolan-2-yl)phenyl)pyrrolidin-2-one (5.00 g, crude) as a yellow gum.

Step 2: Preparation of 1-(4-(2-chloropyrimidin-5-yl)-3-methylphenyl)pyrrolidin-2-one

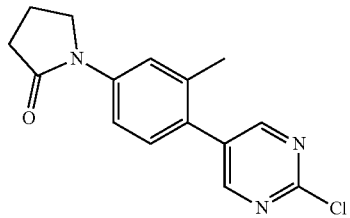 [SMILES: Cc1cc(N2CCCC2=O)ccc1-c1cnc(Cl)nc1]

1-(3-methyl-4-(4,4,5,5-tetramethyl-1,3,2-dioxaborolan-2-yl)phenyl)pyrrolidin-2-one (1.71 g, 5.69 mmol), 5-bromo-2-chloropyrimidine (1.00 g, 5.17 mmol), K₃PO₄ (3.29 g, 15.5 mmol), Pd(dppf)Cl₂ (151 mg, 0.207 mmol) were taken up in dioxane (25 mL) and H₂O (5 mL). The resulting mixture was stirred at 80° C. for 4 hours. A black solution was formed. LCMS showed the purity of product is 46% (Rt=0.644 min; MS Calcd: 287.2; MS Found: 287.9 [M+H]⁺). The reaction mixture was diluted with EtOAc (10 mL) and extracted with EtOAc (10 mL×2). The mixture was concentrated under reduced pressure. The residue was purified by Combi Flash (20% to 50% EtOAc in PE), to give 1-(4-(2-chloropyrimidin-5-yl)-3-methylphenyl)pyrrolidin-2-one (686 mg, yield: 46% for two steps) as a yellow solid.

¹H NMR (400 MHz, CDCl₃) δ 2.16-2.26 (2H, m), 2.33 (3H, s), 2.66 (2H, t, J=8.0 Hz), 3.91 (2H, t, J=7.2 Hz), 7.21 (1H, d, J=8.4 Hz), 7.55-7.59 (1H, dd, J=8.4, 2.4 Hz), 7.65 (1H, d, J=2.4 Hz), 8.61 (2H, s).

Step 3: Preparation of (S)-2-((5-(2-methyl-4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one

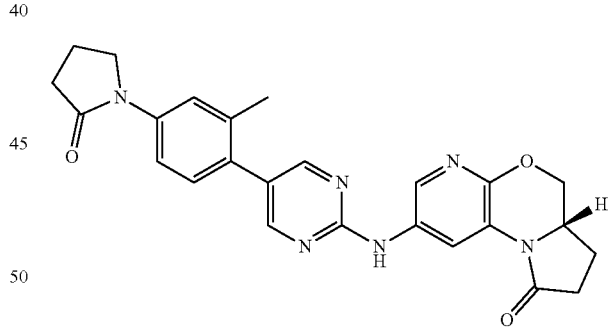

A mixture of 1-(4-(2-chloropyrimidin-5-yl)-3-methylphenyl)pyrrolidin-2-one (60 mg, 0.21 mmol), (S)-2-amino-6,6a,7,8-tetrahydro-9H-pyrido[2,3-b]pyrrolo[1,2-d][1,4]oxazin-9-one (42 mg, 0.21 mmol) and con. HCl (16 uL) in DMF (3 mL) was stirred at 80° C. for 16 hours. A yellow solution was formed. LCMS showed that 1-(4-(2-chloropyrimidin-5-yl)-3-methylphenyl)pyrrolidin-2-one was remained. Then added (S)-2-amino-6,6a,7,8-tetrahydro-9H-pyrido[2,3-b]pyrrolo[1,2-d][1,4]oxazin-9-one (20 mg, 0.10 mmol) and con. HCl (16 uL) in yellow solution was stirred at 80° C. for 6 hours. LCMS showed that 1-(4-(2-chloropyrimidin-5-yl)-3-methylphenyl)pyrrolidin-2-one was remained. The yellow solution was added (S)-2-amino-6,6a,7,8-tetrahydro-9H-pyrido[2,3-b]pyrrolo[1,2-d][1,4]oxazin-9-one (60 mg, 0.30 mmol) and con. HCl (16 uL), stirred at 80° C. for 12 hours. LCMS showed the purity of product is 20% (Rt=0.611 min; MS Calcd: 456.2; MS Found: 457.2 [M+H]$^+$). The yellow solution was purified by HPLC (0.225% FA as an additive) and lyophilized to give (S)-2-((5-(2-methyl-4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one (20 mg, yield: 20%) as an off-white solid.

$^1$H NMR (400 MHz, DMSO-d$_6$) δ 1.63-1.73 (1H, m), 2.02-2.11 (2H, m), 2.14-2.23 (1H, m), 2.31 (3H, s), 2.34-2.43 (1H, m), 2.53 (2H, overlapped with DMSO), 2.64-2.69 (1H, m), 3.84-3.94 (3H, m), 4.03-4.11 (1H, m), 4.59 (1H, dd, J=10.4, 2.8 Hz), 7.28 (1H, d, J=9.2 Hz) 7.57-7.62 (2H, m), 8.29 (1H, d, J=2.4 Hz), 8.47 (2H, s), 9.10 (1H, d, J=2.8 Hz), 9.74 (1H, s).

Example 199: (S)-2-((4-amino-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one

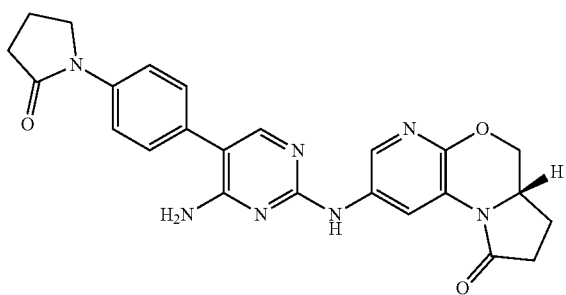 [SMILES: Nc1nc(Nc2cnc3c(c2)N2C(=O)CC[C@H]2CO3)ncc1-c1ccc(N2CCCC2=O)cc1]

Step 1: Preparation of 1-(4-(4-amino-2-chloropyrimidin-5-yl)phenyl)pyrrolidin-2-one

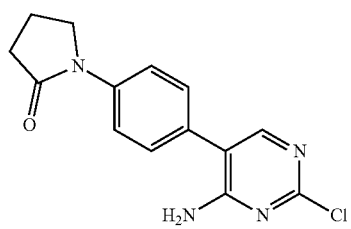 [SMILES: Nc1nc(Cl)ncc1-c1ccc(N2CCCC2=O)cc1]

1-(4-(4,4,5,5-tetramethyl-1,3,2-dioxaborolan-2-yl)phenyl)pyrrolidin-2-one (227 mg, 0.792 mmol), 5-bromo-2-chloro-6-methylpyrimidin-4-amine (150 mg, 0.719 mmol), K$_3$PO$_4$ (458 mg, 2.16 mmol) and Pd(dppf)Cl$_2$ (21 mg, 0.029 mmol) were taken up in dioxane (8 mL) and H$_2$O (2 mL), the resulting mixture was stirred at 80° C. for 4 hours. A black solution was formed. LCMS showed the purity of product is 52% (Rt=0.561 min; MS Calcd: 288.1; MS Found: 288.9 [M+H]$^+$). The reaction mixture was diluted with EtOAc (10 mL), and extracted with EtOAc (10 mL×2). The mixture was concentrated under reduced pressure. The residue was purified by Combi Flash (60% to 100% EtOAc in PE) to give 1-(4-(4-amino-2-chloropyrimidin-5-yl)phenyl)pyrrolidin-2-one (150 mg, yield: 72%) as a white solid.

$^1$H NMR (400 MHz, CDCl$_3$) δ 2.17-2.26 (2H, m), 2.66 (2H, t, J=8.0 Hz), 3.91 (2H, t, J=7.2 Hz), 5.29 (2H, brs), 7.38-7.42 (2H, m), 7.74-7.78 (2H, m), 8.00 (1H, s).

Step 2: Preparation of (S)-2-((4-amino-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one

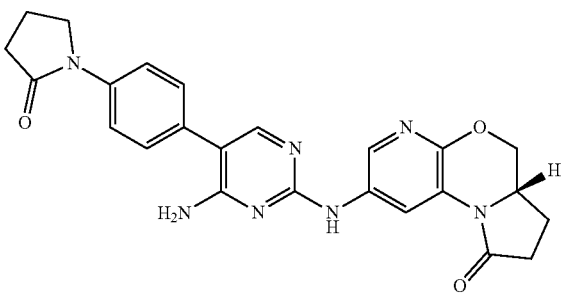

A mixture of 1-(4-(4-amino-2-chloropyrimidin-5-yl)phenyl)pyrrolidin-2-one (50.0 mg, 0.173 mmol), (S)-2-amino-6,6a,7,8-tetrahydro-9H-pyrido[2,3-b]pyrrolo[1,2-d][1,4]oxazin-9-one (35.5 mg, 0.173 mmol) and con. HCl (40 uL) in DMF (3 mL) was stirred at 80° C. for 16 hours. The yellow solution turned to suspension. LCMS showed the purity of product is 75% (Rt=0.527 min; MS Calcd: 457.2; MS Found: 458.2 [M+H]$^+$). The reaction mixture was filtered to give a yellow solid. The yellow solid was purified by HPLC (0.225% FA as additive) and lyophilized to give (S)-2-((4-amino-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one (27.8 mg, yield: 35%) as a white solid.

$^1$H NMR (400 MHz, DMSO-d$_6$) δ 1.63-1.75 (1H, m), 2.04-2.13 (2H, m), 2.17-2.25 (1H, m), 2.33-2.42 (1H, m), 2.53 (2H, overlapped with DMSO), 2.61-2.71 (1H, m), 3.80-3.92 (3H, m), 4.01-4.09 (1H, m), 4.58 (1H, dd, J=10.8, 3.2 Hz), 6.69 (2H, brs), 7.40 (2H, d, J=3.6 Hz), 7.69-7.84 (3H, m), 8.39 (1H, d, J=2.4 Hz), 8.96 (1H, d, J=2.4 Hz), 9.32 (1H, brs).

Example 200: (S)-2'-((4-methoxy-5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one

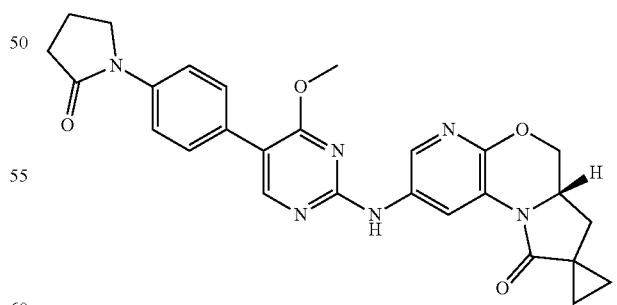

A mixture of 1-(4-(2-chloro-4-methoxypyrimidin-5-yl)phenyl)pyrrolidin-2-one (57.8 mg, 0.190 mmol), (S)-2'-amino-6a',7'-dihydro-6'H,9'H-spiro[cyclopropane-1,8'-pyrido[2,3-b]pyrrolo[1,2-d][1,4]oxazin]-9'-one (40 mg, 0.17 mmol) and con. HCl (39 uL) in DMF (3 mL) was stirred at 80° C. for 16 hours. The yellow solution was formed. LCMS showed the purity of product is 35% (Rt=0.634 min; MS Calcd: 498.2; MS Found: 499.1 [M+H]⁺). The yellow solution was purified by HPLC (0.05% NH₃.H₂O as an additive) and lyophilized to give (S)-2'-((4-methoxy-5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one (10.6 mg, yield: 12%) as a white solid.

¹H NMR (400 MHz, DMSO-d₆) δ 0.80-0.83 (1H, m), 0.89-0.93 (1H, m), 0.96-1.04 (1H, m), 1.05-1.11 (1H, m), 1.96-2.04 (1H, m), 1.99-2.11 (2H, m), 2.14-2.21 (1H, m), 2.49 (2H, overlapped with DMSO), 3.85 (2H, t, J=6.8 Hz), 3.97-4.03 (4H, m), 4.17-4.20 (1H, m), 4.61 (1H, dd, J=10.8, 3.2 Hz), 7.53 (2H, d, J=8.8 Hz), 7.68 (2H, d, J=8.8 Hz), 8.16 (1H, d, J=2.8 Hz), 8.28 (1H, s), 9.23 (1H, d, J=2.8 Hz), 9.71 (1H, s).

Example 201: (S)-2'-((4-methyl-5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one

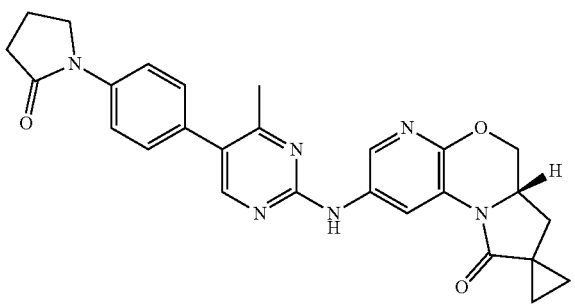

A mixture of 1-(4-(2-chloro-4-methylpyrimidin-5-yl)phenyl)pyrrolidin-2-one (55 mg, 0.19 mmol), (S)-2'-amino-6a',7'-dihydro-6'H,9'H-spiro[cyclopropane-1,8'-pyrido[2,3-b]pyrrolo[1,2-d][1,4]oxazin]-9'-one (40 mg, 0.17 mmol) and con. HCl (39 uL) in DMF (3 mL) was stirred at 80° C. for 16 hours. A yellow solution was formed. LCMS showed the purity of product is 69% (Rt=0.644 min; MS Calcd: 482.2; MS Found: 483.2 [M+H]⁺). The yellow solution was purified by HPLC (0.05% NH₃.H₂O as an additive) and lyophilized to give (S)-2'-((4-methyl-5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one (7.2 mg, yield: 8.6%) as an off-white solid.

¹H NMR (400 MHz, DMSO-d₆) δ 0.80-0.86 (1H, m), 0.91-1.03 (2H, m), 1.06-1.13 (1H, m), 1.96-2.02 (1H, m), 2.05-2.11 (2H, m), 2.15-2.20 (1H, m), 2.37 (3H, s), 2.51 (2H, overlapped with DMSO), 3.87 (2H, t, J=6.8 Hz), 3.96-4.02 (1H, m), 4.17-4.21 (1H, m), 4.60 (1H, dd, J=10.8, 3.2 Hz), 7.41 (2H, d, J=8.8 Hz), 7.74 (2H, d, J=8.4 Hz), 8.22 (1H, d, J=2.8 Hz), 8.25 (1H, s), 9.25 (1H, d, J=2.4 Hz), 9.70 (1H, s).

Example 202: (S)-2'-((4-(methoxymethyl)-5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one

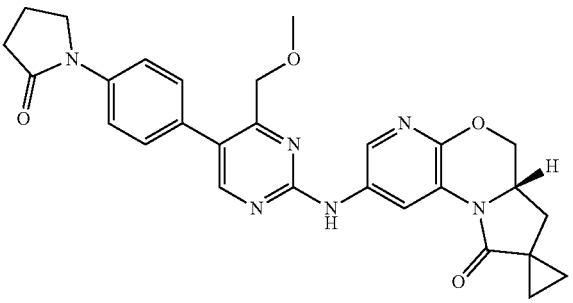 [SMILES: COCc1nc(Nc2cnc3c(c2)N2C(=O)C4(CC4)C[C@H]2CO3)ncc1-c1ccc(N2CCCC2=O)cc1]

The mixture of 1-(4-(4-(methoxymethyl)-2-(methylsulfonyl)pyrimidin-5-yl)phenyl)pyrrolidin-2-one (80 mg, 0.22 mmol), (S)-2'-amino-6a',7'-dihydro-6'H,9'H-spiro[cyclopropane-1,8'-pyrido[2,3-b]pyrrolo[1,2-d][1,4]oxazin]-9'-one (80 mg, 0.35 mmol) and TFA (38 mg, 0.33 mmol) in THF (2 mL) was stirred at 70° C. under N₂ for 55 h to give a brown solution. LCMS showed that the purity of the desired product is 49% (Rt=1.500 min; MS Calcd: 512.2; MS Found: 513.3 [M+H]⁺). The mixture was concentrated. The residue was purified by prep-HPLC (0.225% FA as an additive) and lyophilized. The residue was purified by prep-HPLC (normal phase: [10% DCM in PE-EtOH]), concentrated and lyophilized to give (S)-2'-((4-(methoxymethyl)-5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one (2.8 mg, yield: 2.2% for two steps) as a white solid.

¹H NMR (400 MHz, DMSO-d₆) δ 0.82-0.89 (1H, m), 0.92-0.98 (1H, m), 0.98-1.04 (1H, m), 1.07-1.13 (1H, m), 1.96-2.04 (1H, m), 2.06-2.13 (2H, m), 2.17-2.24 (1H, m), 2.52-2.56 (2H, m), 3.28 (3H, s), 3.88 (2H, t, J=6.8 Hz), 3.96-4.06 (1H, m), 4.14-4.26 (1H, m), 4.35 (2H, s), 4.61 (1H, dd, J=10.8, 3.6 Hz), 7.45 (2H, d, J=8.8 Hz), 7.75 (2H, d, J=8.8 Hz), 8.30 (1H, d, J=2.4 Hz), 8.40 (1H, s), 9.18 (1H, d, J=2.4 Hz), 9.84 (1H, s).

Example 203: (S)-2'-((5-(2-methyl-4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one

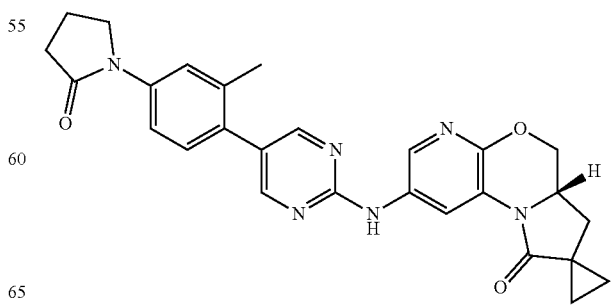

A mixture of 1-(4-(2-chloropyrimidin-5-yl)-3-methylphenyl)pyrrolidin-2-one (27 mg, 0.094 mmol), (S)-2'-amino-6a',7'-dihydro-6'H,9'H-spiro[cyclopropane-1,8'-pyrido[2,3-b]pyrrolo[1,2-d][1,4]oxazin]-9'-one (24 mg, 0.10 mmol), Pd$_2$(dba)$_3$ (9 mg, 0.009 mmol), Brettphos (10 mg, 0.019 mmol) and Cs$_2$CO$_3$ (92 mg, 0.28 mmol) in dioxane (3 mL) was stirred at 100° C. for 17 hours under N$_2$. A black suspension was formed. LCMS showed the purity of product is 14% (Rt=0.599 min; MS Calcd: 481.0; MS Found: 482.2 [M+H]$^+$). The reaction mixture combined with batch (6012-738) was concentrated. The residue was purified by Combi Flash (5% DCM in MeOH) to give impure product. The product was purified by prep-HPLC (0.05% NH$_3$.H$_2$O as an additive) and lyophilized to give (S)-2'-((5-(2-methyl-4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one (9.1 mg, yield: 7%) as a white solid.

$^1$H NMR (400 MHz, DMSO-d$_6$) δ 0.84-0.87 (1H, m), 0.93-0.97 (1H, m), 0.98-1.06 (1H, m), 1.07-1.11 (1H, m), 1.96-2.00 (1H, m), 2.02-2.10 (2H, m), 2.15-2.22 (1H, m), 2.30 (3H, s), 2.56 (2H, overlapped with DMSO), 3.86 (2H, t, J=7.2 Hz), 4.00 (1H, t, J=10.4 Hz), 4.18-4.22 (1H, m), 4.62 (1H, dd, J=10.8, 3.2 Hz), 7.27 (1H, d, J=8.8 Hz), 7.56-7.62 (2H, m), 8.25 (1H, d, J=2.8 Hz), 8.46 (2H, s), 9.08 (1H, d, J=2.8 Hz), 9.75 (1H, s).

Example 204: (S)-2'-((4-amino-5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one

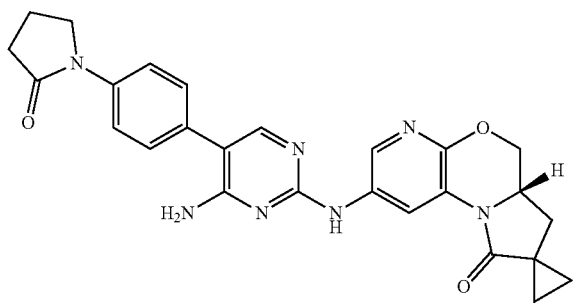 [SMILES: Nc1nc(Nc2cnc3c(c2)N2C(=O)C4(CC4)C[C@H]2CO3)ncc1-c1ccc(N2CCCC2=O)cc1]

A mixture of 1-(4-(4-amino-2-chloropyrimidin-5-yl)phenyl)pyrrolidin-2-one (49 mg, 0.17 mmol), (S)-2'-amino-6a',7'-dihydro-6'H,9'H-spiro[cyclopropane-1,8'-pyrido[2,3-b]pyrrolo[1,2-d][1,4]oxazin]-9'-one (40 mg, 0.17 mmol) and con. HCl (13 uL) in DMF (3 mL) was stirred at 80° C. for 16 hours. The yellow solution turned to suspension. LCMS showed the purity of product is 85% (Rt=0.568 min; MS Calcd: 483.2; MS Found: 484.2 [M+H]$^+$). The reaction mixture was filtered. The filtrate was concentrated to was purified by HPLC (0.05% NH$_3$.H$_2$O as an additive) and lyophilized to give (S)-2'-((4-amino-5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one (15.8 mg, yield: 18%) as a white solid.

$^1$H NMR (400 MHz, DMSO-d$_6$) δ 0.82-0.87 (1H, m), 0.93-1.04 (2H, m), 1.06-1.13 (1H, m), 1.97-2.02 (1H, m), 2.07-2.11 (2H, m), 2.17-2.22 (1H, m), 2.52 (2H, overlapped with DMSO), 3.87 (2H, t, J=2.8 Hz), 3.95-4.01 (1H, m), 4.14-4.23 (1H, m), 4.60 (1H, dd, J=7.6, 3.2 Hz), 6.28 (2H, brs), 7.40 (2H, d, J=8.8 Hz), 7.73 (2H, d, J=8.4 Hz), 7.80 (1H, s), 8.39 (1H, d, J=2.4 Hz), 9.00 (1H, d, J=2.4 Hz), 9.10 (1H, s).

Example 205: (S)-2'-((5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one

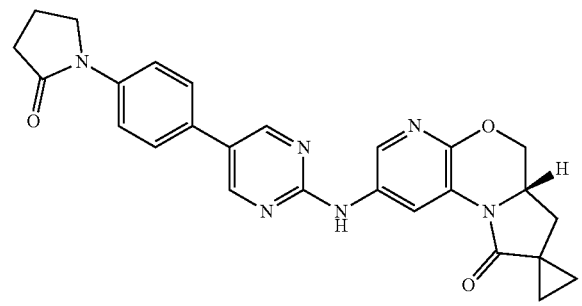 [SMILES: O=C1CCCN1c1ccc(-c2cnc(Nc3cnc4c(c3)N3C(=O)C5(CC5)C[C@H]3CO4)nc2)cc1]

A mixture of 1-(4-(2-chloropyrimidin-5-yl)phenyl)pyrrolidin-2-one (52 mg, 0.19 mmol), (S)-2'-amino-6a',7'-dihydro-6'H,9'H-spiro[cyclopropane-1,8'-pyrido[2,3-b]pyrrolo[1,2-d][1,4]oxazin]-9'-one (40 mg, 0.17 mmol) and con.HCl (39 uL) in EtOH (3 mL) was stirred at 80° C. for 16 hours. The yellow solution turned to suspension. LCMS showed the purity of product is 56% (Rt=0.620 min; MS Calcd: 468.2; MS Found: 469.2 [M+H]$^+$). The reaction mixture was filtered and washed with CH$_3$CN (2 mL). The filtrate was purified by HPLC (0.225% FA as additive) and lyophilized to give (S)-2'-((5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one (2.76 mg, yield: 3%) as a white solid.

$^1$H NMR (400 MHz, DMSO-d$_6$) δ 0.85-1.11 (4H, m), 1.97-2.07 (1H, m), 2.05-2.13 (2H, m), 2.16-2.23 (1H, m), 2.52 (2H, overlapped with DMSO), 3.87 (2H, t, J=7.2 Hz), 3.98-4.03 (1H, m), 4.16-4.25 (1H, m), 4.62 (1H, dd, J=11.2, 3.2 Hz), 7.68-7.79 (4H, m), 8.24 (1H, d, J=2.8 Hz), 8.80 (2H, s), 9.12 (1H, d, J=2.4 Hz), 9.79 (1H, s).

Example 206: (S)-2'-((4-methyl-5-(4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one

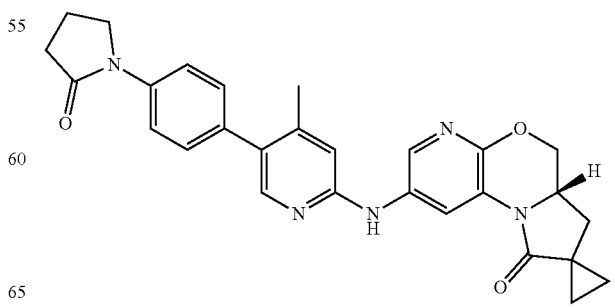

Step 1: Preparation of 1-(4-(6-chloro-4-methylpyridin-3-yl)phenyl)pyrrolidin-2-one

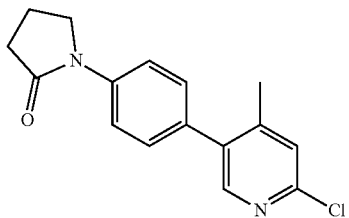

1-(4-(4,4,5,5-tetramethyl-1,3,2-dioxaborolan-2-yl)phenyl)pyrrolidin-2-one (2.08 g, 7.23 mmol), 5-bromo-2-chloro-4-methylpyridine (995 mg, 4.82 mmol), $K_3PO_4$ (3.07 g, 14.5 mmol) and $Pd(dppf)Cl_2$ (141 mg, 0.193 mmol) were taken up in dioxane (25 mL) and $H_2O$ (5 mL). The resulting mixture was stirred at 80° C. for 4 hours. A black solution was formed. LCMS showed the purity of product is 57% (Rt=0.688 min; MS Calcd: 286.1; MS Found: 286.9 [M+H]$^+$). The reaction mixture was diluted with EtOAc (10 mL), and extracted with EtOAc (10 mL×2). The mixture was concentrated under reduced pressure. The residue was purified by Combi Flash (10% to 40% EtOAc in PE) to give 1-(4-(6-chloro-4-methylpyridin-3-yl)phenyl)pyrrolidin-2-one (700 mg, yield: 51%) as a yellow solid.

$^1$H NMR (400 MHz, CDCl$_3$) δ 2.17-2.24 (2H, m), 2.28 (3H, s), 2.65 (2H, t, J=8.0 Hz), 3.91 (2H, t, J=7.2 Hz), 7.24 (1H, s), 7.27-7.32 (2H, m), 7.70-7.74 (2H, m), 8.19 (1H, s).

Step 2: Preparation of (S)-2'-((4-methyl-5-(4-(2-oxopyrrolidin-1-yl)phenyl)pyridin-2-yl)amino)-6a', 7'-dihydro-6'H,9'H-spiro[cyclopropane-1,8'-pyrido[2,3-b]pyrrolo[1,2-d][1,4]oxazin]-9'-one

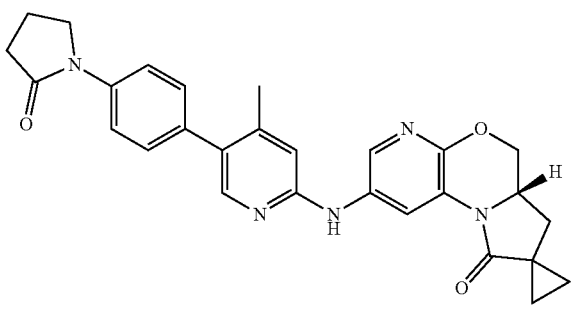 [SMILES: Cc1cc(Nc2cnc3c(c2)N2C(=O)C4(CC4)C[C@H]2CO3)ncc1-c1ccc(N2CCCC2=O)cc1]

A mixture of Pd$_2$(dba)$_3$ (8 mg, 0.008 mmol) and Xantphos (10 mg, 0.017 mmol) in 1,4-dioxane (1 mL) was stirred at 50° C. for 10 min. (S)-2'-amino-6a',7'-dihydro-6'H,9'H-spiro[cyclopropane-1,8'-pyrido[2,3-b]pyrrolo[1,2-d][1,4]oxazin]-9'-one (20 mg, 0.086 mmol), 1-(4-(6-chloro-4-methylpyridin-3-yl)phenyl)pyrrolidin-2-one (30 mg, 0.10 mol) in dioxane (4 mL) and Cs$_2$CO$_3$ (70 mg, 0.22 mmol) were added. The resulting mixture was stirred at 100° C. for 12 hours. A black brown mixture was formed. LCMS showed that the purity of the desired product is 5% (Rt=0.615 min; MS Calcd: 481.2; MS Found: 482.3 [M+H]$^+$). The reaction mixture was work-up together with other batches (es6012-722, es6012-723). The mixture was added H$_2$O (5 mL) dropwise. The formed precipitate was filtered off and washed sequentially with MeOH (10 mL) and dried to give the product as a grey solid. The solid was suspended in MeOH (10 mL) at 15° C. Aq. HCl (1M, 10 mL) was added to give a black solution. Active charcoal (100 mg) was added and the mixture was stirred at 15° C. for 30 min. The mixture was filtered through celite and the celite rinsed with MeOH (10 mL). The filtrate pH adjusted to 7-8 using aq. NaOH (2 M, 3 mL). After 30 min, the precipitate was filtered off, washed sequentially with MeOH (10 mL) to give a yellow solid (100 mg). The residue was triturated with MeCN (5 mL) for 10 hours to give (S)-2'-((4-methyl-5-(4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one (90.3 mg, yield: 73%) as a yellow solid.

$^1$H NMR (400 MHz, DMSO-d$_6$) δ 0.84-0.87 (1H, m), 0.93-0.97 (1H, m), 1.00-1.08 (1H, m), 1.09-1.13 (1H, m), 2.02-2.10 (3H, m), 2.16-2.22 (1H, m), 2.28 (3H, s), 2.56 (2H, overlapped with DMSO), 3.85 (2H, t, J=7.2 Hz), 4.08 (1H, t, J=10.4 Hz), 4.20-4.26 (1H, m), 4.73 (1H, dd, J=10.8, 3.2 Hz), 7.07 (1H, s), 7.37 (2H, d, J=8.8 Hz), 7.75 (2H, d, J=8.4 Hz), 7.80 (1H, s), 8.04 (1H, d, J=2.4 Hz), 8.65 (1H, d, J=2.4 Hz), 10.4 (1H, brs).

Example 207: (S)-2'-((4-(methoxymethyl)-5-(4-(2-oxopyrrolidin-1-yl)phenyl)pyridin-2-yl)amino)-6a', 7'-dihydro-6'H,9'H-spiro[cyclopropane-1,8'-pyrido[2,3-b]pyrrolo[1,2-d][1,4]oxazin]-9'-one

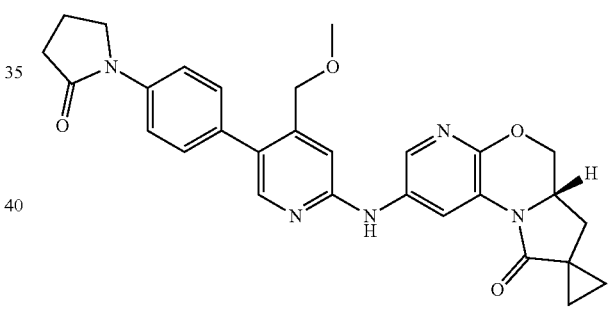

A mixture of 1-(4-(6-chloro-4-(methoxymethyl)pyridin-3-yl)phenyl)pyrrolidin-2-one (60 mg, 0.19 mmol), (S)-2'-amino-6a',7'-dihydro-6'H,9'H-spiro[cyclopropane-1,8'-pyrido[2,3-b]pyrrolo[1,2-d][1,4]oxazin]-9'-one (40 mg, 0.17 mmol), Pd$_2$(dba)$_3$ (15 mg, 0.017 mmol), Brettphos (18 mg, 0.034 mmol) and Cs$_2$CO$_3$ (141 mg, 0.432 mmol) in dioxane (3 mL) was stirred at 100 C for 17 hours under N$_2$. A black suspension was formed. LCMS showed the (S)-2'-amino-6a',7'-dihydro-6'H,9'H-spiro[cyclopropane-1,8'-pyrido[2,3-b]pyrrolo[1,2-d][1,4]oxazin]-9'-one was remained. Then the mixture was added Pd$_2$(dba)$_3$ (10 mg, 0.017 mmol), Brettphos (15 mg, 0.034 mmol), Cs$_2$CO$_3$ (100 mg, 0.432 mmol) and dioxane (2 mL) was stirred at 100° C. for 12 hours under N$_2$. A black suspension was formed. LCMS showed the purity of product is 22% (Rt=0.608 min; MS Calcd: 511.2; MS Found: 512.1 [M+H]$^+$). The reaction mixture was diluted with DCM (10 mL), filtered and concentrated. The residue was purified by HPLC (0.225% FA as additive) and lyophilized, the solid was dissolved with DMF purified by prep-HPLC (0.05% NH$_3$.H$_2$O as an additive) and lyophilized to give (S)-2'-((4-(methoxymethyl)-5-(4-(2-oxopyrrolidin-1-yl)phenyl)pyridin-2-yl)amino)-6a',7'-dihydro- 6'H,9'H-spiro[cyclopropane-1,8'-pyrido[2,3-b]pyrrolo[1,2-d][1,4]oxazin]-9'-one (9.6 mg, yield: 11%) as a white solid.

$^1$H NMR (400 MHz, DMSO-d$_6$) δ 0.80-1.08 (4H, m), 1.96-2.02 (1H, m), 2.05-2.10 (2H, m), 2.15-2.21 (1H, m), 2.52 (2H, overlapped with DMSO), 3.30 (3H, s), 3.87 (2H, t, J=7.2 Hz), 3.98 (1H, t, J=10.0 Hz), 4.16-4.21 (1H, m), 4.33 (2H, s), 4.59 (1H, dd, J=11.2, 2.4 Hz), 6.95 (1H, s), 7.35 (2H, d, J=8.4 Hz), 7.71 (2H, d, J=8.8 Hz), 7.95 (1H, s), 8.32 (1H, d, J=2.4 Hz), 8.97 (1H, d, J=2.4 Hz), 9.21 (1H, s).

Example 208: (S)-2'-((5-(2-methyl-4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one

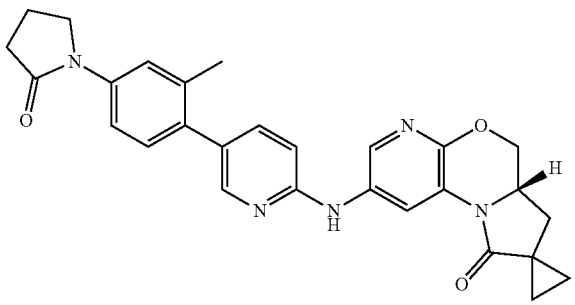 [SMILES: Cc1cc(N2CCCC2=O)ccc1-c1ccc(Nc2cnc3c(c2)N2C(=O)C4(CC4)C[C@H]2CO3)nc1]

Step 1: Preparation of 1-(4-(6-chloropyridin-3-yl)-3-methylphenyl)pyrrolidin-2-one

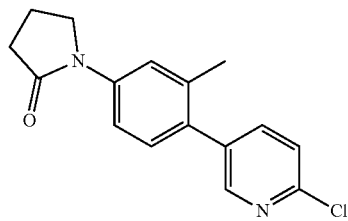 [SMILES: Cc1cc(N2CCCC2=O)ccc1-c1ccc(Cl)nc1]

1-(3-methyl-4-(4,4,5,5-tetramethyl-1,3,2-dioxaborolan-2-yl)phenyl)pyrrolidin-2-one (1.72 g, 5.72 mmol), 5-bromo-2-chloropyridine (1.00 g, 5.20 mmol), K$_3$PO$_4$ (3.31 g, 15.6 mmol) and Pd(dppf)Cl$_2$ (152 mg, 0.208 mmol) were taken up in dioxane (25 mL) and H$_2$O (5 mL). The resulting mixture was stirred at 80° C. for 4 hours. A black solution was formed. LCMS showed the purity of product is 47% (Rt=0.686 min; MS Calcd: 286.2; MS Found: 286.9 [M+H]$^+$). The reaction mixture was diluted with EtOAc (10 mL), and extracted with EtOAc (10 mL×2). The mixture was concentrated under reduced pressure. The residue was purified by Combi Flash (10% to 40% EtOAc in PE) to give 1-(4-(6-chloropyridin-3-yl)-3-methylphenyl)pyrrolidin-2-one (520 mg, yield: 35%) as a yellow solid.

$^1$H NMR (400 MHz, CDCl$_3$) δ 2.15-2.24 (2H, m), 2.29 (3H, s), 2.64 (2H, t, J=7.6 Hz), 3.90 (2H, t, J=7.2 Hz), 7.20 (1H, d, J=8.4 Hz), 7.36-7.41 (1H, m), 7.20 (1H, dd, J=8.4 Hz, 2.4 Hz), 7.58-7.62 (2H, m), 8.35 (1H, d, J=1.6 Hz).

Step 2: Preparation of (S)-2'-((5-(2-methyl-4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one

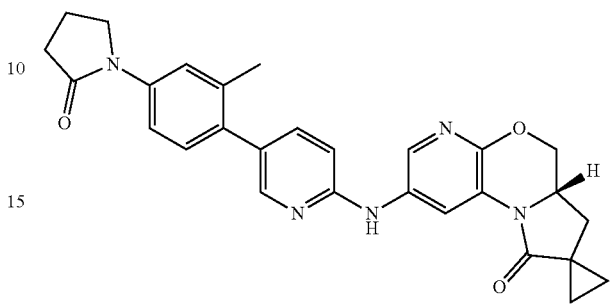

A mixture of 1-(4-(6-chloropyridin-3-yl)-3-methylphenyl)pyrrolidin-2-one (59 mg, 0.21 mmol), (S)-2'-amino-6a',7'-dihydro-6'H,9'H-spiro[cyclopropane-1,8'-pyrido[2,3-b]pyrrolo[1,2-d][1,4]oxazin]-9'-one (40 mg, 0.17 mmol), Pd$_2$(dba)$_3$ (15 mg, 0.017 mmol), Brettphos (18 mg, 0.034 mmol) and Cs$_2$CO$_3$ (141 mg, 0.432 mmol) in dioxane (5 mL) was stirred at 100° C. for 17 hours under N$_2$. A black suspension was formed. LCMS showed the purity of product is 44% (Rt=0.599 min; MS Calcd: 481.2; MS Found: 482.2 [M+H]$^+$). The reaction mixture was diluted with DCM (10 mL), filtered and concentrated. The residue was purified by prep-HPLC (0.225% FA as additive) and lyophilized to give (S)-2'-((5-(2-methyl-4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one (9.7 mg, yield: 12%) as a white solid.

$^1$H NMR (400 MHz, DMSO-d$_6$) δ 0.80-0.87 (1H, m), 0.93-0.97 (1H, m), 0.98-1.05 (1H, m), 1.07-1.13 (1H, m), 1.96-2.11 (3H, m), 2.15-2.23 (1H, m), 2.27 (3H, s), 2.48 (2H, overlapped with DMSO), 3.85 (2H, t, J=8.8 Hz), 3.99 (1H, t, J=7.2 Hz), 4.15-4.27 (1H, m), 4.60 (1H, dd, J=11.2, 2.8 Hz), 6.84 (1H, d, J=8.4 Hz), 7.21 (1H, d, J=9.2 Hz), 7.52-7.62 (3H, m), 8.07 (1H, d, J=2.8 Hz), 8.37 (1H, d, J=2.4 Hz), 8.94 (1H, d, J=2.4 Hz), 9.18 (1H, s).

Example 209: (3S,6R)—N,N-dimethyl-6-(6-(((S)-9-oxo-6a,7,8,9-tetrahydro-6H-pyrido[2,3-b]pyrrolo[1,2-d][1,4]oxazin-2-yl)amino)pyridin-3-yl)tetrahydro-2H-pyran-3-carboxamide

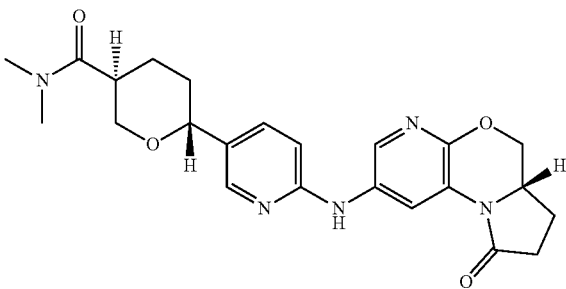 [SMILES: CN(C)C(=O)[C@H]1CC[C@H](c2ccc(Nc3cnc4c(c3)N3C(=O)CC[C@H]3CO4)nc2)OC1]

Step 1: Preparation of 1-(6-chloropyridin-3-yl)but-3-en-1-ol

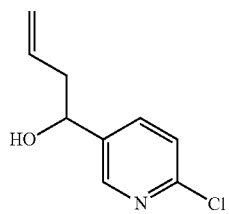

To a solution of 6-chloronicotinaldehyde (2.50 g, 17.7 mmol) in anhydrous THF (25 mL) was added allylmagnesium bromide (21.2 mL, 21.2 mmol, 1M in Et$_2$O) dropwise at 0° C. After the addition, the reaction mixture was stirred at 0° C. for 2 hours. The reaction mixture turned into red suspension from yellow solution. The reaction mixture was quenched with NH$_4$Cl (50 mL, saturated aqueous) and extracted with EtOAc (50 mL×3). The combined organic layer was washed with brine (50 mL), dried over anhydrous Na$_2$SO$_4$ and concentrated. The residue was purified by Combi Flash (20% to 35% EtOAc in PE) to give 1-(6-chloropyridin-3-yl)but-3-en-1-ol (2.45 g, yield: 76%) as blue gum.

$^1$H NMR (400 MHz, CDCl$_3$) δ 2.21 (1H, brs), 2.42-2.60 (2H, m), 4.80 (1H, dd, J=8.0, 4.8 Hz), 5.15-5.25 (2H, m), 5.73-5.85 (1H, m), 7.32 (1H, d, J=8.4 Hz), 7.69 (1H, dd, J=8.0, 2.4 Hz), 8.36 (1H, d, J=2.8 Hz).

Step 2: Preparation of ethyl 2-(((1-(6-chloropyridin-3-yl)but-3-en-1-yl)oxy)methyl)acrylate

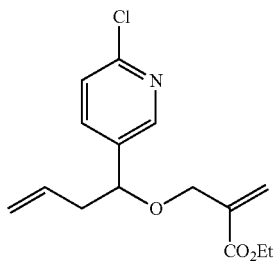 [SMILES: C=CCC(OCC(=C)C(=O)OCC)c1ccc(Cl)nc1]

To a solution of 1-(6-chloropyridin-3-yl)but-3-en-1-ol (2.45 g, 13.3 mmol) in anhydrous THF (60 mL) was added NaH (1.60 g, 40.0 mmol, 60% dispersion in mineral oil) portion-wise at 0° C. Then the reaction mixture was stirred at 10-15° C. for 1 hour. The reaction mixture turned into red suspension from yellow. The mixture was cooled to 0° C. and ethyl 2-(bromomethyl)acrylate (5.15 g, 26.7 mmol) was added dropwise at 0° C. The reaction mixture was stirred at 10-15° C. for another 1 hour. The reaction mixture turned into yellow suspension from red. The reaction mixture was quenched with saturated aqueous NH$_4$Cl (50 mL), then extracted with EtOAc (100 mL×2). The combined organic layer was washed with brine (50 mL), dried over anhydrous Na$_2$SO$_4$ and concentrated. The residue was purified by Combi Flash (10% to 20% EtOAc in PE) to give ethyl 2-(((1-(6-chloropyridin-3-yl)but-3-en-1-yl)oxy)methyl) acrylate (2.70 g, yield: 68%) as colorless gum.

$^1$H NMR (400 MHz, CDCl$_3$) δ 1.29 (3H, t, J=7.2 Hz), 2.38-2.47 (1H, m), 2.56-2.65 (1H, m), 4.00-4.12 (2H, m), 4.20 (2H, q, J=7.2 Hz), 4.42 (1H, t, J=6.8 Hz), 4.99-5.08 (2H, m), 5.67-5.80 (1H, m), 5.88-5.91 (1H, m), 6.29-6.31 (1H, m), 7.33 (1H, d, J=8.0 Hz), 7.63 (1H, dd, J=8.4, 2.4 Hz), 8.30 (1H, d, J=2.4 Hz).

Step 3: Preparation of ethyl 6-(6-chloropyridin-3-yl)-5,6-dihydro-2H-pyran-3-carboxylate

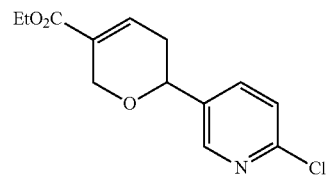 [SMILES: CCOC(=O)C1=CCC(c2ccc(Cl)nc2)OC1]

1$^{st}$ Batch

A mixture of ethyl 2-(((1-(6-chloropyridin-3-yl)but-3-en-1-yl)oxy)methyl)acrylate (800 mg, 2.70 mmol) and Grubbs (II) catalyst (84 mg, 0.14 mmol) in anhydrous DCM (150 mL) was degassed and purged with N$_2$ for 3 times. Then the resulting reaction mixture was stirred at 40° C. for 16 hours under N$_2$ atmosphere. The reaction mixture turned into dark green solution from yellow. The reaction mixture was concentrated and the residue was purified by Combi Flash (5% to 15% EtOAc in PE) to give ethyl 6-(6-chloropyridin-3-yl)-5,6-dihydro-2H-pyran-3-carboxylate (410 mg, yield: 57%) as green gum.

$^1$H NMR (400 MHz, CDCl$_3$) δ 1.31 (3H, t, J=7.2 Hz), 2.42-2.50 (2H, m), 4.24 (2H, q, J=7.2 Hz), 4.42-4.50 (1H, m), 4.54 (1H, dd, J=10.0, 4.0 Hz), 4.61-4.68 (1H, m), 7.07-7.12 (1H, m), 7.34 (1H, d, J=8.4 Hz), 7.70 (1H, dd, J=8.4, 2.4 Hz), 8.38 (1H, d, J=2.4 Hz).

2$^{nd}$ Batch

A mixture of ethyl 2-(((1-(6-chloropyridin-3-yl)but-3-en-1-yl)oxy)methyl)acrylate (1.90 g, 6.42 mmol) and Grubbs (II) catalyst (201 mg, 0.321 mmol) in anhydrous DCM (350 mL) was degassed and purged with N$_2$ for 3 times. Then the resulting reaction mixture was stirred at 40° C. for 16 hours under N$_2$ atmosphere. The reaction mixture turned into dark green solution from yellow. The reaction mixture was concentrated and the residue was purified by Combi Flash (5% to 15% EtOAc in PE) to give ethyl 6-(6-chloropyridin-3-yl)-5,6-dihydro-2H-pyran-3-carboxylate (1.40 g, yield: 81%) as green gum.

Step 4: Preparation of ethyl (3R,6S)-6-(6-chloropyridin-3-yl)tetrahydro-2H-pyran-3-carboxylate

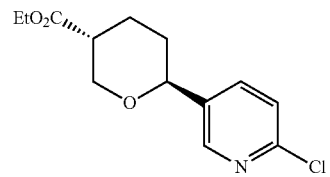 [SMILES: CCOC(=O)[C@@H]1CC[C@@H](c2ccc(Cl)nc2)OC1]

A solution of ethyl 6-(6-chloropyridin-3-yl)-5,6-dihydro-2H-pyran-3-carboxylate (1.10 g, 4.11 mmol) and PtO$_2$ (93 mg, 0.41 mmol) in EtOAc (20 mL) was stirred under H$_2$ 15 psi at 20° C. for 5 hours. The yellow solution turned to black.

LCMS showed the purity of the desired product was 74% (Rt=0.724 min; MS Calcd: 269.1; MS Found: 269.9 [M+H]⁺). TLC indicated one major new spot with larger polarity was detected. The mixture was filtered and the filtrate was concentrated. The residue was purified by Combi Flash (20% EA in PE) to give ethyl (3S,6S)-6-(6-chloropyridin-3-yl)tetrahydro-2H-pyran-3-carboxylate (800 mg, yield: 72%) as a colorless gum and ethyl (3R,6S)-6-(6-chloropyridin-3-yl)tetrahydro-2H-pyran-3-carboxylate (245 mg, yield: 22%) as a yellow gum.

Step 5: Preparation of (3R,6S)-6-(6-chloropyridin-3-yl)tetrahydro-2H-pyran-3-carboxylic acid

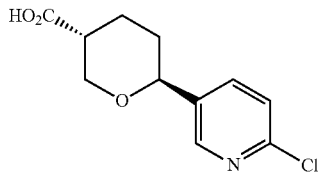 [SMILES: O=C(O)[C@@H]1CC[C@@H](c2ccc(Cl)nc2)OC1]

ethyl (3R,6S)-6-(6-chloropyridin-3-yl)tetrahydro-2H-pyran-3-carboxylate (150 mg, 0.556 mmol) was dissolved in THF (5 mL) and H₂O (5 mL) and treated with LiOH—H₂O (70 mg, 1.7 mmol) at 15° C. for 12 hours. The yellow solution turned to black. Crude LCMS showed that the purity of product was 80% (Rt=0.652 min, MS Calcd.: 241.0; MS Found: 241.9 [M+H]⁺). THF was removed under reduced pressure. The aqueous layer was washed with EtOAc (10 mL). The combined organic layers were washed with NaHCO₃ (5 mL×2, saturated aqueous). The organic extract was added to the original aqueous layers. The pH was the adjusted to 4 with HCl (3 M). The precipitate was filtered, washed with water and dried in vacuo to give (3R,6S)-6-(6-chloropyridin-3-yl)tetrahydro-2H-pyran-3-carboxylic acid (92 mg, yield: 68%) as an off-white solid. Used for the next step without further purification.

¹H NMR (400 MHz, DMSO-d₆) δ 1.44-1.50 (1H, m), 1.68-1.75 (1H, m), 1.88-1.94 (1H, m), 2.08-2.13 (1H, m), 2.54 (1H, overlapped with DMSO), 3.52 (1H, t, J=11.6 Hz), 4.13-4.20 (1H, m), 4.37-4.44 (1H, m), 7.49 (1H, d, J=8.4 Hz), 7.80 (1H, dd, J=8.4, 2.4 Hz), 8.37 (1H, d, J=2.0 Hz), 12.45 (1H, brs).

Step 6: Preparation of (3R,6S)-6-(6-chloropyridin-3-yl)-N,N-dimethyltetrahydro-2H-pyran-3-carboxamide

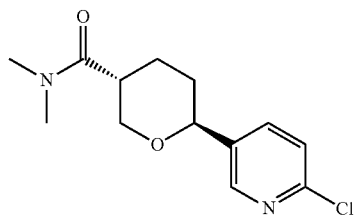 [SMILES: CN(C)C(=O)[C@@H]1CC[C@@H](c2ccc(Cl)nc2)OC1]

To a mixture of (3R,6S)-6-(6-chloropyridin-3-yl)tetrahydro-2H-pyran-3-carboxylic acid (92 mg, 0.38 mmol) in DMF (5 mL) was added EDCI (145 mg, 0.761 mmol), HOBt (103 mg, 0.761 mmol), TEA (115 mg, 1.14 mmol) and Me₂NH.HCl (62 mg, 0.76 mmol), the reaction mixture was stirred at 50° C. for 2 hours to give a grey suspension. LCMS showed the purity of the desired product is 34% (Rt=0.651 min; MS Calcd: 268.1; MS Found: 268.9 [M+H]⁺). TLC indicated one major new spot with lower polarity was detected. The reaction mixture was concentrated. The residue was purified by Combi Flash (68% EA in PE) to give (3R,6S)-6-(6-chloropyridin-3-yl)-N,N-dimethyltetrahydro-2H-pyran-3-carboxamide (100 mg, yield: 98%) as a yellow gum.

Step 7: Preparation of (3S,6R)—N,N-dimethyl-6-(6-(((S)-9-oxo-6a,7,8,9-tetrahydro-6H-pyrido[2,3-b]pyrrolo[1,2-d][1,4]oxazin-2-yl)amino)pyridin-3-yl)tetrahydro-2H-pyran-3-carboxamide

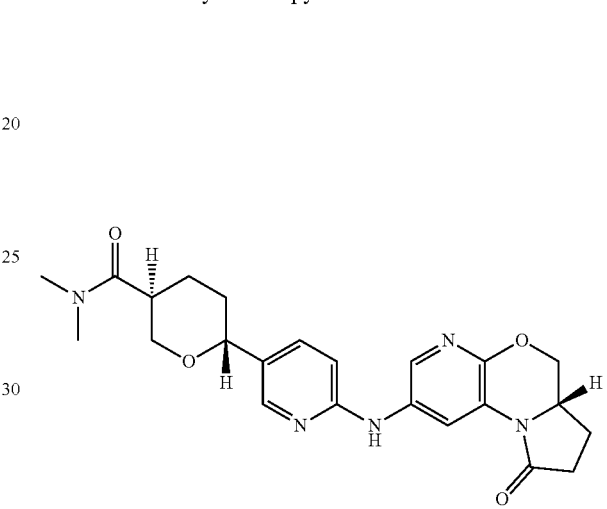

A mixture of Pd₂(dba)₃ (17 mg, 0.018 mmol) and Brettphos (20 mg, 0.037 mmol) in 1,4-dioxane (1 mL) was stirred at 50° C. for 10 min. (3R,6S)-6-(6-chloropyridin-3-yl)-N,N-dimethyltetrahydro-2H-pyran-3-carboxamide (100 mg, 0.372 mmol), (S)-2-amino-6,6a,7,8-tetrahydro-9H-pyrido[2,3-b]pyrrolo[1,2-d][1,4]oxazin-9-one (76 mg, 0.37 mmol) in dioxane (7 mL) and Cs₂CO₃ (266 mg, 0.818 mmol) were added and the resulting mixture was stirred at 100° C. for 15 hours. A black brown mixture was formed. LCMS showed that the purity of the desired product is 19% (Rt=0.596 min; MS Calcd: 437.2; MS Found: 438.1 [M+H]⁺). The reaction mixture was diluted with DCM (10 mL), filtered and concentrated. The residue was purified by prep-HPLC (0.05% NH₃.H₂O as an additive) and lyophilized to give (3S,6R)—N,N-dimethyl-6-(6-(((S)-9-oxo-6a,7,8,9-tetrahydro-6H-pyrido[2,3-b]pyrrolo[1,2-d][1,4]oxazin-2-yl)amino)pyridin-3-yl)tetrahydro-2H-pyran-3-carboxamide (15.0 mg, yield: 9%) as a light yellow solid.

¹H NMR (400 MHz, DMSO-d₆) δ 1.62-1.75 (4H, m), 1.76-1.95 (1H, m), 2.18-2.23 (1H, m), 2.33-2.40 (1H, m), 2.60-2.68 (1H, m), 2.80 (3H, s), 2.85-2.93 (1H, m), 3.05 (3H, s), 3.52 (1H, t, J=11.2 Hz), 3.88 (1H, t, J=10.4 Hz), 3.96-3.99 (1H, m), 4.02-4.08 (1H, m), 4.28 (1H, d, J=11.2 Hz), 4.56 (1H, dd, J=10.8, 3.2 Hz), 6.75 (1H, d, J=8.4 Hz), 7.52 (1H, dd, J=8.4, 2.0 Hz), 8.06 (1H, d, J=2.0 Hz), 8.33-8.36 (1H, m), 8.93-8.95 (1H, m), 9.07 (1H, brs).

Example 210: (S)-2'-((4-isopropyl-5-(4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one

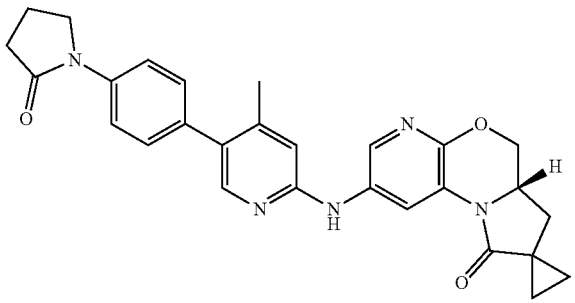 [SMILES: Cc1cc(Nc2cnc3c(c2)N2C(=O)C4(CC4)C[C@H]2CO3)ncc1-c1ccc(N2CCCC2=O)cc1]

A mixture of 1-(4-(6-chloro-4-isopropylpyridin-3-yl)phenyl)pyrrolidin-2-one (60 mg, 0.19 mmol), (S)-2'-amino-6a',7'-dihydro-6'H,9'H-spiro[cyclopropane-1,8'-pyrido[2,3-b]pyrrolo[1,2-d][1,4]oxazin]-9'-one (40 mg, 0.17 mmol), Pd$_2$(dba)$_3$ (16 mg, 0.017 mmol) Brettphos (19 mg, 0.035 mmol) and Cs$_2$CO$_3$ (141 mg, 0.432 mmol) in dioxane (3 mL) was stirred at 100° C. for 16 hours under N$_2$. A black suspension was formed. LCMS showed that the purity of the desired product is 45% (Rt=0.588 min; MS Calcd: 497.2; MS Found: 498.0 [M+H]$^+$). The reaction mixture was diluted with DCM (10 mL) filtered and concentrated. The residue was purified by prep-HPLC (0.05% NH$_3$.H$_2$O as an additive) and lyophilized. 1H NMR-1 indicated the product is impure. It was further purified by prep-TLC (DCM/MeOH, 10/1) and lyophilized. 1H NMR-2 indicated the product is impure. The residue was purified by prep-HPLC (0.05% NH$_3$.H$_2$O as an additive) and lyophilized to give (S)-2'-((4-isopropyl-5-(4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one (3.11 mg, yield: 4%) as a white solid.

$^1$H NMR (400 MHz, DMSO-d$_6$) δ 0.82-0.87 (1H, m), 0.87-0.95 (1H, m), 0.95-1.02 (1H, m), 1.02-1.07 (1H, m), 1.09 (6H, d, J=6.8 Hz), 1.95-2.01 (1H, m), 2.01-2.13 (2H, m), 2.13-2.21 (1H, m), 2.53 (2H, overlapped with DMSO), 2.93-3.02 (1H, m), 3.88 (2H, t, J=7.2 Hz), 3.98 (1H, t, J=10.4 Hz), 4.17-4.26 (1H, m), 4.56-4.64 (1H, m), 6.79 (1H, s), 7.29 (1H, s), 7.31 (1H, s), 7.71 (1H, s), 7.73 (1H, s), 7.86 (1H, s), 8.31 (1H, d, J=2.4 Hz), 8.94 (1H, d, J=2.4 Hz), 9.11 (1H, s).

Example 211: (S)-2'-((4-cyclopropyl-5-(4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one

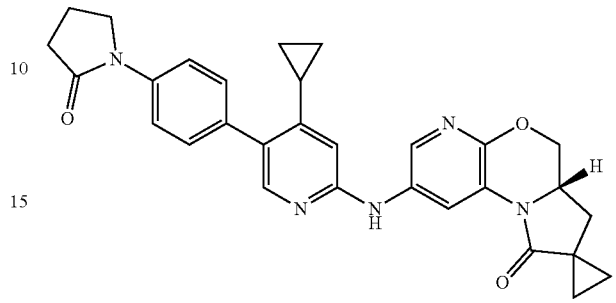

A mixture of 1-(4-(6-chloro-4-cyclopropylpyridin-3-yl)phenyl)pyrrolidin-2-one (54 mg, 0.17 mmol), (S)-2'-amino-6a',7'-dihydro-6'H,9'H-spiro[cyclopropane-1,8'-pyrido[2,3-b]pyrrolo[1,2-d][1,4]oxazin]-9'-one (40 mg, 0.17 mmol), Pd$_2$(dba)$_3$ (16 mg, 0.017 mmol), Brettphos (19 mg, 0.035 mmol) and Cs$_2$CO$_3$ (141 mg, 0.432 mmol) in dioxane (3 mL) was stirred at 100° C. for 16 hours under N$_2$. A black suspension was formed. LCMS showed that the purity of the desired product is 28% (Rt=0.628 min; MS Calcd: 507.2; MS Found: 508.0 [M+H]$^+$). The reaction mixture was diluted with DCM (10 mL), filtered and concentrated. The residue was purified by prep-HPLC (0.05% NH$_3$.H$_2$O as an additive) and lyophilized to give (S)-2'-((4-cyclopropyl-5-(4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one (5.5 mg, yield: 6%) as a white solid.

$^1$H NMR (400 MHz, DMSO-d$_6$) δ 0.68-0.77 (2H, m), 0.81-0.86 (1H, m), 0.92-1.04 (4H, m), 1.06-1.14 (1H, m), 1.76-1.84 (1H, m), 1.95-2.03 (1H, m), 2.04-2.14 (2H, m), 2.14-2.21 (1H, m), 2.52 (2H, overlapped with DMSO), 3.87 (2H, t, J=6.8 Hz), 3.94-4.02 (1H, m), 4.14-4.21 (1H, m), 4.59 (1H, dd, J=10.8, 3.2 Hz), 6.33 (1H, s), 7.43 (2H, d, J=8.8 Hz), 7.73 (2H, d, J=8.4 Hz), 7.90 (1H, s), 8.29 (1H, d, J=2.4 Hz), 8.92 (1H, d, J=2.8 Hz), 9.02 (1H, s).

Example 212: (S)-2'-((4-methoxy-5-(4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one

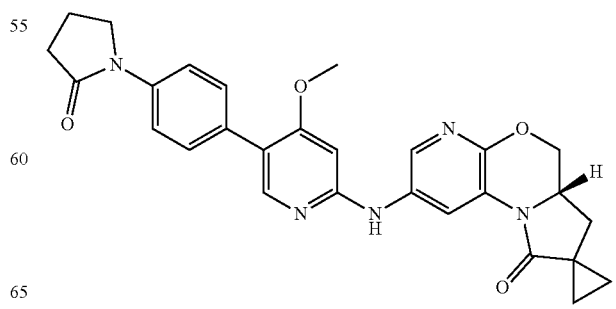

A mixture of 1-(4-(6-chloro-4-methoxypyridin-3-yl)phenyl)pyrrolidin-2-one (58 mg, 0.19 mmol), (S)-2'-amino-6a',7'-dihydro-6'H,9'H-spiro[cyclopropane-1,8'-pyrido[2,3-b]pyrrolo[1,2-d][1,4]oxazin]-9'-one (40 mg, 0.17 mmol), Pd$_2$(dba)$_3$ (16 mg, 0.017 mmol), Brettphos (19 mg, 0.035 mmol) and Cs$_2$CO$_3$ (141 mg, 0.432 mmol) in dioxane (3 mL) was stirred at 100° C. for 16 hours under N$_2$. A black suspension was formed. LCMS showed that the purity of the desired product is 25% (Rt=0.588 min; MS Calcd: 497.2; MS Found: 498.0 [M+H]$^+$). The reaction mixture was diluted with DCM (10 mL) filtered and concentrated. The residue was purified by prep-HPLC (0.05% NH$_3$.H$_2$O as an additive) and lyophilized to give (S)-2'-((4-methoxy-5-(4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one (3.38 mg, yield: 4%) as an off-white solid.

$^1$H NMR (400 MHz, DMSO-d$_6$) δ 0.82-0.87 (1H, m), 0.91-0.97 (1H, m), 0.96-1.04 (1H, m), 1.07-1.13 (1H, m), 1.96-2.04 (1H, m), 2.04-2.10 (2H, m), 2.15-2.12 (1H, m), 2.52 (2H, overlapped with DMSO), 3.80 (3H, s), 3.86 (2H, t, J=7.6 Hz), 3.99 (1H, t, J=10.4 Hz), 4.17-4.23 (1H, m), 4.60 (1H, dd, J=10.8, 2.8 Hz), 6.45 (1H, s), 7.46 (2H, d, J=8.4 Hz), 7.66 (2H, d, J=8.8 Hz), 7.94 (1H, s), 8.32 (1H, d, J=2.4 Hz), 8.95 (1H, d, J=2.4 Hz), 9.15 (1H, s).

Example 213: (S)-2-((4-cyclopropyl-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one

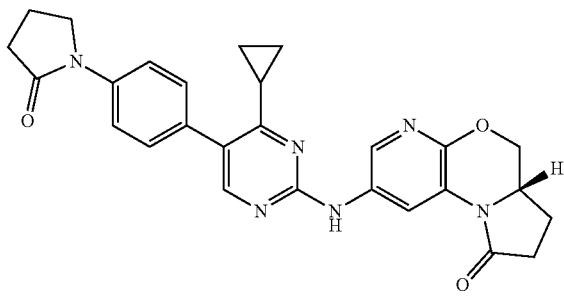 [SMILES: O=C1CCCN1c1ccc(-c2cnc(Nc3cnc4c(c3)N3C(=O)CC[C@H]3CO4)nc2C2CC2)cc1]

Step 1: Preparation of 5-bromo-2-chloro-4-cyclopropylpyrimidine

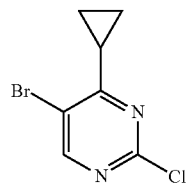 [SMILES: Clc1ncc(Br)c(C2CC2)n1]

A solution of 5-bromo-2,4-dichloropyrimidine (3.00 g, 13.2 mmol), cyclopropylboronic acid (1.13 g, 13.2 mmol), K$_2$CO$_3$ (5.45 g, 39.4 mmol) and Pd(PPh$_3$)$_4$ (500 mg, 0.432 mmol) in DMF (6 mL) and toluene (30 mL) was stirred at 120° C. for 15 hours. A black mixture was formed. LCMS showed the purity of the desired product was 43% (Rt=0.810 min; MS Calcd: 234.0; MS Found: 234.6 [M+H]$^+$). TLC showed the starting material was consumed completely. The mixture was filtered and the filtrate was concentrated. The residue was purified by Combi Flash (9% EA in PE) to give 5-bromo-2-chloro-4-cyclopropylpyrimidine (635 mg, yield: 21%) as colorless oil.

$^1$H NMR (400 MHz, CDCl$_3$) δ 1.20-1.25 (2H, m), 1.27-1.33 (2H, m), 2.42-2.48 (1H, m), 8.49 (1H, s).

Step 2: Preparation of 1-(4-(2-chloro-4-cyclopropylpyrimidin-5-yl)phenyl)pyrrolidin-2-one

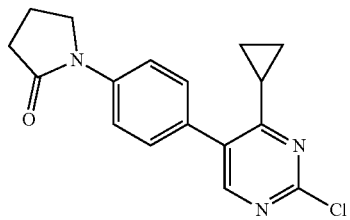 [SMILES: O=C1CCCN1c1ccc(-c2cnc(Cl)nc2C2CC2)cc1]

1-(4-(4,4,5,5-tetramethyl-1,3,2-dioxaborolan-2-yl)phenyl)pyrrolidin-2-one (750 mg, 2.61 mmol), 5-bromo-2-chloro-4-cyclopropylpyrimidine (628 mg, 2.69 mmol), K$_3$PO$_4$ (1.66 g, 7.84 mmol) and Pd(dppf)Cl$_2$ (76 mg, 0.10 mmol) were taken up in dioxane (15 mL) and H$_2$O (3 mL) and the resulting mixture was stirred at 80° C. for 4 hours. A black solution was formed. LCMS showed the purity of the desired product is 70% (Rt=0.805 min; MS Calcd: 313.1; MS Found: 313.9 [M+H]$^+$). The mixture was concentrated under reduced pressure. The residue was purified by Combi Flash (68% EA in PE) to give 1-(4-(2-chloro-4-cyclopropylpyrimidin-5-yl)phenyl)pyrrolidin-2-one (580 mg, yield: 71%) as a yellow solid.

$^1$H NMR (400 MHz, CDCl$_3$) δ 1.03-1.08 (2H, m), 1.30-1.34 (2H, m), 2.05-2.12 (1H, m), 2.19-2.25 (2H, m), 2.66 (2H, t, J=8.0 Hz), 3.92 (2H, t, J=7.2 Hz), 7.43 (2H, d, J=8.8 Hz), 7.76 (2H, d, J=8.8 Hz), 8.30 (1H, s).

Step 3: Preparation of (S)-2-((4-cyclopropyl-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one

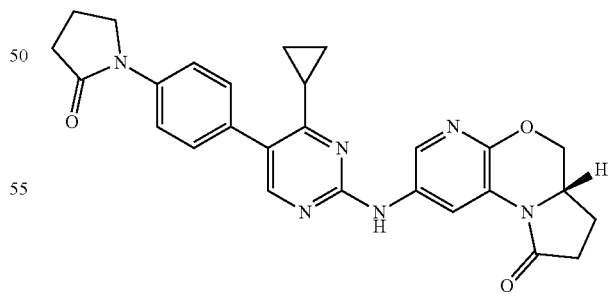

A mixture of (S)-2-amino-6,6a,7,8-tetrahydro-9H-pyrido[2,3-b]pyrrolo[1,2-d][1,4]oxazin-9-one (50 mg, 0.24 mmol), 1-(4-(2-chloro-4-cyclopropylpyrimidin-5-yl)phenyl)pyrrolidin-2-one (76 mg, 0.24 mmol) in DMF (4 mL) was added con. HCl (70 uL). And the mixture was stirred at 80° C. for 30 hours. A red solution was formed. LCMS showed that the purity of the desired product is 20% (Rt=0.734 min; MS Calcd: 482.2; MS Found: 483.0 [M+H]⁺). The solution was purified by prep-HPLC (0.05% NH₃.H₂O as an additive) and lyophilized to give (S)-2-((4-cyclopropyl-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one (11.5 mg, yield: 10%) as a white solid.

¹H NMR (400 MHz, DMSO-d₆) δ 0.94-0.98 (2H, m), 1.16-1.22 (2H, m), 1.68-1.73 (1H, m), 1.98-2.02 (1H, m), 2.05-2.12 (2H, m), 2.18-2.24 (1H, m), 2.35-2.43 (1H, m), 2.53 (2H, t, J=6.4 Hz), 2.62-2.70 (1H, m), 3.83-3.93 (3H, m), 4.02-4.08 (1H, m), 4.58 (1H, dd, J=6.8, 2.4 Hz), 7.46 (2H, d, J=8.8 Hz), 7.76 (2H, d, J=8.8 Hz), 8.18-8.20 (2H, m), 9.08 (1H, d, J=2.0 Hz), 9.54 (1H, brs).

Example 214: (S)-2'-((4-cyclopropyl-5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one

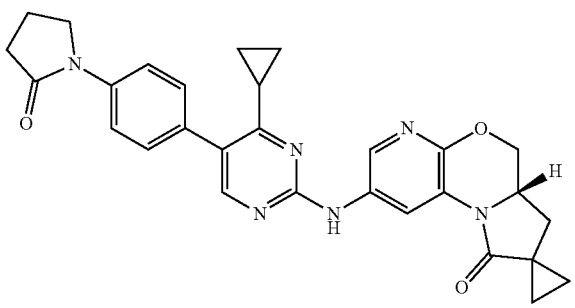 [SMILES: O=C1CCCN1c1ccc(-c2cnc(Nc3cnc4c(c3)N3C(=O)C5(CC5)C[C@H]3CO4)nc2C2CC2)cc1]

A mixture of 1-(4-(2-chloro-4-cyclopropylpyrimidin-5-yl)phenyl)pyrrolidin-2-one (54 mg, 0.17 mmol), (S)-2'-amino-6a',7'-dihydro-6'H,9'H-spiro[cyclopropane-1,8'-pyrido[2,3-b]pyrrolo[1,2-d][1,4]oxazin]-9'-one (40 mg, 0.17 mmol) in DMF (4 mL) was added con.HCl (50 uL). And the mixture was stirred at 80° C. for 30 hours. A red solution was formed. LCMS showed that the purity of the desired product is 13% (Rt=0.775 min; MS Calcd: 508.2; MS Found: 509.1 [M+H]⁺). The solution was purified by prep-HPLC (0.05% NH₃.H₂O as an additive) and lyophilized to give (S)-2'-((4-cyclopropyl-5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one (5.5 mg, yield: 6%) as a yellow solid.

¹H NMR (400 MHz, DMSO-d₆) δ 0.84-0.87 (1H, m), 0.90-0.96 (3H, m), 1.00-1.03 (1H, m), 1.06-1.10 (1H, m), 1.42-1.81 (2H, m), 1.96-2.02 (2H, m), 2.04-2.12 (2H, m), 2.15-2.22 (1H, m), 2.53 (2H, overlapped with DMSO), 3.87 (2H, t, J=7.2 Hz), 3.99 (1H, t, J=10.4 Hz), 4.16-4.21 (1H, m), 4.61 (1H, dd, J=7.2, 2.8 Hz), 7.45 (2H, d, J=8.8 Hz), 7.76 (2H, d, J=8.8 Hz), 8.18-8.20 (2H, m), 9.01 (1H, d, J=2.4 Hz), 9.53 (1H, brs).

Example 215: (S)-2-((4-isopropyl-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one

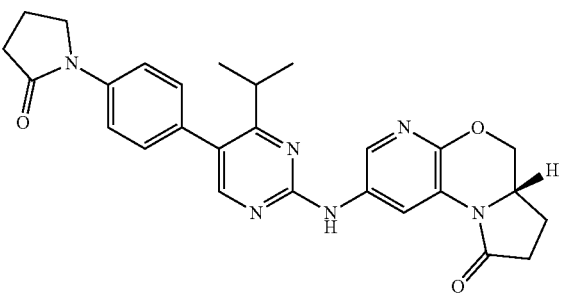 [SMILES: CC(C)c1nc(Nc2cnc3c(c2)N2C(=O)CC[C@H]2CO3)ncc1-c1ccc(N2CCCC2=O)cc1]

Step 1: Preparation of 5-bromo-2-chloro-4-(prop-1-en-2-yl)pyrimidine

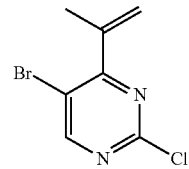

5-bromo-2,4-dichloropyrimidine (1.16 g, 5.09 mmol), potassium trifluoro(prop-1-en-2-yl)borate (753 mg, 5.09 mmol), K₃PO₄ (3.24 g, 15.2 mmol) and Pd(dppf)Cl₂ (148 mg, 0.203 mmol) were taken up in dioxane (20 mL) and H₂O (4 mL) and the resulting mixture was stirred at 80° C. for 14 hours. A black solution was formed. LCMS showed the purity of the desired product is 51% (Rt=0.819 min; MS Calcd: 231.9; MS Found: 232.7 [M+H]⁺). The mixture was concentrated under reduced pressure. The residue was purified by Combi Flash (3% EA in PE) to give 5-bromo-2-chloro-4-(prop-1-en-2-yl)pyrimidine (535 mg, yield: 45%) as light yellow oil.

¹H NMR (400 MHz, CDCl₃) δ 2.17 (3H, s), 5.60 (2H, d, J=15.6 Hz), 8.69 (1H, s).

Step 2: Preparation of 1-(4-(2-chloro-4-(prop-1-en-2-yl)pyrimidin-5-yl)phenyl)pyrrolidin-2-one

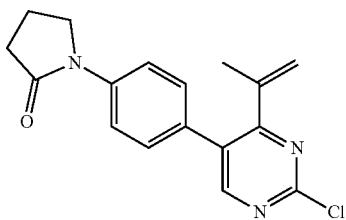 [SMILES: C=C(C)c1nc(Cl)ncc1-c1ccc(N2CCCC2=O)cc1]

1-(4-(4,4,5,5-tetramethyl-1,3,2-dioxaborolan-2-yl)phenyl)pyrrolidin-2-one (600 mg, 2.09 mmol), 5-bromo-2-chloro-4-(prop-1-en-2-yl)pyrimidine (526 mg, 2.26 mmol), K₃PO₄ (1.33 g, 6.27 mmol) and Pd(dppf)Cl₂ (61 mg, 0.083 mmol) were taken up in dioxane (15 mL) and H₂O (3 mL) and the resulting mixture was stirred at 80° C. for 14 hours. A black solution was formed. LCMS showed the purity of the desired product is 85% (Rt=0.802 min; MS Calcd: 313.1; MS Found: 313.8 [M+H]⁺). The mixture was concentrated under reduced pressure. The residue was purified by Combi Flash (48% EA in PE) to give 1-(4-(2-chloro-4-(prop-1-en-2-yl)pyrimidin-5-yl)phenyl)pyrrolidin-2-one (340 mg, yield: 52%) as a yellow solid.

¹H NMR (400 MHz, CDCl₃) δ 1.94 (3H, s), 2.18-2.24 (2H, m), 2.65 (2H, t, J=7.6 Hz), 3.90 (2H, t, J=7.2 Hz), 5.34 (2H, d, J=15.6 Hz), 7.34 (2H, t, J=8.8 Hz), 7.73 (2H, d, J=8.4 Hz), 8.48 (1H, s).

Step 3: Preparation of 1-(4-(2-chloro-4-isopropylpyrimidin-5-yl)phenyl)pyrrolidin-2-one

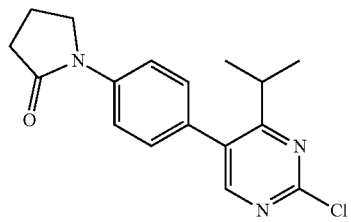 [SMILES: CC(C)c1nc(Cl)ncc1-c1ccc(N2CCCC2=O)cc1]

A solution of 1-(4-(2-chloro-4-(prop-1-en-2-yl)pyrimidin-5-yl)phenyl)pyrrolidin-2-one (280 mg, 0.892 mmol) and PtO₂ (20 mg, 0.089 mmol) in EtOAc (15 mL) was stirred under H₂ 15 psi at 20° C. for 14 hours. The yellow solution turned to black. LCMS showed the purity of the desired product was 67% (Rt=0.825 min; MS Calcd: 315.1; MS Found: 315.8 [M+H]⁺). TLC indicated polarity of the starting material was same as the product. The mixture was filtered and the filtrate was concentrated. The residue was purified by Combi Flash (50% EA in PE) to give 1-(4-(2-chloro-4-isopropylpyrimidin-5-yl)phenyl)pyrrolidin-2-one (221 mg, yield: 78%) as a light yellow solid.

¹H NMR (400 MHz, CDCl₃) δ 1.22 (6H, d, J=6.8 Hz), 2.18-2.25 (2H, m), 2.66 (2H, t, J=8.0 Hz), 3.15-3.22 (1H, m), 3.92 (2H, t, J=6.8 Hz), 7.28 (2H, d, J=8.4 Hz), 7.75 (2H, d, J=8.8 Hz), 8.37 (1H, s).

Step 4: Preparation of (S)-2-((4-isopropyl-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one

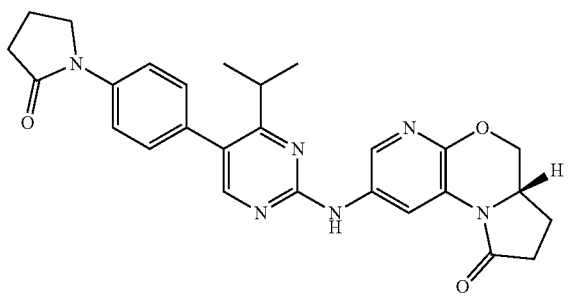 [SMILES: CC(C)c1nc(Nc2cnc3c(c2)N2C(=O)CC[C@H]2CO3)ncc1-c1ccc(N2CCCC2=O)cc1]

To a mixture of 1-(4-(2-chloro-4-isopropylpyrimidin-5-yl)phenyl)pyrrolidin-2-one (60 mg, 0.19 mmol), (S)-2-amino-6,6a,7,8-tetrahydro-9H-pyrido[2,3-b]pyrrolo[1,2-d][1,4]oxazin-9-one (78 mg, 0.38 mmol) in DMF (4 mL) was added con.HCl (50 uL). The reaction mixture was stirred at 80° C. for 48 hours to give a brown solution. LCMS showed the purity of product is 12% (Rt=0.641 min; MS Calcd: 484.2; MS Found: 485.2 [M+H]⁺). The mixture was directly purified by prep-HPLC (0.225% FA as an additive) purification to give (S)-2-((4-isopropyl-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one (18.3 mg, yield: 20%) as an off-white solid.

1H NMR (400 MHz, DMSO-d₆) δ 1.18 (3H, d, J=6.8 Hz), 1.22 (3H, d, J=6.8 Hz), 1.64-1.75 (1H, m), 2.05-2.14 (2H, m), 2.16-2.26 (1H, m), 2.35-2.44 (1H, m), 2.46-2.55 (2H, m), 2.62-2.73 (1H, m), 3.04-3.12 (1H, m), 3.84-3.95 (3H, m), 4.03-4.14 (1H, m), 4.58 (1H, dd, J=10.4, 3.2 Hz), 7.36 (2H, d, J=8.4 Hz), 7.75 (2H, d, J=8.4 Hz), 8.24 (1H, s), 8.28 (1H, d, J=2.4 Hz), 9.31 (1H, d, J=2.4 Hz), 9.68 (1H, brs).

Example 216: (S)-2'-((4-isopropyl-5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one

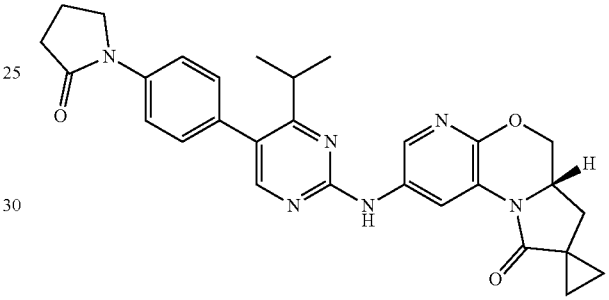

To a mixture of 1-(4-(2-chloro-4-isopropylpyrimidin-5-yl)phenyl)pyrrolidin-2-one (60 mg, 0.19 mmol), (S)-2'-amino-6a',7'-dihydro-6'H,9'H-spiro[cyclopropane-1,8'-pyrido[2,3-b]pyrrolo[1,2-d][1,4]oxazin]-9'-one (88 mg, 0.38 mmol) in DMF (4 mL) was added con.HCl (50 uL). The reaction mixture was stirred at 80° C. for 36 hours to give a brown solution. LCMS showed the purity of product is 8% (Rt=0.905 min; MS Calcd: 510.2; MS Found: 511.4 [M+H]⁺). The mixture was purified by prep-HPLC (0.225% FA as an additive) purification to give (S)-2'-((4-isopropyl-5-(4-(2-oxopyrrolidin-1-yl)phenyl)pyrimidin-2-yl)amino)-6a',7'-dihydro-6'H,9'H-spiro[cyclopropane-1,8'-pyrido[2,3-b]pyrrolo[1,2-d][1,4]oxazin]-9'-one (4.2 mg, yield: 4%) as a white solid.

1H NMR (400 MHz, DMSO-d₆) δ 0.78-0.84 (1H, m), 0.84-0.95 (1H, m), 0.95-1.04 (1H, m), 1.04-1.12 (1H, m), 1.15 (3H, d, J=7.2 Hz), 1.17 (3H, d, J=7.2 Hz), 1.95-2.03 (1H, m), 2.05-2.14 (2H, m), 2.16-2.24 (1H, m), 2.46-2.55 (2H, m), 3.02-3.14 (1H, m), 3.88 (2H, t, J=6.8 Hz), 4.00 (1H, t, J=10.4 Hz), 4.14-4.22 (1H, m), 4.61 (1H, dd, J=10.8, 2.8 Hz), 7.35 (2H, d, J=8.4 Hz), 7.75 (2H, d, J=8.4 Hz), 8.22 (1H, s), 8.30 (1H, d, J=2.8 Hz), 9.17 (1H, d, J=2.4 Hz), 9.66 (1H, brs).

The following compounds were prepared according to the general procedure described herein, as well as the individual procedure for any structurally related compounds. The procedure utilized the appropriate reagents, solvents, and starting materials according to the final products. All reactions were carried out under suitable conditions, including but not limited to temperature, pressure, and time.

Table 1 illustrates compounds of the invention that were prepared in accordance with any of the synthetic method described above using suitable starting materials, reagents and appropriate and necessary conditions to these compounds.

| Example | Compound Name | Structure |
|---|---|---|
| 217 | N,N-dimethyl-4-(6-((1-(methylsulfonyl)-2,3-dihydro-1H-pyrido[2,3-b][1,4]-oxazin-7-yl)amino)-pyridin-3-yl)bnzamide | 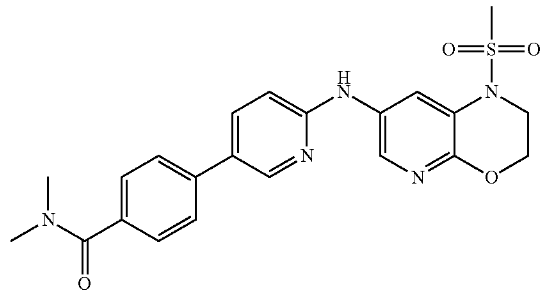 [SMILES: CN(C)C(=O)c1ccc(-c2ccc(Nc3cnc4c(c3)N(S(C)(=O)=O)CCO4)nc2)cc1] |
| 218 | 4-(6-((5-(2-(dimethylamino)-2-oxoethyl)-pyridin-3-yl)amino)-pyridin-3-yl)-N,N-dimethylbenzamide | 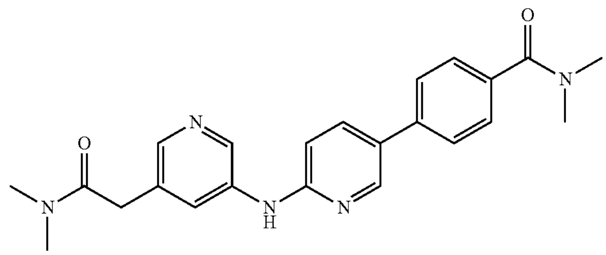 |
| 219 | N-methyl-4-(6-((5-(2-oxopyrrolidin-1-yl)-pyridin-3-yl)amino)-pyridin-3-yl)benzamide | 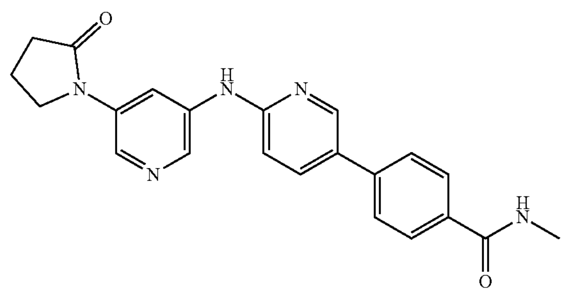 [SMILES: CNC(=O)c1ccc(-c2ccc(Nc3cncc(N4CCCC4=O)c3)nc2)cc1] |
| 220 | 4-(6-acetamido-pyridin-3-yl)-N,N-dimethylbenzamide | 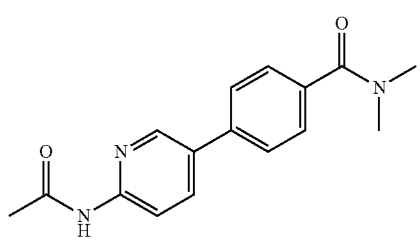 [SMILES: CC(=O)Nc1ccc(-c2ccc(C(=O)N(C)C)cc2)cn1] |
| 221 | N,N-dimethyl-4-(6-((2-oxo-1,2-dihydropyridin-4-yl)amino)-pyridin-3-yl)benzamide | 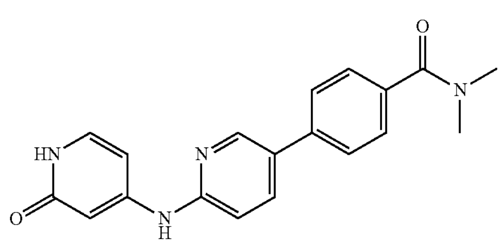 [SMILES: CN(C)C(=O)c1ccc(-c2ccc(Nc3cc[nH]c(=O)c3)nc2)cc1] |

-continued

| Example | Compound Name | Structure |
|---|---|---|
| 222 | 4-(6-((5-(3-(4-amino-benzyl)-2-oxoimid-azolidin-1-yl)pyridin-3-yl)amino)pyridin-3-yl)-N,N-dimethyl-benzamide | 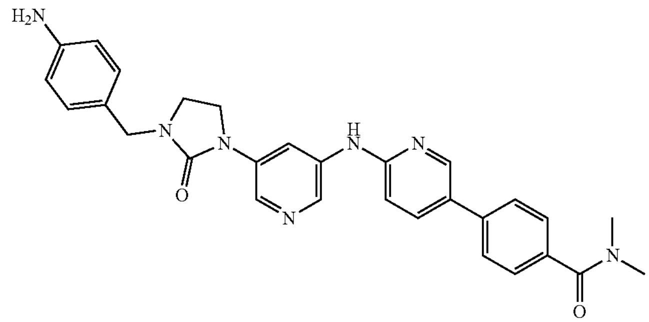 [SMILES: CN(C)C(=O)c1ccc(-c2ccc(Nc3cncc(N4CCN(Cc5ccc(N)cc5)C4=O)c3)nc2)cc1] |
| 223 | 4-(6-((5-(3-(3-amino-benzyl)-2-oxoimid-azolidin-1-yl)pyridin-3-yl)amino)pyridin-3-yl)-N,N-dimethyl-benzamide | 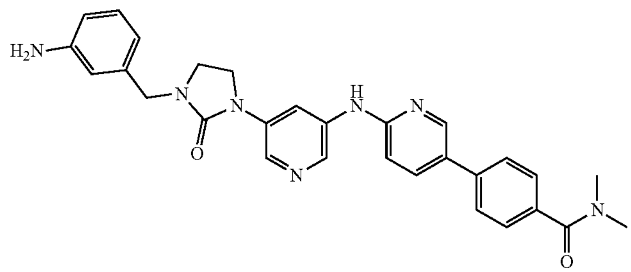 [SMILES: CN(C)C(=O)c1ccc(-c2ccc(Nc3cncc(N4CCN(Cc5cccc(N)c5)C4=O)c3)nc2)cc1] |
| 224 | 4-(6-((5-(3-(3-(3-aminophenyl)propan-amido)benzyl)-2-oxoimidazolidin-1-yl)-pyridin-3-yl)amino)-pyridin-3-yl)-N,N-dimethylbenzamide | 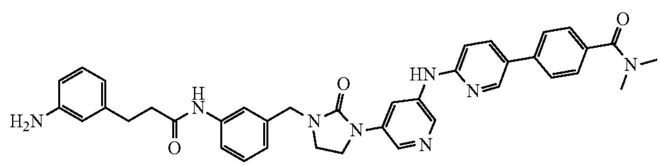 [SMILES: CN(C)C(=O)c1ccc(-c2ccc(Nc3cncc(N4CCN(Cc5cccc(NC(=O)CCc6cccc(N)c6)c5)C4=O)c3)nc2)cc1] |
| 225 | (E)-4-(6-((5-(3-(3-(3-(3-(4-(dimethylamino)-but-2-enamido)phenyl)-propanamido)benzyl)-2-oxoimidazolidin-1-yl)pyridin-3-yl)amino)-pyridin-3-yl)-N,N-dimethylbenzamide | 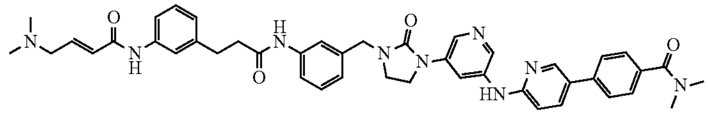 |
| 226 | 4-(6-((5-(3-(3-(2-aminoacetamido)-benzyl)-2-oxoimid-azolidin-1-yl)pyridin-3-yl)amino)pyridin-3-yl)-N,N-dimethyl-benzamide | 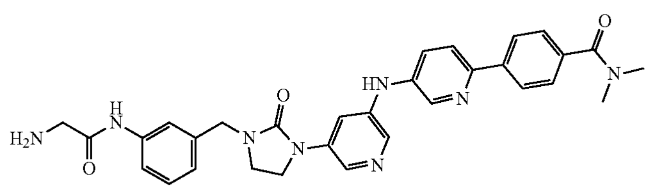 [SMILES: CN(C)C(=O)c1ccc(-c2ccc(Nc3cncc(N4CCN(Cc5cccc(NC(=O)CN)c5)C4=O)c3)cn2)cc1] |
| 227 | (E)-4-(6-((5-(3-(3-(2-(4-(dimethylamino)-but-2-enamido)-acetamido)benzyl)-2-oxoimidazolidin-1-yl)pyridin-3-yl)-amino)pyridin-3-yl)-N,N-dimethylbenz-amide | 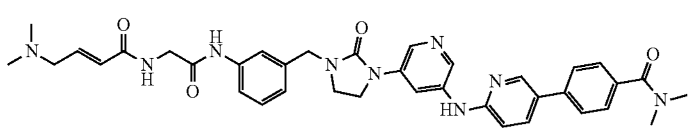 |
| 228 | 4-(6-((5-(3-(4-(2-aminoacetamido)-benzyl)-2-oxoimid-azolidin-1-yl)pyridin-3-yl)amino)pyridin-3-yl)-N,N-dimethyl-benzamide | 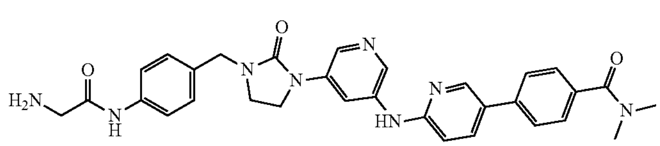 [SMILES: CN(C)C(=O)c1ccc(-c2ccc(Nc3cncc(N4CCN(Cc5ccc(NC(=O)CN)cc5)C4=O)c3)nc2)cc1] |

| Example | Compound Name | Structure |
|---|---|---|
| 229 | (E)-4-(6-((5-(3-(4-(2-(4-(dimethylamino)-but-2-enamido)-acetamido)benzyl)-2-oxoimidazolidin-1-yl)pyridin-3-yl)-amino)pyridin-3-yl)-N,N-dimethylbenz-amide | 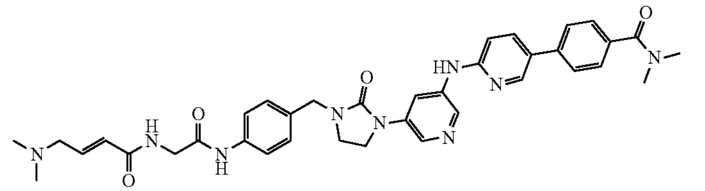 |
| 230 | 4-(6-((5-(3-(4-(3-(3-aminophenyl)propan-amido)benzyl)-2-oxoimidazolidin-1-yl)pyridin-3-yl)amino)pyridin-3-yl)-N,N-dimethylbenz-amide | 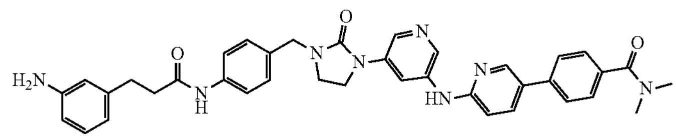 [SMILES: CN(C)C(=O)c1ccc(-c2ccc(Nc3cncc(N4CCN(Cc5ccc(NC(=O)CCc6cccc(N)c6)cc5)C4=O)c3)nc2)cc1] |
| 231 | (E)-4-(6-((5-(3-(4-(3-(3-(4-(dimethyl-amino)-but-2-enamido)phenyl)-propanamido)-benzyl)-2-oxoimid-azolidin-1-yl)pyridin-3-yl)amino)pyridin-3-yl)-N,N-dimethyl-benzamide | 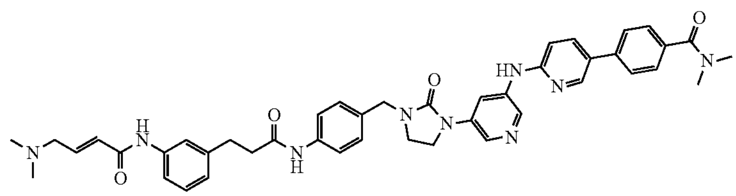 |
| 232 | N-(5-((5-(4-(dimethyl-carbamoyl)phenyl)-pyridin-2-yl)amino)-pyridin-3-yl)-1H-benzo[d]imidazole-7-carboxamide | 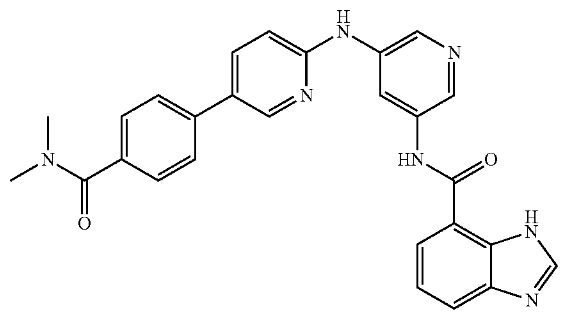 [SMILES: CN(C)C(=O)c1ccc(-c2ccc(Nc3cncc(NC(=O)c4cccc5nc[nH]c45)c3)nc2)cc1] |
| 233 | 1-(4-(6-((1-(1-hydroxy-cyclopropane-1-carbonyl)-2,3-dihydro-1H-pyrido[2,3-b][1,4]-oxazin-7-yl)amino)-pyridin-3-yl)phenyl)-pyrrolidin-2-one | 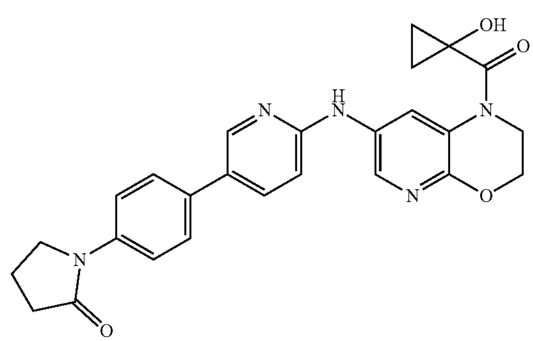 [SMILES: O=C1CCCN1c1ccc(-c2ccc(Nc3cnc4c(c3)N(C(=O)C3(O)CC3)CCO4)nc2)cc1] |
| 234 | 1-(4-(6-((1-(2-hydroxy-propanoyl)-2,3-dihydro-1H-pyrido-[2,3-b][1,4]oxazin-7-yl)amino)pyridin-3-yl)phenyl)pyrrolidin-2-one | 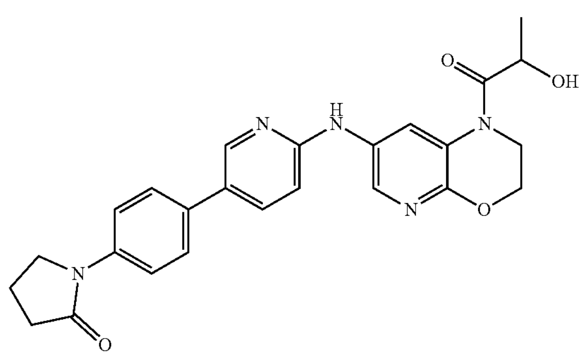 [SMILES: CC(O)C(=O)N1CCOc2ncc(Nc3ccc(-c4ccc(N5CCCC5=O)cc4)cn3)cc21] |

| Example | Compound Name | Structure |
| --- | --- | --- |
| 235 | 1-(4-(6-((1-(2-hydroxy-acetyl)-2,3-dihydro-1H-pyrido[2,3-b][1,4]-oxazin-7-yl)amino)-pyridin-3-yl)phenyl)-pyrrolidin-2-one | 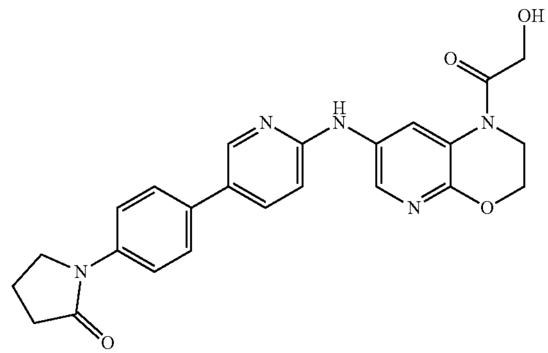 [SMILES: O=C1CCCN1c1ccc(-c2ccc(Nc3cnc4c(c3)N(C(=O)CO)CCO4)nc2)cc1] |
| 236 | (S)-2-((5-(4-((R)-4-hydroxy-2-oxo-pyrrolidin-1-yl)-phenyl)pyridin-2-yl)amino)-6,6a,7,8-tetrahydro-9H-pyrido-[2,3-b]pyrrolo[1,2-d][1,4]oxazin-9-one | 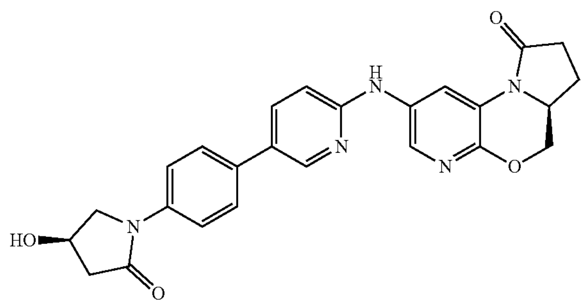 [SMILES: O=C1C[C@@H](O)CN1c1ccc(-c2ccc(Nc3cnc4c(c3)N3C(=O)CC[C@H]3CO4)nc2)cc1] |
| 237 | (S)-2-((5-(4-((S)-4-hydroxy-2-oxo-pyrrolidin-1-yl)-phenyl)pyridin-2-yl)-amino)-6,6a,7,8-tetrahydro-9H-pyrido-[2,3-b]pyrrolo[1,2-d]-[1,4]oxazin-9-one | 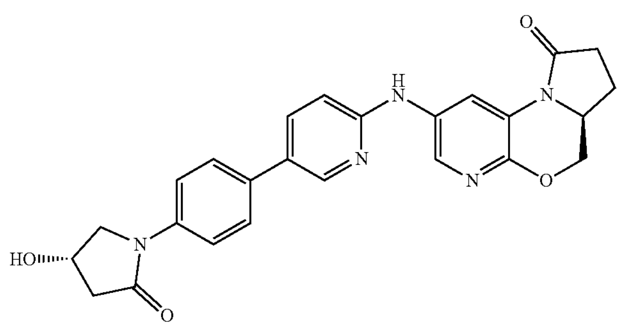 [SMILES: O=C1C[C@H](O)CN1c1ccc(-c2ccc(Nc3cnc4c(c3)N3C(=O)CC[C@H]3CO4)nc2)cc1] |
| 238 | 1-(4-(6-((1-(2-hydroxy-2-methylpropanoyl)-2,3-dihydro-1H-pyrido[2,3-b][1,4]-oxazin-7-yl)amino)-pyridin-3-yl)phenyl)-pyrrolidin-2-one | 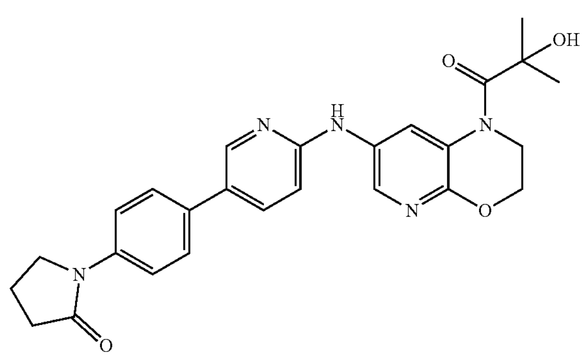 [SMILES: CC(C)(O)C(=O)N1CCOc2ncc(Nc3ccc(-c4ccc(N5CCCC5=O)cc4)cn3)cc21] |

| Example | Compound Name | Structure |
|---|---|---|
| 239 | 5-methoxy-N-(5-((5-(4-(2-oxopyrrolidin-1-yl)phenyl)pyridin-2-yl)amino)pyridin-3-yl)nicotinamide | 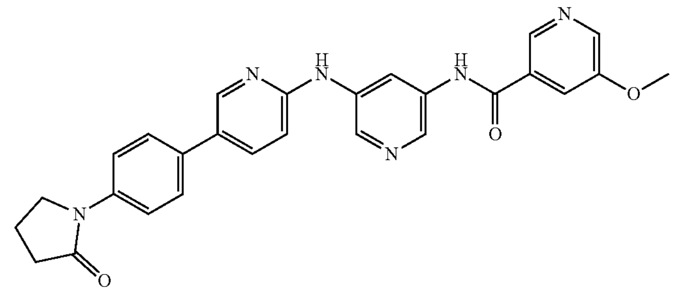 [SMILES: COc1cncc(C(=O)Nc2cncc(Nc3ccc(-c4ccc(N5CCCC5=O)cc4)cn3)c2)c1] |
| 240 | 6-oxo-N-(5-((5-(4-(2-oxopyrrolidin-1-yl)-phenyl)pyridin-2-yl)-amino)pyridin-3-yl)-1,6-dihydropyridine-3-carboxamide | 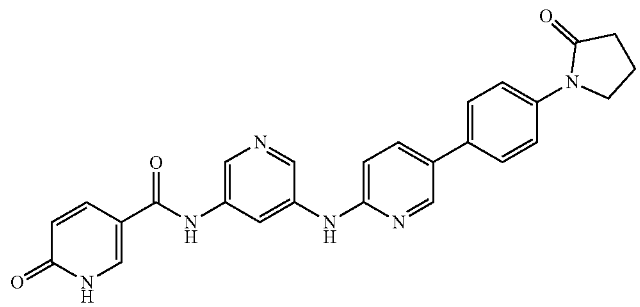 [SMILES: O=C(Nc1cncc(Nc2ccc(-c3ccc(N4CCCC4=O)cc3)cn2)c1)c1ccc(=O)[nH]c1] |
| 241 | 1-(4-(6-((5-(4-(3-methoxypropanoyl)-piperazin-1-yl)-pyridin-3-yl)amino)-pyridin-3-yl)phenyl)-pyrrolidin-2-one | 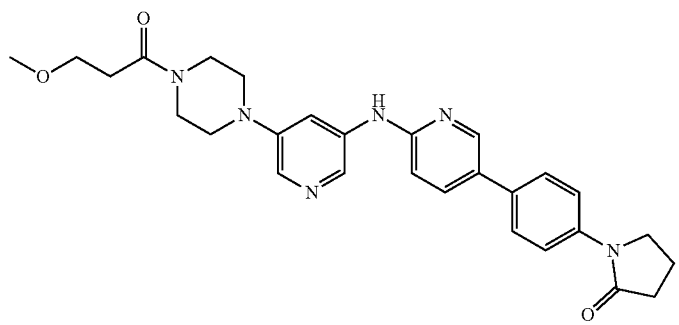 [SMILES: COCCC(=O)N1CCN(c2cncc(Nc3ccc(-c4ccc(N5CCCC5=O)cc4)cn3)c2)CC1] |
| 242 | (S)-N,N-dimethyl-4-(6-((9-oxo-6a,7,8,9-tetrahydro-6H-pyrido-[2,3-b]pyrrolo[1,2-d]-[1,4]oxazin-2-yl)-amino)pyridin-3-yl)-benzamide | 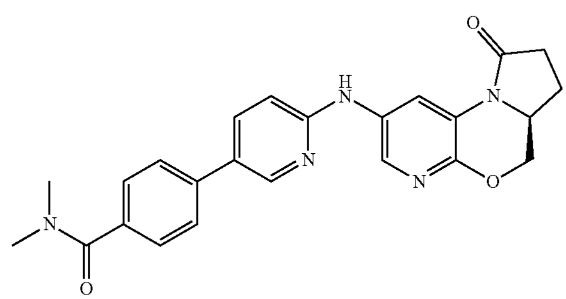 [SMILES: CN(C)C(=O)c1ccc(-c2ccc(Nc3cnc4c(c3)N3C(=O)CC[C@H]3CO4)nc2)cc1] |
| 243 | 2,3-difluoro-N-(5-((5-(4-(2-oxopyrrolidin-1-yl)phenyl)pyridin-2-yl)amino)pyridin-3-yl)benzamide | 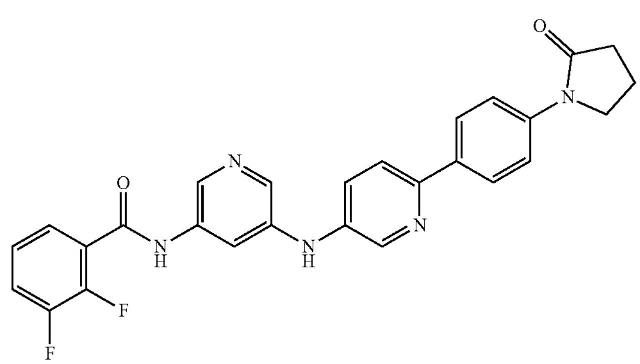 [SMILES: O=C(Nc1cncc(Nc2ccc(-c3ccc(N4CCCC4=O)cc3)nc2)c1)c1cccc(F)c1F] |

-continued

| Example | Compound Name | Structure |
|---|---|---|
| 244 | (R)-1-(4-(6-((5-(4-(tetrahydrofuran-3-carbonyl)piperazin-1-yl)pyridin-3-yl)amino)pyridin-3-yl)phenyl)pyrrolidin-2-one | 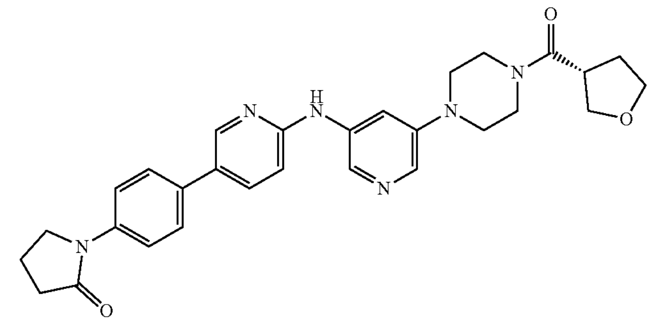 [SMILES: O=C([C@@H]1CCOC1)N1CCN(c2cncc(Nc3ccc(-c4ccc(N5CCCC5=O)cc4)cn3)c2)CC1] |
| 245 | (S)-1-(4-(6-((5-(4-(tetrahydrofuran-3-carbonyl)piperazin-1-yl)pyridin-3-yl)amino)pyridin-3-yl)phenyl)pyrrolidin-2-one | 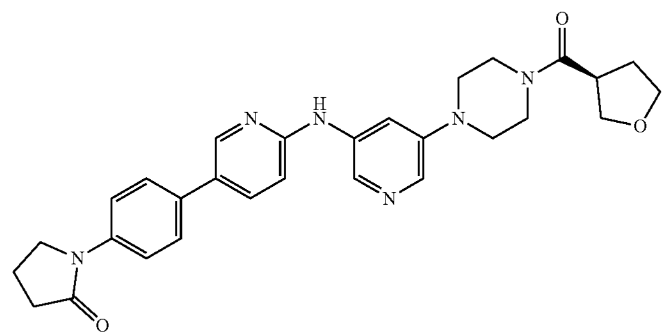 [SMILES: O=C([C@H]1CCOC1)N1CCN(c2cncc(Nc3ccc(-c4ccc(N5CCCC5=O)cc4)cn3)c2)CC1] |
| 246 | (S)-2-((5-(3-fluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one | 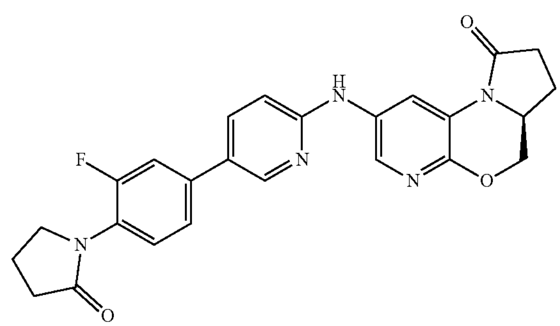 [SMILES: O=C1CCCN1c1ccc(-c2ccc(Nc3cnc4c(c3)N3C(=O)CC[C@H]3CO4)nc2)cc1F] |
| 247 | N-(5-((5-(4-(2-oxo-pyrrolidin-1-yl)-phenyl)pyridin-2-yl)-amino)pyridin-3-yl)-2-phenylcyclopropane-1-carboxamide | 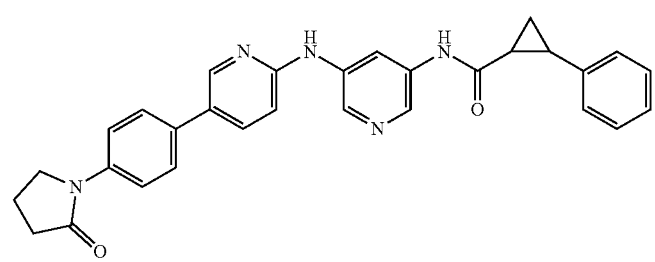 [SMILES: O=C(Nc1cncc(Nc2ccc(-c3ccc(N4CCCC4=O)cc3)cn2)c1)C1CC1c1ccccc1] |
| 248 | 1-ethyl-6-oxo-N-(5-((5-4-(2-oxo-pyrrolidin-1-yl)-phenyl)pyridin-2-yl)amino)pyridin-3-yl)-1,6-dihydropyridine-3-carboxamide | 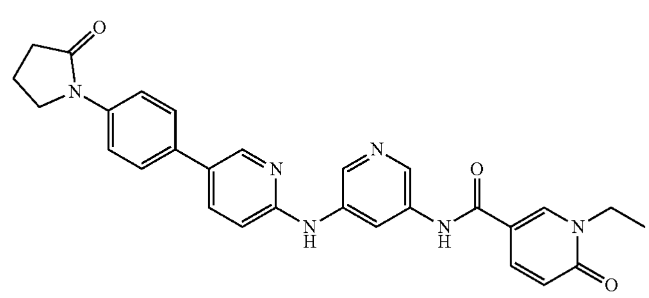 [SMILES: CCn1cc(C(=O)Nc2cncc(Nc3ccc(-c4ccc(N5CCCC5=O)cc4)cn3)c2)ccc1=O] |

| Example | Compound Name | Structure |
|---|---|---|
| 249 | 6-ethoxy-N-(5-((5-(4-(2-oxopyrrolidin-1-yl)phenyl)pyridin-2-yl)amino)pyridin-3-yl)nicotinamide | 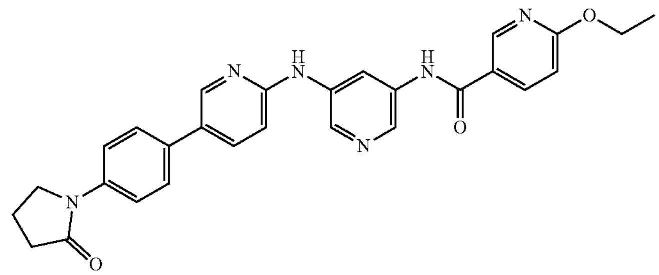 [SMILES: CCOc1ccc(C(=O)Nc2cncc(Nc3ccc(-c4ccc(N5CCCC5=O)cc4)cn3)c2)cn1] |
| 250 | 2-methyl-N-(5-((5-(4-(2-oxopyrrolidin-1-yl)phenyl)pyridin-2-yl)amino)pyridin-3-yl)morpholine-4-carboxamide | 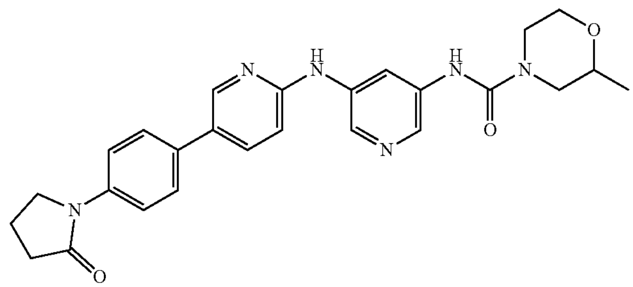 [SMILES: CC1CN(C(=O)Nc2cncc(Nc3ccc(-c4ccc(N5CCCC5=O)cc4)cn3)c2)CCO1] |
| 251 | N-(5-((5-(4-(2-oxo-pyrrolidin-1-yl)-phenyl)pyridin-2-yl)-amino)pyridin-3-yl)-morpholine-4-carboxamide | 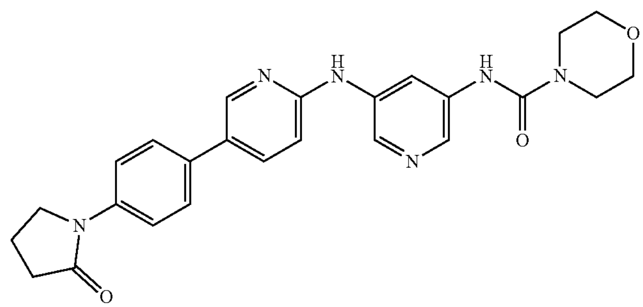 [SMILES: O=C(Nc1cncc(Nc2ccc(-c3ccc(N4CCCC4=O)cc3)cn2)c1)N1CCOCC1] |
| 252 | (1S,2S)-2-ethoxy-N-(5-((5-(4-(2-oxo-pyrrolidin-1-yl)-phenyl)pyridin-2-yl)amino)pyridin-3-yl)cyclopropane-1-carboxamide | 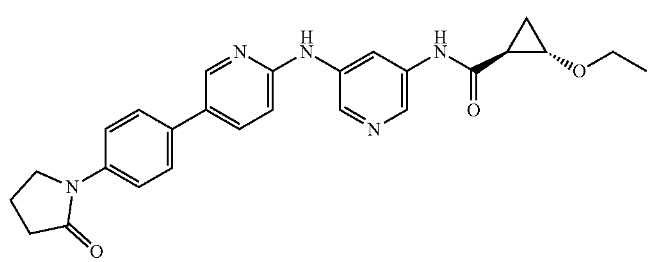 [SMILES: CCO[C@H]1C[C@@H]1C(=O)Nc1cncc(Nc2ccc(-c3ccc(N4CCCC4=O)cc3)cn2)c1] |
| 253 | 5-methoxy-N-(5-((5-(4-(2-oxopyrrolidin-1-yl)phenyl)pyridin-2-yl)amino)pyridin-3-yl)-1H-benzo[d]imidazole-7-carboxamide | 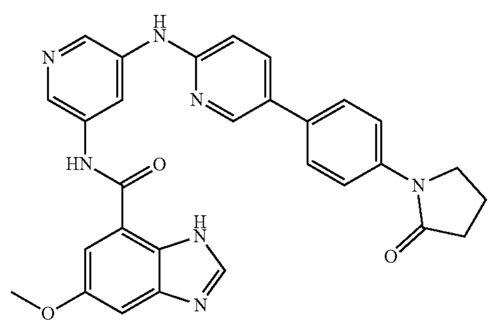 [SMILES: COc1cc(C(=O)Nc2cncc(Nc3ccc(-c4ccc(N5CCCC5=O)cc4)cn3)c2)c2[nH]cnc2c1] |

| Example | Compound Name | Structure |
|---|---|---|
| 254 | N-(5-((5-(4-(2-oxo-pyrrolidin-1-yl)-phenyl)pyridin-2-yl)amino)pyridin-3-yl)-2H-tetrazole-5-carboxamide | 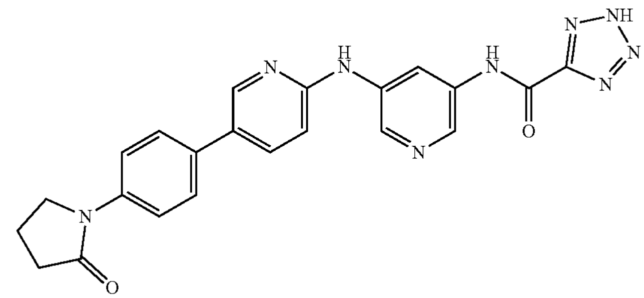 [SMILES: O=C(Nc1cncc(Nc2ccc(-c3ccc(N4CCCC4=O)cc3)cn2)c1)c1nn[nH]n1] |
| 255 | (S)-8,8-dimethyl-2-((5-(4-(2-oxopyrrol-idin-1-yl)phenyl)-pyridin-2-yl)amino)-6,6a,7,8-tetrahydro-9H-pyrido[2,3-b]pyrrolo[1,2-d][1,4]-oxazin-9-one | 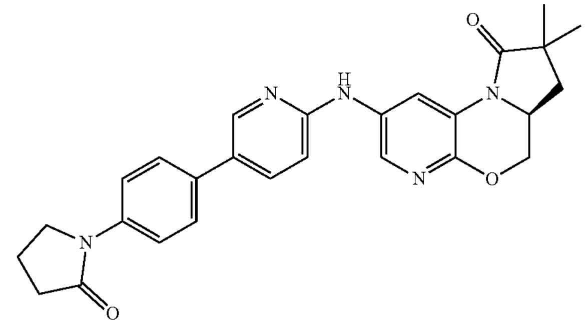 [SMILES: CC1(C)C[C@H]2COc3ncc(Nc4ccc(-c5ccc(N6CCCC6=O)cc5)cn4)cc3N2C1=O] |
| 256 | 3-methyl-N-(5-((5-(4-(2-oxopyrrolidin-1-yl)phenyl)pyridin-2-yl)amino)pyridin-3-yl)piperazine-1-carboxamide | 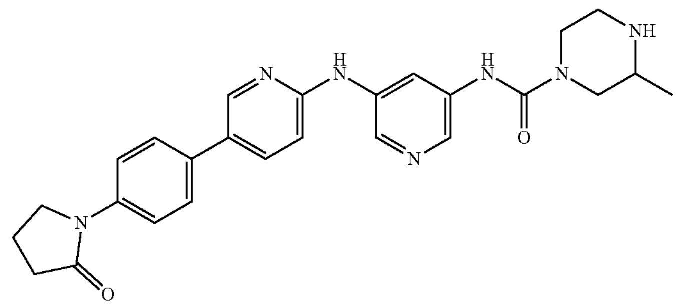 [SMILES: CC1CN(C(=O)Nc2cncc(Nc3ccc(-c4ccc(N5CCCC5=O)cc4)cn3)c2)CCN1] |
| 257 | 3-cyclopropyl-N-(5-((5-(4-(2-oxopyrrol-idin-1-yl)phenyl)-pyridin-2-yl)amino)-pyridin-3-yl)piper-azine-1-carboxamide | 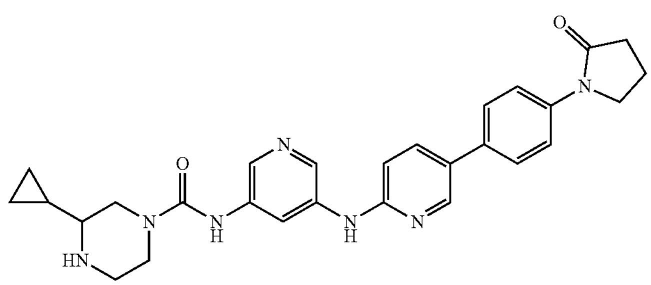 [SMILES: O=C(Nc1cncc(Nc2ccc(-c3ccc(N4CCCC4=O)cc3)cn2)c1)N1CCNC(C2CC2)C1] |
| 258 | (S)-2-((5-(3-fluoro-4-(2-oxopyrrolidin-1-yl)phenyl)pyridin-2-yl)amino)-8,8-dimethyl-6,6a,7,8-tetrahydro-9H-pyrido[2,3-b]pyrrolo-[1,2-d][1,4]oxazin-9-one | 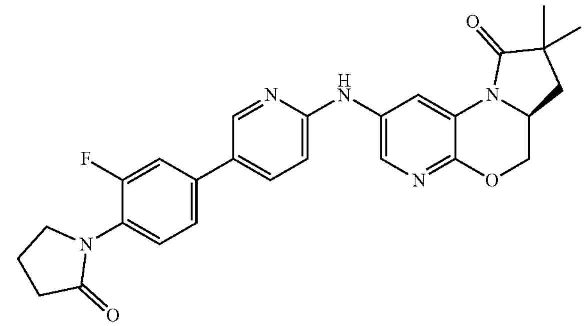 [SMILES: CC1(C)C[C@H]2COc3ncc(Nc4ccc(-c5ccc(N6CCCC6=O)c(F)c5)cn4)cc3N2C1=O] |

| Example | Compound Name |
|---|---|
| 259 | (6aS)-8-methyl-2-((5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one |
| 260 | (S)-2'-((5-(4-(2-oxo-pyrrolidin-1-yl)-phenyl)pyridin-2-yl)amino)-6a',7'-dihydro-6'H,9'H-spiro[cyclopropane-1,8'-pyrido[2,3-b]-pyrrolo[1,2-d][1,4]-oxazin]-9'-one |
| 261 | (6aS)-2-((5-(3-fluoro-4-(2-oxopyrrolidin-1-yl)phenyl)pyridin-2-yl)amino)-8-methyl-6,6a,7,8-tetrahydro-9H-pyrido[2,3-b]-pyrrolo[1,2-d][1,4]-oxazin-9-one |
| 262 | 2-cyclopropyl-N-(5-((5-(4-(2-oxo-pyrrolidin-1-yl)-phenyl)pyridin-2-yl)amino)pyridin-3-yl)morpholine-4-carboxamide |
| 263 | (S)-2-((4'-(difluoro-methyl)-5-(2-oxo-pyrrolidin-1-yl)-[2,3'-bipyridin]-6'-yl)-amino)-6,6a,7,8-tetra-hydro-9H-pyrido[2,3-b]pyrrolo[1,2-d][1,4]-oxazin-9-one |

-continued

| Example | Compound Name | Structure |
|---|---|---|
| 264 | N,N-dimethyl-4-(2-(pyridin-3-ylamino)-pyrimidin-5-yl)-benzamide | 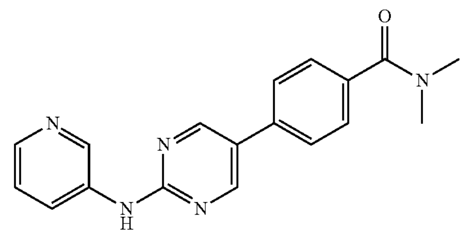 [SMILES: CN(C)C(=O)c1ccc(-c2cnc(Nc3cccnc3)nc2)cc1] |
| 265 | (R)-8-((5-(4-(2-oxopyrrolidin-1-yl)-phenyl)pyridin-2-yl)-amino)-3a,4-dihydro-1H,3H-oxazolo-[3,4-d]pyrido[2,3-b][1,4]oxazin-1-one | 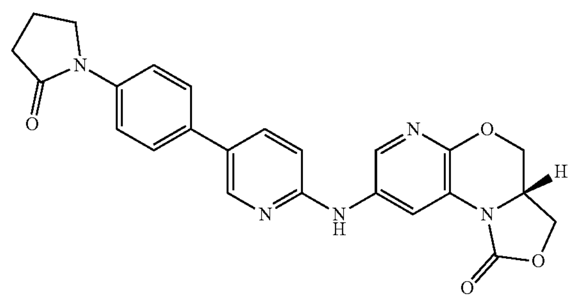 [SMILES: O=C1CCCN1c1ccc(-c2ccc(Nc3cnc4c(c3)N3C(=O)OC[C@H]3CO4)nc2)cc1] |
| 266 | (S)-2-((4-(2-amino-propan-2-yl)-5-(2-fluoro-4-(2-oxo-pyrrolidin-1-yl)-phenyl)pyridin-2-yl)amino)-6,6a,7,8-tetrahydro-9H-pyrido-[2,3-b]pyrrolo[1,2-d]-[1,4]oxazin-9-one | 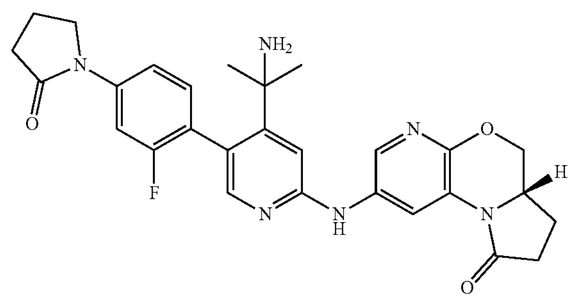 [SMILES: CC(C)(N)c1cc(Nc2cnc3c(c2)N2C(=O)CC[C@H]2CO3)ncc1-c1ccc(N2CCCC2=O)cc1F] |
| 267 | (6aS)-2-((5-(3-fluoro-4-(2-oxopyrrolidin-1-yl)phenyl)pyridin-2-yl)amino)-8-hydroxy-6,6a,7,8-tetrahydro-9H-pyrido[2,3-b]-pyrrolo[1,2-d][1,4]-oxazin-9-one | 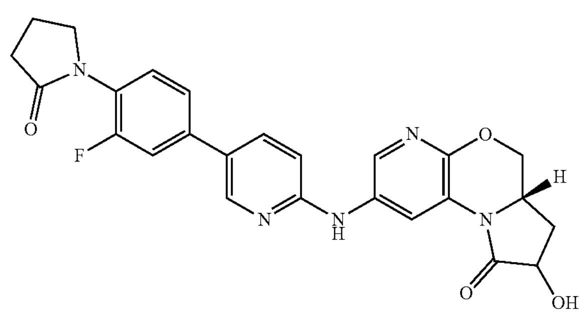 [SMILES: O=C1CCCN1c1ccc(-c2ccc(Nc3cnc4c(c3)N3C(=O)C(O)C[C@H]3CO4)nc2)cc1F] |
| 268 | (6aS)-8-hydroxy-2-((5-(4-(2-oxopyrrol-idin-1-yl)phenyl)-pyridin-2-yl)amino)-6,6a,7,8-tetrahydro-9H-pyrido[2,3-b]-pyrrolo[1,2-d][1,4]-oxazin-9-one | 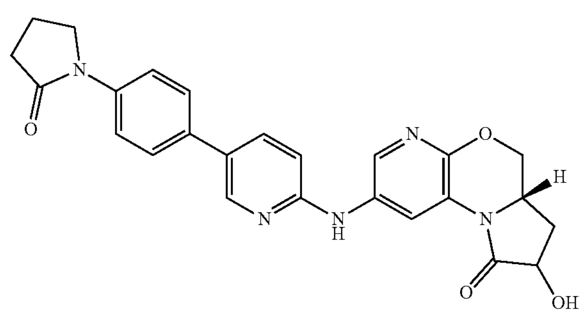 [SMILES: O=C1CCCN1c1ccc(-c2ccc(Nc3cnc4c(c3)N3C(=O)C(O)C[C@H]3CO4)nc2)cc1] |

-continued

| Example | Compound Name |
|---|---|
| 269 | (6aR)-2-((5-(4-(1-methyl-2-oxopyrrolidin-3-yl)phenyl)pyridin-2-yl)amino)-6,6a,7,8-tetrahydro-9H-pyrido[2,3-b]pyrrolo[1,2-d][1,4]oxazin-9-one |
| 270 | (6aS,8R)-2-((5-(3-fluoro-4-(2-oxopyrrolidin-1-yl)phenyl)pyridin-2-yl)amino)-8-hydroxy-8-methyl-6,6a,7,8-tetrahydro-9H-pyrido[2,3-b]pyrrolo[1,2-d][1,4]oxazin-9-one |
| 271 | (6aS,8R)-8-hydroxy-8-methyl-2-((5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one |
| 272 | 1-(5-((5-(3-fluoro-4-(2-oxopyrrolidin-1-yl)phenyl)pyridin-2-yl)amino)pyridin-3-yl)imidazolidin-2-one |
| 273 | (S)-2-((4-(3-methoxycyclobutyl)-5-(4-(2-oxopyrrolidin-1-yl)phenyl)pyrimidin-2-yl)amino)-6,6a7,8-tetrahydro-9H-pyrido[2,3-b]pyrrolo[1,2-d][1,4]oxazin-9-one |

-continued

| Example | Compound Name | Structure |
|---|---|---|
| 274 | (S)-2-((1'-(4-methyl-4H-1,2,4-triazol-3-yl)-1',2',3',6'-tetrahydro-[3,4'-bipyridin]-6-yl)-amino)-6,6a,7,8-tetrahydro-9H-pyrido[2,3-b]pyrrolo[1,2-d][1,4]-oxazin-9-one | 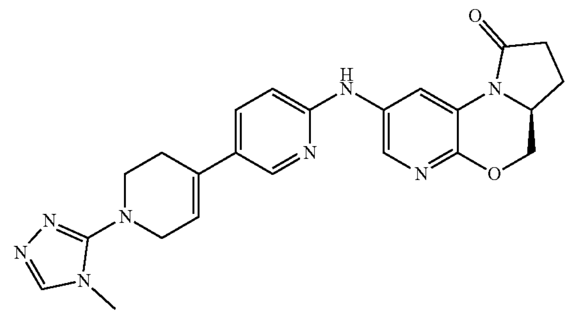 [SMILES: Cn1cnnc1N1CC=C(c2ccc(Nc3cnc4c(c3)N3C(=O)CC[C@H]3CO4)nc2)CC1] |
| 275 | (S)-2-((5-(4-(4-methyl-4H-1,2,4-triazol-3-yl)-piperazin-1-yl)pyridin-2-yl)amino)-6,6a,7,8-tetrahydro-9H-pyrido-[2,3-b]pyrrolo[1,2-d]-[1,4]oxazin-9-one | 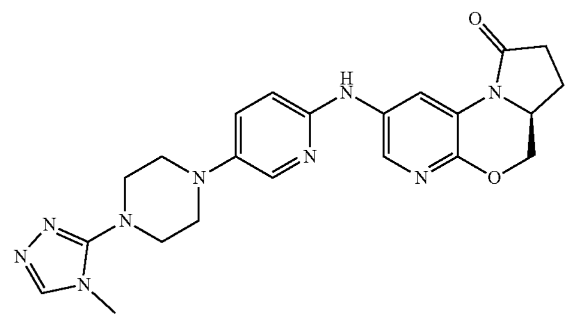 [SMILES: Cn1cnnc1N1CCN(c2ccc(Nc3cnc4c(c3)N3C(=O)CC[C@H]3CO4)nc2)CC1] |
| 276 | (S)-2-((5-(4-(4-methylpyridazin-3-yl)phenyl)pyridin-2-yl)amino)-6,6a,7,8-tetrahydro-9H-pyrido-[2,3-b]pyrrolo[1,2-d]-[1,4]oxazin-9-one | 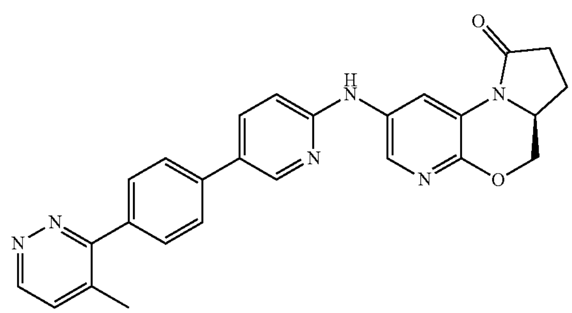 [SMILES: Cc1ccnnc1-c1ccc(-c2ccc(Nc3cnc4c(c3)N3C(=O)CC[C@H]3CO4)nc2)cc1] |
| 277 | (S)-2-((5-(4-(4-methylisoxazol-5-yl)phenyl)pyridin-2-yl)amino)-6,6a,7,8-tetrahydro-9H-pyrido-[2,3-b]pyrrolo[1,2-d]-[1,4]oxazin-9-one | 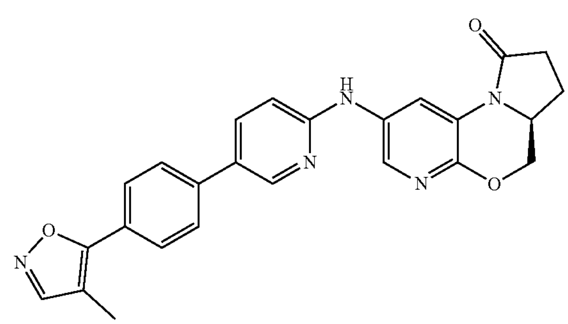 [SMILES: Cc1cnoc1-c1ccc(-c2ccc(Nc3cnc4c(c3)N3C(=O)CC[C@H]3CO4)nc2)cc1] |
| 278 | (S)-2-((4-isopropyl-5-(4-(5-methyl-1H-1,2,3-triazol-1-yl)-phenyl)pyrimidin-2-yl)amino)-6,6a,7,8-tetrahydro-9H-pyrido-[2,3-b]pyrrolo[1,2-d]-[1,4]oxazin-9-one | 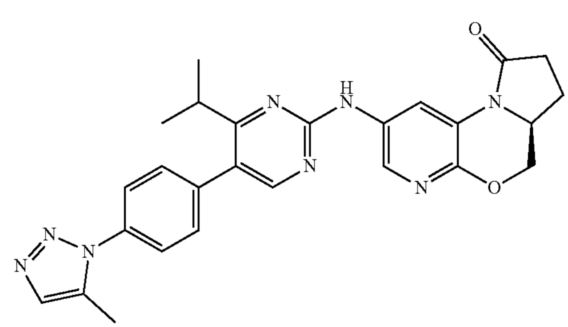 [SMILES: Cc1cnnn1-c1ccc(-c2cnc(Nc3cnc4c(c3)N3C(=O)CC[C@H]3CO4)nc2C(C)C)cc1] |

| Example | Compound Name |
|---|---|
| 279 | (S)-2-((5-(3-methyl-2-oxo-1-oxa-3,8-diaza-spiro[4.5]decan-8-yl)-pyridin-2-yl)amino)-6,6a,7,8-tetrahydro-9H-pyrido[2,3-b]-pyrrolo[1,2-d][1,4]-oxazin-9-one |
| 280 | (S)-2-((4-morpholino-5-(4-(2-oxopyrrolidin-1-yl)phenyl)pyrimidin-2-yl)amino)-6,6a,7,8-tetrahydro-9H-pyrido-[2,3-b]pyrrolo[1,2-d]-[1,4]oxazin-9-one |
| 281 | (S)-2-((4-(4-methyl-piperazin-1-yl)-5-(4-(2-oxopyrrolidin-1-yl)phenyl)pyrimidin-2-yl)amino)-6,6a,7,8-tetrahydro-9H-pyrido-[2,3-b]pyrrolo[1,2-d]-[1,4]oxazin-9-one |
| 282 | (S)-2-((4-(methoxy-methyl)-5-(4-(4-methylisoxazol-3-yl)phenyl)pyridin-2-yl)amino)-6,6a,7,8-tetrahydro-9H-pyrido-[2,3-b]pyrrolo[1,2-d]-[1,4]oxazin-9-one |
| 283 | (S)-2-((5-(4-(4-methyl-isoxazol-3-yl)phenyl)-pyridin-2-yl)amino)-6,6a,7,8-tetrahydro-9H-pyrido[2,3-b]-pyrrolo[1,2-d][1,4]-oxazin-9-one |

| Example | Compound Name |
|---|---|
| 284 | (S)-2-((4-cyclobutoxy-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one |
| 285 | (S)-2-((4-cyclopropyl-5-(4-(4-methyl-4H-1,2,4-triazol-3-yl)phenyl)pyridin-2-yl)amino)-6,6a,7,8-tetrahydro-9H-pyrido[2,3-b]pyrrolo[1,2-d][1,4]oxazin-9-one |
| 286 | (S)-2-((4-(3-methoxyazetidin-1-yl)-5-(4-(2-oxopyrrolidin-1-yl)phenyl)pyrimidin-2-yl)amino)-6,6a,7,8-tetrahydro-9H-pyrido[2,3-b]pyrrolo[1,2-d][1,4]oxazin-9-one |
| 287 | (S)-2-((4-methoxy-5-(4-(4-methyl-4H-1,2,4-triazol-3-yl)phenyl)pyrimidin-2-yl)amino)-6,6a,7,8-tetrahydro-9H-pyrido[2,3-b]pyrrolo[1,2-d][1,4]oxazin-9-one |

| Example | Compound Name | Structure |
|---|---|---|
| 288 | (S)-2-((4-methoxy-5-(4-(5-methyl-1H-1,2,3-triazol-1-yl)-phenyl)pyrimidin-2-yl)amino)-6,6a,7,8-tetrahydro-9H-pyrido-[2,3-b]pyrrolo[1,2-d]-[1,4]oxazin-9-one | 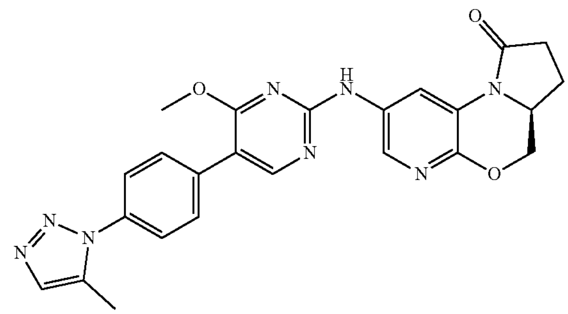 [SMILES: COc1nc(Nc2cnc3c(c2)N2C(=O)CC[C@H]2CO3)ncc1-c1ccc(-n2nncc2C)cc1] |
| 289 | (S)-2-((5-(4-(5-methyl-1H-1,2,3-triazol-1-yl)phenyl)pyridin-2-yl)amino)-6,6a,7,8-tetrahydro-9H-pyrido-[2,3-b]pyrrolo[1,2-d]-[1,4]oxazin-9-one | 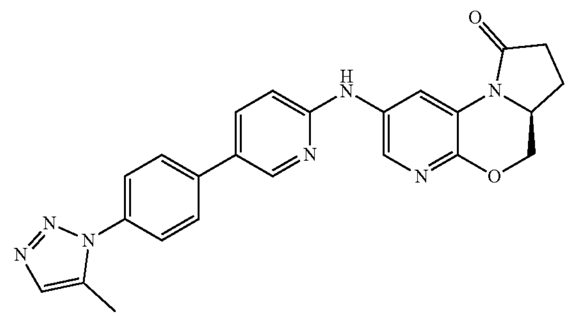 [SMILES: Cc1cnnn1-c1ccc(-c2ccc(Nc3cnc4c(c3)N3C(=O)CC[C@H]3CO4)nc2)cc1] |
| 290 | (S)-2-((4-methoxy-5-(4-(5-methyl-4H-1,2,4-triazol-3-yl)phenyl)-pyridin-2-yl)amino)-6,6a,7,8-tetrahydro-9H-pyrido[2,3-b]pyrrolo-[1,2-d][1,4]oxazin-9-one | 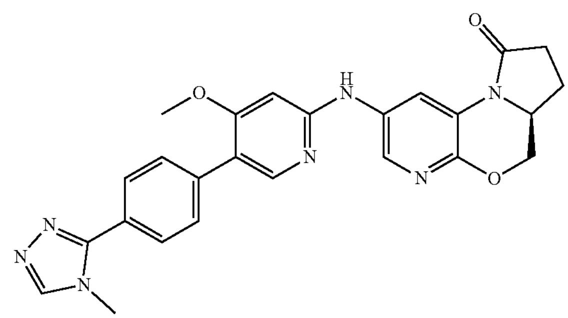 [SMILES: COc1cc(Nc2cnc3c(c2)N2C(=O)CC[C@H]2CO3)ncc1-c1ccc(-c2nncn2C)cc1] |
| 291 | (S)-2-((5-(4-(4-methyl-4H-1,2,4-triazol-3-yl)-phenyl)pyridin-2-yl)-amino)-6,6a,7,8-tetra-hydro-9H-pyrido[2,3-b]pyrrolo[1,2-d][1,4]-oxazin-9-one | 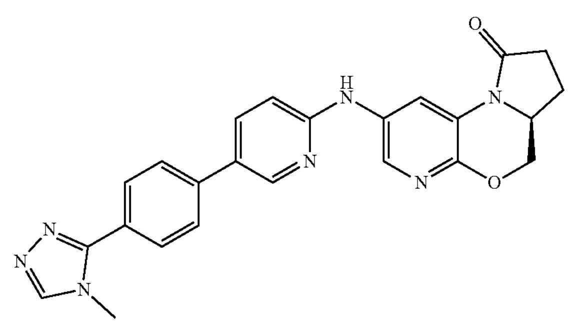 [SMILES: Cn1cnnc1-c1ccc(-c2ccc(Nc3cnc4c(c3)N3C(=O)CC[C@H]3CO4)nc2)cc1] |
| 292 | 4-(4-(2-((2-(2,6-dioxopiperidin-3-yl)-1,3-dioxoisoindolin-4-yl)oxy)acetamido)-butanamido)-N-(5-((5-(4-(2-oxopyrrol-idin-1-yl)phenyl)-pyridin-2-yl)amino)-pyridin-3-yl)benz-amide | 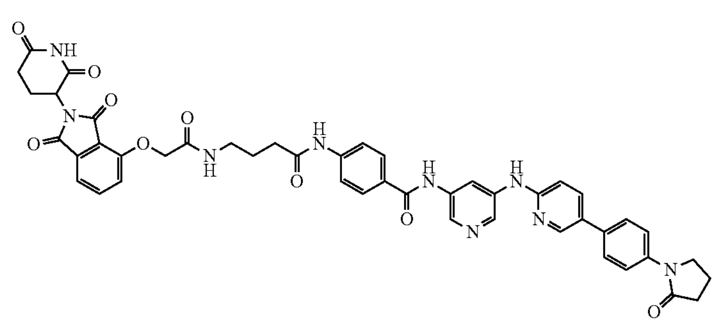 [SMILES: O=C(COc1cccc2c1C(=O)N(C1CCC(=O)NC1=O)C2=O)NCCCC(=O)Nc1ccc(C(=O)Nc2cncc(Nc3ccc(-c4ccc(N5CCCC5=O)cc4)cn3)c2)cc1] |

| Example | Compound Name |
|---|---|
| 293 | (S)-4-(4-(methoxy-methyl)-2-((9-oxo-6a,7,8,9-tetrahydro-6H-pyrido[2,3-b]pyrrolo-[1,2-d][1,4]oxazin-2-yl)amino)pyrimidin-5-yl)-N,N-dimethyl-benzamide |
| 294 | (S)-4-(4-methoxy-2-((9-oxo-6a,7,8,9-tetra-hydro-6H-pyrido[2,3-b]pyrrolo[1,2-d][1,4]-oxazin-2-yl)amino)-pyrimidin-5-yl)-N,N-dimethylbenzamide |
| 295 | (R)-8-((5-(3-fluoro-4-(2-oxopyrrolidin-1-yl)phenyl)pyridin-2-yl)amino)-3a,4-dihydro-1H,3H-oxazolo[3,4-d]pyrido-[2,3-b][1,4]oxazin-1-one |
| 296 | 4-(2-(2-(2-(2-((2-(2,6-dioxopiperidin-3-yl)-1,3-dioxoiso-indolin-4-yl)amino)-ethoxy)ethoxy)-ethoxy)acetamido)-N-(5-((5-(4-(2-oxopyrrolidin-1-yl)-phenyl)pyridin-2-yl)-amino)pyridin-3-yl)-benzamide |
| 297 | (S)-2-((5-(4-(4-iso-butyl-4H-1,2,4-triazol-3-yl)phenyl)pyridin-2-yl)amino)-6,6a,7,8-tetrahydro-9H-pyrido-[2,3-b]pyrrolo[1,2-d]-[1,4]oxazin-9-one |

| Example | Compound Name |
|---|---|
| 298 | (S)-N,N-dimethyl-4-(2-((9'-oxo-6a',7'-dihydro-6'H,9'H-spiro[cyclopropane-1,8'-pyrido[2,3-b]-pyrrolo[1,2-d][1,4]-oxazin]-2'-yl)amino)-pyrimidin-5-yl)benz-amide |
| 299 | (S)-2-fluoro-N,N-dimethyl-4-(2-((9-oxo-6a,7,8,9-tetra-hydro-6H-pyrido[2,3-b]pyrrolo[1,2-d][1,4]-oxazin-2-yl)amino)-pyrimidin-5-yl)benz-amide |
| 300 | (S)-2-((5-(4-((R)-2-methyl-5-oxopyrrol-idin-1-yl)phenyl)-pyridin-2-yl)amino)-6,6a,7,8-tetrahydro-9H-pyrido[2,3-b]-pyrrolo[1,2-d][1,4]-oxazin-9-one |
| 301 | (S)-2-((5-(4-(pyrrol-idine-1-carbonyl)-phenyl)pyrimidin-2-yl)amino)-6,6a,7,8-tetrahydro-9H-pyrido-[2,3-b]pyrrolo[1,2-d][1,4]oxazin-9-one |
| 302 | (S)-2-((5-(4-(azetidine-1-carbonyl)phenyl)-pyrimidin-2-yl)-amino)-6,6a,7,8-tetra-hydro-9H-pyrido[2,3-b]pyrrolo[1,2-d][1,4]-oxazin-9-one |

| Example | Compound Name | Structure |
|---|---|---|
| 303 | (S)-N,N-dimethyl-4-(2-((9-oxo-6a,7,8,9-tetrahydro-6H-pyrido[2,3-b]pyrrolo[1,2-d][1,4]oxazin-2-yl)amino)pyrimidin-5-yl)benzamide | 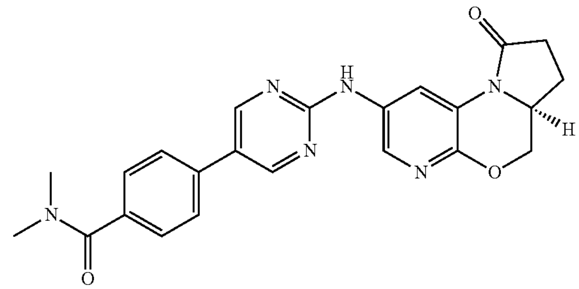 [SMILES: CN(C)C(=O)c1ccc(-c2cnc(Nc3cnc4c(c3)N3C(=O)CC[C@H]3CO4)nc2)cc1] |
| 304 | (S)-2-((9-fluoro-5,5-dimethyl-8-(2-oxopyrrolidin-1-yl)-5H-chromeno[3,4-d]pyrimidin-3-yl)amino)-6,6a,7,8-tetrahydro-9H-pyrido[2,3-b]pyrrolo[1,2-d][1,4]oxazin-9-one | 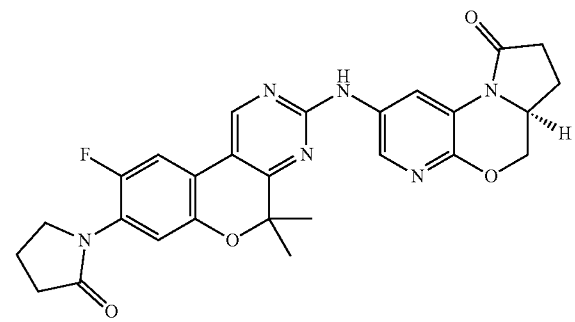 [SMILES: CC1(C)Oc2cc(N3CCCC3=O)c(F)cc2-c2cnc(Nc3cnc4c(c3)N3C(=O)CC[C@H]3CO4)nc21] |
| 305 | (S)-2-((5-(4-(2-oxo-pyrrolidin-1-yl-4,4,5,5-d4)phenyl)-pyridin-2-yl)amino)-6,6a,7,8-tetrahydro-9H-pyrido[2,3-b]-pyrrolo[1,2-d][1,4]-oxazin-9-one | 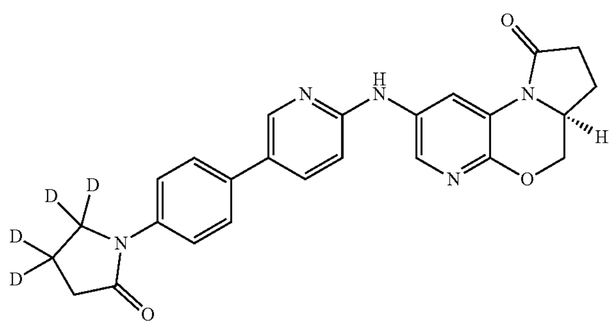 [SMILES: [2H]C1([2H])CC(=O)N(c2ccc(-c3ccc(Nc4cnc5c(c4)N4C(=O)CC[C@H]4CO5)nc3)cc2)C1([2H])[2H]] |

Biochemical Assays

Example 306: ADP-Glo Biochemical Assay

Dilution series of the compounds were prepared in DMSO at 100 times the final assay concentration ($n_1=n_0/3$ in 10 points). The compounds were further diluted to three times the assay concentration in assay buffer (20 mM MOPS pH 7.2, 25 mM magnesium chloride, 0.005% Tween 20). 6 µL of the diluted compounds were added to a 384 well assay plate followed by 9 µL of a mix consisting of 4 nM PIP4K2A (full length protein, SignalChem) and 100 µM PI(5)P diC8 (Tebu-Bio). Enzyme and compounds were pre-incubated at room temperature for 15 minutes.

Then 3 µL of a solution containing 60 µM ATP (Promega) in assay buffer was added to the wells containing compound and enzyme and mixing was performed by pipetting several times. The reaction was incubated at room temperature for 1 h. Then 18 µL of ADP-Glo™ Reagent (Promega) was added to stop the kinase reaction and deplete the unconsumed ATP, mixing was performed by pipetting several times. The plate was incubated at room temperature for 40 minutes before addition of 36 µL of Kinase Detection Reagent (Promega) to convert ADP to ATP and introduce luciferase and luciferin to detect ATP. The reaction was incubated at room temperature for 40 minutes before the luminescence was measured in a in a Victor 3V 1420 multilabel counter (Perkin Elmer).

Percent inhibition of the compounds as compared to dimethyl sulfoxide treated control samples was calculated. Compound concentration versus percent inhibition were fitted to generate $IC_{50}$ values. Results obtained with this assay are disclosed in Tables 2-4 below.

Example 307: Assay Protocol—PIP4KtypeIIA

GST tagged PIP4KtypeIIA and B enzymes were overexpressed in *E. Coli* and purified to >80% homogeneity. Phosphatidyl inositol-5-phosphate (PI5P, Cat. #850152, Avanti Polar Lipids Inc.) was used as the lipid substrate and phosphatidyl ethanolamine (DOPE 18:1, Cat. #850725, Avanti Polar Lipids Inc.) was used as the carrier lipid for assays. Ultrapure ATP and GTP was purchased from Bellbrooke Labs. ADP Glo reagents were obtained from Promega. Transcreener FI reagent was obtained from Bellbrooke labs.

Buffers:
1. HEPES buffer mix: 200 mM HEPES pH 7.4, 50 mM $MgCl_2$, 0.05% v/v triton×100.
2. HNE buffer: 20 mM HEPES, pH 7.4, 100 mM NaCl, 0.5 mM EGTA 3. H:E buffer: 30 mM HEPES, pH 7.4, 1 mM EGTA Enzyme preparation: GST-tagged PIP4KtypeIIA (5 μL, 1.43 mg/mL) was diluted (1:10) to 50 μL using HNE buffer. From the 1:10 diluted stock, a 6.4 μL aliquot was diluted further to 5 mL using HNE buffer to yield 5× enzyme stock (2.5 nM).

GST-tagged PIP4KtypeIIB (3.4 μL, 2.77 mg/mL) was diluted to 5 mL using HNE buffer to yield 5× enzyme stock (25 nM)

Lipid Preparation: In a 10 mL pyrex glass vial, 1 μg of PI5P and 1 μg of DOPE were suspended in 2.5 mL of HEPES buffer mix and 2.5 mL of H:E buffer. The contents were mixed and sonicated for 3 min to yield a translucent lipid stock.

Compound Preparation: Compounds were stored as 5 mM stocks in neat DMSO as room temperature in glass vials. 5 mM stocks were diluted to 2 mM and then serially diluted (3×) in neat DMSO in 96 well polypropylene plates. From the serially diluted stocks, 3 μL was delivered into 250 μL of 25% DMSO (in water) to generate 5× compound stocks. Typically, the highest compound conc. was 24 μM.

Example 308: PIP4KtypeIIA Inhibition Assay

The assay volume was kept at 25 μL. To each well of the reaction plate, 10 μL of lipid stock (1:1 ratio PI5P:DOPE) was delivered. This was followed by the addition of 5 μL of compound in 25% DMSO. Then, to each well, 5 μL of 2.5 nM (5λ) typeIIA enzyme was delivered. The contents were mixed well and incubated for 1 h at 27° C. After 1 h, reaction was initiated by adding 5 μL of 50 μM ATP and the contents were mixed well with a multi-channel pipetteman. The final concentration of the reagents are as follows: 50 mM HEPES, pH 7.3, 10 mM $MgCl_2$, 20 mM NaCl, 0.01% v/v triton-X100, 5% DMSO, 10 μM ATP, 80 μM (2 μg) PI5P, 2 μg DOPE, and 0.5 nM PIP4KIIA. Typically, the highest conc. of compounds was 4.8 μM and the lowest conc. was 0.

After 1 h, the reaction was quenched by adding 25 μL of ADP Glo reagent. The contents were incubated for 1 h. Afterwards, 50 μL of kinase detection reagent was delivered. The contents were incubated for another hour. The luminescence was read using Molecular Devices Paradigm plate reader. Each plate had a "No inhibitor" control (max. activity, 4 wells) and a blank (background noise, 4 wells). The blanks were averaged and subtracted from all other wells. Using a calibration curve, RLU was converted to μM ADP (product). IC50 was calculated by plotting the residual activity (expressed as % No inhibitor control) vs. log [Inh. conc.]

Example 309: PIP4KtypeIIB Inhibition Assay

The assay volume was kept at 25 μL. To each well of the reaction plate, 10 μL of lipid stock (1:1 ratio PI5P:DOPE) was delivered. This was followed by the addition of 5 μL of compound in 25% DMSO. Then, to each well, 5 μL of 25 nM (5×) typeIIB enzyme was delivered. The contents were mixed well and incubated for 1 h at 27° C. After 1 h, reaction was initiated by adding 5 μL of 500 μM GTP and the contents were mixed well with a multi-channel pipetteman. The final concentration of the reagents are as follows: 50 mM HEPES, pH 7.3, 10 mM $MgCl_2$, 20 mM NaCl, 0.01% v/v triton-X100, 5% DMSO, 100 μM GTP, 80 μM (2 μg) PI5P, 2 μg DOPE, and 5 nM PIP4KIIB Typically, the highest conc. of compounds was 4.8 μM and the lowest conc. was 0.

After 2 h, the reaction was quenched by adding 25 μL of transcreener FI reagent. The contents were incubated at rt for 1 h and the Fluorescence (Ex: 584 Em: 623) was read using Molecular Devices Paradigm plate reader. Each plate had a "No inhibitor" control (max. activity, 4 wells) and a blank (background noise, 4 wells). The blanks were averaged and subtracted from all other wells. Using a calibration curve, RFU was converted to μM GDP (product). $IC_{50}$ was calculated by plotting the residual activity (expressed as % No inhibitor control) vs. log [Inh. conc.]

Table 2 represents PI5P4K activity of compounds (Example No.) of the invention arranged in accordance with the inhibition of PIP4K2 A kinase assay.

| Kinase Assay- PIP4K2 A $IC_{50}$ ≤ 1 nM |
|---|
| 81 |
| 222 |
| 223 |
| 226 |
| 227 |
| 183 |
| 177 |
| 179 |
| 278 |
| 280 |
| 284 |
| 288 |
| 215 |
| Kinase Assay- PIP4K2 A 1 < $IC_{50}$ ≤ 10 nM |
| 73 |
| 76 |
| 23 |
| 78 |
| 43 |
| 74 |
| 94 |
| 100 |
| 102 |
| 103 |
| 97 |
| 90 |
| 93 |
| 85 |
| 86 |
| 96 |
| 224 |
| 225 |
| 117 |
| 119 |
| 109 |
| 111 |
| 230 |
| 231 |
| 138 |
| 141 |
| 143 |
| 232 |
| 131 |
| 155 |
| 233 |
| 132 |
| 152 |
| 156 |
| 163 |
| 164 |
| 151 |
| 234 |
| 235 |
| 150 |
| 238 |
| 239 |
| 242 |
| 246 |
| 252 |
| 258 |

| | |
|---|---|
| 190 | 166 |
| 84 | 162 |
| 178 | 240 |
| 191 | 241 |
| 174 | 153 |
| 267 | 192 |
| 268 | 285 |
| 89 | 291 |
| 92 | 293 |
| 276 | 297 |
| 277 | Kinase Assay- PIP4K2 A $100 < IC_{50} \leq 1000$ nM |
| 281 | |
| 282 | 1 |
| 283 | 82 |
| 286 | 19 |
| 287 | 56 |
| 289 | 57 |
| 290 | 14 |
| 294 | 69 |
| 202 | 47 |
| 197 | 218 |
| Kinase Assay- PIP4K2 A $10 < IC_{50} \leq 100$ nM | 34 |
| | 16 |
| 38 | 27 |
| 24 | 41 |
| 40 | 39 |
| 42 | 68 |
| 217 | 65 |
| 11 | 32 |
| 28 | 30 |
| 77 | 67 |
| 52 | 63 |
| 75 | 20 |
| 26 | 21 |
| 25 | 18 |
| 31 | 17 |
| 12 | 104 |
| 72 | 106 |
| 13 | 49 |
| 59 | 48 |
| 46 | 88 |
| 45 | 115 |
| 53 | 61 |
| 80 | 62 |
| 79 | 107 |
| 99 | 125 |
| 101 | 112 |
| 98 | 108 |
| 95 | 110 |
| 87 | 147 |
| 58 | 146 |
| 50 | 148 |
| 91 | 149 |
| 113 | 158 |
| 114 | 161 |
| 116 | 236 |
| 118 | 237 |
| 139 | 264 |
| 140 | 274 |
| 121 | 275 |
| 122 | 292 |
| 123 | 175 |
| 128 | 296 |
| 130 | Kinase Assay- PIP4K2 A $IC_{50} > 1000$ nM |
| 135 | |
| 136 | 10 |
| 137 | 66 |
| 142 | 33 |
| 126 | 3 |
| 120 | 54 |
| 129 | 35 |
| 124 | 9 |
| 157 | 37 |
| 133 | 6 |
| 127 | 36 |
| 134 | 219 |
| 154 | 7 |
| 159 | 2 |
| 165 | 64 |

-continued 70
5
220
4
8
221
22
60
71
51
228
229
29
160
279

Table 3 represents PI5P4K activity of compounds (Example No.) of the invention arranged in accordance with the inhibition of ADP-glo kinase assay PIP4K 2A.

ADP-glo kinase assay PIP4K 2A $IC_{50} \leq 1$ nM 210
211
212
200
195
216

ADP-glo kinase assay PIP4K 2A $1 < IC_{50} \leq 10$ nM 73
81
222
223
224
226
227
109
111
230
231
138
155
233
163
164
151
234
150
238
242
246
247
249
255
258
260
261
183
84
265
266
203
206
198
204
201
199
207
205
182
178
181
177
172
179
176
197
295

ADP-glo kinase assay PIP4K 2A $10 < IC_{50} \leq 100$ nM 80
94
100
102
103
95
85
86
89
96
225
113
116
117
118
119
139
140
121
135
136
137
141
142
143
232
124
131
157
133
146
127
132
134
152
156
154
235
165
166
162
239
252
253
254
256
169
170
168
259
173
167
190
208
196
192
187
191
174
267
268
270
271

ADP-glo kinase assay PIP4K 2A $100 < IC_{50} \leq 1000$ nM 59
46
45
101
98
106
87
58
50
49

114
61
62
107
122
123
125
128
130
126
120
129
112
108
110
147
158
161
159
236
237
240
241
153
244
245
272
250
251
257
262

ADP-glo kinase assay PIP4K 2A IC$_{50}$ > 1000 nM 60
104
71
51
228
229
148
149
29
160
243
194
269

Table 4: represents PI5P4K activity of compounds (Example No.) of the invention arranged in accordance with the inhibition of PIP4K2 B kinase assay.

Trans-FI P kinase assays: PIP4K2B 1 < IC$_{50}$ ≤ 10 nM 260
210
211
203
212
198
204
201
200
199
196
195
207
205
178
177
179
276
278
280
284
286
287
288
289
290
294
215
202
216
197

Trans-FI P kinase assays: PIP4K2B 10 < IC$_{50}$ ≤ 100 nM 73
81
94
100
99
103
95
97
90
93
85
86
89
92
91
96
222
223
224
225
226
113
227
116
117
119
230
231
121
130
135
136
137
138
141
142
143
232
131
155
133
233
134
152
156
163
164
151
154
234
235
150
238
162
239
153
242
246
247
249
253
255
258
169
170
168
259
173
261
167

| | |
|---|---|
| 183 | 175 |
| 190 | 296 |

Trans-FI P kinase assays: PIP4K2B IC$_{50}$ > 1000 nM

| | |
|---|---|
| 84 | |
| 265 | |
| 266 | 60 |
| 208 | 104 |
| 206 | 71 |
| 192 | 51 |
| 182 | 49 |
| 187 | 88 |
| 181 | 115 |
| 191 | 61 |
| 172 | 62 |
| 267 | 228 |
| 268 | 229 |
| 176 | 112 |
| 270 | 108 |
| 271 | 110 |
| 277 | 147 |
| 281 | 148 |
| 282 | 149 |
| 283 | 29 |
| 285 | 160 |
| 291 | 237 |
| 292 | 243 |
| 293 | 194 |
| 295 | 269 |
| 297 | 279 |
| 59 | |
| 46 | |
| 45 | |
| 80 | |
| 101 | |
| 102 | |
| 98 | |
| 106 | |
| 87 | |
| 58 | |
| 50 | |
| 114 | |
| 118 | |
| 109 | |
| 111 | |
| 139 | |
| 140 | |
| 107 | |
| 122 | |
| 123 | |
| 125 | |
| 128 | |
| 126 | |
| 120 | |
| 129 | |
| 124 | |
| 157 | |
| 146 | |
| 127 | |
| 132 | |
| 158 | |
| 161 | |
| 159 | |
| 165 | |
| 236 | |
| 166 | |
| 240 | |
| 241 | |
| 244 | |
| 245 | |
| 272 | |
| 250 | |
| 251 | |
| 252 | |
| 254 | |
| 256 | |
| 257 | |
| 262 | |
| 174 | |
| 274 | |
| 275 | |

Equivalents

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A compound of Formula (Ie):

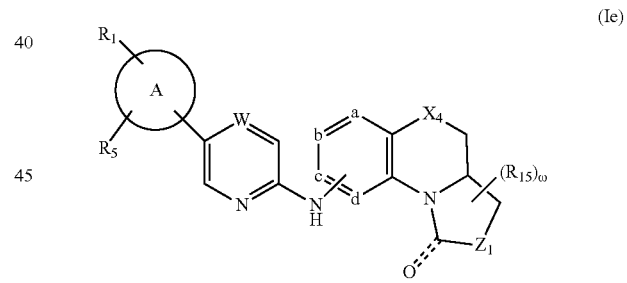

(Ie)

or a pharmaceutically acceptable salt, prodrug, solvate, hydrate, stereoisomer, or tautomer thereof,
wherein:
- - - - - - represents a double bond;
A is $C_{3-8}$ cycloalkyl, $C_{4-8}$ cycloalkenyl, aryl, spiroheterocyclyl, heterocyclyl, or 6-membered heteroaryl;
a, b, c, and d, are each independently C, CH, or N, wherein at least one of a, b, c, and d is N; and no more than two of a, b, c, and d are N;
$X_4$ and $Z_1$ are each independently —O—, —N($R_{15}$)—, or —C($R_{15}$)($R_{15}$)—;
ω is 1, 2, or 3;
W is C($R_6$) or N;
$R_1$ is —N($R_2$)C(O)$R_3$, —C(O)N($R_2$)($R_3$), —S(O)$_2$N($R_2$)($R_3$), —N($R_2$)S(O)$_2R_3$, —R$_2$C(O)N($R_2$)($R_{c3}$), or heteroaryl, wherein heteroaryl is optionally substituted with one or more $R_7$;

$R_2$ is independently, at each occurrence, $C_{1-6}$ alkyl, $C_{2-6}$ alkenyl, or $C_{2-6}$ alkynyl, wherein the $C_{1-6}$ alkyl, $C_{2-6}$ alkenyl, or $C_{2-6}$ alkynyl is optionally substituted with one or more $R_4$;

$R_3$ is independently, at each occurrence, —H, $C_{1-6}$ alkyl, $C_{2-6}$ alkenyl, or $C_{2-6}$ alkynyl, wherein the $C_{1-6}$ alkyl, $C_{2-6}$ alkenyl, or $C_{2-6}$ alkynyl is optionally substituted with one or more $R_4$; or $R_2$ and $R_3$ when taken together with the atom to which they are each attached form a heterocycle optionally substituted with one or more $R_4$;

$R_4$ is independently, at each occurrence, —H, halogen, —OH, —NH$_2$, —NO$_2$, —CN, $C_{1-6}$ alkyl, $C_{1-6}$ alkoxy, $C_{3-8}$ cycloalkyl, heterocyclyl, aryl, or heteroaryl, wherein the $C_{1-6}$ alkyl, $C_{1-6}$ alkoxy, $C_{3-8}$ cycloalkyl, heterocyclyl, aryl, or heteroaryl is optionally substituted with one or more $R_7$;

$R_5$ is —H, halogen, —OH, —CN, $C_{1-6}$ alkyl, methoxy, —O—$C_3$-$C_6$ alkyl, $C_{3-8}$ cycloalkyl, heterocyclyl, aryl, or heteroaryl;

$R_6$ is —H, halogen, —OH, —NH$_2$, —NO$_2$, —CN, —CO$_2$H, —C(O)NH$_2$, $C_{1-6}$ alkoxy, $C_{3-8}$ cycloalkyl, heterocyclyl, —O—$C_{3-8}$ cycloalkyl, or $C_{1-6}$ alkyl, wherein the $C_{1-6}$ alkyl, $C_{1-6}$ alkoxy, heterocyclyl, or $C_{3-8}$ cycloalkyl is optionally substituted with —OH, $C_{1-6}$ alkyl, $C_{1-6}$ alkoxy, $C_{3-8}$ cycloalkyl, —NH$_2$, —NH($C_{1-6}$ alkyl), or —N($C_{1-6}$ alkyl)$_2$; or $R_5$ and $R_6$ when taken together with the carbon atom to which they are each attached form a 5- to 6-membered heteroaryl ring;

$R_7$ is independently, at each occurrence, —H, halogen, —OH, $C_{1-6}$ alkyl, $C_{1-6}$ alkoxy, $C_{3-8}$ cycloalkyl, heterocyclyl, aryl, or heteroaryl, wherein the $C_{1-6}$ alkyl, $C_{1-6}$ alkoxy, $C_{3-8}$ cycloalkyl, heterocyclyl, aryl, or heteroaryl is optionally substituted with one or more $R_{14}$;

$R_{14}$ is independently, at each occurrence, —H, halogen, —CN, —NO$_2$, —OH, —NH$_2$, $C_{1-6}$ alkyl, $C_{3-8}$ cycloalkyl, heterocyclyl, aryl, or heteroaryl;

$R_{15}$ is independently, at each occurrence, —H, halogen, oxo, —OH, —NH$_2$, —NO$_2$, $C_{1-6}$ alkyl, $C_{1-6}$ alkoxy, $C_{3-8}$ cycloalkyl, heterocyclyl, aryl, heteroaryl, —C(O)N(R$_{21}$)(R$_{23}$), —(CH$_2$)$_o$—C(O)R$_{23}$, —OC(O)R$_{23}$, —C(O)OR$_{23}$, —SO$_2$R$_{23}$, —N(R$_{23}$)C(O)—Ar—N(R$_{23}$)-G, or —N(R$_{23}$)C(O)—Ar—N(R$_{23}$)C(O)-G, wherein the $C_{1-6}$ alkyl, $C_{1-6}$ alkoxy, $C_{3-8}$ cycloalkyl, heterocyclyl, heteroaryl, or aryl is optionally substituted with one or more $R_{23}$; or two $R_{15}$ groups, together with the atoms to which they are attached, form a heterocyclyl, $C_{3-6}$ cycloalkyl, $C_{5-6}$ spirocycloalkyl, aryl, or heteroaryl, wherein the $C_{3-6}$ cycloalkyl, heterocyclyl, $C_{5-6}$ spirocycloalkyl, heteroaryl, or aryl is optionally substituted with one or more $R_{20}$;

Ar is aryl;

G is —H, $C_{1-6}$ alkyl, $C_{1-6}$ alkoxy, $C_{2-6}$ alkenyl, $C_{2-6}$ alkynyl, $C_{3-8}$ cycloalkyl, heterocyclyl, aryl, heteroaryl, —C(O)OR$_{23}$, —C(O)CH=CHCH$_2$N(R$_{23}$)(R$_{23}$), or —C(O)N(R$_{21}$)(R$_{23}$); or two $R_{15}$ when on adjacent atoms may be taken together with the atoms to which they are each attached to form a heterocycle optionally substituted with one or more $R_{16}$;

$R_{16}$ is independently, at each occurrence, $C_{1-6}$ alkyl, $C_{3-6}$ cycloalkyl, —C(O)R$_{23}$, —C(O)R$_{23}$, —C(O)OR$_{23}$, —S(O)$_2$R$_{23}$, or oxo;

$R_{20}$ is independently, at each occurrence, —H, halogen, —OH, —NH$_2$, oxo, —C(O)R$_{21}$, —OR$_{23}$, $C_{3-6}$ cycloalkyl, or $C_{1-6}$ alkyl;

$R_{21}$ is independently, at each occurrence, —H, $C_{1-6}$ alkyl, $C_{2-6}$ alkenyl, $C_{2-6}$ alkynyl, $C_{3-8}$ cycloalkyl, heterocyclyl, aryl, or heteroaryl, wherein the $C_{1-6}$ alkyl, $C_{2-6}$ alkenyl, $C_{2-6}$ alkynyl, $C_{3-8}$ cycloalkyl, heterocyclyl, heteroaryl, or aryl is optionally substituted with one or more —H, halogen, —CN, —OH, $C_{1-6}$ alkyl, $C_{1-6}$ alkoxy, $C_{3-8}$ cycloalkyl, heterocyclyl, heteroaryl, or aryl;

each $R_{23}$ is independently, at each occurrence, —H, $C_{1-6}$ alkyl, $C_{1-6}$ alkoxy, $C_{2-6}$ alkenyl, $C_{2-6}$ alkynyl, $C_{3-8}$ cycloalkyl, heterocyclyl, aryl, or heteroaryl, wherein the $C_{1-6}$ alkyl, $C_{2-6}$ alkenyl, $C_{2-6}$ alkynyl, $C_{3-8}$ cycloalkyl, heterocyclyl, heteroaryl, or aryl is optionally substituted with one or more —H, halogen, —CN, —OH, —NH$_2$, $C_{1-6}$ alkyl, $C_{1-6}$ alkoxy, $C_{3-8}$ cycloalkyl, heterocyclyl, heteroaryl, aryl, or $R_{24}$;

$R_{24}$ is independently, at each occurrence, —H, $C_{1-6}$ alkyl, $C_{2-6}$ alkenyl, $C_{2-6}$ alkynyl, $C_{3-8}$ cycloalkyl, heterocyclyl, aryl, heteroaryl, C(O)N($C_{1-6}$ alkyl)($C_{1-6}$ alkyl), —C(O)—$C_{1-6}$ alkyl, —C(O)—$C_{2-6}$ alkenyl, or —C(O)O—$C_{1-6}$ alkyl, wherein the $C_{1-6}$ alkyl, $C_{2-6}$ alkenyl, $C_{2-6}$ alkynyl, $C_{3-8}$ cycloalkyl, heterocyclyl, heteroaryl, or aryl is optionally substituted with one or more —H, halogen, —CN, —OH, —NH$_2$, $C_{1-6}$ alkyl, $C_{1-6}$ alkoxy, $C_{3-8}$ cycloalkyl, heterocyclyl, heteroaryl, or aryl; and each o is independently 0-4.

2. The compound of claim 1 selected from the group consisting of:

(R)-2-((5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((5-(4-((R)-4-hydroxy-2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((5-(4-((S)-4-hydroxy-2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((5-(4-(2-oxopyrrolidin-1-yl)phenyl)pyrazin-2-yl)amino)-6,6a,7,8-tetrahydro-9H-pyrido[2,3-b]pyrrolo[1,2-d][1,4]oxazin-9-one, (S)—N,N-dimethyl-4-(6-((9-oxo-6a,7,8,9-tetrahydro-6H-pyrido[2,3-b]pyrrolo[1,2-d][1,4]oxazin-2-yl)amino)pyridin-3-yl)benzamide, (S)-2-((5-(3-fluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-8,8-dimethyl-2-((5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((5-(3-fluoro-4-(2-oxopyrrolidin-1-yl)phenyl)pyridin-2-yl)amino)-8,8-dimethyl-6,6a,7,8-tetrahydro-9H-pyrido[2,3-b]pyrrolo[1,2-d][1,4]oxazin-9-one, (6aS)-8-methyl-2-((5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (R)-2-((5-(3-fluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2'-((5-(4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one, (6aS)-2-((5-(3-fluoro-4-(2-oxopyrrolidin-1-yl)phenyl)pyridin-2-yl)amino)-8-methyl-6,6a,7,8-tetrahydro-9H-pyrido[2,3-b]pyrrolo[1,2-d][1,4]oxazin-9-one, (S)-2-((5-(3-fluoro-4-(2-oxopyrrolidin-1-yl)phenyl)-4-methoxypyridin-2-yl)amino)-6,6a,7,8-tetrahydro-9H-pyrido[2,3-b]pyrrolo[1,2-d][1,4]oxazin-9-one, (S)-2-((5-(3-fluoro-4-(2-oxopyrrolidin-1-yl)phenyl)-4-methylpyridin-2-yl)amino)-6,6a,7,8-tetrahydro-9H-pyrido[2,3-b]pyrrolo[1,2-d][1,4]oxazin-9-one, (S)-2-((5-(3,5-difluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((5-(2,5-difluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((6-methyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (R)-8-((5-(4-(2-oxopyrrolidin-1-yl)phenyl)pyridin-2-yl)amino)-3a,4-dihydro-1H,3H-oxazolo[3,4-d]pyrido[2,3-b][1,4]oxazin-1-one, (S)-2'-((4-isopropyl-5-(4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one, (S)-2-((4-(2-aminopropan-2-yl)-5-(2-fluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2'-((4-cyclopropyl-5-(4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one, (S)-2'-((4-methoxy-5-(4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one, (S)-2'-((5-(2-methyl-4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one, (S)-2'-((4-methyl-5-(4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one, (S)-2'-((4-(methoxymethyl)-5-(4-(2-oxopyrrolidin-1-yl)phenyl)pyridin-2-yl)amino)-6a',7'-dihydro-6'H,9'H-spiro[cyclopropane-1,8'-pyrido[2,3-b]pyrrolo[1,2-d][1,4]oxazin]-9'-one, (S)-2-((3-methyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((5-(2-methyl-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((4-cyclopropyl-5-(3-fluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((4-cyclopropyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((5-(3-fluoro-4-(2-oxopyrrolidin-1-yl)phenyl)-4-isopropylpyridin-2-yl)amino)-6,6a,7,8-tetrahydro-9H-pyrido[2,3-b]pyrrolo[1,2-d][1,4]oxazin-9-one, (S)-2-((4-isopropyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((5-(2-fluoro-4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (6aS)-2-((5-(3-fluoro-4-(2-oxopyrrolidin-1-yl)phenyl)pyridin-2-yl)amino)-8-hydroxy-6,6a,7,8-tetrahydro-9H-pyrido[2,3-b]pyrrolo[1,2-d][1,4]oxazin-9-one, (6aS)-8-hydroxy-2-((5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((4-methoxy-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((4-methyl-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (6aR)-2-((5-(4-(1-methyl-2-oxopyrrolidin-3-yl)phenyl)pyridin-2-yl)amino)-6,6a,7,8-tetrahydro-9H-pyrido[2,3-b]pyrrolo[1,2-d][1,4]oxazin-9-one, (6aS,8R)-2-((5-(3-fluoro-4-(2-oxopyrrolidin-1-yl)phenyl)pyridin-2-yl)amino)-8-hydroxy-8-methyl-6,6a,7,8-tetrahydro-9H-pyrido[2,3-b]pyrrolo[1,2-d][1,4]oxazin-9-one, (6aS,8R)-8-hydroxy-8-methyl-2-((5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((4-(methoxymethyl)-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (3S,6R)—N,N-dimethyl-6-(6-(((S)-9-oxo-6a,7,8,9-tetrahydro-6H-pyrido[2,3-b]pyrrolo[1,2-d][1,4]oxazin-2-yl)amino)pyridin-3-yl)tetrahydro-2H-pyran-3-carboxamide, (S)-2-((1'-(4-methyl-4H-1,2,4-triazol-3-yl)-1',2',3',6'-tetrahydro-[3,4'-bipyridin]-6-yl)amino)-6,6a,7,8-tetrahydro-9H-pyrido[2,3-b]pyrrolo[1,2-d][1,4]oxazin-9-one, (S)-2-((5-(4-(4-methyl-4H-1,2,4-triazol-3-yl)piperazin-1-yl)pyridin-2-yl)amino)-6,6a,7,8-tetrahydro-9H-pyrido[2,3-b]pyrrolo[1,2-d][1,4]oxazin-9-one, (S)-2-((5-(4-(4-methylpyridazin-3-yl)phenyl)pyridin-2-yl)amino)-6,6a,7,8-tetrahydro-9H-pyrido[2,3-b]pyrrolo[1,2-d][1,4]oxazin-9-one, (S)-2-((5-(4-(4-methylisoxazol-5-yl)phenyl)pyridin-2-yl)amino)-6,6a,7,8-tetrahydro-9H-pyrido[2,3-b]pyrrolo[1,2-d][1,4]oxazin-9-one, (S)-2-((4-(methoxymethyl)-5-(4-(4-methylisoxazol-3-yl)phenyl)pyridin-2-yl)amino)-6,6a,7,8-tetrahydro-9H-pyrido[2,3-b]pyrrolo[1,2-d][1,4]oxazin-9-one, (S)-2-((5-(4-(4-methylisoxazol-3-yl)phenyl)pyridin-2-yl)amino)-6,6a,7,8-tetrahydro-9H-pyrido[2,3-b]pyrrolo[1,2-d][1,4]oxazin-9-one, (S)-2-((4-cyclobutoxy-5-(4-(2-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, (S)-2-((4-cyclopropyl-5-(4-(4-methyl-4H-1,2,4-triazol-3-yl)phenyl)pyridin-2-yl)amino)-6,6a,7,8-tetrahydro-9H-pyrido[2,3-b]pyrrolo[1,2-d][1,4]oxazin-9-one, (S)-2-((5-(4-(5-methyl-TH-1,2,3-triazol-1-yl)phenyl)pyridin-2-yl)amino)-6,6a,7,8-tetrahydro-9H-pyrido[2,3-b]pyrrolo[1,2-d][1,4]oxazin-9-one, (S)-2-((4-methoxy-5-(4-(4-methyl-4H-1,2,4-triazol-3-yl)phenyl)pyridin-2-yl)amino)-6,6a,7,8-tetrahydro-9H-pyrido[2,3-b]pyrrolo[1,2-d][1,4]oxazin-9-one, (S)-2-((5-(4-(4-methyl-4H-1,2,4-triazol-3-yl)phenyl)pyridin-2-yl)amino)-6,6a,7,8-tetrahydro-9H-pyrido[2,3-b]pyrrolo[1,2-d][1,4]oxazin-9-one, (R)-8-((5-(3-fluoro-4-(2-oxopyrrolidin-1-yl)phenyl)pyridin-2-yl)amino)-3a,4-dihydro-1H,3H-oxazolo[3,4-d]pyrido[2,3-b][1,4]oxazin-1-one, (S)-2-((5-(4-(4-isobutyl-4H-1,2,4-triazol-3-yl)phenyl)pyridin-2-yl)amino)-6,6a,7,8-tetrahydro-9H-pyrido[2,3-b]pyrrolo[1,2-d][1,4]oxazin-9-one, (S)-2-((5-(4-((R)-2-methyl-5-oxopyrrolidin-1-yl)phenyl)pyridin-2-yl)amino)-6,6a,7,8-tetrahydro-9H-pyrido[2,3-b]pyrrolo[1,2-d][1,4]oxazin-9-one, and (S)-2-((5-(4-(2-oxopyrrolidin-1-yl-4,4,5,5-d4)phenyl)pyridin-2-yl)amino)-6,6a,7,8-tetrahydro-9H-pyrido[2,3-b]pyrrolo[1,2-d][1,4]oxazin-9-one; or a pharmaceutically acceptable salt, prodrug, solvate, hydrate, stereoisomer, or tautomer thereof.

3. A pharmaceutical composition comprising a compound of claim 1, and a pharmaceutically acceptable carrier.

4. A method of inhibiting PI5P4K comprising, administering to a patient in need thereof an effective amount of a compound of claim 1.

5. The compound of claim 1, wherein A is phenyl.

6. The compound of claim 1, wherein $R_1$ is heteroaryl, wherein the heteroaryl is optionally substituted with $R_7$.

7. The compound of claim 6, wherein $R_7$ is $C_{1-6}$ alkyl.

8. The compound of claim 1, wherein $R_5$ is —H, halogen, —OH, CN, or $C_{1-6}$ alkyl.

9. The compound of claim 1, wherein W is $C(R_6)$.

10. The compound of claim 1, wherein $R_6$ is H.

11. The compound of claim 1, wherein $R_{15}$ is H.

* * * * *